US011242364B1

United States Patent
Migaud et al.

(10) Patent No.: US 11,242,364 B1
(45) Date of Patent: *Feb. 8, 2022

(54) EFFICIENT AND SCALABLE SYNTHESES OF NICOTINOYL RIBOSIDES AND REDUCED NICOTINOYL RIBOSIDES, MODIFIED DERIVATIVES THEREOF, PHOSPHORYLATED ANALOGS THEREOF, ADENYLYL DINUCLEOTIDE CONJUGATES THEREOF, AND NOVEL CRYSTALLINE FORMS THEREOF

(71) Applicants: The Queen's University of Belfast, Belfast (GB); ChromaDex Inc., Irvine, CA (US)

(72) Inventors: Marie Eugenie Migaud, Lurgan (GB); Philip Redpath, Portadown (GB); Kerri Crossey, Magherafelt (GB); Richard Cunningham, Portadown (GB); Aron Erickson, Longmont, CO (US); Richard Nygaard, Longmont, CO (US); Amanda Storjohann, Westminster, CO (US)

(73) Assignees: ChromaDex Inc., Irvine, CA (US); The Queen's University of Belfast, Belfast (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/323,789

(22) Filed: May 18, 2021

Related U.S. Application Data

(60) Continuation of application No. 17/246,090, filed on Apr. 30, 2021, which is a continuation of application No. 16/908,416, filed on Jun. 22, 2020, which is a division of application No. 15/809,753, filed on Nov. 10, 2017, now Pat. No. 10,689,411.

(60) Provisional application No. 62/558,073, filed on Sep. 13, 2017, provisional application No. 62/420,737, filed on Nov. 11, 2016.

(51) Int. Cl.
| | | |
|---|---|---|
| *C07H 19/048* | (2006.01) | |
| *C07D 307/20* | (2006.01) | |
| *C07H 19/20* | (2006.01) | |
| *C07H 19/04* | (2006.01) | |

(52) U.S. Cl.
CPC ......... *C07H 19/048* (2013.01); *C07D 307/20* (2013.01); *C07H 19/20* (2013.01); *C07B 2200/13* (2013.01); *C07H 19/04* (2013.01)

(58) Field of Classification Search
None
See application file for complete search history.

(56) References Cited

U.S. PATENT DOCUMENTS

| | | |
|---|---|---|
| 6,255,291 B1 | 7/2001 | Germano |
| 6,624,150 B2 | 9/2003 | Yerxa et al. |
| 6,867,231 B1 | 3/2005 | Burke et al. |
| 7,022,680 B2 | 4/2006 | Sauve et al. |
| 7,138,122 B2 | 11/2006 | Burke et al. |
| 7,179,791 B2 | 2/2007 | Stamler et al. |
| 7,544,497 B2 | 6/2009 | Sinclair et al. |
| 7,601,332 B2 | 10/2009 | Mahov et al. |
| 7,615,535 B2 | 11/2009 | Stamler et al. |
| 7,776,326 B2 | 8/2010 | Milbrandt et al. |
| 7,977,049 B2 | 7/2011 | Sinclair et al. |
| 8,105,568 B2 | 1/2012 | Mahov et al. |
| 8,106,184 B2 | 1/2012 | Sauve et al. |
| 8,114,626 B2 | 2/2012 | Brenner et al. |

(Continued)

FOREIGN PATENT DOCUMENTS

| | | |
|---|---|---|
| CH | 318073 | 12/1956 |
| CN | 101360421 A | 2/2009 |

(Continued)

OTHER PUBLICATIONS

Kumar, Salt Selection in Drug Development, Pharmaceutical Technology, Pharmaceutical Technology, Mar. 2, 2008, vol. 32, Issue 3. (Year: 2008).*
L.J. Haynes et al., "734. Codehydrogenases. Part II. A Synthesis of Nicotinamide Nucleotide," Journal of the Chemical Society 3727-32 (1957).
M. Jarman, "4-Substituted Nicotinic Acids and Nicotinamides. Part III. Preparation of 4-Methylnicotinic Acid Riboside," Journal of the Chemical Society 918-20 (1969).

(Continued)

*Primary Examiner* — Layla D Berry
(74) *Attorney, Agent, or Firm* — Amin Talati Wasserman LLP; George M. Carrera, Jr.; Jonathan J. Krit

(57) ABSTRACT

The present disclosure provides methods of making nicotinoyl riboside compounds or derivatives of formula (I):

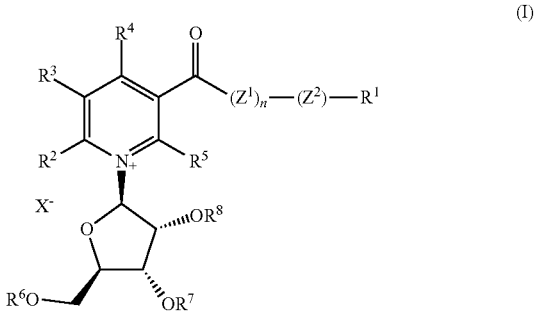

wherein $X^-$, $Z^1$, $Z^2$, n, $R^1$, $R^2$, $R^3$, $R^4$, $R^5$, $R^6$, $R^7$, and $R^8$ are described herein, reduced analogs thereof, modified derivatives thereof, phosphorylated analogs thereof, and adenylyl dinucleotide conjugates thereof, or salts, solvates, or prodrugs thereof, and novel crystalline forms thereof.

39 Claims, 47 Drawing Sheets

(56) References Cited

U.S. PATENT DOCUMENTS

| | | |
|---|---|---|
| 8,197,807 B2 | 6/2012 | Brenner |
| 8,217,006 B2 | 7/2012 | Stamler et al. |
| 8,383,086 B2 | 2/2013 | Brenner |
| 9,000,147 B2 | 4/2015 | Sauve et al. |
| 9,321,797 B2 | 4/2016 | Sauve et al. |
| 2002/0128205 A1 | 9/2002 | Stamler et al. |
| 2004/0224918 A1 | 11/2004 | Yatvin et al. |
| 2005/0227327 A1 | 10/2005 | Brenner |
| 2006/0025337 A1 | 2/2006 | Sinclair et al. |
| 2006/0111435 A1 | 5/2006 | Sinclair et al. |
| 2006/0229265 A1 | 10/2006 | Milburn et al. |
| 2007/0117765 A1 | 5/2007 | Sauve et al. |
| 2008/0194803 A1 | 8/2008 | Sinclair et al. |
| 2008/0318892 A1 | 12/2008 | Pickering et al. |
| 2009/0069444 A1 | 3/2009 | Joseph et al. |
| 2009/0196942 A1 | 8/2009 | Goyarts et al. |
| 2012/0108535 A1 | 5/2012 | Sauve et al. |
| 2012/0172584 A1 | 7/2012 | Sauve et al. |
| 2012/0251463 A1 | 10/2012 | Brenner |
| 2012/0328526 A1 | 12/2012 | Kristian |
| 2012/0329748 A1 | 12/2012 | Sauve et al. |
| 2013/0165398 A1 | 6/2013 | Huber |
| 2015/0056274 A1 | 2/2015 | Zemel et al. |
| 2015/0175645 A1 | 6/2015 | Milburn et al. |
| 2016/0168184 A1 | 6/2016 | Migaud et al. |
| 2016/0250241 A1 | 9/2016 | Deren-Lewis et al. |
| 2016/0272668 A1 | 9/2016 | Dellinger et al. |
| 2016/0355539 A1 | 12/2016 | Migaud et al. |
| 2017/0267709 A1 | 9/2017 | Migaud et al. |
| 2017/0304338 A1 | 10/2017 | Dellinger et al. |

FOREIGN PATENT DOCUMENTS

| | | | |
|---|---|---|---|
| EP | 2805719 A1 | 11/2014 | |
| GB | 2542881 A | 4/2017 | |
| WO | 2003093290 A2 | 11/2003 | |
| WO | 2013045538 A1 | 4/2013 | |
| WO | 2014011676 A1 | 1/2014 | |
| WO | 2014014828 A1 | 1/2014 | |
| WO | 2015014722 A1 | 2/2015 | |
| WO | 2015066382 A1 | 5/2015 | |
| WO | 2015186068 A1 | 12/2015 | |
| WO | 2015186114 A1 | 12/2015 | |
| WO | 2016014927 A2 | 1/2016 | |
| WO | 2016144660 A1 | 9/2016 | |
| WO | 2016149395 A1 | 9/2016 | |
| WO | WO-2017218580 A1 * | 12/2017 | ............... C07H 1/00 |

OTHER PUBLICATIONS

M. Yoshikawa et al., "Studies of Phosphorylation. III. Selective Phosphorylation of Unprotected Nucleosides," 42 Bulletin of the Chemical Society of Japan 3505-08 (1969).

Stephen M. Berge et al., "Pharmaceutical Salts," 66 Journal of Pharmaceutical Sciences 1-19 (1977).

I.A. Mikhailopulo et al., "Synthesis of Glycosides of Nicotinamide and Nicotinamide Mononucleotide," 5 Synthesis 388-89 (1981).

Martin Urberg et al., "Evidence for Synergism Between Chromium and Nicotinic Acid in the Control of Glucose Tolerance in Elderly Humans," 36 Metabolism 896-99 (1987).

Lee Ann Applegate et al., "Identification of the Molecular Target for the Suppression of Contact Hypersensitivity by Ultraviolet Radiation," 4 J. Exp. Med. 1117-31 (1989).

F. Friedlos et al., "Metabolism of NAD(P)H by blood components. Relevance to bioreductively activated prodrugs in a targeted enzyme therapy system," 44 Biochem. Pharmacol. 631-35 (1992), Abstract only.

Akinori Haratake et al., "UVB-Induced Alterations in Permeability Barrier Function: Roles for Epidermal Hyperproliferation and Thymocyte-Mediated Response," 108 Journal of Investigative Dermatology 769-75 (1997).

Krzysztof W. Pankiewicz, "Novel Nicotinamide Adenine Dinucleotide Analogues as Potential Anticancer Agents Quest for Specific Inhibition of Inosine Monophosphate Dehydrogenase," 76 Pharmacol. Ther. 89-100 (1997).

Jaemoon Lee et al., "A chemical synthesis of nicotinamide adenine dinucleotide (NAD+)," Chemical Communications 729-30 (1999).

Agnieszka Bzowska et al., "Purine nucleoside phosphorylases: properties, functions, and clinical aspects," 88 Pharmacology & Therapeutics 349-425 (2000).

V. Plasman et al., "Triterpene Saponins, Quaternary Ammonium Compounds, Phosphatidyl Cholines, and Amino Acids in the Pronatal and Elytral Secretions of Platyphora opima and Desmogramma subtropica," 63 J. Nat. Prod. 1261-64 (2000).

Jorg Breitenbach, "Melt extrusion: from process to drug delivery technology," 54 European Journal of Pharmaceutics and Biopharmaceutics 107-17 (2002).

Kouichi Nakamichi et al., "The role of the kneading paddle and the effects of screw revolution speed and water content on the preparation of solid dispersions using a twin-screw extruder," 241 International Journal of Pharmaceutics 203-11 (2002).

Ning Shan et al., "Mechanochemistry and co-crystal formation: effect of solvent on reaction kinetics," Chemical Communications 2372-73 (2002).

Shinji Tanimori et al., "An Efficient Chemical Synthesis of Nicotinamide Riboside (NAR) and Analogues," 12 Bioorganic & Medicinal Chemistry Letters 1135-37 (2002).

L. Diane Bruce et al., "Properties of hot-melt extruded tablet formulations for the colonic delivery of 5-aminosalicylic acid," 59 European Journal of Pharmaceutics and Biopharmaceutics 85-97 (2005).

Andrew V. Trask et al., "Achieving Polymorphic and Stoichiometric Diversity in Cocrystal Formation: Importance of Solid-State Grinding, Powder X-ray Structure Determination, and Seeding," 5 Crystal Growth & Design 2233-41 (2005).

Andrew V. Trask et al., "Screening for crystalline salts via mechanochemistry," Chemical Communications 51-53 (2006).

E. Verhoeven et al., "Xanthan gum to tailor drug release of sustained-release ethylcellulose mini-matrices prepared via hot-melt extrusion: in vitro and in vivo evaluation," 63 European Journal of Pharmaceutics and Biopharmaceutics 320-30 (2006).

Sandrien Janssens et al., "The use of a new hydrophilic polymer, Kollicoat IR, in the formulation of solid dispersions of Itraconazole," 30 European Journal of Pharmaceutical Sciences 288-94 (2007).

S.J. Jiang et al., "Ultraviolet B-induced alterations of the skin barrier and epidermal calcium gradient," 16 Exp. Dermatol. 985-92 (2007), Abstract only.

Shyam Karki et al., "Screening for Pharmaceutical Cocrystal Hydrates via Neat and Liquid-Assisted Grinding," 4 Molecular Pharmaceutics 347-54 (2007).

Michael A. Repka et al., "Pharmaceutical Applications of Hot-Melt Extrusion: Part I," 33 Drug Development and Industrial Pharmacy 909-26 (2007).

Michael A. Repka et al., "Pharmaceutical Applications of Hot-Melt Extrusion: Part II," 33 Drug Development and Industrial Pharmacy 1043-57 (2007).

H.Y. Thong et al., "Percutaneous penetration enhancers: an overview," 20 Skin Pharmacol. Physiol. 272-82 (2007), Abstract only.

D.A. Miller et al., "Targeted Intestinal Delivery of Supersaturated Itraconazole for Improved Oral Absorption," 25 Pharmaceutical Research 1450-59 (2008).

E. Verhoeven et al., "Influence of formulation and process parameters on the release characteristics of ethylcellulose sustained-release mini-matrices produced by hot-melt extrusion," 69 European Journal of Pharmaceutics and Biopharmaceutics 312-19 (2008).

Kalpana S. Paudel et al., "Challenges and opportunities in dermal/transdermal delivery," 1 Ther. Deliv. 109-31 (2010).

Devita Surjana et al, "Role of Nicotinamide in DNA Damage, Mutagenesis, and DNA Repair," 2010 Journal of Nucleic Acids 157591 (2010).

Ping Xu & Anthony A. Sauve, "Vitamin B3, the nicotinamide adenine dinucleotides and aging," 131 Mechanisms of Ageing and Development 287-98 (2010).

(56) References Cited

OTHER PUBLICATIONS

Ansel's Pharmaceutical Dosage Forms and Drug Delivery Systems, 9th Ed., L.V. Allen, Jr., Ed. (Philadelphia, Penn.: Lippincott Williams & Wilkins, 2011) pp. 272-293.
Christopher Hardacre et al., "Overcoming hydrolytic sensitivity and low solubility of phosphitylation reagents by combining ionic liquids with mechanochemistry," 47 Chemical Communications 5846-48 (2011).
Francesco Ravalico et al., "Rapid synthesis of nucleotide pyrophosphate linkages in a ball mill," 9 Organic & Biomolecular Chemistry 6496-97 (2011).
A. Almeida et al., "Upscaling and in-line process monitoring via spectroscopic techniques of ethylene vinyl acetate hot-melt extruded formulations," 439 International Journal of Pharmaceutics 223-29 (2012).
Kerri Crossey et al., "Exploiting the use of ionic liquids to access phosphorodiamidites," 2 RSC Advances 2988-93 (2012).
Kerri Crossey et al., "Nucleoside phosphitylation using ionic liquid stabilised phosphorodiamidites and mechanochemistry," 48 Chemical Communications 11969-71 (2012).
Huiju Liu et al., "Effects of Screw Configuration on Indomethacin Dissolution Behavior in Eudragit E PO," 31 Advances in Polymer Technology 331-42 (2012).
Mohammed Maniruzzaman et al., "A Review of Hot-Melt Extrusion: Process Technology to Pharmaceutical Products," 2012 ISRN Pharmaceutics 436763 (2012).
Carles Canto et al., "Crosstalk between poly(ADP-ribose) polymerase and sirtuin enzymes," 34 Molecular Aspects of Medicine 1168-201 (2013).
Bing Gong et al., "Nicotinamide riboside restores cognition through an upregulation of proliferator-activated receptor-gamma coactivator 1-alpha regulated beta-secretase 1 degradation and mitochondrial gene expression in Alzheimer's mouse models," 34 Neurobiology of Aging 1581-88 (2013).
Justin R. Hughey et al., "The use of inorganic salts to improve the dissolution characteristics of tablets containing Soluplus-based solid dispersions," 48 European Journal of Pharmaceutical Sciences 758-66 (2013).
Fabrice Krier et al., "PAT tools for the control of co-extrusion implants manufacturing process," 458 International Journal of Pharmaceutics 15-24 (2013).
C. Oba et al., "Collagen hydrolysate intake improves the loss of epidermal barrier function and skin elasticity induced by UVB irradiation in hairless mice," 29 Photodermatol. Photoimmunol. Photomed. 204-11 (2013), Abstract only.
Elena Reitz et al., "Residence time modeling of hot melt extrusion processes," 85 European Journal of Pharmaceutics and Biopharmaceutics 1200-05 (2013).
F. Romanski, et al., "The importance of monitoring process parameters as a method for quality control for hot melt extrusion," AAPS Annual Meeting 2013, San Antonio, USA (2013), Abstract only.
Ashish L. Sarode et al., "Hot melt extrusion (HME) for amorphous solid dispersions: Predictive tools for processing and impact of drug-polymer interactions on supersaturation," 48 European Journal of Pharmaceutical Sciences 371-84 (2013).
Sejal Shah et al., "Melt extrusion with poorly soluble drugs," 453 International Journal of Pharmaceutics 233-52 (2013).
Patrick R. Wahl et al., "Inline monitoring and a PAT strategy for pharmaceutical hot melt extrusion," 455 International Journal of Pharmaceutics 159-68 (2013).
Philip Redpath et al., "Nicotinamide Benzimidazolide Dinucleotides, Non-Cyclisable Analogues of NAD+," 25 Synlett 2331-36 (2014).
Dritan Hasa et al., "Cocrystal Formation through Mechanochemistry: from Neat and Liquid-Assisted Grinding to Polymer-Assisted Grinding," 127 Angewandte Chemie International Edition in English 7371-75 (2015).
J. Thiry et al., "A review of pharmaceutical extrusion: Critical process parameters and scaling-up," 479 International Journal of Pharmaceutics 227-40 (2015).
Jaemoon Lee et al., "A chemical synthesis of nicotinamide adenine dinucleotide (NAD+)," Chem. Commun., 729-730 (1999).
L.J. Haynes et al., "Codehydrogenases. Part II. A Synthesis of Nicotinamide Nucleotide.," J. Chem. Soc., 3727-3721 (1957).
J. Breitenbach, "Melt extrusion from process to drug delivery technology" 54 Eur. J. Pharm. (2002), pp. 107-117.
K. Nakamichi et al., "The role of the kneading paddle and the effects of screw revolution speed and water content on the preparation of SD using twin-screw extruder" 241 Int'l J. Pharm. (2002), pp. 203-211.
A. Almeida et al., "Upscaling and inline process monitoring via spectroscopic techniques of ethylene vinyl acetate hot-melt extruded formulations" 439 Int'l J. Pharm (2012), pp. 223-229.
Baumann et al., "Total Synthesis of the Glycopeptide Recognition Domain of the P-Selectin Glycoprotein Ligand 1" 47 Angew. Chem. Int. Ed. (2008), pp. 3445-3449.
Caira, M R. "Crystalline Polymorphism of Organic Compounds" 198 Topics in Current Chemistry (1998), pp. 164-208.

\* cited by examiner

EFFICIENT AND SCALABLE SYNTHESES OF NICOTINOYL RIBOSIDES AND REDUCED NICOTINOYL RIBOSIDES, MODIFIED DERIVATIVES THEREOF, PHOSPHORYLATED ANALOGS THEREOF, ADENYLYL DINUCLEOTIDE CONJUGATES THEREOF, AND NOVEL CRYSTALLINE FORMS THEREOF

This application is a Continuation of U.S. patent application Ser. No. 17/246,090, filed on Apr. 30, 2021, which is a Continuation of Ser. No. 16/908,416, filed on Jun. 22, 2020, which is a Divisional of U.S. patent application Ser. No. 15/809,753, filed on Nov. 10, 2017, now U.S. Pat. No. 10,689,411, which claims the benefit of each of U.S. Provisional Application No. 62/420,737, filed on Nov. 11, 2016, and U.S. Provisional Application No. 62/558,073, filed on Sep. 13, 2017. The disclosures of each of these prior applications are hereby incorporated by reference herein in their entireties for all purposes.

TECHNICAL FIELD

The present disclosure relates to synthetic processes for the preparation of nicotinoyl ribosides and reduced nicotinoyl ribosides, modified derivatives thereof, phosphorylated analogs thereof, and adenylyl dinucleotide conjugates thereof, the synthetic processes comprising processing of reagents by solvent-based processes, liquid-assisted mixing, milling, grinding, solvent-assisted grinding, and/or extrusion, and crystalline forms of nicotinamide riboside, in particular, nicotinamide riboside chloride, derivatives thereof, crystalline forms of nicotinic acid riboside, derivatives thereof, and crystalline forms of nicotinamide mononucleotide, and derivatives thereof.

BACKGROUND

The dietary vitamin B3, which encompasses nicotinamide ("Nam" or "NM"), nicotinic acid ("NA"), and nicotinamide riboside ("NR"), is a precursor to the coenzyme nicotinamide adenine dinucleotide ("NAD$^+$"), its phosphorylated parent ("NADP$^+$" or "NAD(P)$^+$"), and their respective reduced forms ("NADH" and "NADPH," respectively). Once converted intracellularly to NAD(P)$^+$ and NAD(P)H, vitamin B3 metabolites are used as co-substrates in multiple intracellular protein modification processes, which control numerous essential signaling events (e.g., adenosine diphosphate ribosylation and deacetylation), and as cofactors in over 400 redox enzymatic reactions, thus controlling metabolism. This is demonstrated by a range of metabolic endpoints, which include the deacylation of key regulatory metabolic enzymes, resulting in the restoration of mitochondrial activity and oxygen consumption. Critically, mitochondrial dysfunction and cellular impairment have been correlated to the depletion of the NAD(P)(H)-cofactor pool, when the NAD(P)(H)-cofactor pool is present in sub-optimal intracellular concentrations. Vitamin B3 deficiency yields to evidenced compromised cellular activity through NAD(P)$^+$ depletion, and the beneficial effect of additional NAD(P)$^+$ bioavailability through NA, Nam, NR, and nicotinamide mononucleotide ("NMN") supplementation is primarily observed in cells and tissues where metabolism and mitochondrial function have been compromised.

Despite extensive optimization of solution-based methodologies over many years for nucleotide preparation, difficulties and issues remain in the syntheses of nicotinoyl ribosides, the monophosphorylation of active hydroxyl groups thereof, and subsequent conjugation thereof, with respect to low yields and product stability and isolation from polar solvents. The current methodologies are also plagued by atom and energy inefficiency due, for example, to the use of large solvent excesses and the need for temperature-controlled reaction conditions.

The reported syntheses of nicotinamide riboside (NR) are becoming more scalable, but use corrosive and expensive reagents, and lengthy deprotection steps, and thus still display batch-to-batch quality variation, thereby presenting difficulties in maintaining good standards.

Partially protected nucleosides and nucleotides have found broad-ranging application in order to achieve improved bioavailability of the nucleoside and nucleotide parents. Such partial protection includes hydroxyl modifications with ester, carboxylate, and acetyl groups, in addition to the introduction of hydrolyzable phosphoramidate or mixed anhydride modification of the phosphate monoesters in the form of Protides and CycloSal derivatives. While the former type of protection has become more scalable, the modifications at the phosphorus center remain difficult to accomplish at scale, particularly on nucleosidic entities that are highly sensitive to changes in pH and that are readily degraded by heat.

Reduced nicotinamide riboside ("NRH") has been consistently shown to be more efficient at increasing intracellular NAD$^+$ levels, and surpasses nicotinamide riboside (NR) in that respect. While physiological and potentially therapeutic roles have not yet been examined due to a lack of material accessible in sufficient quantities for broad-ranging studies, it is anticipated that the phosphorylated forms of NRH and reduced nicotinic acid riboside ("NARH"), or derivatives thereof, could also have similar NAD$^+$-boosting capacities.

The reported syntheses of reduced nicotinamide riboside (NRH) are becoming more widely available but remain conducted on small scales, using corrosive and expensive reagents, and lengthy deprotection steps, and thus still display batch-to-batch quality variation, thereby presenting difficulties in maintaining good standards. In the current description, reduced nicotinamide riboside (NRH) generally refers to "reduced pyridine" nucleus, more specifically, the 1,4-dihydropyridine compounds.

Synthetically, the preparation of 5'-nucleotides remains time-consuming, atom-inefficient, and costly, due to the need for numerous protection and deprotection steps. In these preparation methods, the chlorodialkylphosphate, tetraalkylpyrophosphate, chlorophosphite, or phosphoramidite reagents required are also expensive starting materials by virtue of their chemical functionalization and chemical instability, and therefore, consequently associated synthetic difficulties. Phosphorylation reaction conditions are difficult to control and often use non-approved or toxic organic solvents, thus limiting the market of the manufactured compounds.

One known alternative approach to the protection/deprotection method is to use phosphorus oxychloride (P(O)Cl$_3$) (i.e., Yoshikawa conditions), however there are still drawbacks to this method, as follows. While not being bound by theory, in this method, polar trialkyl phosphate solvents, such as P(O)(OMe)$_3$, are used in a large excess, which are believed to enhance reaction rates while limiting the undesirable reactivity of P(O)Cl$_3$ as a chlorinating agent. Thus, it is believed that use of excess P(O)Cl$_3$/P(O)(OR)$_3$ is a better combination for the chemoselective 5'-O-phosphorylation of unprotected ribosides. However, the use of trialkyl phosphate solvents, such as P(O)(OMe)$_3$, precludes their implementation for the preparation of materials for eventual human use, as this class of solvent is highly toxic (known carcinogen, non-GRAS approved) and is difficult to remove from the final polar products. See M. Yoshikawa et al., *Studies of Phosphorylation. III. Selective Phosphorylation of Unprotected Nucleosides*, 42 BULL. CHEM. SOC. JAPAN 3505 (1969); Jaemoon Lee et al., *A chemical synthesis of nicotinamide adenine dinucleotide (NAD$^+$)*, CHEM. COMMUN. 729 (1999); each of which is incorporated by reference herein in its entirety.

Nicotinamide adenine dinucleotide (NAD$^+$) remains an expensive cofactor, and its commercial availability is simply limited by its complex chemical nature and the highly reactive pyrophosphate bond, which is challenging to form at scale.

Nicotinoyl ribosides such as nicotinamide riboside (NR) and nicotinic acid riboside ("NAR"), nicotinamide mononucleotide (NMN), and NAD$^+$ are viewed as useful bioavailable precursors of the NAD(P)(H) pool to combat and treat a broad range of non-communicable diseases, in particular those associated with mitochondrial dysfunction and impaired cellular metabolism. Optimizing the large-scale syntheses of these vitamin B3 derivatives is therefore highly valuable to make these compounds more widely available to society both in terms of nutraceutical and pharmaceutical entities.

Reduced nicotinoyl ribosides, such as reduced nicotinamide riboside (NRH), reduced nicotinic acid riboside (NARH), reduced nicotinamide mononucleotide ("NMNH"), reduced nicotinic acid mononucleotide ("NaMNH"), and reduced nicotinamide adenine dinucleotide ("NADH") are viewed as useful bioavailable precursors of the NAD(P)(H) pool to combat and treat a broad range of non-communicable diseases, in particular those associated with mitochondrial dysfunction and impaired cellular metabolism. Optimizing the large-scale syntheses of these vitamin B3 derivatives is therefore highly valuable to make these compounds more widely available to society, both in terms of nutraceutical and pharmaceutical entities.

Crystalline forms of useful molecules can have advantageous properties relative to the respective amorphous forms of such molecules. For example, crystal forms are often easier to handle and process, for example, when preparing compositions that include the crystal forms. Crystalline forms typically have greater storage stability and are more amenable to purification. The use of a crystalline form of a pharmaceutically useful compound can also improve the performance characteristics of a pharmaceutical product that includes the compound. Obtaining the crystalline form also serves to enlarge the repertoire of materials that formulation scientists have available for formulation optimization, for example by providing a product with different properties, e.g., better processing or handling characteristics, improved dissolution profile, or improved shelf-life.

WO 2016/014927 A2, incorporated by reference herein in its entirety, describes crystalline forms of nicotinamide riboside, including a Form I of nicotinamide riboside chloride. Also disclosed are pharmaceutical compositions comprising the crystalline Form I of nicotinamide riboside chloride, and methods of producing such pharmaceutical compositions.

WO 2016/144660 A1, incorporated by reference herein in its entirety, describes crystalline forms of nicotinamide riboside, including a Form II of nicotinamide riboside chloride. Also disclosed are pharmaceutical compositions comprising the crystalline Form II of nicotinamide riboside chloride, and methods of producing such pharmaceutical compositions.

In view of the above, there is a need for processes that are atom-efficient in terms of reagent and solvent equivalency, that bypass the need for polar, non-GRAS ("generally recognized as safe") solvents, that are versatile in terms of limitations associated with solubility and reagent mixing, that are time- and energy-efficient, and that provide efficient, practical, and scalable methods for the preparation of nicotinoyl ribosides, reduced nicotinoyl ribosides, modified derivatives thereof, phosphorylated analogs thereof, and adenylyl dinucleotide conjugates thereof.

In view of the above, there is a need for novel crystalline forms of nicotinoyl ribosides, reduced nicotinoyl ribosides, modified derivatives thereof, phosphorylated analogs thereof, and adenylyl dinucleotide conjugates thereof.

SUMMARY OF THE INVENTION

In an embodiment, the present disclosure relates to a synthetic sequence that enables the efficient production of nicotinoyl ribosides, derivatives thereof, phosphorylated analogs thereof, and adenylyl dinucleotide conjugates thereof, or salts, solvates, or prodrugs thereof, via processes that are enabled by the processing of reagents by liquid-assisted mixing, grinding, milling, and/or extrusion.

In another embodiment, the present disclosure relates to a synthetic sequence that enables the efficient production of reduced nicotinoyl ribosides, derivatives thereof, phosphorylated analogs thereof, and adenylyl dinucleotide conjugates thereof, or salts, solvates, or prodrugs thereof, via processes that are enabled by the processing of reagents by liquid-assisted mixing, grinding, milling, and/or extrusion.

In yet another embodiment, the present disclosure relates to scalable methods of preparation of nicotinamide riboside (NR) and nicotinic acid riboside (NAR), and derivatives thereof, or salts, solvates, or prodrugs thereof, by liquid assisted mixing and/or extrusion.

In yet another embodiment, the present disclosure relates to scalable methods of preparation of reduced nicotinamide riboside (NRH) and reduced nicotinic acid riboside (NARH), and derivatives thereof, or salts, solvates, or prodrugs thereof, by liquid-assisted mixing, grinding, and/or extrusion.

In yet another embodiment, the present disclosure relates to scalable methods of preparation of nicotinamide riboside triacetate ("NRTA") and nicotinic acid riboside triacetate ("NARTA"), and derivatives thereof, or salts, solvates, or prodrugs thereof, by liquid-assisted mixing, grinding, and/or extrusion.

In yet another embodiment, the present disclosure relates to scalable methods of preparation of reduced nicotinamide riboside triacetate ("NRH-TA") and reduced nicotinic acid riboside triacetate ("NARH-TA"), and derivatives thereof, or salts, solvates, or prodrugs thereof, by biphasic liquid-assisted mixing, grinding, and/or extrusion.

In yet another embodiment, the present disclosure relates to batch and semi-continuous processes that enable the production of nicotinamide riboside (NR) and nicotinic acid riboside (NAR), and triacetate derivatives thereof, or salts, solvates, or prodrugs thereof, whereby the use of solvents is kept to a minimum, and whereby conversion and reaction times are optimized by the use of sealed conditions, continuous liquid-liquid extraction, and/or mechanochemistry, and an optimized purification sequence.

In yet another embodiment, the present disclosure relates to batch and semi-continuous processes that enable the production of reduced nicotinamide riboside (NRH) and reduced nicotinic acid riboside (NARH), and triacetate derivatives thereof, or salts, solvates, or prodrugs thereof, wherein the use of solvents is kept to a minimum, and whereby conversion and reaction times are optimized by the use of sealed conditions, continuous liquid-liquid extraction, and/or mechanochemistry, and an optimized purification sequence.

In yet another embodiment, the present disclosure relates to crystalline forms of nicotinamide riboside (NR), including, but not limited to, a Form I of nicotinamide riboside chloride ("NR—Cl"), and methods of preparation thereof.

In yet another embodiment, the present disclosure relates to crystalline forms of nicotinamide riboside (NR), including, but not limited to, a "NR methanolate Form II" of nicotinamide riboside chloride (NR—Cl), and methods of preparation thereof.

In yet another embodiment, the present disclosure relates to crystalline forms of nicotinic acid riboside (NAR), including, but not limited to, a "Form I" of nicotinic acid riboside (NAR), and methods of preparation thereof.

In yet another embodiment, the present disclosure relates to crystalline forms of nicotinamide riboside triacetate (1-(2',3',5'-triacetyl-beta-D-ribofuranosyl)-nicotinamide, "NR triacetate," or "NRTA"), including, but not limited to, a "Form I" of nicotinamide riboside triacetate (NRTA) chloride, and methods of preparation thereof.

In yet another embodiment, the present disclosure relates to crystalline forms of nicotinic acid riboside triacetate (1-(2',3',5'-triacetyl-beta-D-ribofuranosyl)-nicotinic acid, "NAR triacetate," or "NARTA"), including, but not limited to, a "Form I" of nicotinic acid riboside triacetate (NARTA), and methods of preparation thereof.

In yet another embodiment, the present disclosure relates to crystalline forms of nicotinamide mononucleotide ("NMN"), including, but not limited to, a "Form III" of nicotinamide mononucleotide (NMN), and methods of preparation thereof. In yet another embodiment, the present disclosure relates to an amorphous solid form of nicotinamide mononucleotide (NMN), and methods of preparation thereof.

In yet another embodiment, the present disclosure relates to crystalline forms of nicotinamide mononucleotide (NMN), including, but not limited to, a "Form IV" of nicotinamide mononucleotide (NMN), and methods of preparation thereof.

In yet another embodiment, the present disclosure relates to crystalline forms of compounds or derivatives having formula (IV), or salts, solvates, or prodrugs thereof, and methods of preparation thereof.

In yet another embodiment, the present disclosure relates to crystalline forms of compounds or derivatives having formula (IV-H), or salts, solvates, or prodrugs thereof, and methods of preparation thereof.

In yet another embodiment, the present disclosure relates to crystalline forms of compounds or derivatives having formula (V), or salts, solvates, or prodrugs thereof, and methods of preparation thereof.

In yet another embodiment, the present disclosure relates to crystalline forms of compounds or derivatives having formula (VI), or salts, solvates, or prodrugs thereof, and methods of preparation thereof.

In accordance with one embodiment, the present disclosure provides a novel method for the preparation of compounds or derivatives having formula (I), or salts, solvates, or prodrugs thereof, such as nicotinoyl ribosides and their derivatives, and including but not limited to the triacetylated forms of NR—Cl (nicotinamide riboside chloride salt form) and NAR (nicotinic acid riboside) (compounds or derivatives having formula (I), wherein $R^6$, $R^7$, and $R^8$ are each acetyl groups), and the fully deprotected forms thereof (compounds or derivatives having formula (I), wherein $R^6$, $R^7$, and $R^8$ are each hydrogen), in commercial quantities. In accordance with such an embodiment, the present disclosure provides a novel method whereby mechanic forces and/or sealed conditions are used to minimize solvent and reagent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product nicotinoyl riboside compounds include compounds or derivatives having formula (I), or salts, solvates, or prodrugs thereof:

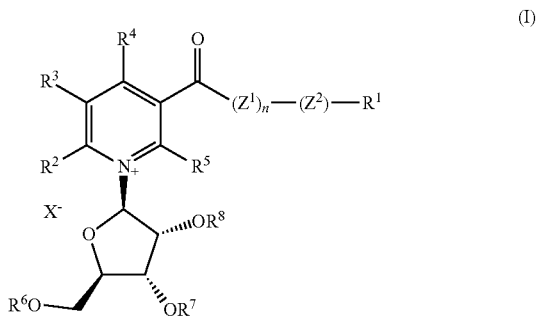

(I)

optionally wherein $X^-$ as counterion is absent, or when $X^-$ is present, $X^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, succinate, sulfonate, trifluoromethanesulfonate, trichloromethanesulfonate, tribromomethanesulfonate, and trifluoroacetate;

optionally wherein when $X^-$ is absent, optionally the counterion is an internal salt;

$Z^1$ and $Z^2$ are independently NH or oxygen;

n is 0 or 1;

$R^1$ is selected from the group consisting of hydrogen, substituted or unsubstituted $(C_1-C_8)$alkyl, substituted or unsubstituted $(C_1-C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl $(C_1-C_4)$alkyl, heterocycle$(C_1-C_4)$alkyl, —N($R^4$)—$CO_2R^C$, —N($R^4$)—$CO_2R^B$, —CH—($R^4$)—$NH_2$, and —CH—($R^4$)—$CO_2R^B$; wherein the substituted $(C_1-C_8)$alkyl, substituted $(C_1-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O ($C_1$-$C_6$)alkyl, —N$R^C$C(O)N$R^C_2$, —N$R^C$$SO_2$N$R^C_2$, —S$R^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

wherein when $R^1$ is hydrogen, $Z^2$ is oxygen, and n is 0, the compound or derivative having formula (I) may optionally take the form of the carboxylate anion conjugate base species of the compound or derivative having formula (I), further optionally associated with a positively charged counterion selected from the group consisting of calcium, magnesium, potassium, sodium, zinc, and ammonium cations;

$R^4$ is selected from the group consisting of —H, —($C_1$-$C_6$)alkyl, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3)_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3)_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$SO$_2$N$R^B_2$, —S$R^B$, —S(O)$R^B$, —SO$_2R^B$, —SO$_2$($C_1$-$C_6$)alkyl, —SO$_2$N$R^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^6$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl($C_1$-$C_4$)alkyl, heterocycle($C_1$-$C_4$)alkyl, —N($R^A$)—CO$_2R^C$, —N($R^A$)—CO$_2R^B$, —CH—($R^A$)—$NH_2$, and —CH—($R^A$)—CO$_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—CO$_2R^C$, —N($R^A$)—CO$_2R^B$, —CH—($R^A$)—$NH_2$, and —CH—($R^A$)—CO$_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$—C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$—N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

provided that the absolute configuration of C** is R or S, or a mixture of R and S.

In accordance with such an embodiment, appropriate starting materials for the methods of the present disclosure for the preparation of compounds or derivatives having formula (I), or salts, solvates, or prodrugs thereof, include compounds or derivatives having formula (1), or salts thereof:

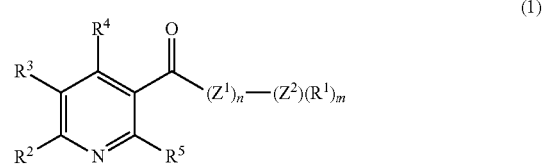

(1)

wherein $Z^1$ and $Z^2$ are independently nitrogen or oxygen;
m is 1 or 2;
n is 0 or 1;
each $R^1$ is independently selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

wherein when each $R^1$ is hydrogen, $Z^2$ is oxygen, m is 1, and n is 0, the compound or derivative having formula (1) may optionally take the form of the carboxylate anion conjugate base species of the compound or derivative having formula (1), further optionally associated with a positively charged counterion selected from the group consisting of calcium, magnesium, potassium, sodium, zinc, and ammonium cations;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$SO$_2$N$R^B_2$, —S$R^B$, —S(O)$R^B$, —SO$_2R^B$, —OSO$_2$($C_1$-$C_6$)alkyl, —SO$_2$N$R^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

provided that the absolute configuration of C** is R or S, or a mixture of R and S.

In accordance with such an embodiment, appropriate starting materials for the methods of the present disclosure for the preparation of compounds or derivatives having formula (I), or salts, solvates, or prodrugs thereof, include compounds or derivatives having formula (2), or salts thereof:

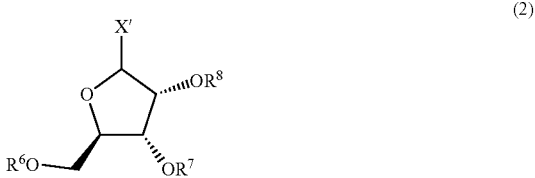

(2)

wherein X' is selected from the group consisting of fluoro, chloro, bromo, iodo, $HCO_2$, acetoxy, propionoxy, butyroxy, glutamyloxy, aspartyloxy, ascorbyloxy, benzoxy, $HOCO_2$, citryloxy, carbamyloxy, gluconyloxy, lactyloxy, succinyloxy, sulfoxy, trifluoromethanesulfoxy, trichloromethanesulfoxy, tribromomethanesulfoxy, and trifluoroacetoxy;

$R^6$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione disulfide ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$—N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —$(C_1-C_8)$alkyl;

each $R^C$ is independently selected from the group consisting of hydrogen, —$(C_1-C_8)$alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —$C(O)R^B$, —$C(O)OR^B$, —$C(O)NR^B_2$, —$C(=NR^B)NR^B_2$, —$OR^B$, —$OC(O)(C_1-C_6)$alkyl, —$OC(O)O(C_1-C_6)$alkyl, —$OC(O)NR^B_2$, —$(C_1-C_6)$alkylene-$NR^B_2$, —$NR^B_2$, —$NR^BC(O)R^B$, —$NR^BC(O)O(C_1-C_6)$alkyl, —$NR^BC(O)NR^B_2$, —$NR^BSO_2NR^B_2$, —$SR^B$, —$S(O)R^B$, —$SO_2R^B$, —$OSO_2(C_1-C_6)$alkyl, —$SO_2NR^B_2$, —$(C_1-C_6)$perfluoroalkyl, and —$(C_1-C_6)$alkylene-$OR^B$;

$R^7$ and $R^8$ are independently selected from the group consisting of hydrogen, —C(O)R', —C(O)OR', —C(O)NHR', substituted or unsubstituted $(C_1-C_8)$alkyl, substituted or unsubstituted $(C_1-C_8)$cycloalkyl, substituted or unsubstituted aryl, substituted or unsubstituted heteroaryl, substituted or unsubstituted heterocycle, substituted or unsubstituted aryl$(C_1-C_4)$alkyl, and substituted or unsubstituted heterocycle$(C_1-C_4)$alkyl; wherein the substituted $(C_1-C_8)$alkyl, substituted $(C_1-C_8)$cycloalkyl, substituted aryl, substituted heteroaryl, substituted heterocycle, substituted aryl$(C_1-C_4)$alkyl, and substituted heterocycle$(C_1-C_4)$alkyl are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1-C_6)$alkyl, —$OC(O)O(C_1-C_6)$alkyl, —$OC(O)NR^C_2$, —$(C_1-C_6)$alkylene-$NR^C_2$, —$NR^C_2$, —$NR^CC(O)R^C$, —$NR^CC(O)O(C_1-C_6)$alkyl, —$NR^CC(O)NR^C_2$—$NR^CSO_2NR^C_2$, —$SR^C$, —$S(O)R^C$, —$SO_2R^C$, —$OSO_2(C_1-C_6)$alkyl, —$SO_2NR^C_2$, —$(C_1-C_6)$perfluoroalkyl, and —$(C_1-C_6)$alkylene-$OR^C$;

provided that the absolute configuration of C** is R or S, or a mixture of R and S.

In accordance with such an embodiment, appropriate starting materials for the methods of the present disclosure for the preparation of compounds or derivatives having formula (2), or salts, solvates, or prodrugs thereof, include compounds or derivatives having formula (2a), or salts thereof:

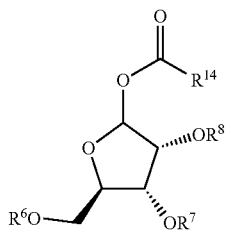

(2a)

wherein $R^6$ is selected from the group consisting of hydrogen, —C(O)R', —C(O)OR', —C(O)NHR', substituted or unsubstituted $(C_1-C_8)$alkyl, substituted or unsubstituted $(C_1-C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl$(C_1-C_4)$alkyl, heterocycle$(C_1-C_4)$alkyl, —$N(R^A)$—$CO_2R^C$, —$N(R^A)$—$CO_2R^B$, —$CH$—$(R^A)$—$NH_2$, and —$CH$—$(R^A)$—$CO_2R^B$; wherein the substituted $(C_1-C_8)$alkyl, substituted $(C_1-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1-C_6)$alkyl, —$OC(O)O(C_1-C_6)$alkyl, —$OC(O)NR^C_2$, —$(C_1-C_6)$alkylene-$NR^C_2$, —$NR^C_2$, —$NR^CC(O)R^C$, —$NR^CC(O)O(C_1-C_6)$alkyl, —$NR^CC(O)NR^C_2$, —$NR^CSO_2NR^C_2$, —$SR^C$, —$S(O)R^C$, —$SO_2R^C$, —$OSO_2(C_1-C_6)$alkyl, —$SO_2NR^C_2$, —$(C_1-C_6)$perfluoroalkyl, and —$(C_1-C_6)$alkylene-$OR^C$;

R' is selected from the group consisting of hydrogen, substituted or unsubstituted $(C_1-C_8)$alkyl, substituted or unsubstituted $(C_1-C_8)$cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl$(C_1-C_4)$alkyl, heterocycle$(C_1-C_4)$alkyl, —$N(R^A)$—$CO_2R^C$, —$N(R^A)$—$CO_2R^B$, —$CH$—$(R^A)$—$NH_2$, and —$CH$—$(R^A)$—$CO_2R^B$; wherein the substituted $(C_1-C_8)$alkyl, substituted $(C_1-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1-C_6)$alkyl, —$OC(O)O(C_1-C_6)$alkyl, —$OC(O)NR^C_2$, —$(C_1-C_6)$alkylene-$NR^C_2$, —$NR^C_2$, —$NR^CC(O)R^C$, —$NR^CC(O)O(C_1-C_6)$alkyl, —$NR^CC(O)NR^C_2$—$NR^CSO_2NR^C_2$, —$SR^C$, —$S(O)R^C$, —$SO_2R^C$, —$OSO_2(C_1-C_6)$alkyl, —$SO_2NR^C_2$, —$(C_1-C_6)$perfluoroalkyl, and —$(C_1-C_6)$alkylene-$OR^C$;

$R^A$ is selected from the group consisting of —H, —$(C_1-C_6)$alkyl, —$(CH_2)_3$—NH—$C(NH_2)(=NH)$, —$CH_2C(=O)NH_2$, —$CH_2COOH$, —$CH_2SH$, —$(CH_2)_2C(=O)$—$NH_2$, —$(CH_2)_2COOH$, —$CH_2$-(2-imidazolyl), —$CH(CH_3)$—$CH_2$—$CH_3$, —$CH_2CH(CH_3)_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —$CH(CH_3)_2$, —$NH_2$, and —$CH_2$—$CH_3$;

each $R^B$ is independently hydrogen or —$(C_1-C_8)$alkyl;

each $R^C$ is independently selected from the group consisting of hydrogen, —$(C_1-C_8)$alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —$C(O)R^B$, —$C(O)OR^B$, —$C(O)NR^B_2$, —$C(=NR^B)NR^B_2$, —$OR^B$, —$OC(O)(C_1-C_6)$alkyl, —$OC(O)O(C_1-C_6)$alkyl, —$OC(O)NR^B_2$, —$(C_1-C_6)$alkylene-$NR^B_2$, —$R^B_2$, —$NR^BC(O)R^B$, —$NR^BC(O)O(C_1-C_6)$alkyl, —$NR^BC(O)NR^B_2$, —$NR^BSO_2NR^B_2$, —$SR^B$, —$S(O)R^B$, —$SO_2R^B$, —$OSO_2(C_1-C_6)$alkyl, —$SO_2NR^B_2$, —$(C_1-C_6)$perfluoroalkyl, and —$(C_1-C_6)$alkylene-$OR^B$;

$R^7$ and $R^8$ are independently selected from the group consisting of hydrogen, —C(O)R', —C(O)OR', —C(O)NHR', substituted or unsubstituted $(C_1-C_8)$alkyl, substituted or unsubstituted $(C_1-C_8)$cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$—C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^{14}$ is methyl or phenyl;

provided that the absolute configuration of C** is R or S, or a mixture of R and S.

Generally, appropriate synthetic processes comprising batch processing or continuous processing of reagents by liquid-assisted mixing, milling, grinding, and/or extrusion are employed as described.

In accordance with an alternative embodiment, appropriate starting materials for the methods of the present disclosure for the preparation of compounds or derivatives having formula (I), or salts, solvates, or prodrugs thereof, include compounds or derivatives having formula (1a), or salts thereof:

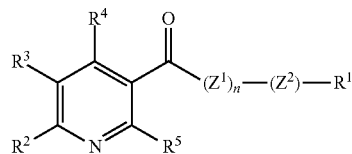

(1a)

wherein Z$^1$ and Z$^2$ are independently NH or oxygen;

n is 0 or 1;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl (C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$) alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein when R$^1$ is hydrogen, Z$^2$ is oxygen, and n is 0, the compound or derivative having formula (1a) may optionally take the form of the carboxylate anion conjugate base species of the compound or derivative having formula (1a), further optionally associated with a positively charged counterion selected from the group consisting of calcium, magnesium, potassium, sodium, zinc, and ammonium cations;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)alkylene-NR$^B_2$, —NR$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$) perfluoroalkyl, and —(C$_1$-C$_6$)alkylene-OR$^B$;

each of R$^2$, R$^3$, R$^4$, and R$^5$ is hydrogen;

provided that the absolute configuration of C** is R or S, or a mixture of R and S.

In accordance with yet another alternative embodiment, appropriate starting materials for the methods of the present disclosure for the preparation of compounds or derivatives having formula (I), or salts, solvates, or prodrugs thereof, include compounds or derivatives having formula (1b), or salts thereof:

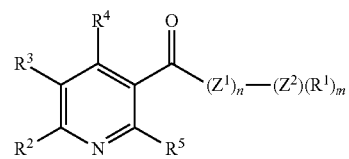

(1b)

wherein Z$^1$ and Z$^2$ are independently nitrogen or oxygen;

m is 1 or 2;

n is 0 or 1;

each R$^1$ is independently selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein when each R$^1$ is hydrogen, Z$^2$ is oxygen, m is 1, and n is 0, the compound or derivative having formula (1b) may optionally take the form of the carboxylate anion conjugate base species of the compound or derivative having formula (1b), further optionally associated with a positively charged counterion selected from the group consisting of calcium, magnesium, potassium, sodium, zinc, and ammonium cations;

R$^4$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)alkylene-NR$^B_2$, —NR$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$)perfluoroalkyl, and —(C$_1$-C$_6$)alkylene-OR$^B$;

each of R$^2$, R$^3$, R$^4$, and R$^5$ is hydrogen;

provided that the absolute configuration of C** is R or S, or a mixture of R and S.

In an embodiment, a method of making a compound or derivative having formula (2), or a salt thereof, can include the steps of:

(a) providing a compound or derivative having formula (2a), or a salt thereof, wherein when R$^{14}$ of the compound or derivative having formula (2a), or salt thereof, is methyl, then X' of the compound or derivative having formula (2), or salt thereof, is not acetoxy, and wherein when R$^{14}$ of the compound or derivative having formula (2a), or salt thereof, is phenyl, then X' of the compound or derivative having formula (2), or salt thereof, is not benzoxy; (b) treating the compound or derivative having formula (2a), or salt thereof, with at least a stoichiometric amount of a Brønsted acid or a nucleophilic substitution reagent in the presence of at least a molar equivalent amount of a polar organic solvent co-reagent; (c) processing the compound or derivative having formula (2a), or salt thereof, the Brønsted acid or nucleophilic substitution reagent, and the polar organic solvent co-reagent so as to produce the compound or derivative having formula (2), or salt thereof, and (d) isolating the compound or derivative having formula (2), or salt thereof.

Processing can be carried out under batch processing conditions or by continuously processing. Continuously processing may include one or more methods of agitation selected from the group consisting of liquid-assisted mixing under sealed conditions, grinding, and extruding. The process described herein effects a preparation of a compound or derivative having formula (2), or salt thereof, under almost solventless conditions.

The polar organic solvent co-reagent and isolation solvent employed in the above method of making a compound or derivative having formula (2), or salt thereof, individually, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, the nucleophilic substitution reagent of step (b) of the above method of making a compound or derivative having formula (2), or a salt thereof, is generated in situ by reacting an acyl chloride with an alcohol in stoichiometrically equivalent amounts.

In an embodiment, a method of making a compound or derivative having formula (I), or a salt, solvate, or prodrug thereof, optionally in a particular anomeric ratio (alpha/beta), can include the steps of:

(a) providing a compound or derivative having formula (2), or a salt thereof; (b) treating the compound or derivative having formula (2), or salt thereof, with a molar equivalent amount of a compound or derivative having formula (1), or a salt thereof, optionally wherein each R$^1$ is a trimethylsilyl ("TMS") group; (c) processing the compound or derivative having formula (2), or salt thereof, and the compound or derivative having formula (1), or salt thereof, optionally wherein each R$^1$ is a TMS group, so as to produce the compound or derivative having formula (I), or salt, solvate, or prodrug thereof, optionally produced in a particular anomeric ratio (alpha/beta); (d) removing by-products resulting from the processing step under reduced pressure and temperature-controlled conditions; (e) separately isolating unreacted compound or derivative having formula (2), or salt thereof; optionally, (e1) adding acetone; optionally, (e2) separately isolating unreacted compound or derivative having formula (1), or salt thereof; and (f) isolating the compound or derivative having formula (I), or salt, solvate, or prodrug thereof.

Processing can be carried out under batch processing conditions or by continuously processing. Continuously processing may include one or more methods of agitation selected from the group consisting of liquid-assisted mixing, milling, grinding, and extruding. The process described herein effects a preparation of a compound or derivative having formula (I), or salt, solvate, or prodrug thereof, optionally in a particular anomeric ratio (alpha/beta).

The polar organic solvent co-reagent and isolation solvent employed in the above method of making a compound or derivative having formula (I), or salt, solvate, or prodrug thereof, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an alternative embodiment of the above method of making a compound or derivative having formula (I), or a salt, solvate, or prodrug thereof, the compound or derivative having formula (2), or salt thereof, is further treated with a molar equivalent of a Lewis acid in step (b).

In yet another alternative embodiment of the above method of making a compound or derivative having formula (I), or salt, solvate, or prodrug thereof, the compound or derivative having formula (I), or salt, solvate, or prodrug thereof, is produced as a mixture of alpha- and beta-anomers in an anomeric ratio by % weight of from about 1.5:1 to about 1:4 alpha-anomer to beta-anomer.

In yet another alternative embodiment of the above method of making a compound or derivative having formula (I), or salt, solvate, or prodrug thereof, the compound or derivative having formula (I), or salt, solvate, or prodrug thereof, is produced as the beta-anomer.

In yet another alternative embodiment of the above method of making a compound or derivative having formula (I), or salt, solvate, or prodrug thereof, the alpha- and beta-anomers of the compound or derivative having formula (I), or salt, solvate, or prodrug thereof, can be separately isolated by a method that can further include the steps of:

(c1) adding acetone to, optionally, the compound or derivative having formula (2), or salt thereof, optionally, the compound or derivative having formula (1), or salt thereof, optionally wherein each $R^1$ is a TMS group, and the compound or derivative having formula (I), or salt, solvate, or prodrug thereof so as to precipitate the beta-anomer of the compound or derivative having formula (I), or salt, solvate, or prodrug thereof; (c2) filtering, optionally, the compound or derivative having formula (2), or salt thereof, optionally, the compound or derivative having formula (1), or salt thereof, optionally wherein each $R^1$ is a TMS group, and the compound or derivative having formula (I), or salt, solvate, or prodrug thereof so as to isolate the beta-anomer of the compound or derivative having formula (I), or salt, solvate, or prodrug thereof; (c3) washing the beta-anomer of the compound or derivative having formula (I), or salt, solvate, or prodrug thereof, with acetone; (c4) combining the acetone from the adding and washing steps; and (c5) removing the acetone under reduced pressure; wherein the steps (c1) to (c5) are performed sequentially, following step (c).

In a particular embodiment, a method of making a crystalline form of the compound or derivative having formula (I), or a salt, solvate, or prodrug thereof, optionally in a particular anomeric ratio (alpha/beta), can include the steps of:

(a) adding a volume of methanol and water in a 95:5 weight:weight ratio to the compound or derivative having formula (I), or salt, solvate, or prodrug thereof, optionally in a particular anomeric ratio (alpha/beta), at room temperature, so as to dissolve approximately 15% of the compound or derivative having formula (I), or salt, solvate, or prodrug thereof, optionally in a particular anomeric ratio (alpha/beta), in the volume of methanol and water; (b) stirring the compound or derivative having formula (I), or salt, solvate, or prodrug thereof, optionally in a particular anomeric ratio (alpha/beta), at 50° C. until all of the compound or derivative having formula (I), or salt, solvate, or prodrug thereof, optionally in a particular anomeric ratio (alpha/beta), apparently dissolves in the volume of methanol and water; (c) cooling the solution of the compound or derivative having formula (I), or salt, solvate, or prodrug thereof, optionally in a particular anomeric ratio (alpha/beta), in the volume of methanol and water, to −10° C. with stirring so as to precipitate the crystalline form of the compound or derivative having formula (I), or salt, solvate, or prodrug thereof, optionally in a particular anomeric ratio (alpha/beta); (d) isolating the crystalline form of the compound or derivative having formula (I), or salt, solvate, or prodrug thereof, optionally in a particular anomeric ratio (alpha/beta); and (e) drying the crystalline form of the compound or derivative having formula (I), or salt, solvate, or prodrug thereof, optionally in a particular anomeric ratio (alpha/beta).

In yet another alternative embodiment of the above method of making a crystalline form of the compound or derivative having formula (I), or salt, solvate, or prodrug thereof, the crystalline form of the compound or derivative having formula (I), or salt, solvate, or prodrug thereof, wherein $R^6$, $R^7$, and $R^8$ are each hydrogen, is crystalline Form I of nicotinamide riboside chloride, having formula (XII):

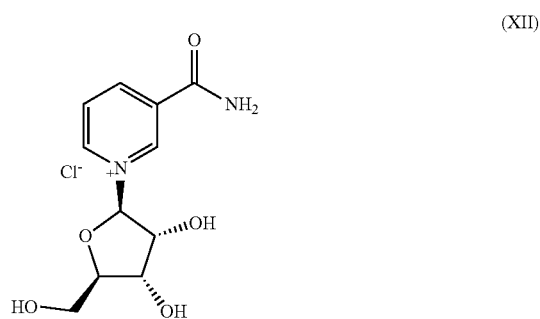 [SMILES: NC(=O)c1ccc[n+]([C@@H]2O[C@H](CO)[C@@H](O)[C@H]2O)c1 ; [Cl-]]

In yet another alternative embodiment, a method of making a compound or derivative having formula (I), or a salt, solvate, or prodrug thereof, optionally in a particular anomeric ratio (alpha/beta), can include the steps of:

(a) providing a compound or derivative having formula (1), or a salt thereof; optionally, (a1) treating the compound or derivative having formula (1), or salt thereof, with excess trimethylsilylating reagent(s), and, optionally, heating the compound or derivative having formula (1), or salt thereof, and the trimethylsilylating reagent(s), to reflux for about 12 hours, so as to produce a compound or derivative having formula (1), or salt thereof, wherein each $R^1$ is a trimethylsilyl ("TMS") group; optionally, (a2) cooling the mixture to room temperature; optionally, (a3) isolating the compound or derivative having formula (1), or salt thereof, wherein each $R^1$ is a TMS group; (b) treating the compound or derivative having formula (1), or salt thereof, optionally wherein each $R^1$ is a TMS group, with a molar equivalent amount of a compound or derivative having formula (2), or a salt thereof, in an organic solvent co-reagent; (c) processing the compound or derivative having formula (1), or salt thereof, optionally wherein each $R^1$ is a TMS group, the compound or derivative having formula (2), or salt thereof, and the organic solvent co-reagent so as to produce the compound or derivative having formula (I), or salt, solvate, or prodrug thereof, optionally wherein each $R^1$ is a TMS group, optionally produced in a particular anomeric ratio (alpha/beta); (d) adding water to, optionally, the compound or derivative having formula (1), or salt thereof, optionally wherein each $R^1$ is a TMS group, optionally, the compound or derivative having formula (2), or salt thereof, the organic solvent co-reagent, and the compound or derivative having formula (I), or salt, solvate, or prodrug thereof, optionally wherein each $R^1$ is a TMS group, optionally in a particular anomeric ratio (alpha/beta); optionally, (d1) adding saturated $NaHCO_3$ solution to, optionally, the compound or derivative having formula (1), or salt thereof, optionally wherein each $R^1$ is a TMS group, optionally, the compound or derivative having formula (2), or salt thereof, the organic solvent co-reagent, the compound or derivative having formula (I), or salt, solvate, or prodrug thereof, optionally wherein each $R^1$ is a TMS group, optionally in a particular anomeric ratio (alpha/beta), and water; (e) adjusting the pH of the aqueous phase; (f) separating the organic phase from the aqueous phase; (g) freeze-drying the aqueous phase to provide the compound or derivative having formula (I), or salt, solvate, or prodrug thereof, optionally in a particular anomeric ratio (alpha/beta); optionally, (g1) treating the compound or derivative having formula (I), or salt, solvate, or prodrug thereof, with a (3<x<100) molar equivalent amount of an alcohol and a reagent selected from the group consisting of at least a sub-molar equivalent amount of a Brønsted inorganic base, a (x≤20) molar equivalent amount of a Brønsted inorganic acid, and a (3≤x<20) molar equivalent amount of an acyl chloride; optionally, (g2) processing the compound or derivative having formula (I), or salt, solvate, or prodrug thereof, the alcohol, and the reagent so as to produce a compound or derivative having formula (I), or salt, solvate, or prodrug thereof, wherein $R^6$, $R^7$, and $R^8$ are each hydrogen; and, optionally, (g3) isolating the compound or derivative having formula (I), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. The process described herein effects a preparation of a compound or derivative having formula (I), or salt, solvate, or prodrug thereof, optionally in a particular anomeric ratio (alpha/beta).

The organic solvent co-reagent employed in the above method of making a compound or derivative having formula (I), or salt, solvate, or prodrug thereof, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another alternative embodiment of the above method of making a compound or derivative having formula (I), or a salt, solvate, or prodrug thereof, wherein the reagent of step (g1) is Brønsted inorganic base, can further include the step of:

(g2a) neutralizing the Brønsted inorganic base using a concentrated acid solution under controlled conditions; wherein the step (g2a) is performed following step (g2).

In yet another alternative embodiment of the above method of making a compound or derivative having formula (I), or a salt, solvate, or prodrug thereof, wherein the reagent of step (g1) is Brønsted inorganic acid, can further include the step of:

(g2a) neutralizing the Brønsted inorganic acid using a concentrated basic solution under controlled conditions, wherein the step (g2a) is performed following step (g2).

In an embodiment, a method of making a compound or derivative having formula (Ia), or a salt, solvate, or prodrug thereof, optionally in a particular anomeric ratio (alpha/beta), can include the steps of:

(a) providing a compound or derivative having formula (2), or a salt thereof; (b) treating the compound or derivative having formula (2), or salt thereof, with a molar equivalent amount of a compound or derivative having formula (1a), or a salt thereof, (c) processing the compound or derivative having formula (2), or salt thereof, and the compound or derivative having formula (1a), or salt thereof, so as to produce the compound or derivative having formula (Ia), or salt, solvate, or prodrug thereof, optionally produced in a particular anomeric ratio (alpha/beta); (d) removing by-products resulting from the processing step under reduced pressure and temperature-controlled conditions; (e) separately isolating unreacted compound or derivative having formula (2), or salt thereof; optionally, (e1) adding acetone; optionally, (e2) separately isolating unreacted compound or derivative having formula (1a), or salt thereof; and (f) isolating the compound or derivative having formula (Ia), or salt, solvate, or prodrug thereof.

Processing can be carried out under batch processing conditions or by continuously processing. Continuously processing may include one or more methods of agitation selected from the group consisting of liquid-assisted mixing, milling, grinding, and extruding. The process described herein effects a preparation of a compound or derivative having formula (Ia), or salt, solvate, or prodrug thereof, optionally in a particular anomeric ratio (alpha/beta).

The polar organic solvent co-reagent and isolation solvent employed in the above method of making a compound or derivative having formula (Ia), or salt, solvate, or prodrug thereof, optionally in a particular anomeric ratio (alpha/beta), can be a polar organic solvent from among, for example, preferably, the Class 2 Residual Sovlents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an alternative embodiment, a method of making a compound or derivative having formula (Ia), or a salt, solvate, or prodrug thereof, optionally in a particular anomeric ratio (alpha/beta), can include the steps of:

(a) providing a compound or derivative having formula (2), or a salt thereof; (b) treating the compound or derivative having formula (2), or salt thereof, with a molar equivalent amount of a compound or derivative having formula (1b), or a salt thereof, (c) processing the compound or derivative having formula (2), or salt thereof, and the compound or derivative having formula (1b), or salt thereof, so as to produce the compound or derivative having formula (Ia), or salt, solvate, or prodrug thereof, optionally produced in a particular anomeric ratio (alpha/beta); (d) removing by-products resulting from the processing step under reduced pressure and temperature-controlled conditions; (e) separately isolating unreacted compound or derivative having formula (2), or salt thereof; optionally, (e1) adding acetone; optionally, (e2) separately isolating unreacted compound or derivative having formula (1b), or salt thereof; and (f) isolating the compound or derivative having formula (Ia), or salt, solvate, or prodrug thereof.

In yet another alternative embodiment of the above method of making a compound or derivative having formula (I), or a salt, solvate, or prodrug thereof, can further include the steps of:

(a1) providing a compound or derivative having formula (2a), or a salt thereof, wherein when $R^{14}$ of the compound or derivative having formula (2a), or salt thereof, is methyl, then X' of the compound or derivative having formula (2), or salt thereof, is not acetoxy, and wherein when $R^{14}$ of the compound or derivative having formula (2a), or salt thereof, is phenyl, then X' of the compound or derivative having formula (2), or salt thereof, is not benzoxy; (a2) treating the compound or derivative having formula (2a), or salt thereof, with at least a stoichiometric equivalent amount of a Brønsted acid or a nucleophilic substitution reagent in the presence of at least a molar equivalent amount of a polar organic solvent co-reagent; (a3) processing the compound or derivative having formula (2a), or salt thereof, the Brønsted acid or nucleophilic substitution reagent, and the polar organic solvent co-reagent so as to produce the compound or derivative having formula (2), or salt thereof; and (a4) isolating the compound or derivative having formula (2), or salt thereof, wherein the steps (a1) to (a4) are performed sequentially, before step (a).

In yet another alternative embodiment, the nucleophilic substitution reagent of step (a2) of the above method of making a compound or derivative having formula (2), or a salt thereof, is generated in situ by reacting an acyl chloride with an alcohol in stoichiometrically equivalent amounts.

In accordance with one embodiment, the present disclosure provides a novel method for the preparation of compounds or derivatives having formula (I-H), or salts, solvates, or prodrugs thereof, wherein $R^6$, $R^7$, and $R^8$ are each hydrogen. In accordance with such an embodiment, the present disclosure provides a novel method whereby mechanic forces are used to minimize solvent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product analogs of nicotinoyl riboside compounds include compounds or derivatives having formula (I-H), or salts, solvates, or prodrugs thereof, wherein $R^6$, $R^7$, and R' are each hydrogen:

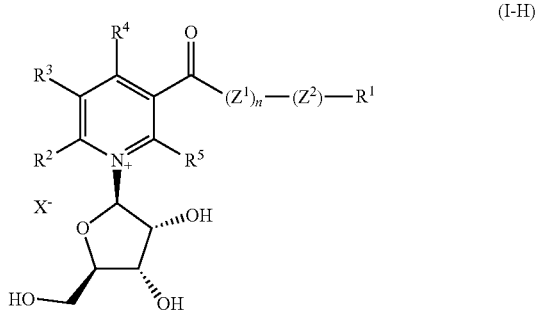

(I-H)

optionally wherein $X^-$ as counterion is absent, or when $X^-$ is present, $X^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when $X^-$ is absent, optionally the counterion is an internal salt;

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl ($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

wherein when $R^1$ is hydrogen, $Z^2$ is oxygen, and n is 0, the compound or derivative having formula (I-H) may optionally take the form of the carboxylate anion conjugate base species of the compound or derivative having formula (I-H), further optionally associated with a positively charged counterion selected from the group consisting of calcium, magnesium, potassium, sodium, zinc, and ammonium cations;

$R^A$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$SO$_2$N$R^B_2$, —S$R^B$, —S(O)$R^B$, —SO$_2R^B$, —OSO$_2$($C_1$-$C_6$)alkyl, —SO$_2$N$R^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

provided that the absolute configuration of C** is R or S, or a mixture of R and S.

In an embodiment, a method of making a compound or derivative having formula (I-H), or a salt, solvate, or prodrug thereof, wherein $R^6$, $R^7$, and $R^8$ are each hydrogen:

(a) providing a compound or derivative having formula (I), or a salt, solvate, or prodrug thereof, wherein $R^6$, $R^7$, and $R^8$ are each —C(O)R', and wherein R' is methyl or —C$_1$alkyl; (b) treating the compound or derivative having formula (I), or salt, solvate, or prodrug thereof, wherein $R^6$, $R^7$, and $R^8$ are each —C(O)R', and wherein R' is methyl or —C$_1$alkyl, with a (3<x<20) molar equivalent amount of an alcohol (e.g., methanol, or ethanol) and a reagent selected from the group consisting of at least a sub-molar equivalent amount of a Brønsted inorganic base, a (x<20) molar equivalent amount of a Brønsted inorganic acid, and a (3<x<20) molar equivalent amount of an acyl chloride; (c) processing the compound or derivative having formula (I), or salt, solvate, or prodrug thereof, wherein $R^6$, $R^7$, and $R^8$ are each —C(O)R', and wherein R' is methyl or —$C_1$alkyl, the alcohol, and the reagent so as to produce the compound or derivative having formula (I-H), or salt, solvate, or prodrug thereof, wherein $R^6$, $R^7$, and $R^8$ are each hydrogen; and (d) isolating the compound or derivative having formula (I-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. The process described herein effects a preparation of a compound or derivative having formula (I-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (I-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an alternative embodiment of the above method of making a compound or derivative having formula (I-H), or a salt, solvate, or prodrug thereof, wherein $R^6$, $R^7$, and $R^8$ are each hydrogen, when the reagent of step (b) is Brønsted inorganic base, the method can further include the step of:

(c1) neutralizing the Brønsted inorganic base using a concentrated acid solution under controlled conditions; wherein the step (c1) is performed following step (c).

In another alternative embodiment of the above method of making a compound or derivative having formula (I-H), or a salt, solvate, or prodrug thereof, wherein $R^6$, $R^7$, and $R^8$ are each hydrogen, when the reagent of step (b) is Brønsted inorganic acid, the method can further include the step of:

(c1) neutralizing the Brønsted inorganic acid using a concentrated basic solution under controlled conditions; wherein the step (c1) is performed following step (c).

In yet another alternative embodiment of the above method of making a compound or derivative having formula (I-H), or a salt, solvate, or prodrug thereof, wherein $R^6$, $R^7$, and $R^8$ are each hydrogen, the method can further include the steps of:

(a1) providing a compound or derivative having formula (1), or a salt thereof, optionally wherein each $R^1$ is a TMS group; (a2) treating the compound or derivative having formula (1), or salt thereof, optionally wherein each $R^1$ is a TMS group, with a molar equivalent amount of a compound or derivative having formula (2), or a salt thereof, wherein $R^6$, $R^7$, and $R^8$ are each —C(O)R', and wherein R' is methyl or —$C_1$alkyl, in an organic solvent co-reagent; (a3) processing the compound or derivative having formula (1), or salt thereof, optionally wherein each $R^1$ is a TMS group, the compound or derivative having formula (2), or salt thereof, wherein $R^6$, $R^7$, and $R^8$ are each —C(O)R', and wherein R' is methyl or —$C_1$alkyl, and the organic solvent co-reagent so as to produce a compound or derivative having formula (I), or salt, solvate, or prodrug thereof, optionally wherein each $R^1$ is a TMS group; (a4) adding water to, optionally, the compound or derivative having formula (1), or salt thereof, optionally wherein each $R^1$ is a TMS group, optionally, the compound or derivative having formula (2), or salt thereof, wherein $R^6$, $R^7$, and $R^8$ are each —C(O)R', and wherein R' is methyl or —$C_1$alkyl, the organic solvent co-reagent, and the compound or derivative having formula (I), or salt, solvate, or prodrug thereof; and (a5) isolating the compound or derivative having formula (I), or salt, solvate, or prodrug thereof, optionally wherein each $R^1$ is a TMS group; wherein the steps (a1) to (a5) are performed sequentially, before step (a).

In yet another alternative embodiment of the above method of making a compound or derivative having formula (I-H), or salt, solvate, or prodrug thereof, the compound or derivative having formula (I), the compound or derivative having formula (1), or salt thereof, optionally wherein each $R^1$ is a TMS group, is further treated with a molar equivalent of a Lewis acid in step (a2).

In a particular embodiment, a method of making a crystalline form of the compound or derivative having formula (I-H), or a salt, solvate, or prodrug thereof, wherein $R^6$, $R^7$, and $R^8$ are each hydrogen, can include the steps of:

(a) adding a volume of methanol and water in a 95:5 weight:weight ratio to the compound or derivative having formula (I-H), or salt, solvate, or prodrug thereof, wherein $R^6$, $R^7$, and $R^8$ are each hydrogen, at room temperature, so as to dissolve approximately 15% of the compound or derivative having formula (I-H), or salt, solvate, or prodrug thereof, wherein $R^6$, $R^7$, and $R^8$ are each hydrogen, in the volume of methanol and water; (b) stirring the compound or derivative having formula (I-H), or salt, solvate, or prodrug thereof, wherein $R^6$, $R^7$, and $R^8$ are each hydrogen, at 50° C. until all of the compound or derivative having formula (I-H), or salt, solvate, or prodrug thereof, wherein $R^6$, $R^7$, and $R^8$ are each hydrogen, apparently dissolves in the volume of methanol and water; (c) cooling the solution of the compound or derivative having formula (I-H), or salt, solvate, or prodrug thereof, wherein $R^6$, $R^7$, and $R^8$ are each hydrogen, in the volume of methanol and water, to −10° C. with stirring so as to precipitate the crystalline form of the compound or derivative having formula (I-H), or salt, solvate, or prodrug thereof, wherein $R^6$, $R^7$, and $R^8$ are each hydrogen; (d) isolating the crystalline form of the compound or derivative having formula (I-H), or salt, solvate, or prodrug thereof, wherein $R^6$, $R^7$, and $R^8$ are each hydrogen; and (e) drying the crystalline form of the compound or derivative having formula (I-H), or salt, solvate, or prodrug thereof, wherein $R^6$, $R^7$, and $R^8$ are each hydrogen.

In accordance with one embodiment, the present disclosure provides a novel method for the preparation of compounds or derivatives having formula (II), or salts, solvates, or prodrugs thereof, such as phosphorylated analogs of nicotinoyl ribosides, in commercial quantities. In accordance with such an embodiment, the present disclosure provides a novel method whereby mechanic forces are used to minimize solvent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product phosphorylated analogs of nicotinoyl riboside compounds include compounds or derivatives having formula (II), or salts, solvates, or prodrugs thereof:

(II)

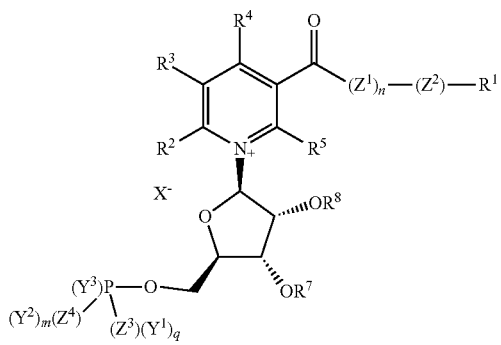

optionally wherein X⁻ as counterion is absent, or when X⁻ is present, X⁻ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when X⁻ is absent, optionally the counterion is an internal salt;

each $Y^1$ and $Y^2$ is independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—$CO_2R^C$, —N($R^A$)—$CO_2R^B$, —CH—($R^A$)—$NH_2$, and —CH—($R^A$)—$CO_2R^B$; wherein the substituted $(C_1$-$C_8)$alkyl, substituted $(C_1$-$C_8)$cycloalkyl, substituted aryl, substituted heteroaryl, substituted heterocycle, and substituted amino are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

or, alternatively, $Y^1$ and $Y^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

optionally wherein $Y^3$ is oxygen, sulfur, or absent;
each of $Z^1$ and $Z^2$ is independently NH or oxygen;
each of $Z^3$ and $Z^4$ is independently nitrogen or oxygen;
m is 1 or 2;
n is 0 or 1;
q is 1 or 2;

$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl $(C_1$-$C_4)$alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

wherein when $R^1$ is hydrogen, $Z^2$ is oxygen, and n is 0, the compound or derivative having formula (II) may optionally take the form of the carboxylate anion conjugate base species of the compound or derivative having formula (II), further optionally associated with a positively charged counterion selected from the group consisting of calcium, magnesium, potassium, sodium, zinc, and ammonium cations;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$SO$_2$N$R^B_2$, —S$R^B$, —S(O)$R^B$, —SO$_2R^B$, —OSO$_2$($C_1$-$C_6$)alkyl, —SO$_2$N$R^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2$$NR^C{}_2$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2$$NR^C{}_2$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

provided that the absolute configuration of C** is R or S, or a mixture of R and S.

In an embodiment, a method of making a compound or derivative having formula (II), or a salt, solvate, or prodrug thereof, wherein $Y^3$ is oxygen, can include the steps of:

(a) providing a compound or derivative having formula (I), or a salt, solvate, or prodrug thereof, wherein $R^6$ is hydrogen; (b) treating the compound or derivative having formula (I), or salt, solvate, or prodrug thereof, wherein $R^6$ is hydrogen, with, optionally, a (0<x≤20) molar equivalent amount of a Brønsted base, and a reagent selected from the group consisting of a phosphitylating reagent, a phosphorylating reagent, and a thiophosphorylating reagent; (c) processing the compound or derivative having formula (I), or salt, solvate, or prodrug thereof, wherein $R^6$ is hydrogen, the reagent, and, optionally, the Brønsted base, so as to produce the compound or derivative having formula (II), or salt, solvate, or prodrug thereof, (d) adding, optionally, the compound or derivative having formula (I), or salt, solvate, or prodrug thereof, wherein $R^6$ is hydrogen, optionally, the reagent, optionally, the Brønsted base, and the compound or derivative having formula (II), or salt, solvate, or prodrug thereof, to iced water; and (e) isolating the compound or derivative having formula (II), or salt, solvate, or prodrug thereof.

In an alternative embodiment of the above method of making a compound or derivative having formula (II), or salt, solvate, or prodrug thereof, the method can further include the step of:

(e1) treating the compound or derivative having formula (II), or salt, solvate, or prodrug thereof, with deprotection reagent(s) in a polar organic solvent co-reagent so as to remove any protecting groups of $R^7$, $R^8$, $Y^1$, and/or $Y^2$; wherein the step (e1) is performed following step (e).

In yet another alternative embodiment of the above method of making a compound or derivative having formula (II), or salt, solvate, or prodrug thereof, wherein the reagent of step (b) is a phosphitylating reagent, the method can further include the steps of:

(c1) adding an oxidizing reagent to, optionally, the compound or derivative having formula (I), or salt, solvate, or prodrug thereof, wherein $R^6$ is hydrogen, optionally, the phosphitylating reagent, optionally, the Brønsted base, and the compound or derivative having formula (II), or salt, solvate, or prodrug thereof, (c2) processing, optionally, the compound or derivative having formula (I), or salt, solvate, or prodrug thereof, wherein $R^6$ is hydrogen, optionally, the phosphitylating reagent, optionally, the Brønsted base, and the compound or derivative having formula (II), or salt, solvate, or prodrug thereof, so as to produce a compound or derivative having formula (II), or salt, solvate, or prodrug thereof, wherein $Y^3$ is sulfur or oxygen; wherein the steps (c1) and (c2) are performed sequentially, following step (c).

Processing can be carried out under batch processing conditions or by continuously processing. Continuously processing may include one or more methods of agitation selected from the group consisting of liquid-assisted grinding and extruding. The process described herein effects a preparation of a compound or derivative having formula (II), or salt, solvate, or prodrug thereof, wherein $Y^3$ is oxygen, under almost solventless conditions.

The polar organic solvent co-reagent and isolation solvent employed in the above method of making a compound or derivative having formula (II), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of methanol and water in a 3:2 volume:volume ratio at room temperature; (b) stirring the compound or derivative having formula (II), or salt, solvate, or prodrug thereof, wherein $Y^3$ is oxygen, and the volume of methanol and water so as to dissolve the compound or derivative having formula (II), or salt, solvate, or prodrug thereof, wherein $Y^3$ is oxygen, in the volume of methanol and water; (c) filtering the solution of the compound or derivative having formula (II), or salt, solvate, or prodrug thereof, wherein $Y^3$ is oxygen, in the volume of methanol and water, so as to remove any undissolved solids; (d) adding a volume of acetone to the solution of the compound or derivative having formula (II), or salt, solvate, or prodrug thereof, wherein $Y^3$ is oxygen, in the volume of methanol and water, wherein the volume of acetone is about 2 to about 5 times the combined volume of methanol and water; (e) cooling the compound or derivative having formula (II), or salt, solvate, or prodrug thereof, wherein $Y^3$ is oxygen, the volume of acetone, and the volume of methanol and water at −20° C. so as to precipitate the crystalline form of the compound or derivative having formula (II), or salt, solvate, or prodrug thereof, wherein $Y^3$ is oxygen; (f) isolating the crystalline form of the compound or derivative having formula (II), or salt, solvate, or prodrug thereof, wherein $Y^3$ is oxygen; and (g) drying the crystalline form of the compound or derivative having formula (II), or salt, solvate, or prodrug thereof, wherein $Y^3$ is oxygen, at room temperature.

In a particular embodiment, an alternative method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of methanol and water in a 3:2 volume:volume ratio at room temperature; (b) stirring the compound or derivative having formula (II), or salt, solvate, or prodrug thereof, wherein $Y^3$ is oxygen, and the volume of methanol and water so as to dissolve the compound or derivative having formula (II), or salt, solvate, or prodrug thereof, wherein $Y^3$ is oxygen, in the volume of methanol and water; (c) filtering the solution of the compound or derivative having formula (II), or salt, solvate, or prodrug thereof, wherein $Y^3$ is oxygen, in the volume of methanol and water, so as to remove any undissolved solids; (d) cooling the compound or derivative having formula (II), or salt, solvate, or prodrug thereof, wherein $Y^3$ is oxygen, and the volume of methanol and water at −20° C. so as to produce an oily layer at the bottom of the volume of methanol and water; (e) decanting the volume of methanol and water from the oily layer at the bottom of the volume of methanol and water; and (f) drying the oily layer at room temperature so as to crystallize the crystalline form of the compound or derivative having formula (II), or salt, solvate, or prodrug thereof, wherein $Y^3$ is oxygen.

In a particular embodiment, another alternative method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of ethanol and water in a 3:2 volume:volume ratio at room temperature, wherein the compound or derivative having formula (II), or salt, solvate, or prodrug thereof, wherein $Y^3$ is oxygen, is added in an amount of about 200 milligrams per milliliter of the volume of ethanol and water; (b) stirring the compound or derivative having formula (II), or salt, solvate, or prodrug thereof, wherein $Y^3$ is oxygen, and the volume of ethanol and water so as to dissolve the compound or derivative having formula (II), or salt, solvate, or prodrug thereof, wherein $Y^3$ is oxygen, in the volume of ethanol and water; (c) filtering the solution of the compound or derivative having formula (II), or salt, solvate, or prodrug thereof, wherein $Y^3$ is oxygen, in the volume of ethanol and water, so as to remove any undissolved solids; (d) cooling the compound or derivative having formula (II), or salt, solvate, or prodrug thereof, wherein $Y^3$ is oxygen, in the volume of ethanol and water, to −10° C. for about 48 hours so as to produce the crystalline form of the compound or derivative having formula (II), or salt, solvate, or prodrug thereof, wherein $Y^3$ is oxygen; (e) decanting the volume of ethanol and water from the crystalline form of the compound or derivative having formula (II), or salt, solvate, or prodrug thereof, wherein $Y^3$ is oxygen, so as to isolate the crystalline form of the compound or derivative having formula (II), or salt, solvate, or prodrug thereof, wherein $Y^3$ is oxygen; and (f) drying the crystalline form of the compound or derivative having formula (II), or salt, solvate, or prodrug thereof, wherein $Y^3$ is oxygen, at room temperature.

In accordance with one embodiment, the present disclosure provides a novel method for the preparation of compounds or derivatives having formula (III), or salts, solvates, or prodrugs thereof, such as adenylyl dinucleotide conjugates of nicotinoyl ribosides, in commercial quantities. In accordance with such an embodiment, the present disclosure provides a novel method whereby mechanic forces are used to minimize solvent quantities, decrease reaction times, increase overall conversion, and facilitate product purification, whereby by-product formation is minimized. Prototype product nicotinoyl riboside compounds include compounds or derivatives having formula (III), or salts, solvates, or prodrugs thereof:

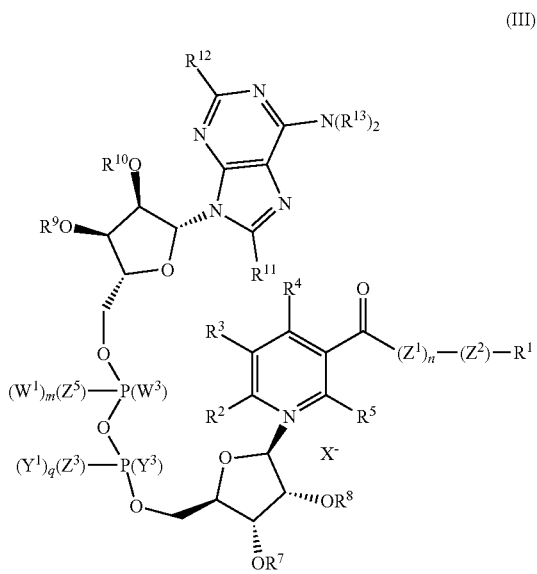

(III)

optionally wherein $X^-$ as counterion is absent, or when $X^-$ is present, $X^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when $X^-$ is absent, optionally the counterion is an internal salt;

each $Y^1$ is independently selected from the group consisting of hydrogen, sodium, potassium, lithium, substituted or unsubstituted $(C_1-C_8)$alkyl, substituted or unsubstituted $(C_1-C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^4$)—$CO_2R^C$, —N($R^4$)—$CO_2R^B$, —CH—($R^4$)—$NH_2$, and —CH—($R^4$)—$CO_2R^B$; wherein the substituted $(C_1-C_8)$alkyl, substituted $(C_1-C_8)$cycloalkyl, substituted aryl, substituted heteroaryl, substituted heterocycle, and substituted amino are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

each $W^1$ is independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, substituted heterocycle, and substituted amino are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

or, alternatively, $Y^1$ and $W^1$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$—C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

optionally wherein $Y^3$ is oxygen, sulfur, or absent;
optionally wherein $W^3$ is oxygen, sulfur, or absent;
each of $Z^1$ and $Z^2$ is independently NH or oxygen;
each of $Z^3$ and $Z^5$ is independently nitrogen or oxygen;
m is 1 or 2;
n is 0 or 1;
q is 1 or 2;
$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

wherein when $R^1$ is hydrogen, $Z^2$ is oxygen, and n is 0, the compound or derivative having formula (III) may optionally take the form of the carboxylate anion conjugate base species of the compound or derivative having formula (III), further optionally associated with a positively charged counterion selected from the group consisting of calcium, magnesium, potassium, sodium, zinc, and ammonium cations;

$R^A$ is selected from the group consisting of —H, —($C_1$-$C_6$)alkyl, —$(CH_2)_3$—NH—C($NH_2$)(=NH), —$CH_2C$(=O)$NH_2$, —$CH_2COOH$, —$CH_2SH$, —$(CH_2)_2C$(=O)—$NH_2$, —$(CH_2)_2COOH$, —$CH_2$-(2-imidazolyl), —CH($CH_3$)—$CH_2$—$CH_3$, —$CH_2CH(CH_3)_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;
each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B_2$, —C(=$NR^B$)$NR^B_2$, —O$R^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$R^B_2$, —$NR^B$C(O)$R^B$, —$NR^B$C(O)O($C_1$-$C_6$)alkyl, —$NR^B$C(O)$NR^B_2$, —$NR^B$$SO_2$$NR^B_2$, —$SR^B$, —S(O)$R^B$, —$SO_2R^B$, —$OSO_2$($C_1$-$C_6$)alkyl, —$SO_2NR^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$—C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)

$NR^C_2$—$NR^CSO_2NR^C_2$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

R' is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl$(C_1$-$C_4)$alkyl, heterocycle$(C_1$-$C_4)$alkyl, —$N(R^A)$—$CO_2R^C$, —$N(R^A)$—$CO_2R^B$, —$CH$—$(R^A)$—$NH_2$, and —$CH$—$(R^A)$—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$—$NR^CSO_2NR^C_2$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$R^9$ and $R^{10}$ are independently selected from the group consisting of hydrogen, —$C(O)R'$, —$C(O)OR'$, —$C(O)NHR'$, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$—$NR^CSO_2NR^C_2$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$R^{11}$ is selected from the group consisting of hydrogen, —$C(O)R'$, —$C(O)OR'$, —$C(O)NHR'$, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C_2$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$R^{12}$ is selected from the group consisting of hydrogen, —$C(O)R'$, —$C(O)OR'$, —$C(O)NHR'$, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C_2$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

each $R^{13}$ is independently selected from the group consisting of hydrogen, —$C(O)R'$, —$C(O)OR'$, —$C(O)NHR'$, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$—$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$—$NR^CSO_2NR^C_2$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

provided that the absolute configuration of C** is R or S, or a mixture of R and S.

In accordance with such an embodiment, appropriate starting materials for the methods of the present disclosure for the preparation of compounds or derivatives having formula (III), or salts, solvates, or prodrugs thereof, include compounds or derivatives having formula (3), or salts thereof:

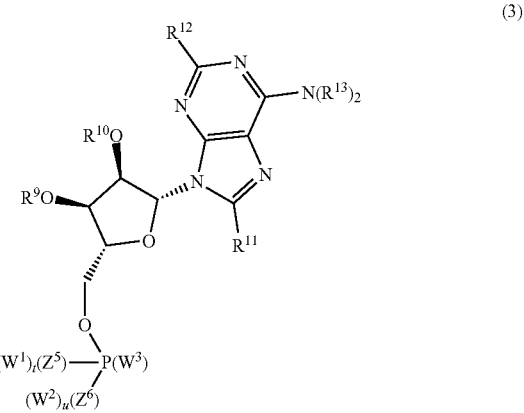

(3)

wherein each $W^1$ and $W^2$ is independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, substituted heterocycle, and substituted amino are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$ —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

or, alternatively, $W^1$ and $W^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

optionally wherein $W^3$ is oxygen, sulfur, or absent;

each of $Z^5$ and $Z^6$ is independently nitrogen or oxygen;

t is 1 or 2;

u is 1 or 2;

$R^9$ and $R^{10}$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$—N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —$R^B_2$, —N$R^B$C(O)$R^B$, —N$R^B$C(O)O($C_1$-$C_6$)alkyl, —N$R^B$C(O)N$R^B_2$, —N$R^B$SO$_2$N$R^B_2$, —S$R^B$, —S(O)$R^B$, —SO$_2R^B$, —OSO$_2$($C_1$-$C_6$)alkyl, —SO$_2$N$R^B_2$, —($C_1$-$C_6$)perfluoroalkyl, and —($C_1$-$C_6$)alkylene-O$R^B$;

$R^{11}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^{12}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl;

wherein the substituted ($C_1$-$C_8$)alkyl, substituted ($C_1$-$C_8$) cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C_2$, —S$R^C$, —S(O)$R^C$, —$SO_2$$R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

each $R^{13}$ is independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$—C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$—N$R^C$$SO_2$N$R^C_2$, —S$R^C$, —S(O)$R^C$, —$SO_2$$R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

provided that the absolute configuration of C** is R or S, or a mixture of R and S.

In an embodiment, a method of making a compound or derivative having formula (III), or a salt, solvate, or prodrug thereof, can include the steps of:

(a) providing a compound or derivative having formula (II), or a salt, solvate, or prodrug thereof; (b) treating the compound or derivative having formula (II), or salt, solvate, or prodrug thereof, with a compound or derivative having formula (3), or a salt thereof, and a reagent selected from the group consisting of a (1<x<10) molar equivalent amount of a carbodiimide reagent, a (0<x<10) molar equivalent amount of an amine, and a (0<x<10) molar equivalent of a Brønsted acid, in the presence of water or an organic solvent co-reagent in an amount of up to 10 molar equivalents; (c) processing the compound or derivative having formula (II), or salt, solvate, or prodrug thereof, the compound or derivative having formula (3), or salt thereof, the reagent, and the water or organic solvent co-reagent, so as to produce the compound or derivative having formula (III), or salt, solvate, or prodrug thereof; (d) adding, optionally, the compound or derivative having formula (II), or salt, solvate, or prodrug thereof, optionally, the compound or derivative having formula (3), or salt thereof, optionally, the reagent, the water or organic solvent co-reagent, and the compound or derivative having formula (III), or salt, solvate, or prodrug thereof, to iced water; and (e) isolating the compound or derivative having formula (III), or salt, solvate, or prodrug thereof.

In an alternative embodiment of the above method of making a compound or derivative having formula (III), or a salt, solvate, or prodrug thereof, the method can further include the step of:

(e1) treating the compound or derivative having formula (III), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$; wherein the step (e1) is performed following step (e).

In another alternative embodiment of the above method of making a compound or derivative having formula (III), or a salt, solvate, or prodrug thereof, the compound or derivative having formula (II), or salt, solvate, or prodrug thereof, compound or derivative having formula (3), or salt thereof, the reagent, and water or organic solvent co-reagent can further be treated with at least a catalytic amount of a divalent metal salt in step (b).

Processing can be carried out under batch processing conditions or by continuously processing. Continuously processing may include one or more methods of agitation selected from the group consisting of continuous grinding and extruding. The process described herein effects a preparation of a compound or derivative having formula (III), or salt, solvate, or prodrug thereof, under almost solventless conditions.

The polar organic solvent co-reagent employed in the above method of making a compound or derivative having formula (III), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In accordance with one embodiment, the present disclosure provides a novel method for the preparation of compounds or derivatives having formula (IV), or salts, solvates, or prodrugs thereof, such as reduced nicotinoyl ribosides and their derivatives, and including, but not limited to, the triacetylated forms of NRH (reduced nicotinamide riboside) and NARH (reduced nicotinic acid riboside) (compounds or derivatives having formula (IV), wherein $R^6$, $R^7$, and R' are each acetyl groups), and the fully deprotected forms thereof (compounds or derivatives having formula (IV-H), wherein $R^6$, $R^7$, and $R^8$ are each hydrogen), in commercial quantities. In accordance with such an embodiment, the present disclosure provides a novel method whereby mechanic forces and/or sealed conditions, and extraction conditions, are used to minimize solvent and reagent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product reduced nicotinoyl riboside compounds include compounds or derivatives having formula (IV), or salts, solvates, or prodrugs thereof:

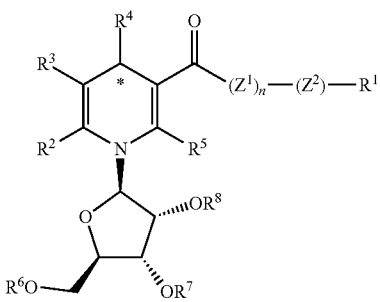

(IV)

wherein $Z^1$ and $Z^2$ are independently NH or oxygen;

n is 0 or 1;

$R^1$ is selected from the group consisting of hydrogen, substituted or unsubstituted $(C_1\text{-}C_8)$alkyl, substituted or unsubstituted $(C_1\text{-}C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl $(C_1\text{-}C_4)$alkyl, heterocycle$(C_1\text{-}C_4)$alkyl, —N($R^A$)—CO$_2$R$^C$, —N($R^A$)—CO$_2$R$^B$, —CH—($R^A$)—NH$_2$, and —CH—($R^A$)—CO$_2$R$^B$; wherein the substituted $(C_1\text{-}C_8)$alkyl, substituted $(C_1\text{-}C_8)$cycloalkyl, substituted aryl, substituted heteroaryl, and substituted heterocycle are substituted with one to five substituents independently selected from the group consisting of —$(C_1\text{-}C_6)$alkyl, —$(C_2\text{-}C_6)$alkenyl, —$(C_2\text{-}C_6)$alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O (C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein when $R^1$ is hydrogen, $Z^2$ is oxygen, and n is 0, the compound or derivative having formula (IV) may optionally take the form of the carboxylate anion conjugate base species of the compound or derivative having formula (IV), further optionally associated with a positively charged counterion selected from the group consisting of calcium, magnesium, potassium, sodium, zinc, and ammonium cations;

$R^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each $R^B$ is independently hydrogen or —(C$_1$-C$_8$)alkyl;

each $R^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)alkylene-NR$^B_2$, —NR$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$)perfluoroalkyl, and —(C$_1$-C$_6$)alkylene-OR$^B$;

$R^2$ and $R^3$ are each independently selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

$R^4$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein C* has an absolute configuration of R or S, or a mixture of R and S;

$R^5$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

$R^6$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl(C$_1$-C$_4$)alkyl, heterocycle(C$_1$-C$_4$)alkyl, —N($R^A$)—CO$_2$R$^C$, —N($R^A$)—CO$_2$R$^B$, —CH—($R^A$)—NH$_2$, and —CH—($R^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N($R^A$)—CO$_2$R$^C$, —N($R^A$)—CO$_2$R$^B$, —CH—($R^A$)—NH$_2$, and —CH—($R^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2$$NR^C{}_2$, —$SR^C$, —S(O)$R^C$, —$SO_2$$R^C$, —$OSO_2$($C_1$-$C_6$)alkyl, —$SO_2$$NR^C{}_2$, —($C_1$-$C_6$)perfluoroalkyl, and —($C_1$-$C_6$)alkylene-O$R^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$) alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$—$NR^C$$SO_2$$NR^C{}_2$, —$SR^C$, —S(O)$R^C$, —$SO_2$$R^C$, —$OSO_2$($C_1$-$C_6$)alkyl, —$SO_2$$NR^C{}_2$, —($C_1$-$C_6$)perfluoroalkyl, and —($C_1$-$C_6$)alkylene-O$R^C$;

provided that the absolute configuration of C** is R or S, or a mixture of R and S.

Generally, appropriate synthetic processes comprising batch and semi-continuous processing of reagents by liquid-assisted mixing, grinding, milling, and/or extrusion are employed as described herein.

In an embodiment, a method of making a compound or derivative having formula (IV), or a salt, solvate, or prodrug thereof, can include the steps of:

(a) providing a compound or derivative having formula (I), or salt, solvate, or prodrug thereof; (b) treating the compound or derivative having formula (I), or salt, solvate, or prodrug thereof, with a (1<x<10) molar equivalent amount of a concentrated basic aqueous solution of reducing agent reagent, in the presence of a (5<x<50) molar equivalent amount of an organic solvent co-reagent; (c) processing the compound or derivative having formula (I), or salt, solvate, or prodrug thereof, the concentrated aqueous solution of reducing agent reagent, and the organic solvent co-reagent so as to produce the compound or derivative having formula (IV), or salt, solvate, or prodrug thereof, (d) adding, optionally, the compound or derivative having formula (I), or salt, solvate, or prodrug thereof, optionally, the concentrated aqueous solution of reducing agent reagent, the organic solvent co-reagent, and the compound or derivative having formula (IV), or salt, solvate, or prodrug thereof, to water; (e) extracting, optionally, the compound or derivative having formula (I), or salt, solvate, or prodrug thereof, optionally, the concentrated aqueous solution of reducing agent reagent, the organic solvent co-reagent, the compound or derivative having formula (IV), or salt, solvate, or prodrug thereof, and water with organic solvent; and (f) isolating the compound or derivative having formula (IV), or salt, solvate, or prodrug thereof.

Processing can be carried out under batch processing conditions or by continuously processing. Continuously processing may include one or more methods of agitation selected from the group consisting of liquid-assisted mixing, grinding, milling, and extruding. The process described herein effects a preparation of a compound or derivative having formula (IV), or salt, solvate, or prodrug thereof, under almost solventless conditions.

The organic solvent co-reagent and isolation solvent employed in the above method of making a compound or derivative having formula (IV), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In accordance with one embodiment, the present disclosure provides a novel method for the preparation of compounds or derivatives having formula (IV-H), or salts, solvates, or prodrugs thereof, wherein $R^6$, $R^7$, and $R^8$ are each hydrogen. In accordance with such an embodiment, the present disclosure provides a novel method whereby mechanic forces are used to minimize solvent and reagent quantities, decrease reaction times, increase overall conversion, and facilitate product purification in a multistep or single-step synthetic sequence, whereby by-product formation is minimized, and whereby by-products that are removed readily by filtration or evaporation are generated. Prototype product reduced nicotinoyl riboside compounds include compounds or derivatives having formula (IV-H), or salts, solvates, or prodrugs thereof, wherein $R^6$, $R^7$, and $R^8$ are each hydrogen:

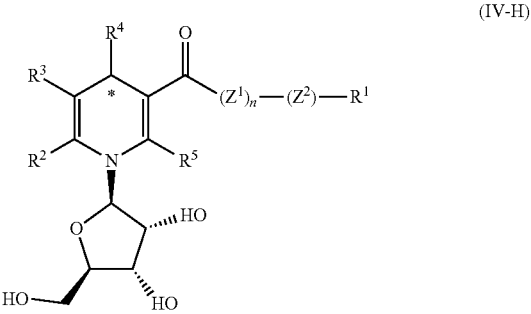

(IV-H)

wherein $Z^1$ and $Z^2$ are independently NH or oxygen;
n is 0 or 1;
$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl ($C_1$-$C_4$)alkyl, heterocycle($C_1$-$C_4$)alkyl, —N($R^A$)—$CO_2$$R^C$, —N($R^A$)—$CO_2$$R^B$, —CH—($R^A$)—$NH_2$, and —CH—($R^A$)—$CO_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O ($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

wherein when R$^1$ is hydrogen, Z$^2$ is oxygen, and n is 0, the compound or derivative having formula (IV-H) may optionally take the form of the carboxylate anion conjugate base species of the compound or derivative having formula (IV-H), further optionally associated with a positively charged counterion selected from the group consisting of calcium, magnesium, potassium, sodium, zinc, and ammonium cations;

R$^4$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —($C_1$-$C_8$)alkyl;

each R$^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)($C_1$-$C_6$)alkyl, —OC(O)O($C_1$-$C_6$)alkyl, —OC(O)NR$^B_2$, —($C_1$-$C_6$)alkylene-NR$^B_2$, —NR$^B_2$, —NR$^B$C(O)R$^B$, —NR$^B$C(O)O($C_1$-$C_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$($C_1$-$C_6$)alkyl, —SO$_2$NR$^B_2$, —($C_1$-$C_6$)perfluoroalkyl, and —($C_1$-$C_6$)alkylene-OR$^B$;

R$^2$ and R$^3$ are each independently selected from the group consisting of hydrogen, —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

R$^4$ is selected from the group consisting of hydrogen, —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

wherein C* has an absolute configuration of R or S, or a mixture of R and S;

R$^5$ is selected from the group consisting of hydrogen, —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

provided that the absolute configuration of C** is R or S, or a mixture of R and S.

In an embodiment, a method of making a compound or derivative having formula (IV-H), or a salt, solvate, prodrug thereof, wherein R$^6$, R$^7$, and R$^8$ are each hydrogen, can include the steps of:

(a) providing a compound or derivative having formula (IV), or a salt, solvate, or prodrug thereof; (b) treating the compound or derivative having formula (IV), or salt, solvate, or prodrug thereof, with a molar (x≤10) equivalent amount of an alcohol (e.g., methanol, or ethanol) and a catalytic amount of a Brønsted base; (c) processing the compound or derivative having formula (IV), or salt, solvate, or prodrug thereof, the alcohol, and the Brønsted base so as to produce the compound or derivative having formula (IV-H), or salt, solvate, or prodrug thereof, wherein R$^6$, R$^7$, and R$^8$ are each hydrogen; and (d) isolating the compound or derivative having formula (IV-H), or salt, solvate, or prodrug thereof, wherein R$^6$, R$^7$, and R$^8$ are each hydrogen.

Processing can be carried out under batch processing conditions or by continuously processing. Continuously processing may include one or more methods of agitation selected from the group consisting of liquid-assisted mixing, milling, grinding, and extruding. The process described herein effects a preparation of a compound or derivative having formula (IV-H), or salt, solvate, or prodrug thereof, wherein R$^6$, R$^7$, and R$^8$ are each hydrogen.

The organic solvent co-reagent and isolation solvent employed in the above method of making a compound or derivative having formula (IV-H), or salt, solvate, or prodrug thereof, wherein R$^6$, R$^7$, and R$^8$ are each hydrogen, can be an alcohol (e.g., methanol, or ethanol), or any polar protic organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an alternative embodiment of the above method of making a compound or derivative having formula (IV-H), or a salt, solvate, or prodrug thereof, wherein R$^6$, R$^7$, and R$^8$ are each hydrogen, the method can further include the steps of:

(a1) providing a compound or derivative having formula (I), or a salt, solvate, or prodrug thereof; (a2) treating the compound or derivative having formula (I), or salt, solvate, or prodrug thereof, with a (1<x<10) molar equivalent amount of a concentrated basic aqueous solution of reducing agent reagent, in the presence of a (5<x<50) molar equivalent amount of a polar organic solvent co-reagent; (a3) processing the compound or derivative having formula (I), or salt, solvate, or prodrug thereof, the concentrated basic aqueous solution of reducing agent reagent, and the polar organic solvent co-reagent so as to produce a compound or derivative having formula (IV), or salt, solvate, or prodrug thereof, while continuously extracting in situ the compound or derivative having formula (IV), or salt, solvate, or prodrug thereof, into organic solvent; and (a4) isolating the compound or derivative having formula (IV), or salt, solvate, or prodrug thereof, wherein the steps (a1) to (a4) are performed sequentially, before step (a).

In accordance with one embodiment, the present disclosure provides a novel method for the preparation of compounds or derivatives having formula (V), or salts, solvates, or prodrugs thereof, such as phosphorylated analogs of reduced nicotinoyl ribosides, in commercial quantities. In accordance with such an embodiment, the present disclosure provides a novel method whereby mechanic forces are used to minimize solvent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product phosphorylated analogs of reduced nicotinoyl riboside compounds include compounds or derivatives having formula (V), or salts, solvates, or prodrugs thereof:

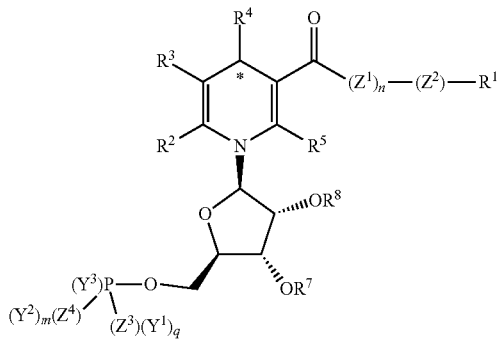

(V)

each $Y^1$ and $Y^2$ is independently selected from the group consisting of hydrogen, sodium, potassium, lithium, substituted or unsubstituted $(C_1-C_8)$alkyl, substituted or unsubstituted $(C_1-C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—$CO_2R^C$, —N($R^A$)—$CO_2R^B$, —CH—($R^A$)—$NH_2$, and —CH—($R^A$)—$CO_2R^B$; wherein the substituted $(C_1-C_8)$alkyl, substituted $(C_1-C_8)$cycloalkyl, substituted aryl, substituted heteroaryl, substituted heterocycle, and substituted amino are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)N$R^C{}_2$, —C(=N$R^C$)N$R^C{}_2$, —O$R^C$, —OC(O)($C_1-C_6$)alkyl, —OC(O)O($C_1-C_6$)alkyl, —OC(O)N$R^C{}_2$, —$(C_1-C_6)$alkylene-N$R^C{}_2$, —N$R^C{}_2$, —N$R^C$C(O)$R^C$, —N$R^C$C(O)O($C_1-C_6$)alkyl, —N$R^C$C(O)N$R^C{}_2$, —N$R^C$SO$_2$N$R^C{}_2$, —S$R^C$, —S(O)$R^C$, —SO$_2R^C$, —OSO$_2$($C_1-C_6$)alkyl, —SO$_2$N$R^C{}_2$, —$(C_1-C_6)$perfluoroalkyl, and —$(C_1-C_6)$alkylene-O$R^C$;

or, alternatively, $Y^1$ and $Y^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)N$R^C{}_2$—C(=N$R^C$)N$R^C{}_2$, —O$R^C$, —OC(O)($C_1-C_6$)alkyl, —OC(O)O($C_1-C_6$)alkyl, —OC(O)N$R^C{}_2$, —$(C_1-C_6)$alkylene-N$R^C{}_2$, —N$R^C{}_2$, —N$R^C$C(O)$R^C$, —N$R^C$C(O)O($C_1-C_6$)alkyl, —N$R^C$C(O)N$R^C{}_2$—N$R^C$SO$_2$N$R^C{}_2$, —S$R^C$, —S(O)$R^C$, —SO$_2R^C$, —OSO$_2$($C_1-C_6$)alkyl, —SO$_2$N$R^C{}_2$, —$(C_1-C_6)$perfluoroalkyl, and —$(C_1-C_6)$alkylene-O$R^C$;

optionally wherein $Y^3$ is oxygen, sulfur, or absent;
each of $Z^1$ and $Z^2$ is independently NH or oxygen;
each of $Z^3$ and $Z^4$ is independently nitrogen or oxygen;
m is 1 or 2;
n is 0 or 1;
q is 1 or 2;

$R^1$ is selected from the group consisting of hydrogen, substituted or unsubstituted $(C_1-C_8)$alkyl, substituted or unsubstituted $(C_1-C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl $(C_1-C_4)$alkyl, heterocycle$(C_1-C_4)$alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted $(C_1-C_8)$alkyl, substituted $(C_1-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)N$R^C{}_2$, —C(=N$R^C$)N$R^C{}_2$, —O$R^C$, —OC(O)($C_1-C_6$)alkyl, —OC(O)O($C_1-C_6$)alkyl, —OC(O)N$R^C{}_2$, —$(C_1-C_6)$alkylene-N$R^C{}_2$, —N$R^C{}_2$, —N$R^C$C(O)$R^C$, —N$R^C$C(O)O($C_1-C_6$)alkyl, —N$R^C$C(O)N$R^C{}_2$, —N$R^C$SO$_2$N$R^C{}_2$, —S$R^C$, —S(O)$R^C$, —SO$_2R^C$, —OSO$_2$($C_1-C_6$)alkyl, —SO$_2$N$R^C{}_2$, —$(C_1-C_6)$perfluoroalkyl, and —$(C_1-C_6)$alkylene-O$R^C$;

wherein when $R^1$ is hydrogen, $Z^2$ is oxygen, and n is 0, the compound or derivative having formula (V) may optionally take the form of the carboxylate anion conjugate base species of the compound or derivative having formula (V), further optionally associated with a positively charged counterion selected from the group consisting of calcium, magnesium, potassium, sodium, zinc, and ammonium cations;

$R^A$ is selected from the group consisting of —H, —$(C_1-C_6)$alkyl, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —$(C_1-C_8)$alkyl;

each $R^C$ is independently selected from the group consisting of hydrogen, —$(C_1-C_8)$alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^B$, —C(O)O$R^B$, —C(O)N$R^B{}_2$, —C(=N$R^B$)N$R^B{}_2$, —O$R^B$, —OC(O)($C_1-C_6$)alkyl, —OC(O)O($C_1-C_6$)alkyl, —OC(O)N$R^B{}_2$, —$(C_1-C_6)$alkylene-N$R^B{}_2$, —N$R^B{}_2$, —N$R^B$C(O)$R^B$, —N$R^B$C(O)O($C_1-C_6$)alkyl, —N$R^B$C(O)N$R^B{}_2$, —N$R^B$SO$_2$N$R^B{}_2$, —S$R^B$, —S(O)$R^B$, —SO$_2R^B$, —OSO$_2$($C_1-C_6$)alkyl, —SO$_2$N$R^B{}_2$, —$(C_1-C_6)$perfluoroalkyl, and —$(C_1-C_6)$alkylene-O$R^B$;

$R^2$ and $R^3$ are each independently selected from the group consisting of hydrogen, —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)N$R^C{}_2$, —C(=N$R^C$)N$R^C{}_2$, —O$R^C$, —OC(O)($C_1-C_6$)alkyl, —OC(O)O($C_1-C_6$)alkyl, —OC(O)N$R^C{}_2$, —$(C_1-C_6)$alkylene-N$R^C{}_2$, —N$R^C{}_2$, —N$R^C$C(O)$R^C$, —N$R^C$C(O)O($C_1-C_6$)alkyl, —N$R^C$C(O)N$R^C{}_2$, —N$R^C$SO$_2$N$R^C{}_2$, —S$R^C$, —S(O)$R^C$, —SO$_2R^C$, —OSO$_2$($C_1-C_6$)alkyl, —SO$_2$N$R^C{}_2$, —$(C_1-C_6)$perfluoroalkyl, and —$(C_1-C_6)$alkylene-O$R^C$;

$R^4$ is selected from the group consisting of hydrogen, —$(C_1-C_6)$alkyl, —$(C_2-C_6)$alkenyl, —$(C_2-C_6)$alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein C* has an absolute configuration of R or S, or a mixture of R and S;

R$^5$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^7$ and R$^8$ are independently selected from the group consisting of, hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$) cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with such an embodiment, appropriate starting materials for the methods of the present disclosure for the preparation of compounds or derivatives having formula (V), or salts, solvates, or prodrugs thereof, include compounds or derivatives having formula (IVb), or salts, solvates, or prodrugs thereof, wherein R$^6$ is hydrogen:

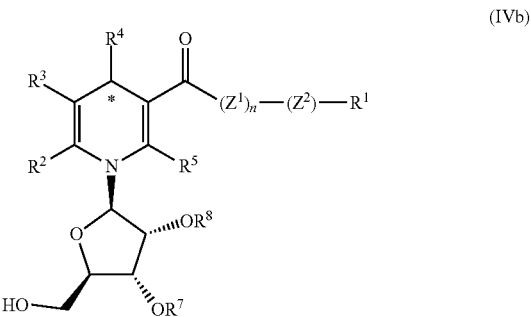

(IVb)

wherein Z$^1$ and Z$^2$ are independently NH or oxygen;

n is 0 or 1;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl (C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$) alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O (C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein when R$^1$ is hydrogen, Z$^2$ is oxygen, and n is 0, the compound or derivative having formula (IVb) may optionally take the form of the carboxylate anion conjugate base species of the compound or derivative having formula (IVb), further optionally associated with a positively charged counterion selected from the group consisting of calcium, magnesium, potassium, sodium, zinc, and ammonium cations;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)alkylene-NR$^B_2$, —NR$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$) perfluoroalkyl, and —(C$_1$-C$_6$)alkylene-OR$^B$;

R$^2$ and R$^3$ are each independently selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^4$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein C* has an absolute configuration of R or S, or a mixture of R and S;

R$^5$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$) cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

provided that the absolute configuration of C** is R or S, or a mixture of R and S.

In an embodiment, a method of making a compound or derivative having formula (V), or a salt, solvate, or prodrug thereof, can include the steps of:

(a) providing a compound or derivative having formula (IVb), or a salt, solvate, or prodrug thereof, wherein R$^6$ is hydrogen; (b) treating the compound or derivative having formula (IVb), or salt, solvate, or prodrug thereof, wherein R$^6$ is hydrogen, optionally, a (0<x≤20) molar equivalent amount of a Brønsted base, and a reagent selected from the group consisting of a phosphitylating reagent, a phosphorylating reagent, and a thiophosphorylating reagent; (c) processing the compound or derivative having formula (IVb), or salt, solvate, or prodrug thereof, wherein R$^6$ is hydrogen, the reagent, and, optionally, the Brønsted base, so as to produce the compound or derivative having formula (V), or salt, solvate, or prodrug thereof, (d) adding, optionally, the compound or derivative having formula (IVb), or salt, solvate, or prodrug thereof, optionally, the reagent, optionally, the Brønsted base, and the compound or derivative having formula (V), or salt, solvate, or prodrug thereof, to iced water; and (e) isolating the compound or derivative having formula (V), or salt, solvate, or prodrug thereof.

In an alternative embodiment of the above method of making a compound or derivative having formula (V), or a salt, solvate, or prodrug thereof, the method can further include the step of:

(e1) treating the compound or derivative having formula (V), or salt, solvate, or prodrug thereof, wherein Y$^3$ is oxygen, with deprotection reagent(s) in a polar organic solvent co-reagent so as to remove any protecting groups of R$^7$, R$^8$, Y$^1$, and/or Y$^2$; wherein the step (e1) is performed following step (e).

In another alternative embodiment of the above method of making a compound or derivative having formula (V), or a salt, solvate, or prodrug thereof, when the reagent of step (b) is phosphitylating reagent, the method can further include the steps of:

(c1) adding an oxidizing reagent to, optionally, the compound or derivative having formula (IVb), or salt, solvate, or prodrug thereof, wherein R$^6$ is hydrogen, optionally, the phosphitylating reagent, optionally, the Brønsted base, and the compound or derivative having formula (V), or salt, solvate, or prodrug thereof; (c2) processing the oxidizing agent reagent, optionally, the compound or derivative having formula (IVb), or salt, solvate, or prodrug thereof, wherein R$^6$ is hydrogen, optionally, the phosphitylating reagent, optionally, the Brønsted base, and the compound or derivative having formula (V), or salt, solvate, or prodrug thereof, so as to produce the compound or derivative having formula (V), or salt, solvate, or prodrug thereof, wherein Y$^3$ is sulfur or oxygen; wherein the steps (c1) and (c2) are performed sequentially, following step (c).

Processing can be carried out under batch processing conditions or by continuously processing. Continuously processing may include one or more methods of agitation selected from the group consisting of liquid-assisted grinding and extruding. The process described herein effects a preparation of a compound or derivative having formula (V), or salt, solvate, or prodrug thereof, wherein $Y^3$ is oxygen, under almost solventless conditions.

The polar organic solvent co-reagent and isolation solvent employed in the above method of making a compound or derivative having formula (V), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In accordance with one embodiment, the present disclosure provides a novel method for the preparation of compounds or derivatives having formula (VI), or salts, solvates, or prodrugs thereof, such as adenylyl dinucleotide conjugates of reduced nicotinoyl ribosides, in commercial quantities. In accordance with such an embodiment, the present disclosure provides a novel method whereby mechanic forces are used to minimize solvent quantities, decrease reaction times, increase overall conversion, and facilitate product purification, whereby by-product formation is minimized. Prototype product reduced nicotinoyl riboside compounds include compounds or derivatives having formula (VI), or salts, solvates, or prodrugs thereof:

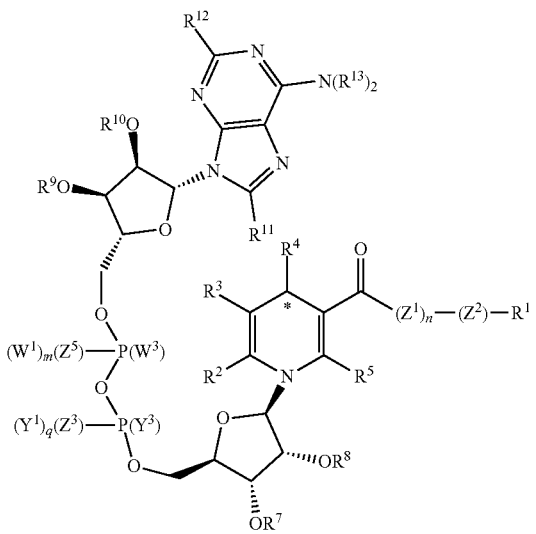

(VI)

wherein each $Y^1$ is independently selected from the group consisting of hydrogen, sodium, potassium, lithium, substituted or unsubstituted $(C_1\text{-}C_8)$alkyl, substituted or unsubstituted $(C_1\text{-}C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), $-N(R^A)-CO_2R^C$, $-N(R^A)-CO_2R^B$, $-C^{}H-(R^A)-NH_2$, and $-C^{}H-(R^A)-CO_2R^B$; wherein the substituted $(C_1\text{-}C_8)$alkyl, substituted $(C_1\text{-}C_8)$cycloalkyl, substituted aryl, substituted heteroaryl, substituted heterocycle, and substituted amino are substituted with one to five substituents independently selected from the group consisting of $-(C_1\text{-}C_6)$alkyl, $-(C_2\text{-}C_6)$alkenyl, $-(C_2\text{-}C_6)$alkynyl, halogen, $-CN$, $-NO_2$, $-C(O)R^C$, $-C(O)OR^C$, $-C(O)NR^C_2$, $-C(=NR^C)NR^C_2$, $-OR^C$, $-OC(O)(C_1\text{-}C_6)$alkyl, $-OC(O)O(C_1\text{-}C_6)$alkyl, $-OC(O)NR^C_2$, $-(C_1\text{-}C_6)$alkylene-$NR^C_2$, $-NR^C_2$, $-NR^CC(O)R^C$, $-NR^CC(O)O(C_1\text{-}C_6)$alkyl, $-NR^CC(O)NR^C_2$, $-NR^CSO_2NR^C_2$, $-SR^C$, $-S(O)R^C$, $-SO_2R^C$, $-OSO_2(C_1\text{-}C_6)$alkyl, $-SO_2NR^C_2$, $-(C_1\text{-}C_6)$perfluoroalkyl, and $-(C_1\text{-}C_6)$alkylene-$OR^C$;

each $W^1$ is independently selected from the group consisting of hydrogen, sodium, potassium, lithium, substituted or unsubstituted $(C_1\text{-}C_8)$alkyl, substituted or unsubstituted $(C_1\text{-}C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), $-N(R^A)-CO_2R^C$, $-N(R^A)-CO_2R^B$, $-C^{}H-(R^A)-NH_2$, and $-C^{}H-(R^A)-CO_2R^B$; wherein the substituted $(C_1\text{-}C_8)$alkyl, substituted $(C_1\text{-}C_8)$cycloalkyl, substituted aryl, substituted heteroaryl, substituted heterocycle, and substituted amino are substituted with one to five substituents independently selected from the group consisting of $-(C_1\text{-}C_6)$alkyl, $-(C_2\text{-}C_6)$alkenyl, $-(C_2\text{-}C_6)$alkynyl, halogen, $-CN$, $-NO_2$, $-C(O)R^C$, $-C(O)OR^C$, $-C(O)NR^C_2$, $-C(=NR^C)NR^C_2$, $-OR^C$, $-OC(O)(C_1\text{-}C_6)$alkyl, $-OC(O)O(C_1\text{-}C_6)$alkyl, $-OC(O)NR^C_2$, $-(C_1\text{-}C_6)$alkylene-$NR^C_2$, $-NR^C_2$, $-NR^CC(O)R^C$, $-NR^CC(O)O(C_1\text{-}C_6)$alkyl, $-NR^CC(O)NR^C_2$, $-NR^CSO_2NR^C_2$, $-SR^C$, $-S(O)R^C$, $-SO_2R^C$, $-OSO_2(C_1\text{-}C_6)$alkyl, $-SO_2NR^C_2$, $-(C_1\text{-}C_6)$perfluoroalkyl, and $-(C_1\text{-}C_6)$alkylene-$OR^C$;

or, alternatively, $Y^1$ and $W^1$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of $-(C_1\text{-}C_6)$alkyl, $-(C_2\text{-}C_6)$alkenyl, $-(C_2\text{-}C_6)$alkynyl, halogen, $-CN$, $-NO_2$, $-C(O)R^C$, $-C(O)OR^C$, $-C(O)NR^C_2$, $-C(=NR^C)NR^C_2$, $-OR^C$, $-OC(O)(C_1\text{-}C_6)$alkyl, $-OC(O)O(C_1\text{-}C_6)$alkyl, $-OC(O)NR^C_2$, $-(C_1\text{-}C_6)$alkylene-$NR^C_2$, $-NR^C_2$, $-NR^CC(O)R^C$, $-NR^CC(O)O(C_1\text{-}C_6)$alkyl, $-NR^CC(O)NR^C_2$, $-NR^CSO_2NR^C_2$, $-SR^C$, $-S(O)R^C$, $-SO_2R^C$, $-OSO_2(C_1\text{-}C_6)$alkyl, $-SO_2NR^C_2$, $-(C_1\text{-}C_6)$perfluoroalkyl, and $-(C_1\text{-}C_6)$alkylene-$OR^C$;

optionally wherein $Y^3$ is oxygen, sulfur, or absent;
optionally wherein $W^3$ is oxygen, sulfur, or absent;
each of $Z^1$ and $Z^2$ is independently NH or oxygen;
each of $Z^3$ and $Z^5$ is independently nitrogen or oxygen;
m is 1 or 2;
n is 0 or 1;
q is 1 or 2;

$R^1$ is selected from the group consisting of hydrogen, substituted or unsubstituted $(C_1\text{-}C_8)$alkyl, substituted or unsubstituted $(C_1\text{-}C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl $(C_1\text{-}C_4)$alkyl, heterocycle$(C_1\text{-}C_4)$alkyl, $-N(R^A)-CO_2R^C$, $-N(R^A)-CO_2R^B$, $-C^{}H-(R^A)-NH_2$, and $-C^{}H-(R^A)-CO_2R^B$; wherein the substituted $(C_1\text{-}C_8)$alkyl, substituted $(C_1\text{-}C_8)$cycloalkyl, substituted aryl, substituted heteroaryl, and substituted heterocycle are substituted with one to five substituents independently selected from the group consisting of $-(C_1\text{-}C_6)$alkyl, $-(C_2\text{-}C_6)$alkenyl, $-(C_2\text{-}C_6)$alkynyl, halogen, $-CN$, $-NO_2$, $-C(O)R^C$, $-C(O)OR^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein when R$^1$ is hydrogen, Z$^2$ is oxygen, and n is 0, the compound or derivative having formula (VI) may optionally take the form of the carboxylate anion conjugate base species of the compound or derivative having formula (VI), further optionally associated with a positively charged counterion selected from the group consisting of calcium, magnesium, potassium, sodium, zinc, and ammonium cations;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)alkylene-NR$^B_2$, —R$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$)perfluoroalkyl, and —(C$_1$-C$_6$)alkylene-OR$^B$;

R$^2$ and R$^3$ are each independently selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^4$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein C* has an absolute configuration of R or S, or a mixture of R and S;

R$^5$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^9$ and R$^{10}$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^{11}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$) cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$) cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O ($C_1$-$C_6$)alkyl, —N$R^C$C(O)N$R^C_2$, —N$R^C$$SO_2$N$R^C_2$, —S$R^C$, —S(O)$R^C$, —$SO_2$$R^C$, —O$SO_2$($C_1$-$C_6$)alkyl, —$SO_2$N$R^C_2$, —($C_1$-$C_6$)perfluoroalkyl, and —($C_1$-$C_6$)alkylene-O$R^C$;

$R^{12}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$) cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$) cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O ($C_1$-$C_6$)alkyl, —N$R^C$C(O)N$R^C_2$, —N$R^C$$SO_2$N$R^C_2$, —S$R^C$, —S(O)$R^C$, —$SO_2$$R^C$, —O$SO_2$($C_1$-$C_6$)alkyl, —$SO_2$N$R^C_2$, —($C_1$-$C_6$)perfluoroalkyl, and —($C_1$-$C_6$)alkylene-O$R^C$;

each $R^{13}$ is independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$) alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C_2$, —S$R^C$, —S(O)$R^C$, —$SO_2$$R^C$, —O$SO_2$($C_1$-$C_6$)alkyl, —$SO_2$N$R^C_2$, —($C_1$-$C_6$)perfluoroalkyl, and —($C_1$-$C_6$)alkylene-O$R^C$;

provided that the absolute configuration of C** is R or S, or a mixture of R and S.

In accordance with such an embodiment, appropriate starting materials for the methods of the present disclosure for the preparation of compounds or derivatives having formula (VI), or salts, solvates, or prodrugs thereof, include compounds or derivatives having formula (3), or salts thereof:

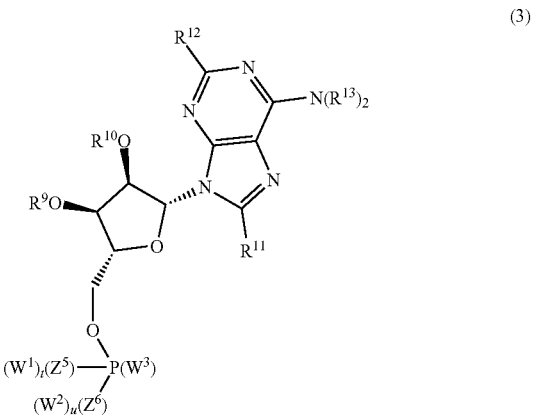

(3)

wherein each $W^1$ and $W^2$ is independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—$CO_2$$R^C$, —N($R^A$)—$CO_2$$R^B$, —CH—($R^A$)—$NH_2$, and —CH—($R^A$)—$CO_2$$R^B$; wherein the substituted ($C_1$-$C_8$)alkyl, substituted ($C_1$-$C_8$)cycloalkyl, substituted aryl, substituted heteroaryl, substituted heterocycle, and substituted amino are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C$, —O$R^C$, —OC(O)($C_1$-$C_6$)alkyl, —OC (O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C_2$, —S$R^C$, —S(O) $R^C$, —$SO_2$$R^C$, —O$SO_2$($C_1$-$C_6$)alkyl, —$SO_2$N$R^C_2$, —($C_1$-$C_6$)perfluoroalkyl, and —($C_1$-$C_6$)alkylene-O$R^C$;

or, alternatively, $W^1$ and $W^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC (O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$—N$R^C$$SO_2$N$R^C_2$, —S$R^C$, —S(O)$R^C$, —$SO_2$$R^C$, —O$SO_2$($C_1$-$C_6$)alkyl, —$SO_2$N$R^C_2$, —($C_1$-$C_6$) perfluoroalkyl, and —($C_1$-$C_6$)alkylene-O$R^C$;

optionally wherein $W^3$ is oxygen, sulfur, or absent;
each of $Z^5$ and $Z^6$ is independently nitrogen or oxygen;
t is 1 or 2;
u is 1 or 2;
$R^9$ and $R^{10}$ are independently selected from the group consisting of hydrogen, —C(O)R', —C(O)OR', —C(O) NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)

alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$—$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B_2$, —C(=$NR^B$)$NR^B_2$, —O$R^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$NR^B_2$, —$NR^B$C(O)$R^B$, —$NR^B$C(O)O($C_1$-$C_6$)alkyl, —$NR^B$C(O)$NR^B_2$, —$NR^B$$SO_2$$NR^B_2$, —$SR^B$, —S(O)$R^B$, —$SO_2R^B$, —$OSO_2$($C_1$-$C_6$)alkyl, —$SO_2NR^B_2$, —($C_1$-$C_6$)perfluoroalkyl, and —($C_1$-$C_6$)alkylene-$OR^B$;

$R^{11}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$R^{12}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

each $R^{13}$ is independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

provided that the absolute configuration of C** is R or S, or a mixture of R and S.

In an embodiment, a method of making a compound or derivative having formula (VI), or a salt, solvate, or prodrug thereof, can include the steps of:

(a) providing a compound or derivative having formula (V), or a salt, solvate, or prodrug thereof, (b) treating the compound or derivative having formula (V), or salt, solvate, or prodrug thereof, with a compound or derivative having formula (3), or a salt thereof, and a reagent selected from the group consisting of a ($1<x\leq10$) molar equivalent amount of a carbodiimide reagent, a ($0<x\leq10$) molar equivalent amount of an amine, and a ($0<x\leq10$) molar equivalent of a Brønsted acid, in the presence of water or an organic solvent co-reagent in an amount of up to 10 molar equivalents; (c) processing the compound or derivative having formula (V), or salt, solvate, or prodrug thereof, the compound or derivative having formula (3), or salt thereof, the reagent, and the water or organic solvent co-reagent, so as to produce the compound or derivative having formula (VI), or salt, solvate, or prodrug thereof; (d) adding, optionally, the compound or derivative having formula (V), or salt, solvate, or prodrug thereof, optionally, the compound or derivative having formula (3), or salt thereof, optionally, the reagent, the water or organic solvent co-reagent, and the compound or derivative having formula (VI), or salt, solvate, or prodrug thereof, to iced water; and (e) isolating the compound or derivative having formula (VI), or salt, solvate, or prodrug thereof.

In an alternative embodiment of the above method of making a compound or derivative having formula (VI), or a salt, solvate, or prodrug thereof, the method can further include the step of:

(e1) treating the compound or derivative having formula (VI), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$; wherein the step (e1) is performed following step (e).

In yet another alternative embodiment of the above method of making a compound or derivative having formula (VI), or a salt, solvate, or prodrug thereof, the compound or derivative having formula (V), or salt, solvate, or prodrug thereof, compound or derivative having formula (3), or salt thereof, the reagent, and water or organic solvent co-reagent can further be treated with at least a catalytic amount of a divalent metal salt in step (b).

Processing can be carried out under batch processing conditions or by continuously processing. Continuously processing may include one or more methods of agitation selected from the group consisting of continuous grinding and extruding. The process described herein effects a preparation of a compound or derivative having formula (VI), or salt, solvate, or prodrug thereof, under almost solventless conditions.

The polar organic solvent co-reagent employed in the above method of making a compound or derivative having formula (VI), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, the present disclosure provides a crystalline NR methanolate Form II of nicotinamide riboside chloride according to formula (VII):

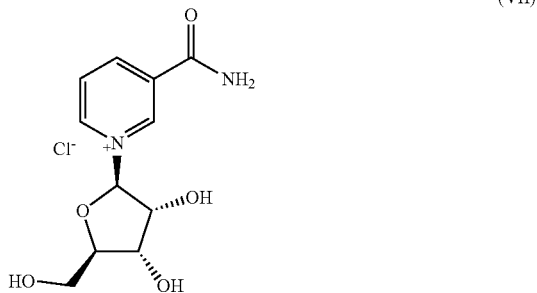

(VII)

In another embodiment, the crystalline NR methanolate Form II can be characterized by a powder X-ray diffraction pattern having peaks at 23.7, 24.5, and 25.4 degrees two theta±0.2 degrees two theta. In yet another embodiment, the crystalline NR methanolate Form II can be characterized by a powder X-ray diffraction pattern having peaks at 12.9, 23.7, 24.5, and 25.4 degrees two theta±0.2 degrees two theta. In yet another embodiment, the crystalline NR methanolate Form II can be characterized by a powder X-ray diffraction pattern having peaks at 12.9, 13.9, 14.8, 23.7, 24.5, and 25.4 degrees two theta±0.2 degrees two theta. In yet another embodiment, the crystalline NR methanolate Form II can be characterized by a powder X-ray diffraction pattern substantially as shown in FIG. 16. In yet another embodiment, the crystalline NR methanolate Form II can be characterized by a powder X-ray diffraction pattern having peaks substantially as provided in Table 7±0.2 degrees two theta.

In yet another embodiment, the crystalline NR methanolate Form II can be characterized by an IR spectrum having peaks at 565.1, 611.3, 638.3, and 680.8 cm$^{-1}$ 0.2 cm$^{-1}$. In yet another embodiment, the crystalline NR methanolate Form II can be characterized by an IR spectrum having peaks at 565.1, 611.3, 638.3, 680.8, 981.6, 1004.8, 1026.0, 1060.7, 1078.0, and 1097.3 cm$^{-1}$ 0.2 cm$^{-1}$. In yet another embodiment, the crystalline NR methanolate Form II can be characterized by an IR spectrum having peaks at 565.1, 611.3, 680.8, 981.6, 1004.8, 1026.0, 1060.7, 1078.0, 1097.3, 1400.1, 1621.9, 1648.9, and 1700.9 cm$^{-1}$±0.2 cm$^{-1}$. In yet another embodiment, the crystalline NR methanolate Form II can be characterized by an IR spectrum substantially as shown in FIG. 22. In yet another embodiment, the crystalline NR methanolate Form II can be characterized by an IR spectrum having peaks substantially as provided in Table 8±0.2 cm$^{-1}$.

In yet another embodiment, the crystalline NR methanolate Form II can be characterized by a DSC thermogram substantially as shown in FIG. 30. In yet another embodiment, the crystalline NR methanolate Form II can be characterized by a DSC thermogram obtained using a heating rate of 10 K/min comprising an endothermic event with an onset temperature of 125° C.±2° C. In yet another embodiment, the crystalline NR methanolate Form II can be characterized by a DSC thermogram obtained using a heating rate of 10 K/min comprising an endothermic event with a peak temperature of 132° C.±2° C. In yet another embodiment, the crystalline NR methanolate Form II can be characterized by a DSC thermogram obtained using a heating rate of 10 K/min comprising an endothermic event with an onset temperature of 125° C.±2° C. and a peak temperature of 132° C.±2° C.

In an embodiment, the crystalline NR methanolate Form II can be prepared by a method that can include the steps of:

(a) adding a volume of methanol and water in a 95:5 weight:weight ratio to the compound or derivative having formula (VII), or salt or solvate thereof, at room temperature, so as to dissolve approximately 15% of the compound or derivative having formula (VII), or salt or solvate thereof, in the volume of methanol and water; (b) stirring the compound or derivative having formula (VII), or salt or solvate thereof, at 50° C. until all of the compound or derivative having formula (VII), or salt or solvate thereof, apparently dissolves in the volume of methanol and water; (c) cooling the solution of the compound or derivative having formula (VII), or salt or solvate thereof, in the volume of methanol and water, to −10° C. with stirring so as to precipitate the crystalline NR methanolate Form II; (d)

isolating the crystalline NR methanolate Form II; and (e) drying the crystalline NR methanolate Form II.

In an alternative embodiment of the above method of preparing crystalline NR methanolate Form II, the method can further include the steps of:

(a1) providing a compound or derivative having formula (Ia), or salt or solvate thereof:

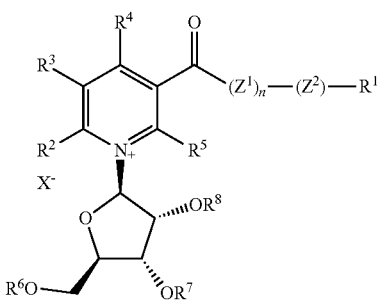

(Ia)

optionally wherein $X^-$ as counterion is absent, or when $X^-$ is present, $X^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

$Z^2$ is NH;

n is 0;

$R^1$ is hydrogen;

each of $R^2$, $R^3$, $R^4$, and $R^5$ is hydrogen;

each of $R^6$, $R^7$, and $R^8$ is —C(O)R';

R' is methyl;

optionally in a particular anomeric ratio (alpha/beta);

(a2) treating the compound or derivative having formula (Ia), or salt or solvate thereof, with a molar equivalent amount of an alcohol and at least a sub-molar equivalent amount of a Brønsted inorganic base; (a3) processing the compound or derivative having formula (Ia), or salt or solvate thereof, the alcohol, and the Brønsted inorganic base so as to produce the compound or derivative having formula (VII), or salt or solvate thereof; (a4) neutralizing the Brønsted inorganic base using a concentrated acid solution; and (a5) isolating the compound or derivative having formula (VII), or salt or solvate thereof, wherein the steps (a1) to (a5) are performed sequentially, before step (a).

Processing can be carried out under batch processing conditions or by continuously processing. Continuously processing may include one or more methods of agitation selected from the group consisting of liquid-assisted mixing, milling, and extruding.

In another alternative embodiment of the above method of preparing crystalline NR methanolate Form II, the method can further include the steps of:

(a1) providing a compound or derivative having formula (Ia), or salt or solvate thereof:

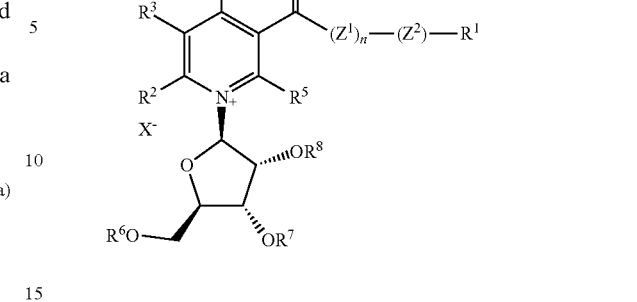

(Ia)

optionally wherein $X^-$ as counterion is absent, or when $X^-$ is present, $X^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

$Z^2$ is NH;

n is 0;

$R^1$ is hydrogen;

each of $R^2$, $R^3$, $R^4$, and $R^5$ is hydrogen;

each of $R^6$, $R^7$, and $R^8$ is —C(O)R';

R' is methyl;

optionally in a particular anomeric ratio (alpha/beta);

(a2) treating the compound or derivative having formula (Ia), or salt or solvate thereof, with a (3<x<100) molar equivalent amount of an alcohol and a (x≤20) molar equivalent amounts of a Brønsted inorganic acid; (a3) processing, under sealed conditions, the compound or derivative having formula (Ia), or salt or solvate thereof, the alcohol, and the Brønsted inorganic acid so as to produce the compound or derivative having formula (VII), or salt or solvate thereof, and (a4) isolating the precipitated compound or derivative having formula (VII), or salt or solvate thereof; wherein the steps (a1) to (a4) are performed sequentially, before step (a).

Processing can be carried out under batch processing conditions or by continuously processing. Continuously processing may include one or more methods of agitation selected from the group consisting of liquid-assisted mixing, milling, and extruding.

In yet another alternative embodiment of the above method of preparing crystalline NR methanolate Form II, the method can further include the step of:

(a3a) neutralizing the Brønsted inorganic acid with a concentrated basic solution under controlled conditions; wherein the step (a3a) is performed following step (a3).

In yet another alternative embodiment of the above method of preparing crystalline NR methanolate Form II, the method can further include the steps of:

(a1) providing a compound or derivative having formula (Ia), or salt or solvate thereof:

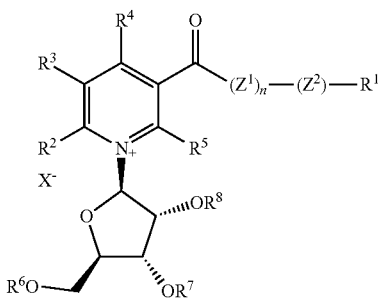

(Ia)

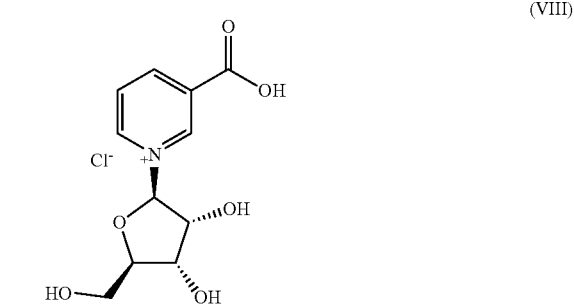 [SMILES: O=C(O)c1ccc[n+]([C@@H]2O[C@H](CO)[C@@H](O)[C@H]2O)c1 ; [Cl-]]

(VIII)

optionally wherein X⁻ as counterion is absent, or when X⁻ is present, X⁻ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

$Z^2$ is NH;

n is 0;

$R^1$ is hydrogen;

each of $R^2$, $R^3$, $R^4$, and $R^5$ is hydrogen;

each of $R^6$, $R^7$, and $R^8$ is —C(O)R';

R' is methyl;

optionally in a particular anomeric ratio (alpha/beta);

(a2) treating the compound or derivative having formula (Ia), or salt or solvate thereof, with a (3<x<100) molar equivalent amount of an alcohol and a (3≤x<20) molar equivalent amount of an acyl chloride; (a3) processing, under sealed conditions, the compound or derivative having formula (Ia), or salt or solvate thereof, the alcohol, and the acyl chloride so as to produce the compound or derivative having formula (VII), or salt or solvate thereof; and (a4) isolating the precipitated compound or derivative having formula (VII), or salt or solvate thereof; wherein the steps (a1) to (a4) are performed sequentially, before step (a).

Processing can be carried out under batch processing conditions or by continuously processing. Continuously processing may include one or more methods of agitation selected from the group consisting of liquid-assisted mixing, milling, and extruding.

In yet another alternative embodiment of the above method of preparing crystalline NR methanolate Form II, the method can further include the step of:

(a3a) adding a concentrated basic solution, under controlled conditions, to, optionally, the compound or derivative having formula (Ia), or salt or solvate thereof, the alcohol, the acyl chloride, and the compound or derivative having formula (VII), or salt or solvate thereof, wherein the step (a3a) is performed following step (a3).

In yet another alternative embodiment of the above method of making a crystalline form of a compound or derivative having formula (I), or a salt, solvate, or prodrug thereof, wherein $R^6$, $R^7$, and $R^8$ are each hydrogen, the crystalline form of the compound or derivative having formula (I), or salt, solvate, or prodrug thereof, wherein $R^6$, $R^7$, and $R^8$ are each hydrogen can be a crystalline Form I of nicotinic acid riboside according to formula (VIII):

In yet another alternative embodiment of the above method, the crystalline Form I can be characterized by a powder X-ray diffraction pattern having peaks at 12.8, 13.2, 15.7, 19.2, 20.5, 21.6, 26.4, 28.3, and 28.9 degrees two theta±0.2 degrees two theta. In yet another alternative embodiment of the above method, the crystalline Form I can be characterized by a powder X-ray diffraction pattern having peaks substantially as provided in Table 4±0.2 degrees two theta.

In yet another alternative embodiment of the above method, the crystalline Form I can be characterized by an IR spectrum having peaks at 534.2, 680.8, 754.0, and 773.3 cm⁻¹ 0.2 cm⁻¹.

In yet another alternative embodiment of the above method, the crystalline Form I can be characterized by an IR spectrum having peaks at 534.2, 680.8, 754.0, 773.3, 1087.7, 1114.7, and 1359.6 cm⁻¹±0.2 cm⁻¹. In yet another alternative embodiment of the above method, the crystalline Form I can be characterized by an IR spectrum having peaks at 534.2, 680.8, 754.0, 773.3, 1087.7, 1114.7, 1359.6, 1579.4, 1612.2, and 1639.2 cm⁻¹ cm⁻¹. In yet another alternative embodiment of the above method, the crystalline Form I can be characterized by an IR spectrum substantially as shown in FIG. 23. In yet another alternative embodiment of the above method, the crystalline Form I can be characterized by an IR spectrum having peaks substantially as provided in Table 5±0.2 cm⁻¹.

In yet another alternative embodiment of the above method, the crystalline Form I can be characterized by a DSC thermogram substantially as shown in FIG. 32. In yet another alternative embodiment of the above method, the crystalline Form I can be characterized by a DSC thermogram obtained using a heating rate of 10 K/min comprising an endothermic vent with an onset temperature of 156° C.±2° C. In yet another alternative embodiment of the above method, the crystalline Form I can be characterized by a DSC thermogram obtained using a heating rate of 10 K/min comprising an endothermic event with a peak temperature of 164° C.±2° C. In yet another alternative embodiment of the above method, the crystalline Form I can be characterized by a DSC thermogram obtained using a heating rate of 10 K/min comprising an endothermic event with an onset temperature of 156° C.±2° C. and a peak temperature of 164° C.±2° C.

In yet another alternative embodiment of the above method of making a compound or derivative having formula (I), or a salt, solvate, or prodrug thereof, the compound or derivative having formula (I), or salt, solvate, or prodrug thereof is nicotinamide riboside triacetate (NRTA) chloride, having formula (IX):

(IX)

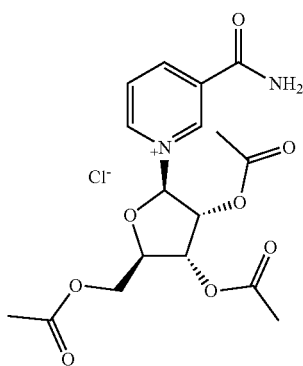

In yet another alternative embodiment of the above method, the nicotinamide riboside triacetate (NRTA) can be crystalline Form I. In yet another alternative embodiment of the above method, the crystalline Form I can be characterized by a powder X-ray diffraction pattern having peaks at 9.8, 14.5, 18.6, 19.2, 19.6, 22.1, 22.5, and 26.6 degrees two theta±0.2 degrees two theta. In yet another alternative embodiment of the above method, the crystalline Form I can be characterized by a powder X-ray diffraction pattern having peaks substantially as provided in Table 2±0.2 degrees two theta.

In yet another alternative embodiment of the above method, the crystalline Form I can be characterized by an IR spectrum having peaks at 626.8, 644.1, and 916.0 cm$^{-1}$ 0.2 cm$^{-1}$. In yet another alternative embodiment of the above method, the crystalline Form I can be characterized by an IR spectrum having peaks at 626.8, 644.1, 916.0, 1058.8, 1101.2, and 1114.7 cm$^{-1}$±0.2 cm$^{-1}$. In yet another alternative embodiment of the above method, the crystalline Form I can be characterized by an IR spectrum having peaks at 626.8, 644.1, 916.0, 1058.8, 1101.2, 1114.7, 1205.3, 1240.0, 1683.6, and 1737.6 cm$^{-1}$ cm$^{-1}$. In yet another alternative embodiment of the above method, the crystalline Form I can be characterized by an IR spectrum substantially as shown in FIG. 24. In yet another alternative embodiment of the above method, the crystalline Form I can be characterized by an IR spectrum having peaks substantially as provided in Table 3 cm$^{-1}$.

In yet another alternative embodiment of the above method, the crystalline Form I can be characterized by a DSC thermogram substantially as shown in FIG. 31. In yet another alternative embodiment of the above method, the crystalline Form I can be characterized by a DSC thermogram obtained using a heating rate of 10 K/min comprising an endothermic event with an onset temperature of 149° C.±2° C. In yet another alternative embodiment of the above method, the crystalline Form I can be characterized by a DSC thermogram obtained using a heating rate of 10 K/min comprising an endothermic event with a peak temperature of 156° C.±2° C. In yet another alternative embodiment, the crystalline Form I can be characterized by a DSC thermogram obtained using a heating rate of 10 K/min comprising an endothermic event with an onset temperature of 149° C.±2° C. and a peak temperature of 156° C.±2° C. In yet another alternative embodiment, the crystalline Form I can be characterized by a DSC thermogram obtained using a heating rate of 10 K/min comprising an endothermic event with an onset temperature of 208° C.±2° C. In yet another alternative embodiment, the crystalline Form I can be characterized by a DSC thermogram obtained using a heating rate of 10 K/min comprising an endothermic event with a peak temperature of 215° C.±2° C. In yet another alternative embodiment, the crystalline Form I can be characterized by a DSC thermogram obtained using a heating rate of 10 K/min comprising an endothermic event with an onset temperature of 208° C.±2° C. and a peak temperature of 215° C.±2° C. In yet another alternative embodiment, the crystalline Form I can be characterized by a DSC thermogram obtained using a heating rate of 10 K/min comprising an endothermic event with an onset temperature of 149° C.±2° C. and a peak temperature of 156° C.±2° C. and an endothermic event with an onset temperature of 208° C.±2° C. and a peak temperature of 215° C.±2° C.

In yet another alternative embodiment of the above method of making a compound or derivative having formula (I), or salt, solvate, or prodrug thereof, the method can further include the steps of:

(d1) adding a volume of methanol and water in a 95:5 weight:weight ratio to the compound or derivative having formula (IX), at room temperature, so as to dissolve approximately 15% of the compound or derivative having formula (IX), in the volume of methanol and water; (d2) stirring the compound or derivative having formula (IX), at 50° C. until all of the compound or derivative having formula (IX) apparently dissolves in the volume of methanol and water; (d3) cooling the solution of the compound or derivative having formula (IX), in the volume of methanol and water, to −10° C. with stirring so as to precipitate the crystalline Form I; (d4) isolating the crystalline Form I; and (d5) drying the crystalline Form I; wherein steps (d1) to (d5) are performed sequentially, following step (d).

In an embodiment, the present disclosure provides a crystalline Form I of nicotinic acid riboside triacetate (NARTA), according to formula (X):

(X)

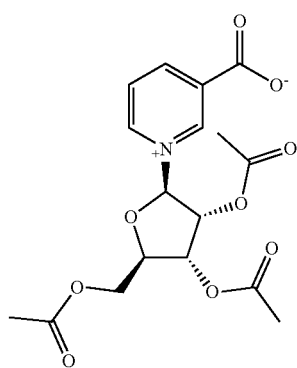

In another embodiment, the crystalline Form I can be characterized by a powder X-ray diffraction pattern having peaks at 4.7, 9.5, and 20.5 degrees two theta±0.2 degrees two theta. In yet another embodiment, the crystalline Form I can be characterized by a powder X-ray diffraction pattern having peaks at 4.7, 9.5, 16.5, 16.8, and 20.5 degrees two theta±0.2 degrees two theta. In yet another embodiment, the crystalline Form I can be characterized by a powder X-ray diffraction pattern having peaks at 4.7, 9.5, 12.0, 16.5, 16.8, 19.9, 20.5, 23.7, and 23.9 degrees two theta±0.2 degrees two theta. In yet another embodiment, the crystalline Form I can be characterized by a powder X-ray diffraction pattern substantially as shown in FIG. 19. In yet another embodiment, the crystalline Form I can be characterized by a powder X-ray diffraction pattern having peaks substantially as provided in Table 9±0.2 degrees two theta.

In yet another embodiment, the crystalline Form I can be characterized by an IR spectrum having peaks at 603.6, 684.6, 763.7, and 781.0 cm$^{-1}$ 0.2 cm$^{-1}$. In yet another embodiment, the crystalline Form I can be characterized by an IR spectrum having peaks at 603.6, 684.6, 763.7, 781.0, 858.2, 894.8, 921.8, 1026.0, 1051.0, and 1066.5 cm$^{-1}$±0.2 cm$^{-1}$. In yet another embodiment, the crystalline Form I can be characterized by an IR spectrum having peaks at 603.6, 684.6, 763.7, 781.0, 858.2, 894.8, 921.8, 1026.0, 1051.0, 1066.5, 1610.3, 1639.2, and 1743.4 cm$^{-1}$±0.2 cm$^{-1}$. In yet another embodiment, the crystalline Form I can be characterized by an IR spectrum substantially as shown in FIG. 25. In yet another embodiment, the crystalline Form I can be characterized by an IR spectrum having peaks substantially as provided in Table 10±0.2 cm$^{-1}$.

In yet another embodiment, the crystalline Form I can be characterized by a DSC thermogram substantially as shown in FIG. 33. In yet another embodiment, the crystalline Form I can be characterized by a DSC thermogram obtained using a heating rate of 10 K/min comprising an endothermic event with an onset temperature of 148° C.±2° C. In yet another embodiment, the crystalline Form I can be characterized by a DSC thermogram obtained using a heating rate of 10 K/min comprising an endothermic event with a peak temperature of 152° C.±2° C. In yet another embodiment, the crystalline Form I can be characterized by a DSC thermogram obtained using a heating rate of 10 K/min comprising an endothermic event with an onset temperature of 148° C.±2° C. and a peak temperature of 152° C.±2° C.

In yet another embodiment, the crystalline Form I can be prepared by a method that can include the steps of:

(a) adding a volume of acetonitrile to the compound or derivative having formula (IX), or a salt or solvate thereof, at room temperature, so as to dissolve the compound or derivative having formula (IX), or salt or solvate thereof, in the volume of acetonitrile; (b) adding a volume of acetone, which is at least equal in volume to the volume of acetonitrile, to the solution of the compound or derivative having formula (IX), or salt or solvate thereof, in the volume of acetonitrile so as to precipitate the crystalline Form I; and (c) isolating the crystalline Form I.

In yet another embodiment, the crystalline Form I can be prepared by a method that can further include the steps of:

(a) providing a compound or derivative having formula (1a), or a salt thereof:

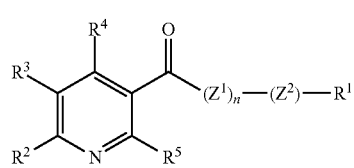

(1a)

wherein $Z^2$ is oxygen;
n is 0;
$R^1$ is hydrogen;
wherein the compound or derivative having formula (1a) may optionally take the form of the carboxylate anion conjugate base species of the compound or derivative having formula (1a), further optionally associated with a positively charged counterion selected from the group consisting of calcium, magnesium, potassium, sodium, zinc, and ammonium cations;
each of $R^2$, $R^3$, $R^4$, and $R^5$ is hydrogen;

(a2) treating the compound or derivative having formula (1a), or salt thereof, with excess trimethylsilylating reagent(s) so as to produce a compound or derivative having formula (1a), or salt thereof, wherein $R^1$ is a TMS group; (a3) removing the trimethylsilylating reagent(s); (a4) treating the compound or derivative having formula (1a), or salt thereof, wherein $R^1$ is a TMS group, with a molar equivalent amount of a compound or derivative having formula (2), or a salt thereof, in an organic solvent co-reagent;

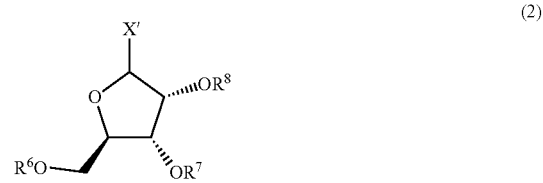

(2)

wherein X' is selected from the group consisting of fluoro, chloro, bromo, iodo, $HCO_2$, acetoxy, propionoxy, butyroxy, glutamyloxy, aspartyloxy, ascorbyloxy, benzoxy, $HOCO_2$, citryloxy, carbamyloxy, gluconyloxy, lactyloxy, succinyloxy, sulfoxy, trifluoromethanesulfoxy, trichloromethanesulfoxy, tribromomethanesulfoxy, and trifluoroacetoxy;

each of $R^6$, $R^7$, and $R^8$ is —C(O)R';

R' is methyl;

(a5) processing the compound or derivative having formula (1a), or salt thereof, wherein $R^1$ is a TMS group, the compound or derivative having formula (2), or salt thereof, and the organic solvent co-reagent so as to produce the compound or derivative having formula (Ia), or salt or solvate thereof, wherein $R^1$ is a TMS group, optionally produced in a particular anomeric ratio (alpha/beta); (a6) adding water to, optionally, the compound or derivative having formula (1a), or salt thereof, wherein $R^1$ is a TMS group, optionally, the compound or derivative having formula (2), or salt thereof, the organic solvent co-reagent, and the compound or derivative having formula (Ia), or salt or solvate thereof, wherein $R^1$ is a TMS group, optionally produced in a particular anomeric ratio (alpha/beta); (a7) adjusting the pH of the aqueous phase; (a8) separating the organic phase from the aqueous phase); and (a9) freeze-drying the aqueous phase to provide the compound or derivative having formula (Ia), or salt or solvate thereof, optionally in a particular anomeric ratio (alpha/beta); wherein steps (a1) to (a9) are performed sequentially, before step (a).

In yet another embodiment of the above method, the compound or derivative having formula (1a), or salt thereof, wherein $R^1$ is a TMS group, the compound or derivative having formula (2), or salt thereof, and the organic solvent co-reagent are further treated with a Lewis acid in step (a4).

In yet another alternative embodiment of the above method of making a compound or derivative having formula (II), or a salt, solvate, or prodrug thereof, the compound or derivative having formula (II), or salt, solvate, or prodrug thereof can be nicotinamide mononucleotide (NMN), having formula (XI):

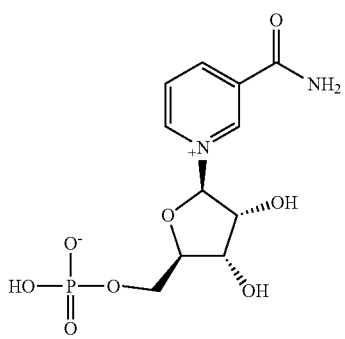

(XI)

In yet another alternative embodiment of the above method, the nicotinamide mononucleotide (NMN) can be crystalline Form III. In yet another alternative embodiment of the above method, the crystalline Form III can be characterized by a powder X-ray diffraction pattern having peaks at 7.9, 15.6, 17.2, 17.9, 21.3, 21.9, 22.9, 24.8, 25.2, and 28.0 degrees two theta±0.2 degrees two theta. In yet another alternative embodiment of the above method, the crystalline Form III can be characterized by a powder X-ray diffraction pattern substantially as shown in FIG. 20. In yet another alternative embodiment of the above method, the crystalline Form III is characterized by a powder X-ray diffraction pattern having peaks substantially as provided in Table 13±0.2 degrees two theta.

In yet another alternative embodiment of the above method, the crystalline Form III can be characterized by an IR spectrum having peaks at 624.8, 626.8, 671.1, 802.3, and 906.4 cm$^{-1}$±0.2 cm$^{-1}$. In yet another alternative embodiment of the above method, the crystalline Form III can be characterized by an IR spectrum having peaks at 624.8, 626.8, 671.1, 802.3, 906.4, 923.8, 952.7, 985.5, 1035.6, 1078.0, 1147.5, and 1182.2 cm$^{-1}$±0.2 cm$^{-1}$. In yet another alternative embodiment of the above method, the crystalline Form III can be characterized by an IR spectrum having peaks at 624.8, 626.8, 671.1, 802.3, 906.4, 923.8, 952.7, 985.5, 1035.6, 1078.0, 1147.5, 1182.2, 1409.7, 1619.9, and 1689.4 cm$^{-1}$±0.2 cm$^{-1}$. In yet another alternative embodiment of the above method, the crystalline Form III can be characterized by an IR spectrum substantially as shown in FIG. 26. In yet another alternative embodiment of the above method, the crystalline Form III can be characterized by an IR spectrum having peaks substantially as provided in Table 14±0.2 cm$^{-1}$.

In yet another alternative embodiment of the above method, the crystalline Form III can be characterized by a DSC thermogram substantially as shown in FIG. 35. In yet another alternative embodiment of the above method, the crystalline Form III can be characterized by a DSC thermogram obtained using a heating rate of 10 K/min comprising an endothermic event with an onset temperature of 105° C.±2° C. In yet another alternative embodiment of the above method, the crystalline Form III can be characterized by a DSC thermogram obtained using a heating rate of 10 K/min comprising an endothermic event with a peak temperature of 157° C.±2° C. In yet another alternative embodiment of the above method, the crystalline Form III can be characterized by a DSC thermogram obtained using a heating rate of 10 K/min comprising an endothermic event with an onset temperature of 105° C.±2° C. and a peak temperature of 157° C.±2° C.

In yet another alternative embodiment of the above method, the method can further include the steps of:
(e1) adding the compound or derivative having formula (XI) to a volume of methanol and water in a 3:2 volume:volume ratio at room temperature; (e2) stirring the compound or derivative having formula (XI) and the volume of methanol and water so as to dissolve the compound or derivative having formula (XI) in the volume of methanol and water; (e3) filtering the solution of the compound or derivative having formula (XI), in the volume of methanol and water, so as to remove any undissolved solids; (e4) adding a volume of acetone to the solution of the compound or derivative having formula (XI), in the volume of methanol and water, wherein the volume of acetone is about 2 to about 5 times the combined volume of methanol and water; (e5) cooling the compound or derivative having formula (XI), in the volume of acetone and the volume of methanol and water, to −20° C. so as to precipitate the crystalline Form III; (e6) isolating the crystalline Form III; and (e7) drying the crystalline Form III at room temperature; wherein the steps (e1) to (e7) are performed sequentially, following step (e).

In yet another alternative embodiment of the above method, the nicotinamide mononucleotide (NMN) can be crystalline Form IV. In yet another alternative embodiment of the above method, the crystalline Form IV can be characterized by a powder X-ray diffraction pattern having peaks at 9.6, 16.2, 16.5, 17.4, 18.9, 19.9, 22.0, 22.8, 25.3, 25.6, 27.1, and 28.7 degrees two theta±0.2 degrees two theta. In yet another alternative embodiment of the above method, the crystalline Form IV can be characterized by a powder X-ray diffraction pattern substantially as shown in FIG. 28. In yet another alternative embodiment of the above method, the crystalline Form IV can be characterized by a powder X-ray diffraction pattern substantially as shown in Table 15±0.2 degrees two theta.

In yet another alternative embodiment of the above method, the crystalline Form IV can be characterized by an IR spectrum having peaks at 624.8, 640.3, 665.3, 725.1, 813.8, and 840.8 cm$^{-1}$ 0.2 cm$^{-1}$. In yet another alternative embodiment of the above method, the crystalline Form IV can be characterized by an IR spectrum having peaks at 624.8, 640.3, 665.3, 725.1, 813.8, 840.8, 867.8, 921.8, 948.8, 985.8, 1029.8, and 1076.1 cm$^{-1}$±0.2 cm$^{-1}$. In yet another alternative embodiment of the above method, the crystalline Form IV can be characterized by an IR spectrum having peaks at 624.8, 640.3, 665.3, 725.1, 813.8, 840.8, 867.8, 921.8, 948.8, 985.5, 1029.8, 1076.1, 1625.7, 1646.9, and 1687.4 cm$^{-1}$±0.2 cm$^{-1}$. In yet another alternative embodiment of the above method, the crystalline Form IV can be characterized by an IR spectrum substantially as shown in FIG. 29. In yet another alternative embodiment of the above method, the crystalline Form IV can be characterized by an IR spectrum substantially as provided in Table 16±0.2 cm$^{-1}$.

In yet another alternative embodiment of the above method, the crystalline Form IV is characterized by a DSC thermogram substantially as shown in FIG. 36. In yet another alternative embodiment of the above method, the crystalline Form IV can be characterized by a DSC thermogram obtained using a heating rate of 10 K/min comprising an endothermic event with an onset temperature of 144° C.±2° C. In yet another alternative embodiment of the above method, the crystalline Form IV can be characterized by a DSC thermogram obtained using a heating rate of 10 K/min comprising an endothermic event with a peak temperature of 165° C.±2° C. In yet another alternative embodiment of the above method, the crystalline Form IV can be characterized by a DSC thermogram obtained using a heating rate of 10 K/min comprising an endothermic event with an onset temperature of 144° C.±2° C. and a peak temperature of 165° C.±2° C.

In yet another alternative embodiment of the above method of making a compound or derivative having formula (II), or a salt, solvate, or prodrug thereof, the method can further include the steps of: (e1) adding the compound or derivative having formula (XI) to a volume of ethanol and water in a 3:2 volume:volume ratio at room temperature, wherein the compound or derivative having formula (XI) is added in an amount of about 200 milligrams per milliliter of the volume of ethanol and water; (e2) stirring the compound or derivative having formula (XI), and the volume of ethanol and water, so as to dissolve the compound or derivative having formula (XI) in the volume of ethanol and water; (e3) filtering the solution of the compound or derivative having formula (XI), in the volume of ethanol and water, so as to remove any undissolved solids; (e4) cooling the compound or derivative having formula (XI), in the volume of ethanol and water, to −10° C. for about 48 hours; (e5) isolating the crystalline Form IV; and (e6) drying the crystalline Form IV at room temperature; wherein the steps (e1) to (e6) are performed sequentially, following step (e).

In yet another embodiment of the above method of making a compound or derivative having formula (I-H), or salt, solvate, or prodrug thereof, the compound or derivative having formula (I-H), or salt, solvate, or prodrug thereof, can be nicotinamide riboside (NR) chloride, having formula (VII):

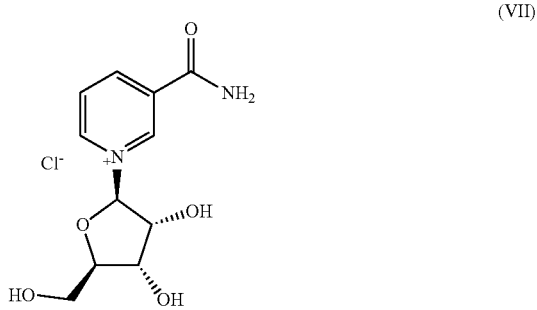 [SMILES: NC(=O)c1ccc[n+]([C@@H]2O[C@H](CO)[C@@H](O)[C@H]2O)c1 ; [Cl-]]

(VII)

In yet another alternative embodiment of the above method of making a compound or derivative having formula (I-H), or a salt, solvate, or prodrug thereof, the reagent of step (b) can be Brønsted inorganic acid. In yet another alternative embodiment of the above method, the Brønsted inorganic acid can be at least three molar equivalents of HCl in methanol at about 5° C. In yet another alternative embodiment of the above method, the acetamide content in the nicotinamide riboside (NR) chloride can be less than 10 ppm as measured by gas chromatography. In yet another alternative embodiment of the above method, the acetamide content in the nicotinamide riboside (NR) chloride can be less than 5 ppm as measured by gas chromatography.

DETAILED DESCRIPTION

Figure 1:
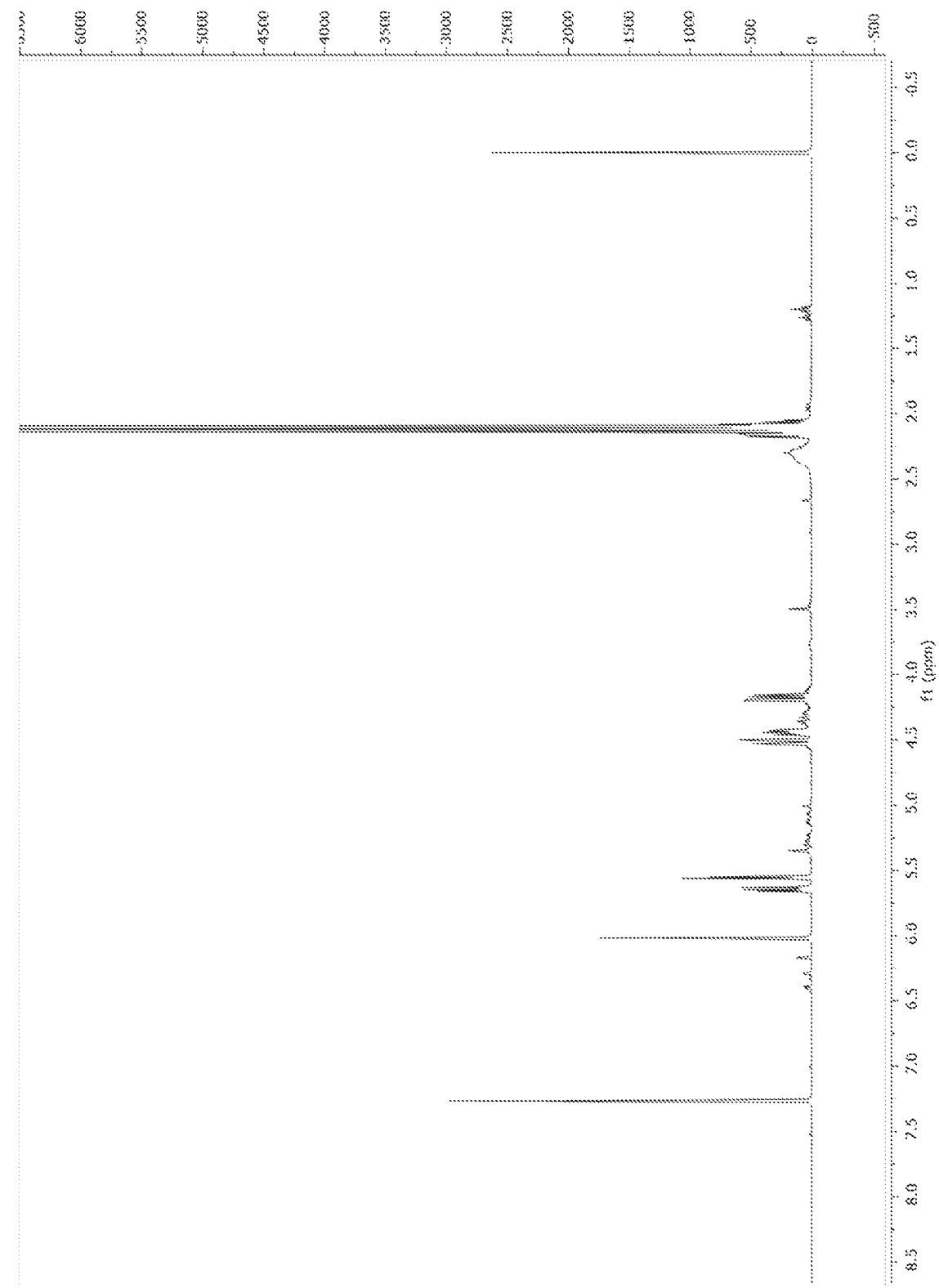
FIG. 1 depicts a $^1$H NMR spectrum of the reaction product mixture for the procedure described in Example 1, Part A, performed in accordance with one embodiment of the described method for the preparation of a compound or derivative having general formula (2) or a salt thereof.

In an embodiment, the present disclosure relates to a synthetic sequence that enables the efficient production of nicotinoyl ribosides, the triacetates thereof, phosphorylated analogs thereof, and adenylyl dinucleotide conjugates thereof, or salts, solvates, or prodrugs thereof, via processes that are enabled by the processing of reagents by liquid-assisted mixing, grinding, milling, and/or extrusion.

In another embodiment, the present disclosure relates to a synthetic sequence that enables the efficient production of reduced nicotinoyl ribosides, the triacetates thereof, phosphorylated analogs thereof, and adenylyl dinucleotide conjugates thereof, or salts, solvates, or prodrugs thereof, via processes that are enabled by the processing of reagents by liquid-assisted mixing, grinding, milling, and/or extrusion.

In yet another embodiment, the present disclosure relates to the scalable methods of preparation of nicotinamide riboside (NR) and nicotinic acid riboside (NAR), and derivatives thereof, or salts, solvates, or prodrugs thereof, by liquid-assisted mixing, grinding, and/or extrusion.

In yet another embodiment, the present disclosure relates to the scalable methods of preparation of reduced nicotinamide riboside (NRH) and reduced nicotinic acid riboside (NARH), and derivatives thereof, or salts, solvates, or prodrugs thereof, by liquid-assisted mixing, grinding, and/or extrusion.

In yet another embodiment, the present disclosure relates to the scalable methods of preparation of reduced nicotinamide riboside triacetate (NRH-TA) and reduced nicotinic acid riboside triacetate (NARH-TA), and derivatives thereof, or salts, solvates, or prodrugs thereof, by biphasic liquid-assisted mixing, grinding, and/or extrusion.

In yet another embodiment, the present disclosure relates to the batch processes that enable the production of nicotinamide riboside (NR) and nicotinic acid riboside (NAR), or salts, solvates, or prodrugs thereof, whereby the use of solvents in kept to a minimum, and whereby conversion and reaction times are optimized by the use of sealed conditions and/or mechanochemistry, and an optimized purification sequence.

In yet another embodiment, the present disclosure relates to the batch and semi-continuous processes that enable the production of reduced nicotinamide riboside (NRH) and reduced nicotinic acid riboside (NARH), and triacetate derivatives thereof, or salts, solvates, or prodrugs thereof, wherein the use of solvents is kept to a minimum, and whereby conversion and reaction times are optimized by the use of sealed conditions, continuous liquid-liquid extraction, and/or mechanochemistry, and an optimized purification sequence.

In yet another embodiment, the present disclosure relates to crystalline forms of nicotinamide riboside (NR), including, but not limited to, a Form I of nicotinamide riboside chloride ("NR—Cl"), and methods of preparation thereof.

In yet another embodiment, the present disclosure relates to crystalline forms of nicotinamide riboside (NR), including, but not limited to, a "NR methanolate Form II" of nicotinamide riboside chloride (NR—Cl), and methods of preparation thereof.

In yet another embodiment, the present disclosure relates to crystalline forms of nicotinic acid riboside (NAR), including, but not limited to, a "Form I" of nicotinic acid riboside (NAR), and methods of preparation thereof.

In yet another embodiment, the present disclosure relates to crystalline forms of nicotinamide riboside triacetate (1-(2',3',5'-triacetyl-beta-D-ribofuranosyl)-nicotinamide, "NR triacetate," or "NRTA"), including, but not limited to, a "Form I" of nicotinamide riboside triacetate (NRTA) chloride, and methods of preparation thereof.

In yet another embodiment, the present disclosure relates to crystalline forms of nicotinic acid riboside triacetate (1-(2',3',5'-triacetyl-beta-D-ribofuranosyl)-nicotininic acid, "NAR triacetate," or "NARTA"), including, but not limited to, a "Form I" of nicotinic acid riboside triacetate (NARTA), and methods of preparation thereof.

In yet another embodiment, the present disclosure relates to crystalline forms of nicotinamide mononucleotide ("NMN"), including, but not limited to, a "Form III" of nicotinamide mononucleotide (NMN), and methods of preparation thereof. In yet another embodiment, the present disclosure relates to an amorphous solid form of nicotinamide mononucleotide (NMN), and methods of preparation thereof. In yet another embodiment, the present disclosure relates to crystalline forms of nicotinamide mononucleotide (NMN), including, but not limited to, a "Form IV" of nicotinamide mononucleotide (NMN), and methods of preparation thereof.

In yet another embodiment, the present disclosure relates to crystalline forms of compounds or derivatives having formula (III), or salts, solvates, or prodrugs thereof, and methods of preparation thereof.

In yet another embodiment, the present disclosure relates to crystalline forms of compounds or derivatives having formula (IV), or salts, solvates, or prodrugs thereof, and methods of preparation thereof.

In yet another embodiment, the present disclosure relates to crystalline forms of compounds or derivatives having formula (IV-H), or salts, solvates, or prodrugs thereof, and methods of preparation thereof.

In yet another embodiment, the present disclosure relates to crystalline forms of compounds or derivatives having formula (V), or salts, solvates, or prodrugs thereof, and methods of preparation thereof.

In yet another embodiment, the present disclosure relates to crystalline forms of compounds or derivatives having formula (VI), or salts, solvates, or prodrugs thereof, and methods of preparation thereof.

In accordance with an embodiment, the present disclosure provides a novel method whereby sealed conditions and/or mechanic forces are used to minimize solvent quantities, decrease reaction times, increase overall conversion, and facilitate product purification in a multistep synthetic sequence, whereby by-product formation is minimized, and whereby primarily by-products that can be removed readily by filtration or evaporation are generated.

Additionally, the methods of the present disclosure address limitations of existing technologies to produce compounds or derivatives such as nicotinoyl ribosides, reduced nicotinoyl ribosides, the triacetates thereof, derivatives thereof, phosphorylated analogs thereof, and adenylyl dinucleotide conjugates thereof, or salts, solvates, or prodrugs thereof.

In accordance with one embodiment, the present disclosure provides a novel method for the preparation of compounds or derivatives having formula (I), or salts, solvates, or prodrugs thereof, such as nicotinoyl ribosides and their derivatives, and including but not limited to the triacetylated forms of NR—Cl (nicotinamide riboside chloride salt form) and NAR (nicotinic acid riboside) (compounds or derivatives having formula (I), wherein $R^6$, $R^7$, and $R^8$ are each acetyl groups), and the fully deprotected forms thereof (compounds or derivatives having formula (I), wherein $R^6$, $R^7$, and $R^8$ are each hydrogens), in commercial quantities. In accordance with such an embodiment, the present disclosure provides a novel method whereby mechanic forces and/or sealed conditions are used to minimize solvent and reagent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product nicotinoyl riboside compounds include compounds or derivatives having formula (I), or salts, solvates, or prodrugs thereof:

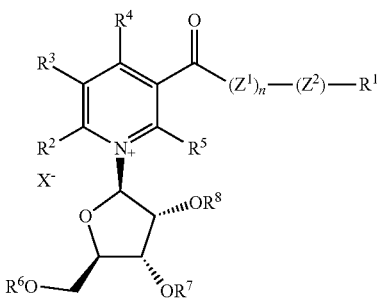
(I)

optionally wherein X⁻ as counterion is absent, or when X⁻ is present, X⁻ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when X⁻ is absent optionally the counterion is an internal salt;

optionally X⁻ is an anion of a substituted or unsubstituted carboxylic acid selected from a monocarboxylic acid, a dicarboxylic acid, or a polycarboxylic acid; and, optionally X⁻ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid, the anion of lactic acid being lactate), or a trihaloacetate selected from trichloroacetate, tribromoacetate, and trifluoroacetate; and, optionally X⁻ is an anion of an unsubstituted monocarboxylic acid selected from formic acid, acetic acid, propionic acid, or butyric acid, being formate, acetate, propionate, and butyrate, respectively; and, optionally X⁻ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally X⁻ is an anion of ascorbic acid, being ascorbate; and, optionally X⁻ is a halide selected from fluoride, chloride, bromide, or iodide; and, optionally X⁻ is an anion of a substituted or unsubstituted sulfonate, further optionally a trihalomethanesulfonate selected from trifluoromethanesulfonate, tribromomethanesulfonate, or trichloromethanesulfonate; and, optionally X⁻ is an anion of a substituted or unsubstituted carbonate, further optionally hydrogen carbonate; and, optionally X⁻ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, substituted carbonate, substituted glutathione, and substituted glutathione disulfide are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —$NR^CC(O)R^C$, —$NR^CC(O)O$($C_1$-$C_6$)alkyl, —$NR^CC(O)NR^C_2$, —$NR^CSO_2NR^C_2$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl ($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —$NR^CC(O)R^C$, —$NR^CC(O)O$($C_1$-$C_6$)alkyl, —$NR^CC(O)NR^C_2$, —$NR^CSO_2NR^C_2$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

wherein when $R^1$ is hydrogen, $Z^2$ is oxygen, and n is 0, the compound or derivative having formula (I) may optionally take the form of the carboxylate anion conjugate base species of the compound or derivative having formula (I), further optionally associated with a positively charged counterion selected from the group consisting of alkali metal, alkaline earth metal, transition metal, and base addition cations;

$R^A$ is selected from the group consisting of —H, —($C_1$-$C_6$)alkyl, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —$R^B_2$, —$NR^BC(O)R^B$, —$NR^BC(O)O$($C_1$-$C_6$)alkyl, —$NR^BC(O)NR^B_2$, —$NR^BSO_2NR^B_2$, —S$R^B$, —S(O)$R^B$, —$SO_2R^B$, —$SO_2$($C_1$-$C_6$)alkyl, —$SO_2NR^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^6$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with such an embodiment, appropriate starting materials for the methods of the present disclosure for the preparation of compounds or derivatives having formula (I), or salts, solvates, or prodrugs thereof, include compounds or derivatives having formula (1), or salts thereof:

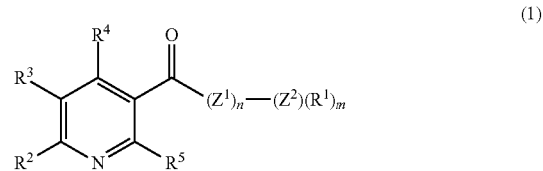

(1)

wherein each Z$^1$ and Z$^2$ is independently nitrogen or oxygen;

m is 1 or 2;

n is 0 or 1;

each R$^1$ is independently selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein when R$^1$ is hydrogen, Z$^2$ is oxygen, m is 1, and n is 0, the compound or derivative having formula (1) may optionally take the form of the carboxylate anion conjugate base species of the compound or derivative having formula (1), further optionally associated with a positively charged counterion selected from the group consisting of alkali metal, alkaline earth metal, transition metal, and base addition cations;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B_2$, —C(=$NR^B$)$NR^B_2$, —$OR^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$R^B_2$, —$NR^BC(O)R^B$, —$NR^BC(O)O(C_1$-$C_6$)alkyl, —$NR^BC(O)NR^B_2$, —$NR^BSO_2NR^B_2$, —$SR^B$, —S(O)$R^B$, —$SO_2R^B$, —$OSO_2(C_1$-$C_6$)alkyl, —$SO_2NR^B_2$, —($C_1$-$C_6$)perfluoroalkyl, and —($C_1$-$C_6$)alkylene-$OR^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C_2$, —$SR^C$, —S(O)$R^C$, —$SO_2R^C$, —$OSO_2(C_1$-$C_6$)alkyl, —$SO_2NR^C_2$, —($C_1$-$C_6$)perfluoroalkyl, and —($C_1$-$C_6$)alkylene-$OR^C$;

provided that the absolute configuration of C** is R or S, or a mixture of R and S.

In accordance with such an embodiment, appropriate starting materials for the methods of the present disclosure for the preparation of compounds or derivatives having formula (I), or salts, solvates, or prodrugs thereof, include compounds or derivatives having formula (2), or salts thereof:

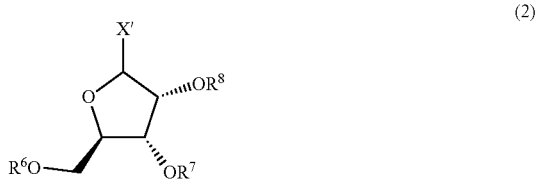

(2)

wherein X' is selected from the group consisting of fluoro, chloro, bromo, iodo, $HCO_2$, acetoxy, propionoxy, butyroxy, glutamyloxy, aspartyloxy, ascorbyloxy, benzoxy, $HOCO_2$, citryloxy, carbamyloxy, gluconyloxy, lactyloxy, methyl bromo, methyl sulfoxy, nitrate, phosphate, diphosphate, succinyloxy, sulfoxy, trifluoromethanesulfoxy, trichloromethanesulfoxy, tribromomethanesulfoxy, and trifluoroacetoxy;

optionally wherein $X^-$ as counterion is absent, or when $X^-$ is present, $X^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when $X^-$ is absent optionally the counterion is an internal salt;

optionally $X^-$ is an anion of a substituted or unsubstituted carboxylic acid selected from a monocarboxylic acid, a dicarboxylic acid, or a polycarboxylic acid; and, optionally $X^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid; the anion of lactic acid being lactate), or a trihaloacetate selected from trichloroacetate, tribromoacetate, and trifluoroacetate; and, optionally $X^-$ is an anion of a substituted monocarboxylic acid selected from formic acid, acetic acid, propionic acid, or butyric acid, being formate, acetate, propionate, and butyrate, respectively; and, optionally $X^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally $X^-$ is an anion of a substituted or unsubstituted carbonate, further optionally hydrogen carbonate; and, optionally $X^-$ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, substituted carbonate, substituted glutathione, and substituted glutathione disulfide are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$—C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$—$NR^CSO_2NR^C_2$, —$SR^C$, —S(O)$R^C$, —$SO_2R^C$, —$OSO_2(C_1$-$C_6$)alkyl, —$SO_2NR^C_2$, —($C_1$-$C_6$)perfluoroalkyl, and —($C_1$-$C_6$)alkylene-$OR^C$;

$R^6$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl($C_1$-$C_4$)alkyl, heterocycle($C_1$-$C_4$)alkyl, —N($R^4$)—$CO_2R^C$, —N($R^4$)—$CO_2R^B$, —CH—($R^4$)—$NH_2$, and —CH—($R^4$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C_2$, —$SR^C$, —S(O)$R^C$, —$SO_2R^C$, —$OSO_2(C_1$-$C_6$)alkyl, —$SO_2NR^C_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B_2$, —C(=$NR^B$)$NR^B_2$, —O$R^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$NR^B_2$, —$NR^B$C(O)$R^B$, —$NR^B$C(O)O($C_1$-$C_6$)alkyl, —$NR^B$C(O)$NR^B_2$, —$NR^B$$SO_2NR^B_2$, —$SR^B$, —S(O)$R^B$, —$SO_2R^B$, —$OSO_2$($C_1$-$C_6$)alkyl, —$SO_2NR^B_2$, —($C_1$-$C_6$)perfluoroalkyl, and —($C_1$-$C_6$)alkylene-$OR^B$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substitutents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$—C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$—$NR^C$$SO_2NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

provided that the absolute configuration of C** is R or S, or a mixture of R and S.

In accordance with an alternative embodiment, prototype product nicotinoyl riboside compounds include compounds or derivatives having formula (Ia), or salts, solvates, or prodrugs thereof:

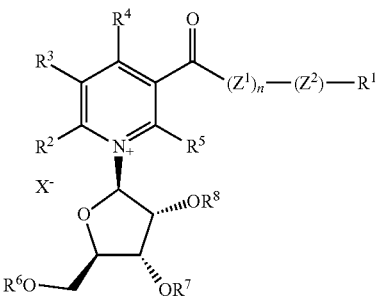

(Ia)

optionally wherein $X^-$ as counterion is absent, or when $X^-$ is present, $X^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when $X^-$ is absent optionally the counterion is an internal salt;

optionally $X^-$ is an anion of a substituted or unsubstituted carboxylic acid selected from a monocarboxylic acid, a dicarboxylic acid, or a polycarboxylic acid; and, optionally $X^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid, the anion of lactic acid being lactate), or a trihaloacetate selected from trichloroacetate, tribromoacetate, and trifluoroacetate; and, optionally $X^-$ is an anion of an unsubstituted monocarboxylic acid selected from formic acid, acetic acid, propionic acid, or butyric acid, being formate, acetate, propionate, and butyrate, respectively; and, optionally $X^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally $X^-$ is an anion of a substituted or unsubstituted carbonate, further optionally hydrogen carbonate; and, optionally $X^-$ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, substituted carbonate, substituted glutathione, and substituted glutathione disulfide are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$—C(=$NR^C$)$NR^C_2$, —O$R^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl($C_1$-$C_4$)alkyl, heterocycle($C_1$-$C_4$)alkyl, —N(R$^4$)—CO$_2$R$^C$, —N(R$^4$)—CO$_2$R$^B$, —CH—(R$^4$)—NH$_2$, and —CH—(R$^4$)—CO$_2$R$^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

wherein when $R^1$ is hydrogen, $Z^2$ is oxygen, and n is 0, the compound or derivative having formula (Ia) may optionally take the form of the carboxylate anion conjugate base species of the compound or derivative having formula (Ia), further optionally associated with a positively charged counterion selected from the group consisting of alkali metal, alkaline earth metal, transition metal, and base addition cations;

$R^A$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —($C_1$-$C_8$)alkyl;

each R$^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)($C_1$-$C_6$)alkyl, —OC(O)O($C_1$-$C_6$)alkyl, —OC(O)NR$^B_2$, —($C_1$-$C_6$)alkylene-NR$^B_2$, —NR$^B_2$, —NR$^B$C(O)R$^B$, —NR$^B$C(O)O($C_1$-$C_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$($C_1$-$C_6$)alkyl, —SO$_2$NR$^B_2$, —($C_1$-$C_6$)perfluoroalkyl, and —($C_1$-$C_6$)alkylene-OR$^B$;

each of $R^2$, $R^3$, $R^4$, and $R^5$ is hydrogen;

$R^6$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl($C_1$-$C_4$)alkyl, heterocycle($C_1$-$C_4$)alkyl, —N(R$^4$)—CO$_2$R$^C$, —N(R$^4$)—CO$_2$R$^B$, —CH—(R$^4$)—NH$_2$, and —CH—(R$^4$)—CO$_2$R$^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N(R$^4$)—CO$_2$R$^C$, —N(R$^4$)—CO$_2$R$^B$, —CH—(R$^4$)—NH$_2$, and —CH—(R$^4$)—CO$_2$R$^B$; wherein the substituted ($C_1$-$C_8$)alkyl, substituted ($C_1$-$C_8$) cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$—C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

provided that the absolute configuration of C** is R or S, or a mixture of R and S.

In accordance with such an embodiment, appropriate starting materials for the methods of the present disclosure for the preparation of compounds or derivatives having formula (Ta), or salts, solvates, or prodrugs thereof, include compounds or derivatives having formula (1a), or salts thereof:

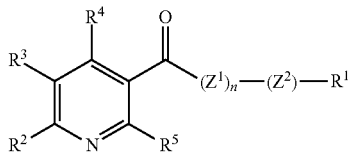

(1a)

wherein $Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl ($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

wherein when $R^1$ is hydrogen, $Z^2$ is oxygen, and n is 0, the compound or derivative having formula (1a) may optionally take the form of the carboxylate anion conjugate base species of the compound or derivative having formula (1a), further optionally associated with a positively charged counterion selected from the group consisting of alkali metal, alkaline earth metal, transition metal, and base addition cations;

$R^A$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester biotinyl; wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —$R^B_2$, —N$R^B$C(O)$R^B$, —N$R^B$C(O)O($C_1$-$C_6$)alkyl, —N$R^B$C(O)N$R^B_2$, —N$R^B$SO$_2$N$R^B_2$, —S$R^B$, —S(O)$R^B$, —SO$_2R^B$, —OSO$_2$($C_1$-$C_6$)alkyl, —SO$_2$N$R^B_2$, —($C_1$-$C_6$)perfluoroalkyl, and —($C_1$-$C_6$)alkylene-O$R^B$;

each of $R^2$, $R^3$, $R^4$, and $R^5$ is hydrogen;

provided that the absolute configuration of C** is R or S, or a mixture of R and S.

In accordance with such an embodiment, appropriate starting materials for the methods of the present disclosure for the preparation of compounds or derivatives having formula (Ia), or salts, solvates, or prodrugs thereof, include compounds or derivatives having formula (1b), or salts thereof:

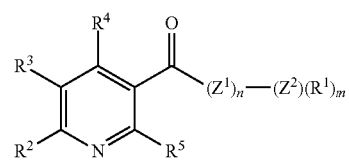

(1b)

wherein each $Z^1$ and $Z^2$ is independently nitrogen or oxygen;

m is 1 or 2;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl ($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

wherein when $R^1$ is hydrogen, $Z^2$ is oxygen, m is 1, and n is 0, the compound or derivative having formula (1b) may optionally take the form of the carboxylate anion conjugate base species of the compound or derivative having formula (1b), further optionally associated with a positively charged counterion selected from the group consisting of alkali metal, alkaline earth metal, transition metal, and base addition cations;

$R^A$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester biotinyl; wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)alkylene-NR$^B_2$, —NR$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$)perfluoroalkyl, and —(C$_1$-C$_6$)alkylene-OR$^B$;

each of R$^2$, R$^3$, R$^4$, and R$^5$ is hydrogen;

provided that the absolute configuration of C** is R or S, or a mixture of R and S.

In accordance with such an embodiment, appropriate starting materials for the methods of the present disclosure for the preparation of compounds or derivatives having formula (Ia), or salts, solvates, or prodrugs thereof, include compounds or derivatives having formula (2), or salts thereof:

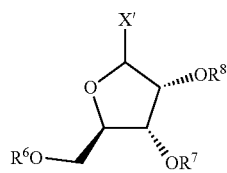

(2)

wherein X' is selected from the group consisting of fluoro, chloro, bromo, iodo, HCO$_2$, acetoxy, propinoxy, butyroxy, glutamyloxy, aspartyloxy, ascorbyloxy, benzoxy, HOCO$_2$, citryloxy, carbamyloxy, gluconyloxy, lactyloxy, methyl bromo, methyl sulfoxy, nitrate, phosphate, diphosphate, succinyloxy, sulfoxy, trifluoromethanesulfoxy, trichloromethanesulfoxy, tribromomethanesulfoxy, and trifluoroacetoxy;

optionally wherein X$^-$ as counterion is absent, or when X$^-$ is present, X$^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when X$^-$ is absent optionally the counterion is an internal salt;

optionally X$^-$ is an anion of a substituted or unsubstituted carboxylic acid selected from a monocarboxylic acid, a dicarboxylic acid, or a polycarboxylic acid; and, optionally X$^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid; the anion of lactic acid being lactate), or a trihaloacetate selected from trichloroacetate, tribromoacetate, and trifluoroacetate; and, optionally X$^-$ is an anion of a substituted monocarboxylic acid selected from formic acid, acetic acid, propionic acid, or butyric acid, being formate, acetate, propionate, and butyrate, respectively; and, optionally X$^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally X$^-$ is an anion of ascorbic acid, being ascorbate; and, optionally X$^-$ is a halide selected from fluoride, chloride, bromide, or iodide; and, optionally X$^-$ is an anion of a substituted or unsubstituted sulfonate, further optionally a trihalomethanesulfonate selected from trifluoromethanesulfonate, tribromomethanesulfonate, or trichloromethanesulfonate; and, optionally X$^-$ is an anion of a substituted or unsubstituted carbonate, further optionally hydrogen carbonate; and, optionally X$^-$ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, substituted carbonate, substituted glutathione, and substituted glutathione disulfide are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^6$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC (O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)alkylene-NR$^B_2$, —NR$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$)perfluoroalkyl, and —(C$_1$-C$_6$)alkylene-OR$^B$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with such an embodiment, appropriate starting materials for the methods of the present disclosure for the preparation of compounds or derivatives having formula (2), or salts thereof, include compounds or derivatives having formula (2a), or salts thereof:

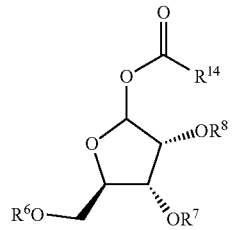

(2a)

wherein R$^6$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^B$, —$C(O)OR^B$, —$C(O)NR^B{}_2$, —$C(=NR^B)NR^B{}_2$, —$OR^B$, —$OC(O)(C_1$-$C_6)$alkyl, —$OC(O)O(C_1$-$C_6)$alkyl, —$OC(O)NR^B{}_2$, —$(C_1$-$C_6)$alkylene-$NR^B{}_2$, —$R^B{}_2$, —$NR^BC(O)R^B$, —$NR^BC(O)O(C_1$-$C_6)$alkyl, —$NR^BC(O)NR^B{}_2$, —$NR^BSO_2NR^B{}_2$, —$SR^B$, —$S(O)R^B$, —$SO_2R^B$, —$OSO_2(C_1$-$C_6)$alkyl, —$SO_2NR^B{}_2$, —$(C_1$-$C_6)$perfluoroalkyl, and —$(C_1$-$C_6)$alkylene-$OR^B$;

$R^7$ and $R^8$ are independently selected from the group consisting of hydrogen, —C(O)R', —C(O)OR', —C(O)NHR', substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C{}_2$, —$C(=NR^C)NR^C{}_2$, —$OR^C$, —$OC(O)(C_1$-$C_6)$alkyl, —$OC(O)O(C_1$-$C_6)$alkyl, —$OC(O)NR^C{}_2$, —$(C_1$-$C_6)$alkylene-$NR^C{}_2$, —$NR^C{}_2$, —$NR^CC(O)R^C$, —$NR^CC(O)O(C_1$-$C_6)$alkyl, —$NR^CC(O)NR^C{}_2$—$NR^CSO_2NR^C{}_2$, —$SR^C$, —$S(O)R^C$, —$SO_2R^C$, —$OSO_2(C_1$-$C_6)$alkyl, —$SO_2NR^C{}_2$, —$(C_1$-$C_6)$perfluoroalkyl, and —$(C_1$-$C_6)$alkylene-$OR^C$;

$R^{14}$ is methyl or phenyl;

provided that the absolute configuration of C** is R or S, or a mixture of R and S.

In accordance with one embodiment, the present disclosure provides a novel method for the preparation of compounds or derivatives having formula (I-H), or salts, solvates, or prodrugs thereof, wherein R6, R7, and R8 are each hydrogen. In accordance with such an embodiment, the present disclosure provides a novel method whereby mechanic forces are used to minimize solvent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product analogs of nicotinoyl riboside compounds include compounds or derivatives having formula (I-H), or salts, solvates, or prodrugs thereof, wherein R6, R7, and R8 are each hydrogen:

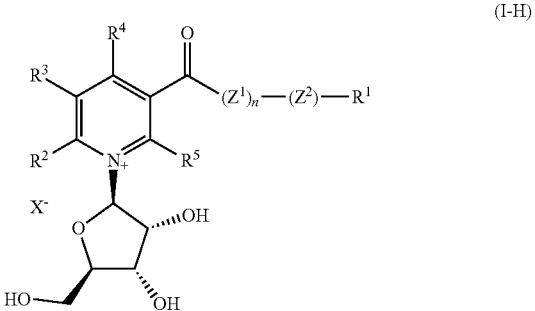

(I-H)

optionally wherein $X^-$ as counterion is absent, or when $X^-$ is present, $X^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when $X^-$ is absent optionally the counterion is an internal salt;

optionally $X^-$ is an anion of a substituted or unsubstituted carboxylic acid selected from a monocarboxylic acid, a dicarboxylic acid, or a polycarboxylic acid; and, optionally $X^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid, the anion of lactic acid being lactate), or a trihaloacetate selected from trichloroacetate, tribromoacetate, and trifluoroacetate; and, optionally $X^-$ is an anion of an unsubstituted monocarboxylic acid selected from formic acid, acetic acid, propionic acid, or butyric acid, being formate, acetate, propionate, and butyrate, respectively; and, optionally $X^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally $X^-$ is an anion of a substituted or unsubstituted carbonate, further optionally hydrogen carbonate; and, optionally $X^-$ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, and substituted carbonate, substituted glutathione, and substituted glutathione disulfide are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C{}_2$, —$C(=NR^C)NR^C{}_2$, —$OR^C$, —$OC(O)(C_1$-$C_6)$alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$—$NR^C$$SO_2$$NR^C_2$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-$OR^C$;

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl ($C_1$-$C_4$)alkyl, heterocycle($C_1$-$C_4$)alkyl, —N($R^A$)—$CO_2$$R^C$, —N($R^A$)—$CO_2$$R^B$, —CH—($R^A$)—$NH_2$, and —CH—($R^A$)—$CO_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-$OR^C$;

wherein when $R^1$ is hydrogen, $Z^2$ is oxygen, and n is 0, the compound or derivative having formula (I-H) may optionally take the form of the carboxylate anion conjugate base species of the compound or derivative having formula (I-H), further optionally associated with a positively charged counterion selected from the group consisting of alkali metal, alkaline earth metal, transition metal, and base addition cations;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)$OR^B$, —C(O)$NR^B_2$, —C(=$NR^B$)$NR^B_2$, —$OR^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$NR^B_2$, —$NR^B$C(O)$R^B$, —$NR^B$C(O)O($C_1$-$C_6$)alkyl, —$NR^B$C(O)$NR^B_2$, —$NR^B$$SO_2$$NR^B_2$, —$SR^B$, —S(O)$R^B$, —$SO_2$$R^B$, —$OSO_2$($C_1$-$C_6$)alkyl, —$SO_2$$NR^B_2$, —($C_1$-$C_6$)perfluoroalkyl, and —($C_1$-$C_6$)alkylene-$OR^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-$OR^C$;

provided that the absolute configuration of C** is R or S, or a mixture of R and S.

In accordance with an alternative embodiment, prototype product analogs of nicotinoyl riboside compounds include compounds or derivatives having formula (Ia-H), or salts, solvates, or prodrugs thereof, wherein $R^6$, $R^7$, and $R^8$ are each hydrogen:

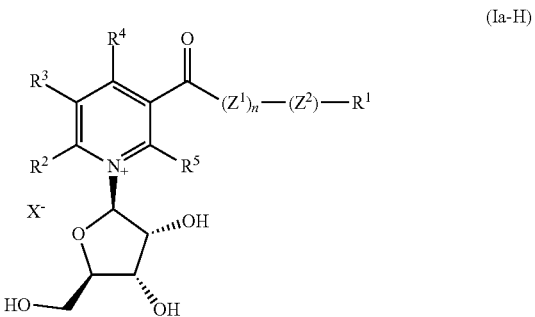

(Ia-H)

optionally wherein $X^-$ as counterion is absent, or when $X^-$ is present, $X^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when $X^-$ is absent optionally the counterion is an internal salt;

optionally $X^-$ is an anion of a substituted or unsubstituted carboxylic acid selected from a monocarboxylic acid, a dicarboxylic acid, or a polycarboxylic acid; and, optionally $X^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid, the anion of lactic acid being lactate), or a trihaloacetate selected from trichloroacetate, tribromoacetate, and trifluoroacetate; and, optionally $X^-$ is an anion of an unsubstituted monocarboxylic acid selected from formic acid, acetic acid, propionic acid, or butyric acid, being formate, acetate, propionate, and butyrate, respectively; and, optionally $X^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally X⁻ is an anion of a substituted or unsubstituted carbonate, further optionally hydrogen carbonate; and, optionally X⁻ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, substituted carbonate, substituted glutathione, and substituted glutathione disulfide are substituted with one to five substituents independently selected from the group consisting of —(C₁-C₆)alkyl, —(C₂-C₆)alkenyl, —(C₂-C₆)alkynyl, halogen, —CN, —NO₂, —C(O)R$^C$, —C(O)OR$^C$, —C(O)NR$^C$₂ —C(=NR$^C$)NR$^C$₂, —OR$^C$, —OC(O)(C₁-C₆)alkyl, —OC(O)O(C₁-C₆)alkyl, —OC(O)NR$^C$₂, —(C₁-C₆)alkylene-NR$^C$₂, —NR$^C$₂, —NR$^C$C(O)R$^C$, —NR$^C$C(O)O(C₁-C₆)alkyl, —NR$^C$C(O)NR$^C$₂—NR$^C$SO₂NR$^C$₂, —SR$^C$, —S(O)R$^C$, —SO₂R$^C$, —OSO₂(C₁-C₆)alkyl, —SO₂NR$^C$₂, —(C₁-C₆)perfluoroalkyl, and —(C₁-C₆)alkylene-OR$^C$;

Z¹ and Z² are independently NH or oxygen;

n is 0 or 1;

R¹ is selected from the group consisting of hydrogen, substituted or unsubstituted (C₁-C₈)alkyl, substituted or unsubstituted (C₁-C₈)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl (C₁-C₄)alkyl, heterocycle(C₁-C₄)alkyl, —N(R$^A$)—CO₂R$^C$, —N(R$^A$)—CO₂R$^B$, —CH—(R$^A$)—NH₂, and —CH—(R$^A$)—CO₂R$^B$; wherein the substituted (C₁-C₈)alkyl, substituted (C₁-C₈)cycloalkyl, substituted aryl, substituted heteroaryl, and substituted heterocycle are substituted with one to five substituents independently selected from the group consisting of —(C₁-C₆)alkyl, —(C₂-C₆)alkenyl, —(C₂-C₆)alkynyl, halogen, —CN, —NO₂, —C(O)R$^C$, —C(O)OR$^C$, —C(O)NR$^C$₂, —C(=NR$^C$)NR$^C$₂, —OR$^C$, —OC(O)(C₁-C₆)alkyl, —OC(O)O(C₁-C₆)alkyl, —OC(O)NR$^C$₂, —(C₁-C₆)alkylene-NR$^C$₂, —NR$^C$₂, —NR$^C$C(O)R$^C$, —NR$^C$C(O)O(C₁-C₆)alkyl, —NR$^C$C(O)NR$^C$₂, —NR$^C$SO₂NR$^C$₂, —SR$^C$, —S(O)R$^C$, —SO₂R$^C$, —OSO₂(C₁-C₆)alkyl, —SO₂NR$^C$₂, —(C₁-C₆)perfluoroalkyl, and —(C₁-C₆)alkylene-OR$^C$;

wherein when R¹ is hydrogen, Z² is oxygen, and n is 0, the compound or derivative having formula (Ia-H) may optionally take the form of the carboxylate anion conjugate base species of the compound or derivative having formula (Ia-H), further optionally associated with a positively charged counterion selected from the group consisting of alkali metal, alkaline earth metal, transition metal, and base addition cations;

R$^A$ is selected from the group consisting of —H, —(C₁-C₆)alkyl, —(CH₂)₃—NH—C(NH₂)(=NH), —CH₂C(=O)NH₂, —CH₂COOH, —CH₂SH, —(CH₂)₂C(=O)—NH₂, —(CH₂)₂COOH, —CH₂-(2-imidazolyl), —CH(CH₃)—CH₂—CH₃, —CH₂CH(CH₃)₂, —(CH₂)₂—NH₂, —(CH₂)₂—S—CH₃, phenyl, —CH₂-phenyl, —CH₂—OH, —CH(OH)—CH₃, —CH₂-(3-indolyl), —CH₂-(4-hydroxyphenyl), —CH(CH₃)₂, —NH₂, and —CH₂—CH₃;

each R$^B$ is independently hydrogen or —(C₁-C₈)alkyl;

each R$^C$ is independently selected from the group consisting of hydrogen, —(C₁-C₈)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C₁-C₆)alkyl, —(C₂-C₆)alkenyl, —(C₂-C₆)alkynyl, halogen, —CN, —NO₂, —C(O)R$^B$, —C(O)OR$^B$, —C(O)NR$^B$₂, —C(=NR$^B$)NR$^B$₂, —OR$^B$, —OC(O)(C₁-C₆)alkyl, —OC(O)O(C₁-C₆)alkyl, —OC(O)NR$^B$₂, —(C₁-C₆)alkylene-NR$^B$₂, —NR$^B$₂, —NR$^B$C(O)R$^B$, —NR$^B$C(O)O(C₁-C₆)alkyl, —NR$^B$C(O)NR$^B$₂, —NR$^B$SO₂NR$^B$₂, —SR$^B$, —S(O)R$^B$, —SO₂R$^B$, —OSO₂(C₁-C₆)alkyl, —SO₂NR$^B$₂, —(C₁-C₆)perfluoroalkyl, and —(C₁-C₆)alkylene-OR$^B$;

R², R³, R⁴, and R⁵ are each hydrogen;

provided that the absolute configuration of C** is R or S, or a mixture of R and S.

In accordance with one embodiment, the present disclosure provides a novel method for the preparation of compounds or derivatives having formula (II), or salts, solvates, or prodrugs thereof, such as phosphorylated analogs of nicotinoyl ribosides, in commercial quantities. In accordance with such an embodiment, the present disclosure provides a novel method whereby mechanic forces are used to minimize solvent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product phosphorylated analogs of nicotinoyl ribosides compounds include compounds or derivatives having formula (II), or salts, solvates, or prodrugs thereof:

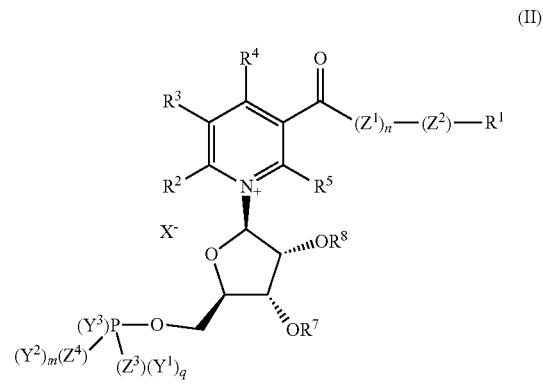

(II)

optionally wherein X⁻ as counterion is absent, or when X⁻ is present, X⁻ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when X⁻ is absent optionally the counterion is an internal salt;

optionally X⁻ is an anion of a substituted or unsubstituted carboxylic acid selected from a monocarboxylic acid, a dicarboxylic acid, or a polycarboxylic acid; and, optionally X⁻ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid, the anion of lactic acid being lactate), or a trihaloacetate selected from trichloroacetate, tribromoacetate, and trifluoroacetate; and, optionally X⁻ is an anion of an unsubstituted monocarboxylic acid selected from formic acid, acetic acid, propionic acid, or butyric acid, being formate, acetate, propionate, and butyrate, respectively; and, optionally X⁻ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally X⁻ is an anion of ascorbic acid, being ascorbate; and, optionally X⁻ is a halide selected from fluoride, chloride, bromide, or iodide; and, optionally X⁻ is an anion of a substituted or unsubstituted sulfonate, further optionally a trihalomethanesulfonate selected from trifluoromethanesulfonate, tribromomethanesulfonate, or trichloromethanesulfonate; and, optionally X⁻ is an anion of a substituted or unsubstituted carbonate, further optionally hydrogen carbonate; and, optionally X⁻ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, substituted carbonate, substituted glutathione, and substituted glutathione disulfide are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$—C(=N$R^C$)N$R^C_2$, —O$R^C$, —OC(O)$(C_1$-$C_6)$alkyl, —OC(O)O$(C_1$-$C_6)$alkyl, —OC(O)N$R^C_2$, —$(C_1$-$C_6)$alkylene-N$R^C_2$, —N$R^C_2$, —N$R^C$C(O)$R^C$, —N$R^C$C(O)O$(C_1$-$C_6)$alkyl, —N$R^C$C(O)N$R^C_2$—N$R^C$SO$_2$N$R^C_2$, —S$R^C$, —S(O)$R^C$, —SO$_2R^C$, —OSO$_2(C_1$-$C_6)$alkyl, —SO$_2$N$R^C_2$, —$(C_1$-$C_6)$perfluoroalkyl, and —$(C_1$-$C_6)$alkylene-O$R^C$;

each $Y^1$ and $Y^2$ is independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^4$)—CO$_2R^C$, —N($R^4$)—CO$_2R^B$, —CH—($R^4$)—NH$_2$, and —CH—($R^4$)—CO$_2R^B$; wherein the substituted $(C_1$-$C_8)$alkyl, substituted $(C_1$-$C_8)$cycloalkyl, substituted aryl, substituted heteroaryl, substituted heterocycle, and substituted amino are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1$-$C_6)$alkyl, OC(O)O$(C_1$-$C_6)$alkyl, —OC(O)N$R^C_2$, —$(C_1$-$C_6)$alkylene-N$R^C_2$, —N$R^C_2$, —N$R^C$C(O)$R^C$, —N$R^C$C(O)O$(C_1$-$C_6)$alkyl, —N$R^C$C(O)N$R^C_2$, —N$R^C$SO$_2$N$R^C_2$, —S$R^C$, —S(O)$R^C$, —SO$_2R^C$, —OSO$_2(C_1$-$C_6)$alkyl, —SO$_2$N$R^C_2$, —$(C_1$-$C_6)$perfluoroalkyl, and —$(C_1$-$C_6)$alkylene-O$R^C$;

or, alternatively, $Y^1$ and $Y^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1$-$C_6)$alkyl, —OC(O)O$(C_1$-$C_6)$alkyl, —OC(O)N$R^C_2$, —$(C_1$-$C_6)$alkylene-N$R^C_2$, —N$R^C_2$, —N$R^C$C(O)$R^C$, —N$R^C$C(O)O$(C_1$-$C_6)$alkyl, —N$R^C$C(O)N$R^C_2$, —N$R^C$SO$_2$N$R^C_2$, —S$R^C$, —S(O)$R^C$, —SO$_2R^C$, —OSO$_2(C_1$-$C_6)$alkyl, —SO$_2$N$R^C_2$, —$(C_1$-$C_6)$perfluoroalkyl, and —$(C_1$-$C_6)$alkylene-O$R^C$;

optionally wherein $Y^3$ is oxygen, sulfur, or absent;

each of $Z^1$ and $Z^2$ is independently NH or oxygen;

each of $Z^3$ and $Z^4$ is independently nitrogen or oxygen;

m is 1 or 2;

n is 0 or 1;

q is 1 or 2;

$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl $(C_1$-$C_4)$alkyl, heterocycle$(C_1$-$C_4)$alkyl, —N($R^4$)—CO$_2R^C$, —N($R^4$)—CO$_2R^B$, —CH—($R^4$)—NH$_2$, and —CH—($R^4$)—CO$_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1$-$C_6)$alkyl, —OC(O)O$(C_1$-$C_6)$alkyl, —OC(O)N$R^C_2$, —$(C_1$-$C_6)$alkylene-N$R^C_2$, —N$R^C_2$, —N$R^C$C(O)$R^C$, —N$R^C$C(O)O$(C_1$-$C_6)$alkyl, —N$R^C$C(O)N$R^C_2$, —N$R^C$SO$_2$N$R^C_2$, —S$R^C$, —S(O)$R^C$, —SO$_2R^C$, —OSO$_2(C_1$-$C_6)$alkyl, —SO$_2$N$R^C_2$, —$(C_1$-$C_6)$perfluoroalkyl, and —$(C_1$-$C_6)$alkylene-O$R^C$;

wherein when $R^1$ is hydrogen, $Z^2$ is oxygen, and n is 0, the compound or derivative having formula (II) may optionally take the form of the carboxylate anion conjugate base species of the compound or derivative having formula (II), further optionally associated with a positively charged counterion selected from the group consisting of alkali metal, alkaline earth metal, transition metal, and base addition cations;

$R^A$ is selected from the group consisting of —H, —$(C_1$-$C_6)$alkyl, —$(CH_2)_3$—NH—C(NH$_2$)(=NH), —CH$_2$C(=O)NH$_2$, —CH$_2$COOH, —CH$_2$SH, —$(CH_2)_2$C(=O)—NH$_2$, —$(CH_2)_2$COOH, —CH$_2$-(2-imidazolyl), —CH(CH$_3$)—CH$_2$—CH$_3$, —CH$_2$CH(CH$_3)_2$, —$(CH_2)_4$—NH$_2$, —$(CH_2)_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3)_2$, —NH$_2$, and —CH$_2$—CH$_3$;

each $R^B$ is independently hydrogen or —$(C_1$-$C_8)$alkyl;

each $R^C$ is independently selected from the group consisting of hydrogen, —$(C_1$-$C_8)$alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)$(C_1$-$C_6)$alkyl, —OC(O)O$(C_1$-$C_6)$alkyl, —OC(O)N$R^B_2$, —$(C_1$-$C_6)$alkylene-N$R^B_2$, —N$R^B_2$, —N$R^B$C(O)$R^B$, —N$R^B$C(O)O$(C_1$-$C_6)$alkyl, —N$R^B$C(O)N$R^B_2$, —N$R^B$SO$_2$N$R^B_2$, —S$R^B$, —S(O)$R^B$, —SO$_2R^B$, —OSO$_2(C_1$-$C_6)$alkyl, —SO$_2$N$R^B_2$, —$(C_1$-$C_6)$perfluoroalkyl, and —$(C_1$-$C_6)$alkylene-O$R^B$;

$R^2$, $R^3$, $R^4$, and $R^5$ are each independently selected from the group consisting of hydrogen, —$(C_1$-$C_6)$alkyl, —$(C_2$-$C_6)$alkenyl, —$(C_2$-$C_6)$alkynyl, halogen, —CN, —$NO_2$, —C(O)R$^C$, —C(O)OR$^C$, —C(O)NR$^C$, —C(=NR$^C$)NR$^C{}_2$, —OR$^C$, —OC(O)(C$_1$-C$_6$)alkyl, —OC(O)O(C$_1$-C$_6$)alkyl, —OC(O)NR$^C{}_2$, —(C$_1$-C$_6$)alkylene-NR$^C{}_2$, —NR$^C{}_2$, —NR$^C$C(O)R$^C$, —NR$^C$C(O)O(C$_1$-C$_6$)alkyl, —NR$^C$C(O)NR$^C{}_2$, —NR$^C$SO$_2$NR$^C{}_2$, —SR$^C$, —S(O)R$^C$, —SO$_2$R$^C$, —OSO$_2$(C$_1$-C$_6$)alkyl, —SO$_2$NR$^C{}_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C{}_2$, —C(=NR$^C$)NR$^C{}_2$, —OR$^C$, —OC(O)(C$_1$-C$_6$)alkyl, —OC(O)O(C$_1$-C$_6$)alkyl, —OC(O)NR$^C{}_2$, —(C$_1$-C$_6$)alkylene-NR$^C{}_2$, —NR$^C{}_2$, —NR$^C$C(O)R$^C$, —NR$^C$C(O)O(C$_1$-C$_6$)alkyl, —NR$^C$C(O)NR$^C{}_2$, —NR$^C$SO$_2$NR$^C{}_2$, —SR$^C$, —S(O)R$^C$, —SO$_2$R$^C$, —OSO$_2$(C$_1$-C$_6$)alkyl, —SO$_2$NR$^C{}_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$) cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C{}_2$, —C(=NR$^C$)NR$^C{}_2$, —OR$^C$, —OC(O)(C$_1$-C$_6$)alkyl, —OC(O)O(C$_1$-C$_6$)alkyl, —OC(O)NR$^C{}_2$, —(C$_1$-C$_6$)alkylene-NR$^C{}_2$, —NR$^C{}_2$, —NR$^C$C(O)R$^C$, —NR$^C$C(O)O(C$_1$-C$_6$)alkyl, —NR$^C$C(O)NR$^C{}_2$, —NR$^C$SO$_2$NR$^C{}_2$, —SR$^C$, —S(O)R$^C$, —SO$_2$R$^C$, —OSO$_2$(C$_1$-C$_6$)alkyl, —SO$_2$NR$^C{}_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with an alternative embodiment, the present disclosure provides a novel method for the preparation of compounds or derivatives having formula (IIa), or salts, solvates, or prodrugs thereof, such as phosphorylated analogs of nicotinoyl ribosides, in commercial quantities. In accordance with such an embodiment, the present disclosure provides a novel method whereby mechanic forces are used to minimize solvent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product phosphorylated analogs of nicotinoyl riboside compounds include compounds or derivatives having formula (IIa), or salts, solvates, or prodrugs thereof:

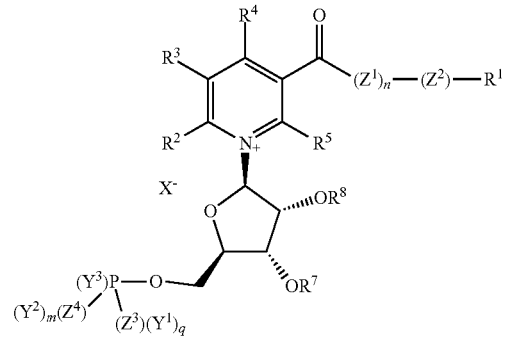

(IIa)

optionally wherein X$^-$ as counterion is absent, or when X$^-$ is present, X$^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when X$^-$ is absent optionally the counterion is an internal salt;

optionally X$^-$ is an anion of a substituted or unsubstituted carboxylic acid selected from a monocarboxylic acid, a dicarboxylic acid, or a polycarboxylic acid; and, optionally X$^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid, the anion of lactic acid being lactate), or a trihaloacetate selected from trichloroacetate, tribromoacetate, and trifluoroacetate; and, optionally X$^-$ is an anion of an unsubstituted monocarboxylic acid selected from formic acid, acetic acid, propionic acid, or butyric acid, being formate, acetate, propionate, and butyrate, respectively; and, optionally X$^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally X$^-$ is an anion of ascorbic acid, being ascorbate; and, optionally X$^-$ is a halide selected from fluoride, chloride, bromide, or iodide; and, optionally X$^-$ is an anion of a substituted or unsubstituted sulfonate, further optionally a trihalomethanesulfonate selected from trifluoromethanesulfonate, tribromomethanesulfonate, or trichloromethanesulfonate; and, optionally X$^-$ is an anion of a substituted or unsubstituted carbonate, further optionally hydrogen carbonate; and, optionally X$^-$ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, substituted carbonate, substituted glutathione, and substituted glutathione disulfide are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$—C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

each Y$^1$ and Y$^2$ is independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, substituted heterocycle, and substituted amino are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

or, alternatively, Y$^1$ and Y$^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

optionally wherein Y$^3$ is oxygen, sulfur, or absent;
each of Z$^1$ and Z$^2$ is independently NH or oxygen;
each of Z$^3$ and Z$^4$ is independently nitrogen or oxygen;
m is 1 or 2;
n is 0 or 1;
q is 1 or 2;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein when R$^1$ is hydrogen, Z$^2$ is oxygen, and n is 0, the compound or derivative having formula (IIa) may optionally take the form of the carboxylate anion conjugate base species of the compound or derivative having formula (IIa), further optionally associated with a positively charged counterion selected from the group consisting of alkali metal, alkaline earth metal, transition metal, and base addition cations;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)alkylene-NR$^B_2$, —NR$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$)perfluoroalkyl, and —(C$_1$-C$_6$)alkylene-OR$^B$;

each of R$^2$, R$^3$, R$^4$, and R$^5$ is hydrogen;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$;

wherein the substituted (C$_1$-C$_8$)alkyl, substituted (C$_1$-C$_8$) cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with one embodiment, the present disclosure provides a novel method for the preparation of compounds or derivatives having formula (III), or salts, solvates, or prodrugs thereof, in commercial quantities. In accordance with such an embodiment, the present disclosure provides a novel method whereby mechanic forces are used to minimize solvent quantities, decrease reaction times, increase overall conversion, and facilitate product purification, whereby by-product formation is minimized. Prototype product nicotinyl riboside compounds include compounds or derivatives having formula (III), or salts, solvates, or prodrugs thereof:

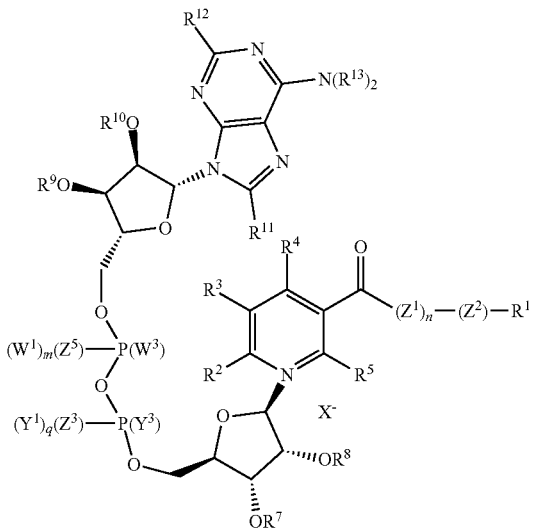

(III)

optionally wherein X$^-$ as counterion is absent, or when X$^-$ is present, X$^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein X$^-$ is absent optionally the counterion is an internal salt;

optionally X$^-$ is an anion of a substituted or unsubstituted carboxylic acid selected from a monocarboxylic acid, a dicarboxylic acid, or a polycarboxylic acid; and, optionally X$^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxylpropanoic acid (being lactic acid, the anion of lactic acid being lactate), or a trihaloacetate selected from trichloroacetate, tribromoacetate, and trifluoroacetate; and, optionally X$^-$ is an anion of an unsubstituted monocarboxylic acid selected from formic acid, acetic acid, propionic acid, or butyric acid, being formate, acetate, propionate, and butyrate, respectively; and, optionally X$^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally X$^-$ is an anion of ascorbic acid, being ascorbate; and, optionally X$^-$ is a halide selected from fluoride, chloride, bromide, or iodide; and, optionally X$^-$ is an anion of a substituted or unsubstituted sulfonate, further optionally a trihalomethanesulfonate selected from trifluoromethanesulfonate, tribromomethanesulfonate, or trichloromethanesulfonate; and, optionally X$^-$ is an anion of a substituted or unsubstituted carbonate, further optionally hydrogen carbonate; and, optionally X$^-$ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, substituted carbonate, substituted glutathione, and substituted glutathione disulfide are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$—C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

each Y$^1$ is independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N(R$^4$)—CO$_2$R$^C$, —N(R$^4$)—CO$_2$R$^B$, —CH—(R$^4$)—NH$_2$, and —CH—(R$^4$)—CO$_2$R$^B$; wherein the substituted (C$_1$-C$_8$)alkyl, substituted (C$_1$-C$_8$)cycloalkyl, substituted aryl, substituted heteroaryl, substituted heterocycle, and substituted amino are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

each W$^1$ is independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, substituted heterocycle, and substituted amino are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2NR^C_2$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

or, alternatively, $Y^1$ and $W^1$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2NR^C_2$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

optionally wherein $Y^3$ is oxygen, sulfur, or absent;
optionally wherein $W^3$ is oxygen, sulfur, or absent;
each of $Z^1$ and $Z^2$ is independently NH or oxygen;
each of $Z^3$ and $Z^5$ is independently nitrogen or oxygen;
m is 1 or 2;
n is 0 or 1;
q is 1 or 2;
$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2NR^C_2$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

wherein when $R^1$ is hydrogen, $Z^2$ is oxygen, and n is 0, the compound or derivative having formula (III) may optionally take the form of the carboxylate anion conjugate base species of the compound or derivative having formula (III), further optionally associated with a positively charged counterion selected from the group consisting of alkali metal, alkaline earth metal, transition metal, and base addition cations;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;
each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B_2$, —C(=$NR^B$)$NR^B_2$, —O$R^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$NR^B_2$, —$NR^B$C(O)$R^B$, —$NR^B$C(O)O($C_1$-$C_6$)alkyl, —$NR^B$C(O)$NR^B_2$, —$NR^B$$SO_2NR^B_2$, —S$R^B$, —S(O)$R^B$, —$SO_2R^B$, —$OSO_2$($C_1$-$C_6$)alkyl, —$SO_2NR^B_2$, —($C_1$-$C_6$) perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2NR^C_2$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$) alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$—C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2NR^C_2$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—(R^A)—NH$_2$, and —CH—(R^A)—CO$_2$R^B; wherein the substituted (C$_1$-C$_8$)alkyl, substituted (C$_1$-C$_8$) cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R^C, —C(O)OR^C, —C(O)NR^C$_2$, —C(=NR^C)NR^C$_2$, —OR^C, —OC(O)(C$_1$-C$_6$)alkyl, —OC(O)O(C$_1$-C$_6$)alkyl, —OC(O)NR^C$_2$, —(C$_1$-C$_6$)alkylene-NR^C$_2$, —NR^C$_2$, —NR^CC(O)R^C, —NR^CC(O)O(C$_1$-C$_6$)alkyl, —NR^CC(O)NR^C$_2$ —NR^CSO$_2$NR^C$_2$, —SR^C, —S(O)R^C, —SO$_2$R^C, —OSO$_2$(C$_1$-C$_6$)alkyl, —SO$_2$NR^C$_2$, —(C$_1$-C$_6$)perfluoroalkyl, and —(C$_1$-C$_6$)alkylene-OR^C;

R$^9$ and R$^{10}$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R^C, —C(O)OR^C, —C(O)NR^C$_2$, —C(=NR^C)NR^C$_2$, —OR^C, —OC(O)(C$_1$-C$_6$)alkyl, —OC(O)O(C$_1$-C$_6$)alkyl, —OC(O)NR^C$_2$, —(C$_1$-C$_6$)alkylene-NR^C$_2$, —NR^C$_2$, —NR^CC(O)R^C, —NR^CC(O)O(C$_1$-C$_6$)alkyl, —NR^CC(O)NR^C$_2$, —NR^CSO$_2$NR^C$_2$, —SR^C, —S(O)R^C, —SO$_2$R^C, —OSO$_2$(C$_1$-C$_6$)alkyl, —SO$_2$NR^C$_2$, —(C$_1$-C$_6$)perfluoroalkyl, and —(C$_1$-C$_6$)alkylene-OR^C;

R$^{11}$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$) cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$) cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$) alkynyl, halogen, —CN, —NO$_2$, —C(O)R^C, —C(O)OR^C, —C(O)NR^C$_2$, —C(=NR^C)NR^C, —OR^C, —OC(O)(C$_1$-C$_6$) alkyl, —OC(O)O(C$_1$-C$_6$)alkyl, —OC(O)NR^C$_2$, —(C$_1$-C$_6$) alkylene-NR^C$_2$, —NR^C$_2$, —NR^CC(O)R^C, —NR^CC(O)O (C$_1$-C$_6$)alkyl, —NR^CC(O)NR^C$_2$, —NR^CSO$_2$NR^C$_2$, —SR^C, —S(O)R^C, —SO$_2$R^C, —OSO$_2$(C$_1$-C$_6$)alkyl, —SO$_2$NR^C$_2$, —(C$_1$-C$_6$)perfluoroalkyl, and —(C$_1$-C$_6$)alkylene-OR^C;

R$^{12}$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$) cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$) cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$) alkynyl, halogen, —CN, —NO$_2$, —C(O)R^C, —C(O)OR^C, —C(O)NR^C$_2$, —C(=NR^C)NR^C, —OR^C, —OC(O)(C$_1$-C$_6$) alkyl, —OC(O)O(C$_1$-C$_6$)alkyl, —OC(O)NR^C$_2$, —(C$_1$-C$_6$) alkylene-NR^C$_2$, —NR^C$_2$, —NR^CC(O)R^C, —NR^CC(O)O (C$_1$-C$_6$)alkyl, —NR^CC(O)NR^C$_2$, —NR^CSO$_2$NR^C$_2$, —SR^C, —S(O)R^C, —SO$_2$R^C, —OSO$_2$(C$_1$-C$_6$)alkyl, —SO$_2$NR^C$_2$, —(C$_1$-C$_6$)perfluoroalkyl, and —(C$_1$-C$_6$)alkylene-OR^C;

each R$^{13}$ is independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R^C, —C(O)OR^C, —C(O)NR^C$_2$—C(=NR^C) NR^C$_2$, —OR^C, —OC(O)(C$_1$-C$_6$)alkyl, —OC(O)O(C$_1$-C$_6$) alkyl, —OC(O)NR^C$_2$, —(C$_1$-C$_6$)alkylene-NR^C$_2$, —NR^C$_2$, —NR^CC(O)R^C, —NR^CC(O)O(C$_1$-C$_6$)alkyl, —NR^CC(O) NR^C$_2$, —NR^CSO$_2$NR^C$_2$, —SR^C, —S(O)R^C, —SO$_2$R^C, —OSO$_2$(C$_1$-C$_6$)alkyl, —SO$_2$NR^C$_2$, —(C$_1$-C$_6$)perfluoroalkyl, and —(C$_1$-C$_6$)alkylene-OR^C;

provided that the absolute configuration of C** is R or S, or a mixture of R and S.

In accordance with such an embodiment, appropriate starting materials for the methods of the present disclosure for the preparation of compounds or derivatives having formula (III), or salts, solvates, or prodrugs thereof, include compounds or derivatives having formula (3), or salts thereof:

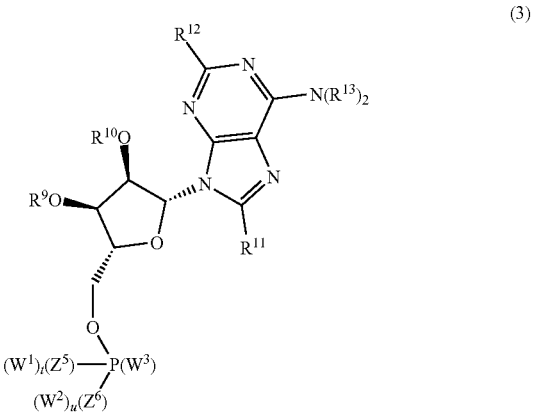

(3)

wherein each W$^1$ and W$^2$ is independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N(R$^A$)—CO$_2$R^C, —N(R$^A$)—CO$_2$R^B, —CH—(R$^A$)—NH$_2$, and —CH—(R$^A$)—CO$_2$R^B; wherein the substituted (C$_1$-C$_8$)alkyl, substituted (C$_1$-C$_8$)cycloalkyl, substituted aryl, substituted heteroaryl, substituted heterocycle, and substituted amino are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

or, alternatively, $W^1$ and $W^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

optionally wherein $W^3$ is oxygen, sulfur, or absent;

each of $Z^5$ and $Z^6$ is independently nitrogen or oxygen;

t is 1 or 2;

u is 1 or 2;

$R^9$ and $R^{10}$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$—C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$—$NR^C$$SO_2$$NR^C_2$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2$$R^C$, —N($R^A$)—$CO_2$$R^B$, —CH—($R^A$)—$NH_2$, and —CH—($R^A$)—$CO_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$—$NR^C$$SO_2$$NR^C_2$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B_2$, —C(=$NR^B$)$NR^B_2$, —O$R^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$R^B_2$, —$NR^B$C(O)$R^B$, —$NR^B$C(O)O($C_1$-$C_6$)alkyl, —$NR^B$C(O)$NR^B_2$, —$NR^B$$SO_2$$NR^B_2$, —$SR^B$, —S(O)$R^B$, —$SO_2$$R^B$, —$OSO_2$($C_1$-$C_6$)alkyl, —$SO_2$$NR^B_2$, —($C_1$-$C_6$)perfluoroalkyl, and —($C_1$-$C_6$)alkylene-O$R^B$;

$R^{11}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

$R^{12}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

each R$^{13}$ is independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$—C(=NR$^C$) NR$^C_2$, —OR$^C$, —OC(O)(C$_1$-C$_6$)alkyl, —OC(O)O(C$_1$-C$_6$) alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O) NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with an alternative embodiment, the present disclosure provides a novel method for the preparation of compounds or derivatives having formula (IIIa), or salts, solvates, or prodrugs thereof, in commercial quantities. In accordance with such an embodiment, the present disclosure provides a novel method whereby mechanic forces are used to minimize solvent quantities, decrease reaction times, increase overall conversion, and facilitate product purification, whereby by-product formation is minimized. Prototype product nicotinoyl riboside compounds include compounds or derivatives having formula (IIIa), or salts, solvates, or prodrugs thereof:

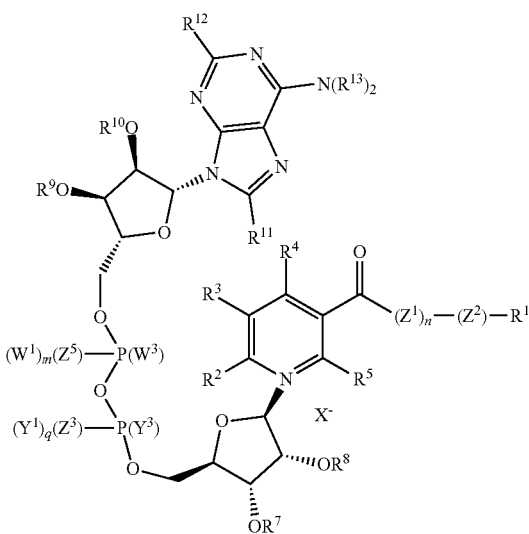

(IIIa)

optionally wherein X$^-$ as counterion is absent, or when X$^-$ is present, X$^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when X$^-$ is absent optionally the counterion is an internal salt;

optionally X$^-$ is an anion of a substituted or unsubstituted carboxylic acid selected from a monocarboxylic acid, a dicarboxylic acid, or a polycarboxylic acid; and, optionally X$^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid, the anion of lactic acid being lactate), or a trihaloacetate selected from trichloroacetate, tribromoacetate, and trifluoroacetate; and, optionally X$^-$ is an anion of an unsubstituted monocarboxylic acid selected from formic acid, acetic acid, propionic acid, or butyric acid, being formate, acetate, propionate, and butyrate, respectively; and, optionally X$^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally X$^-$ is an anion ascorbic acid, being ascorbate; and, optionally X$^-$ is a halide selected from fluoride, chloride, bromide, or iodide; and, optionally X$^-$ is an anion of a substituted or unsubstituted sulfonate, further optionally a trihalomethanesulfonate selected from trifluoromethanesulfonate, tribromomethanesulfonate, or trichloromethanesulfonate; and, optionally X$^-$ is an anion of a substituted or unsubstituted carbonate, further optionally hydrogen carbonate; and, optionally X$^-$ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, substituted carbonate, substituted glutathione, and substituted glutathione disulfide are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O) NR$^C_2$—C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

each Y$^1$ is independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N(R$^A$)—CO$_2$R$^C$, —N(R$^A$)—CO$_2$R$^B$, —CH—(R$^A$)—NH$_2$, and —CH— (R$^A$)—CO$_2$R$^B$; wherein the substituted (C$_1$-C$_8$)alkyl, substituted (C$_1$-C$_8$)cycloalkyl, substituted aryl, substituted heteroaryl, substituted heterocycle, and substituted amino are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

each W$^1$ is independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, substituted heterocycle, and substituted amino are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

or, alternatively, Y$^1$ and W$^1$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

optionally wherein Y$^3$ is oxygen, sulfur, or absent;
optionally wherein W$^3$ is oxygen, sulfur, or absent;
each of Z$^1$ and Z$^2$ is independently NH or oxygen;
each of Z$^3$ and Z$^5$ is independently nitrogen or oxygen;
m is 1 or 2;
n is 0 or 1;
q is 1 or 2;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein when R$^1$ is hydrogen, Z$^2$ is oxygen, and n is 0, the compound or derivative having formula (IIIa) may optionally take the form of the carboxylate anion conjugate base species of the compound or derivative having formula (IIIa), further optionally associated with a positively charged counterion selected from the group consisting of alkali metal, alkaline earth metal, transition metal, and base addition cations;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;
each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)alkylene-NR$^B_2$, —NR$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$)perfluoroalkyl, and —(C$_1$-C$_6$)alkylene-OR$^B$;

each of R$^2$, R$^3$, R$^4$, and R$^5$ is hydrogen;
R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$) cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

R$^9$ and R$^{10}$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$—C(=NR$^C$)NR$^C$$_2$, —OR$^C$, —OC(O)(C$_1$-C$_6$)alkyl, —OC(O)O(C$_1$-C$_6$) alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$—NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

R$^{11}$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$) cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$) cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$) alkynyl, halogen, —CN, —NO$_2$, —C(O)R$^C$, —C(O)OR$^C$, —C(O)NR$^C$$_2$, —C(=NR$^C$)NR$^C$, —OR$^C$, —OC(O)(C$_1$-C$_6$) alkyl, —OC(O)O(C$_1$-C$_6$)alkyl, —OC(O)NR$^C$$_2$, —(C$_1$-C$_6$) alkylene-NR$^C$$_2$, —NR$^C$$_2$, —NR$^C$C(O)R$^C$, —NR$^C$C(O)O (C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

R$^{12}$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$) cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$) cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$) alkynyl, halogen, —CN, —NO$_2$, —C(O)R$^C$, —C(O)OR$^C$, —C(O)NR$^C$$_2$, —C(=NR$^C$)NR$^C$, —OR$^C$, —OC(O)(C$_1$-C$_6$) alkyl, —OC(O)O(C$_1$-C$_6$)alkyl, —OC(O)NR$^C$$_2$, —(C$_1$-C$_6$) alkylene-NR$^C$$_2$, —NR$^C$$_2$, —NR$^C$C(O)R$^C$, —NR$^C$C(O)O (C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

each R$^{13}$ is independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O) R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with such an embodiment, appropriate starting materials for the methods of the present disclosure for the preparation of compounds or derivatives having formula (IIIa), or salts, solvates, or prodrugs thereof, include compounds or derivatives having formula (3), or salts thereof:

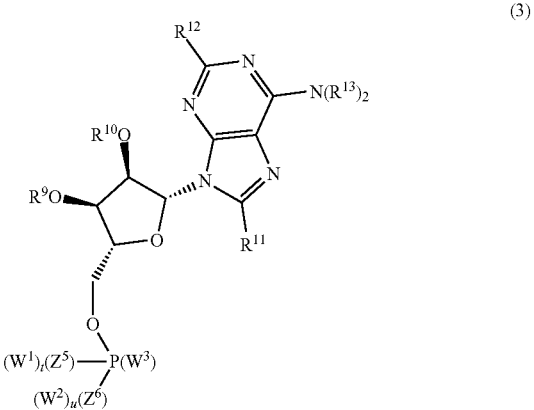

(3)

wherein each W$^1$ and W$^2$ is independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, substituted heterocycle, and substituted amino are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

or, alternatively, $W^1$ and $W^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

optionally wherein $W^3$ is oxygen, sulfur, or absent;

each of $Z^5$ and $Z^6$ is independently nitrogen or oxygen;

t is 1 or 2;

u is 1 or 2;

$R^9$ and $R^{10}$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$—C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$—$NR^C$$SO_2$$NR^C_2$, —$SR^C$, —S(O)$R^C$, —$SO_2R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$—$NR^C$$SO_2$$NR^C_2$, —$SR^C$, —S(O)$R^C$, —$SO_2R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B_2$, —C(=$NR^B$)$NR^B_2$, —O$R^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$R^B_2$, —$NR^B$C(O)$R^B$, —$NR^B$C(O)O($C_1$-$C_6$)alkyl, —$NR^B$C(O)$NR^B_2$, —$NR^B$$SO_2$$NR^B_2$, —$SR^B$, —S(O)$R^B$, —$SO_2R^B$, —$OSO_2$($C_1$-$C_6$)alkyl, —$SO_2$$NR^B_2$, —($C_1$-$C_6$)perfluoroalkyl, and —($C_1$-$C_6$)alkylene-O$R^B$;

$R^{11}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

$R^{12}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

each R$^{13}$ is independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$—C(=NR$^C$) NR$^C$$_2$, —OR$^C$, —OC(O)(C$_1$-C$_6$)alkyl, —OC(O)O(C$_1$-C$_6$) alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O) NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with one embodiment, the present disclosure provides a novel method for the preparation of compounds or derivatives having formula (IV), or salts, solvates, or prodrugs thereof, such as reduced nicotinoyl ribosides and their derivatives, and including, but not limited to, the triacetylated forms of NRH (reduced nicotinamide riboside) and NARH (reduced nicotinic acid riboside) (compounds or derivatives having formula (IV), wherein R$^6$, R$^7$, and R$^8$ are each acetyl groups), and the fully deprotected forms thereof (compounds or derivatives having formula (IV-H), wherein R$^6$, R$^7$, and R$^8$ are each hydrogen), in commercial quantities. In accordance with such an embodiment, the present disclosure provides a novel method whereby mechanic forces and/or sealed conditions, and extraction conditions, are used to minimize solvent and reagent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product reduced nicotinoyl riboside compounds include compounds or derivatives having formula (IV), or salts, solvates, or prodrugs thereof:

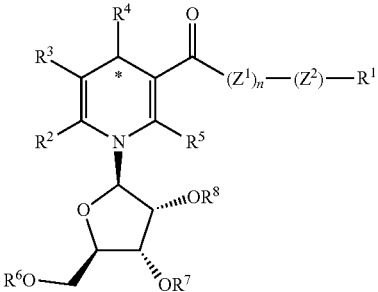

(IV)

wherein Z$^1$ and Z$^2$ are independently NH or oxygen;
n is 0 or 1;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl (C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$) alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O (C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

wherein when R$^1$ is hydrogen, Z$^2$ is oxygen, and n is 0, the compound or derivative having formula (IV) may optionally take the form of the carboxylate anion conjugate base species of the compound or derivative having formula (IV), further optionally associated with a positively charged counterion selected from the group consisting of alkali metal, alkaline earth metal, transition metal, and base addition cations;

R$^A$ is selected from the group consisting of —H, —(C$_1$-C$_6$)alkyl, —(CH$_2$)$_3$—NH—C(NH$_2$)(=NH), —CH$_2$C(=O) NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B$$_2$, —C(=NR$^B$)NR$^B$$_2$, —OR$^B$, —OC(O)(C$_1$-C$_6$)alkyl, —OC(O)O(C$_1$-C$_6$)alkyl, —OC(O)NR$^B$$_2$, —(C$_1$-C$_6$)alkylene-NR$^B$$_2$, —NR$^B$$_2$, —NR$^B$C(O)R$^B$, —NR$^B$C(O)O(C$_1$-C$_6$)alkyl, —NR$^B$C(O)NR$^B$$_2$, —NR$^B$SO$_2$NR$^B$$_2$, —SR$^B$, —S(O)R$^B$, —SO$_2$R$^B$, —OSO$_2$(C$_1$-C$_6$)alkyl, —SO$_2$NR$^B$$_2$, —(C$_1$-C$_6$) perfluoroalkyl, and —(C$_1$-C$_6$)alkylene-OR$^B$;

R$^2$ and R$^3$ are each independently selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O) NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$ (C$_1$-C$_6$)alkyl, —SO$_2$NR$^C$$_2$, —(C$_1$-C$_6$)perfluoroalkyl, and —(C$_1$-C$_6$)alkylene-OR$^C$;

R$^4$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein C* has an absolute configuration of R or S, or a mixture of R and S;

R$^5$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^6$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with an alternative embodiment, prototype product reduced nicotinoyl riboside compounds include compounds or derivatives having formula (IVa), or salts, solvates, or prodrugs thereof:

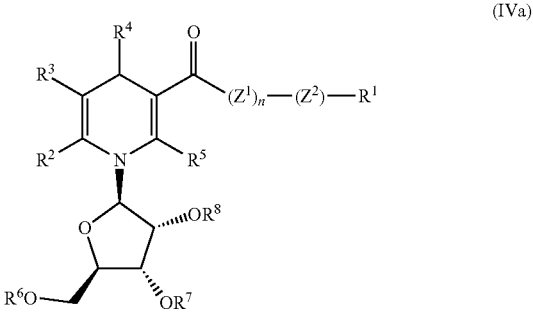

(IVa)

wherein Z$^1$ and Z$^2$ are independently NH or oxygen;

n is 0 or 1;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl (C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein when R$^1$ is hydrogen, Z$^2$ is oxygen, and n is 0, the compound or derivative having formula (IVa) may optionally take the form of the carboxylate anion conjugate base species of the compound or derivative having formula (IVa), further optionally associated with a positively charged counterion selected from the group consisting of alkali metal, alkaline earth metal, transition metal, and base addition cations;

$R^A$ is selected from the group consisting of —H, —($C_1$-$C_6$)alkyl, —$(CH_2)_3$—NH—$C(NH_2)(=NH)$, —$CH_2C(=O)$ $NH_2$, —$CH_2COOH$, —$CH_2SH$, —$(CH_2)_2C(=O)$—$NH_2$, —$(CH_2)_2COOH$, —$CH_2$-(2-imidazolyl), —$CH(CH_3)$—$CH_2$—$CH_3$, —$CH_2CH(CH_3)_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —$CH(CH_3)_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —$C(O)R^B$, —$C(O)OR^B$, —$C(O)NR^B_2$, —$C(=NR^B)NR^B_2$, —$OR^B$, —$OC(O)(C_1$-$C_6)$alkyl, —$OC(O)O(C_1$-$C_6)$alkyl, —$OC(O)NR^B_2$, —($C_1$-$C_6$)alkylene-$NR^B_2$, —$NR^B_2$, —$NR^BC(O)R^B$, —$NR^BC(O)O(C_1$-$C_6)$alkyl, —$NR^BC(O)NR^B_2$, —$NR^BSO_2NR^B_2$, —$SR^B$, —$S(O)R^B$, —$SO_2R^B$, —$OSO_2(C_1$-$C_6)$alkyl, —$SO_2NR^B_2$, —($C_1$-$C_6$)perfluoroalkyl, and —($C_1$-$C_6$)alkylene-$OR^B$;

each of $R^2$, $R^3$, $R^4$, and $R^5$ is hydrogen;

$R^6$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —($C_1$-$C_6$)alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C_2$, —$SR^C$, —$S(O)R^C$, —$SO_2R^C$, —$OSO_2(C_1$-$C_6)$alkyl, —$SO_2NR^C_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —($C_1$-$C_6$)alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C_2$, —$SR^C$, —$S(O)R^C$, —$SO_2R^C$, —$OSO_2(C_1$-$C_6)$alkyl, —$SO_2NR^C_2$, —($C_1$-$C_6$)perfluoroalkyl, and —($C_1$-$C_6$)alkylene-$OR^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —$C(O)R^C$, —$C(O)OR^C$, —$C(O)NR^C_2$—$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —($C_1$-$C_6$)alkylene-$NR^C_2$, —$NR^C_2$, —$NR^CC(O)R^C$, —$NR^CC(O)O(C_1$-$C_6)$alkyl, —$NR^CC(O)NR^C_2$—$NR^CSO_2NR^C_2$, —$SR^C$, —$S(O)R^C$, —$SO_2R^C$, —$OSO_2(C_1$-$C_6)$alkyl, —$SO_2NR^C_2$, —($C_1$-$C_6$)perfluoroalkyl, and —($C_1$-$C_6$)alkylene-$OR^C$;

provided that the absolute configuration of C** is R or S, or a mixture of R and S.

In accordance with one embodiment, the present disclosure provides a novel method for the preparation of compounds or derivatives having formula (IV-H), or salts, solvates, or prodrugs thereof, wherein $R^6$, $R^7$, and $R^8$ are each hydrogen. In accordance with such an embodiment, the present disclosure provides a novel method whereby mechanic forces are used to minimize solvent and reagent quantities, decrease reaction times, increase overall conversion, and facilitate product purification in a multistep or single-step synthetic sequence, whereby by-product formation is minimized, and whereby by-products that are removed readily by filtration or evaporation are generated. Prototype product reduced nicotinoyl riboside compounds include compounds or derivatives having formula (IV-H), or salts, solvates, or prodrugs thereof, wherein $R^6$, $R^7$, and $R^8$ are each hydrogen:

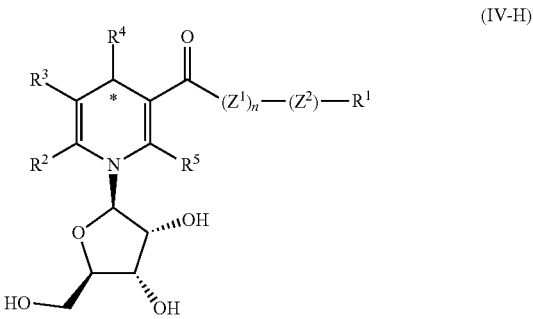

(IV-H)

wherein $Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl($C_1$-$C_4$)alkyl, heterocycle($C_1$-$C_4$)alkyl, —N($R^A$)—$CO_2R^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

wherein when R$^1$ is hydrogen, Z$^2$ is oxygen, and n is 0, the compound or derivative having formula (IV-H) may optionally take the form of the carboxylate anion conjugate base species of the compound or derivative having formula (IV-H), further optionally associated with a positively charged counterion selected from the group consisting of alkali metal, alkaline earth metal, transition metal, and base addition cations;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B$$_2$, —C(=NR$^B$)NR$^B$$_2$, —OR$^B$, —OC(O)(C$_1$-C$_6$)alkyl, —OC(O)O(C$_1$-C$_6$)alkyl, —OC(O)NR$^B$$_2$, —(C$_1$-C$_6$)alkylene-NR$^B$$_2$, —NR$^B$$_2$, —NR$^B$C(O)R$^B$, —NR$^B$C(O)O(C$_1$-C$_6$)alkyl, —NR$^B$C(O)NR$^B$$_2$, —NR$^B$SO$_2$NR$^B$$_2$, —SR$^B$, —S(O)R$^B$, —SO$_2$R$^B$, —OSO$_2$(C$_1$-C$_6$)alkyl, —SO$_2$NR$^B$$_2$, —(C$_1$-C$_6$)perfluoroalkyl, and —(C$_1$-C$_6$)alkylene-OR$^B$;

R$^2$ and R$^3$ are each independently selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$—NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

R$^4$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$—OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

wherein C* has an absolute configuration of R or S, or a mixture of R and S;

R$^5$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$—OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with an alternative embodiment, prototype product reduced nicotinoyl riboside compounds include compounds or derivatives having formula (IVa-H), or salts, solvates, or prodrugs thereof, wherein R$^6$, R$^7$, and R$^8$ are each hydrogen:

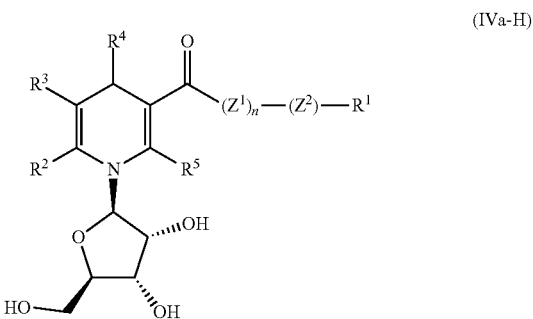

(IVa-H)

wherein Z$^1$ and Z$^2$ are independently NH or oxygen;

n is 0 or 1;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl (C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

wherein when R$^1$ is hydrogen, Z$^2$ is oxygen, and n is 0, the compound or derivative having formula (IVa-H) may optionally take the form of the carboxylate anion conjugate base species of the compound or derivative having formula (IVa-H), further optionally associated with a positively charged counterion selected from the group consisting of alkali metal, alkaline earth metal, transition metal, and base addition cations;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—

$CH_2$—$CH_3$, —$CH_2CH(CH_3)_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —$CH(CH_3)_2$, —$NH_2$, and —$CH_2$—$CH_3$;

each $R^B$ is independently hydrogen or —$(C_1$-$C_8)$alkyl;

each $R^C$ is independently selected from the group consisting of hydrogen, —$(C_1$-$C_8)$alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^B$, —$C(O)OR^B$, —$C(O)NR^B{}_2$, —$C(=NR^B)NR^B{}_2$, —$OR^B$, —$OC(O)(C_1$-$C_6)$alkyl, —$OC(O)O(C_1$-$C_6)$alkyl, —$OC(O)NR^B{}_2$, —$(C_1$-$C_6)$alkylene-$NR^B{}_2$, —$NR^B{}_2$, —$NR^BC(O)R^B$, —$NR^BC(O)O(C_1$-$C_6)$alkyl, —$NR^BC(O)NR^B{}_2$, —$NR^BSO_2NR^B{}_2$, —$SR^B$, —$S(O)R^B$, —$SO_2R^B$, —$OSO_2(C_1$-$C_6)$alkyl, —$SO_2NR^B{}_2$, —$(C_1$-$C_6)$perfluoroalkyl, and —$(C_1$-$C_6)$alkylene-$OR^B$;

each of $R^2$, $R^3$, $R^4$, and $R^5$ is hydrogen;

provided that the absolute configuration of C** is R or S, or a mixture of R and S.

In accordance with one embodiment, the present disclosure provides a novel method for the preparation of compounds or derivatives having formula (V), or salts, solvates, or prodrugs thereof, such as phosphorylated analogs of reduced nicotinoyl ribosides, in commercial quantities. In accordance with such an embodiment, the present disclosure provides a novel method whereby mechanic forces are used to minimize solvent quantities, decrease reaction times, increase overall conversion, and facilitate product purification in a multistep synthetic sequence, whereby by-product formation is minimized, and whereby primarily by-products that can be removed readily by filtration or evaporation are generated. Prototype product phosphorylated analogs of reduced nicotinoyl riboside compounds include compounds or derivatives having formula (V), or salts, solvates, or prodrugs thereof:

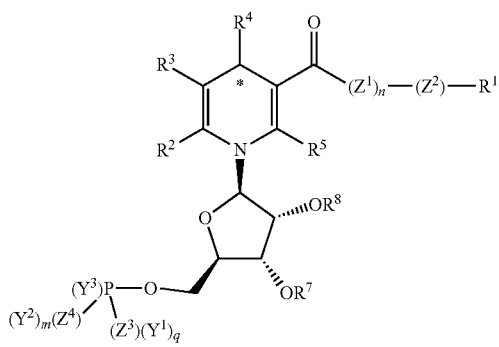

(V)

wherein each $Y^1$ and $Y^2$ is independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —$N(R^4)$—$CO_2R^C$, —$N(R^4)$—$CO_2R^B$, —$CH$—$(R^A)$—$NH_2$, and —$CH$—$(R^A)$—$CO_2R^B$; wherein the substituted $(C_1$-$C_8)$alkyl, substituted $(C_1$-$C_8)$cycloalkyl, substituted aryl, substituted heteroaryl, substituted heterocycle, and substituted amino are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C{}_2$, —$C(=NR^C)NR^C{}_2$, —$OR^C$, —$OC(O)(C_1$-$C_6)$alkyl, —$OC(O)O(C_1$-$C_6)$alkyl, —$OC(O)NR^C{}_2$, —$(C_1$-$C_6)$alkylene-$NR^C{}_2$, —$NR^C{}_2$, —$NR^CC(O)R^C$, —$NR^CC(O)O(C_1$-$C_6)$alkyl, —$NR^CC(O)NR^C{}_2$, —$NR^CSO_2NR^C{}_2$, —$SR^C$, —$S(O)R^C$, —$SO_2R^C$, —$OSO_2(C_1$-$C_6)$alkyl, —$SO_2NR^C{}_2$, —$(C_1$-$C_6)$perfluoroalkyl, and —$(C_1$-$C_6)$alkylene-$OR^C$;

or, alternatively, $Y^1$ and $Y^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C{}_2$, —$C(=NR^C)NR^C{}_2$, —$OR^C$, —$OC(O)(C_1$-$C_6)$alkyl, —$OC(O)O(C_1$-$C_6)$alkyl, —$OC(O)NR^C{}_2$, —$(C_1$-$C_6)$alkylene-$NR^C{}_2$, —$NR^C{}_2$, —$NR^CC(O)R^C$, —$NR^CC(O)O(C_1$-$C_6)$alkyl, —$NR^CC(O)NR^C{}_2$, —$NR^CSO_2NR^C{}_2$, —$SR^C$, —$S(O)R^C$, —$SO_2R^C$, —$OSO_2(C_1$-$C_6)$alkyl, —$SO_2NR^C{}_2$, —$(C_1$-$C_6)$perfluoroalkyl, and —$(C_1$-$C_6)$alkylene-$OR^C$;

optionally wherein $Y^3$ is oxygen, sulfur, or absent;

each of $Z^1$ and $Z^2$ is independently NH or oxygen;

each of $Z^3$ and $Z^4$ is independently nitrogen or oxygen;

m is 1 or 2;

n is 0 or 1;

q is 1 or 2;

$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl $(C_1$-$C_4)$alkyl, heterocycle$(C_1$-$C_4)$alkyl, —$N(R^4)$—$CO_2R^C$, —$N(R^4)$—$CO_2R^B$, —$CH$—$(R^A)$—$NH_2$, and —$CH$—$(R^A)$—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C{}_2$, —$C(=NR^C)NR^C{}_2$, —$OR^C$, —$OC(O)(C_1$-$C_6)$alkyl, —$OC(O)O(C_1$-$C_6)$alkyl, —$OC(O)NR^C{}_2$, —$(C_1$-$C_6)$alkylene-$NR^C{}_2$, —$NR^C{}_2$, —$NR^CC(O)R^C$, —$NR^CC(O)O(C_1$-$C_6)$alkyl, —$NR^CC(O)NR^C{}_2$, —$NR^CSO_2NR^C{}_2$, —$SR^C$, —$S(O)R^C$, —$SO_2R^C$, —$OSO_2(C_1$-$C_6)$alkyl, —$SO_2NR^C{}_2$, —$(C_1$-$C_6)$perfluoroalkyl, and —$(C_1$-$C_6)$alkylene-$OR^C$;

wherein when $R^1$ is hydrogen, $Z^2$ is oxygen, and n is 0, the compound or derivative having formula (V) may optionally take the form of the carboxylate anion conjugate base species of the compound or derivative having formula (V), further optionally associated with a positively charged counterion selected from the group consisting of alkali metal, alkaline earth metal, transition metal, and base addition cations;

$R^A$ is selected from the group consisting of —H, —$(C_1$-$C_6)$alkyl, —$(CH_2)_3$—NH—$C(NH_2)(=NH)$, —$CH_2C(=O)NH_2$, —$CH_2COOH$, —$CH_2SH$, —$(CH_2)_2C(=O)$—$NH_2$, —$(CH_2)_2COOH$, —$CH_2$-(2-imidazolyl), —$CH(CH_3)$—$CH_2$—$CH_3$, —$CH_2CH(CH_3)_2$, —$(CH_2)_4$—$NH_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B$$_2$, —C(=NR$^B$)NR$^B$$_2$, —OR$^B$, —OC(O)(C$_1$-C$_6$)alkyl, —OC(O)O(C$_1$-C$_6$)alkyl, —OC(O)NR$^B$$_2$, —(C$_1$-C$_6$)alkylene-NR$^B$$_2$, —R$^B$$_2$, —NR$^B$C(O)R$^B$, —NR$^B$C(O)O(C$_1$-C$_6$)alkyl, —NR$^B$C(O)NR$^B$$_2$, —NR$^B$SO$_2$NR$^B$$_2$, —SR$^B$, —S(O)R$^B$, —SO$_2$R$^B$, —OSO$_2$(C$_1$-C$_6$)alkyl, —SO$_2$NR$^B$$_2$, —(C$_1$-C$_6$)perfluoroalkyl, and —(C$_1$-C$_6$)alkylene-OR$^B$;

R$^2$ and R$^3$ are each independently selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

R$^4$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

wherein C* has an absolute configuration of R or S, or a mixture of R and S;

R$^5$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$, —NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$—NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$) perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$) cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-C$_6$)alkyl, —OC(O)O(C$_1$-C$_6$)alkyl, —OC(O)NR$^C$$_2$, —(C$_1$-C$_6$)alkylene-NR$^C$$_2$, —NR$^C$$_2$, —NR$^C$C(O)R$^C$, —NR$^C$C(O)O(C$_1$-C$_6$)alkyl, —NR$^C$C(O)NR$^C$$_2$—NR$^C$SO$_2$NR$^C$$_2$, —SR$^C$, —S(O)R$^C$, —SO$_2$R$^C$, —OSO$_2$(C$_1$-C$_6$)alkyl, —SO$_2$NR$^C$$_2$, —(C$_1$-C$_6$) perfluoroalkyl, and —(C$_1$-C$_6$)alkylene-OR$^C$;

provided that the absolute configuration of C** is R or S, or a mixture of R and S.

In accordance with such an embodiment, appropriate starting materials for the methods of the present disclosure for the preparation of compounds or derivatives having formula (V), or salts, solvates, or prodrugs thereof, include compounds or derivatives having formula (IVb), or salts, solvates, or prodrugs thereof:

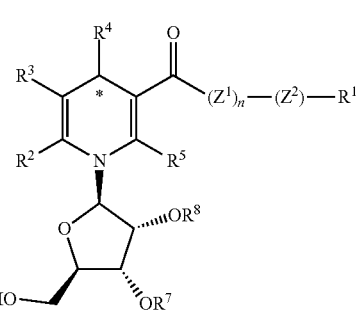

(IVb)

Z$^1$ and Z$^2$ are independently NH or oxygen;

n is 0 or 1;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl (C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C$$_2$, —C(=NR$^C$)NR$^C$$_2$, —OR$^C$, —OC(O)(C$_1$-

$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

wherein when R$^1$ is hydrogen, Z$^2$ is oxygen, and n is 0, the compound or derivative having formula (IVb) may optionally take the form of the carboxylate anion conjugate base species of the compound or derivative having formula (IVb), further optionally associated with a positively charged counterion selected from the group consisting of alkali metal, alkaline earth metal, transition metal, and base addition cations;

R$^4$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —($C_1$-$C_8$)alkyl;

each R$^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)($C_1$-$C_6$)alkyl, —OC(O)O($C_1$-$C_6$)alkyl, —OC(O)NR$^B_2$, —($C_1$-$C_6$)alkylene-NR$^B_2$, —NR$^B_2$, —NR$^B$C(O)R$^B$, —NR$^B$C(O)O($C_1$-$C_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$($C_1$-$C_6$)alkyl, —SO$_2$NR$^B_2$, —($C_1$-$C_6$)perfluoroalkyl, and —($C_1$-$C_6$)alkylene-OR$^B$;

R$^2$ and R$^3$ are each independently selected from the group consisting of hydrogen, —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

R$^4$ is selected from the group consisting of hydrogen, —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

wherein C* has an absolute configuration of R or S, or a mixture of R and S;

R$^5$ is selected from the group consisting of hydrogen, —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

R$^7$ and R$^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

provided that the absolute configuration of C** is R or S, or a mixture of R and S.

In accordance with an alternative embodiment, the present disclosure provides a novel method for the preparation of compounds or derivatives having formula (Va), or salts, solvates, or prodrugs thereof, such as phosphorylated analogs of reduced nicotinoyl ribosides, in commercial quantities. In accordance with such an embodiment, the present disclosure provides a novel method whereby mechanic forces are used to minimize solvent quantities, decrease reaction times, increase overall conversion, and facilitate product purification in a multistep synthetic sequence, whereby by-product formulation is minimized, and whereby primarily by-products that can be removed readily by filtration or evaporation are generated. Prototype product phosphorylated analogs of reduced nicotinoyl riboside compounds include compounds or derivatives having formula (Va), or salts, solvates, or prodrugs thereof:

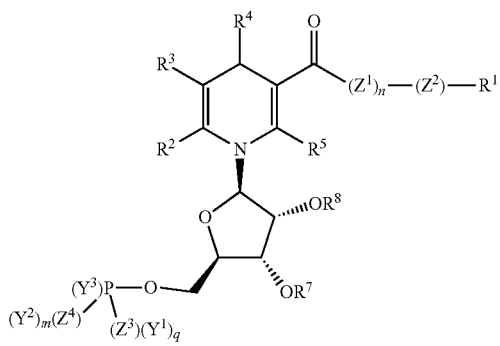

(Va)

wherein each $Y^1$ and $Y^2$ is independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—CO$_2$$R^C$, —N($R^A$)—CO$_2$$R^B$, —CH—($R^A$)—NH$_2$, and —CH—($R^A$)—CO$_2$$R^B$; wherein the substituted $(C_1$-$C_8)$alkyl, substituted $(C_1$-$C_8)$cycloalkyl, substituted aryl, substituted heteroaryl, substituted heterocycle, and substituted amino are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —NO$_2$, —C(O)$R^C$, —C(O)O$R^C$, —C(O)N$R^C$$_2$, —C(=N$R^C$)N$R^C$$_2$, —O$R^C$, —OC(O)$(C_1$-$C_6)$alkyl, —OC(O)O$(C_1$-$C_6)$alkyl, —OC(O)N$R^C$$_2$, —$(C_1$-$C_6)$alkylene-N$R^C$$_2$, —N$R^C$$_2$, —N$R^C$C(O)$R^C$, —N$R^C$C(O)O$(C_1$-$C_6)$alkyl, —N$R^C$C(O)N$R^C$$_2$, —N$R^C$SO$_2$N$R^C$$_2$, —S$R^C$, —S(O)$R^C$, —SO$_2$$R^C$, —OSO$_2$$(C_1$-$C_6)$alkyl, —SO$_2$N$R^C$$_2$, —$(C_1$-$C_6)$perfluoroalkyl, and —$(C_1$-$C_6)$alkylene-O$R^C$;

or, alternatively, $Y^1$ and $Y^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —$(C_1$-$C_6)$alkyl, —$(C_2$-$C_6)$alkenyl, —$(C_2$-$C_6)$alkynyl, halogen, —CN, —NO$_2$, —C(O)$R^C$, —C(O)O$R^C$, —C(O)N$R^C$$_2$, —C(=N$R^C$)N$R^C$$_2$, —O$R^C$, —OC(O)$(C_1$-$C_6)$alkyl, —OC(O)O$(C_1$-$C_6)$alkyl, —OC(O)N$R^C$$_2$, —$(C_1$-$C_6)$alkylene-N$R^C$$_2$, —N$R^C$$_2$, —N$R^C$C(O)$R^C$, —N$R^C$C(O)O$(C_1$-$C_6)$alkyl, —N$R^C$C(O)N$R^C$$_2$, —N$R^C$SO$_2$N$R^C$$_2$, —S$R^C$, —S(O)$R^C$, —SO$_2$$R^C$, —OSO$_2$$(C_1$-$C_6)$alkyl, —SO$_2$N$R^C$$_2$, —$(C_1$-$C_6)$perfluoroalkyl, and —$(C_1$-$C_6)$alkylene-O$R^C$;

optionally wherein $Y^3$ is oxygen, sulfur, or absent;
each of $Z^1$ and $Z^2$ is independently NH or oxygen;
each of $Z^3$ and $Z^4$ is independently nitrogen or oxygen;
m is 1 or 2;
n is 0 or 1;
q is 1 or 2;
$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl $(C_1$-$C_4)$alkyl, heterocycle$(C_1$-$C_4)$alkyl, —N($R^A$)—CO$_2$$R^C$, —N($R^A$)—CO$_2$$R^B$, —CH—($R^A$)—NH$_2$, and —CH—($R^A$)—CO$_2$$R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —NO$_2$, —C(O)$R^C$, —C(O)O$R^C$, —C(O)N$R^C$$_2$, —C(=N$R^C$)N$R^C$$_2$, —O$R^C$, —OC(O)$(C_1$-$C_6)$alkyl, —OC(O)O$(C_1$-$C_6)$alkyl, —OC(O)N$R^C$$_2$, —$(C_1$-$C_6)$alkylene-N$R^C$$_2$, —N$R^C$$_2$, —N$R^C$C(O)$R^C$, —N$R^C$C(O)O$(C_1$-$C_6)$alkyl, —N$R^C$C(O)N$R^C$$_2$, —N$R^C$SO$_2$N$R^C$$_2$, —S$R^C$, —S(O)$R^C$, —SO$_2$$R^C$, —OSO$_2$$(C_1$-$C_6)$alkyl, —SO$_2$N$R^C$$_2$, —$(C_1$-$C_6)$perfluoroalkyl, and —$(C_1$-$C_6)$alkylene-O$R^C$;

wherein when $R^1$ is hydrogen, $Z^2$ is oxygen, and n is 0, the compound or derivative having formula (Va) may optionally take the form of the carboxylate anion conjugate base species of the compound or derivative having formula (Va), further optionally associated with a positively charged counterion selected from the group consisting of alkali metal, alkaline earth metal, transition metal, and base addition cations;

$R^A$ is selected from the group consisting of —H, —$(C_1$-$C_6)$alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each $R^B$ is independently hydrogen or —$(C_1$-$C_8)$alkyl;
each $R^C$ is independently selected from the group consisting of hydrogen, —$(C_1$-$C_8)$alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —NO$_2$, —C(O)$R^B$, —C(O)O$R^B$, —C(O)N$R^B$$_2$, —C(=N$R^B$)N$R^B$$_2$, —O$R^B$, —OC(O)$(C_1$-$C_6)$alkyl, —OC(O)O$(C_1$-$C_6)$alkyl, —OC(O)N$R^B$$_2$, —$(C_1$-$C_6)$alkylene-N$R^B$$_2$, —N$R^B$$_2$, —N$R^B$C(O)$R^B$, —N$R^B$C(O)O$(C_1$-$C_6)$alkyl, —N$R^B$C(O)N$R^B$$_2$, —N$R^B$SO$_2$N$R^B$$_2$, —S$R^B$, —S(O)$R^B$, —SO$_2$$R^B$, —OSO$_2$$(C_1$-$C_6)$alkyl, —SO$_2$N$R^B$$_2$, —$(C_1$-$C_6)$perfluoroalkyl, and —$(C_1$-$C_6)$alkylene-O$R^B$;

each of $R^2$, $R^3$, $R^4$, and $R^5$ is hydrogen;
$R^7$ and $R^8$ are independently selected from the group consisting of hydrogen, —C(O)R', —C(O)OR', —C(O)NHR', substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —NO$_2$, —C(O)$R^C$, —C(O)O$R^C$, —C(O)N$R^C$$_2$—C(=N$R^C$)N$R^C$$_2$, —O$R^C$, —OC(O)$(C_1$-$C_6)$alkyl, —OC(O)O$(C_1$-$C_6)$alkyl, —OC(O)N$R^C$$_2$, —$(C_1$-$C_6)$alkylene-N$R^C$$_2$, —N$R^C$$_2$, —N$R^C$C(O)$R^C$, —N$R^C$C(O)O$(C_1$-$C_6)$alkyl, —N$R^C$C(O)N$R^C$$_2$—N$R^C$SO$_2$N$R^C$$_2$, —S$R^C$, —S(O)$R^C$, —SO$_2$$R^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

provided that the absolute configuration of C** is R or S, or a mixture of R and S.

In accordance with such an embodiment, appropriate starting materials for the methods of the present disclosure for the preparation of compounds or derivatives having formula (Va), or salts, solvates, or prodrugs thereof, include compounds or derivatives having formula (IVc), or salts, solvates, or prodrugs thereof:

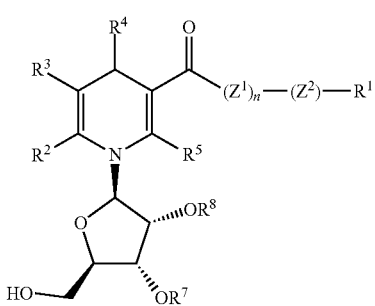

(IVc)

Z$^1$ and Z$^2$ are independently NH or oxygen;

n is 0 or 1;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl (C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

wherein when R$^1$ is hydrogen, Z$^2$ is oxygen, and n is 0, the compound or derivative having formula (IVc) may optionally take the form of the carboxylate anion conjugate base species of the compound or derivative having formula (IVc), further optionally associated with a positively charged counterion selected from the group consisting of alkali metal, alkaline earth metal, transition metal, and base addition cations;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, —NH$_2$, and —CH$_2$—CH$_3$;

each R$^B$ is independently hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)alkylene-NR$^B_2$, —NR$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$)perfluoroalkyl, and —(C$_1$-C$_6$)alkylene-OR$^B$;

each of R$^2$, R$^3$, R$^4$, and R$^5$ is hydrogen;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$—C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$;

wherein the substituted $(C_1$-$C_8)$alkyl, substituted $(C_1$-$C_8)$ cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —$(C_1$-$C_6)$alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2$$R^C$, —OSO$_2$($C_1$-$C_6$)alkyl, —SO$_2$N$R^C_2$, —$(C_1$-$C_6)$perfluoroalkyl, and —$(C_1$-$C_6)$alkylene-O$R^C$;

provided that the absolute configuration of C** is R or S, or a mixture of R and S.

In accordance with one embodiment, the present disclosure provides a novel method for the preparation of compounds or derivatives having formula (VI), or salts, solvates, or prodrugs thereof, such as adenylyl dinucleotide conjugates of reduced nicotinoyl ribosides, in commercial quantities. In accordance with such an embodiment, the present disclosure provides a novel method whereby mechanic forces are used to minimize solvent quantities, decrease reaction times, increase overall conversion, and facilitate product purification, whereby by-product formation is minimized. Prototype product reduced nicotinoyl riboside compounds include compounds or derivatives having formula (VI), or salts, solvates, or prodrugs thereof:

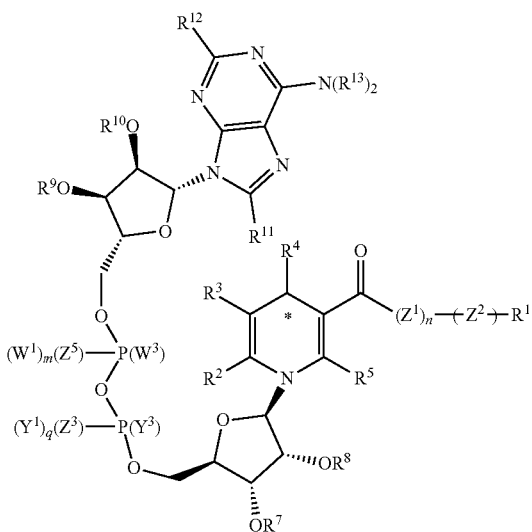

(VI)

wherein each $Y^1$ is independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^4$)—CO$_2$$R^C$, —N($R^4$)—CO$_2$$R^B$, —CH—($R^4$)—NH$_2$, and —CH—($R^4$)—CO$_2$$R^B$; wherein the substituted $(C_1$-$C_8)$alkyl, substituted $(C_1$-$C_8)$cycloalkyl, substituted aryl, substituted heteroaryl, substituted heterocycle, and substituted amino are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —NO$_2$, —C(O)$R^C$, —C(O)O$R^C$, —C(O)NR$^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —$(C_1$-$C_6)$alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2$$R^C$, —OSO$_2$($C_1$-$C_6$)alkyl, —SO$_2$N$R^C_2$, —$(C_1$-$C_6)$perfluoroalkyl, and —$(C_1$-$C_6)$alkylene-O$R^C$;

each $W^1$ is independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^4$)—CO$_2$$R^C$, —N($R^4$)—CO$_2$$R^B$, —CH—($R^4$)—NH$_2$, and —CH—($R^4$)—CO$_2$$R^B$; wherein the substituted $(C_1$-$C_8)$alkyl, substituted $(C_1$-$C_8)$cycloalkyl, substituted aryl, substituted heteroaryl, substituted heterocycle, and substituted amino are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —NO$_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —$(C_1$-$C_6)$alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2$$R^C$, —OSO$_2$($C_1$-$C_6$)alkyl, —SO$_2$N$R^C_2$, —$(C_1$-$C_6)$perfluoroalkyl, and —$(C_1$-$C_6)$alkylene-O$R^C$;

or, alternatively, $Y^1$ and $W^1$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —$(C_1$-$C_6)$alkyl, —$(C_2$-$C_6)$alkenyl, —$(C_2$-$C_6)$alkynyl, halogen, —CN, —NO$_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —$(C_1$-$C_6)$alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C_2$, —S$R^C$, —S(O)$R^C$, —SO$_2$$R^C$, —OSO$_2$($C_1$-$C_6$)alkyl, —SO$_2$N$R^C_2$, —$(C_1$-$C_6)$perfluoroalkyl, and —$(C_1$-$C_6)$alkylene-O$R^C$;

optionally wherein $Y^3$ is oxygen, sulfur, or absent;
optionally wherein $W^3$ is oxygen, sulfur, or absent;
each of $Z^1$ and $Z^2$ is independently NH or oxygen;
each of $Z^3$ and $Z^5$ is independently nitrogen or oxygen;
m is 1 or 2;
n is 0 or 1;
q is 1 or 2;

$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl $(C_1$-$C_4)$alkyl, heterocycle($C_1$-$C_4$)alkyl, —N($R^4$)—CO$_2$$R^C$, —N($R^4$)—CO$_2$$R^B$, —CH—($R^4$)—NH$_2$, and —CH—($R^4$)—CO$_2$$R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —NO$_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —$(C_1$-

$C_6$)alkylene-$NR^C_2$, —$NR^C_2$, —$NR^CC(O)R^C$, —$NR^CC(O)O$ ($C_1$-$C_6$)alkyl, —$NR^CC(O)NR^C_2$, —$NR^CSO_2NR^C_2$, —$SR^C$, —$S(O)R^C$, —$SO_2R^C$, —$OSO_2(C_1$-$C_6)$alkyl, —$SO_2NR^C_2$, —($C_1$-$C_6$)perfluoroalkyl, and —($C_1$-$C_6$)alkylene-$OR^C$;

wherein when $R^1$ is hydrogen, $Z^2$ is oxygen, and n is 0, the compound or derivative having formula (VI) may optionally take the form of the carboxylate anion conjugate base species of the compound or derivative having formula (VI), further optionally associated with a positively charged counterion selected from the group consisting of alkali metal, alkaline earth metal, transition metal, and base addition cations;

$R^4$ is selected from the group consisting of —H, —($C_1$-$C_6$)alkyl, —$(CH_2)_3$—NH—$C(NH_2)(=NH)$, —$CH_2C(=O)NH_2$, —$CH_2COOH$, —$CH_2SH$, —$(CH_2)_2C(=O)$—$NH_2$, —$(CH_2)_2COOH$, —$CH_2$-(2-imidazolyl), —$CH(CH_3)$—$CH_2$—$CH_3$, —$CH_2CH(CH_3)_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —$CH(CH_3)_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —$C(O)R^B$, —$C(O)OR^B$, —$C(O)NR^B_2$, —$C(=NR^B)NR^B_2$, —$OR^B$, —$OC(O)(C_1$-$C_6)$alkyl, —$OC(O)O(C_1$-$C_6)$alkyl, —$OC(O)NR^B_2$, —($C_1$-$C_6$)alkylene-$NR^B_2$, —$NR^B_2$, —$NR^BC(O)R^B$, —$NR^BC(O)O(C_1$-$C_6)$alkyl, —$NR^BC(O)NR^B_2$, —$NR^BSO_2NR^B_2$, —$SR^B$, —$S(O)R^B$, —$SO_2R^B$, —$OSO_2(C_1$-$C_6)$alkyl, —$SO_2NR^B_2$, —($C_1$-$C_6$)perfluoroalkyl, and —($C_1$-$C_6$)alkylene-$OR^B$;

$R^2$ and $R^3$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —($C_1$-$C_6$)alkylene-$NR^C_2$, —$NR^C_2$, —$NR^CC(O)R^C$, —$NR^CC(O)O(C_1$-$C_6)$alkyl, —$NR^CC(O)NR^C_2$—$NR^CSO_2NR^C_2$, —$SR^C$, —$S(O)R^C$, —$SO_2R^C$, —$OSO_2(C_1$-$C_6)$alkyl, —$SO_2NR^C_2$, —($C_1$-$C_6$)perfluoroalkyl, and —($C_1$-$C_6$)alkylene-$OR^C$;

$R^4$ is selected from the group consisting of hydrogen, —($C_1$-$C_6$)alkyl, —($C_2$-$C_6$)alkenyl, —($C_2$-$C_6$)alkynyl, halogen, —CN, —$NO_2$, —$C(O)R^C$, —$C(O)OR^C$, —$C(O)NR^C_2$, —$C(=NR^C)NR^C$, —$OR^C$, —$OC(O)(C_1$-$C_6)$alkyl, —$OC(O)O(C_1$-$C_6)$alkyl, —$OC(O)NR^C_2$, —($C_1$-$C_6$)alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C_2$, —$SR^C$, —$S(O)R^C$, —$SO_2R^C$, —$OSO_2(C_1$-$C_6)$alkyl, —$SO_2NR^C_2$, —($C_1$-$C_6$)perfluoroalkyl, and —($C_1$-$C_6$)alkylene-$OR^C$;

wherein C* has an absolute configuration of R or S, or a mixture of R and S;

$R^5$ is selected from the group consisting of hydrogen, —($C_1$-$C_6$)alkyl, —($C_2$-$C_6$)alkenyl, —($C_2$-$C_6$)alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —($C_1$-$C_6$)alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C_2$, —$SR^C$, —$S(O)R^C$, —$SO_2R^C$, —$OSO_2(C_1$-$C_6)$alkyl, —$SO_2NR^C_2$, —($C_1$-$C_6$)perfluoroalkyl, and —($C_1$-$C_6$)alkylene-$OR^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —$C(O)R^C$, —$C(O)OR^C$, —$C(O)NR^C_2$—$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —($C_1$-$C_6$)alkylene-$NR^C_2$, —$NR^C_2$, —$NR^CC(O)R^C$, —$NR^CC(O)O(C_1$-$C_6)$alkyl, —$NR^CC(O)NR^C_2$—$NR^CSO_2NR^C_2$, —$SR^C$, —$S(O)R^C$, —$SO_2R^C$, —$OSO_2(C_1$-$C_6)$alkyl, —$SO_2NR^C_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —($C_1$-$C_6$)alkylene-$NR^C_2$, —$NR^C_2$, —$NR^CC(O)R^C$, —$NR^CC(O)O(C_1$-$C_6)$alkyl, —$NR^CC(O)NR^C_2$—$NR^CSO_2NR^C_2$, —$SR^C$, —$S(O)R^C$, —$SO_2R^C$, —$OSO_2(C_1$-$C_6)$alkyl, —$SO_2NR^C_2$, —($C_1$-$C_6$) perfluoroalkyl, and —($C_1$-$C_6$)alkylene-$OR^C$;

$R^9$ and $R^{10}$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —($C_1$-$C_6$)alkylene-$NR^C_2$, —$NR^C_2$, —$NR^CC(O)R^C$, —$NR^CC(O)O(C_1$-$C_6)$alkyl, —$NR^CC(O)NR^C_2$—$NR^CSO_2NR^C_2$, —$SR^C$, —$S(O)R^C$, —$SO_2R^C$, —$OSO_2(C_1$-$C_6)$alkyl, —$SO_2NR^C_2$, —($C_1$-$C_6$) perfluoroalkyl, and —($C_1$-$C_6$)alkylene-$OR^C$;

$R^{11}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$) cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$) cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O ($C_1$-$C_6$)alkyl, —N$R^C$C(O)N$R^C_2$, —N$R^C$S$O_2$N$R^C_2$, —S$R^C$, —S(O)$R^C$, —S$O_2R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

$R^{12}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$) cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$) cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O ($C_1$-$C_6$)alkyl, —N$R^C$C(O)N$R^C_2$, —N$R^C$S$O_2$N$R^C_2$, —S$R^C$, —S(O)$R^C$, —S$O_2R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

each $R^{13}$ is independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$) alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$ —C(=N$R^C$) N$R^C_2$, —O$R^C$, —OC(O)($C_1$-$C_6$)alkyl, —OC(O)O($C_1$-$C_6$) alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O) N$R^C_2$, —N$R^C$S$O_2$N$R^C_2$, —S$R^C$, —S(O)$R^C$, —S$O_2R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

provided that the absolute configuration of C** is R or S, or a mixture of R and S.

In accordance with such an embodiment, appropriate starting materials for the methods of the present disclosure for the preparation of compounds or derivatives having formula (VI), or salts, solvates, or prodrugs thereof, include compounds or derivatives having formula (3), or salts thereof:

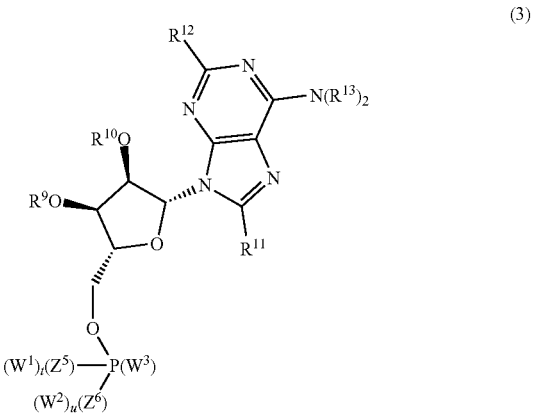

(3)

wherein each $W^1$ and $W^2$ is independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—$CO_2R^C$, —N($R^A$)—$CO_2R^B$, —CH—($R^A$)— $NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, substituted heterocycle, and substituted amino are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C$, —O$R^C$, —OC(O)($C_1$-$C_6$)alkyl, —OC (O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$S$O_2$N$R^C_2$, —S$R^C$, —S(O) $R^C$, —S$O_2R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

or, alternatively, $W^1$ and $W^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC (O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$S$O_2$N$R^C_2$, —S$R^C$, —S(O) $R^C$, —S$O_2R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

optionally wherein $W^3$ is oxygen, sulfur, or absent;
each of $Z^5$ and $Z^6$ is independently nitrogen or oxygen;
t is 1 or 2;
u is 1 or 2;
$R^9$ and $R^{10}$ are independently selected from the group consisting of hydrogen, —C(O)R', —C(O)OR', —C(O) NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)

alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B_2$, —C(=$NR^B$)$NR^B_2$, —$OR^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$NR^B_2$, —$NR^B$C(O)$R^B$, —$NR^B$C(O)O($C_1$-$C_6$)alkyl, —$NR^B$C(O)$NR^B_2$, —$NR^B$$SO_2$$NR^B_2$, —$SR^B$, —S(O)$R^B$, —$SO_2R^B$, —$OSO_2$($C_1$-$C_6$)alkyl, —$SO_2NR^B_2$, —($C_1$-$C_6$)perfluoroalkyl, and —($C_1$-$C_6$)alkylene-$OR^B$;

$R^{11}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$R^{12}$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

each $R^{13}$ is independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$—C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$—$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

provided that the absolute configuration of C** is R or S, or a mixture of R and S.

In accordance with an alternative embodiment, the present disclosure provides a novel method for the preparation of compounds or derivatives having formula (VIa), or salts, solvates, or prodrugs thereof, such as adenylyl dinucleotide conjugates of reduced nicotinoyl ribosides, in commercial quantities. In accordance with such an embodiment, the present disclosure provides a novel method whereby mechanic forces are used to minimize solvent quantities, decrease reaction times, increase overall conversion, and facilitate product purification, whereby by-product formation is minimized. Prototype product nicotinoyl riboside compounds include compounds or derivatives having formula (VIa), or salts, solvates, or prodrugs thereof:

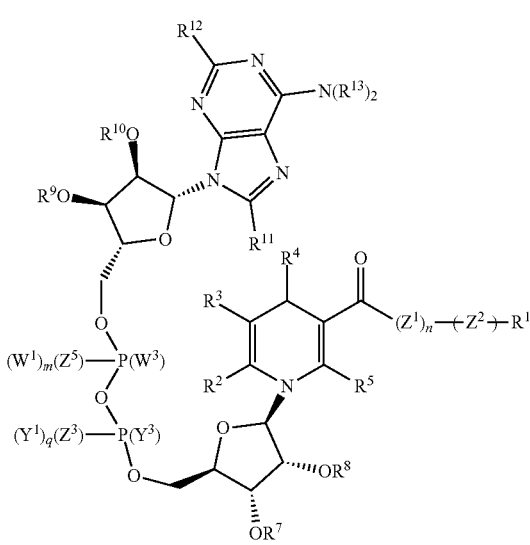

(VIa)

wherein each $Y^1$ is independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—$CO_2R^C$, —N($R^A$)—$CO_2R^B$, —CH—($R^A$)—$NH_2$, and —CH—($R^A$)—$CO_2R^B$; wherein the substituted $(C_1$-$C_8)$alkyl, substituted $(C_1$-$C_8)$cycloalkyl, substituted aryl, substituted heteroaryl, substituted heterocycle, and substituted amino are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C_2$, —$SR^C$, —S(O)$R^C$, —$SO_2R^C$, —$OSO_2(C_1$-$C_6$)alkyl, —$SO_2NR^C_2$, —($C_1$-$C_6$)perfluoroalkyl, and —($C_1$-$C_6$)alkylene-$OR^C$;

each $W^1$ is independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—$CO_2R^C$, —N($R^A$)—$CO_2R^B$, —CH—($R^A$)—$NH_2$, and —CH—($R^A$)—$CO_2R^B$; wherein the substituted $(C_1$-$C_8)$alkyl, substituted $(C_1$-$C_8)$cycloalkyl, substituted aryl, substituted heteroaryl, substituted heterocycle, and substituted amino are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C_2$, —$SR^C$, —S(O)$R^C$, —$SO_2R^C$, —$OSO_2(C_1$-$C_6$)alkyl, —$SO_2NR^C_2$, —($C_1$-$C_6$)perfluoroalkyl, and —($C_1$-$C_6$)alkylene-$OR^C$;

or, alternatively, $Y^1$ and $W^1$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C_2$, —$SR^C$, —S(O)$R^C$, —$SO_2R^C$, —$OSO_2(C_1$-$C_6$)alkyl, —$SO_2NR^C_2$, —($C_1$-$C_6$)perfluoroalkyl, and —($C_1$-$C_6$)alkylene-$OR^C$;

optionally wherein $Y^3$ is oxygen, sulfur, or absent;
optionally wherein $W^3$ is oxygen, sulfur, or absent;
each of $Z^1$ and $Z^2$ is independently NH or oxygen;
each of $Z^3$ and $Z^5$ is independently nitrogen or oxygen;
m is 1 or 2;
n is 0 or 1;
q is 1 or 2;

$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl $(C_1$-$C_4)$alkyl, heterocycle$(C_1$-$C_4)$alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C_2$, —$SR^C$, —S(O)$R^C$, —$SO_2R^C$, —$OSO_2(C_1$-$C_6$)alkyl, —$SO_2NR^C_2$, —($C_1$-$C_6$)perfluoroalkyl, and —($C_1$-$C_6$)alkylene-$OR^C$;

wherein when $R^1$ is hydrogen, $Z^2$ is oxygen, and n is 0, the compound or derivative having formula (VIa) may optionally take the form of the carboxylate anion conjugate base species of the compound or derivative having formula (VIa), further optionally associated with a positively charged counterion selected from the group consisting of alkali metal, alkaline earth metal, transition metal, and base addition cations;

$R^A$ is selected from the group consisting of —H, —$(C_1$-$C_6)$alkyl, —$(CH_2)_3$—NH—C($NH_2$)(=NH), —$CH_2$C(=O)$NH_2$, —$CH_2COOH$, —$CH_2SH$, —$(CH_2)_2C$(=O)—$NH_2$, —$(CH_2)_2COOH$, —$CH_2$-(2-imidazolyl), —CH($CH_3$)—$CH_2$—$CH_3$, —$CH_2CH(CH_3)_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3)_2$, —$NH_2$, and —$CH_2$—$CH_3$;

each $R^B$ is independently hydrogen or —$(C_1$-$C_8)$alkyl;

each $R^C$ is independently selected from the group consisting of hydrogen, —$(C_1$-$C_8)$alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)$(C_1$-$C_6)$alkyl, —OC(O)O$(C_1$-$C_6)$alkyl, —OC(O)N$R^B_2$, —$(C_1$-$C_6)$alkylene-N$R^B_2$, —$R^B_2$, —N$R^B$C(O)$R^B$, —N$R^B$C(O)O$(C_1$-$C_6)$alkyl, —N$R^B$C(O)N$R^B_2$, —N$R^B$$SO_2$N$R^B_2$, —S$R^B$, —S(O)$R^B$, —$SO_2$$R^B$, —$OSO_2$$(C_1$-$C_6)$alkyl, —$SO_2$N$R^B_2$, —$(C_1$-$C_6)$perfluoroalkyl, and —$(C_1$-$C_6)$alkylene-O$R^B$;

each of $R^2$, $R^3$, $R^4$, and $R^5$ is hydrogen;

$R^7$ and $R^8$ are independently selected from the group consisting of hydrogen, —C(O)R', —C(O)OR', —C(O)NHR', substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1$-$C_6)$alkyl, —OC(O)O$(C_1$-$C_6)$alkyl, —OC(O)N$R^C_2$, —$(C_1$-$C_6)$alkylene-N$R^C_2$, —N$R^C_2$, —N$R^C$C(O)$R^C$, —N$R^C$C(O)O$(C_1$-$C_6)$alkyl, —N$R^C$C(O)N$R^C_2$—N$R^C$$SO_2$N$R^C_2$, —S$R^C$, —S(O)$R^C$, —$SO_2$$R^C$, —$OSO_2$$(C_1$-$C_6)$alkyl, —$SO_2$N$R^C_2$, —$(C_1$-$C_6)$perfluoroalkyl, and —$(C_1$-$C_6)$alkylene-O$R^C$;

R' is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl$(C_1$-$C_4)$alkyl, heterocycle$(C_1$-$C_4)$alkyl, —N$(R^A)$—$CO_2$$R^C$, —N$(R^A)$—$CO_2$$R^B$, —CH—$(R^A)$—$NH_2$, and —CH—$(R^A)$—$CO_2$$R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1$-$C_6)$alkyl, —OC(O)O$(C_1$-$C_6)$alkyl, —OC(O)N$R^C_2$, —$(C_1$-$C_6)$alkylene-N$R^C_2$, —N$R^C_2$, —N$R^C$C(O)$R^C$, —N$R^C$C(O)O$(C_1$-$C_6)$alkyl, —N$R^C$C(O)N$R^C_2$, —N$R^C$$SO_2$N$R^C_2$, —S$R^C$, —S(O)$R^C$, —$SO_2$$R^C$, —$OSO_2$$(C_1$-$C_6)$alkyl, —$SO_2$N$R^C_2$, —$(C_1$-$C_6)$perfluoroalkyl, and —$(C_1$-$C_6)$alkylene-O$R^C$;

$R^9$ and $R^{10}$ are independently selected from the group consisting of hydrogen, —C(O)R', —C(O)OR', —C(O)NHR', substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1$-$C_6)$alkyl, —OC(O)O$(C_1$-$C_6)$alkyl, —OC(O)N$R^C_2$, —$(C_1$-$C_6)$alkylene-N$R^C_2$, —N$R^C_2$, —N$R^C$C(O)$R^C$, —N$R^C$C(O)O$(C_1$-$C_6)$alkyl, —N$R^C$C(O)N$R^C_2$—N$R^C$$SO_2$N$R^C_2$, —S$R^C$, —S(O)$R^C$, —$SO_2$$R^C$, —$OSO_2$$(C_1$-$C_6)$alkyl, —$SO_2$N$R^C_2$, —$(C_1$-$C_6)$perfluoroalkyl, and —$(C_1$-$C_6)$alkylene-O$R^C$;

$R^{11}$ is selected from the group consisting of hydrogen, —C(O)R', —C(O)OR', —C(O)NHR', substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1$-$C_6)$alkyl, —OC(O)O$(C_1$-$C_6)$alkyl, —OC(O)N$R^C_2$, —$(C_1$-$C_6)$alkylene-N$R^C_2$, —N$R^C_2$, —N$R^C$C(O)$R^C$, —N$R^C$C(O)O$(C_1$-$C_6)$alkyl, —N$R^C$C(O)N$R^C_2$, —N$R^C$$SO_2$N$R^C_2$, —S$R^C$, —S(O)$R^C$, —$SO_2$$R^C$, —$OSO_2$$(C_1$-$C_6)$alkyl, —$SO_2$N$R^C_2$, —$(C_1$-$C_6)$perfluoroalkyl, and —$(C_1$-$C_6)$alkylene-O$R^C$;

$R^{12}$ is selected from the group consisting of hydrogen, —C(O)R', —C(O)OR', —C(O)NHR', substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1$-$C_6)$alkyl, —OC(O)O$(C_1$-$C_6)$alkyl, —OC(O)N$R^C_2$, —$(C_1$-$C_6)$alkylene-N$R^C_2$, —N$R^C_2$, —N$R^C$C(O)$R^C$, —N$R^C$C(O)O$(C_1$-$C_6)$alkyl, —N$R^C$C(O)N$R^C_2$, —N$R^C$$SO_2$N$R^C_2$, —S$R^C$, —S(O)$R^C$, —$SO_2$$R^C$, —$OSO_2$$(C_1$-$C_6)$alkyl, —$SO_2$N$R^C_2$, —$(C_1$-$C_6)$perfluoroalkyl, and —$(C_1$-$C_6)$alkylene-O$R^C$;

each $R^{13}$ is independently selected from the group consisting of hydrogen, —C(O)R', —C(O)OR', —C(O)NHR', substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$—C(=N$R^C$)N$R^C_2$, —O$R^C$, —OC(O)$(C_1$-$C_6)$alkyl, —OC(O)O$(C_1$-$C_6)$alkyl, —OC(O)N$R^C_2$, —$(C_1$-$C_6)$alkylene-N$R^C_2$, —N$R^C_2$, —N$R^C$C(O)$R^C$, —N$R^C$C(O)O$(C_1$-$C_6)$alkyl, —N$R^C$C(O)

$NR^C{}_2$—$NR^CSO_2NR^C{}_2$, —$SR^C$, —$S(O)R^C$, —$SO_2R^C$, —$OSO_2(C_1\text{-}C_6)$alkyl, —$SO_2NR^C{}_2$, —$(C_1\text{-}C_6)$perfluoroalkyl, and —$(C_1\text{-}C_6)$alkylene-$OR^C$;

provided that the absolute configuration of C** is R or S, or a mixture of R and S.

In accordance with such an embodiment, appropriate starting materials for the method of the present disclosure for the preparation of compounds or derivatives having formula (VIa), or salts, solvates, or prodrugs thereof, include compounds or derivatives having formula (3), or salts thereof:

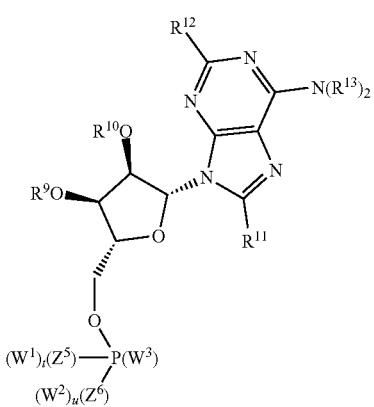

(3)

wherein each $W^1$ and $W^2$ is independently selected from the group consisting of hydrogen, sodium, potassium, lithium, substituted or unsubstituted $(C_1\text{-}C_8)$alkyl, substituted or unsubstituted $(C_1\text{-}C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —$N(R^A)$—$CO_2R^C$, —$N(R^A)$—$CO_2R^B$, —$C^{}H$—$(R^A)$—$NH_2$, and —$C^{}H$—$(R^A)$—$CO_2R^B$; wherein the substituted $(C_1\text{-}C_8)$alkyl, substituted $(C_1\text{-}C_8)$cycloalkyl, substituted aryl, substituted heteroaryl, substituted heterocycle, and substituted amino are substituted with one to five substituents independently selected from the group consisting of —$(C_1\text{-}C_6)$alkyl, —$(C_2\text{-}C_6)$alkenyl, —$(C_2\text{-}C_6)$alkynyl, halogen, —CN, —$NO_2$, —$C(O)R^C$, —$C(O)OR^C$, —$C(O)NR^C{}_2$, —$C(=NR^C)NR^C{}_2$, —$OR^C$, —$OC(O)(C_1\text{-}C_6)$alkyl, —$OC(O)O(C_1\text{-}C_6)$alkyl, —$OC(O)NR^C{}_2$, —$(C_1\text{-}C_6)$alkylene-$NR^C{}_2$, —$NR^C{}_2$, —$NR^CC(O)R^C$, —$NR^CC(O)O(C_1\text{-}C_6)$alkyl, —$NR^CC(O)NR^C{}_2$, —$NR^CSO_2NR^C{}_2$, —$SR^C$, —$S(O)R^C$, —$SO_2R^C$, —$OSO_2(C_1\text{-}C_6)$alkyl, —$SO_2NR^C{}_2$, —$(C_1\text{-}C_6)$perfluoroalkyl, and —$(C_1\text{-}C_6)$alkylene-$OR^C$;

or, alternatively, $W^1$ and $W^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —$(C_1\text{-}C_6)$alkyl, —$(C_2\text{-}C_6)$alkenyl, —$(C_2\text{-}C_6)$alkynyl, halogen, —CN, —$NO_2$, —$C(O)R^C$, —$C(O)OR^C$, —$C(O)NR^C{}_2$, —$C(=NR^C)NR^C{}_2$, —$OR^C$, —$OC(O)(C_1\text{-}C_6)$alkyl, —$OC(O)O(C_1\text{-}C_6)$alkyl, —$OC(O)NR^C{}_2$, —$(C_1\text{-}C_6)$alkylene-$NR^C{}_2$, —$NR^C{}_2$, —$NR^CC(O)R^C$, —$NR^CC(O)O(C_1\text{-}C_6)$alkyl, —$NR^CC(O)NR^C{}_2$, —$NR^CSO_2NR^C{}_2$, —$SR^C$, —$S(O)R^C$, —$SO_2R^C$, —$OSO_2(C_1\text{-}C_6)$alkyl, —$SO_2NR^C{}_2$, —$(C_1\text{-}C_6)$perfluoroalkyl, and —$(C_1\text{-}C_6)$alkylene-$OR^C$;

optionally wherein $W^3$ is oxygen, sulfur, or absent;
each of $Z^5$ and $Z^6$ are independently nitrogen or oxygen;
t is 1 or 2;
u is 1 or 2;
$R^9$ and $R^{10}$ are independently selected from the group consisting of hydrogen, —C(O)R', —C(O)OR', —C(O)NHR', substituted or unsubstituted $(C_1\text{-}C_8)$alkyl, substituted or unsubstituted $(C_1\text{-}C_8)$cycloalkyl, substituted or unsubstituted aryl, substituted or unsubstituted heteroaryl, substituted or unsubstituted heterocycle, substituted or unsubstituted aryl$(C_1\text{-}C_4)$alkyl, and substituted or unsubstituted heterocycle$(C_1\text{-}C_4)$alkyl; wherein the substituted $(C_1\text{-}C_8)$ alkyl, substituted $(C_1\text{-}C_8)$cycloalkyl, substituted aryl, substituted heteroaryl, substituted heterocycle, substituted aryl $(C_1\text{-}C_4)$alkyl, and substituted heterocycle$(C_1\text{-}C_4)$alkyl are substituted with one to five substituents independently selected from the group consisting of —$(C_1\text{-}C_6)$alkyl, —$(C_2\text{-}C_6)$alkenyl, —$(C_2\text{-}C_6)$alkynyl, halogen, —CN, —$NO_2$, —$C(O)R^C$, —$C(O)OR^C$, —$C(O)NR^C{}_2$, —$C(=NR^C)NR^C{}_2$, —$OR^C$, —$OC(O)(C_1\text{-}C_6)$alkyl, —$OC(O)O(C_1\text{-}C_6)$alkyl, —$OC(O)NR^C{}_2$, —$(C_1\text{-}C_6)$alkylene-$NR^C{}_2$, —$NR^C{}_2$, —$NR^CC(O)R^C$, —$NR^CC(O)O(C_1\text{-}C_6)$alkyl, —$NR^CC(O)NR^C{}_2$, —$NR^CSO_2NR^C{}_2$, —$SR^C$, —$S(O)R^C$, —$SO_2R^C$, —$OSO_2(C_1\text{-}C_6)$alkyl, —$SO_2NR^C{}_2$, —$(C_1\text{-}C_6)$perfluoroalkyl, and —$(C_1\text{-}C_6)$alkylene-$OR^C$;

R' is selected from the group consisting of hydrogen, substituted or unsubstituted $(C_1\text{-}C_8)$alkyl, substituted or unsubstituted $(C_1\text{-}C_8)$cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl$(C_1\text{-}C_4)$alkyl, heterocycle$(C_1\text{-}C_4)$alkyl, —$N(R^A)$—$CO_2R^C$, —$N(R^A)$—$CO_2R^B$, —$C^{}H$—$(R^A)$—$NH_2$, and —$C^{}H$—$(R^A)$—$CO_2R^B$; wherein the substituted $(C_1\text{-}C_8)$alkyl, substituted $(C_1\text{-}C_8)$ cycloalkyl, substituted aryl, substituted heteroaryl, and substituted heterocycle are substituted with one to five substituents independently selected from the group consisting of —$(C_1\text{-}C_6)$alkyl, —$(C_2\text{-}C_6)$alkenyl, —$(C_2\text{-}C_6)$alkynyl, halogen, —CN, —$NO_2$, —$C(O)R^C$, —$C(O)OR^C$, —$C(O)NR^C{}_2$, —$C(=NR^C)NR^C{}_2$, —$OR^C$, —$OC(O)(C_1\text{-}C_6)$alkyl, —$OC(O)O(C_1\text{-}C_6)$alkyl, —$OC(O)NR^C{}_2$, —$(C_1\text{-}C_6)$alkylene-$NR^C{}_2$, —$NR^C{}_2$, —$NR^CC(O)R^C$, —$NR^CC(O)O(C_1\text{-}C_6)$alkyl, —$NR^CC(O)NR^C{}_2$, —$NR^CSO_2NR^C{}_2$, —$SR^C$, —$S(O)R^C$, —$SO_2R^C$, —$OSO_2(C_1\text{-}C_6)$alkyl, —$SO_2NR^C{}_2$, —$(C_1\text{-}C_6)$perfluoroalkyl, and —$(C_1\text{-}C_6)$alkylene-$OR^C$;

$R^A$ is selected from the group consisting of —H, —$(C_1\text{-}C_6)$alkyl, —$(CH_2)_3$—NH—$C(NH_2)(=NH)$, —$CH_2C(=O)NH_2$, —$CH_2COOH$, —$CH_2SH$, —$(CH_2)_2C(=O)$—$NH_2$, —$(CH_2)_2COOH$, —$CH_2$-(2-imidazolyl), —$CH(CH_3)$—$CH_2$—$CH_3$, —$CH_2CH(CH_3)_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —$CH(CH_3)_2$, —$NH_2$, and —$CH_2$—$CH_3$;

each $R^B$ is independently hydrogen or —$(C_1\text{-}C_8)$alkyl;

each $R^C$ is independently selected from the group consisting of hydrogen, —$(C_1\text{-}C_8)$alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —$(C_1\text{-}C_6)$alkyl, —$(C_2\text{-}C_6)$alkenyl, —$(C_2\text{-}C_6)$alkynyl, halogen, —CN, —$NO_2$, —$C(O)R^B$, —$C(O)OR^B$, —$C(O)NR^B{}_2$, —$C(=NR^B)NR^B{}_2$, —$OR^B$, —$OC(O)(C_1\text{-}C_6)$alkyl, —$OC(O)O(C_1\text{-}C_6)$alkyl, —$OC(O)NR^B{}_2$, —$(C_1\text{-}C_6)$alkylene-$NR^B{}_2$, —$NR^B{}_2$, —$NR^BC(O)R^B$, —$NR^BC(O)O(C_1\text{-}C_6)$alkyl, —NR$^B$C(O)NR$^B_2$, —NR$^B$SO$_2$NR$^B_2$, —SR$^B$, —S(O)R$^B$, —SO$_2$R$^B$, —OSO$_2$(C$_1$-C$_6$)alkyl, —SO$_2$NR$^B_2$, —(C$_1$-C$_6$)perfluoroalkyl, and —(C$_1$-C$_6$)alkylene-OR$^B$;

R$^{11}$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^{12}$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, —(C$_1$-C$_6$)alkylene-OR$^C$;

each R$^{13}$ is independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

provided that the absolute configuration of C** is R or S, or a mixture of R and S.

Definitions

As used in the specification and the appended claims, the singular forms of "a," "an," and "the" include plural references unless the context clearly dictates otherwise.

As used herein, the term "Lewis acid" refers to any chemical species that can accept a pair of nonbonding valence electrons, i.e., an electron-pair acceptor. Without limitation, non-limiting examples of Lewis acids include BF$_3$, TMSOTf, and SnCl$_4$.

As used herein, the term "solvent" refers to a compound or mixture of compounds including, but not limited to, water, water in which an ionic compound has been dissolved, acetic acid, acetone, acetonitrile, benzene, 1-butanol, 2-butanol, t-butyl alcohol ("TBA"), 2-butanone, carbon tetrachloride, chlorobenzene, chloroform, cyclohexane, 1,2-dichloroethane ("DCE"), diethylene glycol, diethyl ether ("Et$_2$O"), diglyme (diethylene glycol dimethyl ether), 1,2-dimethoxyethane ("DME"), N,N-dimethylformamide ("DMF"), dimethylsulfoxide ("DMSO"), 1,4-dioxane, ethanol, ethyl acetate ("EtOAc"), ethylene glycol, glycerin, heptanes, hexamethylphosphoramide ("HMPA"), hexamethylphosphorus triamide ("HMPT"), hexane, methanol ("MeOH"), methyl t-butyl ether ("MTBE"), methylene chloride ("DCM," "CH$_2$Cl$_2$"), N-methyl-2-pyrrolidinone ("NMP"), nitromethane, pentane, petroleum ether, 1-propanol ("n-propanol," "n-PrOH"), 2-propanol ("isopropanol," "iPrOH"), pyridine, tetrahydrofuran ("THF"), toluene, triethylamine ("TEA," "Et$_3$N"), o-xylene, m-xylene, and/or p-xylene, and the like. Solvent classes may include hydrocarbon, aromatic, aprotic, polar, alcoholic, and mixtures thereof.

As used herein, the terms "mechano-chemical mixing," "mechanochemistry," and "mechanical processing" refer to standard techniques known to those of ordinary skill in the art, in which chemical starting materials and/or reagents with disparate solubility properties are reacted, for example, by direct milling, liquid assisted-milling, triturating, mixing, or grinding, generally in the absence of solvents. Interchangeable terms may include "mechanic-chemical," or the like. See F. Ravalico et al., *Rapid synthesis of nucleotide pyrophosphate linkages in a ball mill*, 9 ORG. BIOL. CHEM. 6496 (2011); Dritan Hasa et al., *Cocrystal Formation through Mechanochemistry: From Neat and Liquid-Assisted Grinding to Polymer-Assisted Grinding*, 127 ANGEWANDTE CHEMIE 7371 (2015); and references cited therein, all of which are incorporated by reference herein in their entireties.

As used herein, the term "liquid-assisted mixing" refers to a standard technique known to those of ordinary skill in the art, in which the kinetics of solid-state grinding is accelerated by addition of a small amount of liquid during mixing. It was discovered in 2001 that not only did small amounts of liquid speed up the solid-state reaction, but in numerous cases, addition of small amounts of liquid allowed the formation of new solid forms that could not otherwise be made. See N. Shan et al., *Mechanochemistry and co-crystal formation: effect of solvent on reaction kinetics*, CHEM. COMMC'NS 2732 (2002), incorporated by reference herein in its entirety. Between 2002 and 2005 it was discovered that the exact outcome of the solid-state grinding could be controlled by careful choice of the added liquid. See A. V. Trask et al., *Achieving Polymorphic and Stoichiometric Diversity in Cocrystal Formation: Importance of Solid-State*

*Grinding, Powder X-ray Structure Differentiation, and Seeding,* 5 CRYSTAL GROWTH & DESIGN 2233 (2005), incorporated by reference herein in its entirety. Between 2005 and 2007, it was further demonstrated that this liquid-assisted mixing approach is significantly more effective in searching for alternate solid forms of drug candidates than other previously used methods, e.g., conventional solution crystallization or melt growth. See S. Karki et al., *Screening for pharmaceutical cocrystal hydrates via neat and liquid-assisted grinding,* 4 MOLECULAR PHARMACEUTICS 347 (2007); A. V. Trask et al., *Screening for crystalline salts via mechanochemistry,* CHEM. COMMC'NS 51 (2006); each of which is incorporated by reference herein in its entirety. Liquid-assisted mixing is a method that is rapid and environmentally friendly because it eliminates the need to use large amounts of solvents, cutting down on waste and lost revenue.

As used therein, the term "extrusion" refers to a standard technique known to those of ordinary skill in the art, in which a raw material is chemically converted into a product of unique shape and density by forcing it through a die under defined conditions. See J. Thiry et al., *A review of pharmaceutical extrusion: Critical process parameters and scaling-up,* 479 INT'L J. PHARMACEUTICS 227 (2015), incorporated by reference herein in its entirety. An extruder is composed of two different parts: a conveying system and a die system. The conveying system transports the material through the barrel via the action of Archimedes' infinite screws, which can also impart a degree of distributive mixing if needed. The die system then forms the material into the desired shape. See id. Pharmaceutical extrudates are generally produced by heating and then softening a mixture of a drug and a thermoplastic polymer, followed by extrusion of the molten mass through a die, resulting in the production of cylinders of films depending on the shape of the die. In addition, other excipients, such as surfactants, salts, superdisintegrants, plasticizers, and antioxidants may be added during the extrusion process if required. See K. Hughey et al., *The use of inorganic salts to improve the dissolution characteristics of tablets containing Soluplus®-based solid dispersions,* 48 EUR. J. PHARM. SCI. 758 (2013); M. A. Repka et al., *Pharmaceutical applications of hot-melt extrusion: part II,* 33 DRUG DEV. INDUS. PHARM. 1043 (2007), each of which is incorporated by reference herein in its entirety. The most common additives are plasticizers, which facilitate the extrusion process by reducing the glass transition temperature of the polymers. See M. M. Crowley et al., *Pharmaceutical applications of hot-melt extrusion: part I,* 33 DRUG DEV. INDUS. PHARM. 909 (2007), incorporated by reference herein in its entirety. The release of the active pharmaceutical ingredient ("API") and the quality of the final product can be fine-tuned by modifying the excipients. For example, some polymers have a different dissolution pH, which can allow the targeting of a specific part of the gastro-intestinal tract. See D. A. Miller et al., *Targeted intestinal delivery of supersaturated itraconazole for improved oral absorption,* 25 PHARM. RES. 1450 (2008), incorporated by reference herein in its entirety. Some polymers can also control the release of the API in order to observe an immediate, delayed, or sustained release. See S. Janssens et al., *The use of a new hydrophilic polymer, Kollicoat IR® in the formulation of solid dispersions of itraconazole,* 30 EUR. J. PHARM. SCI. 288 (2007); L. D. Bruce et al., *Properties of hot-melt extruded tablet formulations for the colonic delivery of 5-aminosalicylic acid,* 59 EUR. J. PHARM. BIOPHARM. 85 (2005); E. Verhoeven et al., *Xanthan gum to tailor drug release of sustained-release ethylcellulose mini-matrices prepared via hot-melt extrusion: in vitro and in vivo evaluation,* 63 EUR. J. PHARM. BIOPHARM. 320 (2006); each of which is incorporated by reference herein in its entirety. Another very important aspect to bear in mind is the affinity between the API and the polymer matrix, especially when aiming for enhancement of the bioavailability of poorly soluble drugs. See Shah et al., *Melt extrusion with poorly soluble drugs,* 453 INT'L J. PHARM. 233 (2013), incorporated by reference herein in its entirety. It is for this reason that a screening process of different polymers is generally needed in order to obtain the best solid dispersion. See Sarode et al., *Hot melt extrusion (HME) for amorphous solid dispersions: predictive tools for processing and impact of drug-polymer interactions on supersaturation,* 48 EUR. J. PHARM. SCI. 371 (2002), incorporated by reference here in its entirety. The formulation step is therefore very important, because it will have a critical impact on the final quality of the product.

Because extrusion is a complex process, which is very versatile and flexible, the process parameters need to be taken into account in order to obtain the best final product. See Romanski et al., *The importance of monitoring process parameters as a method for quality control for hot melt extrusion,* AAPS ANNUAL MEETING, SAN ANTONIO, TX (2013), incorporated by reference herein in its entirety. A typical extrusion setup consists of: a motor, which acts as a drive unit; an extrusion barrel; a rotating screw; and an extrusion die. See R. Chokshi & H. Zia, *Hot-melt extrusion technique: a review,* 3 IRAN J. PHARM. RES. 3 (2004), incorporated by reference herein in its entirety. The extruder must be able to rotate the screw at a predetermined speed. At the same time, the torque and shear generated by the extruded material, and the screws must be compensated. The extruder is connected to a central control unit in order to control the process parameters, such as screw speed and temperature, and therefore pressure. This electronic control unit will also act as a monitoring system. See M. Maniruzzaman et al., *A review of hot-melt extrusion: process technology to pharmaceutical products,* ISRN PHARM. (2012), incorporated by reference herein in its entirety. A very important characteristic to consider, regardless of whether the extrusion equipment is a single screw ("ssEr") or twin screw extruder ("tsEr"), is the length to diameter ratio (L/D) of the screws. The L/D typically ranges from about 20 to about 40:1 (mm). Another important characteristic is the diameter of the screws, because this will determine the size of the equipment and its throughput. The screw diameters of pilot extruders range from about 12 to about 30 mm, while the production machines for pharmaceutical scaling-up are much larger, with diameters typically exceeding about 50 to about 60 mm. See G. Andrews et al., *A Basic Guide: Hot-Melt Extrusion,* 13 UKICRS (2008), incorporated by reference herein in its entirety. Process analytical technology such as near infrared ("NIR") and Raman, can also be applied to the extruder setup via probes in order to control in-line the quality of the final product. See F. Krier et al., *PAT tools for the control of co-extrusion implants manufacturing process,* 458 INT'L J. PHARM. 15 (2013), incorporated by reference herein in its entirety. Throughout the whole process, the temperature of the different sections is controlled by electrical heating bands around the barrel or by heating cartridges inside the barrel, and is monitored by thermocouples.

Temperature is the first factor to take into account in the extrusion process, because the polymer has to be processed above its glass transition temperature ($T_g$), but below its degradation temperature ($T_{deg}$). The API can be processed below or above its melting temperature ($T_m$) depending on whether a miscibility regime or a solubilization regime, respectively, is being used. See M. A. Repka et al., *Melt extrusion*, AAPS (2013), incorporated by reference herein in its entirety. It is well known that the temperature influences the viscosity of the melt. See J. Breitenbach, *Melt extrusion from process to drug delivery technology*, 54 EUR. J. PHARM. BIOPHARM. 107 (2002), incorporated by reference herein in its entirety. Therefore, an equilibrium has to be found between, on the one hand, a low temperature where the melt shows high viscosity, and thus a high torque, and on the other hand, an elevated temperature where the torque is reduced due to the low viscosity of the melt but where both the polymer and the API could be degraded. The product temperature can consequently be a major determinant factor in the quality of the final product. It is important to note that the product temperature will be different from the barrel temperature. Indeed, mechanical energy is often transferred from the screws into the molten material.

It is well known that modification of the screw configuration allows for modification of the production method, as the different screw elements can be optimized to suit particular applications. See Breitenbach (2002); Chokshi & Zia (2004). Moreover, the residence time of the mix in the barrel will also be influenced by the type of element used during the process. For example, adding kneading elements will increase the residence time. See H. Liu et al., *Effects of screw configuration on indomethacin dissolution behavior in eudragit E PO*, 31 ADV. POLYM. TECH. 331 (2012); P. R. Wahl et al., *Inline monitoring and a PAT strategy for pharmaceutical hot melt extrusion*, 455 INT'L J. PHARM. 159 (2013); each of which is incorporated by reference herein in its entirety. Screw configuration is a very important parameter in the amorphization of the API using twin screw hot melt extrusion ("tsHME"). In their study, Nakamichi et al. concluded that at least one mixing zone was needed in order to obtain smooth and homogeneous extrudates while processing nifedipine and hydroxypropylmethylcellulose phthalate with the kneading paddle positioned at the level of the second third of the barrel. K. Nakamichi et al., *The role of the kneading paddle and the effects of screw revolution speed and water content on the preparation of SD using twin-screw extruder*, 241 INT'L J. PHARM. 203 (2002), incorporated by reference herein in its entirety. The samples were recovered from the screw directly and analyzed by DSC and x-ray diffraction ("XRD"). Moreover, when studying the release of the drug in vitro, supersaturation was only observed when the kneading paddle was present. Verhoeven et al. observed the same result while extruding ethylcellulose with metoprolol tartrate ("MPT"). Further, these authors changed the number of mixing zones and their position within the barrel, but mixing efficacy and drug release were found not to be effected by those changes. See E. Verhoeven et al., *Influence of formulation and process parameters on the release characteristics of ethylcellulose sustained-release mini-matrices produced by hot-melt extrusion*, 69 EUR. J. PHARM. BIOPHARM. 312 (2008), incorporated by reference herein in its entirety.

The screw speed also needs to be adapted for each purpose, because it has an impact on several factors involved in the extrusion process. On the one hand, if amorphization is targeted, the screw speed would need to be high in order to obtain a high shear mixing with reduced residence time. On the other hand, in order to obtain high purity cocrystals, the screw speed would need to be reduced so as to increase the residence time, and consequently, the mixing time.

Regarding feeding material into the extruder, first of all, varying the feed rate, while maintaining the screw speed as constant, will change the fill level of the extrusion barrel, because increasing the feed rate will increase the filling rate. See E. Reitz et al., *Residence time modeling of hot melt extrusion processes*, 85 EUR. J. PHARM. BIOPHARM. 1200 (2013), incorporated by reference herein in its entirety. Almeida et al. concluded that a balance needs to be found between feed rate and screw speed in order to maintain a constant melt flow. See A. Almeida et al., *Upscaling and inline process monitoring via spectroscopic techniques of ethylene vinyl acetate hot-melt extruded formulations*, 439 INT'L J. PHARM. 223 (2012), incorporated by reference herein in its entirety. Generally, the filling percentage of the extruder barrel is comprised between about 20% and about 50%, and this can be calculated by using the following equation:

$$\text{Filling \%} = \frac{FR \times RTD}{\rho \times V_{free}} \times 100$$

where "FR" is the feed rate (g/min), "RTD" is the mean residence time (min), "$\rho$" is the bulk viscosity of the polymer/mix (g/mL), and "$V_{free}$" is the extruder free volume (mL). See A. Swanborough, *A practical approach to scale-up from bench-top. Twin Screw Extruders*, THERMO FISHER SCIENTIFIC INC. (2006), incorporated by reference herein in its entirety.

Before scaling up the extrusion process, it is recommended to measure the specific mechanical energy ("SME") on a laboratory scale extruder to allow the prediction of the performance of a production extruder, operating under similar conditions of screw speed and residence time. See Swanborough, 2006. Therefore, all of the parameters described above need to be adapted in order to obtain the same results. When scaling up the extrusion process, larger screws, higher screw speeds, and higher feeding rates will be used. However, two factors—the SME and the residence time-must be maintained at a similar level, even if the scale of the process is increased. Therefore, the critical parameters of the process must be adapted in order to fit these two factors.

In accordance with one embodiment, methods for preparation of the present disclosure comprise processing by extruding, wherein the extruder is a 11-millimeter, stainless steel, twin screw jacketed extruder, and wherein the processing by extruding includes interchangeable mixing elements, independent heating and cooling zones, programmable feeding, and liquid injection ports.

Without limitation, non-limiting examples of Brønsted acids include HI, HCl, HBr, $H_2SO_4$, $H_3O^+$, $HNO_3$, $H_3PO_4$, and $CH_3CO_2H$. Without limitation, non-limiting examples of Brønsted bases include $CH_3^-$, $CH_2=CH^-$, $H^-$, $NH_2^-$, $HC\equiv C^-$, $CH_3O^-$, $HO^-$, $HS^-$, $CO_3^{-2}$, $NH_3$, $HCO_2^-$, $MeO^-$, and $EtO^-$.

Without limitation, and without being bound by theory, as used herein, the terms "oxidizing agent," "oxidant," and "electron acceptor" refer to species that gain electrons and are reduced in a chemical reaction. An oxidizing agent is normally in one of its higher possible oxidation states because it will gain electrons and be reduced. Without limitation, non-limiting examples of oxidizing agents include, but are not limited to, $O_2$, $O_3$, $H_2SO_4$, and the halogen elements.

Without limitation, and without being bound by theory, as used herein, the terms "reducing agent," "reductant," and "electron donor" refer to species that lose electrons and are oxidized in a chemical reaction. A reducing agent is typically in one of its lower possible oxidation states because it will lose electrons and be oxidized. Without limitation, non-limiting examples of reducing agents include, but are not limited to, $H_2$, CO, Fe, Zn, and the alkali metal elements.

Without limitation, and without being bound by theory, as used herein, the term "catalysis" or "catalytic" refers an increase in the rate of a chemical reaction of a substrate species due to the participation of an additional chemical species called a "catalyst," which is not consumed in the catalyzed reaction and can continue to act repeatedly in subsequent repetitions of the same chemical reaction. In particular embodiments, by "catalytic amount" is meant that a chemical species is present in no greater an amount than 10% molar equivalent amount relative to the amount of substrate. In other embodiments, by "catalytic amount" is meant that a chemical species is present in no greater an amount than 5% molar equivalent amount relative to the amount of substrate. In yet other embodiments, by "catalytic amount" is meant that a chemical species is present in no greater an amount than 3% molar equivalent amount relative to the amount of substrate. In yet other embodiments, by "catalytic amount" is meant that a chemical species is present in no greater an amount than 1% molar equivalent amount relative to the amount of substrate.

According to particular embodiments, the compounds or derivatives prepared according to embodiments of the methods of the present disclosure can comprise compounds or derivatives, or salts, solvates, or prodrugs thereof, or crystalline forms thereof, substantially free of solvents or other by-products, generally, or a particular solvent or by-product. In certain embodiments, by "substantially free" is meant greater than about 80% free of solvents or by-products, or greater than about 80% free of a particular solvent or by-product, more preferably greater than about 90% free of solvents or by-products, or greater than about 90% free of a particular solvent or by-product, even more preferably greater than about 95% free of solvents or by-products, or greater than about 95% free of a particular solvent or by-product, even more preferably greater than about 98% free of solvents or by-products, or greater than about 98% free of a particular solvent or by-product, even more preferably greater than about 99% free of solvents or by-products, or greater than about 99% free of a particular solvent or by-product, even more preferably greater than about 99.99% free of solvents or by-products, or greater than about 99.99% free of a particular solvent or by-product, and most preferably quantitatively free of solvents or by-products, or quantitatively free of a particular solvent or by-product.

According to particular embodiments, the compounds or derivatives prepared according to embodiments of the methods of the present disclosure can comprise compounds or derivatives, or salts, solvates, or prodrugs thereof, or crystalline forms thereof, substantially free of solvents or other by-products, generally, or a particular solvent or by-product. In certain embodiments, by "substantially free" is meant less than about 10,000 ppm of solvents or by-products, or less than about 10,000 ppm of a particular solvent or by-product, even more preferably less than about 1,000 ppm of solvents or by-products, or less than about 1,000 ppm of a particular solvent or by-product, even more preferably less than about 100 ppm of solvents or by-products, or less than about 100 ppm of a particular solvent or by-product, even more preferably less than about 10 ppm of solvents or by-products, or less than about 10 ppm of a particular solvent or by-product, even more preferably less than 5 ppm of solvents or by-products, or less than 5 ppm of a particular solvent or by-product, and most preferably, an undetectable amount of solvents or by-products, or an undetectable amount of a particular solvent or by-product.

The term "alkyl," by itself or as part of another substituent means, unless otherwise stated, a straight, branched, or cyclic chain hydrocarbon ("cycloalkyl") having the number of carbon atoms designated (i.e., $C_1$-$C_6$ means one to six carbons). Examples include methyl, ethyl, propyl, isopropyl, butyl, isobutyl, tert-butyl, pentyl, neopentyl, hexyl, cyclohexyl, and cyclopropyl. Most preferred are —($C_1$-$C_3$)alkyl, particularly ethyl, methyl, and isopropyl.

The term "alkenyl," employed alone or in combination with other terms, means unless otherwise stated, a stable mono-unsaturated or di-unsaturated straight chain, the unsaturation meaning a carbon-carbon double bond (—CH=CH—), branched chain, or cyclic hydrocarbon group having the stated number of carbon atoms. Examples include vinyl, propenyl, allyl, crotyl, isopentenyl, butadienyl, 1,3-pentadienyl, 1,4-pentadienyl, cyclopentenyl, cyclopentadienyl, and the higher homologs and isomers. Functional groups representing an alkene are exemplified by —CH=CH—$CH_2$— and $CH_2$=CH—$CH_2$—.

"Substituted alkyl" or "substituted alkenyl" mean alkyl or alkenyl, respectively, as defined above, substituted by one, two, or three substituents. The substituents may, for example, be selected from the group consisting of halogen, —OH, —$NH_2$, —N($CH_3$)$_2$, —C(=O)OH, —C(=O)O($C_1$-$C_4$)alkyl, methoxy, ethoxy, trifluoromethyl, —C(=O)$NH_2$, —$SO_2NH_2$, —C(=NH)$NH_2$, —C≡N, and —$NO_2$, preferably selected from halogen and —OH. Examples of substituted alkyls include, but are not limited to, 2,2-difluoromethyl, 2-carboxycyclopentyl, and 3-chloropropyl.

The term "alkynyl," employed alone or in combination with other terms, means, unless otherwise stated, a stable carbon-carbon triple bond-containing radical (—C≡C—), branched chain, or cyclic hydrocarbon group having the stated number of carbon atoms. Examples include ethynyl and propargyl.

The term "alkoxy," employed alone or in combination with other terms, means, unless otherwise stated, an alkyl group having the designated number of carbon atoms, as defined above, connected to the rest of the molecule via an oxygen atom, such as, for example, methoxy, ethoxy, 1-propoxy, 2-propoxy ("isopropoxy"), and the higher homologs and isomers. Preferred are —($C_1$-$C_3$)alkoxy, particularly ethoxy and methoxy.

The terms "carbamyl" or "carbamoyl" mean the group —C(=O)NRR', wherein R and R' are independently selected from hydrogen or a hydrocarbyl functional group, or wherein R and R' combined form a heterocycle. Examples of carbamyl groups include: —C(=O)$NH_2$ and —C(=O)N($CH_3$)$_2$.

The term "cyano" refers to a —C≡N group.

The term "heteroalkyl," by itself or in combination with another term, means, unless otherwise stated, a stable straight or branched chain alkyl group consisting of the stated number of carbon atoms and one or two heteroatoms selected from the group consisting of O, N, and S, and wherein the nitrogen and sulfur heteroatoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2$—$CH_2$—S (=O)—CH$_3$. Up to two heteroatoms may be consecutive, such as, for example, —CH$_2$—NH—OCH$_3$, or —CH$_2$—CH$_2$—S—S—CH$_3$.

The terms "halo" or "halogen," by themselves or as part of another substituent, mean, unless otherwise stated, a monovalent fluorine, chlorine, bromine, or iodine atom.

The term "nitro" refers to a —NO$_2$ group.

The term "(C$_x$-C$_y$)perfluoroalkyl," wherein x<y, means an alkyl group with a minimum of x carbons and a maximum of y carbons, wherein all hydrogen atoms are replaced by fluorine atoms. Preferred is —(C$_1$-C$_6$)perfluoroalkyl, more preferred is —(C$_1$-C$_3$)perfluoroalkyl, most preferred is —CF$_3$.

The term "aromatic" generally refers to a carbocycle or heterocycle having one or more polyunsaturated rings having aromatic character (i.e., having (4n+2) delocalized π (pi) electrons where n is an integer).

The term "aryl," employed alone or in combination with other terms, means, unless otherwise stated, a carbocyclic aromatic system containing one or more rings (typically one, two, or three rings) wherein such rings may be attached together in a pendant manner, such as a biphenyl, or may be fused, such as naphthalene. Examples include phenyl; anthracyl; and naphthyl. Preferred are phenyl and naphthyl, most preferred is phenyl.

The term "2-(methylenyl)phenyl," employed alone or in combination with other terms, means, unless otherwise stated, a substituted phenyl diradical having the following structural formula:

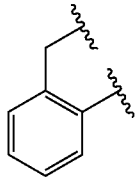 [SMILES: *Cc1ccccc1*]

The terms "heterocycle" or "heterocyclyl" or "heterocyclic," by themselves or as part of another substituent, mean, unless otherwise stated, an unsubstituted or substituted, stable, mono- or multi-cyclic heterocyclic ring system that consists of carbon atoms and at least one heteroatom independently selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure.

The terms "heteroaryl" or "heteroaromatic" refer to a heterocyclic having aromatic character. Similarly, the term "heteroaryl(C$_1$-C$_3$)alkyl" means a functional group wherein a one to three carbon alkylene chain is attached to a heteroaryl group, e.g., —CH$_2$—CH$_2$-pyridyl. The term "substituted heteroaryl(C$_1$-C$_3$)alkyl" means a heteroaryl(C$_1$-C$_3$)alkyl functional group in which the heteroaryl group is substituted. A polycyclic heteroaryl may include fused rings. Examples include indole, 1H-indazole, 1H-pyrrolo[2,3-b]pyridine, and the like. A polycyclic heteroaryl may include one or more rings that are partially saturated. Examples include indoline, tetrahydroquinoline, and 2,3-dihydrobenzofuryl.

The term "heterocycle(C$_1$-C$_3$)alkyl," by itself or as part of another substituent, means, unless otherwise stated, a functional group wherein a (C$_1$-C$_3$)alkylene chain is attached to a heterocyclic group, e.g., morpholino-CH$_2$—CH$_2$—. As used herein, the term "substituted heterocycle(C$_1$-C$_3$)alkyl" means a heterocycle(C$_1$-C$_3$)alkyl functional group in which the heterocycle group is substituted.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,4-dihydropyridine, 1,2,3,6-tetrahydropyridine, piperazine, N-methylpiperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

Examples of heteroaryl groups include: pyridyl; pyrazinyl; pyrimidinyl, particularly 2- and 4-pyrimidinyl; pyridazinyl; thienyl; furyl; pyrrolyl, particularly 2-pyrrolyl; imidazolyl; thiazolyl; oxazolyl; pyrazolyl, particularly 3- and 5-pyrazolyl; isothiazolyl; 1,2,3-triazolyl; 1,2,4-triazolyl; 1,3,4-triazolyl; tetrazolyl; 1,2,3-thiadiazolyl; 1,2,3-oxadiazolyl; 1,3,4-thiadiazolyl; and 1,3,4-oxadiazolyl.

Polycyclic heterocycles include both aromatic and non-aromatic polycyclic heterocycles. Examples of polycyclic heterocycles include: indolyl, particularly 3-, 4-, 5-, 6-, and 7-indolyl; indolinyl; indazolyl, particularly 1H-indazol-5-yl; quinolyl; tetrahydroquinolyl; isoquinolyl, particularly 1- and 5-isoquinolyl; 1,2,3,4-tetrahydroisoquinolyl; cinnolyl; quinoxalinyl, particularly 2- and 5-quinoxalinyl; quinazolinyl; phthalazinyl; naphthyridinyl, particularly 1,5- and 1,8-naphthyridinyl; 1,4-benzodioxanyl; coumaryl; dihydrocoumaryl; benzofuryl, particularly 3-, 4-, 5-, 6-, and 7-benzofuryl; 2,3-dihydrobenzofuryl; 1,2-benzisoxazolyl; benzothienyl, particularly 3-, 4-, 5-, 6-, and 7-benzoethienyl; benzoxazolyl; benzothiazolyl, particularly 2- and 5-benzothiazolyl; purinyl; benzimidazolyl, particularly 2-benzimidazolyl; benztriazolyl; thioxanthinyl; carbazolyl; carbolinyl; acridinyl; pyrrolizidinyl; pyrrolo[2,3-b]pyridinyl, particularly 1H-pyrrolo[2,3-b]pyridine-5-yl; and quinolizidinyl. Particularly preferred are 4-indolyl, 5-indolyl, 6-indolyl, 1H-indazol-5-yl, and 1H-pyrrolo[2,3-b]pyridine-5-yl.

The aforementioned listing of heterocyclic and heteroaryl moieties is intended to be representative and not limiting.

The term "substituted" means that an atom or group of atoms has replaced hydrogen as the substituent attached to another group. For aryl and heteroaryl groups, the term "substituted" refers to any levels of substitution, namely mono-, di-, tri-, tetra-, or penta-substitution, where such substitution is permitted. The substituents are independently selected, and substitution may be at any chemically accessible position.

D-Ribose stereochemistry has been indicated in compounds or derivatives having formulae (2), (I), (I-H), (II), (III), (IV), (IV-H), (V), and (VI), or salts, solvates, or prodrugs thereof. It is understood that the configuration at the anomeric carbon can be reversed (i.e., L-), or can be a mixture of D- and L-.

Synthetic Preparation of Compounds or Derivatives Having Formulae (I), (I-H), (II), (III), (IV), (IV-H), (V), and (VI), or Salts, Solvates, or Prodrugs Thereof In an embodiment, a method of making a compound or derivative having formula (2), or a salt thereof, can include the steps of:

(a) providing a compound or derivative having formula (2a), or a salt thereof, wherein when R$^{14}$ of the compound or derivative having formula (2a), or salt thereof, is methyl, then X' of the compound or derivative having formula (2), or salt thereof, is not acetoxy, and wherein when R$^{14}$ of the compound or derivative having formula (2a), or salt thereof, is phenyl, then X' of the compound or derivative having formula (2), or salt thereof, is not benzoxy;

(b) treating the compound or derivative having formula (2a), or salt thereof, with at least a stoichiometric amount of a Brønsted acid or a nucleophilic substitution reagent, optionally generated in situ from an alcohol and an acyl chloride, in the presence of at least a molar equivalent amount of a polar organic solvent co-reagent;

(c) processing the compound or derivative having formula (2a), or salt thereof, the Brønsted acid or nucleophilic substitution reagent, optionally generated in situ from an alcohol and an acyl chloride, and the polar organic solvent co-reagent so as to produce the compound or derivative having formula (2), or salt thereof;

optionally, (c1) removing by-products resulting from the processing step under reduced pressure and temperature-controlled conditions;

optionally, (c2) separately isolating unreacted compound or derivative having formula (2a), or salt thereof, and (d) isolating the compound or derivative having formula (2), or salt thereof.

Processing can be carried out under batch processing conditions or by continuously processing. Continuously processing may include one or more methods of agitation selected from the group consisting of liquid-assisted mixing under sealed conditions, milling, grinding, and extruding. Liquid-assisted mixing under sealed conditions may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (2), or salt thereof, under almost solventless conditions.

The polar organic solvent co-reagent and isolation solvent employed in the above method of making a compound or derivative having formula (2), or salt thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (2), or a salt thereof, can include the steps of:

(a) providing a compound or derivative having formula (2a), or a salt thereof, wherein when $R^{14}$ of the compound or derivative having formula (2a), or salt thereof, is methyl, then X' of the compound or derivative having formula (2), or salt thereof, is not acetoxy, and wherein when $R^{14}$ of the compound or derivative having formula (2a), or salt thereof, is phenyl, then X' of the compound or derivative having formula (2), or salt thereof, is not benzoxy;

(b) treating the compound or derivative having formula (2a), or salt thereof, with a (1<x<10) equivalent amount of a nucleophilic substitution reagent, optionally generated in situ by reacting an acyl chloride with an alcohol, in stoichiometrically equivalent molar amounts and in the presence of a molar (0<x<10) equivalent amount of a polar organic solvent co-reagent;

(c) processing the compound or derivative having formula (2a), or salt thereof, the nucleophilic substitution reagent, and the polar organic solvent co-reagent, so as to produce the compound or derivative having formula (2), or salt thereof;

optionally, (c1) evaporating any volatile by-products resulting from the processing step under reduced pressure and temperature-controlled conditions; and (d) isolating the compound or derivative having formula (2), or salt thereof.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (2), or salt thereof, under almost solventless conditions.

The polar organic solvent co-reagent and isolation solvent employed in the above method of making a compound or derivative having formula (2), or salt thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (I), or a salt, solvate, or prodrug thereof, optionally in a particular anomeric ratio (alpha/beta), can include the steps of:

(a) providing a compound or derivative having formula (2), or a salt thereof;

(b) treating the compound or derivative having formula (2), or salt thereof, with a molar equivalent amount of a compound or derivative having formula (1), or a salt thereof, optionally, (b1) treating the compound or derivative having formula (2), or salt thereof, and the compound or derivative having formula (1), or salt thereof, with a molar equivalent amount of TMSOTf;

(c) processing the compound or derivative having formula (2), or salt thereof, the compound or derivative having formula (1), or salt thereof, and, optionally, the TMSOTf so as to produce the compound or derivative having formula (I), or salt, solvate, or prodrug thereof, optionally produced in a particular anomeric ratio (alpha/beta);

optionally, (c1) removing by-products resulting from the processing step under reduced pressure and temperature-controlled conditions;

optionally, (c2) separately isolating unreacted compound or derivative having formula (2), or salt thereof;

optionally, (c3) adding acetone;

optionally, (c4) separately isolating unreacted compound or derivative having formula (1), or salt thereof; and (d) isolating the compound or derivative having formula (I), or salt, solvate, or prodrug thereof, optionally in a particular anomeric ratio.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (I), or salt, solvate, or prodrug thereof, optionally in a particular anomeric ratio (alpha/beta).

The polar organic solvent co-reagent and isolation solvent employed in the above method of making a compound or derivative having formula (I), or salt, solvate, or prodrug thereof, optionally in a particular anomeric ratio (alpha/beta) can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (I), or a salt, solvate, or prodrug thereof, optionally in a particular anomeric ratio (alpha/beta), can include the steps of:

(a) adding a volume of methanol and water in a 95:5 weight:weight ratio to the compound or derivative having formula (I), or salt, solvate, or prodrug thereof, optionally in a particular anomeric ratio (alpha/beta), at room temperature, so as to dissolve approximately 15% of the compound or derivative having formula (I), or salt, solvate, or prodrug thereof, optionally in a particular anomeric ratio (alpha/beta), in the volume of methanol and water;

(b) stirring the compound or derivative having formula (I), or salt, solvate, or prodrug thereof, optionally in a particular anomeric ratio (alpha/beta), at 50° C. until all of the compound or derivative having formula (I), or salt, solvate, or prodrug thereof, optionally in a particular anomeric ratio (alpha/beta), apparently dissolves in the volume of methanol and water;

(c) cooling the solution of the compound or derivative having formula (I), or salt, solvate, or prodrug thereof, optionally in a particular anomeric ratio (alpha/beta), in the volume of methanol and water, to −10° C. with stirring so as to precipitate the crystalline form of the compound or derivative having formula (I), or salt, solvate, or prodrug thereof, optionally in a particular anomeric ratio (alpha/beta);

(d) filtering the volume of methanol and water and the crystalline form of the compound or derivative having formula (I), or salt, solvate, or prodrug thereof, optionally in a particular anomeric ratio (alpha/beta), so as to isolate the crystalline form of the compound or derivative having formula (I), or salt, solvate, or prodrug thereof, optionally in a particular anomeric ratio (alpha/beta); and (e) drying the crystalline form of the compound or derivative having formula (I), or salt, solvate, or prodrug thereof, optionally in a particular anomeric ratio (alpha/beta).

The process described herein effects a preparation of a crystalline form of a compound or derivative having formula (I), or salt, solvate, or prodrug thereof, optionally in a particular anomeric ratio (alpha/beta).

In another embodiment, a method of making a compound or derivative having formula (I), or a salt, solvate, or prodrug thereof, optionally in a particular anomeric ratio (alpha/beta), can include the steps of:

(a) providing riboside tetraacetate;

(b) treating the riboside tetraacetate with a molar equivalent amount of a compound or derivative having formula (1), or a salt thereof;

optionally, (b1) treating the riboside tetraacetate and the compound or derivative having formula (1), or salt thereof, with a molar equivalent amount of TMSOTf;

(c) processing the riboside tetraacetate, the compound or derivative having formula (1), or salt thereof, and, optionally, the TMSOTf so as to produce the compound or derivative having formula (I), or salt, solvate, or prodrug thereof, optionally produced in a particular anomeric ratio (alpha/beta);

optionally, (c1) removing by-products resulting from the processing step under reduced pressure and temperature-controlled conditions;

optionally, (c2) separately isolating unreacted riboside tetraacetate;

optionally, (c3) adding acetone;

optionally, (c4) separately isolating unreacted compound or derivative having formula (1), or salt thereof; and (d) isolating the compound or derivative having formula (I), or salt, solvate, or prodrug thereof, optionally in a particular anomeric ratio.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (I), or salt, solvate, or prodrug thereof, optionally in a particular anomeric ratio (alpha/beta).

The polar organic solvent co-reagent and isolation solvent employed in the above method of making a compound or derivative having formula (I), or salt, solvate, or prodrug thereof, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (I), or a salt, solvate, or prodrug thereof, optionally in a particular anomeric ratio (alpha/beta), can include the steps of:

(a) adding a volume of methanol and water in a 95:5 weight:weight ratio to the compound or derivative having formula (I), or salt, solvate, or prodrug thereof, optionally in a particular anomeric ratio (alpha/beta), at room temperature, so as to dissolve approximately 15% of the compound or derivative having formula (I), or salt, solvate, or prodrug thereof, optionally in a particular anomeric ratio (alpha/beta), in the volume of methanol and water;

(b) stirring the compound or derivative having formula (I), or salt, solvate, or prodrug thereof, optionally in a particular anomeric ratio (alpha/beta), at 50° C. until all of the compound or derivative having formula (I), or salt, solvate, or prodrug thereof, optionally in a particular anomeric ratio (alpha/beta), apparently dissolves in the volume of methanol and water;

(c) cooling the solution of the compound or derivative having formula (I), or salt, solvate, or prodrug thereof, optionally in a particular anomeric ratio (alpha/beta), in the volume of methanol and water, to −10° C. with stirring so as to precipitate the crystalline form of the compound or derivative having formula (I), or salt, solvate, or prodrug thereof, optionally in a particular anomeric ratio (alpha/beta);

(d) filtering the volume of methanol and water and the crystalline form of the compound or derivative having formula (I), or salt, solvate, or prodrug thereof, optionally in a particular anomeric ratio (alpha/beta), so as to isolate the crystalline form of the compound or derivative having formula (I), or salt, solvate, or prodrug thereof, optionally in a particular anomeric ratio (alpha/beta); and (e) drying the crystalline form of the compound or derivative having formula (I), or salt, solvate, or prodrug thereof, optionally in a particular anomeric ratio (alpha/beta).

The process described herein effects a preparation of a crystalline form of a compound or derivative having formula (I), or salt, solvate, or prodrug thereof, optionally in a particular anomeric ratio (alpha/beta).

In yet another embodiment, a method of making a compound or derivative having formula (I), or a salt, solvate, or prodrug thereof, optionally in a particular anomeric ratio (alpha/beta), can include the steps of:

(a) providing a compound or derivative having formula (1), or a salt thereof;

optionally, (a1) treating the compound or derivative having formula (1), or salt thereof, with excess trimethylsilylating reagent(s), and, optionally, heating the compound or derivative having formula (1), or salt thereof, and the trimethylsilylating reagent(s), to reflux for about 12 hours, so as to produce a compound or derivative having formula (1), or salt thereof, optionally wherein each $R^1$ is a TMS group;

optionally, (a2) cooling the mixture to room temperature;

optionally, (a3) removing the trimethylsilylating reagent(s);

(b) treating the compound or derivative having formula (1), or salt thereof, optionally wherein each $R^1$ is a TMS group, with a molar equivalent amount of a compound or derivative having formula (2), or a salt thereof, in an organic solvent co-reagent;

optionally, (b1) treating the compound or derivative having formula (1), or salt thereof, optionally wherein each $R^1$ is a TMS group, and the compound or derivative having formula (2), or salt thereof, in an organic solvent co-reagent, with a molar equivalent amount of TMSOTf;

(c) processing the compound or derivative having formula (1), or salt thereof, optionally wherein each $R^1$ is a TMS group, the compound or derivative having formula (2), or salt thereof, optionally, the TMSOTf, and the organic solvent co-reagent so as to produce the compound or derivative having formula (I), or salt, solvate, or prodrug thereof, optionally wherein each $R^1$ is a TMS group, optionally produced in a particular anomeric ratio (alpha/beta);

(d) adding water to, optionally, the compound or derivative having formula (1), or salt thereof, optionally wherein each $R^1$ is a TMS group, optionally, the compound or derivative having formula (2), or salt thereof, optionally, the TMSOTf, the organic solvent co-reagent, and the compound or derivative having formula (I), or salt, solvate, or prodrug thereof, optionally wherein each $R^1$ is a TMS group, optionally in a particular anomeric ratio (alpha/beta);

optionally, (d1) adding saturated $NaHCO_3$ solution to, optionally, the compound or derivative having formula (1), or salt thereof, optionally wherein each $R^1$ is a TMS group, optionally, the compound or derivative having formula (2), or salt thereof, optionally, the TMSOTf, the organic solvent co-reagent, and the compound or derivative having formula (I), or salt, solvate, or prodrug thereof, optionally wherein each $R^1$ is a TMS group, optionally in a particular anomeric ratio (alpha/beta), and water;

optionally, (d2) adjusting the pH of the aqueous phase;

optionally, (d3) separating the organic phase from the aqueous phase;

(e) freeze-drying the aqueous phase to provide the compound or derivative having formula (I), or salt, solvate, or prodrug thereof, optionally in a particular anomeric ratio (alpha/beta);

optionally, (e1) dissolving the compound or derivative having formula (I), or salt, solvate, or prodrug thereof, optionally in a particular anomeric ratio (alpha/beta), in methanol in a gas pressure tube;

optionally, (e2) cooling the solution of the compound or derivative having formula (I), or salt, solvate, or prodrug thereof, optionally in a particular anomeric ratio (alpha/beta), in methanol to −78° C.;

optionally, (e3) bubbling ammonia gas into the solution of the compound or derivative having formula (I), or salt, solvate, or prodrug thereof, optionally in a particular anomeric ratio (alpha/beta), in methanol;

optionally, (e4) sealing the pressure tube;

optionally, (e5) raising the temperature to −20° C.;

optionally, (e6) cooling the pressure tube at −20° C. for about 12 hours to about 4 days, so as to produce a compound or derivative having formula (I), or salt, solvate, or prodrug thereof, wherein $R^6$, $R^7$, and $R^8$ are each hydrogen;

optionally, (e7) unsealing the gas pressure tube; and optionally, (e8) isolating the compound or derivative having formula (I), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (I), or salt, solvate, or prodrug thereof, optionally in a particular anomeric ratio (alpha/beta).

The organic solvent co-reagent employed in the above method of making a compound or derivative having formula (I), or salt, solvate, or prodrug thereof, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (I), or a salt, solvate, or prodrug thereof, optionally in a particular anomeric ratio (alpha/beta), can include the steps of:

(a) dissolving the compound or derivative having formula (I), or salt, solvate, or prodrug thereof, optionally in a particular anomeric ratio (alpha/beta), in a volume of methanol;

(b) adding a volume of acetone, of an equal volume to the volume of methanol, to the compound or derivative having formula (I), or salt, solvate, or prodrug thereof, optionally in a particular anomeric ratio (alpha/beta), in the volume of methanol;

(c) precipitating the compound or derivative having formula (I), or salt, solvate, or prodrug thereof, optionally in a particular anomeric ratio (alpha/beta);

(d) isolating the compound or derivative having formula (I), or salt, solvate, or prodrug thereof, optionally in a particular anomeric ratio (alpha/beta); and (e) washing the compound or derivative having formula (I), or salt, solvate, or prodrug thereof, optionally in a particular anomeric ratio (alpha/beta), with cold methanol.

The process described herein effects a preparation of a crystalline form of a compound or derivative having formula (I), or salt, solvate, or prodrug thereof, optionally in a particular anomeric ratio (alpha/beta).

In yet another embodiment, a method of making a compound or derivative having formula (I), or a salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta), can include the steps of:

(a) providing a compound or derivative having formula (2), or a salt thereof;

(b) treating the compound or derivative having formula (2), or salt thereof, with a molar equivalent amount of a compound or derivative having formula (1), or a salt thereof;

optionally, (b1) treating the compound or derivative having formula (2), or salt thereof, and the compound or derivative having formula (1), or salt thereof, with a molar equivalent amount of TMSOTf;

(c) processing the compound or derivative having formula (2), or salt thereof, the compound or derivative having formula (1), or salt thereof, and, optionally, the TMSOTf so as to produce the compound or derivative having formula (I), or salt, solvate, or prodrug thereof, wherein $R^6$, $R^7$, and $R^8$ are each —C(O)R', and R' is methyl or —$C_1$alkyl, optionally produced in a particular anomeric ratio (alpha/beta);

optionally, (c1) removing by-products resulting from the processing step under reduced pressure and temperature-controlled conditions;

optionally, (c2) separately isolating unreacted compound or derivative having formula (2), or salt thereof;

optionally, (c3) adding acetone;

optionally, (c4) separately isolating unreacted compound or derivative having formula (1), or salt thereof; and (d) isolating the compound or derivative having formula (I), or salt, solvate, or prodrug thereof, optionally in a particular anomeric ratio.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (I), or salt, solvate, or prodrug thereof, wherein $R^6$, $R^7$, and $R^8$ are each —C(O) R', and wherein R' is methyl or —$C_1$alkyl, optionally in a particular anomeric ratio (alpha/beta).

The polar organic solvent co-reagent and isolation solvent employed in the above method of making a compound or derivative having formula (I), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (I), or a salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta), can include the steps of:

(a) providing riboside tetraacetate;

(b) treating the riboside tetraacetate with a stoichiometrically equivalent amount of a compound or derivative having formula (1), or a salt thereof;

optionally, (b1) treating the riboside tetraacetate and the compound or derivative having formula (1), or salt thereof, with a molar equivalent amount of TMSOTf;

(c) processing the riboside tetraacetate, compound or derivative having formula (1), or salt thereof, and, optionally, the TMSOTf so as to produce the compound or derivative having formula (I), or salt, solvate, or prodrug thereof, wherein $R^6$, $R^7$, and $R^8$ are each —C(O)R', and wherein R' is methyl or —$C_1$alkyl, optionally produced in a particular anomeric ratio (alpha/beta);

optionally, (c1) removing by-products resulting from the processing step under reduced pressure and temperature-controlled conditions;

optionally, (c2) separately isolating unreacted riboside tetraacetate;

optionally, (c3) adding acetone;

optionally, (c4) separately isolating unreacted compound or derivative having formula (1), or salt thereof; and (d) isolating the compound or derivative having formula (I), or salt, solvate, or prodrug thereof, wherein $R^6$, $R^7$, and $R^8$ are each —C(O)R', and wherein R' is methyl or —$C_1$alkyl, optionally in a particular anomeric ratio.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (I), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta).

The polar organic solvent co-reagent and isolation solvent employed in the above method of making a compound or derivative having formula (I), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (I), or a salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta), can include the steps of:

(a) providing a compound or derivative having formula (1), or a salt thereof;

optionally, (a1) treating the compound or derivative having formula (1), or salt thereof, with excess trimethylsilylating reagent(s), and, optionally, heating the compound or derivative having formula (1), or salt thereof, and the trimethylsilylating reagent(s), to reflux for about 12 hours, so as to produce a compound or derivative having formula (1), or salt thereof, optionally wherein each $R^1$ is a TMS group;

optionally, (a2) cooling the mixture to room temperature;

optionally, (a3) removing the trimethylsilylating reagent(s);

(b) treating the compound or derivative having formula (1), or salt thereof, optionally wherein each $R^1$ is a TMS group, with a molar equivalent amount of a compound or derivative having formula (2), or a salt thereof, in an organic solvent co-reagent;

optionally, (b1) treating the compound or derivative having formula (1), or salt thereof, optionally wherein each $R^1$ is a TMS group, the compound or derivative having formula (2), or salt thereof, in an organic solvent co-reagent, with a molar equivalent amount of TMSOTf;

(c) processing the compound or derivative having formula (1), or salt thereof, optionally wherein each $R^1$ is a TMS group, the compound or derivative having formula (2), or salt thereof, optionally, the TMSOTf, and the organic solvent co-reagent so as to produce the compound or derivative having formula (I), or salt, solvate, or prodrug thereof, wherein $R^6$, $R^7$, and $R^8$ are each —C(O)R', and wherein R' is methyl or —$C_1$alkyl, optionally wherein each $R^1$ is a TMS group, optionally produced in a particular anomeric ratio (alpha/beta);

(d) adding water to, optionally, the compound or derivative having formula (1), or salt thereof, optionally wherein each $R^1$ is a TMS group, optionally, the compound or derivative having formula (2), or salt thereof, optionally, the TMSOTf, the organic solvent co-reagent, and the compound or derivative having formula (I), or salt, solvate, or prodrug thereof, wherein $R^6$, $R^7$, and $R^8$ are each —C(O)R', and wherein R' is methyl or —$C_1$alkyl, optionally wherein each $R^1$ is a TMS group, optionally in a particular anomeric ratio (alpha/beta);

optionally, (d1) adding saturated $NaHCO_3$ solution to, optionally, the compound or derivative having formula (1), or salt thereof, optionally wherein each $R^1$ is a TMS group, optionally, the compound or derivative having formula (2), or salt thereof, optionally, the TMSOTf, the organic solvent co-reagent, and the compound or derivative having formula (I), or salt, solvate, or prodrug thereof, wherein $R^6$, $R^7$, and $R^8$ are each —C(O)R', and wherein R' is methyl or —$C_1$alkyl, optionally wherein each $R^1$ is a TMS group, optionally in a particular anomeric ratio (alpha/beta), and water;

optionally, (d2) adjusting the pH of the aqueous phase;

optionally, (d3) separating the organic phase from the aqueous phase; and (e) freeze-drying the aqueous phase to provide the compound or derivative having formula (I), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta).

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (I), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta).

The organic solvent co-reagent employed in the above method of making a compound of derivative having formula (I), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (Ia), or a salt, solvate, or prodrug thereof, optionally in a particular anomeric ratio (alpha/beta), can include the steps of:

(a) providing a compound or derivative having formula (2), or a salt thereof;

(b) treating the compound or derivative having formula (2), or salt thereof, with a molar equivalent amount of a compound or derivative having formula (1a), or a salt thereof optionally, (b1) treating the compound or derivative having formula (2), or salt thereof, and the compound or derivative having formula (1a), or salt thereof, with a molar equivalent amount of TMSOTf;

(c) processing the compound or derivative having formula (2), or salt thereof, the compound or derivative having formula (1a), or salt thereof, and, optionally, the TMSOTf so as to produce the compound or derivative having formula (Ia), or salt, solvate, or prodrug thereof, optionally produced in a particular anomeric ratio (alpha/beta);

optionally, (c1) removing by-products resulting from the processing step under reduced pressure and temperature-controlled conditions;

optionally, (c2) separately isolating unreacted compound or derivative having formula (2), or salt thereof;

optionally, (c3) adding acetone;

optionally, (c4) separately isolating unreacted compound or derivative having formula (Ia), or salt thereof, and (d) isolating the compound or derivative having formula (Ia), or salt, solvate, or prodrug thereof, optionally in a particular anomeric ratio.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Ia), or salt, solvate, or prodrug thereof, optionally in a particular anomeric ratio (alpha/beta).

The polar organic solvent co-reagent and isolation solvent employed in the above method of making a compound or derivative having formula (Ia), or salt, solvate, or prodrug thereof, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of a compound or derivative having formula (Ia), or a salt, solvate, or prodrug thereof, optionally in a particular anomeric ratio (alpha/beta), can include the steps of:

(a) adding a volume of methanol and water in a 95:5 weight:weight ratio to the compound or derivative having formula (Ia), or salt, solvate, or prodrug thereof, optionally in a particular anomeric ratio (alpha/beta), at room temperature, so as to dissolve approximately 15% of the compound or derivative having formula (Ia), or salt, solvate, or prodrug thereof, optionally in a particular anomeric ratio (alpha/beta), in the volume of methanol and water;

(b) stirring the compound or derivative having formula (Ia), or salt, solvate, or prodrug thereof, optionally in a particular anomeric ratio (alpha/beta), at 50° C. until all of the compound or derivative having formula (Ia), or salt, solvate, or prodrug thereof, optionally in a particular anomeric ratio (alpha/beta), apparently dissolves in the volume of methanol and water;

(c) cooling the solution of the compound or derivative having formula (Ia), or salt, solvate, or prodrug thereof, optionally in a particular anomeric ratio (alpha/beta), in the volume of methanol and water, to −10° C. with stirring so as to precipitate the crystalline form of the compound or derivative having formula (Ia), or salt, solvate, or prodrug thereof, optionally in a particular anomeric ratio (alpha/beta);

(d) filtering the volume of methanol and water and the crystalline form of the compound or derivative having formula (Ia), or salt, solvate, or prodrug thereof, optionally in a particular anomeric ratio (alpha/beta), so as to isolate the crystalline form of the compound or derivative having formula (Ia), or salt, solvate, or prodrug thereof, optionally in a particular anomeric ratio (alpha/beta); and (e) drying the crystalline form of the compound or derivative having formula (Ia), or salt, solvate, or prodrug thereof, optionally in a particular anomeric ratio (alpha/beta).

The process described herein effects a preparation of a crystalline form of a compound or derivative having formula (Ia), or salt, solvate, or prodrug thereof, optionally in a particular anomeric ratio (alpha/beta).

In another embodiment, a method of making a compound or derivative having formula (Ia), or a salt, solvate, or prodrug thereof, optionally in a particular anomeric ratio (alpha/beta), can include the steps of:

(a) providing riboside tetraacetate;

(b) treating the riboside tetraacetate with a molar equivalent amount of a compound or derivative having formula (1a), or a salt thereof;

optionally, (b1) treating the riboside tetraacetate and the compound or derivative having formula (1a), or salt thereof, with a molar equivalent amount of TMSOTf;

(c) processing the riboside tetraacetate, the compound or derivative having formula (1a), or salt thereof, and, optionally, the TMSOTf so as to produce the compound or derivative having formula (Ia), or salt, solvate, or prodrug thereof, optionally produced in a particular anomeric ratio (alpha/beta);

optionally, (c1) removing by-products resulting from the processing step under reduced pressure and temperature-controlled conditions;

optionally, (c2) separately isolating unreacted riboside tetraacetate;

optionally, (c3) adding acetone;

optionally, (c4) separately isolating unreacted compound or derivative having formula (1a), or salt thereof, and (d) isolating the compound or derivative having formula (Ia), or salt, solvate, or prodrug thereof, optionally in a particular anomeric ratio.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Ia), or salt, solvate, or prodrug thereof, optionally in a particular anomeric ratio (alpha/beta).

The polar organic solvent co-reagent and isolation solvent employed in the above method of making a compound or derivative having formula (Ia), or salt, solvate, or prodrug thereof, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (Ia), or a salt, solvate, or prodrug thereof, optionally in a particular anomeric ratio (alpha/beta), can include the steps of:

(a) adding a volume of methanol and water in a 95:5 weight:weight ratio to the compound or derivative having formula (Ia), or salt, solvate, or prodrug thereof, optionally in a particular anomeric ratio (alpha/beta), at room temperature, so as to dissolve approximately 15% of the compound or derivative having formula (Ia), or salt, solvate, or prodrug thereof, optionally in a particular anomeric ratio (alpha/beta), in the volume of methanol and water;

(b) stirring the compound or derivative having formula (Ia), or salt, solvate, or prodrug thereof, optionally in a particular anomeric ratio (alpha/beta), at 50° C. until all of the compound or derivative having formula (Ia), or salt, solvate, or prodrug thereof, optionally in a particular anomeric ratio (alpha/beta), apparently dissolves in the volume of methanol and water;

(c) cooling the solution of the compound or derivative having formula (Ia), or salt, solvate, or prodrug thereof, optionally in a particular anomeric ratio (alpha/beta), in the volume of methanol and water, to −10° C. with stirring so as to precipitate the crystalline form of the compound or derivative having formula (Ia), or salt, solvate, or prodrug thereof, optionally in a particular anomeric ratio (alpha/beta);

(d) filtering the volume of methanol and water and the crystalline form of the compound or derivative having formula (Ia), or salt, solvate, or prodrug thereof, optionally in a particular anomeric ratio (alpha/beta), so as to isolate the crystalline form of the compound or derivative having formula (Ia), or salt, solvate, or prodrug thereof, optionally in a particular anomeric ratio (alpha/beta); and (e) drying the crystalline form of the compound or derivative having formula (Ia), or salt, solvate, or prodrug thereof, optionally in a particular anomeric ratio (alpha/beta).

The process described herein effects a preparation of a crystalline form of a compound or derivative having formula (Ia), or a salt, solvate, or prodrug thereof, optionally in a particular anomeric ratio (alpha/beta).

In yet another embodiment, a method of making a compound or derivative having formula (Ia), or a salt, solvate, or prodrug thereof, optionally in a particular anomeric ratio (alpha/beta), can include the steps of:

(a) providing a compound or derivative having formula (1a), or a salt thereof;

optionally, (a1) treating the compound or derivative having formula (1a), or salt thereof, with excess trimethylsilylating reagent(s), and, optionally, heating the compound or derivative having formula (1a), or salt thereof, and the trimethylsilylating reagent(s), to reflux for about 12 hours, so as to produce a compound or derivative having formula (1a), or salt thereof, optionally wherein each $R^1$ is a TMS group;

optionally, (a2) cooling the mixture to room temperature;

optionally, (a3) removing the trimethylsilylating reagent(s);

(b) treating the compound or derivative having formula (1a), or salt thereof, optionally wherein each $R^1$ is a TMS group, with a molar equivalent amount of a compound or derivative having formula (2), or a salt thereof, in an organic solvent co-reagent;

optionally, (b1) treating the compound or derivative having formula (1a), or salt thereof, wherein each $R^1$ is a TMS group, with a molar equivalent amount of a compound or derivative having formula (2), or salt thereof, in an organic solvent co-reagent, with a molar equivalent amount of TMSOTf, (c) processing the compound or derivative having formula (1a), or salt thereof, optionally wherein each $R^1$ is a TMS group, the compound or derivative having formula (2), or salt thereof, optionally, the TMSOTf, and the organic solvent co-reagent so as to produce the compound or derivative having formula (Ia), or salt, solvate, or prodrug thereof, optionally wherein each $R^1$ is a TMS group, optionally produced in a particular anomeric ratio (alpha/beta);

(d) adding water to, optionally, the compound or derivative having formula (1a), or salt thereof, optionally wherein each $R^1$ is a TMS group, optionally, the compound or derivative having formula (2), or salt thereof, optionally, the TMSOTf, the organic solvent co-reagent, and the compound or derivative having formula (Ia), or salt, solvate, or prodrug thereof, optionally wherein each $R^1$ is a TMS group, optionally in a particular anomeric ratio (alpha/beta);

optionally, (d1) adding saturated $NaHCO_3$ solution to, optionally, the compound or derivative having formula (1a), or salt thereof, optionally wherein each $R^1$ is a TMS group, optionally, the compound or derivative having formula (2), or salt thereof, optionally, the TMSOTf, the organic solvent co-reagent, and the compound or derivative having formula (Ia), or salt, solvate, or prodrug thereof, optionally wherein each $R^1$ is a TMS group, optionally in a particular anomeric ratio (alpha/beta), and water;

optionally, (d2) adjusting the pH of the aqueous phase;

optionally, (d3) separating the organic phase from the aqueous phase;

(e) freeze-drying the aqueous phase to provide the compound or derivative having formula (Ia), or salt, solvate, or prodrug thereof, optionally in a particular anomeric ratio (alpha/beta);

optionally, (e1) dissolving the compound or derivative having formula (Ia), or salt, solvate, or prodrug thereof, optionally in a particular anomeric ratio (alpha/beta), in methanol in a gas pressure tube;

optionally, (e2) cooling the solution of the compound or derivative having formula (Ia), or salt, solvate, or prodrug thereof, optionally in a particular anomeric ratio (alpha/beta), in methanol to −78° C.;

optionally, (e3) bubbling ammonia gas into the solution of the compound or derivative having formula (Ia), or salt, solvate, or prodrug thereof, optionally in a particular anomeric ratio (alpha/beta), in methanol;

optionally, (e4) sealing the pressure tube;

optionally, (e5) raising the temperature to −20° C.;

optionally, (e6) cooling the pressure tube at −20° C. for about 12 hours to about 4 days, so as to produce a compound or derivative having formula (Ia), or salt, solvate, or prodrug thereof, wherein $R^6$, $R^7$, and $R^8$ are each hydrogen;

optionally, (e7) unsealing the gas pressure tube; and optionally, (e8) isolating the compound or derivative having formula (Ia), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Ia), or salt, solvate, or prodrug thereof, optionally in a particular anomeric ratio (alpha/beta).

The organic solvent co-reagent employed in the above method of making a compound or derivative having formula (Ia), or salt, solvate, or prodrug thereof, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467), incorporated by reference herein in its entirety.

In a particular embodiment, a method of making a crystalline form of the compound or derivative having formula (Ia), or a salt, solvate, or prodrug thereof, optionally in a particular anomeric ratio (alpha/beta), can include the steps of:

(a) dissolving the compound or derivative having formula (Ia), or salt, solvate, or prodrug thereof, optionally in a particular anomeric ratio (alpha/beta), in a volume of methanol;

(b) adding a volume of acetone, of an equal volume to the volume of methanol, to the compound or derivative having formula (Ia), or salt, solvate, or prodrug thereof, optionally in a particular anomeric ratio (alpha/beta), in the volume of methanol;

(c) precipitating the crystalline form of the compound or derivative having formula (Ia), or salt, solvate, or prodrug thereof, optionally in a particular anomeric ratio (alpha/beta);

(d) isolating the crystalline form of the compound or derivative having formula (Ia), or salt, solvate, or prodrug thereof, optionally in a particular anomeric ratio (alpha/beta); and (e) washing the crystalline form of the compound or derivative having formula (Ia), or salt, solvate, or prodrug thereof, optionally in a particular anomeric ratio (alpha/beta), with cold methanol.

The process described herein effects a preparation of a crystalline form of a compound or derivative having formula (Ia), or salt, solvate, or prodrug thereof, optionally in a particular anomeric ratio (alpha/beta).

In yet another embodiment, a method of making a compound or derivative having formula (Ia), or a salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta), can include the steps of:

(a) providing a compound or derivative having formula (2), or a salt thereof;

(b) treating the compound or derivative having formula (2), or salt thereof, with a molar equivalent amount of a compound or derivative having formula (1a), or a salt thereof;

optionally, (b1) treating the compound or derivative having formula (2), or salt thereof, and the compound or derivative having formula (1a), or salt thereof, with a molar equivalent amount of TMSOTf;

(c) processing the compound or derivative having formula (2), or salt thereof, the compound or derivative having formula (1a), or salt thereof, and, optionally, the TMSOTf so as to produce the compound or derivative having formula (Ia), or salt, solvate, or prodrug thereof, wherein $R^6$, $R^7$, and $R^8$ are each —C(O)R', and wherein R' is methyl or —$C_1$alkyl, optionally produced in a particular anomeric ratio (alpha/beta);

optionally, (c1) removing by-products resulting from the processing step under reduced pressure and temperature-controlled conditions;

optionally, (c2) separately isolating unreacted compound or derivative having formula (2), or salt thereof;

optionally, (c3) adding acetone;

optionally, (c4) separately isolating unreacted compound or derivative having formula (1a), or salt thereof, and (d) isolating the compound or derivative having formula (Ia), or salt, solvate, or prodrug thereof, wherein $R^6$, $R^7$, and $R^8$ are each —C(O)R', and wherein R' is methyl or —$C_1$alkyl, optionally in a particular anomeric ratio.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Ia), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta).

The polar organic solvent co-reagent and isolation solvent employed in the above method of making a compound or derivative having formula (Ia), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (Ia), or a salt, solvate, or prodrug thereof, wherein $R^6$, $R^7$, and $R^8$ are each —C(O)R', and wherein R' is methyl or —C$_1$alkyl, optionally in a particular anomeric ratio (alpha/beta), can include the steps of:

(a) providing riboside tetraacetate;

(b) treating the riboside tetraacetate with a stoichiometrically equivalent amount of a compound or derivative having formula (1a), or a salt thereof;

optionally, (b1) treating the riboside tetraacetate and the compound or derivative having formula (1a), or salt thereof, with a molar equivalent amount of TMSOTf;

(c) processing the riboside tetraacetate, the compound or derivative having formula (1a), or salt thereof, and, optionally, the TMSOTf so as to produce the compound or derivative having formula (Ia), or salt, solvate, or prodrug thereof, wherein R$^6$, R$^7$, and R$^8$ are each —C(O)R', and wherein R' is methyl or —C$_1$alkyl, optionally produced in a particular anomeric ratio (alpha/beta);

optionally, (c1) removing by-products resulting from the processing step under reduced pressure and temperature-controlled conditions;

optionally, (c2) separately isolating unreacted riboside tetraacetate;

optionally, (c3) adding acetone;

optionally, (c4) separately isolating unreacted compound or derivative having formula (1a), or salt thereof, and (d) isolating the compound or derivative having formula (Ia), or salt, solvate, or prodrug thereof, wherein R$^6$, R$^7$, and R$^8$ are each —C(O)R', and wherein R' is methyl or —C$_1$alkyl, optionally in a particular anomeric ratio.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Ia), or salt, solvate, or prodrug thereof, wherein R$^6$, R$^7$, and R$^8$ are each —C(O)R', and wherein R' is methyl or —C$_1$alkyl, optionally in a particular anomeric ratio (alpha/beta).

The polar organic solvent co-reagent and isolation solvent employed in the above method of making a compound or derivative having formula (Ia), or salt, solvate, or prodrug thereof, wherein R$^6$, R$^7$, and R$^8$ are each —C(O)R', and wherein R' is methyl or —C$_1$alkyl, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (Ia), or a salt, solvate, or prodrug thereof, wherein R$^6$, R$^7$, and R$^8$ are each —C(O)R', and wherein R' is methyl or —C$_1$alkyl, optionally in a particular anomeric ratio (alpha/beta), can include the steps of:

(a) providing a compound or derivative having formula (1a), or a salt thereof;

optionally, (a1) treating the compound or derivative having formula (1a), or salt thereof, with excess trimethylsilylating reagent(s), and, optionally, heating the compound or derivative having formula (1a), or salt thereof, and the trimethylsilylating reagent(s), to reflux for about 12 hours, so as to produce a compound or derivative having formula (1a), or salt thereof, optionally wherein each R$^1$ is a TMS group;

optionally, (a2) cooling the mixture to room temperature;

optionally, (a3) removing the trimetylsilylating reagent(s);

(b) treating the compound or derivative having formula (1a), or salt thereof, optionally wherein each R$^1$ is a TMS group, with a molar equivalent amount of a compound or derivative having formula (2), or a salt thereof, in an organic solvent co-reagent;

optionally, (b1) treating the compound or derivative having formula (1a), or salt thereof, optionally wherein each R$^1$ is a TMS group, with a compound or derivative having formula (2), or salt thereof, in an organic solvent co-reagent, with a molar equivalent amount of TMSOTf;

(c) processing the compound or derivative having formula (1a), or salt thereof, optionally wherein each R$^1$ is a TMS group, the compound or derivative having formula (2), or salt thereof, optionally, the TMSOTf, and the organic solvent co-reagent so as to produce the compound or derivative having formula (Ia), or salt, solvate, or prodrug thereof, wherein R$^6$, R$^7$, and R$^8$ are each —C(O)R', and wherein R' is methyl or —C$_1$alkyl, optionally wherein each R$^1$ is a TMS group, optionally produced in a particular anomeric ratio (alpha/beta);

(d) adding water to, optionally, the compound or derivative having formula (1a), or salt thereof, optionally wherein each R$^1$ is a TMS group, optionally, the compound or derivative having formula (2), or salt thereof, optionally, the TMSOTf, the organic solvent co-reagent, and the compound or derivative having formula (Ia), or salt, solvate, or prodrug thereof, wherein R$^6$, R$^7$, and R$^8$ are each —C(O)R', and wherein R' is methyl or —C$_1$alkyl, optionally wherein each R$^1$ is a TMS group, optionally in a particular anomeric ratio (alpha/beta);

optionally, (d1) adding saturated NaHCO$_3$ solution to, optionally, the compound or derivative having formula (1a), or salt thereof, optionally wherein each R$^1$ is a TMS group, optionally, the compound or derivative having formula (2), or salt thereof, optionally, the TMSOTf, the organic solvent co-reagent, and the compound or derivative having formula (Ia), or salt, solvate, or prodrug thereof, wherein R$^6$, R$^7$, and R$^8$ are each —C(O)R', and wherein R' is methyl or —C$_1$alkyl, optionally wherein each R$^1$ is a TMS group, optionally in a particular anomeric ratio (alpha/beta), and water;

optionally, (d2) adjusting the pH of the aqueous phase;

optionally, (d3) separating the organic phase from the aqueous phase; and (e) freeze-drying the aqueous phase to provide the compound or derivative having formula (Ia), or salt, solvate, or prodrug thereof, wherein R$^6$, R$^7$, and R$^8$ are each —C(O)R', and wherein R' is methyl or —C$_1$alkyl, optionally in a particular anomeric ratio (alpha/beta).

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10

Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Ia), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta).

The organic solvent co-reagent and isolation solvent employed in the above method of making a compound or derivative having formula (Ia), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (I-H), or a salt, solvate, or prodrug thereof, wherein $R^6$, $R^7$, and $R^8$ are each hydrogen:

(a) providing a compound or derivative having formula (I), or a salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta);

(b) treating the compound or derivative having formula (I), or salt, solvate, or prodrug thereof, wherein $R^6$, $R^7$, and $R^8$ are each —C(O)R', and wherein R' is methyl or —$C_1$alkyl, with a molar equivalent amount of an alcohol (e.g., methanol, or ethanol) and at least a sub-molar equivalent amount of a Brønsted inorganic base;

(c) processing the compound or derivative having formula (I), or salt, solvate, or prodrug thereof, wherein $R^6$, $R^7$, and $R^8$ are each —C(O)R', and wherein R' is methyl or —$C_1$alkyl, the alcohol, and the Brønsted inorganic base so as to produce the compound or derivative having formula (I-H), or salt, solvate, or prodrug thereof, wherein $R^6$, $R^7$, and $R^8$ are each hydrogen;

optionally, (c1) neutralizing the Brønsted inorganic base using a concentrated acid solution under controlled conditions;

optionally, (c2) evaporating any volatile by-products resulting from the processing and neutralizing steps;

(d) isolating the compound or derivative having formula (I-H), or salt, solvate, or prodrug thereof, wherein $R^6$, $R^7$, and $R^8$ are each hydrogen;

optionally, (d1) separately isolating the unreacted compound or derivative having formula (I), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta); and optionally, (d2) drying the compound or derivative having formula (I-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (I-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (I-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (I-H), or a salt, solvate, or prodrug thereof, wherein $R^6$, $R^7$, and $R^8$ are each hydrogen, can include the steps of:

(a) adding a volume of methanol and water in a 95:5 weight:weight ratio to the compound or derivative having formula (I-H), or salt, solvate, or prodrug thereof, wherein $R^6$, $R^7$, and $R^8$ are each hydrogen, at room temperature, so as to dissolve approximately 15% of the compound or derivative having formula (I-H), or salt, solvate, or prodrug thereof, wherein $R^6$, $R^7$, and $R^8$ are each hydrogen, in the volume of methanol and water;

(b) stirring the compound or derivative having formula (I-H), or salt, solvate, or prodrug thereof, wherein $R^6$, $R^7$, and $R^8$ are each hydrogen, at 50° C. until all of the compound or derivative having formula (I-H), or salt, solvate, or prodrug thereof, wherein $R^6$, $R^7$, and $R^8$ are each hydrogen, apparently dissolves in the volume of methanol and water;

(c) cooling the solution of the compound or derivative having formula (I-H), or salt, solvate, or prodrug thereof, wherein $R^6$, $R^7$, and $R^8$ are each hydrogen, in the volume of methanol and water, to −10° C. with stirring so as to precipitate the crystalline form of the compound or derivative having formula (I-H), or salt, solvate, or prodrug thereof, wherein $R^6$, $R^7$, and $R^8$ are each hydrogen;

(d) filtering the volume of methanol and water and the crystalline form of the compound or derivative having formula (I-H), or salt, solvate, or prodrug thereof, wherein $R^6$, $R^7$, and R' are each hydrogen, so as to isolate the crystalline form of the compound or derivative having formula (I-H), or salt, solvate, or prodrug thereof, wherein $R^6$, $R^7$, and $R^8$ are each hydrogen; and (e) drying the crystalline form of the compound or derivative having formula (I-H), or salt, solvate, or prodrug thereof, wherein $R^6$, $R^7$, and $R^8$ are each hydrogen.

The process described herein effects a preparation of a crystalline form of a compound or derivative having formula (I-H), or salt, solvate, or prodrug thereof, wherein $R^6$, $R^7$, and $R^8$ are each hydrogen.

In another embodiment, a method of making a compound or derivative having formula (I-H), or a salt, solvate, or prodrug thereof, wherein $R^6$, $R^7$, and $R^8$ are each hydrogen, can include the steps of:

(a) providing a compound or derivative having formula (I), or a salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta);

(b) treating the compound or derivative having formula (I), or salt, solvate, or prodrug thereof, wherein $R^6$, $R^7$, and $R^8$ are each —C(O)R', and wherein R' is methyl or —$C_1$alkyl, with molar equivalent amounts (3<x<100) of an alcohol (e.g., methanol, or ethanol) and molar equivalent amounts (x≤20) of a Brønsted inorganic acid;

(c) processing, under sealed conditions, the compound or derivative having formula (I), or salt, solvate, or prodrug thereof, wherein $R^6$, $R^7$, and $R^8$ are each —C(O)R', and wherein R' is methyl or —$C_1$alkyl, the alcohol (e.g., methanol, or ethanol), and the Brønsted inorganic acid so as to produce the compound or derivative having formula (I-H), or salt, solvate, or prodrug thereof, wherein $R^6$, $R^7$, and $R^8$ are each hydrogen;

(d) isolating the compound or derivative having formula (I-H), or salt, solvate, or prodrug thereof, wherein $R^6$, $R^7$, and $R^8$ are each hydrogen;

optionally, (d1) separately isolating the unreacted compound or derivative having formula (I), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta);

optionally, (d2) washing the compound or derivative having formula (I-H), or salt, solvate, or prodrug thereof, wherein $R^6$, $R^7$, and $R^8$ are each hydrogen, with cold alcohol (e.g., methanol, or ethanol); and optionally, (d3) drying the compound or derivative having formula (I-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (I-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (I-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (I-H), or a salt, solvate, or prodrug thereof, wherein $R^6$, $R^7$, and $R^8$ are each hydrogen, can include the steps of:

(a) adding a volume of methanol and water in a 95:5 weight:weight ratio to the compound or derivative having formula (I-H), or salt, solvate, or prodrug thereof, wherein $R^6$, $R^7$, and $R^8$ are each hydrogen, at room temperature, so as to dissolve approximately 15% of the compound or derivative having formula (I-H), or salt, solvate, or prodrug thereof, wherein $R^6$, $R^7$, and $R^8$ are each hydrogen, in the volume of methanol and water;

(b) stirring the compound or derivative having formula (I-H), or salt, solvate, or prodrug thereof, wherein $R^6$, $R^7$, and $R^8$ are each hydrogen, at 50° C. until all of the compound or derivative having formula (I-H), or salt, solvate, or prodrug thereof, wherein $R^6$, $R^7$, and $R^8$ are each hydrogen, apparently dissolves in the volume of methanol and water;

(c) cooling the solution of the compound or derivative having formula (I-H), or salt, solvate, or prodrug thereof, wherein $R^6$, $R^7$, and $R^8$ are each hydrogen, in the volume of methanol and water, to −10° C. with stirring so as to precipitate the crystalline form of the compound or derivative having formula (I-H), or salt, solvate, or prodrug thereof, wherein $R^6$, $R^7$, and $R^8$ are each hydrogen;

(d) filtering the volume of methanol and water and the crystalline form of the compound or derivative having formula (I-H), or salt, solvate, or prodrug thereof, wherein $R^6$, $R^7$, and R' are each hydrogen, so as to isolate the crystalline form of the compound or derivative having formula (I-H), or salt, solvate, or prodrug thereof, wherein $R^6$, $R^7$, and $R^8$ are each hydrogen; and (e) drying the crystalline form of the compound or derivative having formula (I-H), or salt, solvate, or prodrug thereof, wherein $R^6$, $R^7$, and $R^8$ are each hydrogen.

The process described herein effects a preparation of a crystalline form of a compound or derivative having formula (I-H), or salt, solvate, or prodrug thereof, wherein $R^6$, $R^7$, and $R^8$ are each hydrogen.

In yet another embodiment, a method of making a compound or derivative having formula (I-H), or a salt, solvate, or prodrug thereof, wherein $R^6$, $R^7$, and $R^8$ are each hydrogen, can include the steps of:

(a) providing a compound or derivative having formula (I), or a salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta);

(b) treating the compound or derivative having formula (I), or salt, solvate, or prodrug thereof, wherein $R^6$, $R^7$, and $R^8$ are each —C(O)R', and wherein R' is methyl or —$C_1$alkyl, with molar equivalent amounts (3<x<100) of an alcohol (e.g., methanol, or ethanol) and molar equivalent amounts (3≤x<20) of an acyl chloride;

(c) processing, under sealed conditions, the compound or derivative having formula (I), or salt, solvate, or prodrug thereof, wherein $R^6$, $R^7$, and $R^8$ are each —C(O)R', and wherein R' is methyl or —$C_1$alkyl, the alcohol (e.g., methanol, or ethanol), and the acyl chloride, so as to generate HCl in situ and produce the compound or derivative having formula (I-H), or salt, solvate, or prodrug thereof, wherein $R^6$, $R^7$, and $R^8$ are each hydrogen;

(d) isolating the compound or derivative having formula (I-H), or salt, solvate, or prodrug thereof, wherein $R^6$, $R^7$, and $R^8$ are each hydrogen;

optionally, (d1) separately isolating the unreacted compound or derivative having formula (I), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta);

optionally, (d2) washing the compound or derivative having formula (I-H), or salt, solvate, or prodrug thereof, wherein $R^6$, $R^7$, and $R^8$ are each hydrogen, with cold alcohol (e.g., methanol, or ethanol); and optionally, (d3) drying the compound or derivative having formula (I-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (I-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (I-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (I-H), or a salt, solvate, or prodrug thereof, wherein $R^6$, $R^7$, and $R^8$ are each hydrogen, can include the steps of:

(a) adding a volume of methanol and water in a 95:5 weight:weight ratio to the compound or derivative having formula (I-H), or salt, solvate, or prodrug thereof, wherein $R^6$, $R^7$, and $R^8$ are each hydrogen, at room temperature, so as to dissolve approximately 15% of the compound or derivative having formula (I-H), or salt, solvate, or prodrug thereof, wherein $R^6$, $R^7$, and $R^8$ are each hydrogen, in the volume of methanol and water;

(b) stirring the compound or derivative having formula (I-H), or salt, solvate, or prodrug thereof, wherein $R^6$, $R^7$, and $R^8$ are each hydrogen, at 50° C. until all of the compound or derivative having formula (I-H), or salt, solvate, or prodrug thereof, wherein $R^6$, $R^7$, and $R^8$ are each hydrogen, apparently dissolves in the volume of methanol and water;

(c) cooling the solution of the compound or derivative having formula (I-H), or salt, solvate, or prodrug thereof, wherein $R^6$, $R^7$, and $R^8$ are each hydrogen, in the volume of methanol and water, to −10° C. with stirring so as to precipitate the crystalline form of the compound or derivative having formula (I-H), or salt, solvate, or prodrug thereof, wherein $R^6$, $R^7$, and $R^8$ are each hydrogen;

(d) filtering the volume of methanol and water and the crystalline form of the compound or derivative having formula (I-H), or salt, solvate, or prodrug thereof, wherein $R^6$, $R^7$, and $R'$ are each hydrogen, so as to isolate the crystalline form of the compound or derivative having formula (I-H), or salt, solvate, or prodrug thereof, wherein $R^6$, $R^7$, and $R^8$ are each hydrogen; and (e) drying the crystalline form of the compound or derivative having formula (I-H), or salt, solvate, or prodrug thereof, wherein $R^6$, $R^7$, and $R^8$ are each hydrogen.

The process described herein effects a preparation of a crystalline form of a compound or derivative having formula (I-H), or salt, solvate, or prodrug thereof, wherein $R^6$, $R^7$, and $R^8$ are each hydrogen.

In yet another embodiment, a method of making a compound or derivative having formula (I-H), or a salt, solvate, or prodrug thereof, wherein $R^6$, $R^7$, and $R^8$ are each hydrogen, optionally in a particular anomeric ratio (alpha/beta), can include the steps of:

(a) providing a compound or derivative having formula (1), or a salt thereof;

optionally, (a1) treating the compound or derivative having formula (1), or salt thereof, with excess trimethylsilylating reagent(s), and, optionally, heating the compound or derivative having formula (1), or salt thereof, the trimethylsilylating reagent(s), to reflux for about 12 hours, so as to produce a compound or derivative having formula (1), or salt thereof, generally wherein each $R^1$ is a TMS group;

optionally, (a2) cooling the mixture to room temperature;

optionally, (a3) removing the trimethylsilylating reagent(s);

(b) treating the compound or derivative having formula (1), or salt thereof, optionally wherein each $R^1$ is a TMS group, with a molar equivalent amount of a compound or derivative having formula (2), or a salt thereof, in an organic solvent co-reagent;

optionally, (b1) treating the compound or derivative having formula (1), or salt thereof, optionally wherein each $R^1$ is a TMS group, and the compound or derivative having formula (2), or salt thereof, in an organic solvent co-reagent, with a molar equivalent amount of TMSOTf;

(c) processing the compound or derivative having formula (1), or salt thereof, optionally wherein each $R^1$ is a TMS group, the compound or derivative having formula (2), or salt thereof, optionally, the TMSOTf, and the organic solvent co-reagent so as to produce a compound or derivative having formula (I), or salt, solvate, or prodrug thereof, optionally wherein each $R^1$ is a TMS group, optionally produced in a particular anomeric ratio (alpha/beta);

(d) adding water to, optionally, the compound or derivative having formula (1), or salt thereof, optionally wherein each $R^1$ is a TMS group, optionally, the compound or derivative having formula (2), or salt thereof, optionally, the TMSOTf, the organic solvent co-reagent, and the compound or derivative having formula (I), or salt, solvate, or prodrug thereof, optionally wherein each $R^1$ is a TMS group, optionally in a particular anomeric ratio (alpha/beta);

optionally, (d1) adding saturated $NaHCO_3$ solution to, optionally, the compound or derivative having formula (1), or salt thereof, optionally wherein each $R^1$ is a TMS group, optionally, the compound or derivative having formula (2), or salt thereof, optionally, the TMSOTf, the organic solvent co-reagent, and the compound or derivative having formula (I), or salt, solvate, or prodrug thereof, optionally wherein each $R^1$ is a TMS group, optionally in a particular anomeric ratio (alpha/beta), and water;

optionally, (d2) adjusting the pH of the aqueous phase;

optionally, (d3) separating the organic phase from the aqueous phase;

(e) freeze-drying the aqueous phase to provide the compound or derivative having formula (I), or salt, solvate, or prodrug thereof, optionally in a particular anomeric ratio (alpha/beta);

(f) dissolving the compound or derivative having formula (I), or salt, solvate, or prodrug thereof, optionally in a particular anomeric ratio (alpha/beta), in methanol in a gas pressure tube;

(g) cooling the solution of the compound or derivative having formula (I), or salt, solvate, or prodrug thereof, optionally in a particular anomeric ratio (alpha/beta), in methanol to −78° C.;

(h) bubbling ammonia gas into the solution of the compound or derivative having formula (I), or salt, solvate, or prodrug thereof, optionally in a particular anomeric ratio (alpha/beta), in methanol, so as to produce the compound or derivative having formula (I-H), or salt, solvate, or prodrug thereof, wherein $R^6$, $R^7$, and $R^8$ are each hydrogen, optionally in a particular anomeric ratio (alpha/beta);

(i) sealing the pressure tube;

(j) raising the temperature to −20° C.;

(k) cooling the pressure tube at −20° C. for about 12 hours to about 4 days;

(l) unsealing the gas pressure tube; and (m) isolating the compound or derivative having formula (I-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (I-H), or salt, solvate, or prodrug thereof, wherein $R^6$, $R^7$, and $R^8$ are each hydrogen, optionally in a particular anomeric ratio (alpha/beta).

The organic solvent co-reagent employed in the above method of making a compound or derivative having formula (I-H), or salt, solvate, or prodrug thereof, wherein $R^6$, $R^7$, and $R^8$ are each hydrogen, optionally in a particular anomeric ratio (alpha/beta), can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (I-H), or a salt, solvate, or prodrug thereof, wherein $R^6$, $R^7$, and $R^8$ are each hydrogen, optionally in a particular anomeric ratio (alpha/beta), can include the steps of:

(a) dissolving the compound or derivative having formula (I-H), or salt, solvate, or prodrug thereof, wherein $R^6$, $R^7$, and $R^8$ are each hydrogen, optionally in a particular anomeric ratio (alpha/beta), in a volume of methanol;

(b) adding a volume of acetone, of an equal volume to the volume of methanol, to the compound or derivative having formula (I-H), or salt, solvate, or prodrug thereof, wherein $R^6$, $R^7$, and $R^8$ are each hydrogen, optionally in a particular anomeric ratio (alpha/beta), in the volume of methanol;

(c) precipitating the crystalline form of the compound or derivative having formula (I-H), or salt, solvate, or prodrug thereof, wherein $R^6$, $R^7$, and $R^8$ are each hydrogen, optionally in a particular anomeric ratio (alpha/beta);

(d) isolating the crystalline form of the compound or derivative having formula (I-H), or salt, solvate, or prodrug thereof, wherein $R^6$, $R^7$, and $R^8$ are each hydrogen, optionally in a particular anomeric ratio (alpha/beta); and (e) washing the crystalline form of the compound or derivative having formula (I-H), or salt, solvate, or prodrug thereof, wherein $R^6$, $R^7$, and $R^8$ are each hydrogen, optionally in a particular anomeric ratio (alpha/beta), with cold methanol.

The process described herein effects a preparation of a crystalline form of a compound or derivative having formula (I-H), or salt, solvate, or prodrug thereof, wherein $R^6$, $R^7$, and $R^8$ are each hydrogen, optionally in a particular anomeric ratio (alpha/beta).

In an embodiment, a method of making a compound or derivative having formula (Ia-H), or a salt, solvate, or prodrug thereof, wherein $R^6$, $R^7$, and $R^8$ are each hydrogen, can include the steps of:

(a) providing a compound or derivative having formula (Ia), or a salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta);

(b) treating the compound or derivative having formula (Ia), or salt, solvate, or prodrug thereof, wherein $R^6$, $R^7$, and $R^8$ are each —C(O)R', and wherein R' is methyl or —$C_1$alkyl, with a molar equivalent amount of an alcohol (e.g., methanol, or ethanol) and at least a sub-molar equivalent amount of a Brønsted inorganic base;

(c) processing the compound or derivative having formula (Ia), or salt, solvate, or prodrug thereof, wherein $R^6$, $R^7$, and $R^8$ are each —C(O)R', and wherein R' is methyl or —$C_1$alkyl, the alcohol, and the Brønsted inorganic base so as to produce the compound or derivative having formula (Ia-H), or salt, solvate, or prodrug thereof, wherein $R^6$, $R^7$, and $R^8$ are each hydrogen;

optionally, (c1) neutralizing the base using a concentrated acid solution under controlled conditions;

optionally, (c2) evaporating volatile by-products resulting from the processing and neutralizing steps from the neutralized reaction mixture;

(d) isolating the compound or derivative having formula (Ia-H), or salt, solvate, or prodrug thereof, wherein $R^6$, $R^7$, and $R^8$ are each hydrogen;

optionally, (d1) separately isolating the unreacted compound or derivative having formula (Ia), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta); and optionally, (d2) drying the compound or derivative having formula (Ia-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Ia-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (Ia-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (Ia-H), or a salt, solvate, or prodrug thereof, wherein $R^6$, $R^7$, and $R^8$ are each hydrogen, can include the steps of:

(a) adding a volume of methanol and water in a 95:5 weight:weight ratio to the compound or derivative having formula (Ia-H), or salt, solvate, or prodrug thereof, wherein $R^6$, $R^7$, and $R^8$ are each hydrogen, at room temperature, so as to dissolve approximately 15% of the compound or derivative having formula (Ia-H), or salt, solvate, or prodrug thereof, wherein $R^6$, $R^7$, and $R^8$ are each hydrogen, in the volume of methanol and water;

(b) stirring the compound or derivative having formula (Ia-H), or salt, solvate, or prodrug thereof, wherein $R^6$, $R^7$, and $R^8$ are each hydrogen, at 50° C. until all of the compound or derivative having formula (Ia-H), or salt, solvate, or prodrug thereof, wherein $R^6$, $R^7$, and $R^8$ are each hydrogen, apparently dissolves in the volume of methanol and water;

(c) cooling the solution of the compound or derivative having formula (Ia-H), or salt, solvate, or prodrug thereof, wherein $R^6$, $R^7$, and $R^8$ are each hydrogen, in the volume of methanol and water, to −10° C. with stirring so as to precipitate the crystalline form of the compound or derivative having formula (Ia-H), or salt, solvate, or prodrug thereof, wherein $R^6$, $R^7$, and $R^8$ are each hydrogen;

(d) filtering the volume of methanol and water and the crystalline form of the compound or derivative having formula (Ia-H), or salt, solvate, or prodrug thereof, wherein $R^6$, $R^7$, and R' are each hydrogen, so as to isolate the crystalline form of the compound or derivative having formula (Ia-H), or salt, solvate, or prodrug thereof, wherein $R^6$, $R^7$, and $R^8$ are each hydrogen; and (e) drying the crystalline form of the compound or derivative having formula (Ia-H), or salt, solvate, or prodrug thereof, wherein $R^6$, $R^7$, and $R^8$ are each hydrogen.

The process described herein effects a preparation of a crystalline form of a compound or derivative having formula (Ia-H), or salt, solvate, or prodrug thereof, wherein $R^6$, $R^7$, and $R^8$ are each hydrogen.

In another embodiment, a method of making a compound or derivative having formula (Ia-H), or a salt, solvate, or prodrug thereof, wherein $R^6$, $R^7$, and $R^8$ are each hydrogen, can include the steps of:

(a) providing a compound or derivative having formula (Ia), or a salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta);

(b) treating the compound or derivative having (Ia), or salt, solvate, or prodrug thereof, wherein $R^6$, $R^7$, and $R^8$ are each —C(O)R', and wherein R' is methyl or —$C_1$alkyl, with molar equivalent amounts (3<x<100) of alcohol (e.g., methanol, or ethanol) and molar equivalent amounts (x≤20) of a Brønsted inorganic acid;

(c) processing, under sealed conditions, the compound or derivative having formula (Ia), or salt, solvate, or prodrug thereof, wherein $R^6$, $R^7$, and $R^8$ are each —C(O)R', and wherein R' is methyl or —$C_1$alkyl, the alcohol (e.g., methanol, or ethanol), and the Brønsted inorganic acid so as to produce the compound or derivative having formula (Ia-H), or salt, solvate, or prodrug thereof, wherein $R^6$, $R^7$, and $R^8$ are each hydrogen;

(d) isolating the compound or derivative having formula (Ia-H), or salt, solvate, or prodrug thereof, wherein $R^6$, $R^7$, and $R^8$ are each hydrogen;

optionally, (d1) separately isolating the unreacted compound or derivative having formula (Ia), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta);

optionally, (d2) washing the compound or derivative having formula (Ia-H), or salt, solvate, or prodrug thereof, wherein $R^6$, $R^7$, and $R^8$ are each hydrogen, with cold alcohol (e.g., methanol, or ethanol); and optionally, (d3) drying the compound or derivative having formula (Ia-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Ia-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (Ia-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (Ia-H), or a salt, solvate, or prodrug thereof, wherein $R^6$, $R^7$, and $R^8$ are each hydrogen, can include the steps of:

(a) adding a volume of methanol and water in a 95:5 weight:weight ratio to the compound or derivative having formula (Ia-H), or salt, solvate, or prodrug thereof, wherein $R^6$, $R^7$, and $R^8$ are each hydrogen, at room temperature, so as to dissolve approximately 15% of the compound or derivative having formula (Ia-H), or salt, solvate, or prodrug thereof, wherein $R^6$, $R^7$, and $R^8$ are each hydrogen, in the volume of methanol and water;

(b) stirring the compound or derivative having formula (Ia-H), or salt, solvate, or prodrug thereof, wherein $R^6$, $R^7$, and $R^8$ are each hydrogen, at 50° C. until all of the compound or derivative having formula (Ia-H), or salt, solvate, or prodrug thereof, wherein $R^6$, $R^7$, and $R^8$ are each hydrogen, apparently dissolves in the volume of methanol and water;

(c) cooling the solution of the compound or derivative having formula (Ia-H), or salt, solvate, or prodrug thereof, wherein $R^6$, $R^7$, and $R^8$ are each hydrogen, in the volume of methanol and water, to −10° C. with stirring so as to precipitate the crystalline form of the compound or derivative having formula (Ia-H), or salt, solvate, or prodrug thereof, wherein $R^6$, $R^7$, and $R^8$ are each hydrogen;

(d) filtering the volume of methanol and water and the crystalline form of the compound or derivative having formula (Ia-H), or salt, solvate, or prodrug thereof, wherein $R^6$, $R^7$, and R' are each hydrogen, so as to isolate the crystalline form of the compound or derivative having formula (Ia-H), or salt, solvate, or prodrug thereof, wherein $R^6$, $R^7$, and $R^8$ are each hydrogen; and (e) drying the crystalline form of the compound or derivative having formula (Ia-H), or salt, solvate, or prodrug thereof, wherein $R^6$, $R^7$, and $R^8$ are each hydrogen.

The process described herein effects a preparation of a crystalline form of a compound or derivative having formula (Ia-H), or salt, solvate, or prodrug thereof, wherein $R^6$, $R^7$, and $R^8$ are each hydrogen.

In yet another embodiment, a method of making a compound or derivative having formula (Ia-H), or a salt, solvate, or prodrug thereof, wherein $R^6$, $R^7$, and $R^8$ are each hydrogen, can include the steps of:

(a) providing a compound or derivative having formula (Ia), or a salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta);

(b) treating the compound or derivative having formula (Ia), or salt, solvate, or prodrug thereof, wherein $R^6$, $R^7$, and $R^8$ are each —C(O)R', and wherein R' is methyl or —$C_1$alkyl, with molar equivalent amounts (3<x<100) of an alcohol (e.g., methanol, or ethanol) and molar equivalent amounts (3≤x<20) of an acyl chloride;

(c) processing, under sealed conditions, the compound having formula (Ia), or salt, solvate, or prodrug thereof, wherein $R^6$, $R^7$, and $R^8$ are each —C(O)R', and wherein R' is methyl or —$C_1$alkyl, the alcohol (e.g., methanol, or ethanol), and the acyl chloride, so as to generate HCl in situ and produce the compound or derivative having formula (Ia-H), or salt, solvate, or prodrug thereof, wherein $R^6$, $R^7$, and $R^8$ are each hydrogen;

(d) isolating the compound or derivative having formula (Ia-H), or salt, solvate, or prodrug thereof, wherein $R^6$, $R^7$, and $R^8$ are each hydrogen;

optionally, (d1) separately isolating the unreacted compound or derivative having formula (Ia), or salt, solvate, or prodrug thereof, wherein $R^6$, $R^7$, and $R^8$ are each —C(O)R', and wherein R' is methyl or —$C_1$alkyl, optionally in a particular anomeric ratio (alpha/beta);

optionally, (d2) washing the compound or derivative having formula (Ia-H), or salt, solvate, or prodrug thereof, wherein $R^6$, $R^7$, and $R^8$ are each hydrogen, with cold alcohol (e.g., methanol, or ethanol); and optionally, (d3) drying the compound or derivative having formula (Ia-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Ia-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (Ia-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (Ia-H), or a salt, solvate, or prodrug thereof, wherein $R^6$, $R^7$, and $R^8$ are each hydrogen, can include the steps of:

(a) adding a volume of methanol and water in a 95:5 weight:weight ratio to the compound or derivative having formula (Ia-H), or salt, solvate, or prodrug thereof, wherein $R^6$, $R^7$, and $R^8$ are each hydrogen, at room temperature, so as to dissolve approximately 15% of the compound or derivative having formula (Ia-H), or salt, solvate, or prodrug thereof, wherein $R^6$, $R^7$, and $R^8$ are each hydrogen, in the volume of methanol and water;

(b) stirring the compound or derivative having formula (Ia-H), or salt, solvate, or prodrug thereof, wherein $R^6$, $R^7$, and $R^8$ are each hydrogen, at 50° C. until all of the compound or derivative having formula (Ia-H), or salt, solvate, or prodrug thereof, wherein $R^6$, $R^7$, and $R^8$ are each hydrogen, apparently dissolves in the volume of methanol and water;

(c) cooling the solution of the compound or derivative having formula (Ia-H), or salt, solvate, or prodrug thereof, wherein $R^6$, $R^7$, and $R^8$ are each hydrogen, in the volume of methanol and water, to −10° C. with stirring so as to precipitate the crystalline form of the compound or derivative having formula (Ia-H), or salt, solvate, or prodrug thereof, wherein $R^6$, $R^7$, and $R^8$ are each hydrogen;

(d) filtering the volume of methanol and water and the crystalline form of the compound or derivative having formula (Ia-H), or salt, solvate, or prodrug thereof, wherein $R^6$, $R^7$, and R' are each hydrogen, so as to isolate the crystalline form of the compound or derivative having formula (Ia-H), or salt, solvate, or prodrug thereof, wherein $R^6$, $R^7$, and $R^8$ are each hydrogen; and (e) drying the crystalline form of the compound or derivative having formula (Ia-H), or salt, solvate, or prodrug thereof, wherein $R^6$, $R^7$, and $R^8$ are each hydrogen.

The process described herein effects a preparation of a crystalline form of a compound or derivative having formula (Ia-H), or salt, solvate, or prodrug thereof, wherein $R^6$, $R^7$, and $R^8$ are each hydrogen.

In yet another embodiment, a method of making a compound or derivative having formula (Ia-H), or a salt, solvate, or prodrug thereof, wherein $R^6$, $R^7$, and $R^8$ are each hydrogen, optionally in a particular anomeric ratio (alpha/beta), can include the steps of:

(a) providing a compound or derivative having formula (1a), or a salt thereof;

optionally, (a1) treating the compound or derivative having formula (1a), or salt thereof, with excess trimethylsilylating reagent(s), and, optionally, heating the compound or derivative having formula (1a), or salt thereof, the trimethylsilylating reagent(s), to reflux for about 12 hours, so as to produce a compound or derivative having formula (1a), or salt thereof, optionally wherein $R^1$ is a TMS group;

optionally, (a2) cooling the mixture to room temperature;

optionally, (a3) removing the trimethylsilylating reagent(s);

(b) treating the compound or derivative having formula (1a), or salt thereof, optionally wherein $R^1$ is a TMS group, with a molar equivalent amount of a compound or derivative having formula (2), or a salt thereof, in an organic solvent co-reagent;

optionally, (b1) treating the compound or derivative having formula (1a), or salt thereof, optionally wherein $R^1$ is a TMS group, and the compound or derivative having formula (2), or salt thereof, in an organic solvent co-reagent, with a molar equivalent amount of TMSOTf;

(c) processing the compound or derivative having formula (1a), or salt thereof, optionally wherein $R^1$ is a TMS group, the compound or derivative having formula (2), or salt thereof, optionally, the TMSOTf, and the organic solvent co-reagent so as to produce a compound or derivative having formula (Ia), or a salt, solvate, or prodrug thereof, optionally wherein $R^1$ is a TMS group, optionally in a particular anomeric ratio (alpha/beta);

(d) adding water to, optionally, the compound or derivative having formula (1a), or salt thereof, optionally wherein $R^1$ is a TMS group, optionally, the compound or derivative having formula (2), or salt thereof, optionally, the TMSOTf, the organic solvent co-reagent, and the compound or derivative having formula (Ia), or salt, solvate, or prodrug thereof, optionally wherein $R^1$ is a TMS group, optionally in a particular anomeric ratio (alpha/beta);

optionally, (d1) adding saturated $NaHCO_3$ solution to, optionally, the compound or derivative having formula (1a), or salt thereof, optionally wherein $R^1$ is a TMS group, optionally, the compound or derivative having formula (2), or salt thereof, optionally, the TMSOTf, the organic solvent co-reagent, and the compound or derivative having formula (Ia), or salt, solvate, or prodrug thereof, optionally wherein $R^1$ is a TMS group, optionally in a particular anomeric ratio (alpha/beta), and water;

optionally, (d2) adjusting the pH of the aqueous phase;

optionally, (d3) separating the organic phase from the aqueous phase;

(e) freeze-drying the aqueous phase to provide the compound or derivative having formula (Ia), or salt, solvate, or prodrug thereof, optionally in a particular anomeric ratio (alpha/beta);

(f) dissolving the compound or derivative having formula (Ia), or salt, solvate, or prodrug thereof, optionally in a particular anomeric ratio (alpha/beta), in methanol in a gas pressure tube;

(g) cooling the solution of the compound or derivative having formula (Ia), or salt, solvate, or prodrug thereof, optionally in a particular anomeric ratio (alpha/beta), in methanol to −78° C.;

(h) bubbling ammonia gas into the solution of the compound or derivative having formula (Ia), or salt, solvate, or prodrug thereof, optionally in a particular anomeric ratio (alpha/beta), in methanol, so as to produce the compound or derivative having formula (Ia-H), or salt, solvate, or prodrug thereof, wherein $R^6$, $R^7$, and $R^8$ are each hydrogen, optionally in a particular anomeric ratio (alpha/beta);

(i) sealing the pressure tube;

(j) raising the temperature to −20° C.;

(k) cooling the pressure tube at −20° C. for about 12 hours to about 4 days;

(l) unsealing the gas pressure tube; and (m) isolating the compound or derivative having formula (Ia-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Ia-H), or salt, solvate, or prodrug thereof, wherein $R^6$, $R^7$, and $R^8$ are each hydrogen, optionally in a particular anomeric ratio (alpha/beta).

The organic solvent co-reagent employed in the above method of making a compound or derivative having formula (Ia-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (Ia-H), or a salt, solvate, or prodrug thereof, wherein $R^6$, $R^7$, and $R^8$ are each hydrogen, optionally in a particular anomeric ratio (alpha/beta), can include the steps of:

(a) dissolving the compound or derivative having formula (Ia-H), or salt, solvate, or prodrug thereof, wherein $R^6$, $R^7$, and $R^8$ are each hydrogen, optionally in a particular anomeric ratio (alpha/beta), in a volume of methanol;

(b) adding a volume of acetone, of an equal volume to the volume of methanol, to the compound or derivative having formula (Ia-H), or salt, solvate, or prodrug thereof, wherein $R^6$, $R^7$, and $R^8$ are each hydrogen, optionally in a particular anomeric ratio (alpha/beta), in the volume of methanol;

(c) precipitating the crystalline form of the compound or derivative having formula (Ia-H), or salt, solvate, or prodrug thereof, wherein $R^6$, $R^7$, and $R^8$ are each hydrogen, optionally in a particular anomeric ratio (alpha/beta);

(d) isolating the crystalline form of the compound or derivative having formula (Ia-H), or salt, solvate, or prodrug thereof, wherein $R^6$, $R^7$, and $R^8$ are each hydrogen, optionally in a particular anomeric ratio (alpha/beta); and (e) washing the crystalline form of the compound or derivative having formula (Ia-H), or salt, solvate, or prodrug thereof, wherein $R^6$, $R^7$, and $R^8$ are each hydrogen, optionally in a particular anomeric ratio (alpha/beta), with cold methanol.

The process described herein effects a preparation of a crystalline form of a compound or derivative having formula (Ia-H), or salt, solvate, or prodrug thereof, wherein $R^6$, $R^7$, and $R^8$ are each hydrogen, optionally in a particular anomeric ratio (alpha/beta).

In an embodiment, a method of making a compound or derivative having formula (II), or a salt, solvate, or prodrug thereof, wherein $Y^3$ is oxygen, can include the steps of:

(a) providing a compound or derivative having formula (I), or a salt, solvate, or prodrug thereof, wherein $R^6$ is hydrogen;

(b) treating the compound or derivative having formula (I), or salt, solvate, or prodrug thereof, wherein $R^6$ is hydrogen, with a phosphorylating reagent;

optionally, (b1) treating the compound or derivative having formula (I), or salt, solvate, or prodrug thereof, wherein $R^6$ is hydrogen, and the phosphorylating reagent, with a (0<x≤20) molar equivalent amount of a Brønsted acid or base;

(c) processing the compound or derivative having formula (I), or salt, solvate, or prodrug thereof, wherein $R^6$ is hydrogen, the phosphorylating reagent, and, optionally, the Brønsted acid or base, so as to produce the compound or derivative having formula (II), or salt, solvate, or prodrug thereof, wherein $Y^3$ is oxygen;

(d) adding, optionally, the compound or derivative having formula (I), or salt, solvate, or prodrug thereof, wherein $R^6$ is hydrogen, optionally, the phosphorylating reagent, optionally, the Brønsted acid or base, and the compound or derivative having formula (II), or salt, solvate, or prodrug thereof, wherein $Y^3$ is oxygen, to iced water;

optionally, (d1) adjusting the pH of the aqueous phase with an aqueous base;

optionally, (d2) isolating the unreacted compound or derivative having formula (I), or salt, solvate, or prodrug thereof, wherein $R^6$ is hydrogen;

(e) isolating the compound or derivative having formula (II), or salt, solvate, or prodrug thereof, wherein $Y^3$ is oxygen; and optionally, (e1) treating the compound or derivative having formula (II), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (II), or salt, solvate, or prodrug thereof, wherein $Y^3$ is oxygen, under almost solventless conditions.

The polar organic solvent co-reagent and isolation solvent employed in the above method of making a compound or derivative having formula (II), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of methanol and water in a 3:2 volume:volume ratio at room temperature;

(b) stirring the compound or derivative having formula (II), or salt, solvate, or prodrug thereof, wherein $Y^3$ is oxygen, and the volume of methanol and water so as to dissolve the compound or derivative having formula (II), or salt, solvate, or prodrug thereof, wherein $Y^3$ is oxygen, in the volume of methanol and water;

(c) filtering the solution of the compound or derivative having formula (II), or salt, solvate, or prodrug thereof, wherein $Y^3$ is oxygen, in the volume of methanol and water, so as to remove any undissolved solids;

(d) adding a volume of acetone to the solution of the compound or derivative having formula (II), or salt, solvate, or prodrug thereof, wherein $Y^3$ is oxygen, in the volume of methanol and water, wherein the volume of acetone is about 2 to about 5 times the combined volume of methanol and water;

(e) cooling the compound or derivative having formula (II), or salt, solvate, or prodrug thereof, wherein $Y^3$ is oxygen, the volume of acetone, and the volume of methanol and water at −20° C. so as to precipitate the crystalline form of the compound or derivative having formula (II), or salt, solvate, or prodrug thereof, wherein $Y^3$ is oxygen;

(f) filtering the crystalline form of the compound or derivative having formula (II), or salt, solvate, or prodrug thereof, wherein $Y^3$ is oxygen, the volume of acetone, and the volume of methanol and water so as to isolate the crystalline form of the compound or derivative having formula (II), or salt, solvate, or prodrug thereof, wherein $Y^3$ is oxygen; and (g) drying the crystalline form of the compound or derivative having formula (II), or salt, solvate, or prodrug thereof, wherein $Y^3$ is oxygen, at room temperature.

The process described herein effects a preparation of a crystalline form of a compound or derivative having formula (II), or salt, solvate, or prodrug thereof, wherein $Y^3$ is oxygen.

In a particular embodiment, an alternative method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of methanol and water in a 3:2 volume:volume ratio at room temperature;

(b) stirring the compound or derivative having formula (II), or salt, solvate, or prodrug thereof, wherein $Y^3$ is oxygen, and the volume of methanol and water so as to dissolve the compound or derivative having formula (II), or salt, solvate, or prodrug thereof, wherein $Y^3$ is oxygen, in the volume of methanol and water;

(c) filtering the solution of the compound or derivative having formula (II), or salt, solvate, or prodrug thereof, wherein $Y^3$ is oxygen, in the volume of methanol and water, so as to remove any undissolved solids;

(d) cooling the compound or derivative having formula (II), or salt, solvate, or prodrug thereof, wherein $Y^3$ is oxygen, and the volume of methanol and water at −20° C. so as to produce an oily layer at the bottom of the volume of methanol and water;

(e) decanting the volume of methanol and water from the oily layer at the bottom of the volume of methanol and water; and (f) drying the oily layer at room temperature so as to crystallize the crystalline form of the compound or derivative having formula (II), or salt, solvate, or prodrug thereof, wherein $Y^3$ is oxygen.

The process described herein effects a preparation of a crystalline form of a compound or derivative having formula (II), or salt, solvate, or prodrug thereof, wherein $Y^3$ is oxygen.

In a particular embodiment, another alternative method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of ethanol and water in a 3:2 volume:volume ratio at room temperature, wherein the compound or derivative having formula (II), or salt, solvate, or prodrug thereof, wherein $Y^3$ is oxygen, is added in an amount of about 200 milligrams per milliliter of the volume of ethanol and water;

(b) stirring the compound or derivative having formula (II), or salt, solvate, or prodrug thereof, wherein $Y^3$ is oxygen, and the volume of ethanol and water so as to dissolve the compound or derivative having formula (II), or salt, solvate, or prodrug thereof, wherein $Y^3$ is oxygen, in the volume of ethanol and water;

(c) filtering the solution of the compound or derivative having formula (II), or salt, solvate, or prodrug thereof, wherein $Y^3$ is oxygen, in the volume of ethanol and water, so as to remove any undissolved solids;

(d) cooling the compound or derivative having formula (II), or salt, solvate, or prodrug thereof, wherein $Y^3$ is oxygen, in the volume of ethanol and water, to −10° C. for about 48 hours so as to produce the crystalline form of the compound or derivative having formula (II), or salt, solvate, or prodrug thereof, wherein $Y^3$ is oxygen;

(e) decanting the volume of ethanol and water from the crystalline form of the compound or derivative having formula (II), or salt, solvate, or prodrug thereof, wherein $Y^3$ is oxygen, so as to isolate the crystalline form of the compound or derivative having formula (II), or salt, solvate, or prodrug thereof, wherein $Y^3$ is oxygen; and (f) drying the crystalline form of the compound or derivative having formula (II), or salt, solvate, or prodrug thereof, wherein $Y^3$ is oxygen, at room temperature.

The process described herein effects a preparation of a crystalline form of a compound or derivative having formula (II), or salt, solvate, or prodrug thereof, wherein $Y^3$ is oxygen.

In another embodiment, a method of making a compound or derivative having formula (II), or a salt, solvate, or prodrug thereof, wherein $Y^3$ is oxygen, can include the steps of:

(a) providing a compound or derivative having formula (I), or a salt, solvate, or prodrug thereof, wherein $R^6$ is hydrogen;

(b) treating the compound or derivative having formula (I), or salt, solvate, or prodrug thereof, wherein $R^6$ is hydrogen, with a phosphitylating reagent;

optionally, (b1) treating the compound or derivative having formula (I), or salt, solvate, or prodrug thereof, wherein $R^6$ is hydrogen, and the phosphitylating reagent, with a (0<x≤20) molar equivalent amount of a Brønsted acid or base;

(c) processing the compound or derivative having formula (I), or salt, solvate, or prodrug thereof, wherein $R^6$ is hydrogen, the phosphitylating reagent, and, optionally, the Brønsted acid or base so as to produce a compound or derivative having formula (II), or salt, solvate, or prodrug thereof, wherein $Y^3$ is absent;

(d) adding an oxidizing agent reagent to, optionally, the compound or derivative having formula (I), or salt, solvate, or prodrug thereof, wherein $R^6$ is hydrogen, optionally, the phosphitylating reagent, optionally, the Brønsted acid or base, and the compound or derivative having formula (II), or salt, solvate, or prodrug thereof, wherein $Y^3$ is absent;

(e) processing the oxidizing agent reagent, optionally, the compound or derivative having formula (I), or salt, solvate, or prodrug thereof, wherein $R^6$ is hydrogen, optionally, the phosphitylating reagent, optionally, the Brønsted acid or base, and the compound or derivative having formula (II), or salt, solvate, or prodrug thereof, wherein $Y^3$ is absent, so as to produce the compound or derivative having formula (II), or salt, solvate, or prodrug thereof, wherein $Y^3$ is oxygen;

(f) adding, optionally, the oxidizing agent reagent, optionally, the compound or derivative having formula (I), or salt, solvate, or prodrug thereof, wherein $R^6$ is hydrogen, optionally, the phosphitylating reagent, optionally, the Brønsted acid or base, optionally, the compound or derivative having formula (II), or salt, solvate, or prodrug thereof, wherein $Y^3$ is absent, and the compound or derivative having formula (II), or salt, solvate, or prodrug thereof, wherein $Y^3$ is oxygen, to iced water;

optionally, (f1) adjusting the pH of the aqueous phase with an aqueous base;

(g) isolating the compound or derivative having formula (II), or salt, solvate, or prodrug thereof, wherein $Y^3$ is oxygen; and optionally, (g1) treating the compound or derivative having formula (II), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (II), or salt, solvate, or prodrug thereof, wherein $Y^3$ is oxygen, under almost solventless conditions.

The polar organic solvent co-reagent and isolation solvent employed in the above method of making a compound or derivative having formula (II), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of methanol and water in a 3:2 volume:volume ratio at room temperature;

(b) stirring the compound or derivative having formula (II), or salt, solvate, or prodrug thereof, wherein $Y^3$ is oxygen, and the volume of methanol and water so as to dissolve the compound or derivative having formula (II), or salt, solvate, or prodrug thereof, wherein $Y^3$ is oxygen, in the volume of methanol and water;

(c) filtering the solution of the compound or derivative having formula (II), or salt, solvate, or prodrug thereof, wherein $Y^3$ is oxygen, in the volume of methanol and water, so as to remove any undissolved solids;

(d) adding a volume of acetone to the solution of the compound or derivative having formula (II), or salt, solvate, or prodrug thereof, wherein $Y^3$ is oxygen, in the volume of methanol and water, wherein the volume of acetone is about 2 to about 5 times the combined volume of methanol and water;

(e) cooling the compound or derivative having formula (II), or salt, solvate, or prodrug thereof, wherein $Y^3$ is oxygen, the volume of acetone, and the volume of methanol and water at −20° C. so as to precipitate the crystalline form of the compound or derivative having formula (II), or salt, solvate, or prodrug thereof, wherein $Y^3$ is oxygen;

(f) filtering the crystalline form of the compound or derivative having formula (II), or salt, solvate, or prodrug thereof, wherein $Y^3$ is oxygen, the volume of acetone, and the volume of methanol and water so as to isolate the crystalline form of the compound or derivative having formula (II), or salt, solvate, or prodrug thereof, wherein $Y^3$ is oxygen; and (g) drying the crystalline form of the compound or derivative having formula (II), or salt, solvate, or prodrug thereof, wherein $Y^3$ is oxygen, at room temperature.

The process described herein effects a preparation of a crystalline form of a compound or derivative having formula (II), or salt, solvate, or prodrug thereof, wherein $Y^3$ is oxygen.

In a particular embodiment, an alternative method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of methanol and water in a 3:2 volume:volume ratio at room temperature;

(b) stirring the compound or derivative having formula (II), or salt, solvate, or prodrug thereof, wherein $Y^3$ is oxygen, and the volume of methanol and water so as to dissolve the compound or derivative having formula (II), or salt, solvate, or prodrug thereof, wherein $Y^3$ is oxygen, in the volume of methanol and water;

(c) filtering the solution of the compound or derivative having formula (II), or salt, solvate, or prodrug thereof, wherein $Y^3$ is oxygen, in the volume of methanol and water, so as to remove any undissolved solids;

(d) cooling the compound or derivative having formula (II), or salt, solvate, or prodrug thereof, wherein $Y^3$ is oxygen, and the volume of methanol and water at −20° C. so as to produce an oily layer at the bottom of the volume of methanol and water;

(e) decanting the volume of methanol and water from the oily layer at the bottom of the volume of methanol and water; and (f) drying the oily layer at room temperature so as to crystallize the crystalline form of the compound or derivative having formula (II), or salt, solvate, or prodrug thereof, wherein $Y^3$ is oxygen.

The process described herein effects a preparation of a crystalline form of a compound or derivative having formula (II), or salt, solvate, or prodrug thereof, wherein $Y^3$ is oxygen.

In a particular embodiment, another alternative method of making a crystalline form of the compound or derivative having formula (II), or salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of ethanol and water in a 3:2 volume:volume ratio at room temperature, wherein the compound or derivative having formula (II), or salt, solvate, or prodrug thereof, wherein $Y^3$ is oxygen, is added in an amount of about 200 milligrams per milliliter of the volume of ethanol and water;

(b) stirring the compound or derivative having formula (II), or salt, solvate, or prodrug thereof, wherein $Y^3$ is oxygen, and the volume of ethanol and water so as to dissolve the compound or derivative having formula (II), or salt, solvate, or prodrug thereof, wherein $Y^3$ is oxygen, in the volume of ethanol and water;

(c) filtering the solution of the compound or derivative having formula (II), or salt, solvate, or prodrug thereof, wherein $Y^3$ is oxygen, in the volume of ethanol and water, so as to remove any undissolved solids;

(d) cooling the compound or derivative having formula (II), or salt, solvate, or prodrug thereof, wherein $Y^3$ is oxygen, in the volume of ethanol and water, to −10° C. for about 48 hours so as to produce the crystalline form of the compound or derivative having formula (II), or salt, solvate, or prodrug thereof, wherein $Y^3$ is oxygen;

(e) decanting the volume of ethanol and water from the crystalline form of the compound or derivative having formula (II), or salt, solvate, or prodrug thereof, wherein $Y^3$ is oxygen, so as to isolate the crystalline form of the compound or derivative having formula (II), or salt, solvate, or prodrug thereof, wherein $Y^3$ is oxygen; and (f) drying the crystalline form of the compound or derivative having formula (II), or salt, solvate, or prodrug thereof, wherein $Y^3$ is oxygen, at room temperature.

The process described herein effects a preparation of a crystalline form of a compound or derivative having formula (II), or salt, solvate, or prodrug thereof, wherein $Y^3$ is oxygen.

In yet another embodiment, a method of making a compound or derivative having formula (II), or a salt, solvate, or prodrug thereof, wherein $Y^3$ is absent, can include the steps of:

(a) providing a compound or derivative having formula (I), or a salt, solvate, or prodrug thereof, wherein $R^6$ is hydrogen;

(b) treating the compound or derivative having formula (I), or salt, solvate, or prodrug thereof, wherein $R^6$ is hydrogen, with a phosphitylating reagent;

optionally, (b1) treating the compound or derivative having formula (I), or salt, solvate, or prodrug thereof, wherein $R^6$ is hydrogen, and the phosphitylating reagent, with a (0<x≤20) molar equivalent amount of a Brønsted acid or base;

(c) processing the compound or derivative having formula (I), or salt, solvate, or prodrug thereof, wherein $R^6$ is hydrogen, the phosphitylating reagent, and, optionally, the Brønsted acid or base so as to produce the compound or derivative having formula (II), or salt, solvate, or prodrug thereof, wherein $Y^3$ is absent;

(d) adding, optionally, the compound or derivative having formula (I), or salt, solvate, or prodrug thereof, wherein $R^6$ is hydrogen, optionally, the phosphitylating reagent, optionally, the Brønsted acid or base, and the compound or derivative having formula (II), or salt, solvate, or prodrug thereof, wherein $Y^3$ is absent, to iced water;

optionally, (d1) adjusting the pH of the aqueous phase with an aqueous base;

(e) isolating the compound or derivative having formula (II), or salt, solvate, or prodrug thereof, wherein $Y^3$ is absent; and optionally, (e1) treating the compound or derivative having formula (II), or salt, solvate, or prodrug thereof, wherein $Y^3$ is absent, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (II), or salt, solvate, or prodrug thereof, wherein $Y^3$ is absent, under almost solventless conditions.

The polar organic solvent co-reagent and isolation solvent employed in the above method of making a compound or derivative having formula (II), or salt, solvate, or prodrug thereof, wherein $Y^3$ is absent, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (II), or a salt, solvate, or prodrug thereof, wherein $Y^3$ is sulfur, can include the steps of:

(a) providing a compound or derivative having formula (I), or a salt, solvate, or prodrug thereof, wherein $R^6$ is hydrogen;

(b) treating the compound or derivative having formula (I), or salt, solvate, or prodrug thereof, wherein $R^6$ is hydrogen, with a phosphitylating reagent;

optionally, (b1) treating the compound or derivative having formula (I), or salt, solvate, or prodrug thereof, wherein $R^6$ is hydrogen, and the phosphitylating reagent, with a (0<x≤20) molar equivalent amount of a Brønsted acid or base;

(c) processing the compound or derivative having formula (I), or salt, solvate, or prodrug thereof, wherein $R^6$ is hydrogen, the phosphitylating reagent, and, optionally, the Brønsted acid or base so as to produce a compound or derivative having formula (II), or a salt, solvate, or prodrug thereof, wherein $Y^3$ is absent;

(d) adding an oxidizing agent reagent to, optionally, the compound or derivative having formula (I), or salt, solvate, or prodrug thereof, wherein $R^6$ is hydrogen, optionally, the phosphitylating reagent, optionally, the Brønsted acid or base, and the compound or derivative having formula (II), or salt, solvate, or prodrug thereof, wherein $Y^3$ is absent;

(e) processing the oxidizing agent reagent, optionally, the compound or derivative having formula (I), or salt, solvate, or prodrug thereof, wherein $R^6$ is hydrogen, optionally, the phosphitylating reagent, optionally, the Brønsted acid or base, and the compound or derivative having formula (II), or salt, solvate, or prodrug thereof, wherein $Y^3$ is absent, so as to produce the compound or derivative having formula (II), or salt, solvate, or prodrug thereof, wherein $Y^3$ is sulfur;

(f) adding, optionally, the oxidizing agent reagent, optionally, the compound or derivative having formula (I), or salt, solvate, or prodrug thereof, wherein $R^6$ is hydrogen, optionally, the phosphitylating reagent, optionally, the Brønsted acid or base, optionally, the compound or derivative having formula (II), or salt, solvate, or prodrug thereof, wherein $Y^3$ is absent, and the compound or derivative having formula (II), or salt, solvate, or prodrug thereof, wherein $Y^3$ is sulfur, to iced water;

optionally, (f1) adjusting the pH of the aqueous phase with an aqueous base;

(g) isolating the compound or derivative having formula (II), or salt, solvate, or prodrug thereof, wherein $Y^3$ is sulfur; and optionally, (g1) treating the compound or derivative having formula (II), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (II), or salt, solvate, or prodrug thereof, wherein $Y^3$ is sulfur, under almost solventless conditions.

The polar organic solvent co-reagent and isolation solvent employed in the above method of making a compound or derivative having formula (II), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (II), or a salt, solvate, or prodrug thereof, wherein $Y^3$ is sulfur, can include the steps of:

(a) providing a compound or derivative having formula (I), or a salt, solvate, or prodrug thereof, wherein $R^6$ is hydrogen;

(b) treating the compound or derivative having formula (I), or salt, solvate, or prodrug thereof, wherein $R^6$ is hydrogen, with a thiophosphorylating reagent;

optionally, (b1) treating the compound or derivative having formula (I), or salt, solvate, or prodrug thereof, wherein $R^6$ is hydrogen, and the thiophosphorylating reagent, with a (0<x≤20) molar equivalent amount of a Brønsted acid or base;

(c) processing the compound or derivative having formula (I), or salt, solvate, or prodrug thereof, wherein $R^6$ is hydrogen, the thiophosphorylating reagent, and, optionally, the Brønsted acid or base, so as to produce the compound or derivative having formula (II), or salt, solvate, or prodrug thereof, wherein $Y^3$ is sulfur;

(d) adding, optionally, the compound or derivative having formula (I), or salt, solvate, or prodrug thereof, wherein $R^6$ is hydrogen, optionally, the thiophosphorylating reagent, optionally, the Brønsted acid or base, and the compound or derivative having formula (II), or salt, solvate, or prodrug thereof, wherein $Y^3$ is sulfur, to iced water;

optionally, (d1) adjusting the pH of the aqueous phase with an aqueous base;

optionally, (d2) isolating the unreacted compound or derivative having formula (I), or salt, solvate, or prodrug thereof, wherein $R^6$ is hydrogen;

(e) isolating the compound or derivative having formula (II), or salt, solvate, or prodrug thereof, wherein $Y^3$ is sulfur; and optionally, (e1) treating the compound or derivative having formula (II), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (II), or salt, solvate, or prodrug thereof, wherein $Y^3$ is sulfur, under almost solventless conditions.

The polar organic solvent co-reagent and isolation solvent employed in the above method of making a compound or derivative having formula (II), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (II), or a salt, solvate, or prodrug thereof, wherein $Y^3$ is oxygen, can include the steps of:

(a) providing a compound or derivative having formula (I-H), or a salt, solvate, or prodrug thereof, wherein $R^6$, $R^7$, and $R^8$ are each hydrogen;

(b) treating the compound or derivative having formula (I-H), or salt, solvate, or prodrug thereof, wherein $R^6$, $R^7$, and $R^8$ are each hydrogen, with a phosphorylating reagent;

optionally, (b1) treating the compound or derivative having formula (I-H), or salt, solvate, or prodrug thereof, wherein $R^6$, $R^7$, and $R^8$ are each hydrogen, and the phosphorylating reagent, with a (0<x≤20) molar equivalent amount of a Brønsted acid or base;

(c) processing the compound or derivative having formula (I-H), or salt, solvate, or prodrug thereof, wherein $R^6$, $R^7$, and $R^8$ are each hydrogen, the phosphorylating reagent, and, optionally, the Brønsted acid or base, so as to produce the compound or derivative having formula (II), or salt, solvate, or prodrug thereof, wherein $Y^3$ is oxygen;

(d) adding, optionally, the compound or derivative having formula (I-H), or salt, solvate, or prodrug thereof, wherein $R^6$, $R^7$, and $R^8$ are each hydrogen, optionally, the phosphorylating reagent, optionally, the Brønsted acid or base, and the compound or derivative having formula (II), or salt, solvate, or prodrug thereof, wherein $Y^3$ is oxygen, to iced water;

optionally, (d1) adjusting the pH of the aqueous phase with an aqueous base;

optionally, (d2) isolating the unreacted compound or derivative having formula (I-H), or salt, solvate, or prodrug thereof, wherein $R^6$, $R^7$, and $R^8$ are each hydrogen; and (e) isolating the compound or derivative having formula (II), or salt, solvate, or prodrug thereof, wherein $Y^3$ is oxygen; and optionally, (e1) treating the compound or derivative having formula (II), wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (II), or salt, solvate, or prodrug thereof, wherein $Y^3$ is oxygen, under almost solventless conditions.

The polar organic solvent co-reagent and isolation solvent employed in the above method of making a compound or derivative having formula (II), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of methanol and water in a 3:2 volume:volume ratio at room temperature;

(b) stirring the compound or derivative having formula (II), or salt, solvate, or prodrug thereof, wherein $Y^3$ is oxygen, and the volume of methanol and water so as to dissolve the compound or derivative having formula (II), or salt, solvate, or prodrug thereof, wherein $Y^3$ is oxygen, in the volume of methanol and water;

(c) filtering the solution of the compound or derivative having formula (II), or salt, solvate, or prodrug thereof, wherein $Y^3$ is oxygen, in the volume of methanol and water, so as to remove any undissolved solids;

(d) adding a volume of acetone to the solution of the compound or derivative having formula (II), or salt, solvate, or prodrug thereof, wherein $Y^3$ is oxygen, in the volume of methanol and water, wherein the volume of acetone is about 2 to about 5 times the combined volume of methanol and water;

(e) cooling the compound or derivative having formula (II), or salt, solvate, or prodrug thereof, wherein $Y^3$ is oxygen, the volume of acetone, and the volume of methanol and water at −20° C. so as to precipitate the crystalline form of the compound or derivative having formula (II), or salt, solvate, or prodrug thereof, wherein $Y^3$ is oxygen;

(f) filtering the crystalline form of the compound or derivative having formula (II), or salt, solvate, or prodrug thereof, wherein $Y^3$ is oxygen, the volume of acetone, and the volume of methanol and water so as to isolate the crystalline form of the compound or derivative having formula (II), or salt, solvate, or prodrug thereof, wherein $Y^3$ is oxygen; and (g) drying the crystalline form of the compound or derivative having formula (II), or salt, solvate, or prodrug thereof, wherein $Y^3$ is oxygen, at room temperature.

The process described herein effects a preparation of a crystalline form of a compound or derivative having formula (II), or salt, solvate, or prodrug thereof, wherein $Y^3$ is oxygen.

In a particular embodiment, an alternative method of making a crystalline form of a compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of methanol and water in a 3:2 volume:volume ratio at room temperature;

(b) stirring the compound or derivative having formula (II), or salt, solvate, or prodrug thereof, wherein $Y^3$ is oxygen, and the volume of methanol and water so as to dissolve the compound or derivative having formula (II), or salt, solvate, or prodrug thereof, wherein $Y^3$ is oxygen, in the volume of methanol and water;

(c) filtering the solution of the compound or derivative having formula (II), or salt, solvate, or prodrug thereof, wherein $Y^3$ is oxygen, in the volume of methanol and water, so as to remove any undissolved solids;

(d) cooling the compound or derivative having formula (II), or salt, solvate, or prodrug thereof, wherein $Y^3$ is oxygen, and the volume of methanol and water at −20° C. so as to produce an oily layer at the bottom of the volume of methanol and water;

(e) decanting the volume of methanol and water from the oily layer at the bottom of the volume of methanol and water; and (f) drying the oily layer at room temperature so as to crystallize the crystalline form of the compound or derivative having formula (II), or salt, solvate, or prodrug thereof, wherein $Y^3$ is oxygen.

The process described herein effects a preparation of a crystalline form of a compound or derivative having formula (II), or salt, solvate, or prodrug thereof, wherein $Y^3$ is oxygen.

In a particular embodiment, another alternative method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of ethanol and water in a 3:2 volume:volume ratio at room temperature, wherein the compound or derivative having formula (II), or salt, solvate, or prodrug thereof, wherein $Y^3$ is oxygen, is added in an amount of about 200 milligrams per milliliter of the volume of ethanol and water;

(b) stirring the compound or derivative having formula (II), or salt, solvate, or prodrug thereof, wherein $Y^3$ is oxygen, and the volume of ethanol and water so as to dissolve the compound or derivative having formula (II), or salt, solvate, or prodrug thereof, wherein $Y^3$ is oxygen, in the volume of ethanol and water;

(c) filtering the solution of the compound or derivative having formula (II), or salt, solvate, or prodrug thereof, wherein $Y^3$ is oxygen, in the volume of ethanol and water, so as to remove any undissolved solids;

(d) cooling the compound or derivative having formula (II), or salt, solvate, or prodrug thereof, wherein $Y^3$ is oxygen, in the volume of ethanol and water, to −10° C. for about 48 hours so as to produce the crystalline form of the compound or derivative having formula (II), or salt, solvate, or prodrug thereof, wherein $Y^3$ is oxygen;

(e) decanting the volume of ethanol and water from the crystalline form of the compound or derivative having formula (II), or salt, solvate, or prodrug thereof, wherein $Y^3$ is oxygen, so as to isolate the crystalline form of the compound or derivative having formula (II), or salt, solvate, or prodrug thereof, wherein $Y^3$ is oxygen; and (f) drying the crystalline form of the compound or derivative having formula (II), or salt, solvate, or prodrug thereof, wherein $Y^3$ is oxygen, at room temperature.

The process described herein effects a preparation of a crystalline form of a compound or derivative having formula (II), or salt, solvate, or prodrug thereof, wherein $Y^3$ is oxygen.

In yet another embodiment, a method of making a compound or derivative having formula (II), or a salt, solvate, or prodrug thereof, wherein $Y^3$ is oxygen, can include the steps of:

(a) providing a compound or derivative having formula (I-H), or a salt, solvate, or prodrug thereof, wherein $R^6$, $R^7$, and $R^8$ are each hydrogen;

(b) treating the compound or derivative having formula (I-H), or salt, solvate, or prodrug thereof, wherein $R^6$, $R^7$, and $R^8$ are each hydrogen, with a phosphitylating reagent;

optionally, (b1) treating the compound or derivative having formula (I-H), or salt, solvate, or prodrug thereof, wherein $R^6$, $R^7$, and $R^8$ are each hydrogen, and the phosphitylating reagent, with a (0<x≤20) molar equivalent amount of a Brønsted acid or base;

(c) processing the compound or derivative having formula (I-H), or salt, solvate, or prodrug thereof, wherein $R^6$, $R^7$, and $R^8$ are each hydrogen, the phosphitylating reagent, and, optionally, the Brønsted acid or base so as to produce a compound or derivative having formula (II), or salt, solvate, or prodrug thereof, wherein $Y^3$ is absent;

(d) adding an oxidizing agent reagent to, optionally, the compound or derivative having formula (I-H), or salt, solvate, or prodrug thereof, wherein $R^6$, $R^7$, and $R^8$ are each hydrogen, optionally, the phosphitylating reagent, optionally, the Brønsted acid or base, and the compound or derivative having formula (II), or salt, solvate, or prodrug thereof, wherein $Y^3$ is absent;

(e) processing the oxidizing agent reagent, optionally, the compound or derivative having formula (I-H), or salt, solvate, or prodrug thereof, wherein $R^6$, $R^7$, and $R^8$ are each hydrogen, optionally, the phosphitylating reagent, optionally, the Brønsted acid or base, and the compound or derivative having formula (II), or salt, solvate, or prodrug thereof, wherein $Y^3$ is absent, so as to produce the compound or derivative having formula (II), or salt, solvate, or prodrug thereof, wherein $Y^3$ is oxygen;

(f) adding, optionally, the oxidizing agent reagent, optionally, the compound or derivative having formula (I-H), or salt, solvate, or prodrug thereof, wherein $R^6$, $R^7$, and $R^8$ are each hydrogen, optionally, the phosphitylating reagent, optionally, the Brønsted acid or base, optionally, the compound or derivative having formula (II), or salt, solvate, or prodrug thereof, wherein $Y^3$ is absent, and the compound or derivative having formula (II), or salt, solvate, or prodrug thereof, wherein $Y^3$ is oxygen, to iced water;

optionally, (f1) adjusting the pH of the aqueous phase with an aqueous base;

(g) isolating the compound or derivative having formula (II), or salt, solvate, or prodrug thereof, wherein $Y^3$ is oxygen; and optionally, (g1) treating the compound or derivative having formula (II), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (II), or salt, solvate, or prodrug thereof, wherein $Y^3$ is oxygen, under almost solventless conditions.

The polar organic solvent co-reagent and isolation solvent employed in the above method of making a compound or derivative having formula (II), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of methanol and water in a 3:2 volume:volume ratio at room temperature;

(b) stirring the compound or derivative having formula (II), or salt, solvate, or prodrug thereof, wherein $Y^3$ is oxygen, and the volume of methanol and water so as to dissolve the compound or derivative having formula (II), or salt, solvate, or prodrug thereof, wherein $Y^3$ is oxygen, in the volume of methanol and water;

(c) filtering the solution of the compound or derivative having formula (II), or salt, solvate, or prodrug thereof, wherein $Y^3$ is oxygen, in the volume of methanol and water, so as to remove any undissolved solids;

(d) adding a volume of acetone to the solution of the compound or derivative having formula (II), or salt, solvate, or prodrug thereof, wherein $Y^3$ is oxygen, in the volume of methanol and water, wherein the volume of acetone is about 2 to about 5 times the combined volume of methanol and water;

(e) cooling the compound or derivative having formula (II), or salt, solvate, or prodrug thereof, wherein $Y^3$ is oxygen, the volume of acetone, and the volume of methanol and water at −20° C. so as to precipitate the crystalline form of the compound or derivative having formula (II), or salt, solvate, or prodrug thereof, wherein $Y^3$ is oxygen;

(f) filtering the crystalline form of the compound or derivative having formula (II), or salt, solvate, or prodrug thereof, wherein $Y^3$ is oxygen, the volume of acetone, and the volume of methanol and water so as to isolate the crystalline form of the compound or derivative having formula (II), or salt, solvate, or prodrug thereof, wherein $Y^3$ is oxygen; and (g) drying the crystalline form of the compound or derivative having formula (II), or salt, solvate, or prodrug thereof, wherein $Y^3$ is oxygen, at room temperature.

The process described herein effects a preparation of a crystalline form of a compound or derivative having formula (II), or salt, solvate, or prodrug thereof, wherein $Y^3$ is oxygen.

In a particular embodiment, an alternative method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of methanol and water in a 3:2 volume:volume ratio at room temperature;

(b) stirring the compound or derivative having formula (II), or salt, solvate, or prodrug thereof, wherein $Y^3$ is oxygen, and the volume of methanol and water so as to dissolve the compound or derivative having formula (II), or salt, solvate, or prodrug thereof, wherein $Y^3$ is oxygen, in the volume of methanol and water;

(c) filtering the solution of the compound or derivative having formula (II), or salt, solvate, or prodrug thereof, wherein $Y^3$ is oxygen, in the volume of methanol and water, so as to remove any undissolved solids;

(d) cooling the compound or derivative having formula (II), or salt, solvate, or prodrug thereof, wherein $Y^3$ is oxygen, and the volume of methanol and water at −20° C. so as to produce an oily layer at the bottom of the volume of methanol and water;

(e) decanting the volume of methanol and water from the oily layer at the bottom of the volume of methanol and water; and (f) drying the oily layer at room temperature so as to crystallize the crystalline form of the compound or derivative having formula (II), or salt, solvate, or prodrug thereof, wherein $Y^3$ is oxygen.

The process described herein effects a preparation of a crystalline form of a compound or derivative having formula (II), or salt, solvate, or prodrug thereof, wherein $Y^3$ is oxygen.

In a particular embodiment, another alternative method of making a crystalline form of the compound or derivative having formula (II), or a salt, solvate, or prodrug thereof, wherein $Y^3$ is oxygen, can include the steps of:

(a) adding the compound or derivative having formula (II), or salt, solvate, or prodrug thereof, wherein $Y^3$ is oxygen, to a volume of ethanol and water in a 3:2 volume:volume ratio at room temperature, wherein the compound or derivative having formula (II), or salt, solvate, or prodrug thereof, wherein $Y^3$ is oxygen, is added in an amount of about 200 milligrams per milliliter of the volume of ethanol and water;

(b) stirring the compound or derivative having formula (II), or salt, solvate, or prodrug thereof, wherein $Y^3$ is oxygen, and the volume of ethanol and water so as to dissolve the compound or derivative having formula (II), or salt, solvate, or prodrug thereof, wherein $Y^3$ is oxygen, in the volume of ethanol and water;

(c) filtering the solution of the compound or derivative having formula (II), or salt, solvate, or prodrug thereof, wherein $Y^3$ is oxygen, in the volume of ethanol and water, so as to remove any undissolved solids;

(d) cooling the compound or derivative having formula (II), or salt, solvate, or prodrug thereof, wherein $Y^3$ is oxygen, in the volume of ethanol and water, to −10° C. for about 48 hours so as to produce the crystalline form of the compound or derivative having formula (II), or salt, solvate, or prodrug thereof, wherein $Y^3$ is oxygen;

(e) decanting the volume of ethanol and water from the crystalline form of the compound or derivative having formula (II), or salt, solvate, or prodrug thereof, wherein $Y^3$ is oxygen, so as to isolate the crystalline form of the compound or derivative having formula (II), or salt, solvate, or prodrug thereof, wherein $Y^3$ is oxygen; and (f) drying the crystalline form of the compound or derivative having formula (II), or salt, solvate, or prodrug thereof, wherein $Y^3$ is oxygen, at room temperature.

The process described herein effects a preparation of a crystalline form of a compound or derivative having formula (II), or salt, solvate, or prodrug thereof, wherein $Y^3$ is oxygen.

In yet another embodiment, a method of making a compound or derivative having formula (II), or a salt, solvate, or prodrug thereof, wherein $Y^3$ is absent, can include the steps of:

(a) providing a compound or derivative having formula (I-H), or a salt, solvate, or prodrug thereof, wherein $R^6$, $R^7$, and $R^8$ are each hydrogen;

(b) treating the compound or derivative having formula (I-H), or salt, solvate, or prodrug thereof, wherein $R^6$, $R^7$, and $R^8$ are each hydrogen, with a phosphitylating reagent optionally, (b1) treating the compound or derivative having formula (I-H), or salt, solvate, or prodrug thereof, wherein $R^6$, $R^7$, and $R^8$ are each hydrogen, and the phosphitylating reagent, with a (0<x≤20) molar equivalent amount of a Brønsted acid or base;

(c) processing the compound or derivative having formula (I-H), or salt, solvate, or prodrug thereof, wherein $R^6$, $R^7$, and $R^8$ are each hydrogen, the phosphitylating reagent, and, optionally, the Brønsted acid or base so as to produce the compound or derivative having formula (II), or salt, solvate, or prodrug thereof, wherein $Y^3$ is absent;

(d) adding, optionally, the compound or derivative having formula (I-H), or salt, solvate, or prodrug thereof, wherein $R^6$, $R^7$, and $R^8$ are each hydrogen, optionally, the phosphitylating reagent, optionally, the Brønsted acid or base, and the compound or derivative having formula (II), or salt, solvate, or prodrug thereof, wherein $Y^3$ is absent, to iced water;

optionally, (d1) adjusting the pH of the aqueous phase with an aqueous base;

(e) isolating the compound or derivative having formula (II), or salt, solvate, or prodrug thereof, wherein $Y^3$ is absent; and optionally, (e1) treating the compound or derivative having formula (II), or salt, solvate, or prodrug thereof, wherein $Y^3$ is absent, with deprotection agent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (II), or salt, solvate, or prodrug thereof, wherein $Y^3$ is absent, under almost solventless conditions.

The polar organic solvent co-reagent and isolation solvent employed in the above method of making a compound or derivative having formula (II), or salt, solvate, or prodrug thereof, wherein $Y^3$ is absent, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (II), or a salt, solvate, or prodrug thereof, wherein $Y^3$ is sulfur, can include the steps of:

(a) providing a compound or derivative having formula (I-H), or a salt, solvate, or prodrug thereof, wherein $R^6$, $R^7$, and $R^8$ are each hydrogen;

(b) treating the compound or derivative having formula (I-H), or salt, solvate, or prodrug thereof, wherein $R^6$, $R^7$, and $R^8$ are each hydrogen, with a phosphitylating reagent;

optionally, (b1) treating the compound or derivative having formula (I-H), or salt, solvate, or prodrug thereof, wherein $R^6$, $R^7$, and $R^8$ are each hydrogen, and the phosphitylating reagent, with a (0<x≤20) molar equivalent amount of a Brønsted acid or base;

(c) processing the compound or derivative having formula (I-H), or salt, solvate, or prodrug thereof, wherein $R^6$, $R^7$, and $R^8$ are each hydrogen, the phosphitylating reagent, and, optionally, the Brønsted acid or base so as to produce a compound or derivative having formula (II), or a salt, solvate, or prodrug thereof, wherein $Y^3$ is absent;

(d) adding an oxidizing agent reagent to, optionally, the compound or derivative having formula (I-H), wherein $R^6$, $R^7$, and $R^8$ are each hydrogen, optionally, the phosphitylating reagent, optionally, the Brønsted acid or base, and the compound or derivative having formula (II), or salt, solvate, or prodrug thereof, wherein $Y^3$ is absent;

(e) processing the oxidizing agent reagent, optionally, the compound or derivative having formula (I-H), or salt, solvate, or prodrug thereof, wherein $R^6$, $R^7$, and $R^8$ are each hydrogen, optionally, the phosphitylating reagent, optionally, the Brønsted acid or base, and the compound or derivative having formula (II), or salt, solvate, or prodrug thereof, wherein $Y^3$ is absent, so as to produce the compound or derivative having formula (II), or salt, solvate, or prodrug thereof, wherein $Y^3$ is sulfur;

(f) adding, optionally, the oxidizing agent reagent, optionally, the compound or derivative having formula (I-H), or salt, solvate, or prodrug thereof, wherein $R^6$, $R^7$, and $R^8$ are each hydrogen, optionally, the phosphitylating reagent, optionally, the Brønsted acid or base, optionally, the compound or derivative having formula (II), or salt, solvate, or prodrug thereof, wherein $Y^3$ is absent, and the compound or derivative having formula (II), or salt, solvate, or prodrug thereof, wherein $Y^3$ is sulfur, to iced water;

optionally, (f1) adjusting the pH of the aqueous phase with an aqueous base;

(g) isolating the compound or derivative having formula (II), or salt, solvate, or prodrug thereof, wherein $Y^3$ is sulfur; and optionally, (g1) treating the compound or derivative having formula (II), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (II), or salt, solvate, or prodrug thereof, wherein $Y^3$ is sulfur, under almost solventless conditions.

The polar organic solvent co-reagent and isolation solvent employed in the above method of making a compound or derivative having formula (II), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (II), or a salt, solvate, or prodrug thereof, wherein $Y^3$ is sulfur, can include the steps of:

(a) providing a compound or derivative having formula (I-H), or a salt, solvate, or prodrug thereof, wherein $R^6$, $R^7$, and $R^8$ are each hydrogen;

(b) treating the compound or derivative having formula (I-H), or salt, solvate, or prodrug thereof, wherein $R^6$, $R^7$, and $R^8$ are each hydrogen, with a thiophosphorylating reagent;

optionally, (b1) treating the compound or derivative having formula (I-H), or salt, solvate, or prodrug thereof, wherein $R^6$, $R^7$, and $R^8$ are each hydrogen, and the thiophosphorylating reagent, with a (0<x≤20) molar equivalent amount of a Brønsted acid or base;

(c) processing the compound or derivative having formula (I-H), or salt, solvate, or prodrug thereof, wherein $R^6$, $R^7$, and $R^8$ are each hydrogen, the thiophosphorylating reagent, and, optionally, the Brønsted acid or base, so as to produce the compound or derivative having formula (II), or salt, solvate, or prodrug thereof, wherein $Y^3$ is sulfur;

(d) adding, optionally, the compound or derivative having formula (I-H), or salt, solvate, or prodrug thereof, wherein $R^6$, $R^7$, and $R^8$ are each hydrogen, optionally, the thiophosphorylating reagent, optionally, the Brønsted acid or base, and the compound or derivative having formula (II), or salt, solvate, or prodrug thereof, wherein $Y^3$ is sulfur, to iced water;

optionally, (d1) adjusting the pH of the aqueous phase with an aqueous base;

optionally, (d2) isolating the unreacted compound or derivative having formula (I-H), or salt, solvate, or prodrug thereof, wherein $R^6$, $R^7$, and $R^8$ are each hydrogen;

(e) isolating the compound or derivative having formula (II), or salt, solvate, or prodrug thereof, wherein $Y^3$ is sulfur; and optionally, (e1) treating the compound or derivative having formula (II), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (II), or salt, solvate, or prodrug thereof, wherein $Y^3$ is sulfur, under almost solventless conditions.

The polar organic solvent co-reagent and isolation solvent employed in the above method of making a compound or derivative having formula (II), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (IIa), or a salt, solvate, or prodrug thereof, wherein $Y^3$ is oxygen, can include the steps of:

(a) providing a compound or derivative having formula (Ia), or a salt, solvate, or prodrug thereof, wherein $R^6$ is hydrogen;

(b) treating the compound or derivative having formula (Ia), or salt, solvate, or prodrug thereof, wherein $R^6$ is hydrogen, with a phosphorylating reagent;

optionally, (b1) treating the compound or derivative having formula (Ia), or salt, solvate, or prodrug thereof, wherein $R^6$ is hydrogen, and the phosphorylating reagent, with a (0<x≤20) molar equivalent amount of a Brønsted acid or base;

(c) processing the compound or derivative having formula (Ia), or salt, solvate, or prodrug thereof, wherein $R^6$ is hydrogen, the phosphorylating reagent, and, optionally, the Brønsted acid or base, so as to produce the compound or derivative having formula (IIa), or salt, solvate, or prodrug thereof, wherein $Y^3$ is oxygen;

(d) adding, optionally, the compound or derivative having formula (Ia), or salt, solvate, or prodrug thereof, wherein $R^6$ is hydrogen, optionally, the phosphorylating reagent, optionally, the Brønsted acid or base, and the compound or derivative having formula (IIa), or salt, solvate, or prodrug thereof, wherein $Y^3$ is oxygen, to iced water;

optionally, (d1) adjusting the pH of the aqueous phase with an aqueous base;

optionally, (d2) isolating the unreacted compound or derivative having formula (Ta), or salt, solvate, or prodrug thereof, wherein $R^6$ is hydrogen;

(e) isolating the compound or derivative having formula (IIa), or salt, solvate, or prodrug thereof, wherein $Y^3$ is oxygen; and optionally, (e1) treating the compound or derivative having formula (IIa), or salt, solvate, or prodrug thereof, wherein $Y^3$ is oxygen, with deprotection agent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIa), or salt, solvate, or prodrug thereof, wherein $Y^3$ is oxygen, under almost solventless conditions.

The polar organic solvent co-reagent and isolation solvent employed in the above method of making a compound or derivative having formula (IIa), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of methanol and water in a 3:2 volume:volume ratio at room temperature;

(b) stirring the compound or derivative having formula (IIa), or salt, solvate, or prodrug thereof, wherein $Y^3$ is oxygen, and the volume of methanol and water so as to dissolve the compound or derivative having formula (IIa), or salt, solvate, or prodrug thereof, wherein $Y^3$ is oxygen, in the volume of methanol and water;

(c) filtering the solution of the compound or derivative having formula (IIa), or salt, solvate, or prodrug thereof, wherein $Y^3$ is oxygen, in the volume of methanol and water, so as to remove any undissolved solids;

(d) adding a volume of acetone to the solution of the compound or derivative having formula (IIa), or salt, solvate, or prodrug thereof, wherein $Y^3$ is oxygen, in the volume of methanol and water, wherein the volume of acetone is about 2 to about 5 times the combined volume of methanol and water;

(e) cooling the compound or derivative having formula (IIa), or salt, solvate, or prodrug thereof, wherein $Y^3$ is oxygen, the volume of acetone, and the volume of methanol and water at −20° C. so as to precipitate the crystalline form of the compound or derivative having formula (IIa), or salt, solvate, or prodrug thereof, wherein $Y^3$ is oxygen;

(f) filtering the crystalline form of the compound or derivative having formula (IIa), or salt, solvate, or prodrug thereof, wherein $Y^3$ is oxygen, the volume of acetone, and the volume of methanol and water so as to isolate the crystalline form of the compound or derivative having formula (IIa), or salt, solvate, or prodrug thereof, wherein $Y^3$ is oxygen; and (g) drying the crystalline form of the compound or derivative having formula (IIa), or salt, solvate, or prodrug thereof, wherein $Y^3$ is oxygen, at room temperature.

The process described herein effects a preparation of a crystalline form of a compound or derivative having formula (IIa), or salt, solvate, or prodrug thereof, wherein $Y^3$ is oxygen.

In a particular embodiment, an alternative method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of methanol and water in a 3:2 volume:volume ratio at room temperature;

(b) stirring the compound or derivative having formula (IIa), or salt, solvate, or prodrug thereof, wherein $Y^3$ is oxygen, and the volume of methanol and water so as to dissolve the compound or derivative having formula (IIa), or salt, solvate, or prodrug thereof, wherein $Y^3$ is oxygen, in the volume of methanol and water;

(c) filtering the solution of the compound or derivative having formula (IIa), or salt, solvate, or prodrug thereof, wherein $Y^3$ is oxygen, in the volume of methanol and water, so as to remove any undissolved solids;

(d) cooling the compound or derivative having formula (IIa), or salt, solvate, or prodrug thereof, wherein $Y^3$ is oxygen, and the volume of methanol and water at −20° C. so as to produce an oily layer at the bottom of the volume of methanol and water;

(e) decanting the volume of methanol and water from the oily layer at the bottom of the volume of methanol and water; and (f) drying the oily layer at room temperature so as to crystallize the crystalline form of the compound or derivative having formula (IIa), or salt, solvate, or prodrug thereof, wherein $Y^3$ is oxygen.

The process described herein effects a preparation of a crystalline form of a compound or derivative having formula (IIa), or salt, solvate, or prodrug thereof, wherein $Y^3$ is oxygen.

In a particular embodiment, another alternative method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of ethanol and water in a 3:2 volume:volume ratio at room temperature, wherein the compound or derivative having formula (IIa), or salt, solvate, or prodrug thereof, wherein $Y^3$ is oxygen, is added in an amount of about 200 milligrams per milliliter of the volume of ethanol and water;

(b) stirring the compound or derivative having formula (IIa), or salt, solvate, or prodrug thereof, wherein $Y^3$ is oxygen, and the volume of ethanol and water so as to dissolve the compound or derivative having formula (IIa), or salt, solvate, or prodrug thereof, wherein $Y^3$ is oxygen, in the volume of ethanol and water;

(c) filtering the solution of the compound or derivative having formula (IIa), or salt, solvate, or prodrug thereof, wherein $Y^3$ is oxygen, in the volume of ethanol and water, so as to remove any undissolved solids;

(d) cooling the compound or derivative having formula (IIa), or salt, solvate, or prodrug thereof, wherein $Y^3$ is oxygen, in the volume of ethanol and water, to $-10°$ C. for about 48 hours so as to produce the crystalline form of the compound or derivative having formula (IIa), or salt, solvate, or prodrug thereof, wherein $Y^3$ is oxygen;

(e) decanting the volume of ethanol and water from the crystalline form of the compound or derivative having formula (IIa), or salt, solvate, or prodrug thereof, wherein $Y^3$ is oxygen, so as to isolate the crystalline form of the compound or derivative having formula (IIa), or salt, solvate, or prodrug thereof, wherein $Y^3$ is oxygen; and (f) drying the crystalline form of the compound or derivative having formula (IIa), or salt, solvate, or prodrug thereof, wherein $Y^3$ is oxygen, at room temperature.

The process described herein effects a preparation of a crystalline form of a compound or derivative having formula (IIa), or salt, solvate, or prodrug thereof, wherein $Y^3$ is oxygen.

In another embodiment, a method of making a compound or derivative having formula (IIa), or a salt, solvate, or prodrug thereof, wherein $Y^3$ is oxygen, can include the steps of:

(a) providing a compound or derivative having formula (Ia), or a salt, solvate, or prodrug thereof, wherein $R^6$ is hydrogen;

(b) treating the compound or derivative having formula (Ia), or salt, solvate, or prodrug thereof, wherein $R^6$ is hydrogen, with a phosphitylating reagent;

optionally, (b1) treating the compound or derivative having formula (Ia), or salt, solvate, or prodrug thereof, wherein $R^6$ is hydrogen, and the phosphitylating reagent, with a (0<x≤20) molar equivalent amount of a Brønsted acid or base;

(c) processing the compound or derivative having formula (Ia), or salt, solvate, or prodrug thereof, wherein $R^6$ is hydrogen, the phosphitylating reagent, and, optionally, the Brønsted acid or base so as to produce a compound or derivative having formula (IIa), or salt, solvate, or prodrug thereof, wherein $Y^3$ is absent;

(d) adding an oxidizing agent reagent to, optionally, the compound or derivative having formula (Ia), or salt, solvate, or prodrug thereof, wherein $R^6$ is hydrogen, optionally, the phosphitylating reagent, optionally, the Brønsted acid or base, and the compound or derivative having formula (IIa), or salt, solvate, or prodrug thereof, wherein $Y^3$ is absent;

(e) processing the oxidizing agent reagent, optionally, the compound or derivative having formula (Ia), or salt, solvate, or prodrug thereof, wherein $R^6$ is hydrogen, optionally, the phosphitylating reagent, optionally, the Brønsted acid or base, and the compound or derivative having formula (IIa), or salt, solvate, or prodrug thereof, wherein $Y^3$ is absent, so as to produce the compound or derivative having formula (IIa), or salt, solvate, or prodrug thereof, wherein $Y^3$ is oxygen;

(f) adding, optionally, the oxidizing agent reagent, optionally, the compound or derivative having formula (Ia), or salt, solvate, or prodrug thereof, wherein $R^6$ is hydrogen, optionally, the phosphitylating reagent, optionally, the Brønsted acid or base, optionally, the compound or derivative having formula (IIa), or salt, solvate, or prodrug thereof, wherein $Y^3$ is absent, and the compound or derivative having formula (IIa), or salt, solvate, or prodrug thereof, wherein $Y^3$ is oxygen, to iced water;

optionally, (f1) adjusting the pH of the aqueous phase with an aqueous base;

(g) isolating the compound or derivative having formula (IIa), or salt, solvate, or prodrug thereof, wherein $Y^3$ is oxygen; and optionally, (g1) treating the compound or derivative having formula (IIa), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIa), or salt, solvate, or prodrug thereof, wherein $Y^3$ is oxygen, under almost solventless conditions.

The polar organic solvent co-reagent and isolation solvent employed in the above method of making a compound or derivative having formula (IIa), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of methanol and water in a 3:2 volume:volume ratio at room temperature;

(b) stirring the compound or derivative having formula (IIa), or salt, solvate, or prodrug thereof, wherein $Y^3$ is oxygen, and the volume of methanol and water so as to dissolve the compound or derivative having formula (IIa), or salt, solvate, or prodrug thereof, wherein $Y^3$ is oxygen, in the volume of methanol and water;

(c) filtering the solution of the compound or derivative having formula (IIa), or salt, solvate, or prodrug thereof, wherein $Y^3$ is oxygen, in the volume of methanol and water, so as to remove any undissolved solids;

(d) adding a volume of acetone to the solution of the compound or derivative having formula (IIa), or salt, solvate, or prodrug thereof, wherein $Y^3$ is oxygen, in the volume of methanol and water, wherein the volume of acetone is about 2 to about 5 times the combined volume of methanol and water;

(e) cooling the compound or derivative having formula (IIa), or salt, solvate, or prodrug thereof, wherein $Y^3$ is oxygen, the volume of acetone, and the volume of methanol and water at $-20°$ C. so as to precipitate the crystalline form of the compound or derivative having formula (IIa), or salt, solvate, or prodrug thereof, wherein $Y^3$ is oxygen;

(f) filtering the crystalline form of the compound or derivative having formula (IIa), or salt, solvate, or prodrug thereof, wherein $Y^3$ is oxygen, the volume of acetone, and the volume of methanol and water so as to isolate the crystalline form of the compound or derivative having formula (IIa), or salt, solvate, or prodrug thereof, wherein $Y^3$ is oxygen; and (g) drying the crystalline form of the compound or derivative having formula (IIa), or salt, solvate, or prodrug thereof, wherein $Y^3$ is oxygen, at room temperature.

The process described herein effects a preparation of a crystalline form of a compound or derivative having formula (IIa), or salt, solvate, or prodrug thereof, wherein $Y^3$ is oxygen.

In a particular embodiment, an alternative method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of methanol and water in a 3:2 volume:volume ratio at room temperature;

(b) stirring the compound or derivative having formula (IIa), or salt, solvate, or prodrug thereof, wherein $Y^3$ is oxygen, and the volume of methanol and water so as to dissolve the compound or derivative having formula (IIa), or salt, solvate, or prodrug thereof, wherein $Y^3$ is oxygen, in the volume of methanol and water;

(c) filtering the solution of the compound or derivative having formula (IIa), or salt, solvate, or prodrug thereof, wherein $Y^3$ is oxygen, in the volume of methanol and water, so as to remove any undissolved solids;

(d) cooling the compound or derivative having formula (IIa), or salt, solvate, or prodrug thereof, wherein $Y^3$ is oxygen, and the volume of methanol and water at −20° C. so as to produce an oily layer at the bottom of the volume of methanol and water;

(e) decanting the volume of methanol and water from the oily layer at the bottom of the volume of methanol and water; and (f) drying the oily layer at room temperature so as to crystallize the crystalline form of the compound or derivative having formula (IIa), or salt, solvate, or prodrug thereof, wherein $Y^3$ is oxygen.

The process described herein effects a preparation of a crystalline form of a compound or derivative having formula (IIa), or salt, solvate, or prodrug thereof, wherein $Y^3$ is oxygen.

In a particular embodiment, another alternative method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of ethanol and water in a 3:2 volume:volume ratio at room temperature, wherein the compound or derivative having formula (IIa), or salt, solvate, or prodrug thereof, wherein $Y^3$ is oxygen, is added in an amount of about 200 milligrams per milliliter of the volume of ethanol and water;

(b) stirring the compound or derivative having formula (IIa), or salt, solvate, or prodrug thereof, wherein $Y^3$ is oxygen, and the volume of ethanol and water so as to dissolve the compound or derivative having formula (IIa), or salt, solvate, or prodrug thereof, wherein $Y^3$ is oxygen, in the volume of ethanol and water;

(c) filtering the solution of the compound or derivative having formula (IIa), or salt, solvate, or prodrug thereof, wherein $Y^3$ is oxygen, in the volume of ethanol and water, so as to remove any undissolved solids;

(d) cooling the compound or derivative having formula (IIa), or salt, solvate, or prodrug thereof, wherein $Y^3$ is oxygen, in the volume of ethanol and water, to −10° C. for about 48 hours so as to produce the crystalline form of the compound or derivative having formula (IIa), or salt, solvate, or prodrug thereof, wherein $Y^3$ is oxygen;

(e) decanting the volume of ethanol and water from the crystalline form of the compound or derivative having formula (IIa), or salt, solvate, or prodrug thereof, wherein $Y^3$ is oxygen, so as to isolate the crystalline form of the compound or derivative having formula (IIa), or salt, solvate, or prodrug thereof, wherein $Y^3$ is oxygen; and (f) drying the crystalline form of the compound or derivative having formula (IIa), or salt, solvate, or prodrug thereof, wherein $Y^3$ is oxygen, at room temperature.

The process described herein effects a preparation of a crystalline form of a compound or derivative having formula (IIa), or salt, solvate, or prodrug thereof, wherein $Y^3$ is oxygen.

In yet another embodiment, a method of making a compound or derivative having formula (IIa), or a salt, solvate, or prodrug thereof, wherein $Y^3$ is absent, can include the steps of:

(a) providing a compound or derivative having formula (Ia), or a salt, solvate, or prodrug thereof, wherein $R^6$ is hydrogen;

(b) treating the compound or derivative having formula (Ia), or salt, solvate, or prodrug thereof, wherein $R^6$ is hydrogen, with a phosphitylating reagent;

optionally, (b1) treating the compound or derivative having formula (Ia), or salt, solvate, or prodrug thereof, wherein $R^6$ is hydrogen, and the phosphitylating reagent, with a (0<x≤20) molar equivalent amount of a Brønsted acid or base;

(c) processing the compound or derivative having formula (Ia), or salt, solvate, or prodrug thereof, wherein $R^6$ is hydrogen, the phosphitylating reagent, and, optionally, the Brønsted acid or base so as to produce the compound or derivative having formula (IIa), or salt, solvate, or prodrug thereof, wherein $Y^3$ is absent;

(d) adding, optionally, the compound or derivative having formula (Ia), or salt, solvate, or prodrug thereof, wherein $R^6$ is hydrogen, optionally, the phosphitylating reagent, optionally, the Brønsted acid or base, and the compound or derivative having formula (IIa), or salt, solvate, or prodrug thereof, wherein $Y^3$ is absent, to iced water;

optionally, (d1) adjusting the pH of the aqueous phase with an aqueous base;

(e) isolating the compound or derivative having formula (IIa), or salt, solvate, or prodrug thereof, wherein $Y^3$ is absent; and optionally, (e1) treating the compound or derivative having formula (IIa), or salt, solvate, or prodrug thereof, wherein $Y^3$ is absent, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIa), or salt, solvate, or prodrug thereof, wherein $Y^3$ is absent, under almost solventless conditions.

The polar organic solvent co-reagent and isolation solvent employed in the above method of making a compound or derivative having formula (IIa), or salt, solvate, or prodrug thereof, wherein $Y^3$ is absent, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (IIa), or a salt, solvate, or prodrug thereof, wherein $Y^3$ is sulfur, can include the steps of:

(a) providing a compound or derivative having formula (Ia), or a salt, solvate, or prodrug thereof, wherein $R^6$ is hydrogen;

(b) treating the compound or derivative having formula (Ia), or salt, solvate, or prodrug thereof, wherein $R^6$ is hydrogen, with a phosphitylating reagent;

optionally, (b1) treating the compound or derivative having formula (Ia), or salt, solvate, or prodrug thereof, wherein $R^6$ is hydrogen, and the phosphitylating reagent, with a (0<x≤20) molar equivalent amount of a Brønsted acid or base;

(c) processing the compound or derivative having formula (Ia), or salt, solvate, or prodrug thereof, wherein $R^6$ is hydrogen, the phosphitylating reagent, and, optionally, the Brønsted acid or base so as to produce a compound or derivative having formula (IIa), or a salt, solvate, or prodrug thereof, wherein $Y^3$ is absent;

(d) adding an oxidizing agent reagent to, optionally, the compound or derivative having formula (Ia), or salt, solvate, or prodrug thereof, wherein $R^6$ is hydrogen, optionally, the phosphitylating reagent, optionally, the Brønsted acid or base, and the compound or derivative having formula (IIa), or salt, solvate, or prodrug thereof, wherein $Y^3$ is absent;

(e) processing the oxidizing agent reagent, optionally, the compound or derivative having formula (Ia), or salt, solvate, or prodrug thereof, wherein $R^6$ is hydrogen, optionally, the phosphitylating reagent, optionally, the Brønsted acid or base, and the compound or derivative having formula (IIa), or salt, solvate, or prodrug thereof, wherein $Y^3$ is absent, so as to produce the compound or derivative having formula (IIa), or salt, solvate, or prodrug thereof, wherein $Y^3$ is sulfur;

(f) adding, optionally, the oxidizing agent reagent, optionally, the compound or derivative having formula (Ia), or salt, solvate, or prodrug thereof, wherein $R^6$ is hydrogen, optionally, the phosphitylating reagent, optionally, the Brønsted acid or base, optionally, the compound or derivative having formula (IIa), or salt, solvate, or prodrug thereof, wherein $Y^3$ is absent, and the compound or derivative having formula (IIa), or salt, solvate, or prodrug thereof, wherein $Y^3$ is sulfur, to iced water;

optionally, (f1) adjusting the pH of the aqueous phase with an aqueous base;

(g) isolating the compound or derivative having formula (IIa), or salt, solvate, or prodrug thereof, wherein $Y^3$ is sulfur; and optionally, (g1) treating the compound or derivative having formula (IIa), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIa), or salt, solvate, or prodrug thereof, wherein $Y^3$ is sulfur, under almost solventless conditions.

The polar organic solvent co-reagent and isolation solvent employed in the above method of making a compound or derivative having formula (IIa), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (IIa), or a salt, solvate, or prodrug thereof, wherein $Y^3$ is sulfur, can include the steps of:

(a) providing a compound or derivative having formula (Ia), or a salt, solvate, or prodrug thereof, wherein $R^6$ is hydrogen;

(b) treating the compound or derivative having formula (Ia), or salt, solvate, or prodrug thereof, wherein $R^6$ is hydrogen, with a thiophosphorylating reagent;

optionally, (b1) treating the compound or derivative having formula (Ia), or salt, solvate, or prodrug thereof, wherein $R^6$ is hydrogen, and the thiophosphorylating reagent, with a (0<x≤20) molar equivalent amount of a Brønsted acid or base;

(c) processing the compound or derivative having formula (Ia), or salt, solvate, or prodrug thereof, wherein $R^6$ is hydrogen, the thiophosphorylating reagent, and, optionally, the Brønsted acid or base, so as to produce the compound or derivative having formula (IIa), or salt, solvate, or prodrug thereof, wherein $Y^3$ is sulfur;

(d) adding, optionally, the compound or derivative having formula (Ia), or salt, solvate, or prodrug thereof, wherein $R^6$ is hydrogen, optionally, the thiophosphorylating reagent, optionally, the Brønsted acid or base, and the compound or derivative having formula (IIa), or salt, solvate, or prodrug thereof, wherein $Y^3$ is sulfur, to iced water;

optionally, (d1) adjusting the pH of the aqueous phase with an aqueous base;

optionally, (d2) isolating the unreacted compound or derivative having formula (Ia), or salt, solvate, or prodrug thereof, wherein $R^6$ is hydrogen;

(e) isolating the compound or derivative having formula (IIa), or salt, solvate, or prodrug thereof, wherein $Y^3$ is sulfur; and optionally, (e1) treating the compound or derivative having formula (IIa), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIa), or salt, solvate, or prodrug thereof, wherein $Y^3$ is sulfur, under almost solventless conditions.

The polar organic solvent co-reagent and isolation solvent employed in the above method of making a compound or derivative having formula (IIa), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (IIa), or a salt, solvate, or prodrug thereof, wherein $Y^3$ is oxygen, can include the steps of:

(a) providing a compound or derivative having formula (Ia-H), or a salt, solvate, or prodrug thereof, wherein $R^6$, $R^7$, and $R^8$ are each hydrogen;

(b) treating the compound or derivative having formula (Ia-H), or salt, solvate, or prodrug thereof, wherein $R^6$, $R^7$, and $R^8$ are each hydrogen, with a phosphorylating reagent;

optionally, (b1) treating the compound or derivative having formula (Ia-H), or salt, solvate, or prodrug thereof, wherein $R^6$, $R^7$, and $R^8$ are each hydrogen, and the phosphorylating reagent, with a (0<x≤20) molar equivalent amount of a Brønsted acid or base;

(c) processing the compound or derivative having formula (Ia-H), or salt, solvate, or prodrug thereof, wherein $R^6$, $R^7$, and $R^8$ are each hydrogen, the phosphorylating reagent, and, optionally, the Brønsted acid or base, so as to produce the compound or derivative having formula (IIa), or salt, solvate, or prodrug thereof, wherein $Y^3$ is oxygen;

(d) adding, optionally, the compound or derivative having formula (Ia-H), or salt, solvate, or prodrug thereof, wherein $R^6$, $R^7$, and $R^8$ are each hydrogen, optionally, the phosphorylating reagent, optionally, the Brønsted acid or base, and the compound or derivative having formula (IIa), or salt, solvate, or prodrug thereof, wherein $Y^3$ is oxygen, to iced water;

optionally, (d1) adjusting the pH of the aqueous phase with an aqueous base;

optionally, (d2) isolating the unreacted compound or derivative having formula (Ia-H), or salt, solvate, or prodrug thereof, wherein $R^6$, $R^7$, and $R^8$ are each hydrogen;

(e) isolating the compound or derivative having formula (IIa), or salt, solvate, or prodrug thereof, wherein $Y^3$ is oxygen; and optionally, (e1) treating the compound or derivative having formula (IIa), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIa), or salt, solvate, or prodrug thereof, wherein $Y^3$ is oxygen, under almost solventless conditions.

The polar organic solvent co-reagent and isolation solvent employed in the above method of making a compound or derivative having formula (IIa), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of methanol and water in a 3:2 volume:volume ratio at room temperature;

(b) stirring the compound or derivative having formula (IIa), or salt, solvate, or prodrug thereof, wherein $Y^3$ is oxygen, and the volume of methanol and water so as to dissolve the compound or derivative having formula (IIa), or salt, solvate, or prodrug thereof, wherein $Y^3$ is oxygen, in the volume of methanol and water;

(c) filtering the solution of the compound or derivative having formula (IIa), or salt, solvate, or prodrug thereof, wherein $Y^3$ is oxygen, in the volume of methanol and water, so as to remove any undissolved solids;

(d) adding a volume of acetone to the solution of the compound or derivative having formula (IIa), or salt, solvate, or prodrug thereof, wherein $Y^3$ is oxygen, in the volume of methanol and water, wherein the volume of acetone is about 2 to about 5 times the combined volume of methanol and water;

(e) cooling the compound or derivative having formula (IIa), or salt, solvate, or prodrug thereof, wherein $Y^3$ is oxygen, the volume of acetone, and the volume of methanol and water at −20° C. so as to precipitate the crystalline form of the compound or derivative having formula (IIa), or salt, solvate, or prodrug thereof, wherein $Y^3$ is oxygen;

(f) filtering the crystalline form of the compound or derivative having formula (IIa), or salt, solvate, or prodrug thereof, wherein $Y^3$ is oxygen, the volume of acetone, and the volume of methanol and water so as to isolate the crystalline form of the compound or derivative having formula (IIa), or salt, solvate, or prodrug thereof, wherein $Y^3$ is oxygen; and (g) drying the crystalline form of the compound or derivative having formula (IIa), or salt, solvate, or prodrug thereof, wherein $Y^3$ is oxygen, at room temperature.

The process described herein effects a preparation of a crystalline form of a compound or derivative having formula (IIa), or salt, solvate, or prodrug thereof, wherein $Y^3$ is oxygen.

In a particular embodiment, an alternative method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of methanol and water in a 3:2 volume:volume ratio at room temperature;

(b) stirring the compound or derivative having formula (IIa), or salt, solvate, or prodrug thereof, wherein $Y^3$ is oxygen, and the volume of methanol and water so as to dissolve the compound or derivative having formula (IIa), or salt, solvate, or prodrug thereof, wherein $Y^3$ is oxygen, in the volume of methanol and water;

(c) filtering the solution of the compound or derivative having formula (IIa), or salt, solvate, or prodrug thereof, wherein $Y^3$ is oxygen, in the volume of methanol and water, so as to remove any undissolved solids;

(d) cooling the compound or derivative having formula (IIa), or salt, solvate, or prodrug thereof, wherein $Y^3$ is oxygen, and the volume of methanol and water at −20° C. so as to produce an oily layer at the bottom of the volume of methanol and water;

(e) decanting the volume of methanol and water from the oily layer at the bottom of the volume of methanol and water; and (f) drying the oily layer at room temperature so as to crystallize the crystalline form of the compound or derivative having formula (IIa), or salt, solvate, or prodrug thereof, wherein $Y^3$ is oxygen.

The process described herein effects a preparation of a crystalline form of a compound or derivative having formula (IIa), or salt, solvate, or prodrug thereof, wherein $Y^3$ is oxygen.

In a particular embodiment, another alternative method of making a crystalline form of the compound or derivative having formula (IIa), or salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of ethanol and water in a 3:2 volume:volume ratio at room temperature, wherein the compound or derivative having formula (IIa), or salt, solvate, or prodrug thereof, wherein $Y^3$ is oxygen, is added in an amount of about 200 milligrams per milliliter of the volume of ethanol and water;

(b) stirring the compound or derivative having formula (IIa), or salt, solvate, or prodrug thereof, wherein $Y^3$ is oxygen, and the volume of ethanol and water so as to dissolve the compound or derivative having formula (IIa), or salt, solvate, or prodrug thereof, wherein $Y^3$ is oxygen, in the volume of ethanol and water;

(c) filtering the solution of the compound or derivative having formula (IIa), or salt, solvate, or prodrug thereof, wherein $Y^3$ is oxygen, in the volume of ethanol and water, so as to remove any undissolved solids;

(d) cooling the compound or derivative having formula (IIa), or salt, solvate, or prodrug thereof, wherein $Y^3$ is oxygen, in the volume of ethanol and water, to −10° C. for about 48 hours so as to produce the crystalline form of the compound or derivative having formula (IIa), or salt, solvate, or prodrug thereof, wherein $Y^3$ is oxygen;

(e) decanting the volume of ethanol and water from the crystalline form of the compound or derivative having formula (IIa), or salt, solvate, or prodrug thereof, wherein $Y^3$ is oxygen, so as to isolate the crystalline form of the compound or derivative having formula (IIa), or salt, solvate, or prodrug thereof, wherein $Y^3$ is oxygen; and (f) drying the crystalline form of the compound or derivative having formula (IIa), or salt, solvate, or prodrug thereof, wherein $Y^3$ is oxygen, at room temperature.

The process described herein effects a preparation of a crystalline form of a compound or derivative having formula (IIa), or salt, solvate, or prodrug thereof, wherein $Y^3$ is oxygen.

In yet another embodiment, a method of making a compound or derivative having formula (IIa), or a salt, solvate, or prodrug thereof, wherein $Y^3$ is oxygen, can include the steps of:

(a) providing a compound or derivative having formula (Ia-H), or a salt, solvate, or prodrug thereof, wherein $R^6$, $R^7$, and $R^8$ are each hydrogen;

(b) treating the compound or derivative having formula (Ia-H), or salt, solvate, or prodrug thereof, wherein $R^6$, $R^7$, and $R^8$ are each hydrogen, with a phosphitylating reagent;

optionally, (b1) treating the compound or derivative having formula (Ia-H), or salt, solvate, or prodrug thereof, wherein $R^6$, $R^7$, and $R^8$ are each hydrogen, and the phosphitylating reagent, with a ($0<x\leq20$) molar equivalent amount of a Brønsted acid or base;

(c) processing the compound or derivative having formula (Ia-H), or salt, solvate, or prodrug thereof, wherein $R^6$, $R^7$, and $R^8$ are each hydrogen, the phosphitylating reagent, and, optionally, the Brønsted acid or base so as to produce a compound or derivative having formula (IIa), or salt, solvate, or prodrug thereof, wherein $Y^3$ is absent;

(d) adding an oxidizing agent reagent to, optionally, the compound or derivative having formula (Ia-H), or salt, solvate, or prodrug thereof, wherein $R^6$, $R^7$, and $R^8$ are each hydrogen, optionally, the phosphitylating reagent, optionally, the Brønsted acid or base, and the compound or derivative having formula (IIa), or salt, solvate, or prodrug thereof, wherein $Y^3$ is absent;

(e) processing the oxidizing agent reagent, optionally, the compound or derivative having formula (Ia-H), or salt, solvate, or prodrug thereof, wherein $R^6$, $R^7$, and $R^8$ are each hydrogen, optionally, the phosphitylating reagent, optionally, the Brønsted acid or base, and the compound or derivative having formula (IIa), or salt, solvate, or prodrug thereof, wherein $Y^3$ is absent, so as to produce the compound or derivative having formula (IIa), or salt, solvate, or prodrug thereof, wherein $Y^3$ is oxygen;

(f) adding, optionally, the oxidizing agent reagent, optionally, the compound or derivative having formula (Ia-H), or salt, solvate, or prodrug thereof, wherein $R^6$, $R^7$, and $R^8$ are each hydrogen, optionally, the phosphitylating reagent, optionally, the Brønsted acid or base, optionally, the compound or derivative having formula (IIa), or salt, solvate, or prodrug thereof, wherein $Y^3$ is absent, and the compound or derivative having formula (IIa), or salt, solvate, or prodrug thereof, wherein $Y^3$ is oxygen, to iced water;

optionally, (f1) adjusting the pH of the aqueous phase with an aqueous base;

(g) isolating the compound or derivative having formula (IIa), or salt, solvate, or prodrug thereof, wherein $Y^3$ is oxygen; and optionally, (g1) treating the compound or derivative having formula (IIa), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIa), or salt, solvate, or prodrug thereof, wherein $Y^3$ is oxygen, under almost solventless conditions.

The polar organic solvent co-reagent and isolation solvent employed in the above method of making a compound or derivative having formula (IIa), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In a particular embodiment, a method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of methanol and water in a 3:2 volume:volume ratio at room temperature;

(b) stirring the compound or derivative having formula (IIa), or salt, solvate, or prodrug thereof, wherein $Y^3$ is oxygen, and the volume of methanol and water so as to dissolve the compound or derivative having formula (IIa), or salt, solvate, or prodrug thereof, wherein $Y^3$ is oxygen, in the volume of methanol and water;

(c) filtering the solution of the compound or derivative having formula (IIa), or salt, solvate, or prodrug thereof, wherein $Y^3$ is oxygen, in the volume of methanol and water, so as to remove any undissolved solids;

(d) adding a volume of acetone to the solution of the compound or derivative having formula (IIa), or salt, solvate, or prodrug thereof, wherein $Y^3$ is oxygen, in the volume of methanol and water, wherein the volume of acetone is about 2 to about 5 times the combined volume of methanol and water;

(e) cooling the compound or derivative having formula (IIa), or salt, solvate, or prodrug thereof, wherein $Y^3$ is oxygen, the volume of acetone, and the volume of methanol and water at −20° C. so as to precipitate the crystalline form of the compound or derivative having formula (IIa), or salt, solvate, or prodrug thereof, wherein $Y^3$ is oxygen;

(f) filtering the crystalline form of the compound or derivative having formula (IIa), or salt, solvate, or prodrug thereof, wherein $Y^3$ is oxygen, the volume of acetone, and the volume of methanol and water so as to isolate the crystalline form of the compound or derivative having formula (IIa), or salt, solvate, or prodrug thereof, wherein $Y^3$ is oxygen; and (g) drying the crystalline form of the compound or derivative having formula (IIa), or salt, solvate, or prodrug thereof, wherein $Y^3$ is oxygen, at room temperature.

The process described herein effects a preparation of a crystalline form of a compound or derivative having formula (IIa), or salt, solvate, or prodrug thereof, wherein $Y^3$ is oxygen.

In a particular embodiment, an alternative method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of methanol and water in a 3:2 volume:volume ratio at room temperature;

(b) stirring the compound or derivative having formula (IIa), or salt, solvate, or prodrug thereof, wherein $Y^3$ is oxygen, and the volume of methanol and water so as to dissolve the compound or derivative having formula (IIa), or salt, solvate, or prodrug thereof, wherein $Y^3$ is oxygen, in the volume of methanol and water;

(c) filtering the solution of the compound or derivative having formula (IIa), or salt, solvate, or prodrug thereof, wherein $Y^3$ is oxygen, in the volume of methanol and water, so as to remove any undissolved solids;

(d) cooling the compound or derivative having formula (IIa), or salt, solvate, or prodrug thereof, wherein $Y^3$ is oxygen, and the volume of methanol and water at −20° C. so as to produce an oily layer at the bottom of the volume of methanol and water;

(e) decanting the volume of methanol and water from the oily layer at the bottom of the volume of methanol and water; and (f) drying the oily layer at room temperature so as to crystallize the crystalline form of the compound or derivative having formula (IIa), or salt, solvate, or prodrug thereof, wherein $Y^3$ is oxygen.

The process described herein effects a preparation of a crystalline form of a compound or derivative having formula (IIa), or salt, solvate, or prodrug thereof, wherein $Y^3$ is oxygen.

In a particular embodiment, another alternative method of making a crystalline form of the compound or derivative having formula (IIa), or a salt, solvate, or prodrug thereof, wherein $Y^3$ is oxygen, can include the steps of:

(a) adding the compound or derivative having formula (IIa), or salt, solvate, or prodrug thereof, wherein $Y^3$ is oxygen, to a volume of ethanol and water in a 3:2 volume:volume ratio at room temperature, wherein the compound or derivative having formula (IIa), or salt, solvate, or prodrug thereof, wherein $Y^3$ is oxygen, is added in an amount of about 200 milligrams per milliliter of the volume of ethanol and water;

(b) stirring the compound or derivative having formula (IIa), or salt, solvate, or prodrug thereof, wherein $Y^3$ is oxygen, and the volume of ethanol and water so as to dissolve the compound or derivative having formula (IIa), or salt, solvate, or prodrug thereof, wherein $Y^3$ is oxygen, in the volume of ethanol and water;

(c) filtering the solution of the compound or derivative having formula (IIa), or salt, solvate, or prodrug thereof, wherein $Y^3$ is oxygen, in the volume of ethanol and water, so as to remove any undissolved solids;

(d) cooling the compound or derivative having formula (IIa), or salt, solvate, or prodrug thereof, wherein $Y^3$ is oxygen, in the volume of ethanol and water, to −10° C. for about 48 hours so as to produce the crystalline form of the compound or derivative having formula (IIa), or salt, solvate, or prodrug thereof, wherein $Y^3$ is oxygen;

(e) decanting the volume of ethanol and water from the crystalline form of the compound or derivative having formula (IIa), or salt, solvate, or prodrug thereof, wherein $Y^3$ is oxygen, so as to isolate the crystalline form of the compound or derivative having formula (IIa), or salt, solvate, or prodrug thereof, wherein $Y^3$ is oxygen; and (f) drying the crystalline form of the compound or derivative having formula (IIa), or salt, solvate, or prodrug thereof, wherein $Y^3$ is oxygen, at room temperature.

The process described herein effects a preparation of a crystalline form of a compound or derivative having formula (IIa), or salt, solvate, or prodrug thereof, wherein $Y^3$ is oxygen.

In yet another embodiment, a method of making a compound or derivative having formula (IIa), or a salt, solvate, or prodrug thereof, wherein $Y^3$ is absent, can include the steps of:

(a) providing a compound or derivative having formula (Ia-H), or a salt, solvate, or prodrug thereof, wherein $R^6$, $R^7$, and $R^8$ are each hydrogen;

(b) treating the compound or derivative having formula (Ia-H), or salt, solvate, or prodrug thereof, wherein $R^6$, $R^7$, and $R^8$ are each hydrogen, with a phosphitylating reagent;

optionally, (b1) treating the compound or derivative having formula (Ia-H), or salt, solvate, or prodrug thereof, wherein $R^6$, $R^7$, and $R^8$ are each hydrogen, and the phosphitylating reagent, with a (0<x≤20) molar equivalent amount of a Brønsted acid or base;

(c) processing the compound or derivative having formula (Ia-H), or salt, solvate, or prodrug thereof, wherein $R^6$, $R^7$, and $R^8$ are each hydrogen, the phosphitylating reagent, and, optionally, the Brønsted acid or base so as to produce the compound or derivative having formula (IIa), or salt, solvate, or prodrug thereof, wherein $Y^3$ is absent;

(d) adding, optionally, the compound or derivative having formula (Ia-H), or salt, solvate, or prodrug thereof, wherein $R^6$, $R^7$, and $R^8$ are each hydrogen, optionally, the phosphitylating reagent, optionally, the Brønsted acid or base, and the compound or derivative having formula (IIa), or salt, solvate, or prodrug thereof, wherein $Y^3$ is absent, to iced water;

optionally, (d1) adjusting the pH of the aqueous phase with an aqueous base;

(e) isolating the compound or derivative having formula (IIa), or salt, solvate, or prodrug thereof, wherein $Y^3$ is absent; and optionally, (e1) treating the compound or derivative having formula (IIa), or salt, solvate, or prodrug thereof, wherein $Y^3$ is absent, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIa), or salt, solvate, or prodrug thereof, wherein $Y^3$ is absent, under almost solventless conditions.

The polar organic solvent co-reagent and isolation solvent employed in the above method of making a compound or derivative having formula (IIa), or salt, solvate, or prodrug thereof, wherein $Y^3$ is absent, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (IIa), or a salt, solvate, or prodrug thereof, wherein $Y^3$ is sulfur, can include the steps of:

(a) providing a compound or derivative having formula (Ia-H), or a salt, solvate, or prodrug thereof, wherein $R^6$, $R^7$, and $R^8$ are each hydrogen;

(b) treating the compound or derivative having formula (Ia-H), or salt, solvate, or prodrug thereof, wherein $R^6$, $R^7$, and $R^8$ are each hydrogen, with a phosphitylating reagent;

optionally, (b1) treating the compound or derivative having formula (Ia-H), or salt, solvate, or prodrug thereof, wherein $R^6$, $R^7$, and $R^8$ are each hydrogen, and the phosphitylating reagent, with a (0<x≤20) molar equivalent amount of a Brønsted acid or base;

(c) processing the compound or derivative having formula (Ia-H), or salt, solvate, or prodrug thereof, wherein $R^6$, $R^7$, and $R^8$ are each hydrogen, the phosphitylating reagent, and, optionally, the Brønsted acid or base so as to produce a compound or derivative having formula (IIa), or a salt, solvate, or prodrug thereof, wherein $Y^3$ is absent;

(d) adding an oxidizing agent reagent to, optionally, the compound or derivative having formula (Ia-H), wherein $R^6$, $R^7$, and $R^8$ are each hydrogen, optionally, the phosphitylating reagent, optionally, the Brønsted acid or base, and the compound or derivative having formula (IIa), or salt, solvate, or prodrug thereof, wherein $Y^3$ is absent;

(e) processing the oxidizing agent reagent, optionally, the compound or derivative having formula (Ia-H), or salt, solvate, or prodrug thereof, wherein $R^6$, $R^7$, and $R^8$ are each hydrogen, optionally, the phosphitylating reagent, optionally, the Brønsted acid or base, and the compound or derivative having formula (IIa), or salt, solvate, or prodrug thereof, wherein $Y^3$ is absent, so as to produce the compound or derivative having formula (IIa), or salt, solvate, or prodrug thereof, wherein $Y^3$ is sulfur;

(f) adding, optionally, the oxidizing agent reagent, optionally, the compound or derivative having formula (Ia-H), or salt, solvate, or prodrug thereof, wherein $R^6$, $R^7$, and $R^8$ are each hydrogen, optionally, the phosphitylating reagent, optionally, the Brønsted acid or base, optionally, the compound or derivative having formula (IIa), or salt, solvate, or prodrug thereof, wherein $Y^3$ is absent, and the compound or derivative having formula (IIa), or salt, solvate, or prodrug thereof, wherein $Y^3$ is sulfur, to iced water;

optionally, (f1) adjusting the pH of the aqueous phase with an aqueous base;

(g) isolating the compound or derivative having formula (IIa), or salt, solvate, or prodrug thereof, wherein $Y^3$ is sulfur; and optionally, (g1) treating the compound or derivative having formula (IIa), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIa), or salt, solvate, or prodrug thereof, wherein $Y^3$ is sulfur, under almost solventless conditions.

The polar organic solvent co-reagent and isolation solvent employed in the above method of making a compound or derivative having formula (IIa), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (IIa), or salt, solvate, or prodrug thereof, wherein $Y^3$ is sulfur, can include the steps of:

(a) providing a compound or derivative having formula (Ia-H), or a salt, solvate, or prodrug thereof, wherein $R^6$, $R^7$, and $R^8$ are each hydrogen;

(b) treating the compound or derivative having formula (Ia-H), or salt, solvate, or prodrug thereof, wherein $R^6$, $R^7$, and $R^8$ are each hydrogen, with a thiophosphorylating reagent;

optionally, (b1) treating the compound or derivative having formula (Ia-H), or salt, solvate, or prodrug thereof, wherein $R^6$, $R^7$, and $R^8$ are each hydrogen, and the thiophosphorylating reagent, with a (0<x≤20) molar equivalent amount of a Brønsted acid or base;

(c) processing the compound or derivative having formula (Ia-H), or salt, solvate, or prodrug thereof, wherein $R^6$, $R^7$, and $R^8$ are each hydrogen, the thiophosphorylating reagent, and, optionally, the Brønsted acid or base, so as to produce the compound or derivative having formula (IIa), or salt, solvate, or prodrug thereof, wherein $Y^3$ is sulfur;

(d) adding, optionally, the compound or derivative having formula (Ia-H), or salt, solvate, or prodrug thereof, wherein $R^6$, $R^7$, and $R^8$ are each hydrogen, optionally, the thiophosphorylating reagent, optionally, the Brønsted acid or base, and the compound or derivative having formula (IIa), or salt, solvate, or prodrug thereof, wherein $Y^3$ is sulfur, to iced water;

optionally, (d1) adjusting the pH of the aqueous phase with an aqueous base;

optionally, (d2) isolating the unreacted compound or derivative having formula (Ia-H), or salt, solvate, or prodrug thereof, wherein $R^6$, $R^7$, and $R^8$ are each hydrogen;

(e) isolating the compound or derivative having formula (IIa), or salt, solvate, or prodrug thereof, wherein $Y^3$ is sulfur; and optionally, (e1) treating the compound or derivative having formula (IIa), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of compound or derivative having formula (IIa), or salt, solvate, or prodrug thereof, wherein $Y^3$ is sulfur, under almost solventless conditions.

The polar organic solvent co-reagent and isolation solvent employed in the above method of making a compound or derivative having formula (IIa), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (III), or a salt, solvate, or prodrug thereof, can include the steps of:

(a) providing a compound or derivative having formula (II), or a salt, solvate, or prodrug thereof;

(b) treating the compound or derivative having formula (II), or salt, solvate, or prodrug thereof, with a compound or derivative having formula (3), or a salt thereof, and a (1<x≤10) molar equivalent amount of a carbodiimide reagent, in the presence of water or an organic solvent co-reagent in an amount of up to 10 molar equivalents;

optionally, (b1) treating the compound or derivative having formula (II), or salt, solvate, or prodrug thereof, the compound or derivative having formula (3), or salt thereof, the carbodiimide reagent, and the water or organic solvent co-reagent, with at least a catalytic amount of a divalent metal salt;

(c) processing the compound or derivative having formula (II), or salt, solvate, or prodrug thereof, the compound or derivative having formula (3), or salt thereof, the carbodiimide reagent, the water or organic solvent co-reagent, and, optionally, the divalent metal salt, so as to produce the compound or derivative having formula (III), or salt, solvate, or prodrug thereof;

(d) adding, optionally, the compound or derivative having formula (II), or salt, solvate, or prodrug thereof, optionally, the compound or derivative having formula (3), or salt thereof, optionally, the carbodiimide reagent, the water or organic solvent co-reagent, optionally, the divalent metal salt, and the compound or derivative having formula (III), or salt, solvate, or prodrug thereof, to iced water;

optionally, (d1) adjusting the pH of the aqueous phase with an aqueous base;

optionally, (d2) isolating the unreacted compound or derivative having formula (II), or salt, solvate, or prodrug thereof;

optionally, (d3) isolating the unreacted compound or derivative having formula (3), or salt thereof;

(e) isolating the compound or derivative having formula (III), or salt, solvate, or prodrug thereof; and optionally, (e1) treating the compound or derivative having formula (III), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (III), or salt, solvate, or prodrug thereof, under almost solventless conditions.

The polar organic solvent co-reagent employed in the above method of making a compound or derivative having formula (III), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (III), or a salt, solvate, or prodrug thereof, can include the steps of:

(a) providing a compound or derivative having formula (II), or a salt, solvate, or prodrug thereof;

(b) treating the compound or derivative having formula (II), or salt, solvate, or prodrug thereof, with a compound or derivative having formula (3), or a salt thereof, and a ($0<x\leq10$) molar equivalent amount of an amine, in the presence of water or an organic solvent co-reagent in an amount of up to 10 molar equivalents;

optionally, (b1) treating the compound or derivative having formula (II), or salt, solvate, or prodrug thereof, the compound or derivative having formula (3), or salt thereof, the amine, and the water or organic solvent co-reagent, with at least a catalytic amount of a divalent metal salt;

(c) processing the compound or derivative having formula (II), or salt, solvate, or prodrug thereof, the compound or derivative having formula (3), or salt thereof, the amine, the water or organic solvent co-reagent, and, optionally, the divalent metal salt, so as to produce the compound or derivative having formula (III), or salt, solvate, or prodrug thereof;

(d) adding, optionally, the compound or derivative having formula (II), or salt, solvate, or prodrug thereof, optionally, the compound or derivative having formula (3), or salt thereof, optionally, the amine, the water or organic solvent co-reagent, optionally, the divalent metal salt, and the compound or derivative having formula (III), or salt, solvate, or prodrug thereof, to iced water;

optionally, (d1) adjusting the pH of the aqueous phase with an aqueous base;

optionally, (d2) isolating the unreacted compound or derivative having formula (II), or salt, solvate, or prodrug thereof;

optionally, (d3) isolating the unreacted compound or derivative having formula (3), or salt thereof;

(e) isolating the compound or derivative having formula (III), or salt, solvate, or prodrug thereof; and optionally, (e1) treating the compound or derivative having formula (III), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (III), or salt, solvate, or prodrug thereof, under almost solventless conditions.

The polar organic solvent co-reagent employed in the above method of making a compound or derivative having formula (III), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (III), or a salt, solvate, or prodrug thereof, can include the steps of:

(a) providing a compound or derivative having formula (II), or a salt, solvate, or prodrug thereof;

(b) treating the compound or derivative having formula (II), or salt, solvate, or prodrug thereof, with a compound or derivative having formula (3), or a salt thereof, and a ($0<x\leq10$) molar equivalent amount of a Brønsted acid, in the presence of water or an organic solvent co-reagent in an amount of up to 10 molar equivalents;

optionally, (b1) treating the compound or derivative having formula (II), or salt, solvate, or prodrug thereof, the compound or derivative having formula (3), or salt thereof, the Brønsted acid, and the water or organic solvent co-reagent, with at least a catalytic amount of a divalent metal salt;

(c) processing the compound or derivative having formula (II), or salt, solvate, or prodrug thereof, the compound or derivative having formula (3), or salt thereof, the Brønsted acid, the water or organic solvent co-reagent, and, optionally, the divalent metal salt, so as to produce the compound or derivative having formula (III), or salt, solvate, or prodrug thereof;

(d) adding, optionally, the compound or derivative having formula (II), or salt, solvate, or prodrug thereof, optionally, the compound or derivative having formula (3), or salt thereof, optionally, the Brønsted acid, the water or organic solvent co-reagent, optionally, the divalent metal salt, and the compound or derivative having formula (III), or salt, solvate, or prodrug thereof, to iced water;

optionally, (d1) adjusting the pH of the aqueous phase with an aqueous base;

optionally, (d2) isolating the unreacted compound or derivative having formula (II), or salt, solvate, or prodrug thereof;

optionally, (d3) isolating the unreacted compound or derivative having formula (3), or salt thereof;

(e) isolating the compound or derivative having formula (III), or salt, solvate, or prodrug thereof; and optionally, (e1) treating the compound or derivative having formula (III), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (III), or salt, solvate, or prodrug thereof, under almost solventless conditions.

The polar organic solvent co-reagent employed in the above method of making a compound or derivative having formula (III), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (IIIa), or a salt, solvate, or prodrug thereof, can include the steps of:

(a) providing a compound or derivative having formula (IIa), or a salt, solvate, or prodrug thereof;

(b) treating the compound or derivative having formula (IIa), or salt, solvate, or prodrug thereof, with a compound or derivative having formula (3), or a salt thereof, and a ($1<x\leq10$) molar equivalent amount of a carbodiimide reagent, in the presence of water or an organic solvent co-reagent;

optionally, (b1) treating the compound or derivative having formula (IIa), or salt, solvate, or prodrug thereof, the compound or derivative having formula (3), or salt thereof, the carbodiimide reagent, and the water or organic solvent co-reagent, with at least a catalytic amount of a divalent metal salt;

(c) processing the compound or derivative having formula (IIa), or salt, solvate, or prodrug thereof, the compound or derivative having formula (3), or salt thereof, the carbodiimide reagent, the water or organic solvent co-reagent, and, optionally, the divalent metal salt, so as to produce the compound or derivative having formula (IIIa), or salt, solvate, or prodrug thereof;

(d) adding, optionally, the compound or derivative having formula (IIa), or salt, solvate, or prodrug thereof, optionally, the compound or derivative having formula (3), or salt thereof, optionally, the carbodiimide reagent, the water or organic solvent co-reagent, optionally, the divalent metal salt, and the compound or derivative having formula (IIIa), or salt, solvate, or prodrug thereof, to iced water;

optionally, (d1) adjusting the pH of the aqueous phase with an aqueous base;

optionally, (d2) isolating the unreacted compound or derivative having formula (IIa), or salt, solvate, or prodrug thereof, optionally, (d2) isolating the unreacted compound or derivative having formula (3), or salt thereof;

(e) isolating the compound or derivative having formula (IIIa), or salt, solvate, or prodrug thereof;

optionally, (e1) treating the compound or derivative having formula (IIIa), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIIa), or salt, solvate, or prodrug thereof, under almost solventless conditions.

The polar organic solvent co-reagent employed in the above method of making a compound or derivative having formula (IIIa), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (IIIa), or a salt, solvate, or prodrug thereof, can include the steps of:

(a) providing a compound or derivative having formula (IIa), or a salt, solvate, or prodrug thereof;

(b) treating the compound or derivative having formula (IIa), or salt, solvate, or prodrug thereof, with a compound or derivative having formula (3), or a salt thereof, and a ($0<x\leq10$) molar equivalent amount of an amine, in the presence of water or an organic solvent co-reagent in an amount of up to 10 molar equivalents;

optionally, (b1) treating the compound or derivative having formula (IIa), or salt, solvate, or prodrug thereof, the compound or derivative having formula (3), or salt thereof, the amine, and the water or organic solvent co-reagent, with at least a catalytic amount of a divalent metal salt;

(c) processing the compound or derivative having formula (IIa), or salt, solvate, or prodrug thereof, the compound or derivative having formula (3), or salt thereof, the amine, the water or organic solvent co-reagent, and, optionally, the divalent metal salt, so as to produce the compound or derivative having formula (IIIa), or salt, solvate, or prodrug thereof;

(d) adding, optionally, the compound or derivative having formula (IIa), or salt, solvate, or prodrug thereof, optionally, the compound or derivative having formula (3), or salt thereof, optionally, the amine, the water or organic solvent co-reagent, optionally, the divalent metal salt, and the compound or derivative having formula (IIIa), or salt, solvate, or prodrug thereof, to iced water;

optionally, (d1) adjusting the pH of the aqueous phase with an aqueous base;

optionally, (d2) isolating the unreacted compound or derivative having formula (IIa), or salt, solvate, or prodrug thereof;

optionally, (d3) isolating the unreacted compound or derivative having formula (3), or salt thereof;

(e) isolating the compound or derivative having formula (IIIa), or salt, solvate, or prodrug thereof, and optionally, (e1) treating the compound or derivative having formula (IIIa), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIIa), or salt, solvate, or prodrug thereof, under almost solventless conditions.

The polar organic solvent co-reagent employed in the above method of making a compound or derivative having formula (IIIa), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (IIIa), or a salt, solvate, or prodrug thereof, can include the steps of:

(a) providing a compound or derivative having formula (IIa), or a salt, solvate, or prodrug thereof;

(b) treating the compound or derivative heaving formula (IIa), or salt, solvate, or prodrug thereof, with a compound or derivative having formula (3), or a salt thereof, and a ($0 < x \leq 10$) molar equivalent amount of a Brønsted acid, in the presence of water or an organic solvent co-reagent in an amount of up to 10 molar equivalents;

optionally, (b1) treating the compound or derivative having formula (IIa), or salt, solvate, or prodrug thereof, the compound or derivative having formula (3), or salt thereof, the Brønsted acid, and the water or organic solvent co-reagent, with at least a catalytic amount of a divalent metal salt;

(c) processing the compound or derivative having formula (IIa), or salt, solvate, or prodrug thereof, the compound or derivative having formula (3), or salt thereof, the Brønsted acid, the water or organic solvent co-reagent, and, optionally, the divalent metal salt, so as to produce the compound or derivative having formula (IIIa), or salt, solvate, or prodrug thereof;

(d) adding, optionally, the compound or derivative having formula (IIa), or salt, solvate, or prodrug thereof, optionally, the compound or derivative having formula (3), or salt thereof, optionally, the Brønsted acid, the water or organic solvent co-reagent, optionally, the divalent metal salt, and the compound or derivative having formula (IIIa), or salt, solvate, or prodrug thereof, to iced water;

optionally, (d1) adjusting the pH of the aqueous phase with an aqueous base;

optionally, (d2) isolating the unreacted compound or derivative having formula (IIa), or salt, solvate, or prodrug thereof;

optionally, (d3) isolating the unreacted compound or derivative having formula (3), or salt thereof;

(e) isolating the compound or derivative having formula (IIIa), or salt, solvate, or prodrug thereof, and optionally, (e1) treating the compound or derivative having formula (IIIa), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IIIa), or salt, solvate, or prodrug thereof, under almost solventless conditions.

The polar organic solvent co-reagent employed in the above method of making a compound or derivative having formula (IIIa), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (IV), or a salt, solvate, or prodrug thereof, can include the steps of:

(a) providing a compound or derivative having formula (I), or salt, solvate, or prodrug thereof;

(b) treating the compound or derivative having formula (I), or salt, solvate, or prodrug thereof, with a ($1 < x < 10$) molar equivalent amount of a concentrated basic aqueous solution of reducing agent reagent, in the presence of a ($5 < x < 50$) molar equivalent amount of an organic solvent co-reagent;

(c) processing the compound or derivative having formula (I), or salt, solvate, or prodrug thereof, the concentrated aqueous solution of reducing agent reagent, and the organic solvent co-reagent so as to produce the compound or derivative having formula (IV), or salt, solvate, or prodrug thereof;

(d) adding, optionally, the compound or derivative having formula (I), or salt, solvate, or prodrug thereof, optionally, the concentrated aqueous solution of reducing agent reagent, the organic solvent co-reagent, and the compound or derivative having formula (IV), or salt, solvate, or prodrug thereof, to water;

(e) extracting, optionally, the compound or derivative having formula (I), or salt, solvate, or prodrug thereof, optionally, the concentrated aqueous solution of reducing agent reagent, the organic solvent co-reagent, the compound or derivative having formula (IV), or salt, solvate, or prodrug thereof, and water with organic solvent; and (f) isolating the compound or derivative having formula (IV), or salt, solvate, or prodrug thereof.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IV), or salt, solvate, or prodrug thereof, under almost solventless conditions.

The polar organic solvent co-reagent and isolation solvent employed in the above method of making a compound or derivative having formula (IV), or salt, solvate, or prodrug thereof, can be a polar organic solvent from among, for example, preferably, the Class 2 Residual Solvents listed in Table 2, or optionally, for non-human use, the Class 3

Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (IV), or a salt, solvate, or prodrug thereof, wherein $R^6$, $R^7$, and $R^8$ are each —C(O)R', and wherein R' is methyl or —$C_1$alkyl, can include the steps of:

(a) providing a compound or derivative having formula (I), or a salt, solvate, or prodrug thereof, wherein $R^6$, $R^7$, and $R^8$ are each —C(O)R', and wherein R' is methyl or —$C_1$alkyl;

(b) treating the compound or derivative having formula (I), or salt, solvate, or prodrug thereof, wherein $R^6$, $R^7$, and $R^8$ are each —C(O)R', and wherein R' is methyl or —$C_1$alkyl, with a molar equivalent amount of a reducing agent reagent, in the presence of a (1<x≤10) molar equivalent amount of an organic solvent co-reagent;

(c) processing the compound or derivative having formula (I), or salt, solvate, or prodrug thereof, wherein $R^6$, $R^7$, and $R^8$ are each —C(O)R', and wherein R' is methyl or —$C_1$alkyl, the reducing agent reagent, and the organic solvent co-reagent so as to produce the compound or derivative having formula (IV), or salt, solvate, or prodrug thereof, wherein $R^6$, $R^7$, and $R^8$ are each —C(O)R', and wherein R' is methyl or —$C_1$alkyl;

optionally, (c1) removing by-products resulting from the processing step under reduced pressure and temperature-controlled conditions;

optionally, (c2) separately isolating unreacted compound or derivative having formula (I), or salt, solvate, or prodrug thereof, wherein $R^6$, $R^7$, and $R^8$ are each —C(O)R', and wherein R' is methyl or —$C_1$alkyl; and (d) isolating the compound or derivative having formula (IV), or salt, solvate, or prodrug thereof, wherein $R^6$, $R^7$, and $R^8$ are each —C(O)R', and wherein R' is methyl or —$C_1$alkyl.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IV), or salt, solvate, or prodrug thereof, wherein $R^6$, $R^7$, and $R^8$ are each —C(O)R', and wherein R' is methyl or —$C_1$alkyl, under almost solventless conditions.

The polar organic solvent co-reagent and isolation solvent employed in the above method of making a compound or derivative having formula (IV), or salt, solvate, or prodrug thereof, wherein $R^6$, $R^7$, and $R^8$ are each —C(O)R', and wherein R' is methyl or —$C_1$alkyl, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (IVa), or a salt, solvate, or prodrug thereof, can include the steps of:

(a) providing a compound or derivative having formula (Ia), or salt, solvate, or prodrug thereof;

(b) treating the compound or derivative having formula (Ia), or salt, solvate, or prodrug thereof, with a (1<x<10) molar equivalent amount of a concentrated basic aqueous solution of reducing agent reagent, in the presence of a (5<x<50) molar equivalent amount of an organic solvent co-reagent;

(c) processing the compound or derivative having formula (Ia), or salt, solvate, or prodrug thereof, the concentrated aqueous solution of reducing agent reagent, and the organic solvent co-reagent so as to produce the compound or derivative having formula (IVa), or salt, solvate, or prodrug thereof;

(d) adding, optionally, the compound or derivative having formula (Ia), or salt, solvate, or prodrug thereof, optionally, the concentrated aqueous solution of reducing agent reagent, the organic solvent co-reagent, and the compound or derivative having formula (IVa), or salt, solvate, or prodrug thereof, to water;

(e) extracting, optionally, the compound or derivative having formula (Ia), or salt, solvate, or prodrug thereof, optionally, the concentrated aqueous solution of reducing agent reagent, the organic solvent co-reagent, the compound or derivative having formula (IVa), or salt, solvate, or prodrug thereof, and water with organic solvent; and (f) isolating the compound or derivative having formula (IVa), or salt, solvate, or prodrug thereof.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IVa), or salt, solvate, or prodrug thereof, under almost solventless conditions.

The polar organic solvent co-reagent and isolation solvent employed in the above method of making a compound or derivative having formula (IVa), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (IVa), or a salt, solvate, or prodrug thereof, wherein $R^6$, $R^7$, and $R^8$ are each —C(O)R', and wherein R' is methyl or —$C_1$alkyl, can include the steps of:

(a) providing a compound or derivative having formula (Ia), or a salt, solvate, or prodrug thereof, wherein $R^6$, $R^7$, and $R^8$ are each —C(O)R', and wherein R' is methyl or —$C_1$alkyl;

(b) treating the compound or derivative having formula (Ia), or salt, solvate, or prodrug thereof, wherein $R^6$, $R^7$, and $R^8$ are each —C(O)R', and wherein R' is methyl or —C$_1$alkyl, with a molar equivalent amount of a reducing agent reagent, in the presence of a (1<x≤10) molar equivalent amount of an organic solvent co-reagent;

(c) processing the compound or derivative having formula (Ia), or salt, solvate, or prodrug thereof, wherein $R^6$, $R^7$, and $R^8$ are each —C(O)R', and wherein R' is methyl or —C$_1$alkyl, the reducing agent reagent, and the organic solvent co-reagent so as to produce the compound or derivative having formula (IVa), or salt, solvate, or prodrug thereof, wherein $R^6$, $R^7$, and $R^8$ are each —C(O)R', and wherein R' is methyl or —C$_1$alkyl;

optionally, (c1) removing by-products resulting from the processing step under reduced pressure and temperature-controlled conditions;

optionally, (c2) separately isolating unreacted compound or derivative having formula (Ia), or salt, solvate, or prodrug thereof, wherein $R^6$, $R^7$, and $R^8$ are each —C(O)R', and wherein R' is methyl or —C$_1$alkyl; and (d) isolating the compound or derivative having formula (IVa), or salt, solvate, or prodrug thereof, wherein $R^6$, $R^7$, and $R^8$ are each —C(O)R', and wherein R' is methyl or —C$_1$alkyl.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IVa), or salt, solvate, or prodrug thereof, wherein $R^6$, $R^7$, and $R^8$ are each —C(O)R', and wherein R' is methyl or —C$_1$alkyl, under almost solventless conditions.

The polar organic solvent co-reagent and isolation solvent employed in the above method of making a compound or derivative having formula (IVa), or salt, solvate, or prodrug thereof, wherein $R^6$, $R^7$, and $R^8$, are each —C(O)R', and wherein R' is methyl or —C$_1$alkyl, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (IV-H), or a salt, solvate, or prodrug thereof, wherein $R^6$, $R^7$, and $R^8$ are each hydrogen, can include the steps of:

(a) providing a compound or derivative having formula (IV), or a salt, solvate, or prodrug thereof;

(b) treating the compound or derivative having formula (IV), or salt, solvate, or prodrug thereof, with a molar (x≤10) equivalent amount of an alcohol (e.g., methanol, or ethanol) and at least a catalytic amount of a Brønsted inorganic base;

(c) processing the compound or derivative having formula (IV), or salt, solvate, or prodrug thereof, the alcohol, and the Brønsted inorganic base so as to produce the compound or derivative having formula (IV-H), or salt, solvate, or prodrug thereof, wherein $R^6$, $R^7$, and $R^8$ are each hydrogen;

optionally, (c1) evaporating any volatile by-products resulting from the processing step;

(d) isolating the compound or derivative having formula (IV-H), or salt, solvate, or prodrug thereof, wherein $R^6$, $R^7$, and $R^8$ are each hydrogen;

optionally, (d1) separately isolating the unreacted compound or derivative having formula (IV), or salt, solvate, or prodrug thereof, and optionally, (d2) drying the compound or derivative having formula (IV-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IV-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (IV-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (IV-H), or a salt, solvate, or prodrug thereof, wherein $R^6$, $R^7$, and $R^8$ are each hydrogen, can include the steps of:

(a) providing a compound or derivative having formula (IV), or a salt, solvate, or prodrug thereof, wherein $R^6$, $R^7$, and $R^8$ are each —C(O)R', and wherein R' is methyl or —C$_1$alkyl;

(b) treating the compound or derivative having formula (IV), or salt, solvate, or prodrug thereof, wherein $R^6$, $R^7$, and $R^8$ are each —C(O)R', and wherein R' is methyl or —C$_1$alkyl, with a molar (x≤10) equivalent amount of an alcohol (e.g., methanol, or ethanol) and at least a catalytic amount of a Brønsted inorganic base;

(c) processing the compound or derivative having formula (IV), or salt, solvate, or prodrug thereof, wherein $R^6$, $R^7$, and $R^8$ are each —C(O)R', and wherein R' is methyl or —C$_1$alkyl, the alcohol, and the Brønsted inorganic base so as to produce the compound or derivative having formula (IV-H), or salt, solvate, or prodrug thereof, wherein $R^6$, $R^7$, and $R^8$ are each hydrogen;

optionally, (c1) evaporating any volatile by-products resulting from the processing step;

(d) isolating the compound or derivative having formula (IV-H), or salt, solvate, or prodrug thereof, wherein $R^6$, $R^7$, and $R^8$ are each hydrogen;

optionally, (d1) separately isolating the unreacted compound or derivative having formula (IV), or salt, solvate, or prodrug thereof, wherein $R^6$, $R^7$, and $R^8$ are each —C(O)R', and wherein R' is methyl or —$C_1$alkyl; and optionally, (d2) drying the compound or derivative having formula (IV-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IV-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (IV-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (IV-H), or a salt, solvate, or prodrug thereof, wherein $R^6$, $R^7$, and $R^8$ are each hydrogen, can include the steps of:

(a) providing a compound or derivative having formula (I), or a salt, solvate, or prodrug thereof;

(b) treating the compound or derivative having formula (I), or salt, solvate, or prodrug thereof, with a (1<x<10) molar equivalent amount of a concentrated basic aqueous solution of reducing agent reagent, in the presence of a (5<x<50) molar equivalent amount of a polar organic solvent co-reagent;

(c) processing the compound or derivative having formula (I), or salt, solvate, or prodrug thereof, the concentrated aqueous solution of reducing agent reagent, and the polar organic solvent co-reagent so as to produce a compound or derivative having formula (IV), or a salt, solvate, or prodrug thereof, while continuously extracting in situ the compound or derivative having formula (IV), or salt, solvate, or prodrug thereof, into organic solvent;

optionally, (c1) removing by-products resulting from processing step (c) by continuously extracting with water;

(d) separating the organic solvent phase, in which the compound or derivative having formula (IV), or salt, solvate, or prodrug thereof, is dissolved, from the aqueous phase;

optionally, (d1) removing the organic solvent under reduced pressure and temperature-controlled conditions so as to provide a viscous paste containing the compound or derivative having formula (IV), or salt, solvate, or prodrug thereof;

(e) treating the compound or derivative having formula (IV), or salt, solvate, or prodrug thereof, and residual organic solvent, with a molar (x≤10) equivalent amount of an alcohol (e.g., methanol, or ethanol) and at least a catalytic amount of a Brønsted inorganic base;

(f) processing the compound or derivative having formula (IV), or salt, solvate, or prodrug thereof, residual organic solvent, the alcohol, and the Brønsted inorganic base so as to produce the compound or derivative having formula (IV-H), or salt, solvate, or prodrug thereof, wherein $R^6$, $R^7$, and $R^8$ are each hydrogen;

optionally, (f1) evaporating any volatile by-products resulting from processing step (f);

(g) isolating the compound or derivative having formula (IV-H), or salt, solvate, or prodrug thereof, wherein $R^6$, $R^7$, and $R^8$ are each hydrogen;

optionally, (g1) separately isolating the unreacted compound or derivative having formula (IV), or salt, solvate, or prodrug thereof, and optionally, (g2) drying the compound or derivative having formula (IV-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IV-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (IV-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (IV-H), or a salt, solvate, or prodrug thereof, wherein $R^6$, $R^7$, and $R^8$ are each hydrogen, can include the steps of:

(a) providing a compound or derivative having formula (I), or a salt, solvate, or prodrug thereof, wherein $R^6$, $R^7$, and $R^8$ are each —C(O)R', and wherein R' is methyl or —$C_1$alkyl;

(b) treating the compound or derivative having formula (I), or salt, solvate, or prodrug thereof, wherein $R^6$, $R^7$, and $R^8$ are each —C(O)R', and wherein R' is methyl or —$C_1$alkyl, with a (1<x<10) molar equivalent amount of a concentrated basic aqueous solution of reducing agent reagent, in the presence of a (5<x<50) molar equivalent amount of a polar organic solvent co-reagent;

(c) processing the compound or derivative having formula (I), or salt, solvate, or prodrug thereof, wherein $R^6$, $R^7$, and $R^8$ are each —C(O)R', and wherein R' is methyl or —$C_1$alkyl, the concentrated aqueous solution of reducing agent reagent, and the polar organic solvent co-reagent so as to produce a compound or derivative having formula (IV), or a salt, solvate or prodrug thereof, wherein $R^6$, $R^7$, and $R^8$ are each —C(O)R', and wherein R' is methyl or —$C_1$alkyl, while continuously extracting in situ the compound or derivative having formula (IV), or salt, solvate, or prodrug thereof, wherein $R^6$, $R^7$, and $R^8$ are each —C(O)R', and wherein R' is methyl or —$C_1$alkyl, into organic solvent;

optionally, (c1) removing by-products resulting from processing step (c) by continuously extracting with water;

(d) separating the organic solvent phase, in which the compound or derivative having formula (IV), or salt, solvate, or prodrug thereof, wherein $R^6$, $R^7$, and $R^8$ are each —C(O)R', and wherein R' is methyl or —$C_1$alkyl, is dissolved, from the aqueous phase;

optionally, (d1) removing the organic solvent under reduced pressure and temperature-controlled conditions so as to provide a viscous paste containing the compound or derivative having formula (IV), or salt, solvate, or prodrug thereof, wherein $R^6$, $R^7$, and $R^8$ are each —C(O)R', and wherein R' is methyl or —$C_1$alkyl;

(e) treating the compound or derivative having formula (IV), or salt, solvate, or prodrug thereof, wherein $R^6$, $R^7$, and $R^8$ are each —C(O)R', and wherein R' is methyl or —$C_1$alkyl, and residual organic solvent, with a molar (x≤10) equivalent amount of an alcohol (e.g., methanol, or ethanol) and at least a catalytic amount of a Brønsted inorganic base;

(f) processing the compound or derivative having formula (IV), or salt, solvate, or prodrug thereof, wherein $R^6$, $R^7$, and $R^8$ are each —C(O)R', and wherein R' is methyl or —$C_1$alkyl, residual organic solvent, the alcohol, and the Brønsted inorganic base so as to produce the compound or derivative having formula (IV-H), or salt, solvate, or prodrug thereof, wherein $R^6$, $R^7$, and $R^8$ are each hydrogen;

optionally, (f1) evaporating any volatile by-products resulting from processing step (f);

(g) isolating the compound or derivative having formula (IV-H), or salt, solvate, or prodrug thereof, wherein $R^6$, $R^7$, and $R^8$ are each hydrogen;

optionally, (g1) separately isolating the unreacted compound or derivative having formula (IV), or salt, solvate, or prodrug thereof, wherein $R^6$, $R^7$, and $R^8$ are each —C(O)R', and wherein R' is methyl or —$C_1$alkyl; and optionally, (g2) drying the compound or derivative having formula (IV-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IV-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (IV-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (IVa-H), or a salt, solvate, or prodrug thereof, wherein $R^6$, $R^7$, and $R^8$ are each hydrogen, can include the steps of:

(a) providing a compound or derivative having formula (IVa), or a salt, solvate, or prodrug thereof;

(b) treating the compound or derivative having formula (IVa), or salt, solvate, or prodrug thereof, with a molar (x≤10) equivalent amount of an alcohol (e.g., methanol, or ethanol) and at least a catalytic amount of a Brønsted inorganic base;

(c) processing the compound or derivative having formula (IVa), or salt, solvate, or prodrug thereof, the alcohol, and the Brønsted inorganic base so as to produce the compound or derivative having formula (IVa-H), or salt, solvate, or prodrug thereof, wherein $R^6$, $R^7$, and R' are each hydrogen;

optionally, (c1) evaporating any volatile by-products resulting from the processing step;

(d) isolating the compound or derivative having formula (IVa-H), or salt, solvate, or prodrug thereof, wherein $R^6$, $R^7$, and $R^8$ are each hydrogen;

optionally, (d1) separately isolating the unreacted compound or derivative having formula (IVa), or salt, solvate, or prodrug thereof, and optionally, (d2) drying the compound or derivative having formula (IVa-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IVa-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (IVa-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (IVa-H), or a salt, solvate, or prodrug thereof, wherein $R^6$, $R^7$, and $R^8$ are each hydrogen, can include the steps of:

(a) providing a compound or derivative having formula (IVa), or a salt, solvate, or prodrug thereof, wherein $R^6$, $R^7$, and $R^8$ are each —C(O)R', and wherein R' is methyl or —$C_1$alkyl;

(b) treating the compound or derivative having formula (IVa), or salt, solvate, or prodrug thereof, wherein $R^6$, $R^7$, and $R^8$ are each —C(O)R', and wherein R' is methyl or —$C_1$alkyl, with a molar (x≤10) equivalent amount of an alcohol (e.g., methanol, or ethanol) and at least a catalytic amount of a Brønsted inorganic base;

(c) processing the compound or derivative having formula (IVa), or salt, solvate, or prodrug thereof, wherein $R^6$, $R^7$, and $R^8$ are each —C(O)R', and wherein R' is methyl or —$C_1$alkyl, the alcohol, and the Brønsted inorganic base so as to produce the compound or derivative having formula (IVa-H), or salt, solvate, or prodrug thereof, wherein $R^6$, $R^7$, and $R^8$ are each hydrogen;

optionally, (c1) evaporating any volatile by-products resulting from the processing step;

(d) isolating the compound or derivative having formula (IVa-H), or salt, solvate, or prodrug thereof, wherein $R^6$, $R^7$, and $R^8$ are each hydrogen;

optionally, (d1) separately isolating the unreacted compound or derivative having formula (IVa), or salt, solvate, or prodrug thereof, wherein $R^6$, $R^7$, and $R^8$ are each —C(O)R', and wherein R' is methyl or —$C_1$alkyl; and optionally, (d2) drying the compound or derivative having formula (IVa-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IVa-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (IVa-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (IVa-H), or a salt, solvate, or prodrug thereof, wherein $R^6$, $R^7$, and $R^8$ are each hydrogen, can include the steps of:

(a) providing a compound or derivative having formula (Ia), or a salt, solvate, or prodrug thereof;

(b) treating the compound or derivative having formula (Ia), or salt, solvate, or prodrug thereof, with a (1<x<10) molar equivalent amount of a concentrated basic aqueous solution of reducing agent reagent, in the presence of a (5<x<50) molar equivalent amount of a polar organic solvent co-reagent;

(c) processing the compound or derivative having formula (Ia), or salt, solvate, or prodrug thereof, the concentrated aqueous solution of reducing agent reagent, and polar organic solvent co-reagent so as to produce a compound or derivative having formula (IVa), or a salt, solvate, or prodrug thereof, while continuously extracting in situ the compound or derivative having formula (IVa), or salt, solvate, or prodrug thereof, into organic solvent;

optionally, (c1) removing by-products resulting from processing step (c) by continuously extracting the organic solvent with water;

(d) separating the organic solvent phase, in which the compound or derivative having formula (IVa), or salt, solvate, or prodrug thereof, is dissolved, from the aqueous phase;

optionally, (d1) removing the organic solvent under reduced pressure and temperature-controlled conditions so as to provide a viscous paste containing the compound or derivative having formula (IVa), or salt, solvate, or prodrug thereof;

(e) treating the compound or derivative having formula (IVa), or salt, solvate, or prodrug thereof, and residual organic solvent, with a molar (x≤10) equivalent amount of an alcohol (e.g., methanol, or ethanol) and at least a catalytic amount of a Brønsted inorganic base;

(f) processing the compound or derivative having formula (IVa), or salt, solvate, or prodrug thereof, residual organic solvent, the alcohol, and the Brønsted inorganic base so as to produce the compound or derivative having formula (IVa-H), or salt, solvate, or prodrug thereof, wherein $R^6$, $R^7$, and $R^8$ are each hydrogen;

optionally, (f1) evaporating any volatile by-products resulting from processing step (f);

(g) isolating the compound or derivative having formula (IVa-H), or salt, solvate, or prodrug thereof, wherein $R^6$, $R^7$, and $R^8$ are each hydrogen;

optionally, (g1) separately isolating the unreacted compound or derivative having formula (IVa), or salt, solvate, or prodrug thereof, and optionally, (g2) drying the compound or derivative having formula (IVa-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (IVa-H), or salt, solvate, or prodrug thereof, wherein $R^6$, $R^7$, and $R^8$ are each hydrogen.

The polar organic solvent co-reagent and isolation solvent employed in the above method of making a compound or derivative having formula (IVa-H), or salt, solvate, or prodrug thereof, wherein $R^6$, $R^7$, and $R^8$ are each hydrogen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (IVa-H), or a salt, solvate, or prodrug thereof, wherein $R^6$, $R^7$, and $R^8$ are each hydrogen, can include the steps of:

(a) providing a compound or derivative having formula (Ia), or a salt, solvate, or prodrug thereof, wherein $R^6$, $R^7$, and $R^8$ are each —C(O)R', and wherein R' is methyl or —$C_1$alkyl;

(b) treating the compound or derivative having formula (Ia), or salt, solvate, or prodrug thereof, wherein $R^6$, $R^7$, and $R^8$ are each —C(O)R', and wherein R' is methyl or —$C_1$alkyl, with a (1<x<10) molar equivalent amount of a concentrated basic aqueous solution of reducing agent reagent, in the presence of a (5<x<50) molar equivalent amount of a polar organic solvent co-reagent;

(c) processing the compound or derivative having formula (Ia), or salt, solvate, or prodrug thereof, wherein $R^6$, $R^7$, and $R^8$ are each —C(O)R', and wherein R' is methyl or —$C_1$alkyl, the concentrated aqueous solution of reducing agent reagent, and the polar organic solvent co-reagent so as to produce a compound or derivative having formula (IVa), or a salt, solvate, or prodrug thereof, wherein $R^6$, $R^7$, and $R^8$ are each —C(O)R', and wherein R' is methyl or —$C_1$alkyl, while continuously extracting in situ the compound or derivative having formula (IVa), or salt, solvate, or prodrug thereof, wherein $R^6$, $R^7$, and $R^8$ are each —C(O)R', and wherein R' is methyl or —$C_1$alkyl, into organic solvent;

optionally, (c1) removing by-products resulting from processing step (c) by continuously extracting the organic solvent with water;

(d) separating the organic solvent phase, in which the compound or derivative having formula (IVa), or salt, solvate, or prodrug thereof, wherein $R^6$, $R^7$, and $R^8$ are each —C(O)R', and wherein R' is methyl or —$C_1$alkyl, is dissolved, from the aqueous phase;

optionally, (d1) removing the organic solvent under reduced pressure and temperature-controlled conditions so as to provide a viscous paste containing the compound or derivative having formula (IVa), or salt, solvate, or prodrug thereof, wherein $R^6$, $R^7$, and $R^8$ are each —C(O)R', and wherein R' is methyl or —$C_1$alkyl;

(e) treating the compound or derivative having formula (IVa), or salt, solvate, or prodrug thereof, wherein $R^6$, $R^7$, and $R^8$ are each —C(O)R', and wherein R' is methyl or —$C_1$alkyl, and residual organic solvent, with a molar (x≤10) equivalent amount of an alcohol (e.g., methanol, or ethanol) and at least a catalytic amount of a Brønsted inorganic base;

(f) processing the compound or derivative having formula (IVa), or salt, solvate, or prodrug thereof, wherein $R^6$, $R^7$, and $R^8$ are each —C(O)R', and wherein R' is methyl or —$C_1$alkyl, residual organic solvent, alcohol, and Brønsted inorganic base so as to produce the compound or derivative having formula (IVa-H), or salt, solvate, or prodrug thereof, wherein $R^6$, $R^7$, and R' are each hydrogen;

optionally, (f1) evaporating any volatile by-products resulting from processing step (f);

(g) isolating the compound or derivative having formula (IVa-H), or salt, solvate, or prodrug thereof, wherein $R^6$, $R^7$, and $R^8$ are each hydrogen;

optionally, (g1) separately isolating the unreacted compound or derivative having formula (IVa), or salt, solvate, or prodrug thereof, wherein $R^6$, $R^7$, and $R^8$ are each —C(O)R', and wherein R' is methyl or —$C_1$alkyl; and optionally, (g2) drying the compound or derivative having formula (IVa-H), or salt, solvate, or prodrug thereof, wherein $R^6$, $R^7$, and $R^8$ are each hydrogen.

Processing can be carried out under batch processing conditions or by continuously processing. Continuously processing may include one or more methods of agitation selected from the group consisting of liquid-assisted mixing, milling, grinding, and extruding. Liquid-assisted mixing may be performed between about 5 Hz and about 50 Hz for about 1 min to about 500 min, preferably between about 10 Hz and about 40 Hz for about 15 min to about 180 min, and most preferably between about 20 Hz and about 30 Hz for about 60 min to about 120 min. Grinding may be performed between about 50 RPM and about 200 RPM, preferably between about 75 RPM and about 150 RPM, and most preferably between about 100 RPM and about 130 RPM.

In an embodiment, a method of making a compound or derivative having formula (V), or a salt, solvate, or prodrug thereof, wherein $Y^3$ is oxygen, can include the steps of:

(a) providing a compound or derivative having formula (IVb), or a salt, solvate, or prodrug thereof;

(b) treating the compound or derivative having formula (IVb), or salt, solvate, or prodrug thereof, with a phosphorylating reagent;

optionally, (b1) treating the compound or derivative having formula (IVb), or salt, solvate, or prodrug thereof, and the phosphorylating reagent, with a (0<x≤20) molar equivalent amount of a Brønsted base;

(c) processing the compound or derivative having formula (IVb), or salt, solvate, or prodrug thereof, the phosphorylating reagent, and, optionally, the Brønsted base, so as to produce the compound or derivative having formula (V), or salt, solvate, or prodrug thereof, wherein $Y^3$ is oxygen;

(d) adding, optionally, the compound or derivative having formula (IVb), or salt, solvate, or prodrug thereof, optionally, the phosphorylating reagent, optionally, the Brønsted base, and the compound or derivative having formula (V), or salt, solvate, or prodrug thereof, wherein $Y^3$ is oxygen, to iced water;

optionally, (d1) adjusting the pH of the aqueous phase with an aqueous base;

optionally, (d2) isolating the unreacted compound or derivative having formula (IVb), or salt, solvate, or prodrug thereof;

(e) isolating the compound or derivative having formula (V), or salt, solvate, or prodrug thereof, wherein $Y^3$ is oxygen;

optionally, (e1) treating the compound or derivative having formula (V), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between 50 RPM and about 200 RPM, preferably between about 75 RPM and about 150 RPM, and most preferably between about 100 RPM and about 130 RPM.

The process described herein effects a preparation of a compound or derivative having formula (V), or salt, solvate, or prodrug thereof, wherein $Y^3$ is oxygen, under almost solventless conditions.

The polar organic solvent co-reagent and isolation solvent employed in the above method of making a compound or derivative having formula (V), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (V), or a salt, solvate, or prodrug thereof, wherein $Y^3$ is oxygen, can include the steps of:

(a) providing a compound or derivative having formula (IVb), or a salt, solvate, or prodrug thereof;

(b) treating the compound or derivative having formula (IVb), or salt, solvate, or prodrug thereof, with a phosphitylating reagent;

optionally, (b1) treating the compound or derivative having formula (IVb), or salt, solvate, or prodrug thereof, and the phosphitylating reagent, with a ($0<x\leq20$) molar equivalent amount of a Brønsted base;

(c) processing the compound or derivative having formula (IVb), or salt, solvate, or prodrug thereof, the phosphitylating reagent, and, optionally, the Brønsted base so as to produce a compound or derivative having formula (V), or a salt, solvate, or prodrug thereof, wherein $Y^3$ is absent;

(d) adding an oxidizing agent reagent to, optionally, the compound or derivative having formula (IVb), or salt, solvate, or prodrug thereof, optionally, the phosphitylating reagent, optionally, the Brønsted base, and the compound or derivative having formula (V), or salt, solvate, or prodrug thereof, wherein $Y^3$ is absent;

(e) processing the oxidizing agent reagent, optionally, the compound or derivative having formula (IVb), or salt, solvate, or prodrug thereof, optionally, the phosphitylating reagent, optionally, the Brønsted base, and the compound or derivative having formula (V), or salt, solvate, or prodrug thereof, wherein $Y^3$ is absent, so as to produce the compound or derivative having formula (V), or salt, solvate, or prodrug thereof, wherein $Y^3$ is oxygen;

(f) adding, optionally, the oxidizing agent reagent, the compound or derivative having formula (IVb), or salt, solvate, or prodrug thereof, optionally, the phosphitylating reagent, optionally, the Brønsted base, optionally, the compound or derivative having formula (V), or salt, solvate, or prodrug thereof, wherein $Y^3$ is absent, and the compound or derivative having formula (V), or salt, solvate, or prodrug thereof, wherein $Y^3$ is oxygen, to iced water;

optionally, (f1) adjusting the pH of the aqueous phase with an aqueous base;

(g) isolating the compound or derivative having formula (V), or salt, solvate, or prodrug thereof, wherein $Y^3$ is oxygen; and optionally, (g1) treating the compound or derivative having formula (V), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (V), or salt, solvate, or prodrug thereof, wherein $Y^3$ is oxygen, under almost solventless conditions.

The polar organic solvent co-reagent and isolation solvent employed in the above method of making a compound or derivative having formula (V), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (V), or a salt, solvate, or prodrug thereof, wherein $Y^3$ is absent, can include the steps of:

(a) providing a compound or derivative having formula (IVb), or a salt, solvate, or prodrug thereof;

(b) treating the compound or derivative having formula (IVb), or salt, solvate, or prodrug thereof, with a phosphitylating reagent;

optionally, (b1) treating the compound or derivative having formula (IVb), or salt, solvate, or prodrug thereof, and the phosphitylating reagent, with a ($0<x\leq20$) molar equivalent amount of a Brønsted base;

(c) processing the compound or derivative having formula (IVb), or salt, solvate, or prodrug thereof, the phosphitylating reagent, and, optionally, the Brønsted base so as to produce the compound or derivative having formula (V), or salt, solvate, or prodrug thereof, wherein $Y^3$ is absent;

(d) adding, optionally, the compound or derivative having formula (IVb), or salt, solvate, or prodrug thereof, optionally, the phosphitylating reagent, optionally, the Brønsted base, and the compound or derivative having formula (V), or salt, solvate, or prodrug thereof, wherein $Y^3$ is absent, to iced water;

optionally, (d1) adjusting the pH of the aqueous phase with an aqueous base;

optionally, (d2) isolating the unreacted compound or derivative having formula (IVb), or salt, solvate, or prodrug thereof;

(e) isolating the compound or derivative having formula (V), or salt, solvate, or prodrug thereof, wherein $Y^3$ is absent; and optionally, (e1) treating the compound or derivative having formula (V), or salt, solvate, or prodrug thereof, wherein $Y^3$ is absent, with deprotection reagent(s) in a polar organic solvent co-reagent so as to remove any protecting groups of $R^7$, $R^8$, $Y^1$ and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (V), or salt, solvate, or prodrug thereof, wherein $Y^3$ is absent, under almost solventless conditions.

The polar organic solvent co-reagent and isolation solvent employed in the above method of making a compound or derivative having formula (V), or salt, solvate, or prodrug thereof, wherein $Y^3$ is absent, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (V), or a salt, solvate, or prodrug thereof, wherein $Y^3$ is sulfur, can include the steps of:

(a) providing a compound or derivative having formula (IVb), or a salt, solvate, or prodrug thereof;

(b) treating the compound or derivative having formula (IVb), or salt, solvate, or prodrug thereof, with a phosphitylating reagent;

optionally, (b1) treating the compound or derivative having formula (IVb), or salt, solvate, or prodrug thereof, and the phosphitylating reagent, with a (0<x≤20) molar equivalent amount of a Brønsted base;

(c) processing the compound or derivative having formula (IVb), or salt, solvate, or prodrug thereof, the phosphitylating reagent, and, optionally, the Brønsted base so as to produce a compound or derivative having formula (V), or a salt, solvate, or prodrug thereof, wherein $Y^3$ is absent;

(d) adding an oxidizing agent reagent to, optionally, the compound or derivative having formula (IVb), or salt, solvate, or prodrug thereof, optionally, the phosphitylating reagent, optionally, the Brønsted base, and the compound or derivative having formula (V), or salt, solvate, or prodrug thereof, wherein $Y^3$ is absent;

(e) processing the oxidizing agent reagent, optionally, the compound or derivative having formula (IVb), or salt, solvate, or prodrug thereof, optionally, the phosphitylating reagent, optionally, the Brønsted base, and the compound or derivative having formula (V), or salt, solvate, or prodrug thereof, wherein $Y^3$ is absent, so as to produce the compound or derivative having formula (V), or salt, solvate, or prodrug thereof, wherein $Y^3$ is sulfur;

(f) adding, optionally, the oxiziding agent reagent, optionally, the compound or derivative having formula (IVb), or salt, solvate, or prodrug thereof, optionally, the phosphitylating reagent, optionally, the Brønsted base, optionally, the compound or derivative having formula (V), or salt, solvate, or prodrug thereof, wherein $Y^3$ is absent, and the compound or derivative having formula (V), or salt, solvate, or prodrug thereof, wherein $Y^3$ is sulfur, to iced water;

optionally, (f1) adjusting the pH of the aqueous phase with an aqueous base;

(g) isolating the compound or derivative having formula (V), or salt, solvate, or prodrug thereof, wherein $Y^3$ is sulfur; and optionally, (g1) treating the compound or derivative having formula (V), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (V), or salt, solvate, or prodrug thereof, wherein $Y^3$ is sulfur, under almost solventless conditions.

The polar organic solvent co-reagent and isolation solvent in the above method of making a compound or derivative having formula (V), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (V), or a salt, solvate, or prodrug thereof, wherein $Y^3$ is sulfur, can include the steps of:

(a) providing a compound or derivative having formula (IVb), or a salt, solvate, or prodrug thereof;

(b) treating the compound or derivative having formula (IVb), or salt, solvate, or prodrug thereof, with a thiophosphorylating reagent;

optionally, (b1) treating the compound or derivative having formula (IVb), or salt, solvate, or prodrug thereof, and the thiophosphorylating reagent, with a (0<x≤20) molar equivalent amount of a Brønsted base;

(c) processing the compound or derivative having formula (IVb), or salt, solvate, or prodrug thereof, the thiophosphorylating reagent, and, optionally, the Brønsted base, so as to produce the compound or derivative having formula (V), or salt, solvate, or prodrug thereof, wherein $Y^3$ is sulfur;

(d) adding, optionally, the compound or derivative having formula (IVb), or salt, solvate, or prodrug thereof, optionally, the thiophosphorylating reagent, optionally, the Brønsted base, and the compound or derivative having formula (V), or salt, solvate, or prodrug thereof, wherein $Y^3$ is sulfur, to iced water;

optionally, (d1) adjusting the pH of the aqueous phase with an aqueous base;

optionally, (d2) isolating the unreacted compound or derivative having formula (IVb), or salt, solvate, or prodrug thereof;

(e) isolating the compound or derivative having formula (V), or salt, solvate, or prodrug thereof, wherein $Y^3$ is sulfur; and optionally, (e1) treating the compound or derivative having formula (V), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (V), or salt, solvate, or prodrug thereof, wherein $Y^3$ is sulfur, under almost solventless conditions.

The polar organic solvent co-reagent and isolation solvent in the above method of making a compound or derivative having formula (V), or salt, solvate, or prodrug thereof, wherein $Y^3$ is sulfur, can be a polar organic solvent from among, for example, preferably, the Class 2 Residual Solvents, listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (V), or a salt, solvate, or prodrug thereof, wherein $Y^3$ is oxygen, can include the steps of:

(a) providing a compound or derivative having formula (TV-H), or a salt, solvate, or prodrug thereof, wherein $R^6$, $R^7$, and $R^8$ are each hydrogen;

(b) treating the compound or derivative having formula (TV-H), or salt, solvate, or prodrug thereof, wherein $R^6$, $R^7$, and $R^8$ are each hydrogen, with a phosphorylating reagent;

optionally, (b1) treating the compound or derivative having formula (TV-H), or salt, solvate, or prodrug thereof, wherein $R^6$, $R^7$, and $R^8$ are each hydrogen, and the phosphorylating reagent, with a (0<x≤20) molar equivalent amount of a Brønsted base;

(c) processing the compound or derivative having formula (TV-H), or salt, solvate, or prodrug thereof, wherein $R^6$, $R^7$, and $R^8$ are each hydrogen, the phosphorylating reagent, and optionally, the Brønsted base, so as to produce the compound or derivative having formula (V), or salt, solvate, or prodrug thereof, wherein $Y^3$ is oxygen;

(d) adding, optionally, the compound or derivative having formula (IV-H), or salt, solvate, or prodrug thereof, wherein $R^6$, $R^7$, and $R^8$ are each hydrogen, optionally, the phosphorylating reagent, optionally, the Brønsted base, and the compound or derivative having formula (V), or salt, solvate, or prodrug thereof, wherein $Y^3$ is oxygen, to iced water;

optionally, (d1) adjusting the pH of the aqueous phase with an aqueous base;

optionally, (d2) isolating the unreacted compound or derivative having formula (IV-H), or salt, solvate, or prodrug thereof, wherein $R^6$, $R^7$, and $R^8$ are each hydrogen; and (e) isolating the compound or derivative having formula (V), or salt, solvate, or prodrug thereof, wherein $Y^3$ is oxygen; and optionally, (e1) treating the compound or derivative having formula (V), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (V), or salt, solvate, or prodrug thereof, wherein $Y^3$ is oxygen, under almost solventless conditions.

The polar organic solvent co-reagent and isolation solvent employed in the above method of making a compound or derivative having formula (V), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (V), or a salt, solvate, or prodrug thereof, wherein $Y^3$ is oxygen, can include the steps of:

(a) providing a compound or derivative having formula (TV-H), or a salt, solvate, or prodrug thereof, wherein $R^6$, $R^7$, and $R^8$ are each hydrogen;

(b) treating the compound or derivative having formula (TV-H), or salt, solvate, or prodrug thereof, wherein $R^6$, $R^7$, and $R^8$ are each hydrogen, with a phosphitylating reagent;

optionally, (b1) treating the compound or derivative having formula (TV-H), or salt, solvate, or prodrug thereof, wherein $R^6$, $R^7$, and $R^8$ are each hydrogen, and the phosphitylating reagent, with a (0<x≤20) molar equivalent amount of a Brønsted base;

(c) processing the compound or derivative having formula (TV-H), or salt, solvate, or prodrug thereof, wherein $R^6$, $R^7$, and $R^8$ are each hydrogen, the phosphitylating reagent, and, optionally, the Brønsted base so as to produce a compound or derivative having formula (V), or a salt, solvate, or prodrug thereof, wherein $Y^3$ is absent;

(d) adding an oxidizing agent reagent to, optionally, the compound or derivative having formula (IV-H), or salt, solvate, or prodrug thereof, wherein $R^6$, $R^7$, and $R^8$ are each hydrogen, optionally, the phosphitylating reagent, optionally, the Brønsted base, and the compound or derivative having formula (V), or salt, solvate, or prodrug thereof, wherein $Y^3$ is absent;

(e) processing the oxidizing agent reagent, optionally, the compound or derivative having formula (IV-H), or salt, solvate, or prodrug thereof, wherein $R^6$, $R^7$, and $R^8$ are each hydrogen, optionally, the phosphitylating reagent, optionally, the Brønsted base, and the compound or derivative having formula (V), or salt, solvate, or prodrug thereof, wherein $Y^3$ is absent, so as to produce the compound or derivative having formula (V), or salt, solvate, or prodrug thereof, wherein $Y^3$ is oxygen;

(f) adding, optionally, the oxidizing agent reagent, the compound or derivative having formula (IV-H), or salt, solvate, or prodrug thereof, optionally, the phosphitylating reagent, optionally, the Brønsted base, optionally, the compound or derivative having formula (V), or salt, solvate, or prodrug thereof, wherein $Y^3$ is absent, and the compound or derivative having formula (V), or salt, solvate, or prodrug thereof, wherein $Y^3$ is oxygen, to iced water;

optionally, (f1) adjusting the pH of the aqueous phase with an aqueous base;

(g) isolating the compound or derivative having formula (V), or salt, solvate, or prodrug thereof, wherein $Y^3$ is oxygen; and optionally, (g1) treating the compound or derivative having formula (V), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (V), or salt, solvate, or prodrug thereof, wherein $Y^3$ is oxygen, under almost solventless conditions.

The polar organic solvent co-reagent and isolation solvent in the above method of making a compound or derivative having formula (V), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (V), or a salt, solvate, or prodrug thereof, wherein $Y^3$ is absent, can include the steps of:

(a) providing a compound or derivative having formula (TV-H), or a salt, solvate, or prodrug thereof, wherein $R^6$, $R^7$, and $R^8$ are each hydrogen;

(b) treating the compound or derivative having formula (TV-H), or salt, solvate, or prodrug thereof, wherein $R^6$, $R^7$, and $R^8$ are each hydrogen, with a phosphitylating reagent;

optionally, (b1) treating the compound or derivative having formula (TV-H), or salt, solvate, or prodrug thereof, and the phosphitylating reagent, with a (0<x≤20) molar equivalent amount of a Brønsted base;

(c) processing the compound or derivative having formula (TV-H), or salt, solvate, or prodrug thereof, wherein $R^6$, $R^7$, and $R^8$ are each hydrogen, the phosphitylating reagent, and, optionally, the Brønsted base so as to produce the compound or derivative having formula (V), or salt, solvate, or prodrug thereof, wherein $Y^3$ is absent;

(d) adding, optionally, the compound or derivative having formula (IV-H), or salt, solvate, or prodrug thereof, wherein $R^6$, $R^7$, and $R^8$ are each hydrogen, optionally, the phosphitylating reagent, optionally, the Brønsted base, and the compound or derivative having formula (V), or salt, solvate, or prodrug thereof, wherein $Y^3$ is absent, to iced water;

optionally, (d1) adjusting the pH of the aqueous phase with an aqueous base;

optionally, (d2) isolating the unreacted compound or derivative having formula (IV-H), or salt, solvate, or prodrug thereof, wherein $R^6$, $R^7$, and $R^8$ are each hydrogen;

(e) isolating the compound or derivative having formula (V), or salt, solvate, or prodrug thereof, wherein $Y^3$ is absent; and optionally, (e1) treating the compound or derivative having formula (V), or salt, solvate, or prodrug thereof, wherein $Y^3$ is absent, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (V), or salt, solvate, or prodrug thereof, wherein $Y^3$ is absent, under almost solventless conditions.

The polar organic solvent co-reagent and isolation solvent in the above method of making a compound or derivative having formula (V), or salt, solvate, or prodrug thereof, wherein $Y^3$ is absent, can be a polar organic solvent from among, for example, preferably the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (V), or a salt, solvate, or prodrug thereof, wherein $Y^3$ is sulfur, can include the steps of:

(a) providing a compound or derivative having formula (TV-H), or a salt, solvate, or prodrug thereof, wherein $R^6$, $R^7$, and $R^8$ are each hydrogen;

(b) treating the compound or derivative having formula (TV-H), or salt, solvate, or prodrug thereof, wherein $R^6$, $R^7$, and $R^8$ are each hydrogen, with a phosphitylating reagent;

optionally, (b1) treating the compound or derivative having formula (TV-H), or salt, solvate, or prodrug thereof, wherein $R^6$, $R^7$, and $R^8$ are each hydrogen, and the phosphitylating reagent, with a (0<x≤20) molar equivalent amount of a Brønsted base;

(c) processing the compound or derivative having formula (TV-H), or salt, solvate, or prodrug thereof, wherein $R^6$, $R^7$, and $R^8$ are each hydrogen, the phosphitylating reagent, and, optionally, the Brønsted base so as to produce a compound or derivative having formula (V), or a salt, solvate, or prodrug thereof, wherein $Y^3$ is absent;

(d) adding an oxidizing agent reagent to, optionally, the compound or derivative having formula (IV-H), or salt, solvate, or prodrug thereof, wherein $R^6$, $R^7$, and $R^8$ are each hydrogen, optionally, the phosphitylating reagent, optionally, the Brønsted base, and the compound or derivative having formula (V), or salt, solvate, or prodrug thereof, wherein $Y^3$ is absent;

(e) processing the oxidizing agent reagent, optionally, the compound or derivative having formula (IV-H), or salt, solvate, or prodrug thereof, wherein $R^6$, $R^7$, and $R^8$ are each hydrogen, optionally, the phosphitylating reagent, optionally, the Brønsted base, and the compound or derivative having formula (V), or salt, solvate, or prodrug thereof, wherein $Y^3$ is absent, so as to produce the compound or derivative having formula (V), or salt, solvate, or prodrug thereof, wherein $Y^3$ is sulfur;

(f) adding, optionally, the oxidizing agent reagent, optionally, the compound or derivative having formula (TV-H), or salt, solvate, or prodrug thereof, wherein $R^6$, $R^7$, and $R^8$ are each hydrogen, optionally, the phosphitylating reagent, optionally, the Brønsted base, optionally, the compound or derivative having formula (V), or salt, solvate, or prodrug thereof, wherein $Y^3$ is absent, and the compound or derivative having formula (V), or salt, solvate, or prodrug thereof, wherein $Y^3$ is sulfur, to iced water;

optionally, (f1) adjusting the pH of the aqueous phase with an aqueous base;

(g) isolating the compound or derivative having formula (V), or salt, solvate, or prodrug thereof, wherein $Y^3$ is sulfur; and optionally, (g1) treating the compound or derivative having formula (V), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (V), or salt, solvate, or prodrug thereof, wherein $Y^3$ is sulfur, under almost solventless conditions.

The polar organic solvent co-reagent and isolation solvent in the above method of making a compound or derivative having formula (V), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (V), or a salt, solvate, or prodrug thereof, wherein $Y^3$ is sulfur, can include the steps of:

(a) providing a compound or derivative having formula (IV-H), or a salt, solvate, or prodrug thereof, wherein $R^6$, $R^7$, and $R^8$ are each hydrogen;

(b) treating the compound or derivative having formula (IV-H), or salt, solvate, or prodrug thereof, wherein $R^6$, $R^7$, and $R^8$ are each hydrogen, with a thiophosphorylating reagent;

optionally, (b1) treating the compound or derivative having formula (IV-H), or salt, solvate, or prodrug thereof, wherein $R^6$, $R^7$, and $R^8$ are each hydrogen, and the thiophosphorylating reagent, with a (0<x≤20) molar equivalent amount of a Brønsted base;

(c) processing the compound or derivative having formula (IV-H), or salt, solvate, or prodrug thereof, wherein $R^6$, $R^7$, and $R^8$ are each hydrogen, the thiophosphorylating reagent, and, optionally, the Brønsted base, so as to produce the compound or derivative having formula (V), or salt, solvate, or prodrug thereof, wherein $Y^3$ is sulfur;

(d) adding, optionally, the compound or derivative having formula (IV-H), or salt, solvate, or prodrug thereof, wherein $R^6$, $R^7$, and $R^8$ are each hydrogen, optionally, the thiophosphorylating reagent, optionally, the Brønsted base, and the compound or derivative having formula (V), or salt, solvate, or prodrug thereof, wherein $Y^3$ is sulfur, to iced water;

optionally, (d1) adjusting the pH of the aqueous phase with an aqueous base;

optionally, (d2) isolating the unreacted compound or derivative having formula (IV-H), or salt, solvate, or prodrug thereof, wherein $R^6$, $R^7$, and $R^8$ are each hydrogen;

(e) isolating the compound or derivative having formula (V), or salt, solvate, or prodrug thereof, wherein $Y^3$ is sulfur; and optionally, (e1) treating the compound or derivative having formula (V), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (V), or salt, solvate, or prodrug thereof, wherein $Y^3$ is sulfur, under almost solventless conditions.

The polar organic solvent co-reagent and isolation solvent employed in the above method of making a compound or derivative having formula (V), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (Va), or a salt, solvate, or prodrug thereof, wherein $Y^3$ is oxygen, can include the steps of:

(a) providing a compound or derivative having formula (IVc), or a salt, solvate, or prodrug thereof;

(b) treating the compound or derivative having formula (IVc), or salt, solvate, or prodrug thereof, with a phosphorylating reagent;

optionally, (b1) treating the compound or derivative having formula (IVc), or salt, solvate, or prodrug thereof, and the phosphorylating reagent, with a (0<x≤20) molar equivalent amount of a Brønsted base;

(c) processing the compound or derivative having formula (IVc), or salt, solvate, or prodrug thereof, the phosphorylating reagent, and optionally, the Brønsted base, so as to produce the compound or derivative having formula (Va), or salt, solvate, or prodrug thereof, wherein $Y^3$ is oxygen;

(d) adding, optionally, the compound or derivative having formula (IVc), or salt, solvate, or prodrug thereof, optionally, the phosphorylating reagent, optionally, the Brønsted base, and the compound or derivative having formula (Va), or salt, solvate, or prodrug thereof, wherein $Y^3$ is oxygen, to iced water;

optionally, (d1) adjusting the pH of the aqueous phase with an aqueous base;

optionally, (d2) isolating the unreacted compound or derivative having formula (IVc), or salt, solvate, or prodrug thereof;

(e) isolating the compound or derivative having formula (Va), or salt, solvate, or prodrug thereof, wherein $Y^3$ is oxygen; and optionally, (e1) treating the compound or derivative having formula (Va), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Va), or salt, solvate, or prodrug thereof, wherein $Y^3$ is oxygen, under almost solventless conditions.

The polar organic solvent co-reagent employed in the above method of making a compound or derivative having formula (Va), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (Va), or a salt, solvate, or prodrug thereof, wherein $Y^3$ is oxygen, can include the steps of:

(a) providing a compound or derivative having formula (IVc), or a salt, solvate, or prodrug thereof;

(b) treating the compound or derivative having formula (IVc), or salt, solvate, or prodrug thereof, with a phosphitylating reagent;

optionally, (b1) treating the compound or derivative having formula (IVc), or salt, solvate, or prodrug thereof, and the phosphitylating reagent, with a (0<x≤20) molar equivalent amount of a Brønsted base;

(c) processing the compound or derivative having formula (IVc), or salt, solvate, or prodrug thereof, the phosphitylating reagent, and, optionally, the Brønsted base so as to produce a compound or derivative having formula (Va), or a salt, solvate, or prodrug thereof, wherein $Y^3$ is absent;

(d) adding an oxidizing agent reagent to, optionally, the compound or derivative having formula (IVc), or salt, solvate, or prodrug thereof, optionally, the phosphitylating reagent, optionally, the Brønsted base, and the compound or derivative having formula (Va), or salt, solvate, or prodrug thereof, wherein $Y^3$ is absent;

(e) processing the oxidizing agent reagent, optionally, the compound or derivative having formula (IVc), or salt, solvate, or prodrug thereof, optionally, the phosphitylating reagent, optionally, the Brønsted base, and the compound or derivative having formula (Va), or salt, solvate, or prodrug thereof, wherein $Y^3$ is absent, so as to produce the compound or derivative having formula (Va), or salt, solvate, or prodrug thereof, wherein $Y^3$ is oxygen;

(f) adding, optionally, the oxidizing agent reagent, the compound or derivative having formula (IVc), or salt, solvate, or prodrug thereof, optionally, the phosphitylating reagent, optionally, the Brønsted base, optionally, the compound or derivative having formula (Va), or salt, solvate, or prodrug thereof, wherein $Y^3$ is absent, and the compound or derivative having formula (Va), or salt, solvate, or prodrug thereof, wherein $Y^3$ is oxygen, to iced water;

optionally, (f1) adjusting the pH of the aqueous phase with an aqueous base;

(g) isolating the compound or derivative having formula (Va), or salt, solvate, or prodrug thereof, wherein $Y^3$ is oxygen; and optionally, (g1) treating the compound or derivative having formula (Va), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Va), or salt, solvate, or prodrug thereof, wherein $Y^3$ is oxygen, under almost solventless conditions.

The polar organic solvent co-reagent and isolation solvent in the above method of making a compound or derivative having formula (Va), or salt, solvate, or prodrug thereof, wherein $Y^3$ is oxygen, can be a polar organic solvent from among, for example, preferably, the Class 2 Residual Solvents, listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (Va), or a salt, solvate, or prodrug thereof, wherein $Y^3$ is absent, can include the steps of:

(a) providing a compound or derivative having formula (IVc), or a salt, solvate, or prodrug thereof;

(b) treating the compound or derivative having formula (IVc), or salt, solvate, or prodrug thereof, with a phosphitylating reagent;

optionally, (b1) treating the compound or derivative having formula (IVc), or salt, solvate, or prodrug thereof, and the phosphitylating reagent, with a (0<x≤20) molar equivalent amount of a Brønsted base;

(c) processing the compound or derivative having formula (IVc), or salt, solvate, or prodrug thereof, the phosphitylating reagent, and, optionally, the Brønsted base so as to produce the compound or derivative having formula (Va), or salt, solvate, or prodrug thereof, wherein $Y^3$ is absent;

(d) adding, optionally, the compound or derivative having formula (IVc), or salt, solvate, or prodrug thereof, optionally, the phosphitylating reagent, optionally, the Brønsted base, and the compound or derivative having formula (Va), or salt, solvate, or prodrug thereof, wherein $Y^3$ is absent, to iced water;

optionally, (d1) adjusting the pH of the aqueous phase with an aqueous base;

optionally, (d2) isolating the unreacted compound or derivative having formula (IVc), or salt, solvate, or prodrug thereof;

(e) isolating the compound or derivative having formula (Va), or salt, solvate, or prodrug thereof, wherein $Y^3$ is absent; and optionally, (e1) treating the compound or derivative having formula (Va), or salt, solvate, or prodrug thereof, wherein $Y^3$ is absent, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Va), or salt, solvate, or prodrug thereof, wherein $Y^3$ is absent, under almost solventless conditions.

The polar organic solvent co-reagent and isolation solvent in the above method of making a compound or derivative having formula (Va), or salt, solvate, or prodrug thereof, wherein $Y^3$ is absent, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (Va), or a salt, solvate, or prodrug thereof, wherein $Y^3$ is sulfur, can include the steps of:

(a) providing a compound or derivative having formula (IVc), or a salt, solvate, or prodrug thereof;

(b) treating the compound or derivative having formula (IVc), or salt, solvate, or prodrug thereof, with a phosphitylating reagent;

optionally, (b1) treating the compound or derivative having formula (IVc), or salt, solvate, or prodrug thereof, and the phosphitylating reagent, with a (0<x≤20) molar equivalent amount of a Brønsted base;

(c) processing the compound or derivative having formula (IVc), or salt, solvate, or prodrug thereof, the phosphitylating reagent, and, optionally, the Brønsted base so as to produce a compound or derivative having formula (Va), or a salt, solvate, or prodrug thereof, wherein $Y^3$ is absent;

(d) adding an oxidizing agent reagent to, optionally, the compound or derivative having formula (IVc), or salt, solvate, or prodrug thereof, optionally, the phosphitylating reagent, optionally, the Brønsted base, and the compound or derivative having formula (Va), or salt, solvate, or prodrug thereof, wherein $Y^3$ is absent;

(e) processing the oxidizing agent reagent, optionally, the compound or derivative having formula (IVc), or salt, solvate, or prodrug thereof, optionally, the phosphitylating reagent, optionally, the Brønsted base, and the compound or derivative having formula (Va), or salt, solvate, or prodrug thereof, wherein $Y^3$ is absent, so as to produce the compound or derivative having formula (Va), or salt, solvate, or prodrug thereof, wherein $Y^3$ is sulfur;

(f) adding, optionally, the oxidizing agent reagent, optionally, the compound or derivative having formula (IVc), or salt, solvate, or prodrug thereof, optionally, the phosphitylating reagent, optionally, the Brønsted base, optionally, the compound or derivative having formula (Va), or salt, solvate, or prodrug thereof, wherein $Y^3$ is absent, and the compound or derivative having formula (Va), or salt, solvate, or prodrug thereof, wherein $Y^3$ is sulfur, to iced water;

optionally, (f1) adjusting the pH of the aqueous phase with an aqueous base;

(g) isolating the compound or derivative having formula (Va), or salt, solvate, or prodrug thereof, wherein $Y^3$ is sulfur; and optionally, (g1) treating the compound or derivative having formula (Va), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Va), or salt, solvate, or prodrug thereof, wherein $Y^3$ is absent, under almost solventless conditions.

The polar organic solvent co-reagent and isolation solvent in the above method of making a compound or derivative having formula (Va), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (Va), or a salt, solvate, or prodrug thereof, wherein $Y^3$ is sulfur, can include the steps of:

(a) providing a compound or derivative having formula (IVc), or a salt, solvate, or prodrug thereof;

(b) treating the compound or derivative having formula (IVc), or salt, solvate, or prodrug thereof, with a thiophosphorylating reagent;

optionally, (b1) treating the compound or derivative having formula (IVc), or salt, solvate, or prodrug thereof, and the thiophosphorylating reagent, with a (0<x≤20) molar equivalent amount of a Brønsted base;

(c) processing the compound or derivative having formula (IVc), or salt, solvate, or prodrug thereof, the thiophosphorylating reagent, and, optionally, the Brønsted base, so as to produce the compound or derivative having formula (Va), or salt, solvate, or prodrug thereof, wherein $Y^3$ is sulfur;

(d) adding, optionally, the compound or derivative having formula (IVc), or salt, solvate, or prodrug thereof, optionally, the thiophosphorylating reagent, optionally, the Brønsted base, and the compound or derivative having formula (Va), or salt, solvate, or prodrug thereof, wherein $Y^3$ is sulfur, to iced water;

optionally, (d1) adjusting the pH of the aqueous phase with an aqueous base;

optionally, (d2) isolating the unreacted compound or derivative having formula (IVc), or salt, solvate, or prodrug thereof;

(e) isolating the compound or derivative having formula (Va), or salt, solvate, or prodrug thereof, wherein $Y^3$ is sulfur; and optionally, (e1) treating the compound or derivative having formula (Va), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Va), or salt, solvate, or prodrug thereof, wherein $Y^3$ is sulfur, under almost solventless conditions.

The polar organic solvent co-reagent and isolation solvent employed in the above method of making a compound or derivative having formula (Va), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (Va), or a salt, solvate, or prodrug thereof, wherein $Y^3$ is oxygen, can include the steps of:

(a) providing a compound or derivative having formula (IVa-H), or a salt, solvate, or prodrug thereof, wherein $R^6$, $R^7$, and $R^8$ are each hydrogen;

(b) treating the compound or derivative having formula (IVa-H), or salt, solvate, or prodrug thereof, wherein $R^6$, $R^7$, and $R^8$ are each hydrogen, with a phosphorylating reagent;

optionally, (b1) treating the compound or derivative having formula (IVa-H), or salt, solvate, or prodrug thereof, wherein $R^6$, $R^7$, and $R^8$ are each hydrogen, and the phosphorylating reagent, with a (0<x≤20) molar equivalent amount of a Brønsted base;

(c) processing the compound or derivative having formula (IVa-H), or salt, solvate, or prodrug thereof, wherein $R^6$, $R^7$, and $R^8$ are each hydrogen, the phosphorylating reagent, and, optionally, the Brønsted base, so as to produce the compound or derivative having formula (Va), or salt, solvate, or prodrug thereof, wherein $Y^3$ is oxygen;

(d) adding, optionally, the compound or derivative having formula (IVa-H), or salt, solvate, or prodrug thereof, wherein $R^6$, $R^7$, and $R^8$ are each hydrogen, optionally, the phosphorylating reagent, optionally, the Brønsted base, and the compound or derivative having formula (Va), or salt, solvate, or prodrug thereof, wherein $Y^3$ is oxygen, to iced water;

optionally, (d1) adjusting the pH of the aqueous phase with an aqueous base;

optionally, (d2) isolating the unreacted compound or derivative having formula (IVa-H), or salt, solvate, or prodrug thereof, wherein $R^6$, $R^7$, and $R^8$ are each hydrogen;

(e) isolating the compound or derivative having formula (Va), or salt, solvate, or prodrug thereof, wherein $Y^3$ is oxygen; and optionally, (e1) treating the compound or derivative having formula (Va), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Va), or salt, solvate, or prodrug thereof, wherein $Y^3$ is oxygen, under almost solventless conditions.

The polar organic solvent co-reagent employed in the above method of making a compound or derivative having formula (Va), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (Va), or a salt, solvate, or prodrug thereof, wherein $Y^3$ is oxygen, can include the steps of:

(a) providing a compound or derivative having formula (IVa-H), or a salt, solvate, or prodrug thereof, wherein $R^6$, $R^7$, and $R^8$ are each hydrogen;

(b) treating the compound or derivative having formula (IVa-H), or salt, solvate, or prodrug thereof, wherein $R^6$, $R^7$, and $R^8$ are each hydrogen, with a phosphitylating reagent;

optionally, (b1) treating the compound or derivative having formula (IVa-H), or salt, solvate, or prodrug thereof, wherein $R^6$, $R^7$, and $R^8$ are each hydrogen, and the phosphitylating reagent, with a (0<x≤20) molar equivalent amount of a Brønsted base;

(c) processing the compound or derivative having formula (IVa-H), or salt, solvate, or prodrug thereof, wherein $R^6$, $R^7$, and $R^8$ are each hydrogen, the phosphitylating reagent, and, optionally, the Brønsted base so as to produce a compound or derivative having formula (Va), or a salt, solvate, or prodrug thereof, wherein $Y^3$ is absent;

(d) adding an oxidizing agent reagent to, optionally, the compound or derivative having formula (IVa-H), or salt, solvate, or prodrug thereof, wherein $R^6$, $R^7$, and $R^8$ are each hydrogen, optionally, the phosphitylating reagent, optionally, the Brønsted base, and the compound or derivative having formula (Va), or salt, solvate, or prodrug thereof, wherein $Y^3$ is absent;

(e) processing the oxidizing agent reagent, optionally, the compound or derivative having formula (IVa-H), or salt, solvate, or prodrug thereof, wherein $R^6$, $R^7$, and $R^8$ are each hydrogen, optionally, the phosphitylating reagent, optionally, the Brønsted base, and the compound or derivative having formula (Va), or salt, solvate, or prodrug thereof, wherein $Y^3$ is absent, so as to produce the compound or derivative having formula (Va), or salt, solvate, or prodrug thereof, wherein $Y^3$ is oxygen;

(f) adding, optionally, the oxidizing agent reagent, the compound or derivative having formula (IVa-H), or salt, solvate, or prodrug thereof, optionally, the phosphitylating reagent, optionally, the Brønsted base, optionally, the compound or derivative having formula (Va), or salt, solvate, or prodrug thereof, wherein $Y^3$ is absent, and the compound or derivative having formula (Va), or salt, solvate, or prodrug thereof, wherein $Y^3$ is oxygen, to iced water;

optionally, (f) adjusting the pH of the aqueous phase with an aqueous base;

(g) isolating the compound or derivative having formula (Va), or salt, solvate, or prodrug thereof, wherein $Y^3$ is oxygen; and optionally, (g1) treating the compound or derivative having formula (Va), or salt, solvate, or prodrug thereof, wherein $Y^3$ is oxygen, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Va), or salt, solvate, or prodrug thereof, wherein $Y^3$ is oxygen, under almost solventless conditions.

The polar organic solvent co-reagent and isolation solvent in the above method of making a compound or derivative having formula (Va), or salt, solvate, or prodrug thereof, wherein $Y^3$ is oxygen, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (Va), or a salt, solvate, or prodrug thereof, wherein $Y^3$ is absent, can include the steps of:

(a) providing a compound or derivative having formula (IVa-H), or a salt, solvate, or prodrug thereof, wherein $R^6$, $R^7$, and $R^8$ are each hydrogen;

(b) treating the compound or derivative having formula (IVa-H), or salt, solvate, or prodrug thereof, wherein $R^6$, $R^7$, and $R^8$ are each hydrogen, with a phosphitylating reagent;

optionally, (b1) treating the compound or derivative having formula (IVa-H), or salt, solvate, or prodrug thereof, wherein $R^6$, $R^7$, and $R^8$ are each hydrogen, and the phosphitylating reagent, with a (0<x≤20) molar equivalent amount of a Brønsted base;

(c) processing the compound or derivative having formula (IVa-H), or salt, solvate, or prodrug thereof, wherein $R^6$, $R^7$, and $R^8$ are each hydrogen, the phosphitylating reagent, and, optionally, the Brønsted base so as to produce the compound or derivative having formula (Va), or salt, solvate, or prodrug thereof, wherein $Y^3$ is absent;

(d) adding, optionally, the compound or derivative having formula (IVa-H), or salt, solvate, or prodrug thereof, wherein $R^6$, $R^7$, and $R^8$ are each hydrogen, optionally, the phosphitylating reagent, optionally, the Brønsted base, and the compound or derivative having formula (Va), or salt, solvate, or prodrug thereof, wherein $Y^3$ is absent, to iced water;

optionally, (d1) adjusting the pH of the aqueous phase with an aqueous base;

optionally, (d2) isolating the unreacted compound or derivative having formula (IVa-H), or salt, solvate, or prodrug thereof, wherein $R^6$, $R^7$, and $R^8$ are each hydrogen;

(e) isolating the compound or derivative having formula (Va), or salt, solvate, or prodrug thereof, wherein $Y^3$ is absent; and optionally, (e1) treating the compound or derivative having formula (Va), or salt, solvate, or prodrug thereof, wherein $Y^3$ is absent, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Va), or salt, solvate, or prodrug thereof, wherein $Y^3$ is absent, under almost solventless conditions.

The polar organic solvent co-reagent and isolation solvent in the above method of making a compound or derivative having formula (Va), or salt, solvate, or prodrug thereof, wherein $Y^3$ is absent, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (Va), or a salt, solvate, or prodrug thereof, wherein $Y^3$ is sulfur, can include the steps of:

(a) providing a compound or derivative having formula (IVa-H), or a salt, solvate, or prodrug thereof, wherein $R^6$, $R^7$, and $R^8$ are each hydrogen;

(b) treating the compound or derivative having formula (IVa-H), or salt, solvate, or prodrug thereof, wherein $R^6$, $R^7$, and $R^8$ are each hydrogen, with a phosphitylating reagent;

optionally, (b1) treating the compound or derivative having formula (IVa-H), or salt, solvate, or prodrug thereof, wherein $R^6$, $R^7$, and $R^8$ are each hydrogen, and the phosphitylating reagent, with a (0<x≤20) molar equivalent amount of a Brønsted base;

(c) processing the compound or derivative having formula (IVa-H), or salt, solvate, or prodrug thereof, wherein $R^6$, $R^7$, and $R^8$ are each hydrogen, the phosphitylating reagent, and, optionally, the Brønsted base so as to produce a compound or derivative having formula (Va), or a salt, solvate, or prodrug thereof, wherein $Y^3$ is absent;

(d) adding an oxidizing agent reagent to, optionally, the compound or derivative having formula (IVa-H), or salt, solvate, or prodrug thereof, wherein $R^6$, $R^7$, and $R^8$ are each hydrogen, optionally, the phosphitylating reagent, optionally, the Brønsted base, and the compound or derivative having formula (Va), or salt, solvate, or prodrug thereof, wherein $Y^3$ is absent;

(e) processing the oxidizing agent reagent, optionally, the compound or derivative having formula (IVa-H), or salt, solvate, or prodrug, wherein $R^6$, $R^7$, and $R^8$ are each hydrogen, optionally, the phosphitylating reagent, optionally, the Brønsted base, and the compound or derivative having formula (Va), or salt, solvate, or prodrug thereof, wherein $Y^3$ is absent, so as to produce the compound or derivative having formula (Va), or salt, solvate, or prodrug thereof, wherein $Y^3$ is sulfur;

(f) adding, optionally, the oxidizing agent reagent, the compound or derivative having formula (IVa-H), or salt, solvate, or prodrug thereof, wherein $R^6$, $R^7$, and $R^8$ are each hydrogen, optionally, the phosphitylating reagent, optionally, the Brønsted base, optionally, the compound or derivative having formula (Va), or salt, solvate, or prodrug thereof, wherein $Y^3$ is absent, and the compound or derivative having formula (Va), or salt, solvate, or prodrug thereof, wherein $Y^3$ is sulfur, to iced water;

optionally, (f1) adjusting the pH of the aqueous phase with an aqueous base;

(g) isolating the compound or derivative having formula (Va), or salt, solvate, or prodrug thereof, wherein $Y^3$ is sulfur; and optionally, (g1) treating the compound or derivative having formula (Va), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Va), or salt, solvate, or prodrug thereof, wherein $Y^3$ is sulfur, under almost solventless conditions.

The polar organic solvent co-reagent and isolation solvent in the above method of making a compound or derivative having formula (Va), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (Va), or a salt, solvate, or prodrug thereof, wherein $Y^3$ is sulfur, can include the steps of:

(a) providing a compound or derivative having formula (IVa-H), or a salt, solvate, or prodrug thereof, wherein $R^6$, $R^7$, and $R^8$ are each hydrogen;

(b) treating the compound or derivative having formula (IVa-H), or salt, solvate, or prodrug thereof, wherein $R^6$, $R^7$, and $R^8$ are each hydrogen, with a thiophosphorylating reagent;

optionally, (b1) treating the compound or derivative having formula (IVa-H), or salt, solvate, or prodrug thereof, wherein $R^6$, $R^7$, and $R^8$ are each hydrogen, and the thiophosphorylating reagent, with a ($0 < x \leq 20$) molar equivalent amount of a Brønsted base;

(c) processing the compound or derivative having formula (IVa-H), or salt, solvate, or prodrug thereof, wherein $R^6$, $R^7$, and $R^8$ are each hydrogen, the thiophosphorylating reagent, and, optionally, the Brønsted base, so as to produce the compound or derivative having formula (Va), or salt, solvate, or prodrug thereof, wherein $Y^3$ is sulfur;

(d) adding, optionally, the compound or derivative having formula (IVa-H), or salt, solvate, or prodrug thereof, wherein $R^6$, $R^7$, and $R^8$ are each hydrogen, optionally, the thiophosphorylating reagent, optionally, the Brønsted base, and the compound or derivative having formula (Va), or salt, solvate, or prodrug thereof, wherein $Y^3$ is sulfur, to iced water;

optionally, (d1) adjusting the pH of the aqueous phase with an aqueous base;

optionally, (d2) isolating the unreacted compound or derivative having formula (IVa-H), or salt, solvate, or prodrug thereof, wherein $R^6$, $R^7$, and $R^8$ are each hydrogen;

(e) isolating the compound or derivative having formula (Va), or salt, solvate, or prodrug thereof, wherein $Y^3$ is sulfur; and optionally, (e1) treating the compound or derivative having formula (Va), or salt, solvate, or prodrug thereof, wherein $Y^3$ is sulfur, with deprotection reagent(s) in a polar organic solvent co-reagent so as to remove any protecting groups of $R^7$, $R^8$, $Y^1$, and/or $Y^2$.

Processing can be carried out under batch processing conditions or by continuously processing. Continuously processing may include one or more methods of agitation selected from the group consisting of liquid-assisted grinding and extruding. Liquid-assisted grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (Va), or salt, solvate, or prodrug thereof, wherein $Y^3$ is sulfur, under almost solventless conditions.

The polar organic solvent co-reagent and isolation solvent employed in the above method of making a compound or derivative having formula (Va), or salt, solvate, or prodrug thereof, wherein $Y^3$ is sulfur, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (VI), or a salt, solvate, or prodrug thereof, can include the steps of:

(a) providing a compound or derivative having formula (V), or a salt, solvate, or prodrug thereof;

(b) treating the compound or derivative having formula (V), or salt, solvate, or prodrug thereof, with a compound or derivative having formula (3), or a salt thereof, and a ($1 < x \leq 10$) molar equivalent amount of a carbodiimide reagent, in the presence of water or an organic solvent co-reagent in an amount of up to 10 molar equivalents;

optionally, (b1) treating the compound or derivative having formula (V), or salt, solvate, or prodrug thereof, the compound or derivative having formula (3), or salt thereof, the carbodiimide reagent, and the water or organic solvent co-reagent, with at least a catalytic amount of a divalent metal salt;

(c) processing the compound or derivative having formula (V), or salt, solvate, or prodrug thereof, the compound or derivative having formula (3), or salt thereof, the carbodiimide reagent, the water or organic solvent co-reagent, and, optionally, the divalent metal salt, so as to produce the compound or derivative having formula (VI), or salt, solvate, or prodrug thereof;

(d) adding, optionally, the compound or derivative having formula (V), or salt, solvate, or prodrug thereof, optionally, the compound or derivative having formula (3), or salt thereof, optionally, the carbodiimide reagent, the water or organic solvent co-reagent, optionally, the divalent metal salt, and the compound or derivative having formula (VI), or salt, solvate, or prodrug thereof, to iced water;

optionally, (d1) adjusting the pH of the aqueous phase with an aqueous base;

optionally, (d2) isolating the unreacted compound or derivative having formula (V), or salt, solvate, or prodrug thereof;

optionally, (d3) isolating the unreacted compound or derivative having formula (3), or salt thereof;

(e) isolating the compound or derivative having formula (VI), or salt, solvate, or prodrug thereof; and optionally, (e1) treating the compound or derivative having formula (VI), or salt, solvate, or prodrug thereof, with deprotection reagent(s) in a polar organic solvent co-reagent so as to remove any protecting groups of, $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (VI), or salt, solvate, or prodrug thereof, under almost solventless conditions.

The polar organic solvent co-reagent employed in the above method of making a compound or derivative having formula (VI), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (VI), or a salt, solvate, or prodrug thereof, can include the steps of:

(a) providing a compound or derivative having formula (V), or a salt, solvate, or prodrug thereof;

(b) treating the compound or derivative having formula (V), or salt, solvate, or prodrug thereof, with a compound or derivative having formula (3), or a salt thereof, and a ($0<x\leq10$) molar equivalent amount of an amine, in the presence of water or an organic solvent co-reagent in an amount of up to 10 molar equivalents;

optionally, (b1) treating the compound or derivative having formula (V), or salt, solvate, or prodrug thereof, the compound or derivative having formula (3), or salt thereof, the amine, and the water or organic solvent co-reagent, with at least a catalytic amount of a divalent metal salt;

(c) processing the compound or derivative having formula (V), or salt, solvate, or prodrug thereof, the compound or derivative having formula (3), or salt thereof, the amine, the water or organic solvent co-reagent, and, optionally, the divalent metal salt, so as to produce the compound or derivative having formula (VI), or salt, solvate, or prodrug thereof;

(d) adding, optionally, the compound or derivative having formula (V), or salt, solvate, or prodrug thereof, optionally, the compound or derivative having formula (3), or salt thereof, optionally, the amine, the water or organic solvent co-reagent, optionally, the divalent metal salt, and the compound or derivative having formula (VI), or salt, solvate, or prodrug thereof, to iced water;

optionally, (d1) adjusting the pH of the aqueous phase with an aqueous base;

optionally, (d2) isolating the compound or derivative having formula (V), or salt, solvate, or prodrug thereof;

optionally, (d3) isolating the unreacted compound or derivative having formula (3), or salt thereof;

(e) isolating the compound or derivative having formula (VI), or salt, solvate, or prodrug thereof; and optionally, (e1) treating the compound or derivative having formula (VI), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (VI), or salt, solvate, or prodrug thereof, under almost solventless conditions.

The polar organic solvent co-reagent employed in the above method of making a compound or derivative having formula (VI), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (VI), or a salt, solvate, or prodrug thereof, can include the steps of:

(a) providing a compound or derivative having formula (V), or salt, solvate, or prodrug thereof;

(b) treating the compound or derivative having formula (V), or salt, solvate, or prodrug thereof, with a compound or derivative having formula (3), or a salt thereof, and a ($0<x\leq10$) molar equivalent amount of a Brønsted acid, in the presence of water or an organic solvent co-reagent in an amount of up to 10 molar equivalents;

optionally, (b1) treating the compound or derivative having formula (V), or salt, solvate, or prodrug thereof, the compound or derivative having formula (3), or salt thereof, the Brønsted acid, and the water or organic solvent co-reagent, with at least a catalytic amount of a divalent metal salt;

(c) processing the compound or derivative having formula (V), or salt, solvate, or prodrug thereof, the compound or derivative having formula (3), or salt thereof, the Brønsted acid, the water or organic solvent co-reagent, and, optionally, the divalent metal salt, so as to produce the compound or derivative having formula (VI), or salt, solvate, or prodrug thereof;

(d) adding, optionally, the compound or derivative having formula (V), or salt, solvate, or prodrug thereof, optionally, the compound or derivative having formula (3), or salt thereof, optionally, the Brønsted acid, the water or organic solvent co-reagent, optionally, the divalent metal salt, and the compound or derivative having formula (VI), or salt, solvate, or prodrug thereof, to iced water;

optionally, (d1) adjusting the pH of the aqueous phase with an aqueous base;

optionally, (d2) isolating the unreacted compound or derivative having formula (V), or salt, solvate, or prodrug thereof;

optionally, (d3) isolating the unreacted compound or derivative having formula (3), or salt thereof;

(e) isolating the compound or derivative having formula (VI), or salt, solvate, or prodrug thereof; and optionally, (e1) treating the compound or derivative having formula (VI), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (VI), or salt, solvate, or prodrug thereof, under almost solventless conditions.

The polar organic solvent co-reagent employed in the above method of making a compound or derivative having formula (VI), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In an embodiment, a method of making a compound or derivative having formula (VIa), or a salt, solvate, or prodrug thereof, can include the steps of:

(a) providing a compound or derivative having formula (Va), or a salt, solvate, or prodrug thereof;

(b) treating the compound or derivative having formula (Va), or salt, solvate, or prodrug thereof, with a compound or derivative having formula (3), or a salt thereof, and a ($1<x\leq10$) molar equivalent amount of a carbodiimide reagent, in the presence of water or an organic solvent co-reagent in an amount of up to 10 molar equivalents;

optionally, (b1) treating the compound or derivative having formula (Va), or salt, solvate, or prodrug thereof, the compound or derivative having formula (3), or salt thereof, the carbodiimide reagent, and the water or organic solvent co-reagent, with at least a catalytic amount of a divalent metal salt;

(c) processing the compound or derivative having formula (Va), or salt, solvate, or prodrug thereof, the compound or derivative having formula (3), or salt thereof, the carbodiimide reagent, the water or organic solvent co-reagent, and, optionally, the divalent metal salt, so as to produce the compound or derivative having formula (VIa), or salt, solvate, or prodrug thereof;

(d) adding, optionally, the compound or derivative having formula (Va), or salt, solvate, or prodrug thereof, optionally, the compound or derivative having formula (3), or salt thereof, optionally, the carbodiimide reagent, the water or organic solvent co-reagent, optionally, the divalent metal salt, and the compound or derivative having formula (VIa), or salt, solvate, or prodrug thereof, to iced water;

optionally, (d1) adjusting the pH of the aqueous phase with an aqueous base;

optionally, (d2) isolating the unreacted compound or derivative having formula (Va), or salt, solvate, or prodrug thereof;

optionally, (d3) isolating the unreacted compound or derivative having formula (3), or salt thereof;

(e) isolating the compound or derivative having formula (VIa), or salt, solvate, or prodrug thereof; and optionally, (e1) treating the compound or derivative having formula (VIa), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (VIa), or salt, solvate, or prodrug thereof, under almost solventless conditions.

The polar organic solvent co-reagent employed in the above method of making a compound or derivative having formula (VIa), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In another embodiment, a method of making a compound or derivative having formula (VIa), or a salt, solvate, or prodrug thereof, can include the steps of:

(a) providing a compound or derivative having formula (Va), or a salt, solvate, or prodrug thereof;

(b) treating the compound or derivative having formula (Va), or salt, solvate, or prodrug thereof, with a compound or derivative having formula (3), or a salt thereof, and a ($0<x\leq10$) molar equivalent amount of an amine, in the presence of water or an organic solvent co-reagent in an amount of up to 10 molar equivalents;

optionally, (b1) treating the compound or derivative having formula (Va), or salt, solvate, or prodrug thereof, the compound or derivative having formula (3), or salt thereof, the amine, and the water or organic solvent co-reagent, with at least a catalytic amount of a divalent metal salt;

(c) processing the compound or derivative having formula (Va), or salt, solvate, or prodrug thereof, the compound or derivative having formula (3), or salt thereof, the amine, the water or organic solvent co-reagent, and, optionally, the divalent metal salt, so as to produce the compound or derivative having formula (VIa), or salt, solvate, or prodrug thereof;

(d) adding, optionally, the compound or derivative having formula (Va), or salt, solvate, or prodrug thereof, optionally, the compound or derivative having formula (3), or salt thereof, optionally, the amine, the water or organic solvent co-reagent, optionally, the divalent metal salt, and the compound or derivative having formula (VIa), or salt, solvate, or prodrug thereof, to iced water;

optionally, (d1) adjusting the pH of the aqueous phase with an aqueous base;

optionally, (d2) isolating the unreacted compound or derivative having formula (Va), or salt, solvate, or prodrug thereof;

optionally, (d3) isolating the unreacted compound or derivative having formula (3), or salt thereof;

(e) isolating the compound or derivative having formula (VIa), or salt, solvate, or prodrug thereof, and optionally, (e1) treating the compound or derivative having formula (VIa), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (VIa), or salt, solvate, or prodrug thereof, under almost solventless conditions.

The polar organic solvent co-reagent employed in the above method of making a compound or derivative having formula (VIa), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

In yet another embodiment, a method of making a compound or derivative having formula (VIa), or a salt, solvate, or prodrug thereof, can include the steps of:

(a) providing a compound or derivative having formula (Va), or a salt, solvate, or prodrug thereof, (b) treating the compound or derivative having formula (Va), or salt, solvate, or prodrug thereof, with a compound or derivative having formula (3), or a salt thereof, and a (0<x≤10) molar equivalent amount of a Brønsted acid, in the presence of water or an organic solvent co-reagent in an amount of up to 10 molar equivalents;

optionally, (b1) treating the compound or derivative having formula (Va), or salt, solvate, or prodrug thereof, the compound or derivative having formula (3), or salt thereof, the Brønsted acid, and the water or organic solvent co-reagent, with at least a catalytic amount of a divalent metal salt;

(c) processing the compound or derivative having formula (Va), or salt, solvate, or prodrug thereof, the compound or derivative having formula (3), or salt thereof, the Brønsted acid, the water or organic solvent co-reagent, and, optionally, the divalent metal salt, so as to produce the compound or derivative having formula (VIa), or salt, solvate, or prodrug thereof;

(d) adding, optionally, the compound or derivative having formula (Va), or salt, solvate, or prodrug thereof, optionally, the compound or derivative having formula (3), or salt thereof, optionally, the Brønsted acid, the water or organic solvent co-reagent, optionally, the divalent metal salt, a the compound or derivative having formula (VIa), or salt, solvate, or prodrug thereof, the polar organic solvent co-reagent, and, optionally, the additional additives, to iced water;

optionally, (d1) adjusting the pH of the aqueous phase with an aqueous base;

optionally, (d2) isolating the unreacted compound or derivative having formula (Va), or salt, solvate, or prodrug thereof;

optionally, (d3) isolating the unreacted compound or derivative having formula (3), or salt thereof;

(e) isolating the compound or derivative having formula (VIa), or salt, solvate, or prodrug thereof, and optionally, (e1) treating the compound or derivative having formula (VIa), or salt, solvate, or prodrug thereof, with deprotection reagent(s) in a polar organic solvent co-reagent so as to remove any protecting groups of $R^7$, $R^8$, $R^9$, $R^{10}$, $Y^1$, and/or $W^1$.

Processing can be carried out under batch processing conditions or by continuously processing. Continuously processing may include one or more methods of agitation selected from the group consisting of continuous grinding and extruding. Continuous grinding may be performed between about 50 RPM and about 200 RPM, preferably between about 75 RPM and about 150 RPM, and most preferably between about 100 RPM and about 130 RPM.

The process described herein effects a preparation of a compound or derivative having formula (VIa), or salt, solvate, or prodrug thereof, under almost solventless conditions.

The polar organic solvent co-reagent employed in the above method of making a compound or derivative having formula (VIa), or salt, solvate, or prodrug thereof, can be a polar organic solvent from among, for example, preferably, the Class 2 Residual Solvents listed in Table 2, or optionally, for non-human use, the Class 3 Residual Solvents listed in Table 3 in THE NATIONAL FORMULARY, UNITED STATES PHARMACOPEIA 30 <467> (U.S. PHARMACOPEIAL CONVENTION 2006) (USP 30 at <467>), incorporated by reference herein in its entirety.

It is understood that the pH can be adjusted to the isoelectric point of the product compound(s) or derivative(s), or near neutral pH. Precipitation of the product compound(s) or derivative(s) can be carried out using an appropriate water miscible, or other generally non-toxic, solvent.

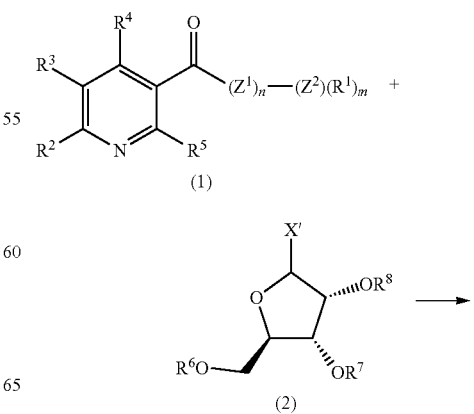

Scheme A

-continued

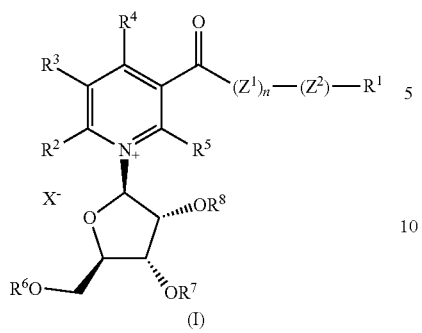
(I)

An embodiment of the chemoselective, and optionally stereoselective, synthesis of a compound or derivative having formula (I), or a salt, solvate, or prodrug thereof, optionally in a particular anomeric ratio (alpha/beta), is shown above in Scheme A.

Scheme B

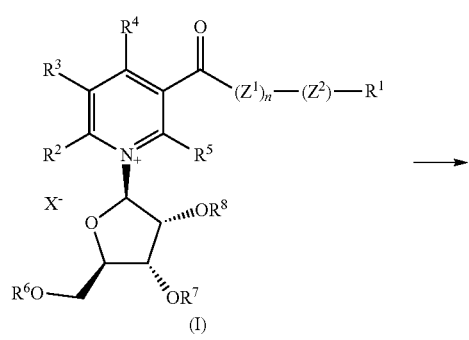
(I)

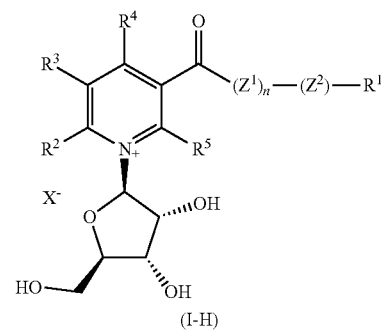
(I-H)

An embodiment of the chemoselective synthesis of a compound or derivative having formula (I-H), or a salt, solvate, or prodrug thereof, is shown above in Scheme B.

Scheme C

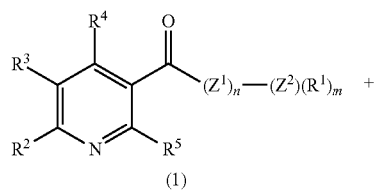
(1)

-continued

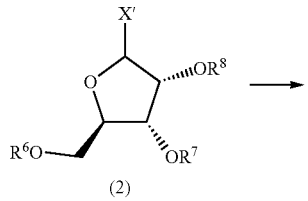
(2)

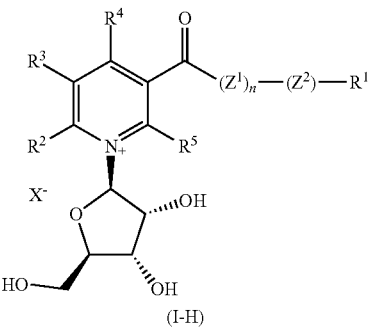
(I-H)

An alternative embodiment of the chemoselective synthesis of a compound or derivative having formula (I-H), or a salt, solvate, or prodrug thereof, is shown above in Scheme C.

Scheme D

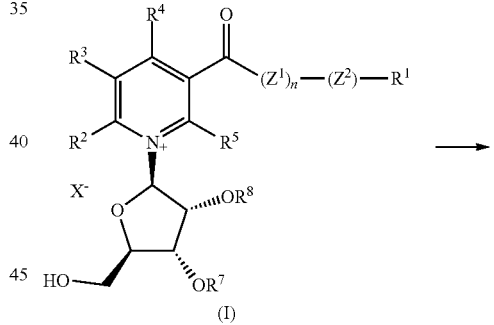
(I)

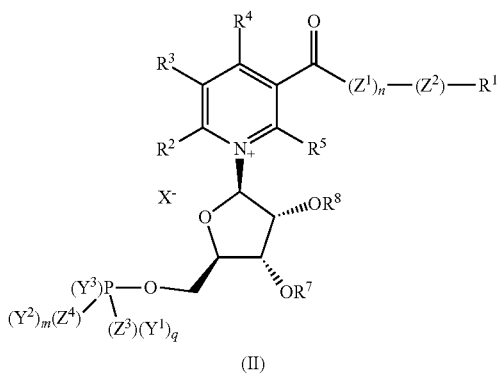
(II)

An embodiment of the chemoselective synthesis of a compound or derivative having formula (II), or a salt, solvate, or prodrug thereof, is shown above in Scheme D.
Scheme E
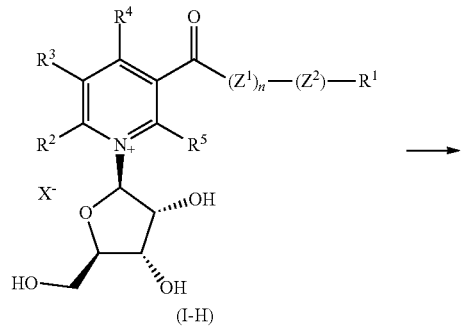
(I-H)
Scheme F
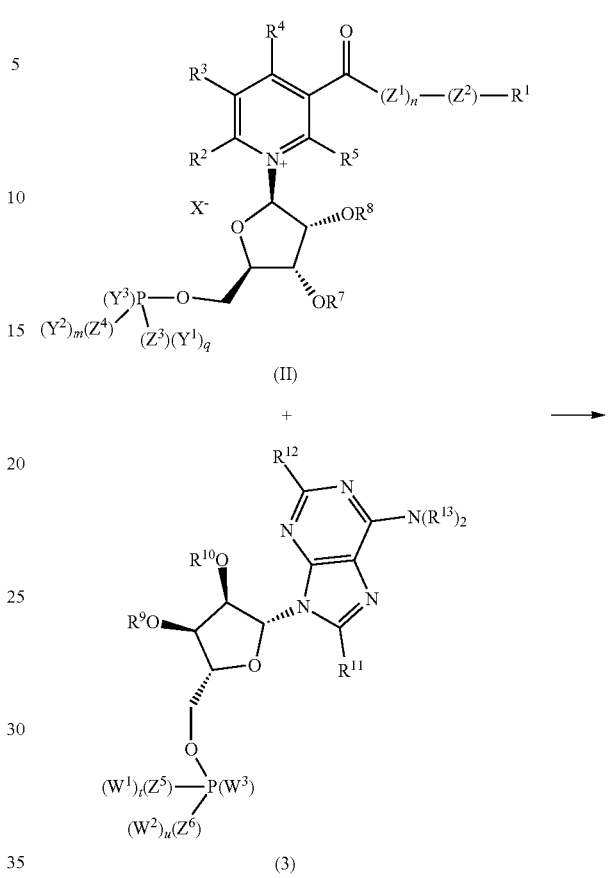
An alternative embodiment of the chemoselective synthesis of a compound or derivative having formula (II), or a salt, solvate, or prodrug thereof, is shown above in Scheme E.
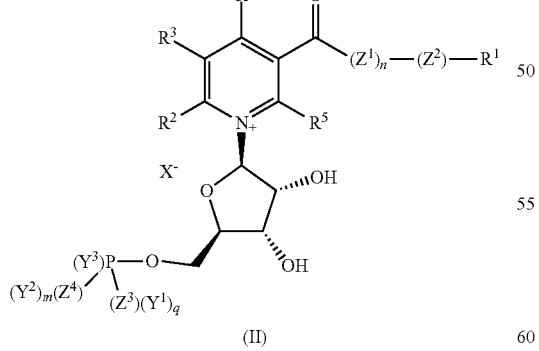
(II)
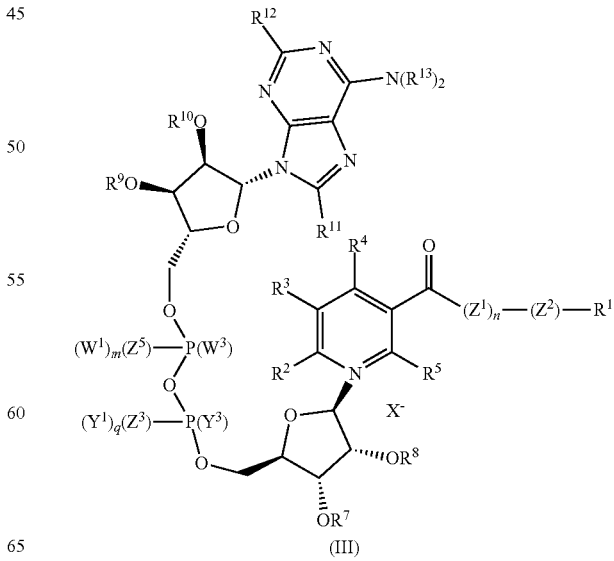
(III)

An embodiment of the chemoselective synthesis of a compound or derivative having formula (III), or a salt, solvate, or prodrug thereof, is shown above in Scheme F.

An embodiment of the chemoselective synthesis of a compound or derivative having formula (IV-H), or a salt, solvate, or prodrug thereof, is shown above in Scheme H.

Scheme G

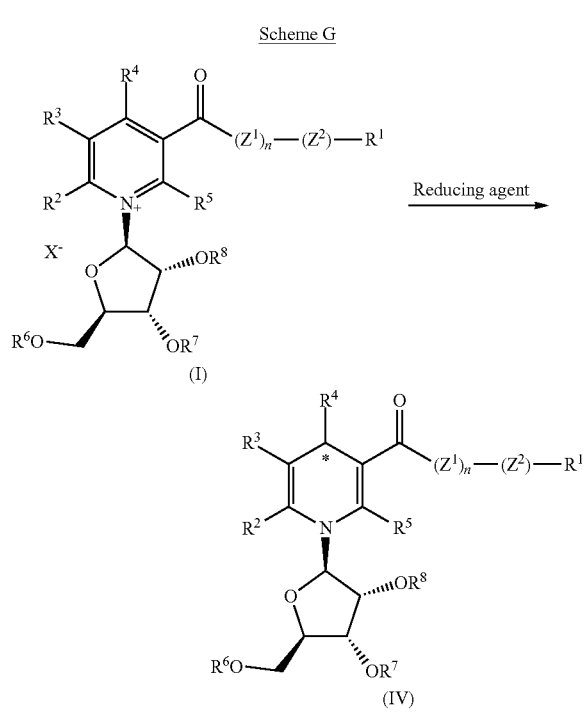

An embodiment of the chemoselective, and optionally stereoselective, synthesis of a compound or derivative having formula (IV), or a salt, solvate, or prodrug thereof, is shown above in Scheme G.

Scheme H

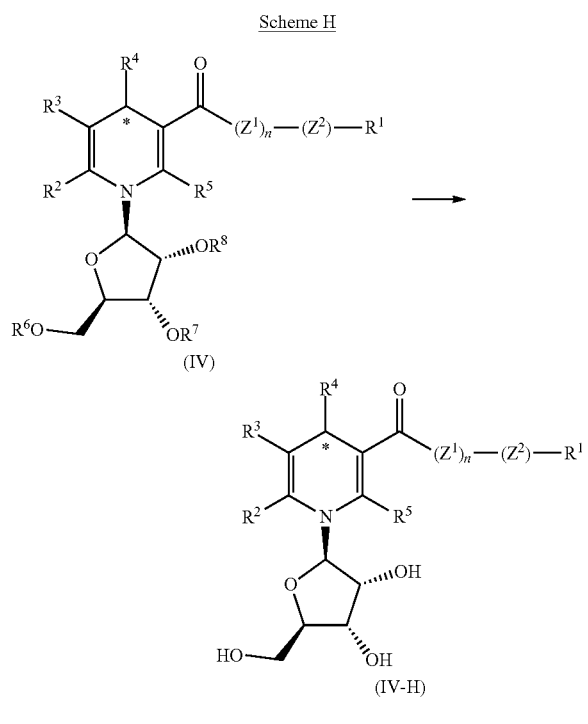

Scheme I

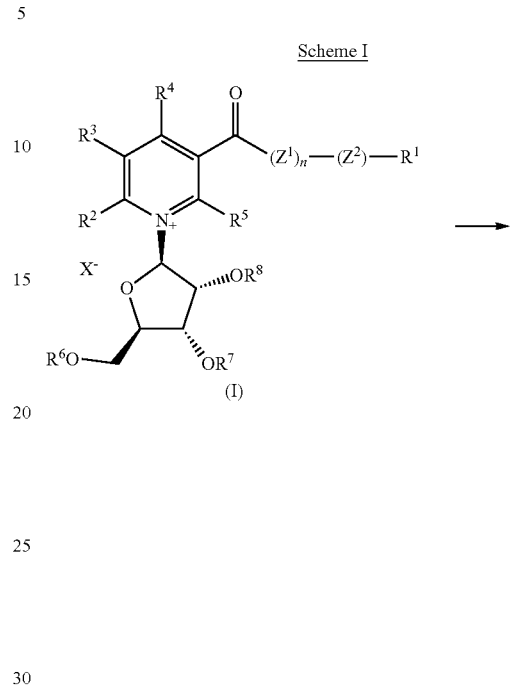

An alternative embodiment of the chemoselective synthesis of a compound or derivative having formula (IV-H), or a salt, solvate, or prodrug thereof, is shown above in Scheme I.

Scheme J

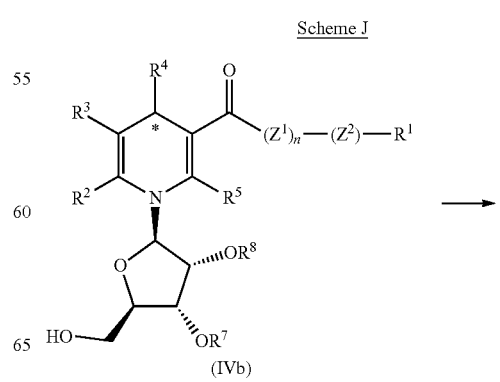

-continued

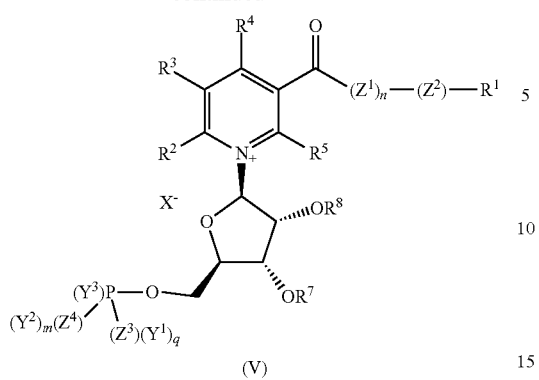

(V)

An embodiment of the chemoselective synthesis of a compound or derivative having formula (V), or a salt, solvate, or prodrug thereof, is shown above in Scheme J.

Scheme K

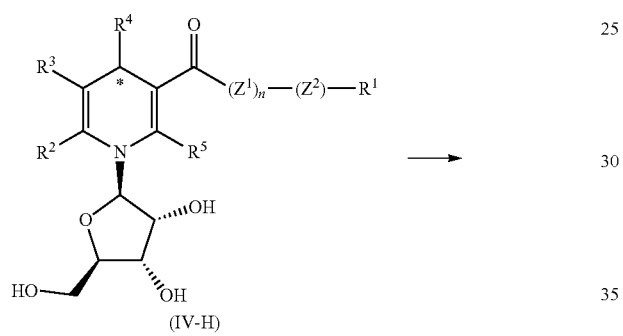

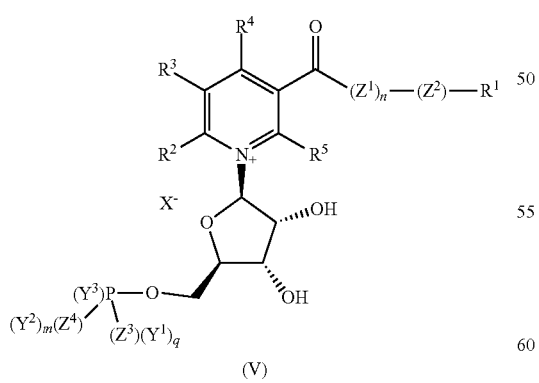

(V)

An alternative embodiment of the chemoselective synthesis of a compound or derivative having formula (V), or a salt, solvate, or prodrug thereof, is shown above in Scheme K.

Scheme L

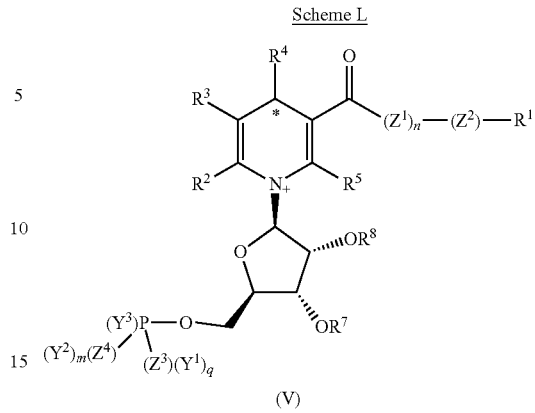

(V)

+

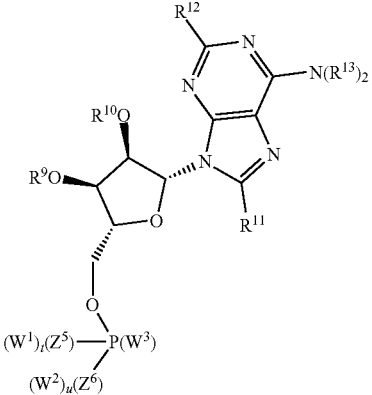

(3)

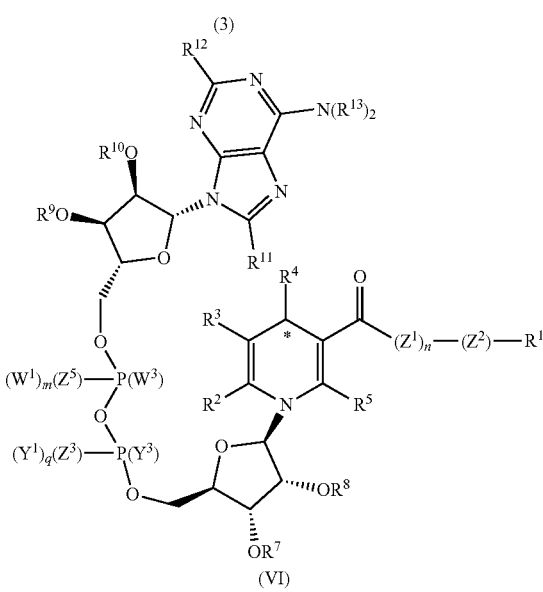

(VI)

An embodiment of the chemoselective synthesis of a compound or derivative having formula (VI), or a salt, solvate, or prodrug thereof, is shown above in Scheme L.

In the embodiments shown above in Schemes A-L:
optionally wherein $X^-$ as counterion is absent, or when $X^-$ is present, $X^-$ is selected from the group consisting of fluoride, chloride, bromide, iodide, formate, acetate, propionate, butyrate, glutamate, aspartate, ascorbate, benzoate, carbonate, citrate, carbamate, gluconate, lactate, methyl bromide, methyl sulfate, nitrate, phosphate, diphosphate, succinate, sulfonate, trifluoromethanesulfonate, trichloromethanesulfonate, tribromomethanesulfonate, and trifluoroacetate;

optionally wherein when $X^-$ is absent, optionally the counterion is an internal salt;

optionally $X^-$ is an anion of a substituted or unsubstituted carboxylic acid selected from a monocarboxylic acid, a dicarboxylic acid, or a polycarboxylic acid; and, optionally $X^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid, the anion of lactic acid being lactate), or a trihaloacetate selected from trichloroacetate, tribromoacetate, and trifluoroacetate; and, optionally $X^-$ is an anion of an unsubstituted monocarboxylic acid selected from formic acid, acetic acid, propionic acid, or butyric acid, being formate, acetate, propionate, and butyrate, respectively; and, optionally $X^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally $X^-$ is an anion of a substituted or unsubstituted carbonate, further optionally hydrogen carbonate; and, optionally $X^-$ is an anion of a substituted or unsubstituted glutathione or glutathione disulfide;

wherein the substituted carboxylic acid, substituted monocarboxylic acid, substituted propanoic acid, substituted acetic acid, substituted amino acid, substituted sulfonate, substituted carbonate, substituted glutathione, and substituted glutathione disulfide are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)N$R^C_2$—C(=N$R^C$)N$R^C_2$, —O$R^C$, —OC(O)$(C_1-C_6)$alkyl, —OC(O)O$(C_1-C_6)$alkyl, —OC(O)N$R^C_2$, —$(C_1-C_6)$alkylene-N$R^C_2$, —N$R^C_2$, —N$R^C$C(O)$R^C$, —N$R^C$C(O)O$(C_1-C_6)$alkyl, —N$R^C$C(O)N$R^C_2$—N$R^C$SO$_2$N$R^C_2$, —S$R^C$, —S(O)$R^C$, —SO$_2$$R^C$, —OSO$_2$$(C_1-C_6)$alkyl, —SO$_2$N$R^C_2$, —$(C_1-C_6)$perfluoroalkyl, and —$(C_1-C_6)$alkylene-O$R^C$;

wherein X' is selected from the group consisting of fluoro, chloro, bromo, iodo, $HCO_2$, acetoxy, propionoxy, butyroxy, glutamyloxy, aspartyloxy, ascorbyloxy, benzoxy, $HOCO_2$, citryloxy, carbamyloxy, gluconyloxy, lactyloxy, methyl bromo, methyl sulfoxy, nitrate, phosphate, diphosphate, succinyloxy, sulfoxy, trifluoromethanesulfoxy, trichloromethanesulfoxy, tribromomethanesulfoxy, and trifluoroacetoxy;

each $Y^1$ and $Y^2$ is independently selected from the group consisting of hydrogen, sodium, potassium, lithium, substituted or unsubstituted $(C_1-C_8)$alkyl, substituted or unsubstituted $(C_1-C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—CO$_2$$R^C$, —N($R^A$)—CO$_2$$R^B$, —CH—($R^A$)—NH$_2$, and —CH—($R^A$)—CO$_2$$R^B$; wherein the substituted $(C_1-C_8)$alkyl, substituted $(C_1-C_8)$cycloalkyl, substituted aryl, substituted heteroaryl, substituted heterocycle, and substituted amino are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1-C_6)$alkyl, —OC(O)O$(C_1-C_6)$alkyl, —OC(O)N$R^C_2$, —$(C_1-C_6)$alkylene-N$R^C_2$, —N$R^C_2$, —N$R^C$C(O)$R^C$, —N$R^C$C(O)O$(C_1-C_6)$alkyl, —N$R^C$C(O)N$R^C_2$—N$R^C$SO$_2$N$R^C_2$, —S$R^C$, —S(O)$R^C$, —SO$_2$$R^C$, —OSO$_2$$(C_1-C_6)$alkyl, —SO$_2$N$R^C_2$, —$(C_1-C_6)$perfluoroalkyl, and —$(C_1-C_6)$alkylene-O$R^C$;

or, alternatively, $Y^1$ and $Y^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1-C_6)$alkyl, —OC(O)O$(C_1-C_6)$alkyl, —OC(O)N$R^C_2$, —$(C_1-C_6)$alkylene-N$R^C_2$, —N$R^C_2$, —N$R^C$C(O)$R^C$, —N$R^C$C(O)O$(C_1-C_6)$alkyl, —N$R^C$C(O)N$R^C_2$, —N$R^C$SO$_2$N$R^C_2$, —S$R^C$, —S(O)$R^C$, —SO$_2$$R^C$, —OSO$_2$$(C_1-C_6)$alkyl, —SO$_2$N$R^C_2$, —$(C_1-C_6)$perfluoroalkyl, and —$(C_1-C_6)$alkylene-O$R^C$;

each $W^1$ and $W^2$ is independently selected from the group consisting of hydrogen, sodium, potassium, lithium, substituted or unsubstituted $(C_1-C_8)$alkyl, substituted or unsubstituted $(C_1-C_8)$cycloalkyl, substituted or unsubstituted aryl, substituted or unsubstituted heteroaryl, substituted or unsubstituted heterocycle, substituted or unsubstituted amino, thiamine (vitamin B1), riboflavin (vitamin B2), niacin (vitamin B3), pyridoxine (vitamin B6), —N($R^A$)—CO$_2$$R^C$, —N($R^A$)—CO$_2$$R^B$, —CH—($R^A$)—NH$_2$, and —CH—($R^A$)—CO$_2$$R^B$; wherein the substituted $(C_1-C_8)$alkyl, substituted $(C_1-C_8)$cycloalkyl, substituted aryl, substituted heteroaryl, substituted heterocycle, and substituted amino are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)N$R^C_2$, —C(=N$R^C$)N$R^C$, —O$R^C$, —OC(O)$(C_1-C_6)$alkyl, —OC(O)O$(C_1-C_6)$alkyl, —OC(O)N$R^C_2$, —$(C_1-C_6)$alkylene-N$R^C_2$, —N$R^C_2$, —N$R^C$C(O)$R^C$, —N$R^C$C(O)O$(C_1-C_6)$alkyl, —N$R^C$C(O)N$R^C_2$, —N$R^C$SO$_2$N$R^C_2$, —S$R^C$, —S(O)$R^C$, —SO$_2$$R^C$, —OSO$_2$$(C_1-C_6)$alkyl, —SO$_2$N$R^C_2$, —$(C_1-C_6)$perfluoroalkyl, and —$(C_1-C_6)$alkylene-O$R^C$;

or, alternatively, $W^1$ and $W^2$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)$(C_1-C_6)$alkyl, —OC(O)O$(C_1-C_6)$alkyl, —OC(O)N$R^C_2$, —$(C_1-C_6)$alkylene-N$R^C_2$, —N$R^C_2$, —N$R^C$C(O)$R^C$, —N$R^C$C(O)O$(C_1-C_6)$alkyl, —N$R^C$C(O)N$R^C_2$, —N$R^C$SO$_2$N$R^C_2$, —S$R^C$, —S(O)$R^C$, —SO$_2$$R^C$, —OSO$_2$$(C_1-C_6)$alkyl, —SO$_2$N$R^C_2$, —$(C_1-C_6)$perfluoroalkyl, and —$(C_1-C_6)$alkylene-O$R^C$;

or, alternatively, $Y^1$ and $W^1$ taken together are selected from the group consisting of sodium, potassium, lithium, magnesium, calcium, strontium, barium, and substituted or unsubstituted 2-(methylenyl)phenyl; wherein the substituted 2-(methylenyl)phenyl is substituted with one to four substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

optionally wherein $Y^3$ is oxygen, sulfur, or absent;
optionally wherein $W^3$ is oxygen, sulfur, or absent;
each of $Z^1$ and $Z^2$ is independently NH or oxygen;
each of $Z^3$, $Z^4$, $Z^5$, and $Z^6$ is independently nitrogen or oxygen;
m is 1 or 2;
n is 0 or 1;
q is 1 or 2;
t is 1 or 2;
u is 1 or 2;

each $R^1$ is independently selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, pterostilbene ester, resveratrol ester, aryl($C_1$-$C_4$)alkyl, TMS, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

wherein when $R^1$ is hydrogen, $Z^2$ is oxygen, m is 1, and n is 0, the compound or derivative may optionally take the form of the carboxylate anion conjugate base species of the compound or derivative, further optionally associated with a positively charged counterion selected from the group consisting of alkali metal, alkaline earth metal, transition metal, and base addition cations;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, —$NH_2$, and —$CH_2$—$CH_3$;

each $R^B$ is independently hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of a compound or derivative having formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B_2$, —C(=$NR^B$)$NR^B_2$, —O$R^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$R^B_2$, —$NR^B$C(O)$R^B$, —$NR^B$C(O)O($C_1$-$C_6$)alkyl, —$NR^B$C(O)$NR^B_2$, —$NR^B$$SO_2$$NR^B_2$, —$SR^B$, —S(O)$R^B$, —$SO_2R^B$, —$OSO_2$($C_1$-$C_6$)alkyl, —$SO_2NR^B_2$, —($C_1$-$C_6$)perfluoroalkyl, and —($C_1$-$C_6$)alkylene-O$R^B$;

$R^2$ and $R^3$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

$R^4$ is selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

wherein C* has an absolute configuration of R or S, or a mixture of R and S;

$R^5$ is selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

$R^6$ is selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, glutathione ester, glutathione disulfide ester, aryl($C_1$-$C_4$)alkyl, heterocycle($C_1$-$C_4$)alkyl, —N($R^A$)—$CO_2R^C$, —N($R^A$)—$CO_2R^B$, —CH—($R^A$)—$NH_2$, and —CH—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C_2$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-

$C_4$)alkyl, —N(R$^A$)—CO$_2$R$^C$, —N(R$^A$)—CO$_2$R$^B$, —CH—(R$^A$)—NH$_2$, and —CH—(R$^A$)—CO$_2$R$^B$; wherein the substituted (C$_1$-C$_8$)alkyl, substituted (C$_1$-C$_8$) cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$—C(=NR$^C$)NR$^C_2$, —OR$^C$, —OC(O)(C$_1$-C$_6$)alkyl, —OC(O)O(C$_1$-C$_6$) alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^9$ and R$^{10}$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$) perfluoroalkyl, and —(C$_1$-C$_6$)alkylene-OR$^C$;

R$^{11}$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$) cycloalkyl, substituted or unsubstituted aryl, substituted or unsubstituted heteroaryl, substituted or unsubstituted heterocycle, substituted or unsubstituted aryl(C$_1$-C$_4$)alkyl, substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^{12}$ is selected from the group consisting of hydrogen, —C(O)R', —C(O)OR', —C(O)NHR', substituted or unsubstituted (C$_1$-C$_8$)alkyl, substituted or unsubstituted (C$_1$-C$_8$) cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$) cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$) alkynyl, halogen, —CN, —NO$_2$, —C(O)R$^C$, —C(O)OR$^C$, —C(O)NR$^C_2$, —C(=NR$^C$)NR$^C$, —OR$^C$, —OC(O)(C$_1$-C$_6$) alkyl, —OC(O)O(C$_1$-C$_6$)alkyl, —OC(O)NR$^C_2$, —(C$_1$-C$_6$) alkylene-NR$^C_2$, —NR$^C_2$, —NR$^C$C(O)R$^C$, —NR$^C$C(O)O (C$_1$-C$_6$)alkyl, —NR$^C$C(O)NR$^C_2$, —NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

each R$^{13}$ is independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$—NR$^C$SO$_2$NR$^C_2$, —SR$^C$, —S(O)R$^C$, —SO$_2$R$^C$, —OSO$_2$(C$_1$-C$_6$)alkyl, —SO$_2$NR$^C_2$, —(C$_1$-C$_6$) perfluoroalkyl, and —(C$_1$-C$_6$)alkylene-OR$^C$;

provided that the absolute configuration of C** is R or S, or a mixture of R and S.

As discussed above, the existing prior art approaches, for the most part, utilize solvent-mediated approaches to prepare the nicotinoyl ribosides and reduced nicotinoyl ribosides, modified derivatives thereof, phosphorylated analogs thereof, and adenylyl dinucleotide conjugates thereof. Such processes are cumbersome, inefficient, and not scalable.

As used herein, the terms "trimethylsilylating agent(s)" or "trimethylsilylating reagent(s)," alone or in combination with other terms, refer to compounds that include one or more tetravalent silicon atoms each covalently bonded to three methyl groups (i.e., trimethylsilyl ("TMS") group) and, upon reaction with organic compounds containing an oxygen-hydrogen or nitrogen-hydrogen covalent bond, yield an organic compound wherein the hydrogen of the oxygen-hydrogen or nitrogen-hydrogen covalent bond has been replaced with the trimethylsilyl (TMS) group such that the silicon atom is instead covalently bonded to the oxygen or nitrogen. The trimethylsilylation is preferably carried out by dissolving the organic compound in excess molar equivalents of hexamethyldisilazane ("HMDS") as a trimethylsilylating reagent, optionally with at least a catalytic amount of ammonium sulfate ("$(NH_4)_2SO_4$"). Preferred reaction conditions include a temperature of 0° C. to reflux and a time of about 2 hours to about 12 hours. It is noted that trimethylsilylation can also be carried out by dissolving an organic compound in an organic solvent and reacting it with excess trimethylsilyl chloride in the presence of an excess of organic amine base, for example, triethylamine ("$Et_3N$" or "TEA"), optionally further in the presence of HMDS. It is noted that trimethylsilylation can alternatively be carried out by using excess bis(trimethylsilyl)acetamide ("BSA") as a trimethylsilylating reagent. The person skilled in the art knows further processes that can be used to introduce trimethylsilyl groups, because trimethylsilylating agent(s) and reagent(s) have been extensively documented in the chemical literature.

As used herein, the terms "phosphorylating agent" or "phosphorylating reagent," alone or in combination with other terms, refer to compounds that include a phosphorus atom in the +5 oxidation state and, upon reaction with hydroxyl-containing compounds, yield a phosphate triester.

One suitable phosphorylating agent or reagent is phosphorus oxychloride ($POCl_3$). Other suitable phosphorylating agents or reagents (or phosphorus reagent systems) include compounds having formula $P(O)Cl(OR^X)(OR^Y)$ that include CAS Numbers 2524-64-3, 6609-64-9, 814-49-3, 14254-41-2, 2574-25-6, 813-77-4, 1499-17-8, 2510-89-6, 819-43-2, 5381-98-6, 538-37-4, 57188-46-2, 81639-99-8, 17672-53-6, 4090-55-5, 17776-78-2, 6630-13-3, 56119-60-9, 77075-54-8, 89104-48-3, 6546-97-0, 6630-15-5, 16383-57-6, 381-44-2, 124648-60-8, 17788-08-8, 58377-73-4, 6630-14-4, 17158-87-1, 17677-92-8, 51103-92-5, 52258-06-7, 56623-07-5, 58377-74-5, 85363-77-5, 112966-13-9, 167907-25-7, 179695-78-4, 877458-32-7, 1424937-89-2, 1424939-04-7, 2035-83-8, 127164-51-6, 6719-79-5, 59819-52-2, 69919-18-2, 77181-80-7, 4040-23-7, 6533-33-1, 6719-82-0, 6719-84-2, 22939-24-8, 27315-40-8, 28888-24-6, 61550-37-6, 73992-66-2, 86531-53-5, 96357-53-8, 108249-87-2, 343863-91-2, 875893-99-5, 714-87-4, 6087-94-1, 13674-83-4, 56883-17-1, 88805-00-9, 92401-83-7, 93115-98-1, 120628-26-4, 130312-59-3, 315179-27-2, 1388636-60-9, 1388636-61-0; and compounds having formula $P(O)Cl_2(OR^Z)$ that include CAS Numbers 770-12-7, 1498-51-7, 15074-54-1, 777-52-6, 677-24-7, 772-79-2, 4167-02-6, 1455-05-6, 31651-76-0, 53676-22-5, 18868-46-7, 53676-18-9, 940-18-1, 84681-46-9, 878-17-1, 105053-57-4, 149864-64-2, 6964-36-9, 18350-98-6, 53676-17-8, 60223-35-0, 25359-51-7, 2035-84-9, 2196-02-3, 382608-79-9, 775-08-6, 30333-08-5, 1479-10-3, 2213-71-0, 5305-82-8, 5995-77-7, 13674-82-3, 13825-97-3, 17788-07-7, 19430-76-3, 19430-77-4, 20056-41-1, 20464-68-0, 31735-82-7, 36196-79-9, 41998-90-7, 52198-45-5, 53121-39-4, 53121-41-8, 99884-77-2, 105053-58-5, 125440-36-0, 140468-02-6, 140468-03-7, 184528-24-5, 870673-87-3, 916893-01-1, 1498-52-8, 20464-67-9, 38135-34-1, 41240-73-7, 62485-00-1, 78840-91-2, 313946-12-2, 1242826-74-9. $R^X$, $R^Y$, and $R^Z$ may be the same or different, and include, but are not limited to, simple alkyl.

As used herein, the terms "phosphitylating agent" or "phosphitylating reagent," alone or in combination with other terms, refer to compounds that include a phosphorus atom in the +3 oxidation state and, upon reaction with hydroxyl-containing compounds, yield a phosphite triester.

As used herein, the term "thiophosphorylating agent," alone or in combination with other terms, refers to compounds that include a phosphorus atom in the +5 oxidation state and with a bond to a sulfur atom, and which, upon reaction with hydroxyl-containing compounds, yield a thiophosphate triester. One suitable thiosphorylating reagent is phoshoryl thiochloride ($P(S)Cl_3$).

As used herein, the term "carbodiimide reagent," alone or in combination with other terms, refers to alkylcarbodiimide reagents, including, but not limited to, dicyclohexylcarbodiimide ("DCC"), diisopropylcarbodiimide ("DCI"), and ethyl-(N',N'-dimethylamino)propylcarbodiimide hydrochloride ("EDC"). Without being bound by theory, it is believed that carbodiimide reagents can activate one phosphate monoester for displacement with another, with subsequent formation of a pyrophosphate linkage.

As used herein, the term "divalent metal salt," alone or in combination with other terms, refers to ionic compounds that include a cationic species arising from a metallic element that can attain a formal charge of +2 (i.e., "divalent"). Such metallic elements include, but are not limited to zinc (i.e., "$Zn^{+2}$"), magnesium (i.e., "$Mg^{+2}$"), manganese (i.e., "$Mn^{+2}$"), and cadmium (i.e., "$Cd^{+2}$"). Without being bound by theory, it is believed that divalent metal salts will facilitate the reaction of activated monophosphates as, for example, morpholidates or phosphoroimidazolates, with another monophosphate, to achieve the desired pyrophosphate linkage and produce the desired adenylyl dinucleotide conjugate.

Without being bound by theory, it is believed that a monophosphate can be activated as a phosphoramidate by reaction with an appropriate amine. The activated monophosphate could then be reacted with another monophosphate to achieve the desired pyrophosphate linkage and produce the desired adenylyl dinucleotide conjugate. Non-limiting examples of amines include, for example, morpholine, and other amines that are presently disclosed herein. Alternatively, without being bound by theory, it is believed that a monophosphate can be activated by reaction with an acid, in an amount ranging from catalytic amounts up to stoichiometric or molar equivalent amounts. Non-limiting examples of acids are presently disclosed herein.

The person of ordinary skill in the art knows further processes that can be used to introduce pyrophosphate linkages, because conditions and reagents for the syntheses of pyrophosphate linkages have been extensively documented in the chemical literature.

The compounds or derivatives having formulae (2), (I), (I-H), (II), (III), (IV), (IV-H), (V), and/or (VI), or salts, solvates, or prodrugs thereof, synthesized by the methods of the present disclosure, and intermediates, may be isolated from their reaction mixtures and purified by standard techniques such as filtration, liquid-liquid extraction, solid phase extraction, distillation, recrystallization, or chromatography, including flash column chromatography, preparative TLC, HPTLC, HPLC, or rp-HPLC. One preferred method for purification of the compounds or derivatives having formulae (2), (I), (I-H), (II), (III), (IV), (IV-H), (V), and/or (VI), or salts, solvates, or prodrugs thereof, comprises crystallizing the compound or derivative, or salt, solvate, or prodrug thereof, from a solvent, to form, preferably, a crystalline form of the compound or derivative, or salt, solvate, or prodrug thereof. Following crystallization, the crystallization solvent is removed by a process other than evaporation, for example, filtration or decanting, and the crystals are then preferably washed using pure solvent (or a mixture of pure solvents). Preferred solvents for crystallization include water; alcohols, particularly alcohols containing up to four carbon atoms, such as methanol, ethanol, isopropanol, butan-1-ol, butan-2-ol, and 2-methyl-2-propanol; ethers, for example diethyl ether, diisopropyl ether, t-butyl methyl ether, 1,2-dimethoxyethane, tetrahydrofuran, and 1,4-dioxane; carboxylic acids, for example formic acid and acetic acid; hydrocarbon solvents, for example pentane, hexane, and toluene; and mixtures thereof, particularly aqueous mixtures such as aqueous methanol, ethanol, isopropanol, and acetone. Pure solvents, preferably at least analytical grade, and more preferably pharmaceutical grade are preferably used. In a preferred embodiment of the processes of the invention, the products are so isolated. In the compounds or derivatives having formulae (2), (I), (I-H), (II), (III), (IV), (IV-H), (V), and/or (VI), or salts, solvates, or prodrugs thereof, synthesized by the methods of the present disclosure, the compounds or derivatives having formula (2), (I), (I-H), (II), (III), (IV), (IV-H), (V), and/or (VI), or salts, solvates, or prodrugs thereof, synthesized by the methods of the present disclosure, are preferably in or prepared from a crystalline form, preferably prepared according to such a process. Alternatively, the compounds or derivatives having formulae (2), (I), (I-H), (II), (III), (IV), (IV-H), (V), and/or (VI), or salts, solvates, or prodrugs thereof, synthesized by the methods of the present disclosure, can be isolated using lyophilization or freeze-drying techniques, following ion-exchange purification, thus avoiding use of non-aqueous solvents.

The synthetic methods described above reflect a convergent synthesis strategy. Thus, two components may be synthesized and elaborated separately prior to condensing or coupling the compounds to form the target compounds. These convergent synthetic schemes allow for arrangement of the assembly steps of the backbone of the target compounds and derivatization of derivatizable functionalities to accommodate functional group sensitivity and/or to allow for functional groups or elements to be introduced either before or after the assembly of the backbone of the target compounds via the condensation or coupling reactions described.

It will be appreciated by one skilled in the art that certain aromatic substituents in compounds synthesized by the methods of the present disclosure, intermediates used in the processes above, or precursors to the compounds synthesized by the methods of the present disclosure, may be introduced by employing aromatic substitution reactions to introduce or replace a substituent, or by using functional group transformations to modify an existing substituent, or a combination thereof. Such reactions may be effected either prior to or immediately following the processes mentioned above, and are included as part of the process aspect of the invention. The reagents and reaction conditions for such procedures are known in the art. Specific examples of procedures that may be employed include, but are not limited to, electrophilic functionalization of an aromatic ring, for example via nitration, halogenation, or acylation; transformation of a nitro group to an amino group, for example via reduction, such as by catalytic hydrogenation; acylation, alkylation, or sulfonylation of an amino or hydroxyl group; replacement of an amino group by another functional group via conversion to an intermediate diazonium salt followed by nucleophilic or free radical substitution of the diazonium salt; or replacement of a halogen by another group, for example via nucleophilic or organometallically-catalyzed substitution reactions.

Additionally, in the aforesaid processes, certain functional groups that would be sensitive to the reaction conditions may be protected by protecting groups. A protecting group is a derivative of a chemical functional group that would otherwise be incompatible with the conditions required to perform a particular reaction that, after the reaction has been carried out, can be removed to regenerate the original functional group, which is thereby considered to have been "protected." Any chemical functionality that is a structural component of any of the reagents used to synthesize compounds synthesized by the methods of the present disclosure may be optionally protected with a chemical protecting group if such a protecting group is useful in the synthesis of compounds synthesized by the methods of the present disclosure. The person skilled in the art knows when protecting groups are indicated, how to select such groups, and processes that can be used for selectively introducing and selectively removing them, because methods of selecting and using protecting groups have been extensively documented in the chemical literature. Techniques for selecting, incorporating, and removing chemical functional groups may be found, for example, in THEODORA W. GREENE & PETER G. M. WUTS, PROTECTIVE GROUPS IN ORGANIC SYNTHESIS (John Wiley & Sons, Inc. 1999), the entire disclosure of which is incorporated herein by reference.

In addition to use of a protecting group, sensitive functional groups may be introduced as synthetic precursors to the functional groups desired in the intermediate or final product. An example of this is an aromatic nitro ($-NO_2$) group. The aromatic nitro group does not undergo any of the nucleophilic reactions of an aromatic amino group. However, the nitro group can serve as the equivalent of a protected amino group because it is readily reduced to the amino group under mild conditions that are selective for the nitro group over most other functional groups.

It will be appreciated by one skilled in the art that the processes described are not the exclusive means by which compounds synthesized by the methods of the present disclosure may be synthesized and that an extremely broad repertoire of synthetic organic reactions is available to be potentially employed in synthesizing compounds synthesized by the methods of the present disclosure. The person skilled in the art knows how to select and implement appropriate synthetic routes. Suitable synthetic methods may be identified by reference to the literature, including reference sources such as COMPREHENSIVE ORGANIC SYNTHESIS (B. M. Trost & I. Fleming eds., Pergamon Press 1991); COMPREHENSIVE ORGANIC FUNCTIONAL GROUP TRANSFORMATIONS (A. R. Katritzky, O. Meth-Cohn, & C. W. Rees eds., Pergamon Press 1996); COMPREHENSIVE ORGANIC FUNCTIONAL GROUP TRANSFORMATIONS II (A. R. Katritzky & R. J. K. Taylor eds., 2d ed., Elsevier 2004); COMPREHENSIVE HETEROCYCLIC CHEMISTRY (A. R. Katritzky & C. W. Rees eds., Pergamon Press 1984); COMPREHENSIVE HETEROCYCLIC CHEMISTRY II (A. R. Katritzky, C. W. Rees, & E. F. V. Scriven eds., Pergamon Press 1996); and J. MARCH, ADVANCED ORGANIC CHEMISTRY (4th ed., John Wiley & Sons, Inc. 1992).

Salts of Compounds or Derivatives Synthesized According to the Methods of the Present Disclosure The compounds or derivatives synthesized by the methods of the present disclosure may take the form of salts. The term "salts" embraces addition salts of free acids or free bases that are compounds or derivatives synthesized by the methods of the present disclosure. The term "pharmaceutically acceptable salt" refers to salts that possess toxicity profiles within a range that affords utility in pharmaceutical applications.

Suitable pharmaceutically acceptable acid solution salts may be prepared from an inorganic acid or from an organic acid. Examples of inorganic acids include hydrochloric, hydrobromic, hydroiodic, nitric, carbonic, sulfuric, and phosphoric acids. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoroacetic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, and galacturonic acid. In the present examples of compounds or derivatives having formulae (2), (I), (I-H), (II), (III), (IV), (IV-H), (V), or (VI), or salts, solvates, or prodrugs thereof, i.e., compounds containing amino groups, pyridine, or reduced pyridine, said compounds can be isolated as salts of inorganic acids or strong organic acids, e.g., hydrochloric acid or trifluoroacetic acid.

Suitable pharmaceutically acceptable base addition salts of compounds or derivatives synthesized by the methods of the present disclosure include, for example, metallic salts including alkali metal, alkaline earth metal, and transition metal salts such as, for example, calcium, magnesium, potassium, sodium, and zinc salts. Further, base addition salts of compounds synthesized by the methods of the present disclosure include, for example, ammonium salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine), tromethamine (tris(hydroxymethyl)aminomethane), and procaine.

All of these salts may be prepared by conventional means from the corresponding compounds or derivatives having formulae (2), (I), (I-H), (II), (III), (IV), (IV-H), (V), (VI), or salts, solvates, or prodrugs thereof, by reacting, for example, the appropriate acid or base with the compound or derivative having formulae (2), (I), (I-H), (II), (III), (IV), (IV-H), (V), or (VI), or salts, solvates, or prodrugs thereof. Preferably, the salts are in crystalline form, or alternatively in dried or freeze-dried form. The person skilled in the art will know how to prepare and select suitable salt forms for example, as described in P. H. STAHL & C. G. WERMUTH, HANDBOOK OF PHARMACEUTICAL SALTS: PROPERTIES, SELECTION, AND USE (Wiley-VCH 2002).

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., —OH, —SH, —COOH, —NR$_2$, associated with the drug, that cleave in vivo. Standard prodrugs include, but are not limited to, carboxylate esters where the group is alkyl, aryl, aralkyl, acyloxyalkyl, alkoxycarbonyloxyalkyl, as well as esters of hydroxyl, thiol, and amines where the group attached is an acyl group, an alkoxycarbonyl, aminocarbonyl, phosphate, or sulfate. The groups illustrated are exemplary, not exhaustive, and one skilled in the art could prepare other known varieties of prodrugs. Such prodrugs of the compounds or derivatives having formula (I), (I-H), (II), (III), (IV), (IV-H), (V), and/or (VI) fall within the scope of the methods of the present invention. Prodrugs must undergo some form of a chemical transformation to produce the compound or derivative that is biologically active or is a precursor of the biologically active compound. In some cases, the prodrug is biologically active, usually less than the drug itself, and serves to improve drug efficacy or safety through improved oral bioavailability, pharmacodynamic half-life, etc. As used herein, the term "derivative," alone or in combination with other terms, can include a prodrug.

The nutraceutical compositions of the present disclosure may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluents, or excipient that is compatible with the other ingredients of the formulation and not deleterious to the user. In accordance with one embodiment, suitable nutraceutically acceptable carriers can include ethanol, aqueous ethanol mixtures, water, fruit, and/or vegetable juices, and combinations thereof.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films, or oral dissolvable strips can be used. Other useful delivery systems comprise oral or nasal sprays or inhalers, and the like.

For oral administration, a compound or derivative having formulae (2), (I), (I-H), (II), (III), (IV), (IV-H), (V), or (VI), or a salt, solvate, or prodrug thereof may be further combined with one or more solid inactive ingredients for the preparation of tablets, capsules, pills, powders, granules, or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

The compounds or derivatives synthesized by the methods of the present disclosure, together with a conventional adjuvant, carrier, or diluents, may thus be placed into the form of pharmaceutical compositions and unit dosages thereof. Such forms include solids, and in particular, tablets, filled capsules, powder, and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principals, and such unit dosage forms may contain any suitable effective amount of the active ingredient commensurate with the intended daily dosage range to be employed.

The compounds or derivatives synthesized by the methods of the present disclosure can be administered in a wide variety of oral and parenteral dosage forms. It will be obvious to those skilled in the art that the following dosage forms may comprise, as the active component, either a chemical compound or derivative synthesized by the methods of the present disclosure or a pharmaceutically acceptable salt, solvate, or prodrug of a chemical compound or derivative synthesized by the methods of the present disclosure.

For preparing pharmaceutical compositions from a chemical compound or derivative synthesized by the methods of the present disclosure, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active components. In tablets, the active component is mixed with the carrier having the necessary binding capacity in suitable proportions and compacted in the shape and size desired.

The powders and tablets preferably contain from about five or ten to about seventy percent of the active compound(s) or derivative(s) synthesized by the methods of the present disclosure. Suitable carriers are microcrystalline cellulose, sugar, lactose, pectin, dextrin, starch, gelatin, tragacanth, methylcellulose, sodium carboxymethylcellulose, a low melting wax, cocoa butter, and the like, and other excipients may include magnesium stearate, stearic acid, talc, silicon dioxide, etc. The term "preparation" is intended to include the formulation of active compound with encapsulating material as carrier providing a capsule in which the active component, with or without carriers, is surrounded by a carrier, which is thus in association with it. Tablets, powders, capsules, pills, sachets, and lozenges are included. Tablets, powders, capsules, pills, sachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution. The chemical compounds or derivatives synthesized by the methods of the present disclosure may thus be formulated for parenteral administration (e.g., by injection, for example bolus injection or continuous infusion) and may be presented in unit dose for example in ampoules, pre-filled syringes, small volume infusion, or in multi-dose containers with an added preservative). The compositions may take such forms as suspensions, solutions, or emulsions in oily or aqueous vehicles, and may contain formulation agents such as suspending, stabilizing, and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Compositions suitable for topical administration in the mouth include lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in suitable liquid carrier.

Solutions or suspensions are applied directly to the nasal cavity by conventional means, for example, with a dropper, pipette, or spray. The compositions may be provided in single or multi-dose form. In compositions intended for administration to the respiratory tract, including intranasal compositions, the compound or derivative will generally have a small particle size, for example, of the order of 5 microns or less. Such a particle size may be obtained by means known in the art, for example by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets, capsules, and lozenges for oral administration and liquids for oral use are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of Remington's Pharmaceutical Sciences (Mack Publishing Co., Easton, Pa.).

Solid nutritional compositions for oral administration may optionally contain, in addition to the above enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; binders including acacia, methylcellulose, sodium carboxymethylcellulose, polyvinylpyrrolidone, hydroxypropyl methylcellulose, ethyl cellulose, and the like; and lubricants such as magnesium stearate, stearic acid, silicone fluid, talc, waxes, oils, colloidal silica, and the like. The usefulness of such excipients is well known in the art.

Liquid nutritional compositions for oral administration in connection with a method for preventing and/or treating inflammation, colds, and/or flu can be prepared in water or other aqueous vehicles. In addition to the above enumerated ingredients or compounds, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods. Various ready-to-drink formulations ("RTDs") are contemplated.

Routes of Administration

The compositions may be administered by any suitable route, including but not limited to oral, sublingual, buccal, ocular, pulmonary, rectal, and parenteral administration, or as an oral or nasal spray (e.g., inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the installation of a pharmaceutical composition in the body of the patient in a controlled formulation, with systemic or local release of the drug to occur at a later time. For example, the drug may be localized in a depot for controlled release to the circulation, or for release to a local site.

Pharmaceutical compositions of the disclosure may be those suitable for oral, rectal, bronchial, nasal, pulmonal, topical (including buccal and sub-lingual), transdermal, vaginal, or parenteral (including cutaneous, subcutaneous, intramuscular, intraperitoneal, intravenous, intraarterial, intracerebral, intraocular injection, or infusion) administration, or those in a form suitable for administration by inhalation or insufflations, including powders and liquid aerosol administration, or by sustained release systems. Suitable examples of sustained release systems include semipermeable matrices of solid hydrophobic polymers containing a compound or derivative synthesized by the methods of the present disclosure, which matrices may be in the form of shaped articles, e.g., films or microcapsules.

The methods described above may be further understood in connection with the following Examples. In addition, the following non-limiting examples are provided to illustrate the invention. The illustrated synthetic pathways are applicable to other embodiments of the present invention. The synthetic procedures described as general methods describe what is believed will be typically effective to perform the synthesis indicated. However, the person skilled in the art will appreciate that it may be necessary to vary the procedures for any given embodiment of the invention, e.g., vary the order or steps and/or the chemical reagents used. Products may be purified by conventional techniques that will vary, for example, according to the amounts of side products produced the physical properties of the compounds or derivatives synthesized by the methods of the present invention.

Example 1

A. Synthetic Preparation of [(2R,3R,4R)-3,4-Diacetoxy-5-Chlorotetrahydrofuran-2-yl]Methyl Acetate (Compound 1): Compound of Formula (2): $R^6=R^7=R^8=$Acetyl, X=Chloride

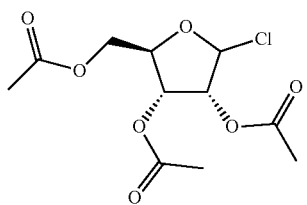

Compound 1

Figure 5:
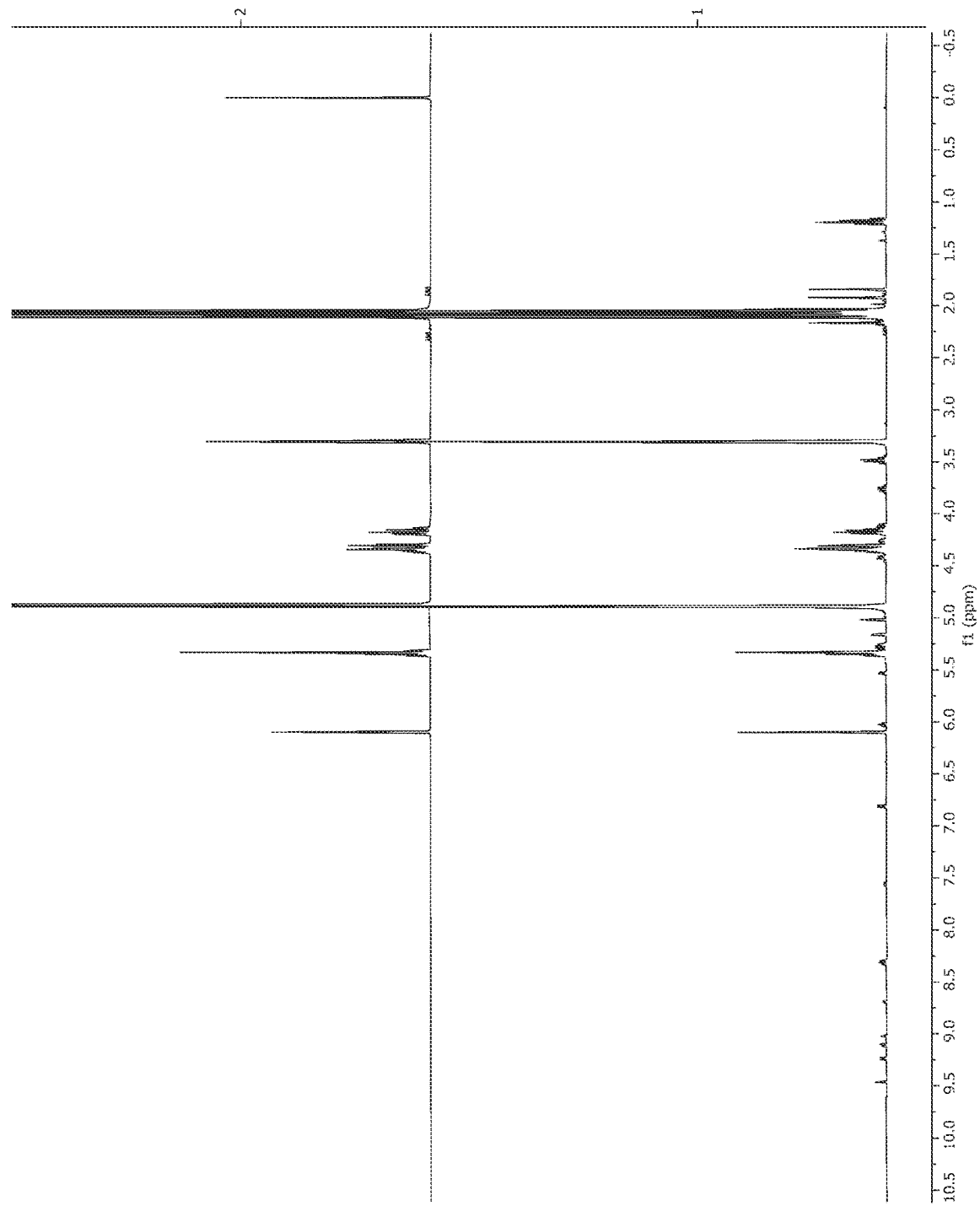
FIG. 5 depicts a $^1$H NMR spectrum of riboside tetraacetate, recycled from the reaction product mixture for the procedure described in Example 1, Part A (bottom), as compared to standard for riboside tetraacetate (top), performed in accordance with one embodiment of the described method for the preparation of a compound or derivative having general formula (2) or a salt thereof.

[(2R,3R,4R)-3,4,5-triacetoxytetrahydrofuran-2-yl]methyl acetate (100 g, 314.19 mmol) was added to a 500 milliliter round-bottom flask and charged with acetyl chloride (111.7 mL, 1579.96 mmol). The mixture was cooled to 0° C. using an ice bath, and ethanol (55.04 mL, 942.58 mmol) was added slowly, dropwise. Once all of the ethanol was added, the solution was allowed to stir at 0° C. for one hour under sealed conditions. The reaction was judged to be complete by $^1$H NMR, and the mixture was carefully concentrated on the rotary evaporator. The product (91.3 g), Compound 1, was used without further purification for the next step. As seen in FIG. 1, NMR showed 87% conversion to the product chlororiboside triacetate (7% unreacted [(2R,3R,4R)-3,4,5-triacetoxytetrahydrofuran-2-yl]methyl acetate, and 6% α-chlororiboside triacetate). FIG. 5 compares $^1$H NMR spectra of recovered, unreacted starting material ([(2R,3R,4R)-3,4,5-triacetoxytetrahydrofuran-2-yl]methyl acetate) (bottom) and a quantitatively pure sample of the same chemical (top).

B. Synthetic Preparation of Nicotinamide Riboside Triacetate Chloride (Compound 2): Compound of Formula (Ia): $R^1=$Hydrogen, n=0, $Z^2=$NH, $R^2=R^3=R^4=R^5=$Hydrogen, $X^-=$Chloride, $R^6=R^7=R^8=$Acetyl

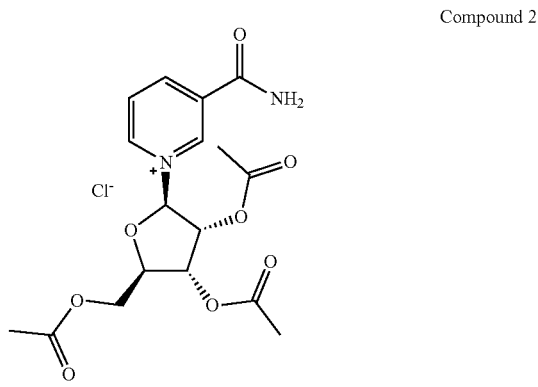 [SMILES: CC(=O)OC[C@H]1O[C@@H]([n+]2cccc(C(N)=O)c2)[C@H](OC(C)=O)[C@@H]1OC(C)=O ; [Cl-]]

Compound 2

Figure 2:
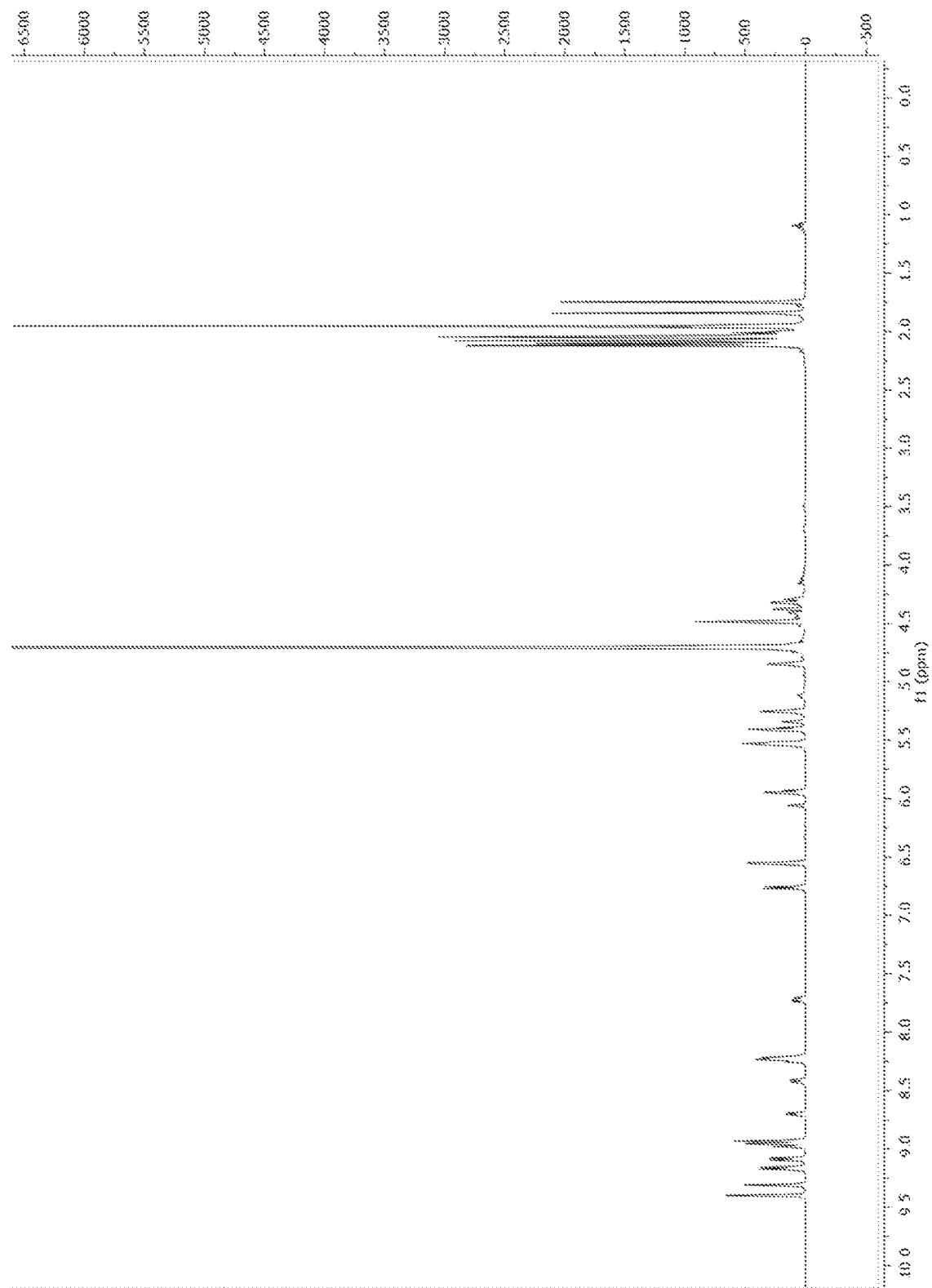
FIG. 2 depicts a $^1$H NMR spectrum of the reaction product mixture for the procedure described in Example 1, Part B, performed in accordance with one embodiment of the described method for the preparation of a compound or derivative having general formula (I) or a salt, solvate, or prodrug thereof.
Figure 3:
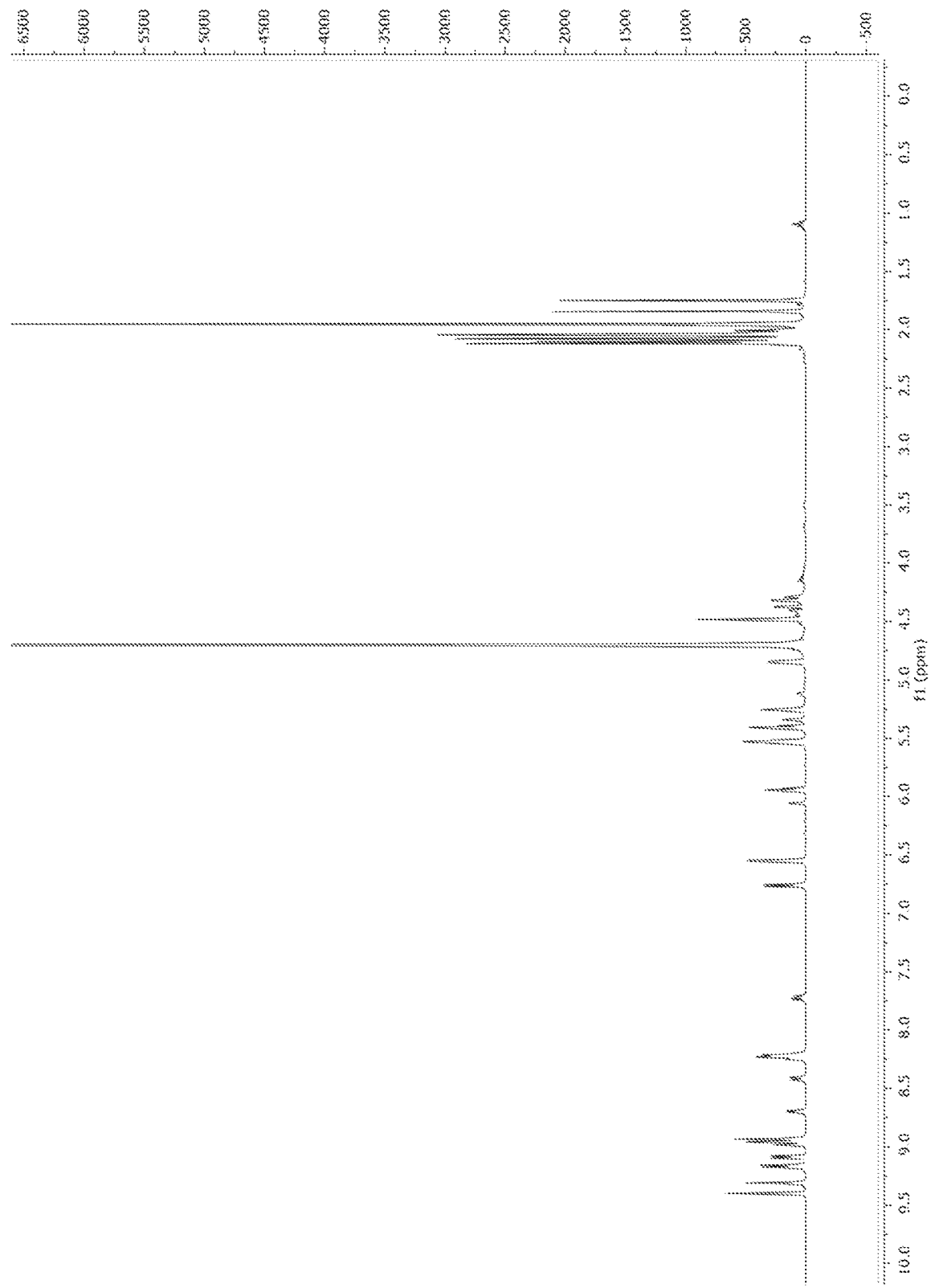
FIG. 3 depicts a $^1$H NMR spectrum of the reaction product mixture for the procedure described in Example 1, Part B, performed in accordance with one embodiment of the described method for the preparation of a compound or derivative having general formula (I) or a salt, solvate, or prodrug thereof, after removal of polar organic solvent co-reagent.

To Compound 1 (86%, 92.59 g, 0.27 mol, 1 eq) was added nicotinamide (33 g, 0.27 mol, 1 eq), and acetonitrile (84.67 mL, 1.62 mol, 6 eq), and the flask fitted with a reflux condenser and heated to 70° C. for 20 minutes. $^1$H NMR showed reaction to be complete. As seen in FIG. 2, $^1$H NMR showed 93% conversion (determined by $^1$H NMR integration), and approximately 7% unreacted nicotinamide. The α:β anomeric ratio was approximately 4:6. It is expected that these results could be improved upon if a proper sealed vessel were to be implemented. FIG. 3 depicts a $^1$H NMR spectra of the reaction mixture after removal of acetonitrile solvent.

Figure 4:
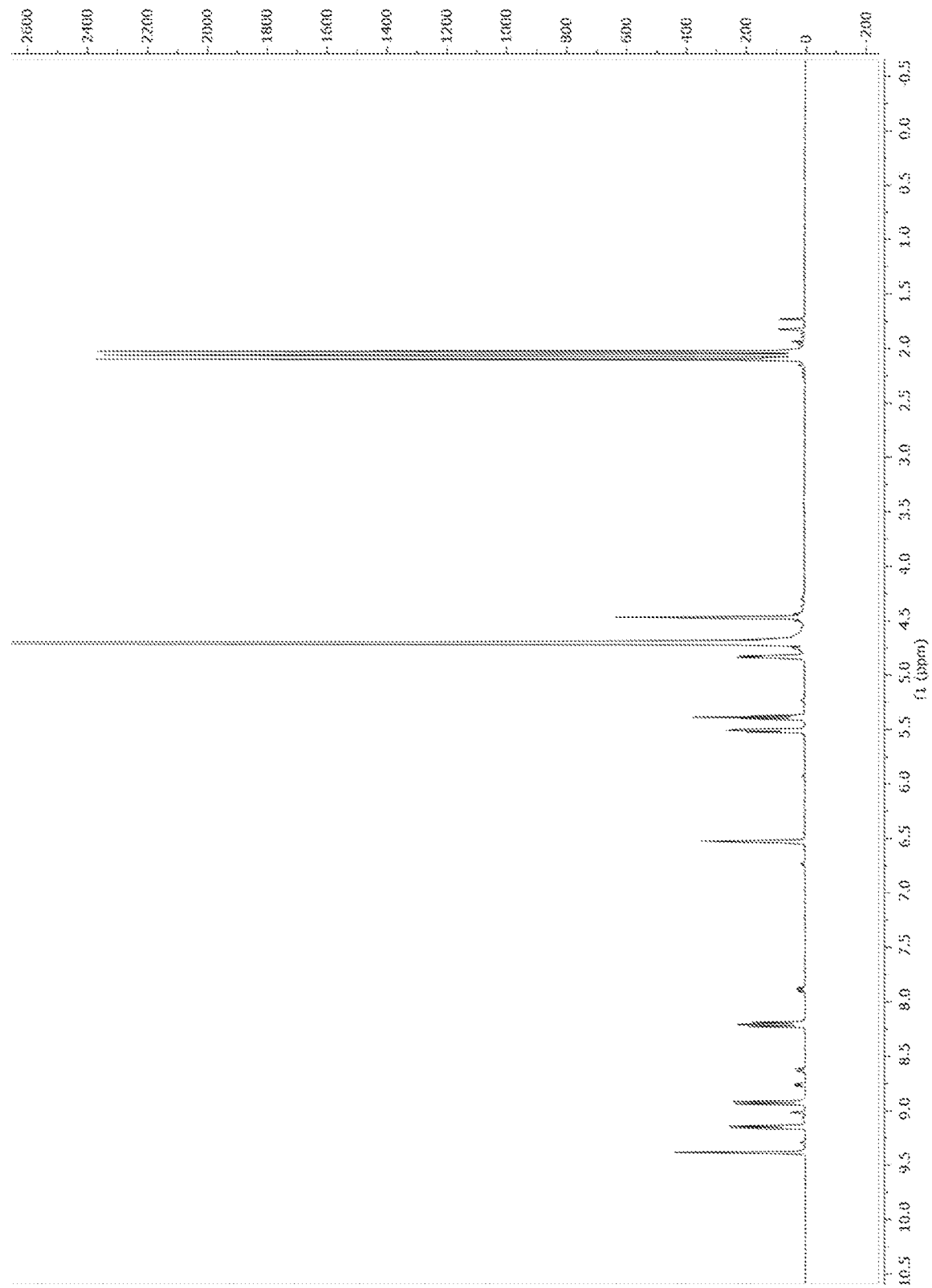
FIG. 4 depicts a $^1$H NMR spectrum of the reaction product precipitated and isolated from the reaction product mixture for the procedure described in Example 1, Part B, performed in accordance with one embodiment of the described method for the preparation of a compound or derivative having general formula (I) or a salt, solvate, or prodrug thereof.

While still at 70° C., acetone was added (~100 mL) and the reaction was filtered under vacuum. It is important to add the acetone immediately upon completion of the glycosylation reaction, when the reaction mixture is still warm, followed by immediate filtration. The cake was washed a further 2 times (2×100-150 mL) with acetone and then the solid was collected and dried under high vacuum. The sample was subsequently washed with acetone until the white solid that had precipitated became a free-flowing white powder, which was then filtered under vacuum. As shown in FIG. 4, $^1$H NMR of the filtrate demonstrated that the white powder was the β-anomer of Compound 2 (approximately 54 g), which was obtained as a free-flowing white powder. $^1$H NMR demonstrated very small traces of α-anomer of Compound 2, and nicotinamide. These could be removed by further washing with acetone, as visual inspection of the final product demonstrated some remaining small clumps therein.

The acetone washings became a viscous yellow oil as the sample became more concentrated, and white crystals began to precipitate. ¹H NMR were taken of the white crystals after washing with ether to remove traces of the yellow oil, and the NMR showed the crystals to be tetraacetate riboside (unreacted from the synthetic preparation of Compound 1). Acetone has proven to be an effective solvent for separating β-anomer of Compound 2 from α-anomer, as well as removing the other impurities. Multiple washings with acetone afforded pure β-anomer.

¹H NMR (400 MHz, MeOD): δ ppm 9.61 (s, 1H, aromatic), 9.30 (dt, J=6.3, 1.4 Hz, 1H, aromatic), 9.10 (dt, J=8.2, 1.4 Hz, 1H, aromatic), 8.37 (dd, J=8.2, 6.3 Hz, 1H, aromatic), 6.60 (d, J=3.9 Hz, 1H, H-1 (anomeric)), 5.60 (dd, J=5.6, 3.9 Hz, 1H, H-2), 5.46 (t, J=5.6 Hz, 1H, H-3), 4.81-4.84 (m, 1H, H-4), 4.61 ($AB_X$, $J_{A,A'}$=13.1 Hz, $J_{A,B}$=3.5 Hz, 1H, H-5), 4.51 ($AB_X$, $J_{A,A'}$=13.0 Hz, $J_{A,B}$=2.8 Hz, 1H, H-5'), 2.20 (s, 3H, OAc), 2.17 (s, 3H, OAc), 2.16 (s, 3H, OAc). ¹³C NMR (100 MHz, MeOD): δ ppm 172.1, 171.6, 171.2 (3×$\underline{C}$(=O)CH₃), 164.9 ($\underline{C}$(=O)NH₂), 147.0, 144.3, 142.3, 136.2, 129.6 (aromatic), 99.4 (C-1 (anomeric)), 84.4 (C-4), 77.6 (C-2), 70.7 (C-3), 63.5 (C-5).

Figure 6:
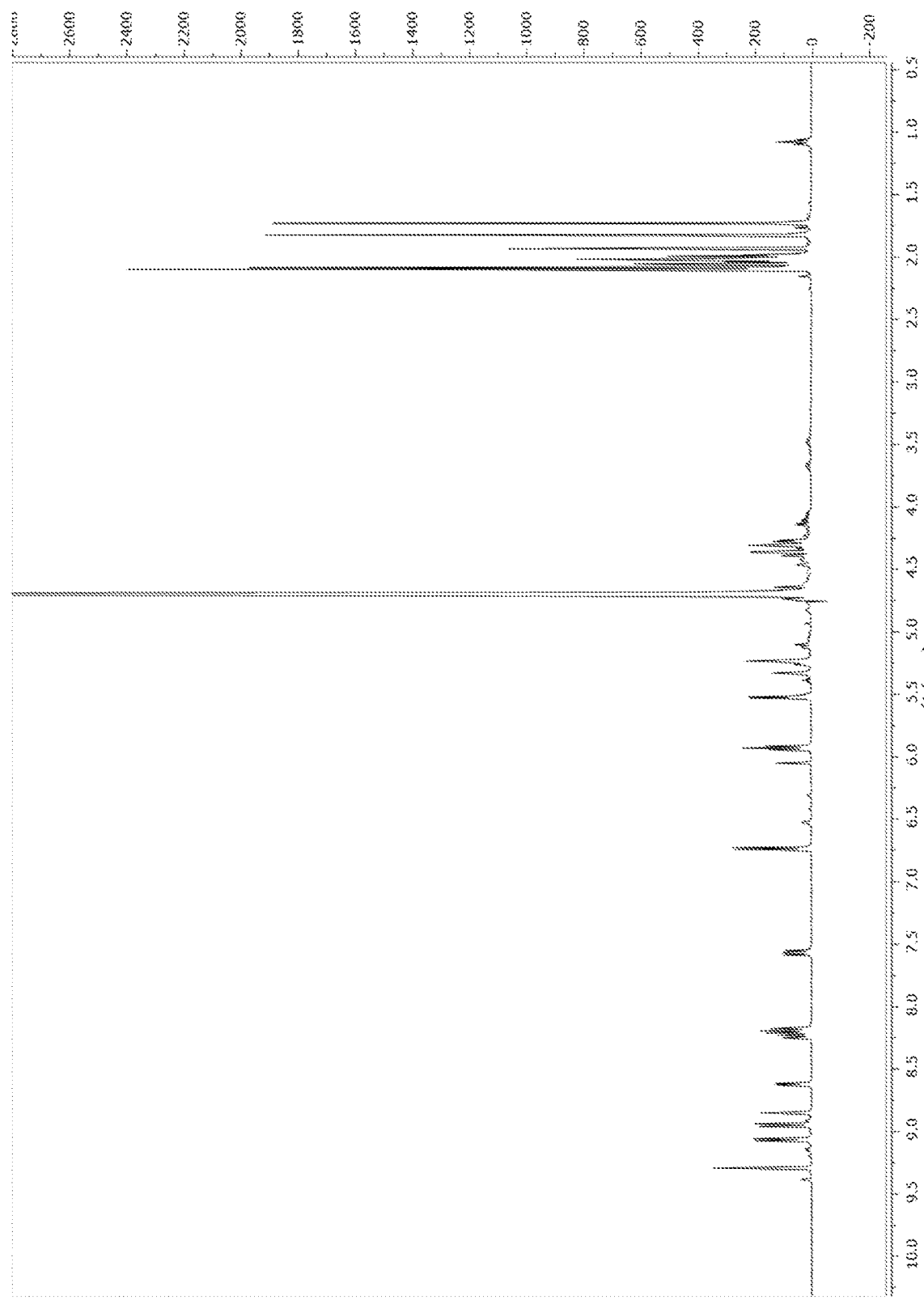
FIG. 6 depicts a $^1$H NMR spectrum of the reaction product isolated from the reaction product mixture for the procedure described in Example 1, Part B, performed in accordance with one embodiment of the described method for the preparation of a compound or derivative having general formula (I) or a salt, solvate, or prodrug thereof.
Figure 7:
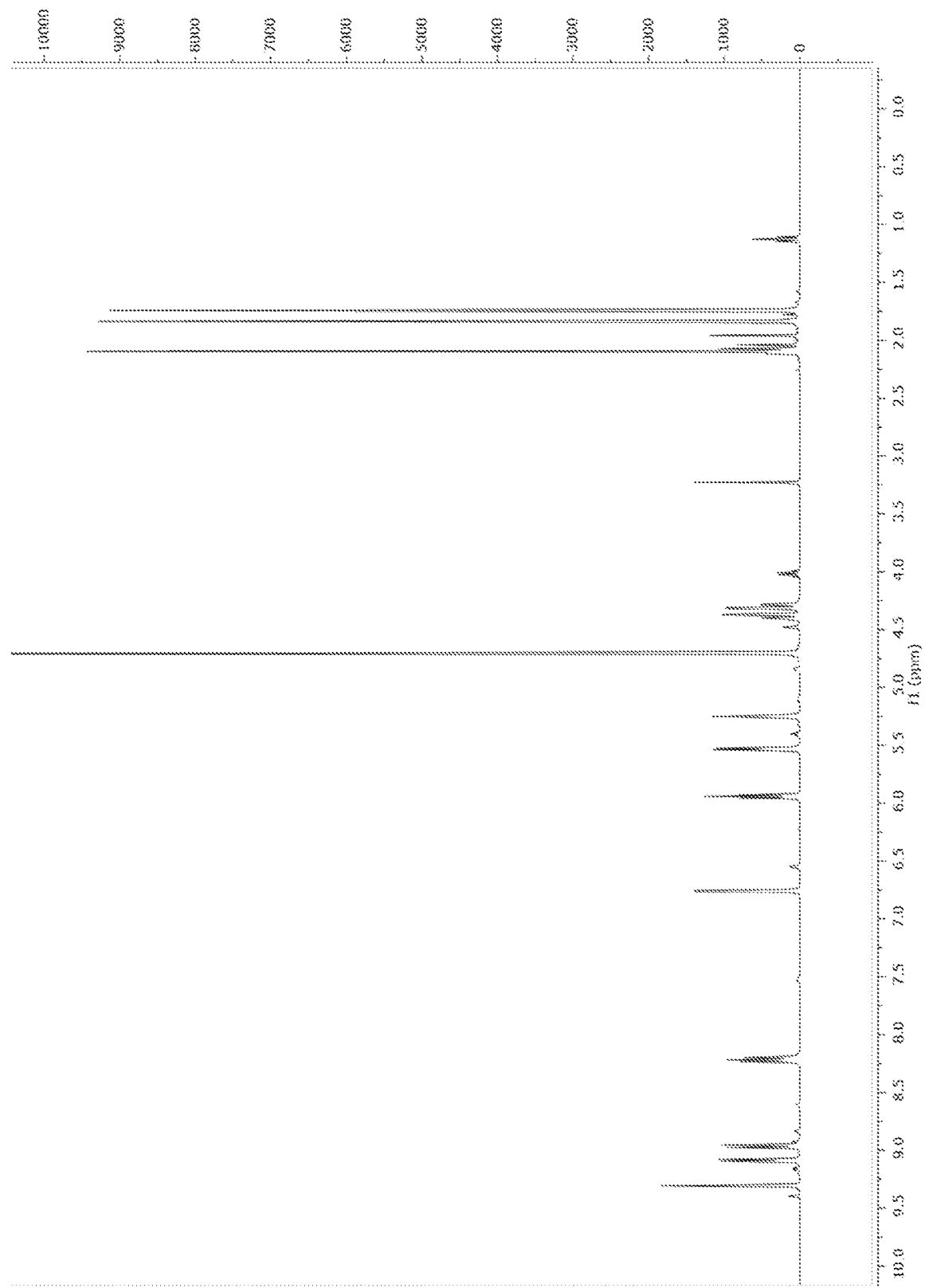
FIG. 7 depicts a $^1$H NMR spectrum of a compound or derivative having general formula (I), purified subsequent to isolation from the reaction product mixture for the procedure described in Example 1, Part B, performed in accordance with one embodiment of the described method for the preparation of a compound or derivative having general formula (I) or a salt, solvate, or prodrug thereof.

The α-anomer of Compound 2 was isolated in order to get full characterization and establish its physical appearance. As such, the combined acetone washes were concentrated. FIG. 6 shows a ¹H NMR spectrum of the concentrated, combined acetone washes. The concentrated material was loaded onto a 340 g silica biotage column with minimal MeOH. The gradient was run using 5% MeOH in EtOAc, increasing to 60% MeOH in EtOAc over approximately 2200 mL. The α-anomer of Compound 2 was isolated as an off-white powder. As shown in FIG. 7, ¹H NMR still demonstrates some minor impurities of β-anomer of Compound 2 and nicotinamide. It is expected that further purification would afford pure α-anomer of Compound 2.

A range of reaction conditions have been explored, and are presented in Table 1, whereby extrusion was used in order to achieve the production of Compound 2 from Compound 1 and nicotinamide (compound of formula (1)). Table 1 describes the conditions, including the use of additives such as microcrystalline cellulose ("MIC") in order to achieve a better flow at the addition state, as well as a better processing step result. While reaction occurred and seemed to have some effect on the α:β anomeric ratio of Compound 2, difficulties were encountered in terms of complete conversion. These results demonstrate that extrusion is suitable for the continuous production of Compound 2 by extrusion with currently optimized yields above 8500, with the possibility of recycling unreacted riboside tetraacetate.

TABLE 1

Summary of Glycosylation Study

| Experiment # | Conditions mol:mol ratio of β-anomer of Compound 1: nicotinamide | Run # | ¹H NMR integration of α-anomer (Compound 2) | ¹H NMR integration of β-anomer (Compound 2) | ¹H NMR integration of nicotinamide | α:β ratio | % Conversion to Compound 2 |
|---|---|---|---|---|---|---|---|
| 1 | 1:1 250 RPM Room temp. | — | 1.05 | 1.00 | 5.92 | 1:1 | 54 |
| 2 | 1:2 250 RPM Room temp. | — | 0.75 | 1.00 | 27.83 | 4:6 | 10 |
| 3 | 1:1 100 RPM Room temp. | — | — | — | — | — | No conversion |
|  | 1:1 100 RPM 45° C. | — | 0.56 | 1.00 | 4.55 | 3.5:6.5 | 54 |
|  | 1:1 100 RPM 55° C. | — | 0.84 | 1.00 | 2.82 | 4.5:5.5 | 70 |
|  | 1:0.5 100 RPM 50° C. | — | 0 | 1.00 | 7.94 | 0:1 | 46 |
|  | 1:0.5 100 RPM 50° C. (2nd cycle) | — | 0.58 | 1.00 | 1.84 | 4:6 | 85 |
|  | 1:0.5 50 RPM 50° C. | — | 0.44 | 1.00 | 9.91 | 3:7 | 50 |
|  | 1:0.5 50 RPM 60° C. | — | 0.44 | 1.00 | 5.25 | 3:7 | 65 |
|  | 1:0.5 250 RPM 60° C. | — | 0.50 | 1.00 | 3.33 | 3:7 | 75 |
| 4 | 1:1 100 RPM 50° C. | — | 0.77 | 1.00 | 43.02 | 4:6 | 12 |
| 5 | 1:1 100 RPM 50° C. 1 eq. MeCN | 1 | 0.58 | 1.00 | 8.66 | 4:6 | 38 |
|  |  | 2 | 0.88 | 1.00 | 5.53 | 1:1 | 54 |
|  |  | 3 | 1.19 | 1.00 | 2.23 | 6:4 | 78 |
| 6 | 1:1 100 RPM 50° C. 0.5 eq. MeCN | 1 | 0.50 | 1.00 | 25.50 | 1:2 | 17 |
|  |  | 2 | 1.04 | 1.00 | 6.83 | 1:1 | 50 |
|  |  | 3 | 1.36 | 1.00 | 4.71 | 6:4 | 63 |

TABLE 1-continued

Summary of Glycosylation Study

| Experiment # | Conditions mol:mol ratio of β-anomer of Compound 1: nicotinamide | Run # | ¹H NMR integration of α-anomer (Compound 2) | ¹H NMR integration of β-anomer (Compound 2) | ¹H NMR integration of nicotinamide | α:β ratio | % Conversion to Compound 2 |
|---|---|---|---|---|---|---|---|
| 7 | 1:1 100 RPM 50° C. 1 eq. EtOAc | 1 2 3 | — 0.77 1.26 | — 1.00 1.00 | 1 27.23 8.38 | — 4:6 6:4 | — 18 47 |
| 8 | 1:1.5 100 RPM 50° C. 1 eq. MeCN | 1 2 3 | 0.71 0.82 1.08 | 1.00 1.00 1.00 | 18.14 5.95 3.76 | 4:6 1:1 1:1 | 18 41 56 |
| 9 | 1:1 100 RPM Room temp. 1 eq. MeCN | 1 2 3 4 | — — — — | — — — — | — — — — | — — — — | — — — — |
| 10 | 1:1 100 RPM 50° C. 1 eq. MeCN MIC (mass:mass with nicotinamide) | 1 2 3 4 | 0.44 0.71 0.57 0.62 | 1.00 1.00 1.00 1.00 | 8.46 3.00 3.58 3.97 | 3:7 4:6 4:6 4:6 | 37 66 60 60 |
| 11 | 1:1 100 RPM 70° C. 1 eq. MeCN | 1 2 3 4 | 0.47 0.73 0.90 1.07 | 1.00 1.00 1.00 1.00 | 8.08 2.98 1.93 1.15 | 3:7 4:6 1:1 1:1 | 38 66 77 86 |
| 12 | 1:1 100 RPM 70° C. 1 eq. MeCN MIC (mass:mass with nicotinamide) | 1 2 3 | 0.59 0.62 0.63 | 1.00 1.00 1.00 | 3.37 3.21 3.54 | 4:6 4:6 4:6 | 62 63 62 |
| 13 | 1:1 100 RPM 70° C. 2 eq. MeCN MIC (mass:mass with nicotinamide) | 1 2 3 4 | 0.33 0.34 0.39 0.39 | 1.00 1.00 1.00 1.00 | 4.14 2.57 2.96 2.45 | 1:3 3:7 3:7 3:7 | 52 65 63 66 |
| 14 | 1:1 100 RPM 70° C. 2 eq. MeCN MIC (mass:mass with nicotinamide) | 1 2 3 4 | 0.24 0.37 0.36 0.35 | 1.00 1.00 1.00 1.00 | 3.98 3.26 2.59 2.59 | 2:8 3:7 3:7 3:7 | 51 59 63 63 |
| 15 | 1:1 100 RPM 70° C. 2 eq. MeCN MIC (0.5 mass:mass with nicotinamide) | 1 2 3 4 | 0.32 0.43 0.59 0.54 | 1.00 1.00 1.00 1.00 | 8.10 3.10 2.06 1.74 | 3:7 3:7 4:6 4:6 | 36 61 67 75 |
| 16 | 1:1 2 eq. MeCN MIC (mass:mass with nicotinamide) Ball mill (30 min, 30 Hz) | — | 1.00 | 2.6 | 8.8 | 3:7 | 58 |
| 17 | 1:1 2 eq. MeCN MIC (mass:mass with nicotinamide) 70° C. Solution-based | — | 1 | 1.8 | 4.1 | 4:6 | 70 |

TABLE 1-continued

Summary of Glycosylation Study

| Experiment # | Conditions mol:mol ratio of β-anomer of Compound 1: nicotinamide | Run # | $^1$H NMR integration of α-anomer (Compound 2) | $^1$H NMR integration of β-anomer (Compound 2) | $^1$H NMR integration of nicotinamide | α:β ratio | % Conversion to Compound 2 |
|---|---|---|---|---|---|---|---|
| 18 | 1:1 2 eq. MeCN 70° C. Solution-based | — | 0.85 | 1.00 | 0.65 | 1:1 | 91 |
| 19 | 1:1 3 eq. MeCN 70° C. Solution-based | 10 min | 1 | 1.74 | 1.45 | 3:7 | 87 |
|  |  | 20 min | 1 | 1.53 | 1.06 | 4:6 | 89 |
|  |  | 30 min | 1 | 1.50 | 1.00 | 4:6 | 90 |
|  |  | 60 min | 1 | 1.42 | 0.96 | 4:6 | 90 |
| 20 | 1:1 MeCN 2 eq. 70° C. Solution-based | 10 min | 1 | 1.52 | 1.06 | 4:6 | 89 |
|  |  | 20 min | 1 | 1.41 | 0.87 | 4:6 | 90 |
|  |  | 30 min | 1 | 1.41 | 0.88 | 4:6 | 90 |
|  |  | 60 min | 1 | 1.40 | 0.86 | 4:6 | 90 |

Crystalline Form I of nicotinamide riboside triacetate (NRTA) chloride may be characterized by a powder X-ray diffraction pattern having peaks at 19.6, 22.1, and 26.6 degrees two theta±0.2 degrees two theta. The crystalline Form I of nicotinamide riboside triacetate (NTRTA) chloride may also or alternatively be characterized by a powder X-ray diffraction pattern having peaks at 9.8, 19.2, 19.6, 22.1, and 26.6 degrees two theta±0.2 degrees two theta. The crystalline Form I of nicotinamide riboside triacetate (NRTA) chloride may also or alternatively be characterized by a powder X-ray diffraction pattern having peaks at 9.8, 14.5, 18.6, 19.2, 19.6, 22.1, 22.5, 26.6 degrees two theta±0.2 degrees two theta.

Figure 18:
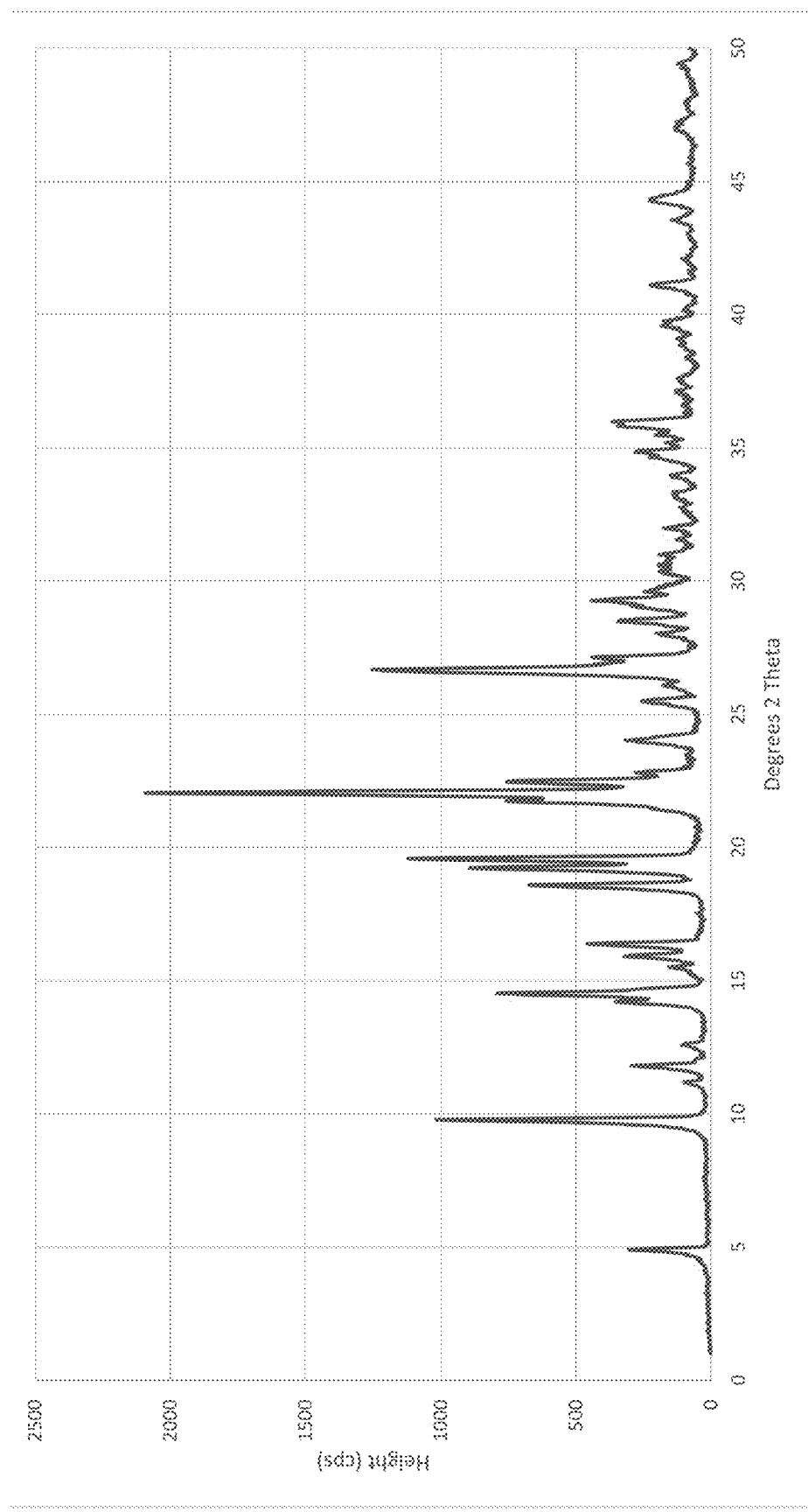
FIG. 18 provides an X-ray powder diffraction pattern for the presently disclosed Form I of crystalline nicotinamide riboside triacetate (1-(2',3',5'-triacetyl-beta-D-ribofuranosyl)-nicotinamide, "NR triacetate," or "NRTA"), the compound having formula (IX), prepared according to an embodiment of the presently disclosed methods for the preparation of a compound or derivative having general formula (Ia), or a salt, solvate, or prodrug thereof.

In other embodiments, the crystalline Form I of nicotinamide riboside triacetate (NRTA) chloride may be characterized by a powder X-ray diffraction pattern substantially as shown in FIG. 18. The crystalline Form I of nicotinamide riboside triacetate (NRTA) chloride may also or alternatively be characterized by a powder X-ray diffraction pattern having peaks substantially as provided in Table 2, below, ±0.2 degrees two theta.

TABLE 2

| Peak No. | Pos. [°2Th.] | d-spacing [Å] | Height [cts] | I/I$_{max}$ [%] |
|---|---|---|---|---|
| 1 | 4.911 | 17.978 | 319 | 13 |
| 2 | 9.787 | 9.03 | 1089 | 46 |
| 3 | 11.194 | 7.898 | 81 | 3 |
| 4 | 11.805 | 7.49 | 283 | 12 |
| 5 | 12.623 | 7.007 | 89 | 4 |
| 6 | 14.199 | 6.232 | 331 | 14 |
| 7 | 14.48 | 6.112 | 778 | 33 |
| 8 | 15.494 | 5.715 | 105 | 4 |
| 9 | 15.916 | 5.564 | 305 | 13 |
| 10 | 16.376 | 5.408 | 488 | 21 |
| 11 | 18.602 | 4.766 | 702 | 30 |
| 12 | 19.239 | 4.6097 | 917 | 39 |
| 13 | 19.587 | 4.5286 | 1266 | 54 |
| 14 | 21.769 | 4.0793 | 633 | 27 |
| 15 | 22.055 | 4.027 | 2363 | 100 |
| 16 | 22.474 | 3.9529 | 806 | 34 |
| 17 | 22.792 | 3.898 | 232 | 10 |

TABLE 2-continued

| Peak No. | Pos. [°2Th.] | d-spacing [Å] | Height [cts] | I/I$_{max}$ [%] |
|---|---|---|---|---|
| 18 | 23.995 | 3.706 | 270 | 11 |
| 19 | 25.496 | 3.491 | 211 | 9 |
| 20 | 26.06 | 3.417 | 87 | 4 |
| 21 | 26.632 | 3.3444 | 1197 | 51 |
| 22 | 27.125 | 3.2848 | 362 | 15 |
| 23 | 27.98 | 3.187 | 116 | 5 |
| 24 | 28.5 | 3.13 | 269 | 11 |
| 25 | 29.193 | 3.0566 | 339 | 14 |
| 26 | 30.97 | 2.885 | 66 | 3 |
| 27 | 34.866 | 2.5712 | 195 | 8 |
| 28 | 35.13 | 2.553 | 83 | 4 |
| 29 | 35.523 | 2.5251 | 122 | 5 |
| 30 | 35.96 | 2.4953 | 314 | 13 |
| 31 | 38.91 | 2.313 | 39 | 2 |
| 32 | 39.6 | 2.274 | 115 | 5 |
| 33 | 41.09 | 2.1947 | 185 | 8 |
| 34 | 43.52 | 2.078 | 72 | 3 |
| 35 | 44.234 | 2.0459 | 176 | 7 |
| 36 | 47.03 | 1.931 | 64 | 3 |

Figure 24:
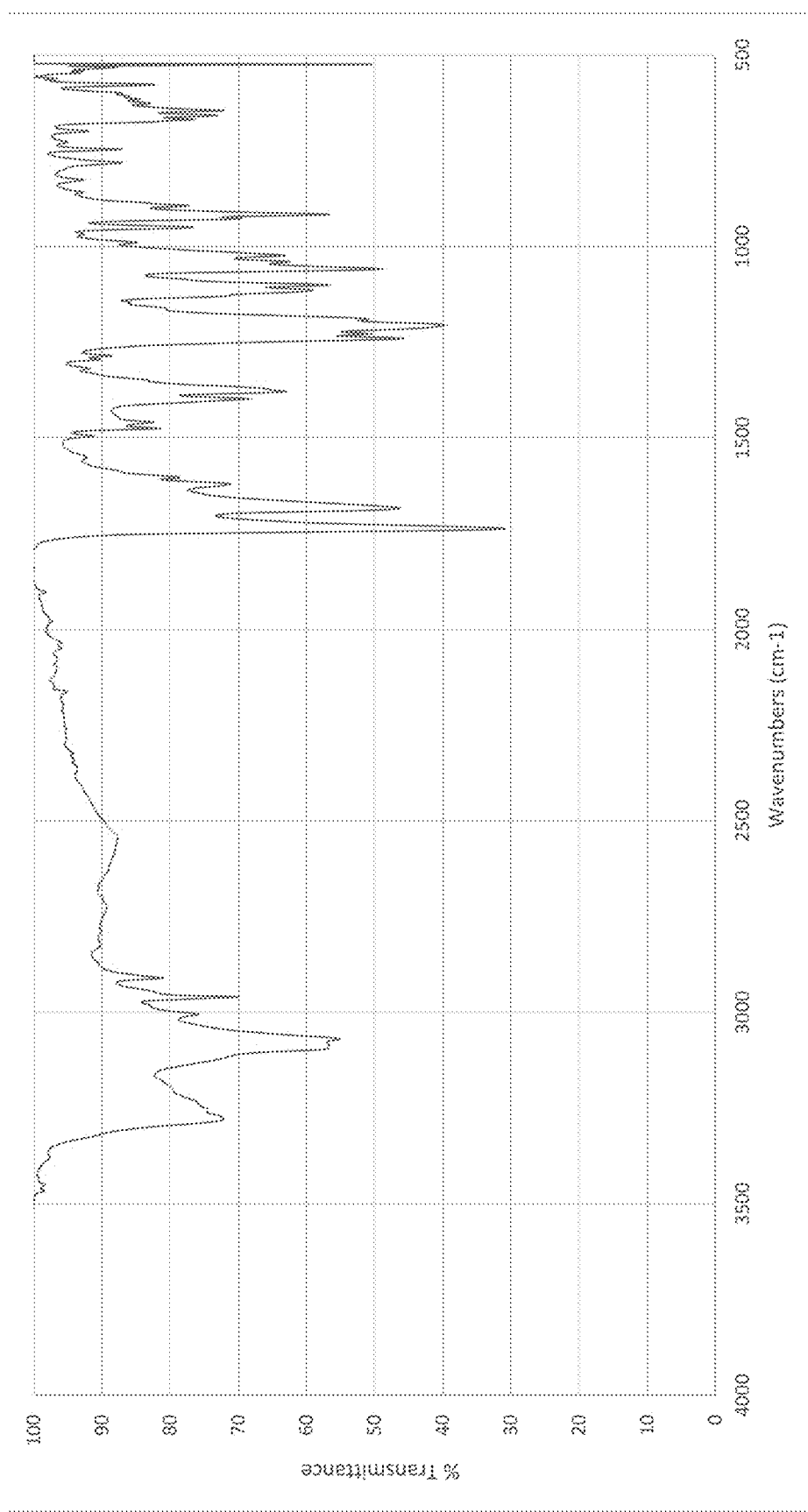
FIG. 24 provides a solid state IR spectrum for the presently disclosed Form I of crystalline nicotinamide riboside triacetate (1-(2',3',5'-triacetyl-beta-D-ribofuranosyl)-nicotinamide, "NR triacetate," or "NRTA"), the compound having formula (IX).

The crystalline Form I of nicotinamide riboside triacetate (NRTA) chloride may also or alternatively be characterized by a solid-state IR spectrum having peaks at 626.8, 644.1, and 916.0 cm$^{-1}$±0.2 cm$^{-1}$. The crystalline Form I of nicotinamide riboside triacetate (NRTA) chloride may also or alternatively be characterized by a solid-state IR spectrum having peaks at 626.8, 644.1, 916.0, 1058.8, 1101.2, and 1114.7 cm$^{-1}$±0.2 cm$^{-1}$. The crystalline Form I of nicotinamide riboside triacetate (NRTA) chloride may also or alternatively be characterized by a solid-state IR spectrum having peaks at 626.8, 644.1, 916.0, 1058.8, 1101.2, 1114.7, 1205.3, 1240.0, 1683.6, and 1737.6 cm$^{-1}$±0.2 cm$^{-1}$. In certain embodiments, the crystalline Form I of nicotinamide riboside triacetate (NRTA) chloride may be characterized by a solid-state IR spectrum substantially as shown in FIG. 24. In further embodiments, the crystalline Form I of nicotinamide riboside triacetate (NRTA) chloride may be characterized by a solid-state IR spectrum having peaks substantially as provided in Table 3, below, 0.2 cm$^{-1}$.

TABLE 3

| IR (cm$^{-1}$) |
| --- |
| 3276.52 |
| 3070.17 |
| 3004.60 |
| 2960.25 |
| 2910.10 |
| 1737.58 |
| 1683.58 |
| 1619.94 |
| 1602.58 |
| 1552.44 |
| 1494.59 |
| 1475.30 |
| 1459.87 |
| 1398.16 |
| 1378.88 |
| 1319.09 |
| 1294.02 |
| 1286.31 |
| 1240.03 |
| 1228.45 |
| 1205.31 |
| 1189.88 |
| 1114.67 |
| 1101.17 |
| 1058.75 |
| 1039.46 |
| 1024.03 |
| 991.25 |
| 950.75 |
| 927.61 |
| 916.04 |
| 892.89 |
| 781.04 |
| 746.33 |
| 698.12 |
| 657.62 |
| 644.12 |
| 626.76 |
| 578.55 |

In another embodiment, crystalline Form I of nicotinamide riboside triacetate (NRTA) chloride is characterized by a DSC thermogram obtained using a heating rate of 10 K/min comprising an endothermic event with an onset temperature of 149° C.±2° C.

In yet another embodiment, crystalline Form I of nicotinamide riboside triacetate (NRTA) chloride is characterized by a DSC thermogram obtained using a heating rate of 10 K/min comprising an endothermic event with a peak temperature of 156° C.±2° C.

In yet another embodiment, crystalline Form I of nicotinamide riboside triacetate (NRTA) chloride is characterized by a DSC thermogram obtained using a heating rate of 10 K/min comprising an endothermic event with an onset temperature of 149° C.±2° C., a peak temperature of 156° C.±2° C., or both.

In yet another embodiment, crystalline Form I of nicotinamide riboside triacetate (NRTA) chloride is characterized by a DSC thermogram obtained using a heating rate of 10 K/min comprising an endothermic event with an onset temperature of 208° C.±2° C.

In yet another embodiment, crystalline Form I of nicotinamide riboside triacetate (NRTA) chloride is characterized by a DSC thermogram obtained using a heating rate of 10 K/min comprising an endothermic event with a peak temperature of 215° C.±2° C.

In yet another embodiment, crystalline Form I of nicotinamide riboside triacetate (NRTA) chloride is characterized by a DSC thermogram obtained using a heating rate of 10 K/min comprising an endothermic event with an onset temperature of 208° C.±2° C., a peak temperature of 215° C.±2° C., or both.

Figure 31:
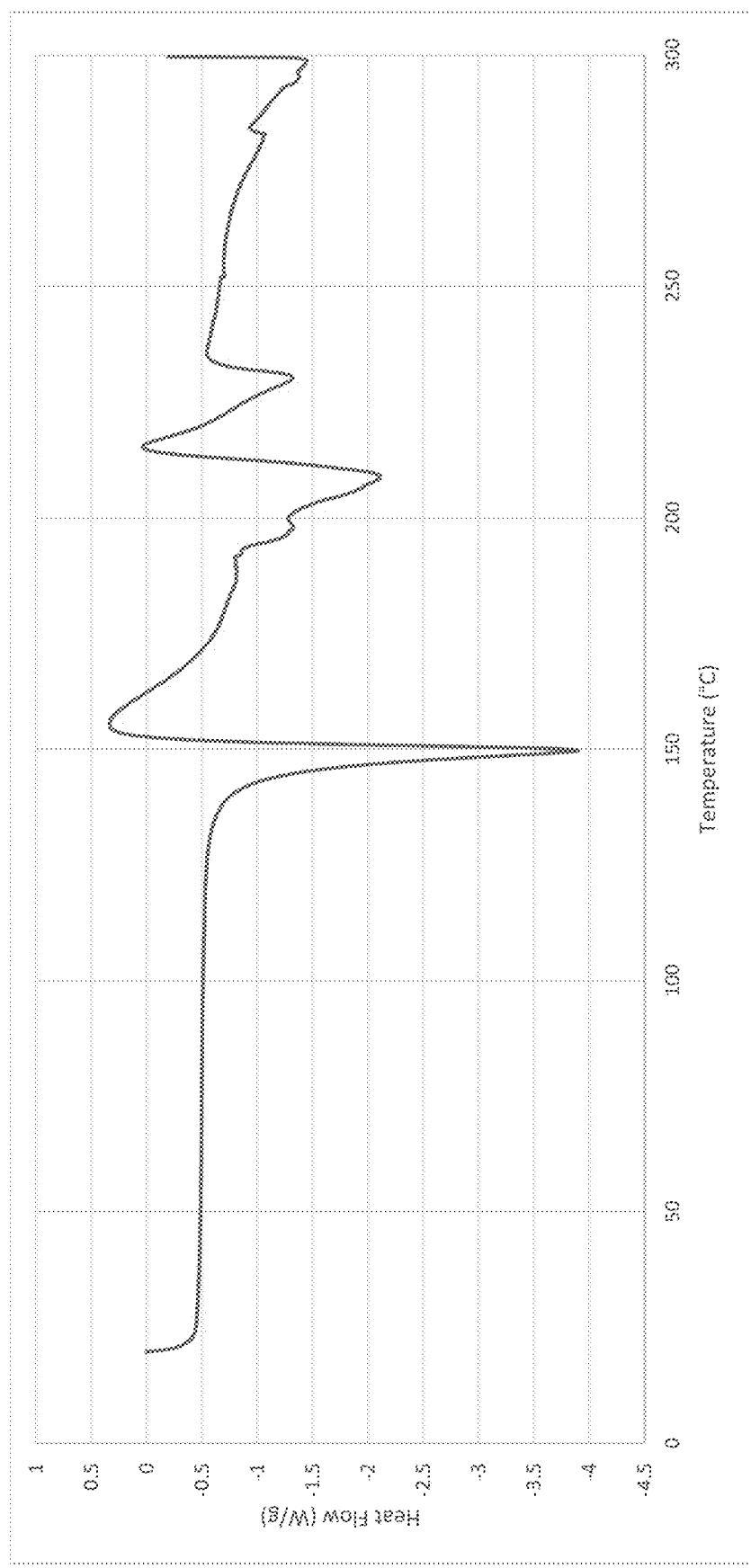
FIG. 31 provides a DSC thermogram for a sample of the presently disclosed Form I of crystalline nicotinamide riboside triacetate (1-(2',3',5'-triacetyl-beta-D-ribofuranosyl)-nicotinamide, "NR triacetate," or "NRTA"), the compound having formula (IX), which was heated at a rate of 10 K/min.

In yet another embodiment, crystalline Form I of nicotinamide riboside triacetate (NRTA) chloride may be characterized by a DSC thermogram substantially as shown in FIG. 31.

C. Synthetic preparation of nicotinamide riboside triflate (Compound 3): Compound of formula (Ia): $R^1$=hydrogen, n=0, $Z^2$=NH, $R^2$=$R^3$=$R^4$=$R^5$=hydrogen, $X^-$=triflate, $R^6$=$R^7$=$R^8$=acetyl.

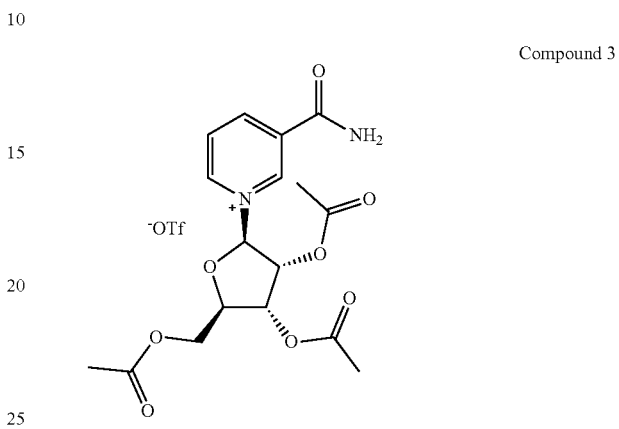

Compound 3

Figure 12:
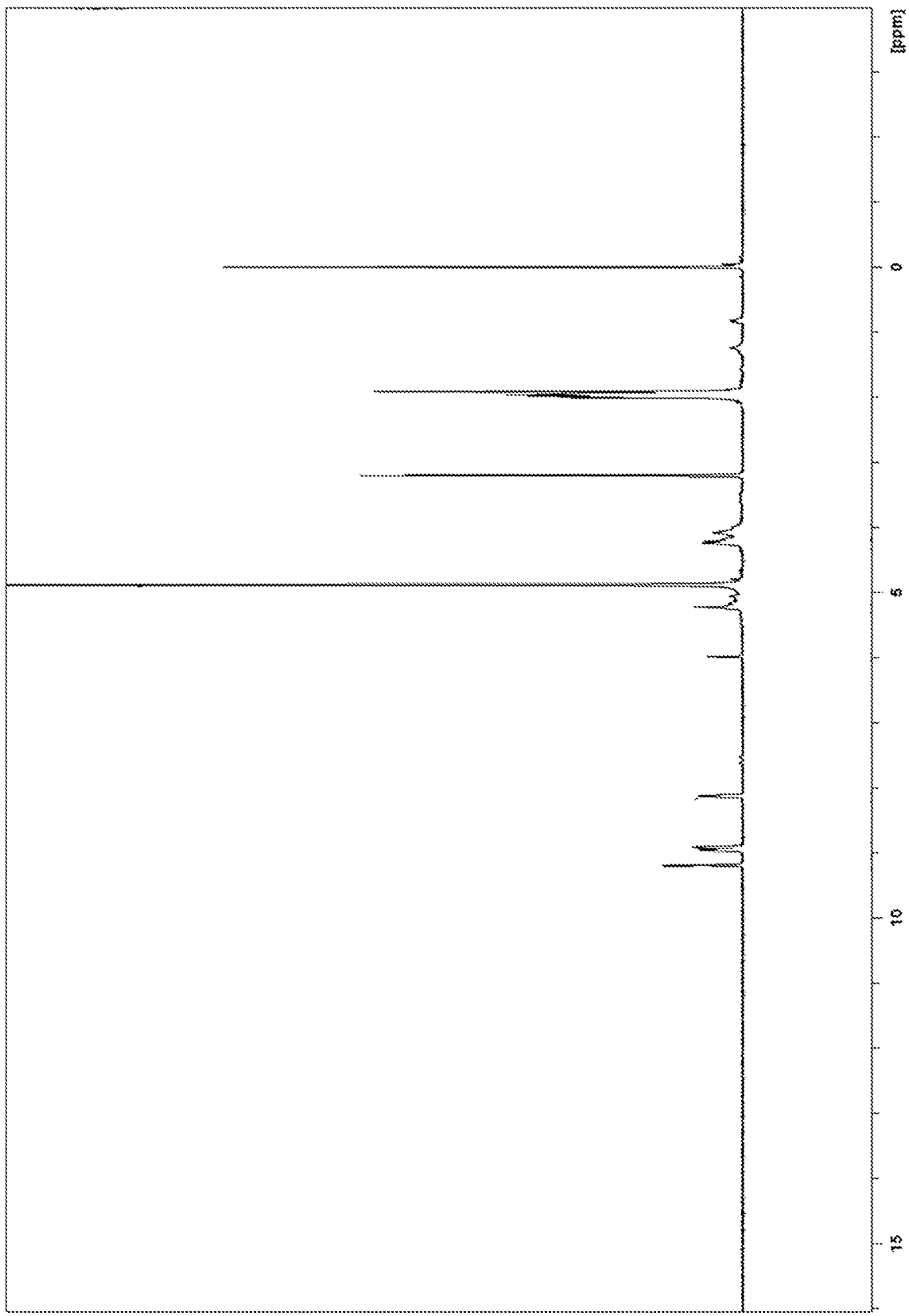
FIG. 12 depicts a $^1$H NMR spectrum of the reaction mixture, performed in accordance with one embodiment of the described method for the preparation of a compound or derivative having general formula (Ia-H), or a salt, solvate, or prodrug thereof, wherein $R^6$, $R^7$, and $R^8$ are each hydrogen, according to the procedure described in Example 1, Part C, wherein reaction was conducted for 10 minutes at 50 RPM.
Figure 13:
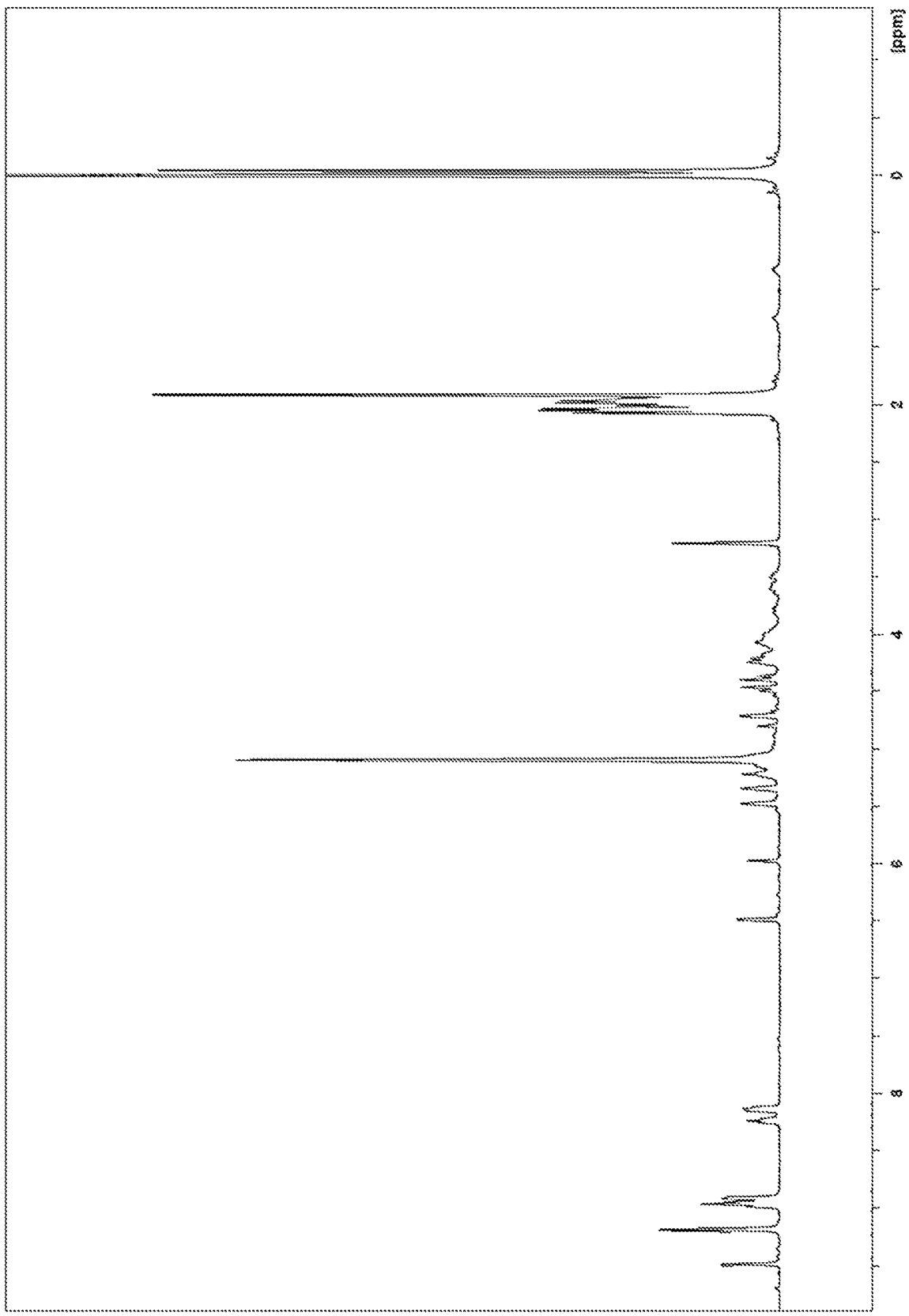
FIG. 13 depicts a $^1$H NMR spectrum of the reaction mixture, performed in accordance with one embodiment of the described method for the preparation of a compound or derivative having general formula (Ia-H), or a salt, solvate, or prodrug thereof, wherein $R^6$, $R^7$, and $R^8$ are each hydrogen, according to the procedure described in Example 1, Part C, wherein reaction was conducted for 10 minutes at 100 RPM.
Figure 14:
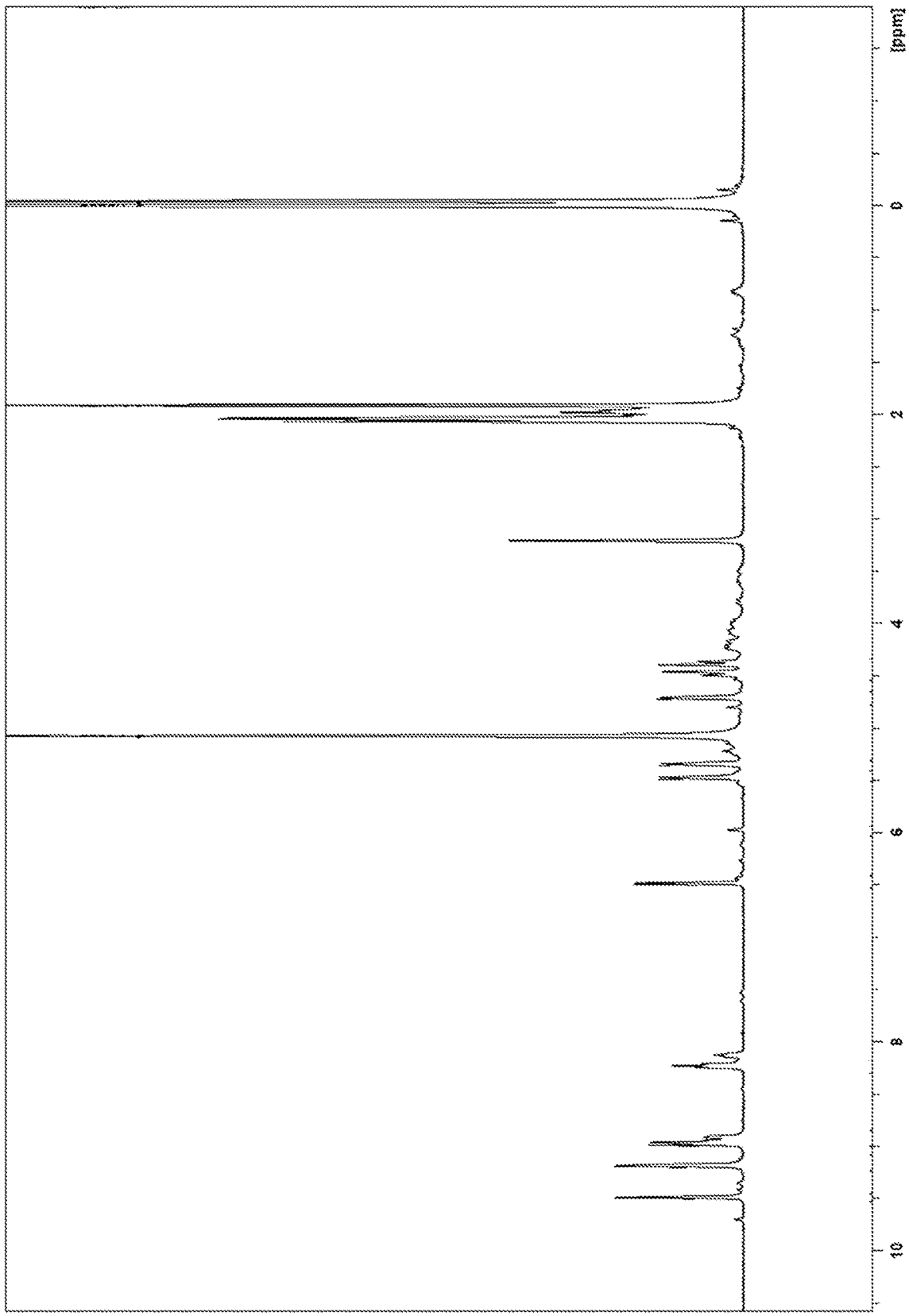
FIG. 14 depicts a $^1$H NMR spectrum of the reaction mixture, performed in accordance with one embodiment of the described method for the preparation of a compound or derivative having general formula (Ia-H), or a salt, solvate, or prodrug thereof, wherein $R^6$, $R^7$, and $R^8$ are each hydrogen, according to the procedure described in Example 1, Part C, wherein reaction was conducted for 15 minutes at 250 RPM.

A range of reaction conditions have been explored, whereby extrusion was used in order to achieve the production of Compound 3 from riboside tetraacetate, TMSOTf, and nicotinamide. Table 1 describes the conditions applied to improve conversion. Reagent addition rate, extruder screw profile, rotation speed, and temperature of the barrel affected the reaction outcomes and the α:β anomeric ratio of Compound 3. For instance, by increasing the extruder speed from 50 RPM to 250 RPM and the residency time from 10 min to 15 min, the crude conversion yields increased from 0 to 9200, as per evidence in FIGS. 12-14. These results demonstrate that extrusion is suitable for the continuous production of Compound 3 by extrusion with currently optimized yields above 92%, with the possibility of recycling unreacted riboside tetraacetate.

D. Synthetic Preparation of Nicotinic Acid Riboside (Compound 4): Compound of Formula (Ia-H):
$R^1$=Hydrogen, n=0. $Z^2$=Oxygen.
$R^2$=$R^3$=$R^4$=$R^5$=$R^6$=$R^7$=$R^8$=Hydrogen

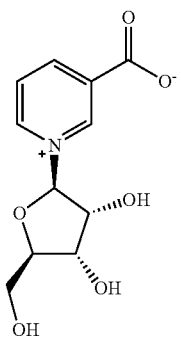

Compound 4

To a dry round-bottom flask was added nicotinic acid (40 g, 324.9 mmol, 1.0 equiv.), followed by HMDS (200 g, 1239.2 mmol, 3.8 equiv.) and a catalytic amount of ammonium sulphate (10% mol equiv.). The suspension was then heated to reflux under an atmosphere of nitrogen gas for 12 hours. The solution was cooled to room temperature, and the excess HMDS was removed under reduced pressure. The gummy oil was then resuspended in freshly distilled dichloroethane (150 mL), followed by the addition of riboside tetraacetate (103 g, 322.6 mmol, 1.0 equiv.) and TMSOTf (58 mL, 322.6 mmol, 1.0 equiv.). The solution was heated to 40° C. and left stirring overnight under nitrogen gas. After NMR analysis indicated that the reaction had reached completion, the solution was allowed to cool to room temperature. With intensive stirring, 100 mL of distilled water was added followed by the rapid addition of a saturated NaHCO$_3$ solution (approximately 50 mL). The pH was adjusted to approximately 6, and the organic phase was separated, then the aqueous layer was washed three additional times with dichloromethane (100 mL), the aqueous layer was then frozen and freeze-dried to give an off-white solid, which was characterized infra as crystalline Form I of nicotinic acid riboside triacetate (NARTA) without further purification. In a glass pressure tube, the crude was suspended into methanol, and ammonia gas was bubbled into the solution for five minutes with the temperature held at −78° C. The tube was then sealed and stored at −20° C. for 4 days, after which the solution was concentrated under reduced pressure. The crude was then resolubilized into methanol and an equivalent volume of acetone was added, causing a phase separation to occur. The precipitate was then filtered under reduced pressure and washed an additional five times with cold methanol to yield nicotinic acid riboside (Compound 4) as a free-flowing orange powder in 74% yield.

$^1$H NMR (400 MHz, D20): δ ppm 9.33 (br s, 1H, aromatic), 9.02 (d, J=6.3 Hz, 1H, aromatic), 8.81 (dt, J=8.0, 1.3 Hz, 1H, aromatic), 8.06 (dd, J=8.0, 6.3 Hz, 1H, aromatic), 6.09 (d, J=4.8 Hz, 1H, H-1 (anomeric)), 4.37 (dd, J=4.8, 4.5 Hz, 1H, H-2), 4.33-4.36 (m, 1H, H-4), 4.23 (t, J=4.5 Hz, 1H, H-3), 3.91 (AB$_X$, J$_{A,A'}$=12.9 Hz, J$_{A,B}$=3.9 Hz, 1H, H-5), 3.78 (AB$_X$, J$_{A,A'}$=12.9 Hz, J$_{A,B}$=2.9 Hz, 1H, H-5'). $^{13}$C NMR (100 MHz, D20): δ ppm 167.5 (COOH), 146.9, 141.3, 140.9, 137.3, 127.9 (aromatic), 99.6 (C-1 (anomeric)), 87.6 (C-4), 77.5 (C-2), 70.0 (C-3), 60.4 (C-5). HRMS (ES, M+H$^+$) calculated 256.0821 for C$_{11}$H$_{13}$NO$_6$, found 256.0818.

Figure 45:
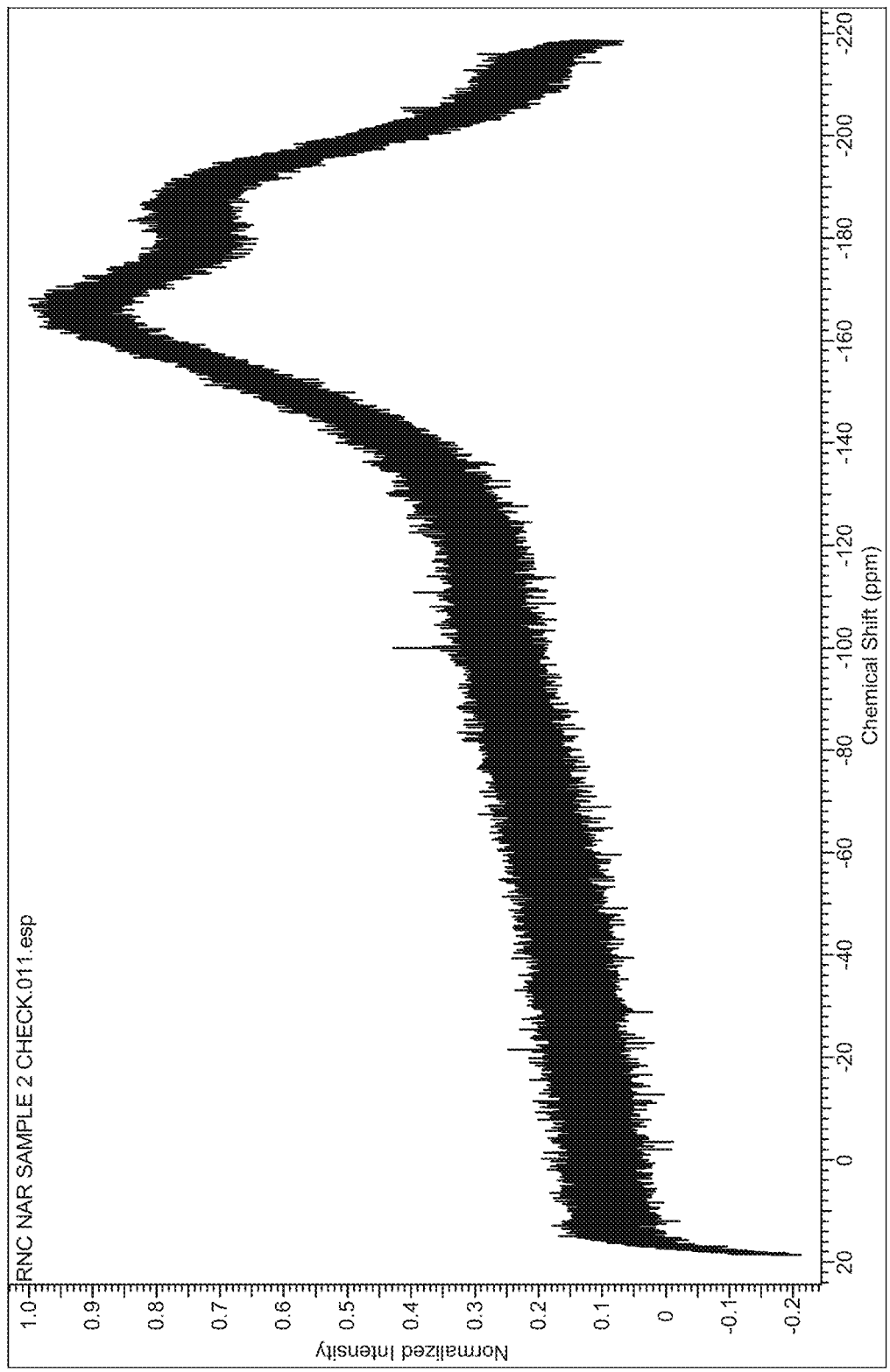
FIG. 45 depicts a $^{19}$F NMR spectrum of product nicotinic acid riboside (NAR), the compound having formula (VIII), prepared according to an embodiment of the described methods for the preparation of a compound or derivative having general formula (Ia-H), or a salt, solvate, or prodrug thereof, wherein $R^6$, $R^7$, and $R^8$ are each hydrogen, showing the absence of any fluorine shifts corresponding to the absence of any fluorine-containing species in the product, and wherein the method includes the use of a Lewis acid including a trifluoromethanesulfonate ("triflate") species.
Figure 46:
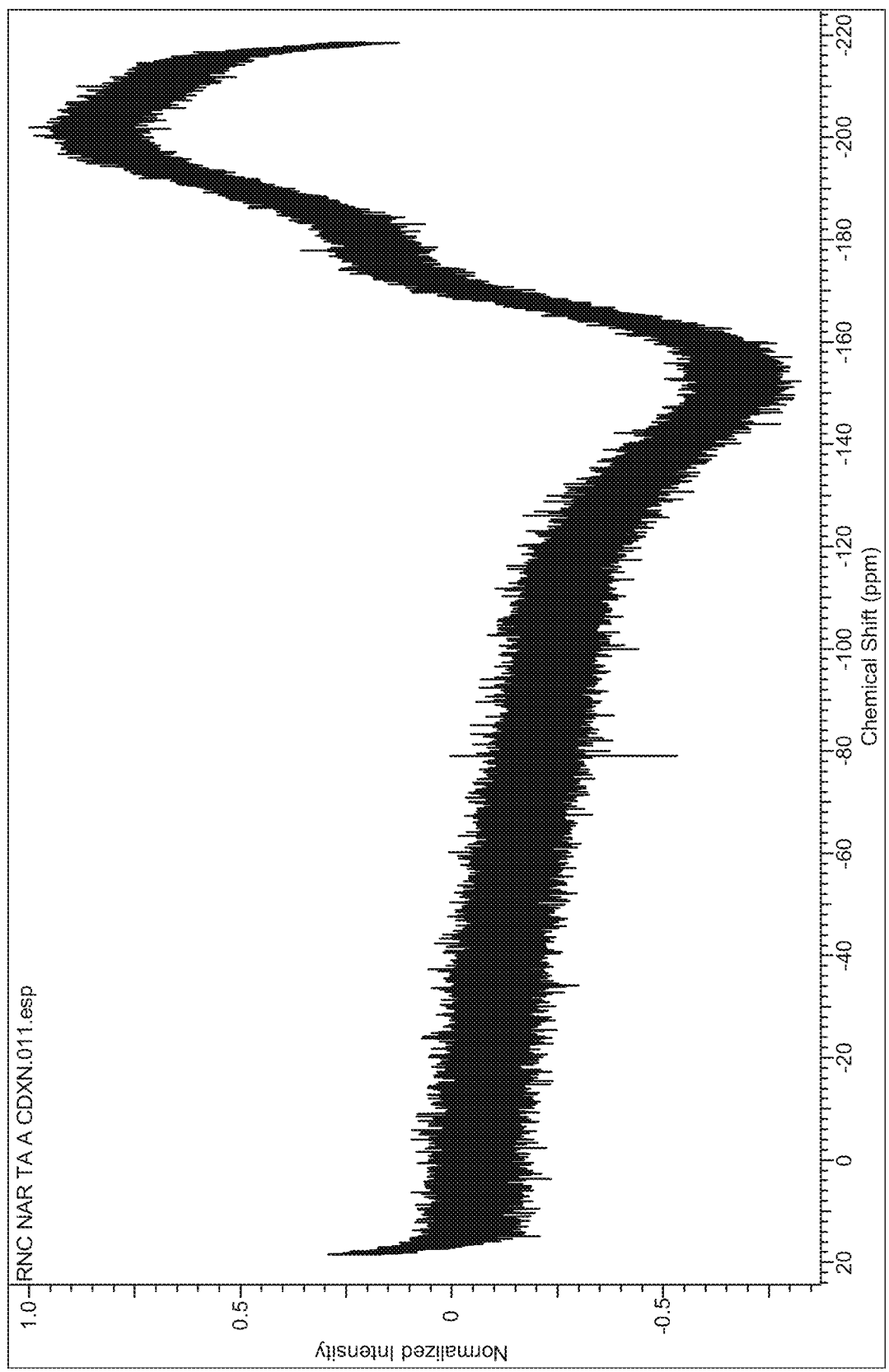
FIG. 46 depicts a $^{19}$F NMR spectrum of product nicotinic acid riboside triacetate (NARTA), the compound having formula (X), prepared according to an embodiment of the described methods for the preparation of a compound or derivative having general formula (Ia), or a salt, solvate, or prodrug thereof, showing the absence of any fluorine shifts corresponding to the absence of any fluorine-containing species in the product, and wherein the method includes the use of a Lewis acid including a trifluoromethanesulfonate ("triflate") species.

Nicotinic acid riboside (Compound 4) was shown to be free of triflate according to $^{19}$F NMR, as shown in FIG. 45. Crude nicotinic acid riboside triacetate (NARTA) was shown to be free of triflate according to $^{19}$F NMR, as shown in FIG. 46.

The crystalline Form I of nicotinic acid riboside (NAR, Compound 4) may be characterized by a powder X-ray diffraction pattern having peaks at 19.2, 21.6, and 26.4 degrees two theta±0.2 degrees two theta. The crystalline Form I of nicotinic acid riboside (NAR) may also or alternatively be characterized by a powder X-ray diffraction pattern having peaks at 15.7, 19.2, 21.6, 26.4, and 28.9 degrees two theta±0.2 degrees two theta. The crystalline Form I of nicotinic acid riboside (NAR) may also or alternatively be characterized by a powder X-ray diffraction pattern having peaks at 12.8, 13.2, 15.7, 19.2, 20.5, 21.6, 26.4, 28.3, 28.9 degrees two theta±0.2 degrees two theta.

Figure 17:
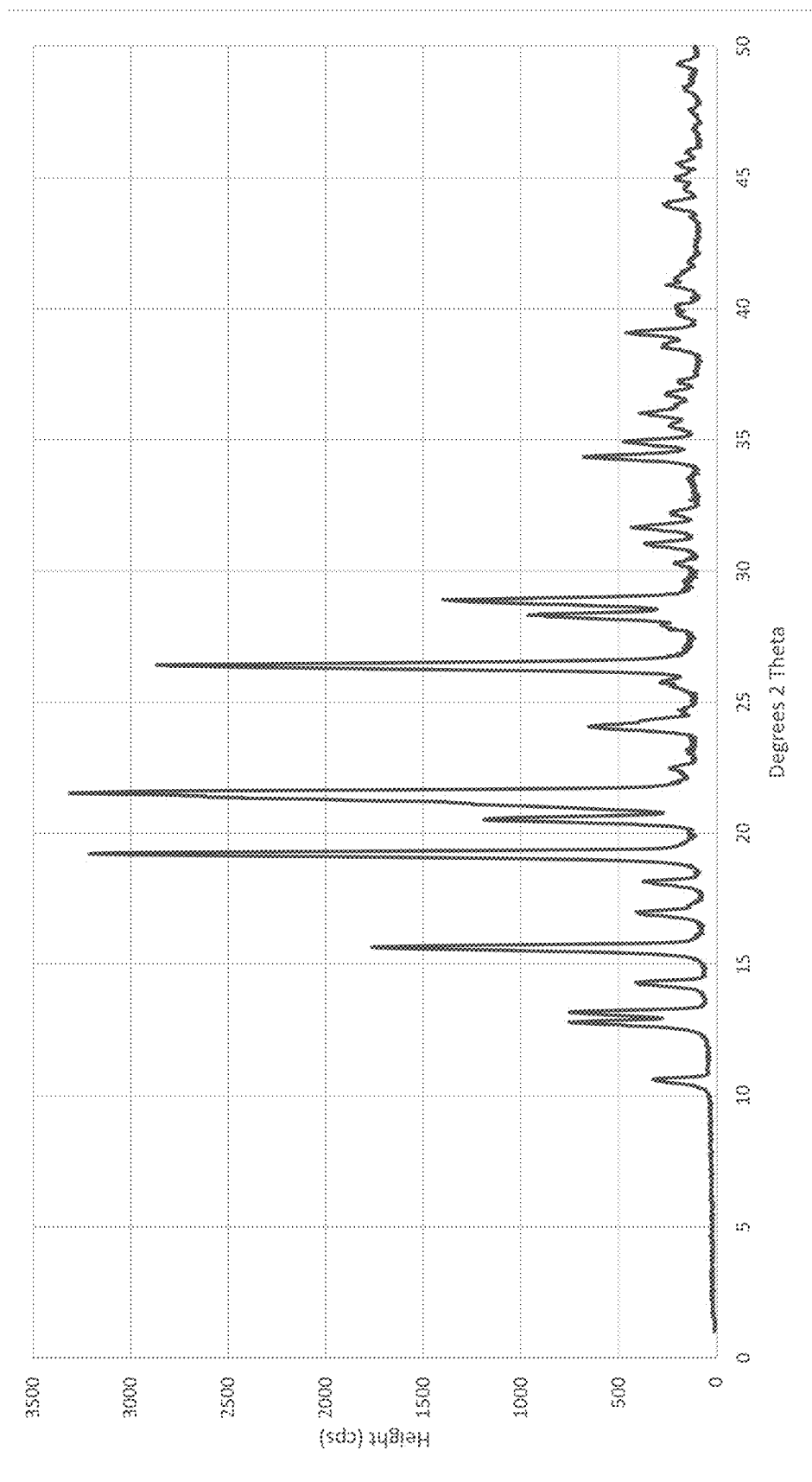
FIG. 17 provides an X-ray powder diffraction pattern for the presently disclosed Form I of crystalline nicotinic acid riboside (NAR), the compound having formula (VIII), prepared according to an embodiment of the presently disclosed methods for the preparation of a compound or derivative having general formula (Ia-H), or a salt, solvate, or prodrug thereof, wherein $R^6$, $R^7$, and $R^8$ are each hydrogen.

In other embodiments, the crystalline Form I of nicotinic acid riboside (NAR) may be characterized by a powder X-ray diffraction pattern substantially as shown in FIG. 17. The crystalline Form I of nicotinic acid riboside (NAR) may also or alternatively be characterized by a powder X-ray diffraction pattern having peaks substantially as provided in Table 4, below, 0.2 degrees two theta.

TABLE 4

| Peak No. | Pos. [°2Th.] | d-spacing [Å] | Height [cts] | I/I$_{max}$ [%] |
|---|---|---|---|---|
| 1 | 10.634 | 8.312 | 321 | 9 |
| 2 | 12.808 | 6.906 | 711 | 20 |
| 3 | 13.179 | 6.713 | 778 | 22 |
| 4 | 14.298 | 6.1894 | 387 | 11 |
| 5 | 15.669 | 5.651 | 1892 | 53 |
| 6 | 16.946 | 5.228 | 346 | 10 |
| 7 | 18.137 | 4.887 | 276 | 8 |
| 8 | 19.237 | 4.61 | 3542 | 100 |
| 9 | 20.548 | 4.3189 | 1233 | 35 |
| 10 | 21.5597 | 4.1184 | 3298 | 93 |
| 11 | 24.019 | 3.702 | 541 | 15 |
| 12 | 25.76 | 3.456 | 150 | 4 |
| 13 | 26.387 | 3.375 | 3098 | 87 |
| 14 | 27.87 | 3.198 | 165 | 5 |
| 15 | 28.3 | 3.151 | 932 | 26 |
| 16 | 28.874 | 3.0897 | 1425 | 40 |
| 17 | 30.26 | 2.951 | 109 | 3 |
| 18 | 30.983 | 2.884 | 276 | 8 |
| 19 | 31.643 | 2.8253 | 339 | 10 |
| 20 | 32.2 | 2.777 | 128 | 4 |
| 21 | 34.336 | 2.6096 | 602 | 17 |
| 22 | 34.931 | 2.5665 | 380 | 11 |
| 23 | 35.51 | 2.526 | 118 | 3 |
| 24 | 35.9 | 2.4994 | 237 | 7 |
| 25 | 36.75 | 2.444 | 148 | 4 |
| 26 | 38.53 | 2.335 | 165 | 5 |
| 27 | 39.042 | 2.3052 | 384 | 11 |
| 28 | 39.95 | 2.255 | 97 | 3 |
| 29 | 40.84 | 2.208 | 121 | 3 |
| 30 | 43.984 | 2.057 | 216 | 6 |
| 31 | 45.04 | 2.0113 | 101 | 3 |
| 32 | 45.412 | 1.9956 | 124 | 4 |

Figure 23:
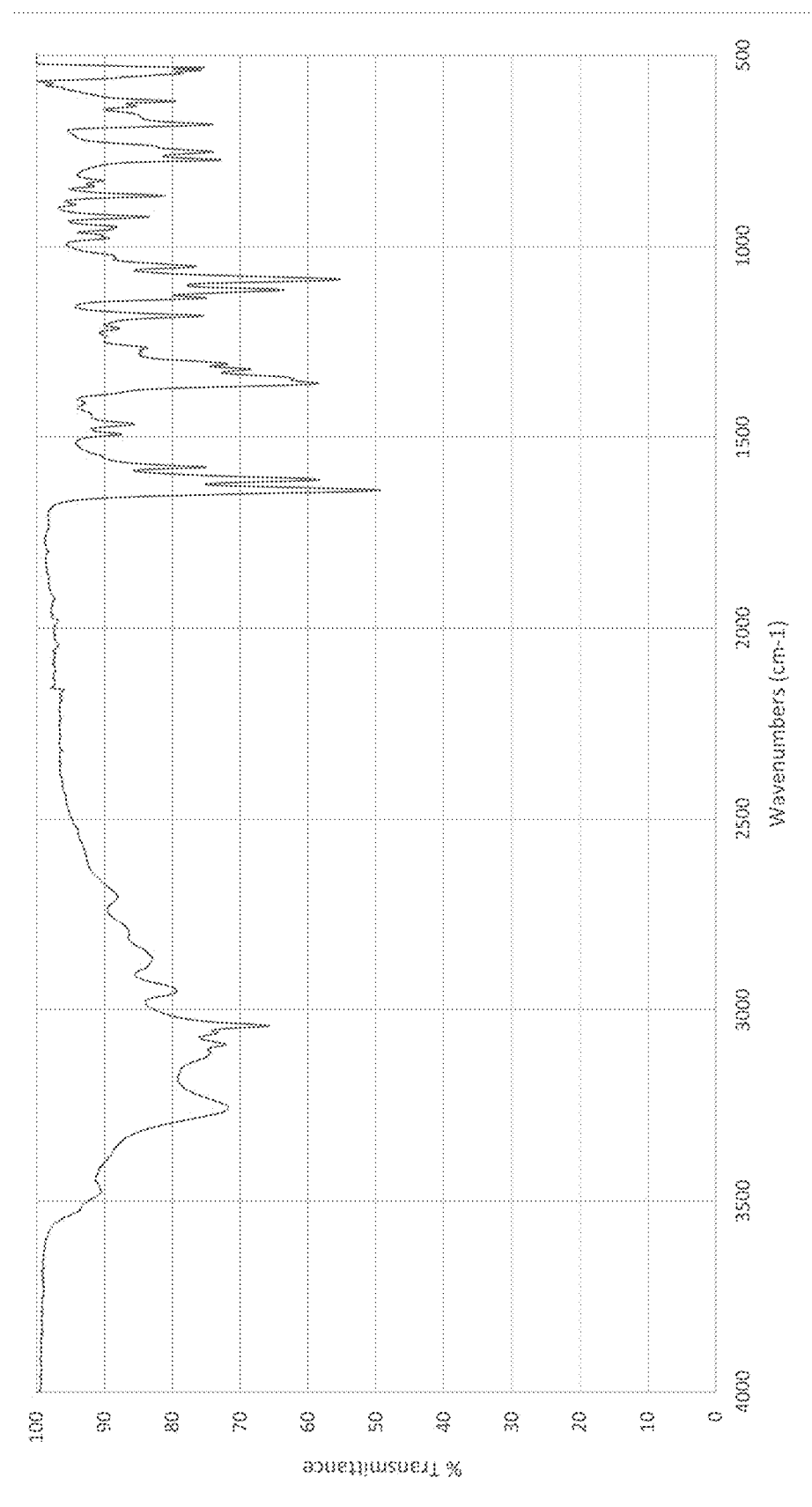
FIG. 23 provides a solid state IR spectrum for the presently disclosed Form I of crystalline nicotinic acid riboside (NAR), the compound having formula (VIII).

The crystalline Form I of nicotinic acid riboside (NAR, Compound 4) may also or alternatively be characterized by a solid-state JR spectrum having peaks at 534.2, 680.8, 754.0, and 773.3 cm$^{-1}$±0.2 cm$^{-1}$. The crystalline Form I of nicotinic acid riboside (NAR) may also or alternatively be characterized by a solid-state JR spectrum having peaks at 534.2, 680.8, 754.0, 773.3, 1087.7, 1114.7, and 1359.6 cm$^{-1}$±0.2 cm$^{-1}$. The crystalline Form I of nicotinic acid riboside (NAR) may also or alternatively be characterized by a solid-state JR spectrum having peaks at 534.2, 680.8, 754.0, 773.3, 1087.7, 1114.7, 1359.6, 1579.4, 1612.2, and 1639.2 cm$^{-1}$±0.2 cm$^{-1}$. In certain embodiments, the crystalline Form I of nicotinic acid riboside (NAR) may also or alternatively be characterized by a solid-state IR spectrum substantially as shown in FIG. 23. In further embodiments, the crystalline Form I of nicotinic acid riboside (NAR) may also or alternatively be characterized by a solid-state IR spectrum having peaks substantially as provided in Table 5, below, 0.2 cm$^{-1}$.

TABLE 5

| IR (cm$^{-1}$) |
|---|
| 3257.23 |
| 3091.38 |
| 3060.53 |
| 3041.24 |
| 2950.60 |
| 1639.22 |
| 1612.23 |
| 1579.44 |
| 1492.66 |
| 1465.66 |
| 1359.59 |

TABLE 5-continued

| IR (cm$^{-1}$) |
| --- |
| 1346.09 |
| 1322.95 |
| 1309.45 |
| 1267.02 |
| 1214.95 |
| 1182.17 |
| 1135.89 |
| 1114.67 |
| 1087.67 |
| 1052.96 |
| 979.67 |
| 948.82 |
| 923.75 |
| 867.82 |
| 773.33 |
| 754.04 |
| 680.76 |
| 632.55 |
| 620.98 |
| 534.19 |

In another embodiment, crystalline Form I of nicotinic acid riboside (NAR) is characterized by a DSC thermogram obtained using a heating rate of 10 K/min comprising an endothermic event with an onset temperature of 156° C.±2° C.

In yet another embodiment, crystalline Form I of nicotinic acid riboside (NAR) is characterized by a DSC thermogram obtained using a heating rate of 10 K/min comprising an endothermic event with a peak temperature of 164° C.±2° C.

In yet another embodiment, crystalline Form I of nicotinic acid riboside (NAR) is characterized by a DSC thermogram obtained using a heating rate of 10 K/min comprising an endothermic event with an onset temperature of 156° C.±2° C., a peak temperature of 164° C.±2° C., or both.

Figure 32:
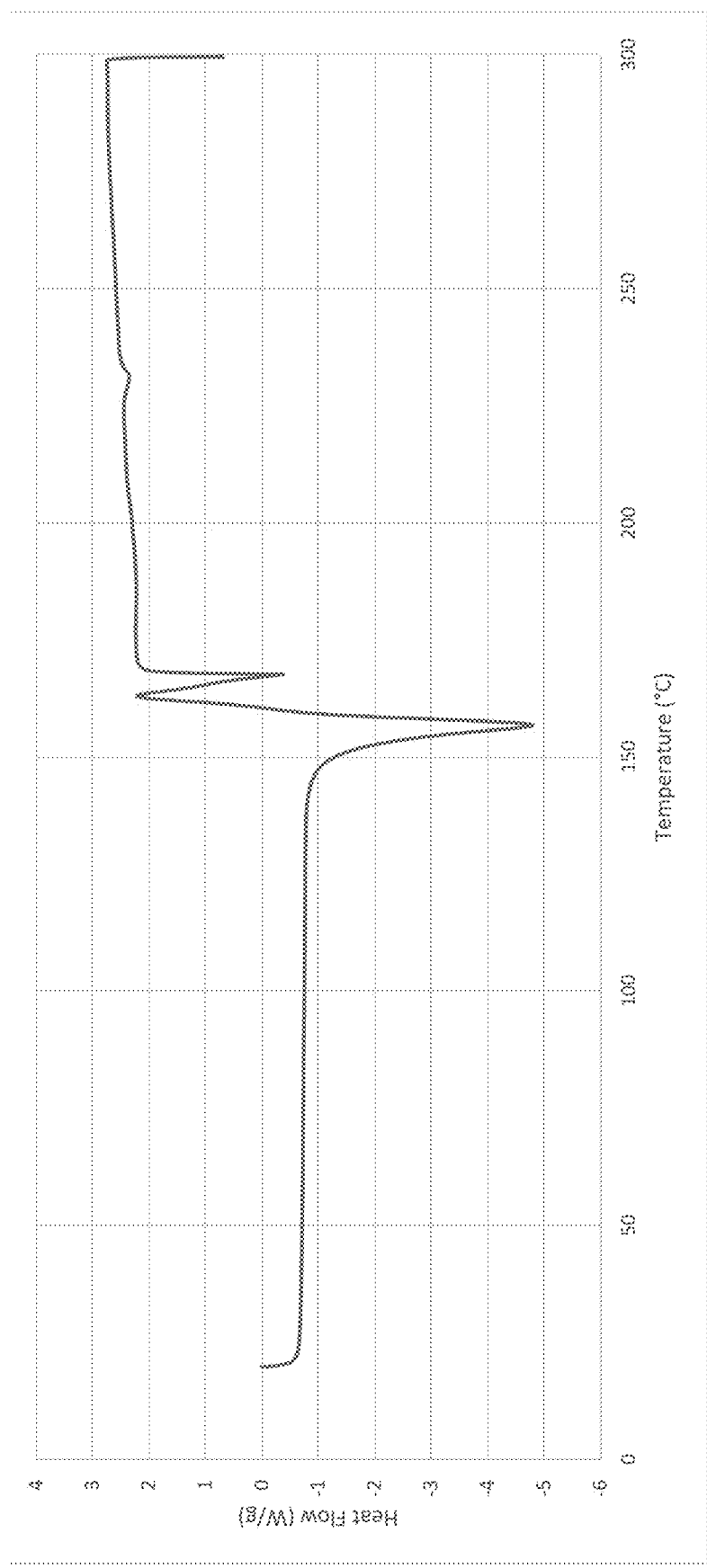
FIG. 32 provides a DSC thermogram for a sample of the presently disclosed Form I of crystalline nicotinic acid riboside (NAR), the compound having formula (VIII), which was heated at a rate of 10 K/min.

In yet another embodiment, crystalline Form I of nicotinic acid riboside (NAR) may be characterized by a DSC thermogram substantially as shown in FIG. 32.

E. Synthetic Preparation of Nicotinamide Riboside Chloride (Compound 5): Compound of Formula (Ia-H): R$^1$=Hydrogen, n=0, Z$^2$=NH, R$^2$=R$^3$=R$^4$=R$^5$=R$^6$=R$^7$=R$^8$=Hydrogen, X$^-$=Chloride

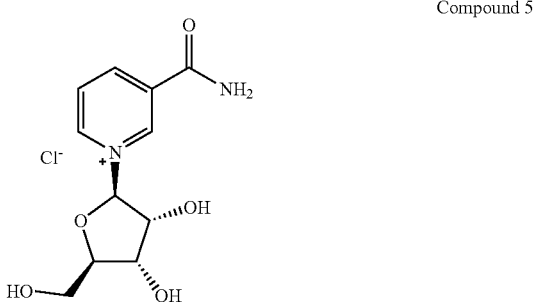 [SMILES: NC(=O)c1ccc[n+]([C@@H]2O[C@H](CO)[C@@H](O)[C@H]2O)c1 ; [Cl-]]

Compound 5

To a screw setup extruder, a premix of 60 g of Compound 2 and 120 g K$_2$CO$_3$ were pre-mixed and fed at approximately 2 grams/minute (4% feed rate). The peristaltic pump was set to 1.6 mL/min, the chiller bath set to −2.5° C., and the extruder was set to 10° C. Methanol was chilled in a −80° C. freezer. The solution was quenched with 2 M aqueous HCl, the pH was brought to 6, and a sample was removed and concentrated. $^1$H NMR demonstrated complete deprotection. Additional equivalents of K$_2$CO$_3$ appear advantageous for the reaction. It is expected that performing the deprotection reaction at a higher temperature with immediate quenching would drive the reaction to completion.

$^1$H NMR (400 MHz, D2O): δ ppm 9.46 (s, 1H, aromatic), 9.12 (dt, J=6.3, 1.4 Hz, 1H, aromatic), 8.83 (dt, J=8.2, 1.4 Hz, 1H, aromatic), 8.13 (dd, J=8.2, 6.3 Hz, 1H, aromatic), 6.13 (d, J=4.3 Hz, 1H, H-1 (anomeric)), 4.37 (t, J=4.7 Hz, 1H, H-2), 4.31-4.34 (m, 1H, H-4), 4.21 (t, J=4.7 Hz, 1H, H-3), 3.90 (AB$_X$, J$_{A,A'}$=13.0 Hz, J$_{A,B}$=3.5 Hz, 1H, H-5), 3.75 (AB$_X$, J$_{A,A'}$=13.0 Hz, J$_{A,B}$=2.8 Hz, 1H, H-5'). $^{13}$C NMR (100 MHz, D2O): δ ppm 165.8 (C(=O)NH$_2$), 145.7, 142.7, 140.4, 134.0, 128.5 (aromatic), 100.0 (C-1 (anomeric)), 87.8 (C-4), 77.5 (C-2), 69.9 (C-3), 60.3 (C-5). HRMS (ES, M+) calculated 255.0981 for C$_{11}$H$_{15}$N$_2$O$_5$, found 255.0986.

In other embodiments of the present invention, extruding can be performed from about 0.5 gram/minute to about 20 grams/minute, preferably from about 0.5 grams/minute to about 10 grams/minute, most preferably from about 0.5 grams/minute to about 5 grams/minute. Extruding can be performed with the peristaltic pump at from about 0.25 mL/min to about 10 mL/min, the chiller bath set from about −10° C. to about 19° C., and the extruder set to from about 5° C. to about 75° C.

Figure 8:
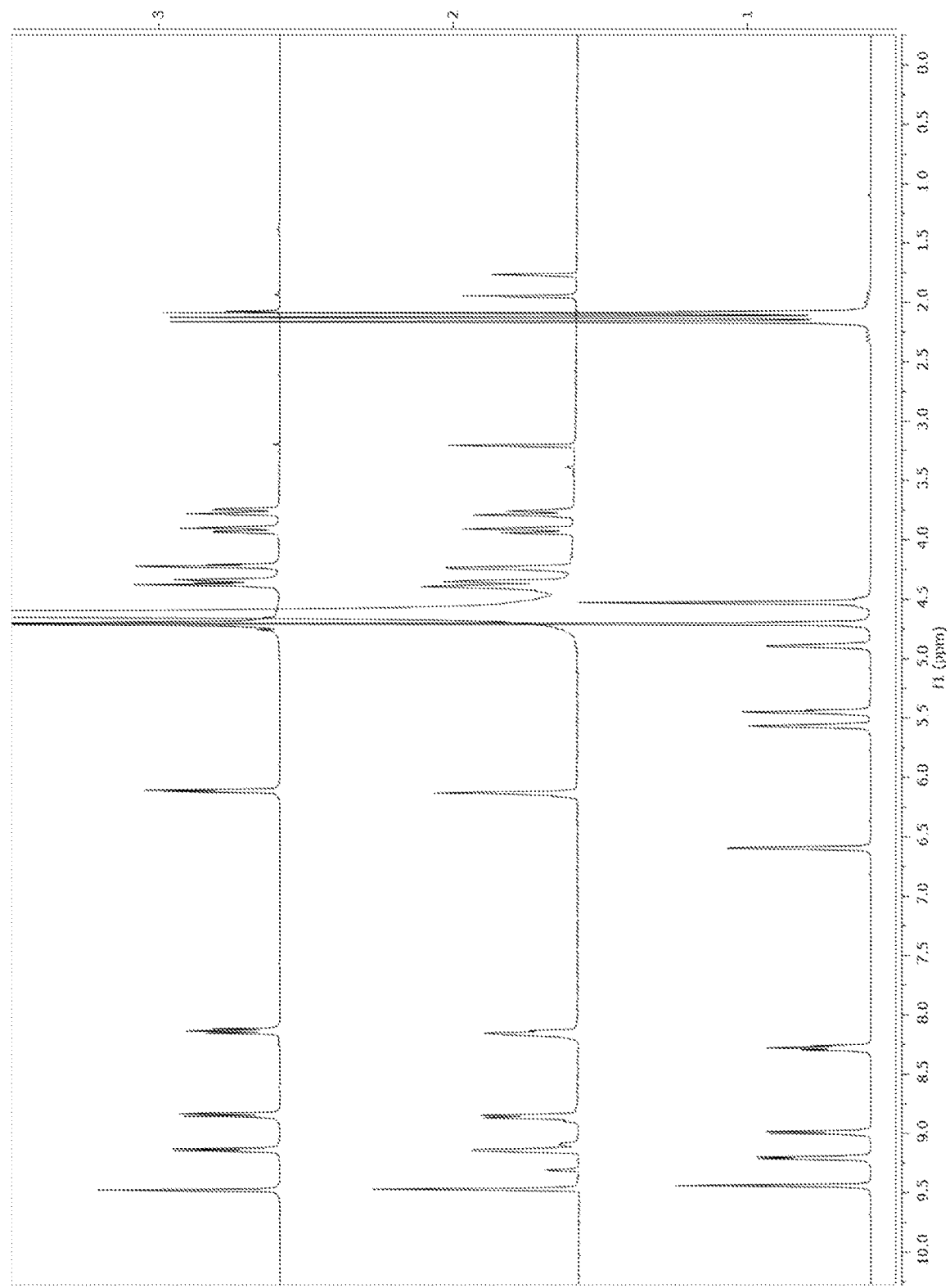
FIG. 8 depicts a comparison of $^1$H NMR spectra of a compound or derivative having general formula (I) as starting material (bottom), the reaction product mixture after treatment at low temperature with a base addition salt according to the procedure described in Example 1, Part D (middle), performed in accordance with one embodiment of the described method for the preparation of a compound or derivative having general formula (I-H) or a salt, solvate, or prodrug thereof, wherein $R^6$, $R^7$, and $R^8$ are each hydrogen, and purified desired product (top).
Figure 9:
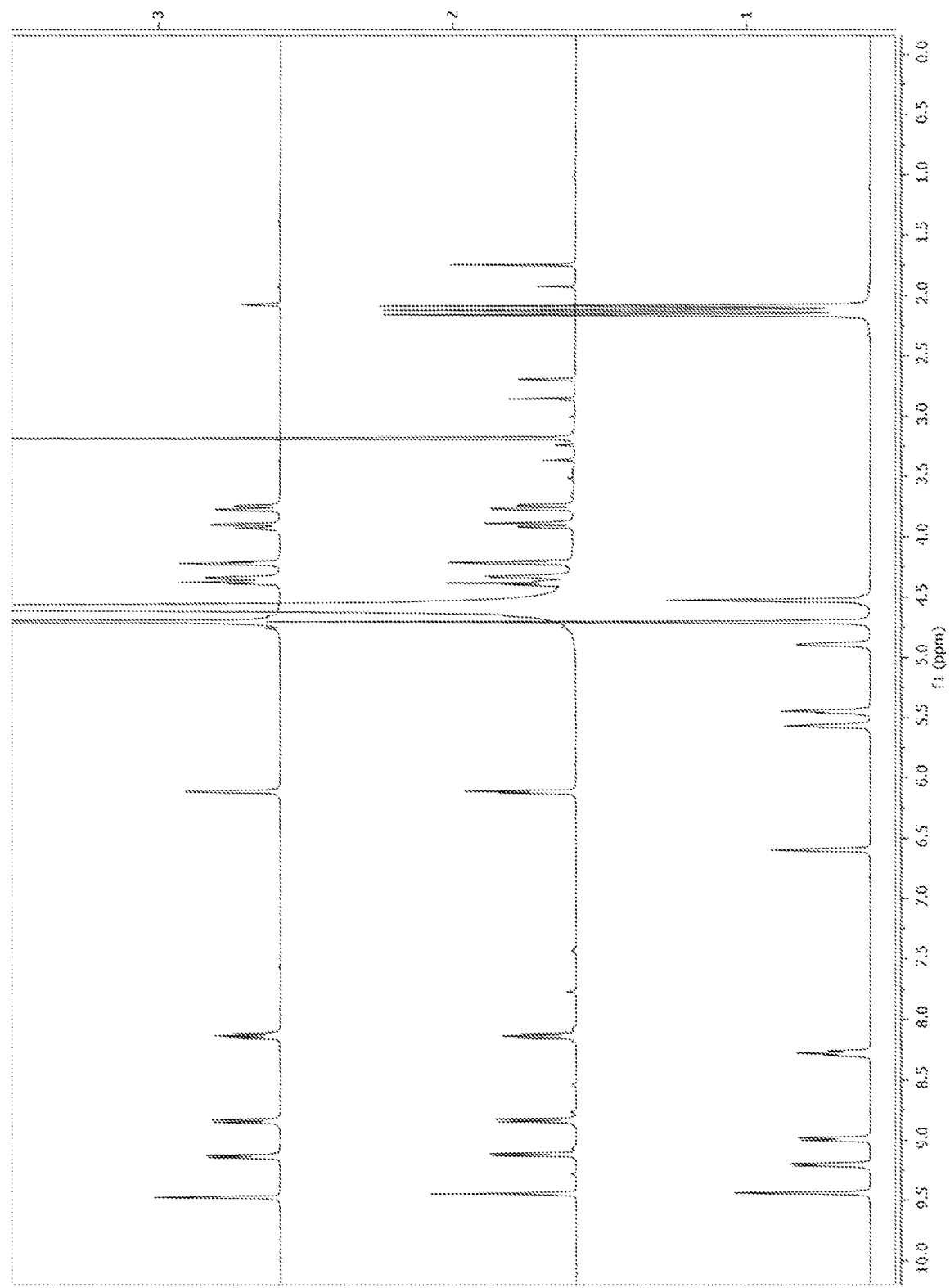
FIG. 9 depicts a comparison of $^1$H NMR spectra of a compound or derivative having general formula (I) as starting material (bottom), the reaction product mixture after treatment at room temperature with a base addition salt according to the procedure described in Example 1, Part D (middle), performed in accordance with one embodiment of the described method for the preparation of a compound or derivative having general formula (I-H) or a salt, solvate, or prodrug thereof, wherein $R^6$, $R^7$, and $R^8$ are each hydrogen, and purified desired product (top).
Figure 10:
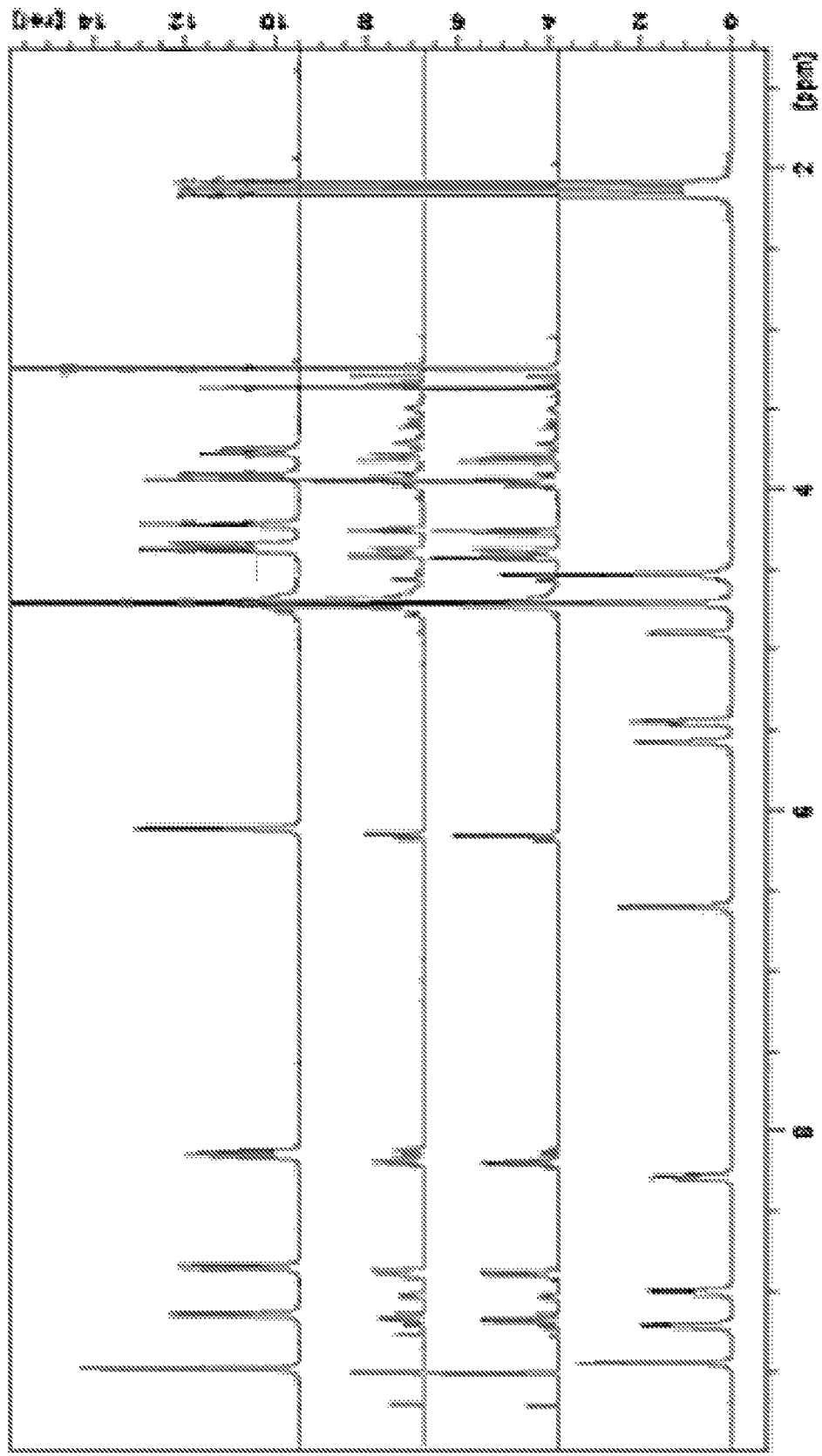
FIG. 10 depicts a comparison of $^1$H NMR spectra of a compound or derivative having general formula (I) as starting material (bottom), the reaction product mixture after treatment at room temperature with acid addition at two different concentrations according to the procedure described in Example 1, Part D (middle), performed in accordance with one embodiment of the described method for the preparation of a compound or derivative having general formula (Ia-H) or a salt, solvate, or prodrug thereof, wherein $R^6$, $R^7$, and $R^8$ are each hydrogen, and purified desired product (top).

The reaction was repeated at room temperature with immediate quenching. To a screw setup extruder, a premix of 60 g of Compound 2 and 120 g K$_2$CO$_3$ were pre-mixed and fed at approximately 2 grams/minute (4% feed rate). The peristaltic pump was set to 2.75, the chiller bath set to 18° C., and the extruder was set to 21° C. Methanol was kept at room temperature. The reaction was quenched with 2 M aqueous HCl, the pH was brought to 6.4, and a sample was taken and concentrated. As shown in FIGS. 8 and 9, by comparison of $^1$H NMR spectra of starting material and product, $^1$H NMR demonstrated 94% conversion to Compound 5 (product mixture, middle; purified product, top), with 4% monoacetylated product and 2% nicotinamide (bottom).

Figure 11A:
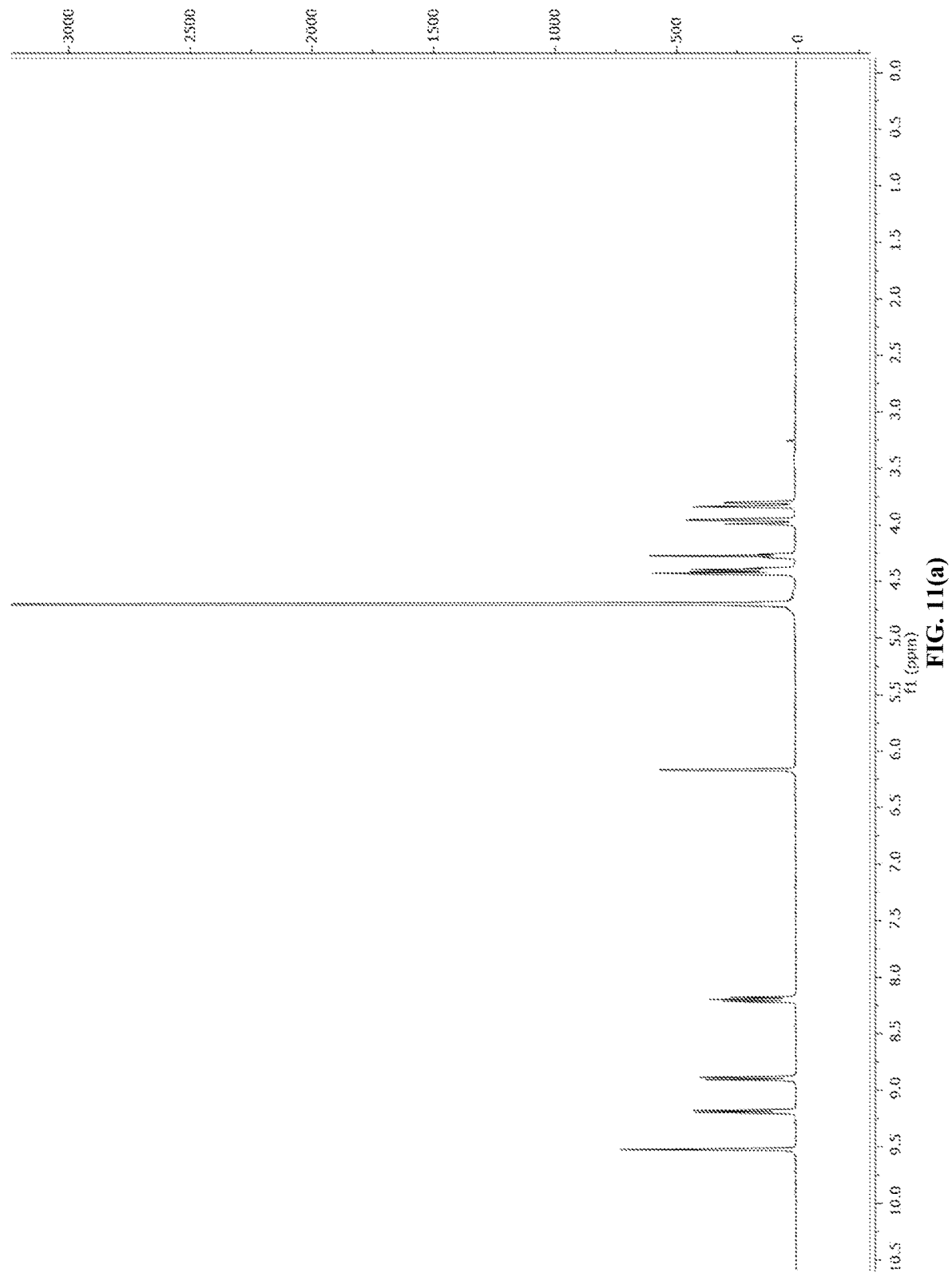
FIG. 11(a) depicts a $^1$H NMR spectrum of a product filtrate of a compound or derivative having general formula (Ia-H), performed in accordance with one embodiment of the described method for the preparation of a compound or derivative having general formula (Ia-H) or a salt, solvate, or prodrug thereof, wherein $R^6$, $R^7$, and $R^8$ are each hydrogen.
Figure 11B:
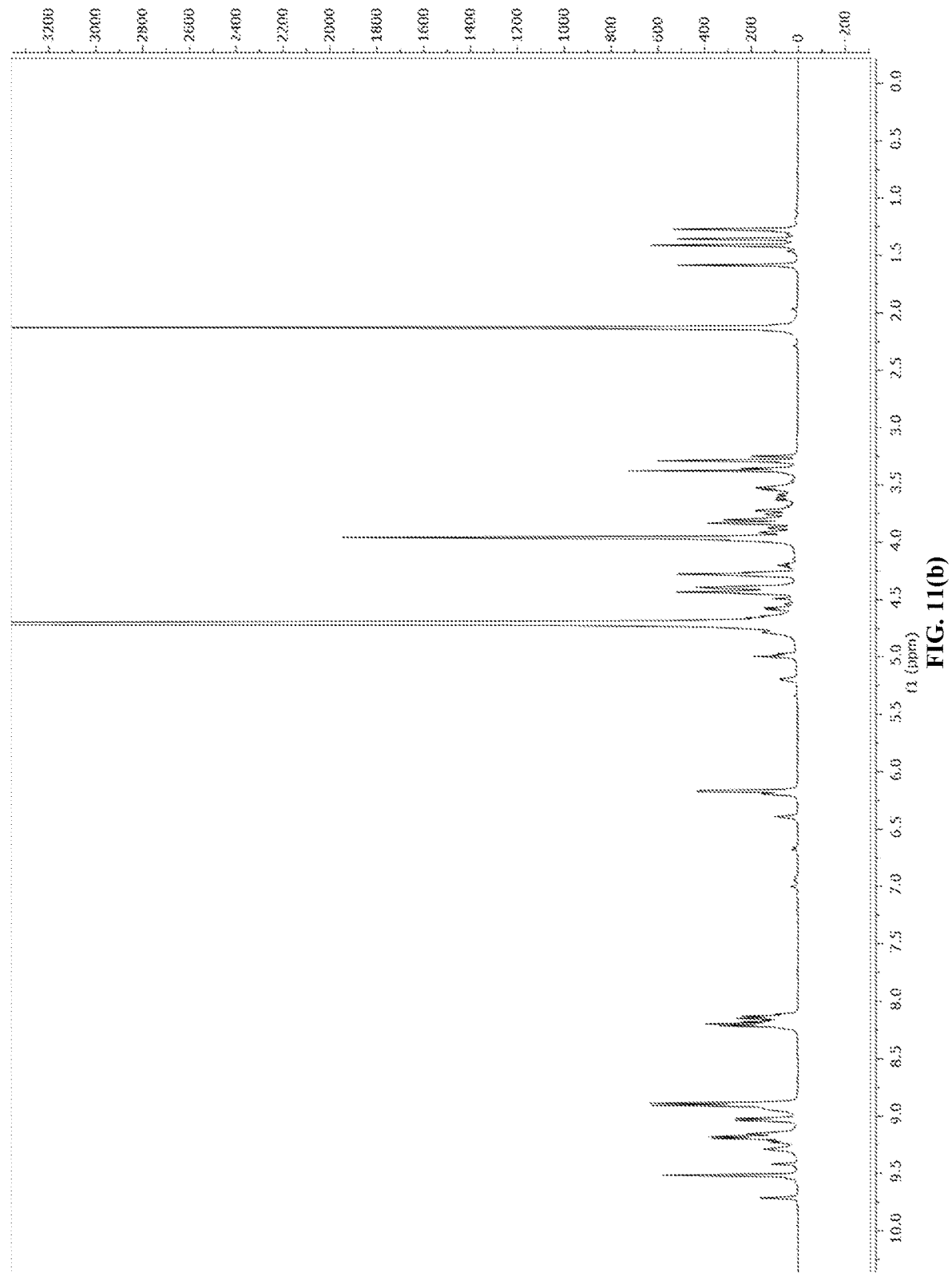
FIG. 11(b) depicts a $^1$H NMR spectrum of the impurity-containing supernatant remaining after filtration of the product filtrate represented by the $^1$H NMR spectrum depicted in FIG. 11(a), performed in accordance with one embodiment of the described method for the preparation of a compound or derivative having general formula (Ia-H) or a salt, solvate, or prodrug thereof, wherein $R^6$, $R^7$, and $R^8$ are each hydrogen.

A bath-based, acid-based deprotection reaction that yielded Compound 5 from Compound 2 was also examined at room temperature, under both sealed methanolic and ethanolic anhydrous acidic conditions. The acidic conditions did not require quenching, as Compound 5 crashed out of solution as the reaction progressed over 24 hours. However, anhydrous conditions are required in order to minimize side-product formation. Four simultaneous reactions were conducted with differing amounts of HCl and MeOH or EtOH. All reactions were performed on a 5-gram scale based on Compound 2. Conditions 1: 3 equiv. 11.65 M concentrated HCl in methanol (3.09 mL MeOH). Conditions 2: 20 equiv. 11.65 M concentrated HCl in methanol (20.59 mL MeOH). Conditions 3: 3 equiv. 1.25 M anhydrous HCl in MeOH (28.79 mL MeOH). Conditions 4: 20 equiv. 1.25 M HCl (191.93 mL MeOH). For reactions using concentrated HCl, although complete deprotection occurred, notable amounts of degradation products were observed after 24 hours. Using 3 equiv. 1.25 M anhydrous HCl gave the best results with complete deprotection after 24 hours with only traces of degradation product. Increasing to 20 equiv. anhydrous HCl only resulted in an increase in the amount of degradation product observed. The use of sealed tubes greatly improved the rate of reaction when compared to open vessels. FIG. 11(a) depicts the $^1$H NMR spectrum of a product filtrate of Compound 4. FIG. 11(b) depicts the $^1$H NMR spectrum of the impurity-containing supernatant remaining after filtration of Compound 5.

Optimized Deprotection Reactions

Reaction in Methanol: The deprotection was conducted on Compound 2 on a 5-gram scale, using 3 equiv. 1.25 M anhydrous HCl in MeOH under sealed conditions. As full deprotection occurred, Compound 5 began to precipitate out of solution. After twelve hours, the suspension in the sealed tube was filtered under reduced pressure and the cake was washed with small volumes of EtOH. NMR of the cake (FIG. 11(a)) and of the supernatant (FIG. 11(b)) were taken. NMR of the cake (FIG. 11(a)) showed complete deprotection with only trace amounts of impurities. The supernatant (FIG. 11(b)) is shown to contain some amount of Compound 5 as well as partially deprotected material and small amounts of reaction by-products.

Reaction in Ethanol: The reaction was performed using 4 equiv. of 1.25 M anhydrous HCl in EtOH under sealed conditions. A precipitate formed as the reaction progressed, and, after 48 hours, the suspension was filtered and the cake was washed with EtOH. NMR of the cake showed complete deprotection with only trace amounts of impurities. The supernatant was shown to contain some amount of Compound 5, as well as partially deprotected material and small amounts of reaction by-products.

Reaction with in situ Generation of HCl in Ethanol: The deprotection reaction was attempted using 4 equiv. AcCl in EtOH (30 mL). Compound 2 was dissolved in EtOH and the reaction cooled to −80° C. AcCl was then added slowly, and the reaction mixture was tube-sealed and allowed to warm to room temperature. The reaction was left to stir overnight and a white solid had precipitated out of solution. This white solid was filtered and washed with EtOH, and an NMR of the white solid was taken. NMR of the cake showed almost complete deprotection, however, some partially deprotected material and traces of by-product could be detected.

Reaction with in situ Generation of HCl in Methanol: The deprotection reaction was attempted using 3 equiv. of AcCl in MeOH (30 mL). Compound 2 was dissolved in MeOH and the reaction cooled to −80° C. AcCl was then added slowly, and the reaction mixture was tube-sealed and allowed to warm to room temperature. The reaction was left to stir overnight and a white solid had precipitated out of solution. This white solid was filtered and washed with EtOH, and an NMR of the white solid was taken. NMR of the cake showed complete deprotection with trace amounts of by-product present. The filtrate was shown to contain partially unprotected material and other by-products.

The crystalline Form I of nicotinamide riboside chloride (NR—Cl, Compound 5) may be characterized by a powder X-ray diffraction pattern having peaks at 15.7, 21.8, and 26.5 degrees two theta±0.2 degrees two theta. The crystalline Form I of nicotinamide riboside chloride may also or alternatively be characterized by a powder X-ray diffraction pattern having peaks at 5.2, 15.7, 21.8, 25.3, and 26.5 degrees two theta±0.2 degrees two theta. The crystalline Form I of nicotinamide riboside chloride may also or alternatively be characterized by a powder X-ray diffraction pattern having peaks at 5.2, 157.7, 18.6, 21.8, 23.5, 23.8, 25.3, 26.5, and 28.1 degrees two theta±0.2 degrees two theta.

Figure 15:
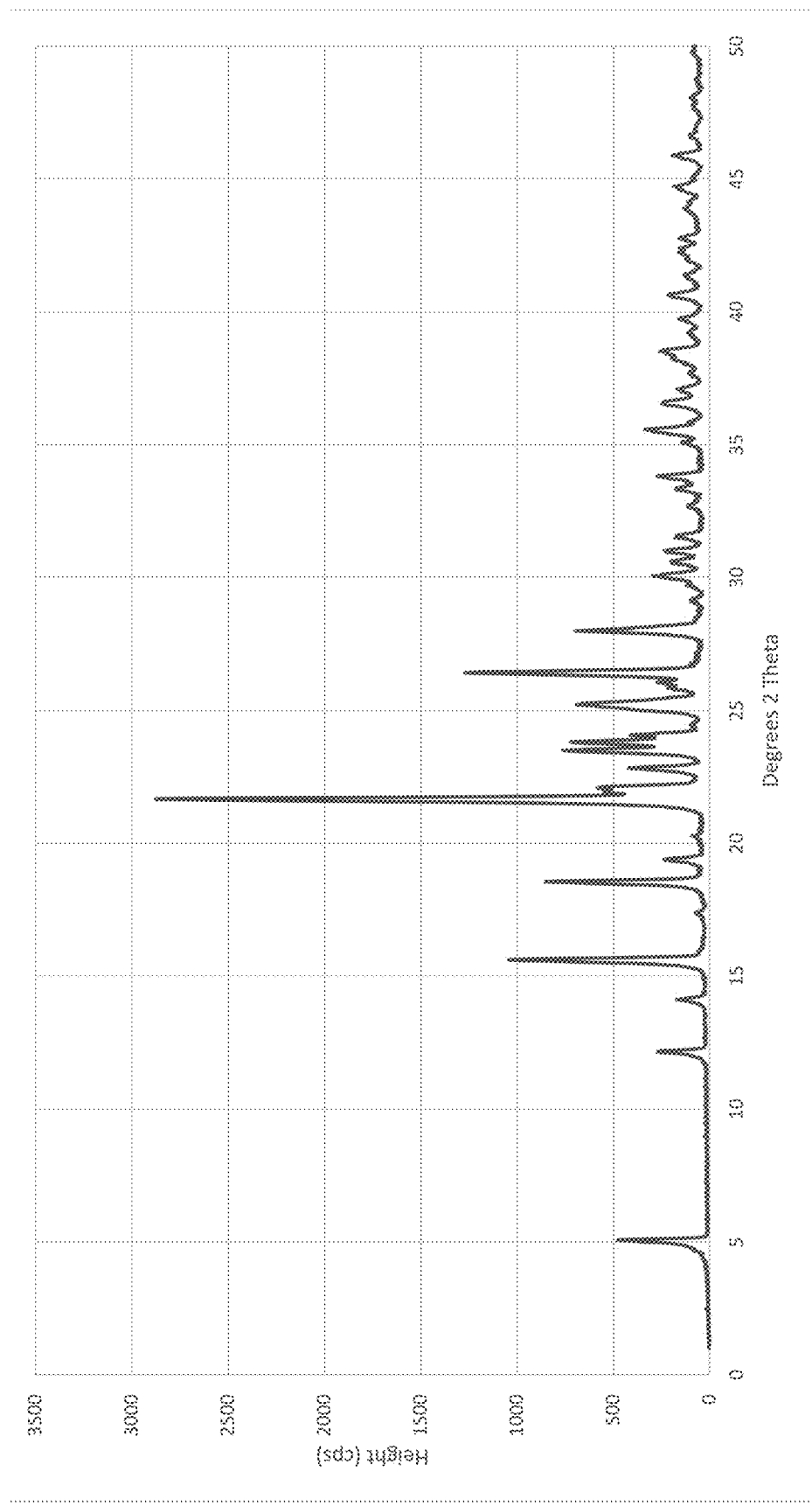
FIG. 15 provides an X-ray powder diffraction pattern for the previously described Form I of crystalline nicotinamide riboside chloride (NR—Cl), the compound having formula (VII), prepared according to an embodiment of the presently disclosed methods for the preparation of a compound or derivative having general formula (Ia-H), or a salt, solvate, or prodrug thereof, wherein $R^6$, $R^7$, and $R^8$ are each hydrogen.

In other embodiments, the crystalline Form I of nicotinamide riboside chloride may be characterized by a powder X-ray diffraction pattern substantially as shown in FIG. 15. The crystalline Form I of nicotinamide riboside chloride may also or alternatively be characterized by a powder X-ray diffraction pattern having peaks substantially as provided in Table 6, below, 0.2 degrees two theta.

TABLE 6

| Peak No. | Pos. [°2Th.] | d-spacing [Å] | Height [cts] | $I/I_{max}$ [%] |
|---|---|---|---|---|
| 1 | 5.152 | 17.14 | 1051 | 57 |
| 2 | 12.247 | 7.221 | 200 | 11 |
| 3 | 14.217 | 6.2248 | 141 | 8 |
| 4 | 15.715 | 5.6346 | 1162 | 63 |
| 5 | 18.627 | 4.76 | 513 | 28 |
| 6 | 19.44 | 4.562 | 135 | 7 |
| 7 | 20.29 | 4.372 | 81 | 4 |
| 8 | 21.754 | 4.0821 | 1855 | 100 |
| 9 | 21.99 | 4.039 | 317 | 17 |
| 10 | 22.19 | 4.003 | 329 | 18 |
| 11 | 22.874 | 3.885 | 260 | 14 |
| 12 | 23.549 | 3.7740 | 638 | 34 |
| 13 | 23.846 | 3.729 | 511 | 28 |
| 14 | 24.113 | 3.688 | 310 | 17 |
| 15 | 25.289 | 3.519 | 1083 | 58 |
| 16 | 25.887 | 3.439 | 166 | 9 |
| 17 | 26.49 | 3.362 | 1105 | 60 |
| 18 | 28.067 | 3.1766 | 670 | 36 |
| 19 | 30.1 | 2.967 | 150 | 8 |
| 20 | 30.624 | 2.9169 | 319 | 17 |
| 21 | 31.06 | 2.877 | 147 | 8 |
| 22 | 31.579 | 2.8309 | 165 | 9 |
| 23 | 33.367 | 2.6832 | 122 | 7 |
| 24 | 33.85 | 2.646 | 159 | 9 |
| 25 | 35.613 | 2.519 | 339 | 18 |
| 26 | 36.54 | 2.457 | 159 | 9 |
| 27 | 37.12 | 2.42 | 72 | 4 |
| 28 | 38.531 | 2.3346 | 94 | 5 |
| 29 | 39.202 | 2.2962 | 70 | 4 |
| 30 | 39.774 | 2.2645 | 97 | 5 |
| 31 | 40.64 | 2.218 | 140 | 8 |
| 32 | 42.2 | 2.14 | 85 | 5 |
| 33 | 42.82 | 2.1101 | 111 | 6 |
| 34 | 44.62 | 2.029 | 117 | 6 |
| 35 | 45.86 | 1.977 | 148 | 8 |
| 36 | 46.69 | 1.9439 | 48 | 3 |
| 37 | 47.91 | 1.897 | 38 | 2 |

Preparation of Crystalline NR Methanolate Form II of Nicotinamide Riboside Chloride (NR—Cl, Compound 5)

Nicotinamide riboside chloride (NR—Cl, Compound 5) was dissolved in a mixture of methanol and water in a 95:5 weight:weight ratio such that approximately 15% of the Compound 5 was dissolved in the solvent mixture. The slurry was stirred as it was heated to 50° C., until all of the solids dissolved. The solution was cooled to −10° C. with stirring, and crystalline NR methanolate Form II of Compound 5 precipitated from the solution. The crystalline NR methanolate Form II of Compound 5 and cold methanol and water were filtered to collect the crystalline NR methanolate Form II of Compound 5. The crystalline NR methanolate Form II of Compound 5 (NR—Cl) was dried under vacuum overnight at room temperature.

Crystalline NR methanolate Form II of nicotinamide riboside chloride may be characterized by a powder X-ray diffraction pattern having peaks at 23.7, 24.5, and 25.4 degrees two theta±0.2 degrees two theta. The crystalline NR methanolate Form II of nicotinamide riboside chloride may also or alternatively be characterized by a powder X-ray diffraction pattern having peaks at 12.9, 23.7, 24.5, and 25.4 degrees two theta±0.2 degrees two theta. The crystalline NR methanolate Form II of nicotinamide riboside chloride may also or alternatively be characterized by a powder X-ray diffraction pattern having peaks at 12.9, 13.9, 14.8, 23.7, 24.5, and 25.4 degrees two theta±0.2 degrees two theta.

Figure 16:
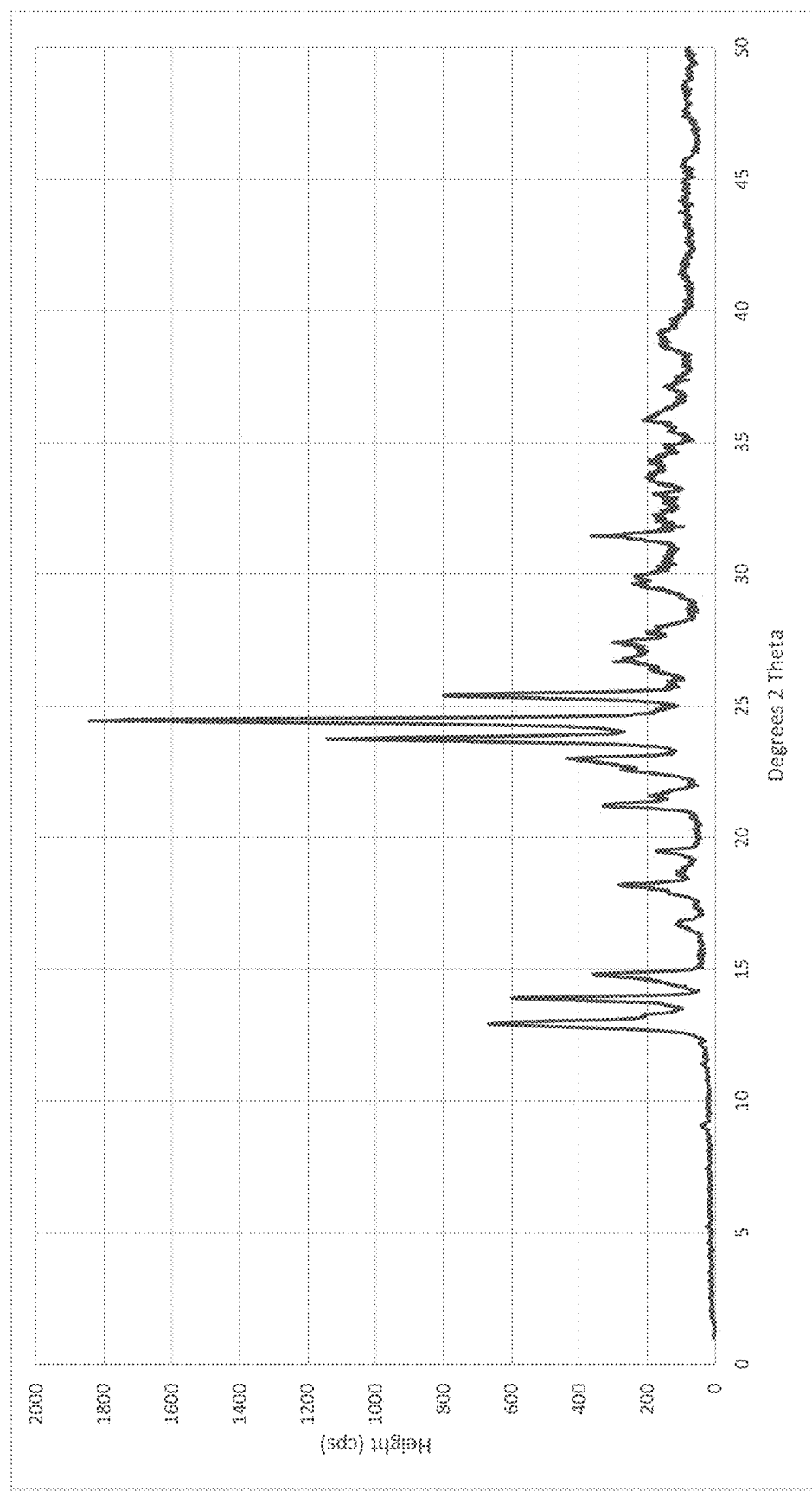
FIG. 16 provides an X-ray powder diffraction pattern for the presently disclosed NR methanolate Form II of crystalline nicotinamide riboside chloride (NR—Cl), the compound having formula (VII), prepared according to am embodiment of the presently disclosed methods for the preparation of a compound or derivative having general formula (Ia-H), or a salt, solvate, or prodrug thereof, wherein $R^6$, $R^7$, and $R^8$ are each hydrogen.

In other embodiments, the crystalline NR methanolate Form II of nicotinamide riboside chloride may be characterized by a powder X-ray diffraction pattern substantially as shown in FIG. 16. The crystalline NR methanolate Form II may also or alternatively be characterized by a powder X-ray diffraction pattern having peaks substantially as provided in Table 7, below, ±0.2 degrees two theta.

TABLE 7

| Peak No. | Pos. [°2Th.] | d-spacing [Å] | Height [cts] | $I/I_{max}$ [%] |
|---|---|---|---|---|
| 1 | 12.938 | 6.837 | 686 | 35 |
| 2 | 13.891 | 6.3701 | 590 | 30 |
| 3 | 14.766 | 5.994 | 383 | 20 |
| 4 | 16.722 | 5.297 | 67 | 3 |
| 5 | 18.14 | 4.886 | 262 | 14 |
| 6 | 19.49 | 4.552 | 130 | 7 |
| 7 | 21.22 | 4.184 | 292 | 15 |
| 8 | 22.54 | 3.942 | 160 | 8 |
| 9 | 22.994 | 3.8646 | 346 | 18 |
| 10 | 23.736 | 3.7456 | 1102 | 57 |
| 11 | 24.475 | 3.634 | 1936 | 100 |
| 12 | 25.384 | 3.5059 | 769 | 40 |
| 13 | 27.19 | 3.277 | 115 | 6 |
| 14 | 29.79 | 2.996 | 142 | 7 |
| 15 | 31.46 | 2.841 | 222 | 11 |
| 16 | 35.93 | 2.497 | 79 | 4 |
| 17 | 38.91 | 2.313 | 85 | 4 |

Figure 22:
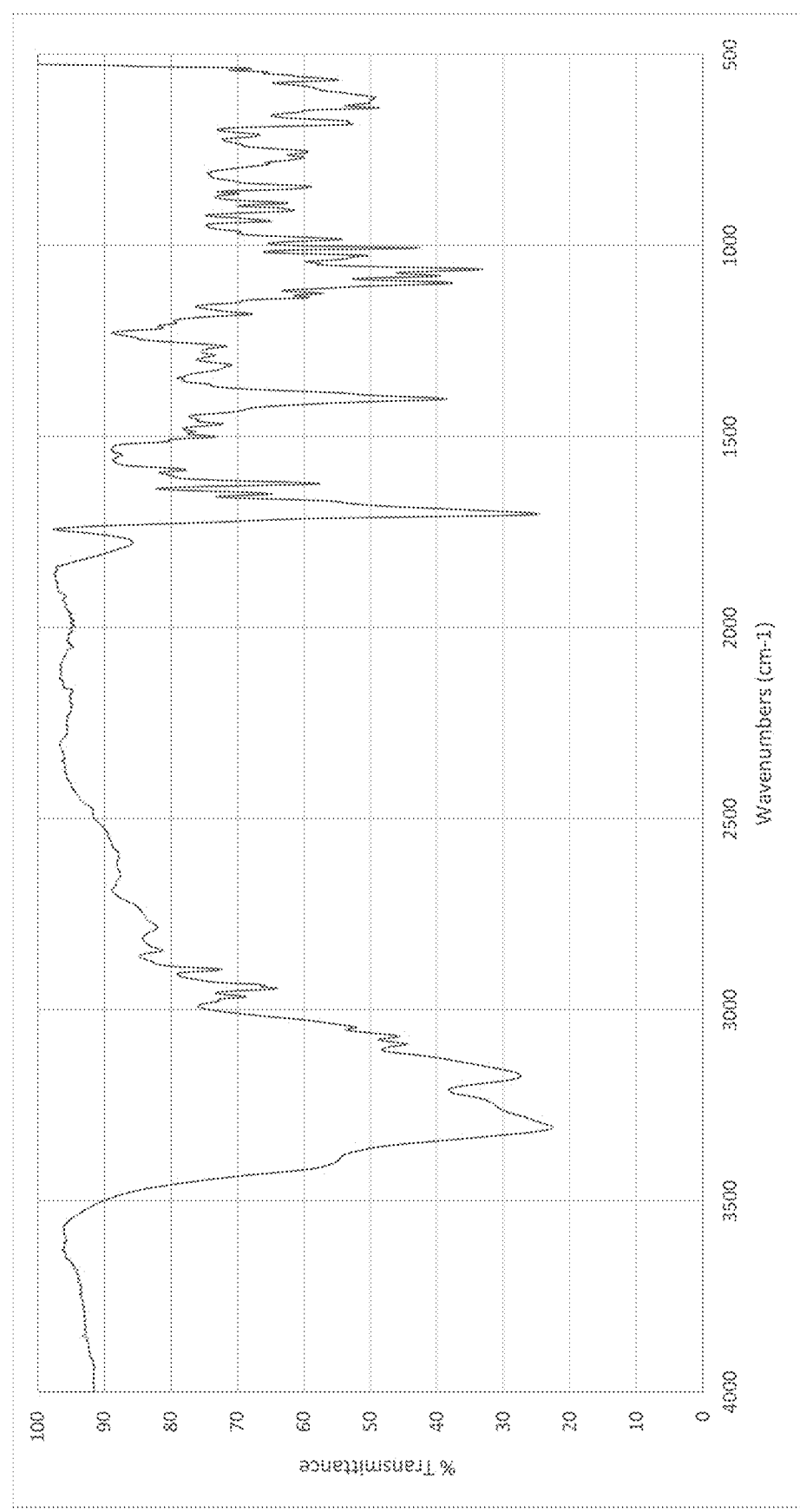
FIG. 22 provides a solid state IR spectrum for the presently disclosed NR methanolate Form II of crystalline nicotinamide riboside chloride (NR—Cl), the compound having formula (VII).

The crystalline NR methanolate Form II may also or alternatively be characterized by a solid-state IR spectrum having peaks at 565.1, 611.3, 638.3, and 680.8 cm$^{-1}$±0.2 cm$^{-1}$. The crystalline NR methanolate Form II may also or alternatively be characterized by a solid-state IR spectrum having peaks at 565.1, 611.3, 638.3, 680.8, 981.6, 1004.8, 1026.0, 1060.7, 1078.0, and 1097.3 cm$^{-1}$±0.2 cm$^{-1}$. The crystalline NR methanolate Form II may also or alternatively be characterized by a solid-state IR spectrum having peaks at 565.1, 611.3, 638.3, 680.8, 981.6, 1004.8, 1026.0, 1060.7, 1078.0, 1097.3, 1400.1, 1621.9, 1648.9, and 1700.9 cm$^{-1}$±0.2 cm$^{-1}$. In certain embodiments, the crystalline NR methanolate Form II may also or alternatively be characterized by a solid-state IR spectrum substantially as shown in FIG. 22. In further embodiments, the crystalline NR methanolate Form II may be characterized by a solid-state IR spectrum having peaks substantially as provided in Table 8, below, 0.2 cm$^{-1}$.

TABLE 8

| IR (cm$^{-1}$) |
|---|
| 3307.38 |
| 3172.38 |
| 3089.46 |
| 3068.24 |
| 2966.03 |
| 2942.89 |
| 2892.75 |
| 1700.94 |
| 1648.87 |
| 1621.87 |
| 1498.44 |
| 1465.66 |
| 1400.09 |
| 1311.38 |
| 1286.31 |
| 1263.17 |
| 1178.31 |
| 1124.32 |
| 1097.32 |
| 1078.03 |
| 1060.67 |
| 1025.96 |
| 1004.75 |
| 981.61 |
| 935.32 |
| 906.39 |
| 887.11 |

TABLE 8-continued

| IR (cm$^{-1}$) |
|---|
| 844.68 |
| 769.47 |
| 752.11 |
| 709.69 |
| 680.76 |
| 638.33 |
| 611.33 |
| 565.05 |

In another embodiment, crystalline NR methanolate Form II of nicotinamide riboside chloride is characterized by a DSC thermogram obtained using a heating rate of 10 K/min comprising an endothermic event with an onset temperature of 125° C.±2° C.

In yet another embodiment, crystalline NR methanolate Form II of nicotinamide riboside chloride is characterized by a DSC thermogram obtained using a heating rate of 10 K/min comprising an endothermic event with a peak temperature of 132° C.±2° C.

In yet another embodiment, crystalline NR methanolate Form II of nicotinamide riboside chloride is characterized by a DSC thermogram obtained using a heating rate of 10 K/min comprising an onset temperature of 125° C.±2° C., an endothermic event with a peak temperature of 132° C. 2° C., or both.

Figure 30:
FIG. 30 provides a DSC thermogram for a sample of the presently disclosed crystalline NR methanolate Form II of nicotinamide riboside chloride that was heated at a rate of 10 K/min.

In yet another embodiment, crystalline NR methanolate Form II of nicotinamide riboside chloride may be characterized by a DSC thermogram substantially as shown in FIG. 30.

Characterization Data for Nicotinic Acid Riboside Triacetate (NARTA)

$^1$H NMR (D$_2$O, 400 MHz): δ ppm 9.28 (s, 1H, aromatic), 8.98 (d, J=6.1 Hz, 1H, aromatic), 8.83 (d, J=7.8 Hz, 1H, aromatic), 8.06 (dd, J=7.8, 6.1 Hz, 1H, aromatic), 6.46 (d, J=3.7 Hz, 1H, H-1 (anomeric)), 5.46 (t, J=4.7 Hz, 1H, H-3), 5.37 (t, J=5.4 Hz, 1H, H-2), 4.77-4.80 (m, 1H, H-4), 4.41-4.44 (m, 2H, H-5), 2.05 (s, 3H, OAc), 2.03 (s, 3H, OAc), 1.99 (s, 3H, OAc). $^{13}$C NMR (D$_2$O, 100 MHz): δ ppm 176.7, 173.5, 172.5, 164.6 (3×C(=O)CH$_3$, COOH), 148.4, 143.7, 141.7, 133.0, 128.8 (aromatic), 97.4 (C-1 (anomeric)), 82.3 (C-3), 76.6 (C-2), 69.7 (C-5), 62.8 (C-4), 20.3 (s, OAc), 20.0 (s, OAc), 19.9 (s, OAc).

Crystalline Form I of Nicotinic Acid Riboside Triacetate (NARTA)

Crystalline Form I of nicotinic acid riboside triacetate (NARTA) may be characterized by a powder X-ray diffraction pattern having peaks at 4.7, 9.5, and 20.5 degrees two theta±0.2 degrees two theta. The crystalline Form I of nicotinic acid riboside triacetate (NARTA) may also or alternatively be characterized by a powder X-ray diffraction pattern having peaks at 4.7, 9.5, 16.5, 16.8, and 20.5 degrees two theta±0.2 degrees two theta. The crystalline Form I of nicotinic acid riboside triacetate (NARTA) may also or alternatively be characterized by a powder X-ray diffraction pattern having peaks at 4.7, 9.5, 12.0, 16.5, 16.8, 19.9, 20.5, 23.7, and 23.9 degrees two theta±0.2 degrees two theta.

Figure 19:
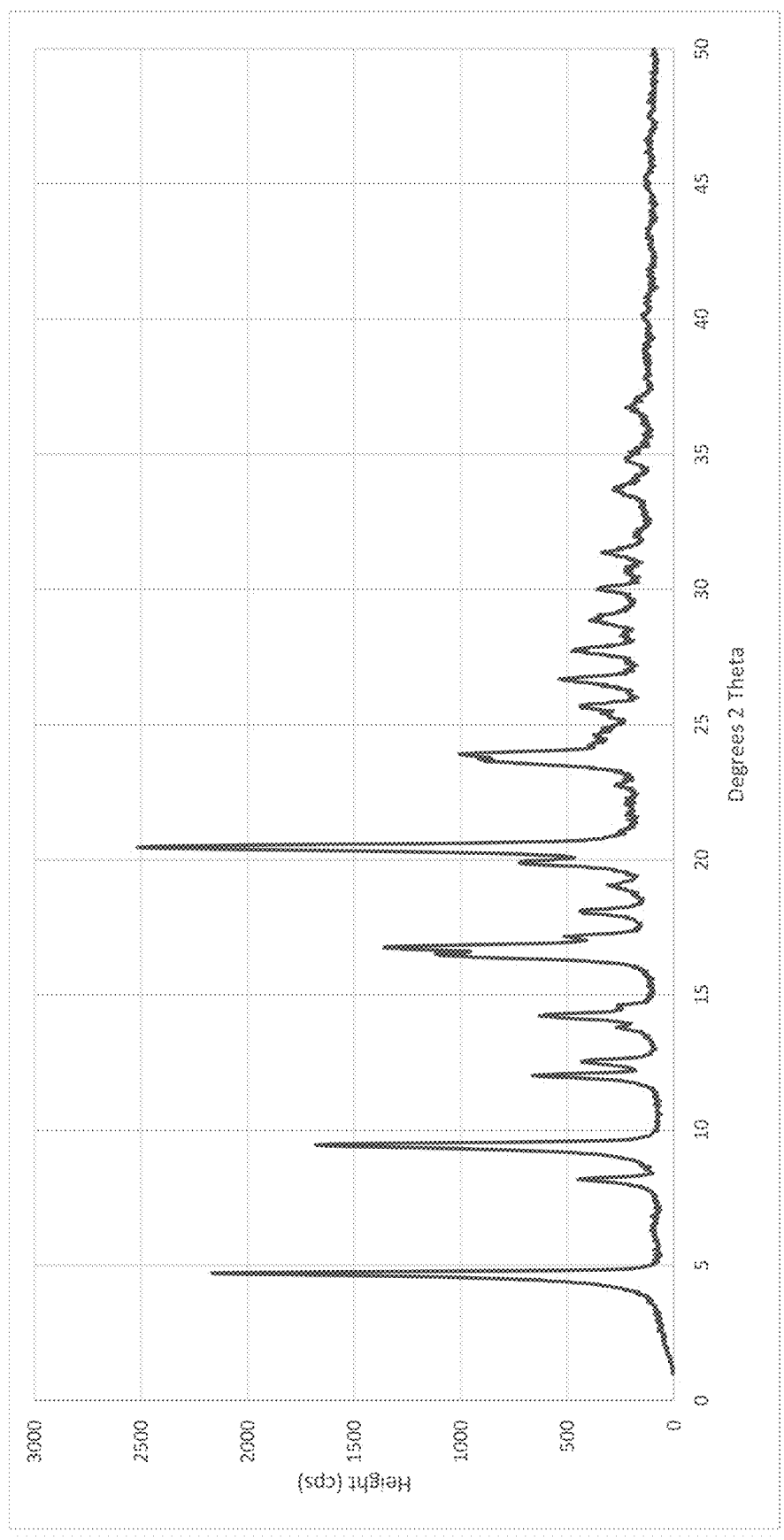
FIG. 19 provides an X-ray powder diffraction pattern for the presently disclosed Form I of crystalline nicotinic acid riboside triacetate (1-(2',3',5'-triacetyl-beta-D-ribofuranosyl)-nicotinic acid, "NAR triacetate," or "NARTA"), the compound having formula (X), prepared according to an embodiment of the presently disclosed methods for the preparation of a compound or derivative having general formula (Ia), or a salt, solvate, or prodrug thereof.

In other embodiments, the crystalline Form I of nicotinic acid riboside triacetate (NARTA) may be characterized by a powder X-ray diffraction pattern substantially as shown in FIG. 19. The crystalline Form I of nicotinic acid riboside triacetate (NARTA) may also or alternatively be characterized by a powder X-ray diffraction pattern having peaks substantially as provided in Table 9, below, ±0.2 degrees two theta.

TABLE 9

| Peak No. | Pos. [°2Th.] | d-spacing [Å] | Height [cts] | I/I$_{max}$ [%] |
|---|---|---|---|---|
| 1 | 4.715 | 18.725 | 2365 | 90 |
| 2 | 8.195 | 10.78 | 357 | 14 |
| 3 | 9.464 | 9.338 | 1819 | 69 |
| 4 | 12.039 | 7.346 | 608 | 23 |
| 5 | 12.552 | 7.046 | 383 | 15 |
| 6 | 13.787 | 6.418 | 140 | 5 |
| 7 | 14.23 | 6.219 | 502 | 19 |
| 8 | 14.58 | 6.07 | 168 | 6 |
| 9 | 16.486 | 5.373 | 848 | 32 |
| 10 | 16.763 | 5.285 | 1337 | 51 |
| 11 | 17.157 | 5.164 | 357 | 14 |
| 12 | 18.079 | 4.903 | 313 | 12 |
| 13 | 19.04 | 4.658 | 114 | 4 |
| 14 | 19.886 | 4.4612 | 573 | 22 |
| 15 | 20.476 | 4.3339 | 2636 | 100 |
| 16 | 23.69 | 3.7527 | 683 | 26 |
| 17 | 23.883 | 3.7228 | 653 | 25 |
| 18 | 24.45 | 3.638 | 164 | 6 |
| 19 | 25.724 | 3.4604 | 217 | 8 |
| 20 | 26.653 | 3.342 | 333 | 13 |
| 21 | 27.739 | 3.2134 | 299 | 11 |
| 22 | 28.82 | 3.095 | 191 | 7 |
| 23 | 30.03 | 29.73 | 196 | 7 |
| 24 | 31.324 | 2.8533 | 167 | 6 |
| 25 | 33.62 | 2.663 | 136 | 5 |
| 26 | 34.78 | 2.578 | 100 | 4 |
| 27 | 26.736 | 2.4445 | 81 | 3 |

Figure 25:
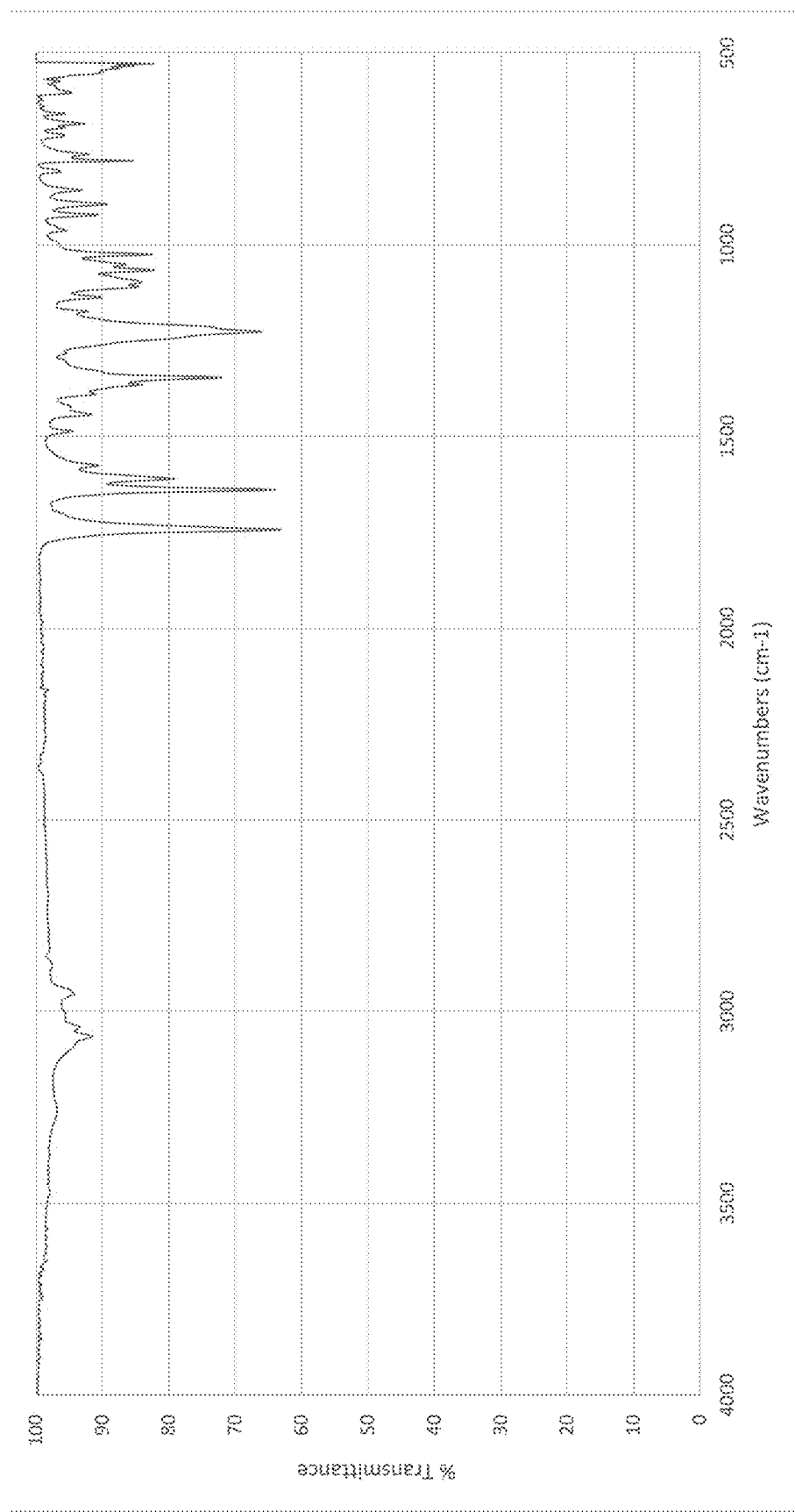
FIG. 25 provides a solid state IR spectrum for the presently disclosed Form I of crystalline nicotinic acid riboside triacetate (1-(2',3',5'-triacetyl-beta-D-ribofuranosyl)-nicotinic acid, "NAR triacetate," or "NARTA"), the compound having formula (X).

The crystalline Form I of nicotinic acid riboside triacetate (NARTA) may also or alternatively be characterized by a solid-state JR spectrum having peaks at 603.6, 684.6, 763.7, and 781.0 cm$^{-1}$±0.2 cm$^{-1}$. The crystalline Form I of nicotinic acid riboside triacetate (NARTA) may also or alternatively be characterized by a solid-state JR spectrum having peaks at 603.6, 684.6, 763.7, 781.0, 858.2, 894.8, 921.8, 1026.0, 1051.0, and 1066.5 cm$^{-1}$±0.2 cm$^{-1}$. The crystalline Form I of nicotinic acid riboside triacetate (NARTA) may also or alternatively be characterized by a solid-state IR spectrum having peaks at 603.6, 684.6, 763.7, 781.0, 858.2, 894.8, 921.8, 1026.0, 1051.0, 1066.5, 1610.3, 1639.2, and 1743.4 cm$^{-1}$±0.2 cm$^{-1}$. In certain embodiments, the crystalline Form I of nicotinic acid riboside triacetate (NARTA) may be characterized by a solid-state IR spectrum substantially as shown in FIG. 25. In further embodiments, the crystalline Form I of nicotinic acid riboside triacetate (NARTA) may be characterized by a solid-state IR spectrum having peaks substantially as provided in Table 10, below, ±0.2 cm$^{-1}$.

TABLE 10

| IR (cm$^{-1}$) |
|---|
| 3064.38 |
| 3041.24 |
| 2954.46 |
| 1743.36 |
| 1639.22 |
| 1610.30 |
| 1346.09 |
| 1226.53 |
| 1110.82 |
| 1097.32 |
| 1066.46 |
| 1051.03 |
| 1025.96 |
| 921.82 |
| 894.82 |
| 858.18 |
| 781.04 |
| 763.69 |

TABLE 10-continued

| IR (cm$^{-1}$) |
|---|
| 684.62 |
| 603.62 |

In another embodiment, crystalline Form I of nicotinic acid riboside triacetate (NARTA) is characterized by a DSC thermogram obtained using a heating rate of 10 K/min comprising an endothermic event with an onset temperature of 148° C.±2° C.

In yet another embodiment, crystalline Form I of nicotinic acid riboside triacetate (NARTA) is characterized by a DSC thermogram obtained using a heating rate of 10 K/min comprising an endothermic event with a peak temperature of 152° C.±2° C.

In yet another embodiment, crystalline Form I of nicotinic acid riboside triacetate (NARTA) is characterized by a DSC thermogram obtained using a heating rate of 10 K/min comprising an endothermic event with an onset temperature of 148° C.±2° C., a peak temperature of 152° C. 2° C., or both.

Figure 33:
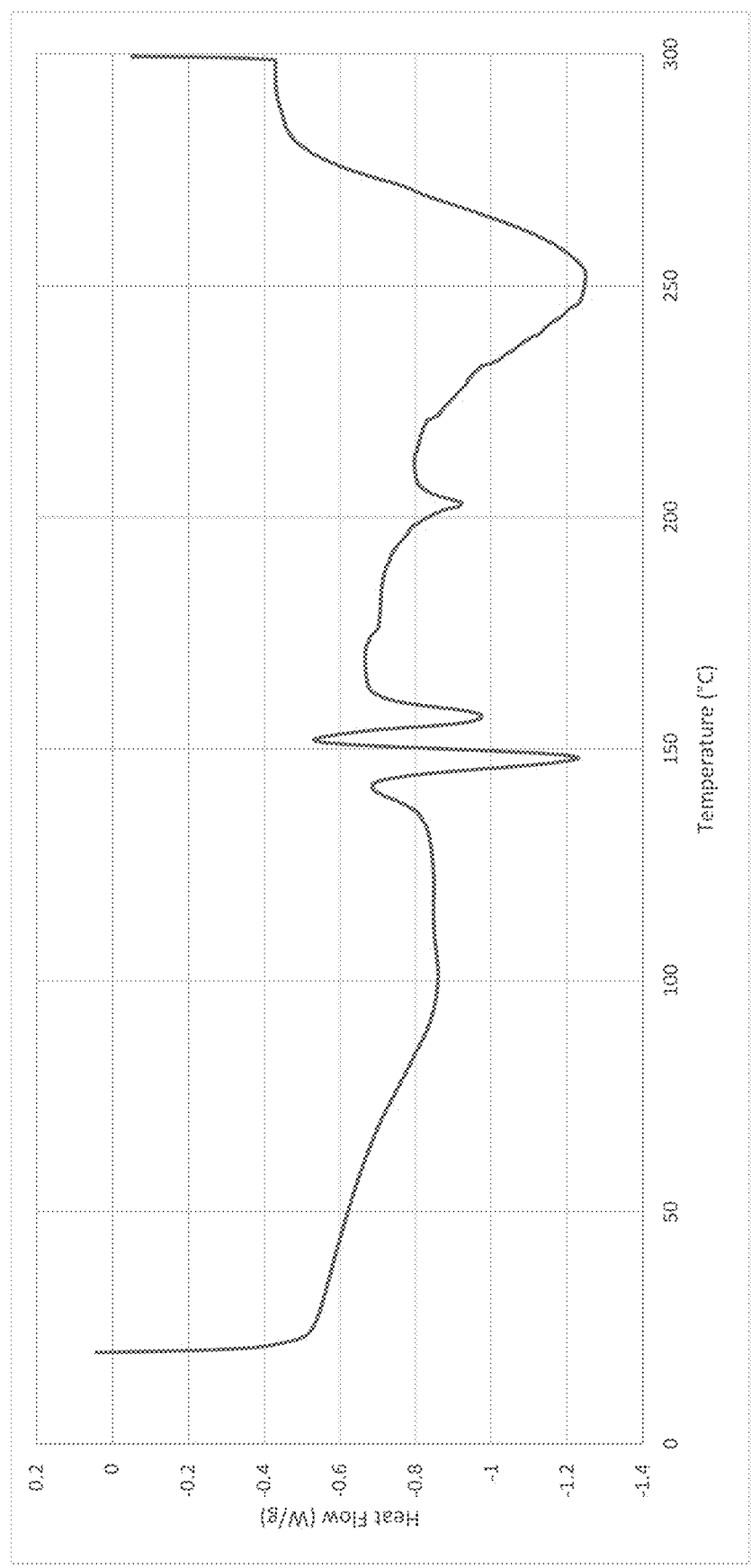
FIG. 33 provides a DSC thermogram for a sample of the presently disclosed Form I of crystalline nicotinic acid riboside triacetate (1-(2',3',5'-triacetyl-beta-D-ribofuranosyl)-nicotinic acid, "NAR triacetate," or "NARTA"), the compound having formula (X), which was heated at a rate of 10 K/min.

In yet another embodiment, crystalline Form I of nicotinic acid riboside triacetate (NARTA) is characterized by a DSC thermogram substantially as shown in FIG. 33.

Example 2

A. Synthetic Preparation of Nicotinamide Mononucleotide (Compound 6): Compound of Formula (IIa): R$^1$=Hydrogen, n=0, Z$^2$=NH, R$^2$=R$^3$=R$^4$=R$^5$=R$^7$=R$^8$=Y$^1$=Y$^2$=Hydrogen, Y$^3$=Oxygen

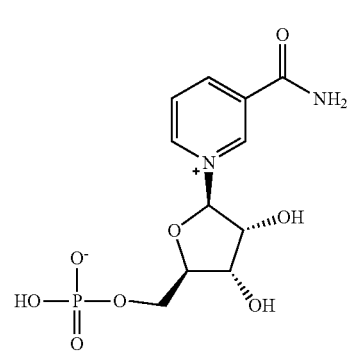

Compound 6

The reaction to produce Compound 6 by extrusion was performed on the ThermoFisher twin screw extruder 11 mm, using a feed rate of 10 g/min with a 1:4 ratio of nicotinamide riboside to POCl$_3$. The extruder came to a grinding halt as it was difficult to control the feed rate of POCl$_3$. The machine was opened and samples were removed from mixing zone 1 and mixing zone 2 and submitted for NMR analysis. Mixing zone 1 showed the material to be slightly charred but conversion to Compound 6 was observed, along with the presence of by-products. Mixing zone 2 did not appear to show any charring. NMR showed approximately 46% conversion to Compound 6, along with the presence of by-products. The extruder was cleaned to clear the mixing zone from the hardened material that had formed in order to prevent torque on the screw, and a second run was attempted.

Run 2 was performed using a feed rate of 7 g/min with a 1:3 ratio of nicotinamide riboside to POCl$_3$. Once again, after the machine came to a halt, the machine was opened and samples were removed from mixing zone 1 and mixing zone 2 and submitted for NMR analysis. Mixing zone 1 showed approximately 30% conversion to Compound 6 with no evidence of apparent darkening of the mixture by observation. Mixing zone 2 showed approximately 15% conversion to Compound 6. A sample of the material that came out of the extruder showed approximately 6% conversion to Compound 6 by NMR.

$^1$H NMR (D$_2$O, 400 MHz): δ ppm 9.32 (s, 1H, aromatic), 9.13 (m, 1H, aromatic), 8.89 (dt, J=8.0, 1.3 Hz, 1H, aromatic), 8.19 (dd, J=8.0, 6.5 Hz, 1H, aromatic), 6.04 (d, J=5.5 Hz, 1H, H-1 (anomeric)), 4.54 (m, 1H, H-2), 4.46 (t, J=5.1 Hz, 1H, H-3), 4.34 (dd, J=5.0, 2.5 Hz, 1H, H-4), 4.21 (AB$_X$, J$_{A,A'}$=12.0, 4.0 Hz, 1H, H-5), 4.05 (AB$_X$, J$_{A,B}$=12.0, 4.0 Hz, 1H, H-5). $^{13}$C NMR (D$_2$O, 100 MHz): δ ppm 165.6 (C(=O)NH$_2$), 146.0, 142.5, 139.9, 133.9, 128.5 (aromatic), 99.9 (C-1 (anomeric)), 89.4 (C-4), 77.7 (C-2), 70.9 (C-3), 64.1 (C-5). $^{31}$P NMR (D$_2$O, 162 MHz): δ ppm 0.03. HRMS (ES, M+H$^+$) calculated 357.0464 for C$_{11}$H$_{15}$N$_2$O$_8$PNa, found 357.0479.

An amorphous solid form of nicotinamide mononucleotide (NMN, Compound 6) may be characterized by a powder X-ray diffraction pattern having a peak at 21.2 degrees two theta±0.2 degrees two theta.

Figure 21:
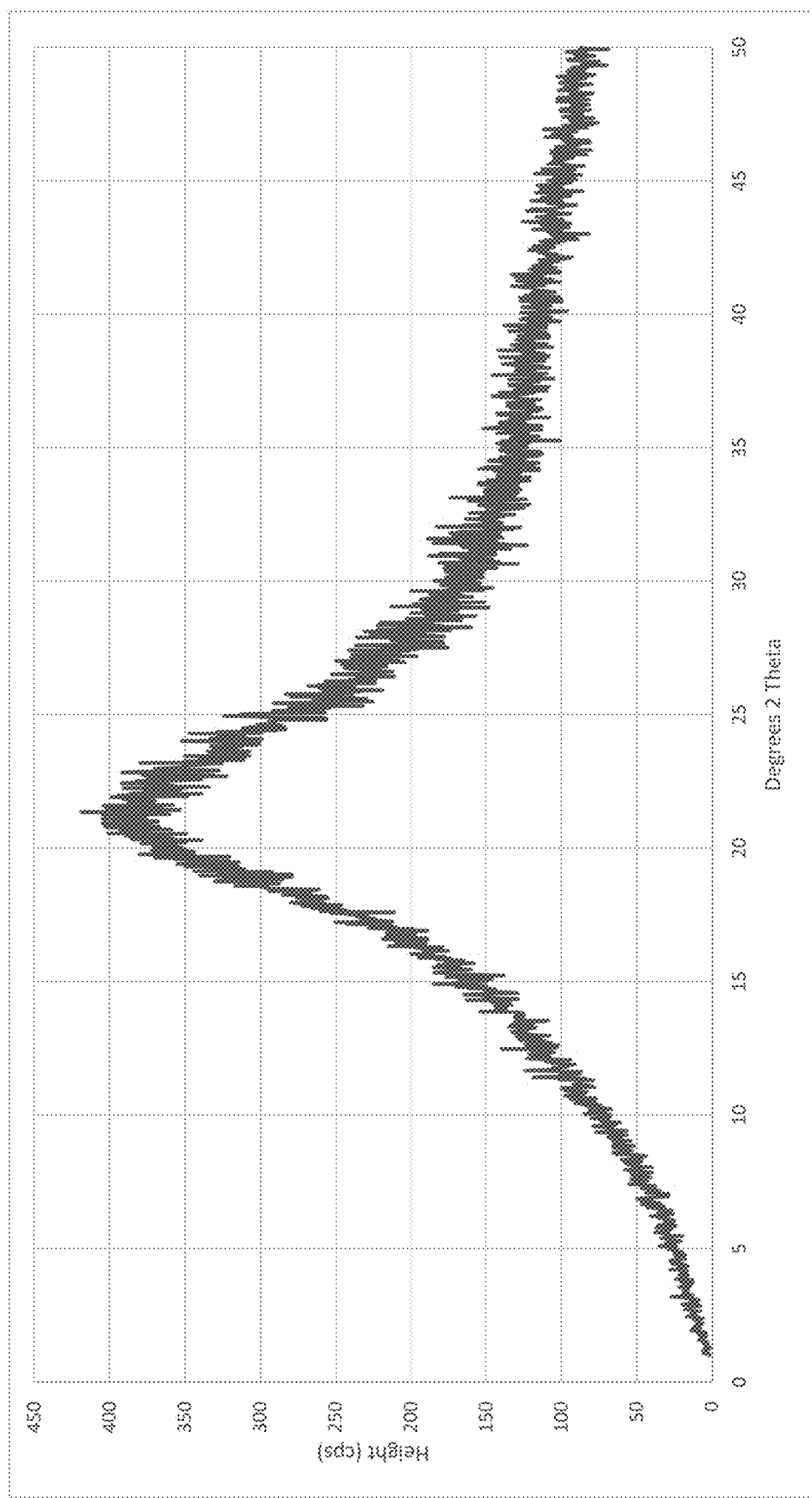
FIG. 21 provides an X-ray powder diffraction pattern for the presently disclosed amorphous solid form of nicotinamide mononucleotide (NMN), the compound having formula (XI), prepared according to an embodiment of the presently disclosed methods for the preparation of a compound or derivative having general formula (IIa), or a salt, solvate, or prodrug thereof.

In other embodiments, the amorphous solid form of nicotinamide mononucleotide (NMN, Compound 6) may be characterized by a powder X-ray diffraction pattern substantially as shown in FIG. 21. The amorphous solid form of nicotinamide mononucleotide (NMN, Compound 6) may be characterized by a powder X-ray diffraction pattern having peaks substantially as provided in Table 11, below, ±0.2 degrees two theta.

TABLE 11

| Peak No. | Pos. [°2Th.] | d-spacing [Å] | Height [cts] | I/I$_{max}$ [%] |
|---|---|---|---|---|
| 1 | 21.18 | 4.192 | 288 | 100 |

The amorphous solid form of nicotinamide mononucleotide (NMN, Compound 6) may also or alternatively be characterized by a solid-state IR spectrum having peaks at 632.6, 673.1, 794.5, and 916.0 cm$^{-1}$±0.2 cm$^{-1}$. The amorphous solid form of nicotinamide mononucleotide (NMN) may also or alternatively be characterized by a solid-state IR spectrum having peaks at 632.6, 673.1, 794.5, 916.0, 991.3, 1058.8, 1405.9, 1452.2, 1502.3, and 1585.2 cm$^{-1}$±0.2 cm$^{-1}$.

Figure 27:
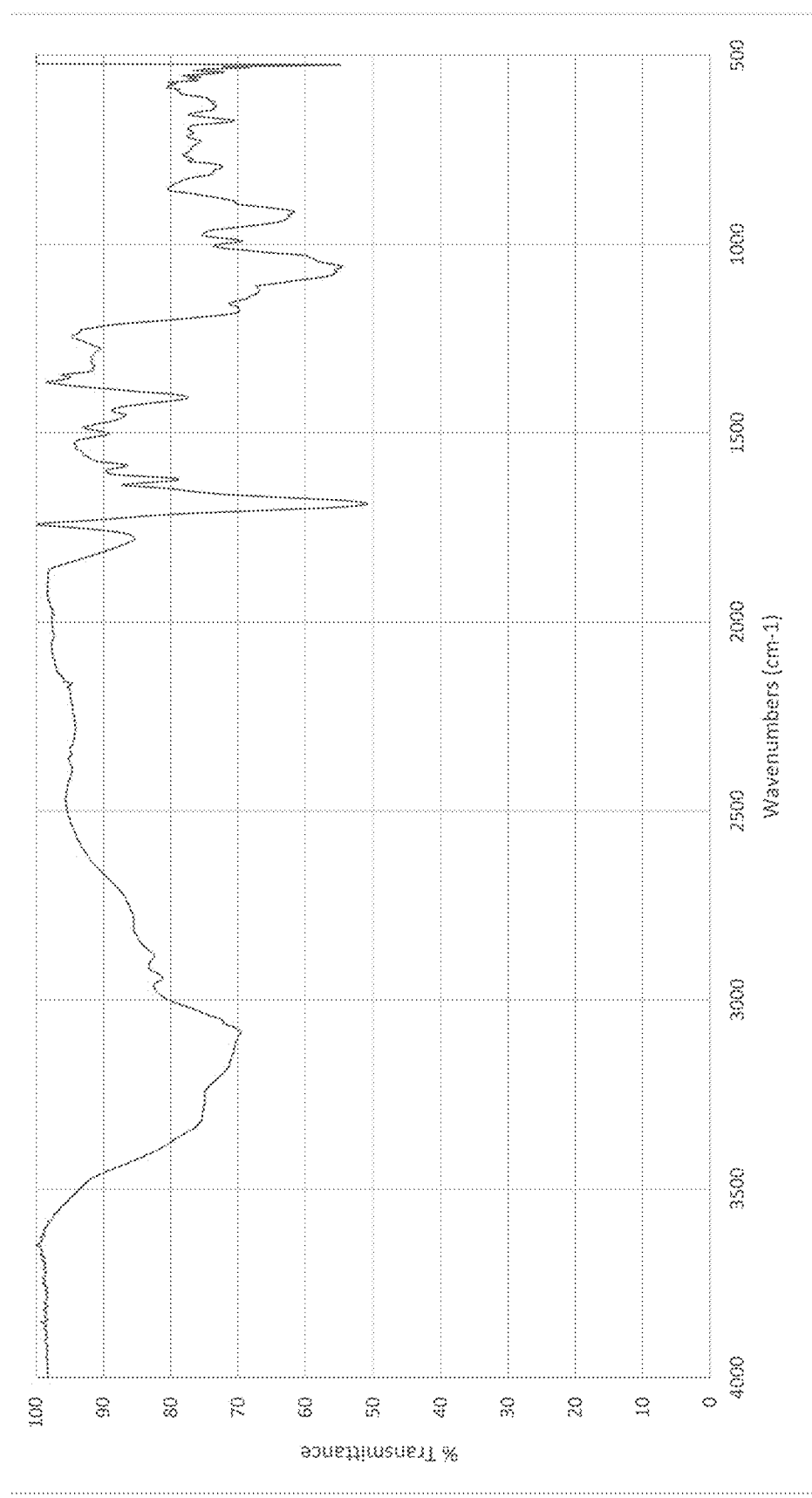
FIG. 27 provides a solid state IR spectrum for the presently disclosed amorphous solid form of nicotinamide mononucleotide (NMN), the compound having formula (XI).

The amorphous solid form of nicotinamide mononucleotide (NMN) may also or alternatively be characterized by a solid-state IR spectrum having peaks at 632.6, 673.1, 794.5, 916.0, 991.3, 1058.5, 1405.9, 1452.2, 1502.3, 1585.2, 1621.9, 1687.4, and 1776.2 cm$^{-1}$±0.2 cm$^{-1}$. In certain embodiments, the amorphous solid form of nicotinamide mononucleotide (NMN) may be characterized by a solid-state IR spectrum substantially as shown in FIG. 27. In further embodiments, the amorphous solid form of nicotinamide mononucleotide (NMN) may be characterized by a solid-state IR spectrum having peaks substantially as provided in Table 12, below, 0.2 cm$^{-1}$.

TABLE 12

| IR (cm$^{-1}$) |
|---|
| 3085.60 |
| 1776.15 |

TABLE 12-continued

| IR (cm$^{-1}$) |
|---|
| 1687.44 |
| 1621.87 |
| 1585.23 |
| 1502.30 |
| 1452.16 |
| 1405.88 |
| 1058.75 |
| 991.25 |
| 916.04 |
| 794.54 |
| 673.05 |
| 632.55 |

In another embodiment, the amorphous solid form of nicotinamide mononucleotide (NMN, Compound 6) is characterized by a DSC thermogram obtained using a heating rate of 10 K/min comprising an endothermic event with a peak temperature of 164° C.±2° C.

Figure 34:
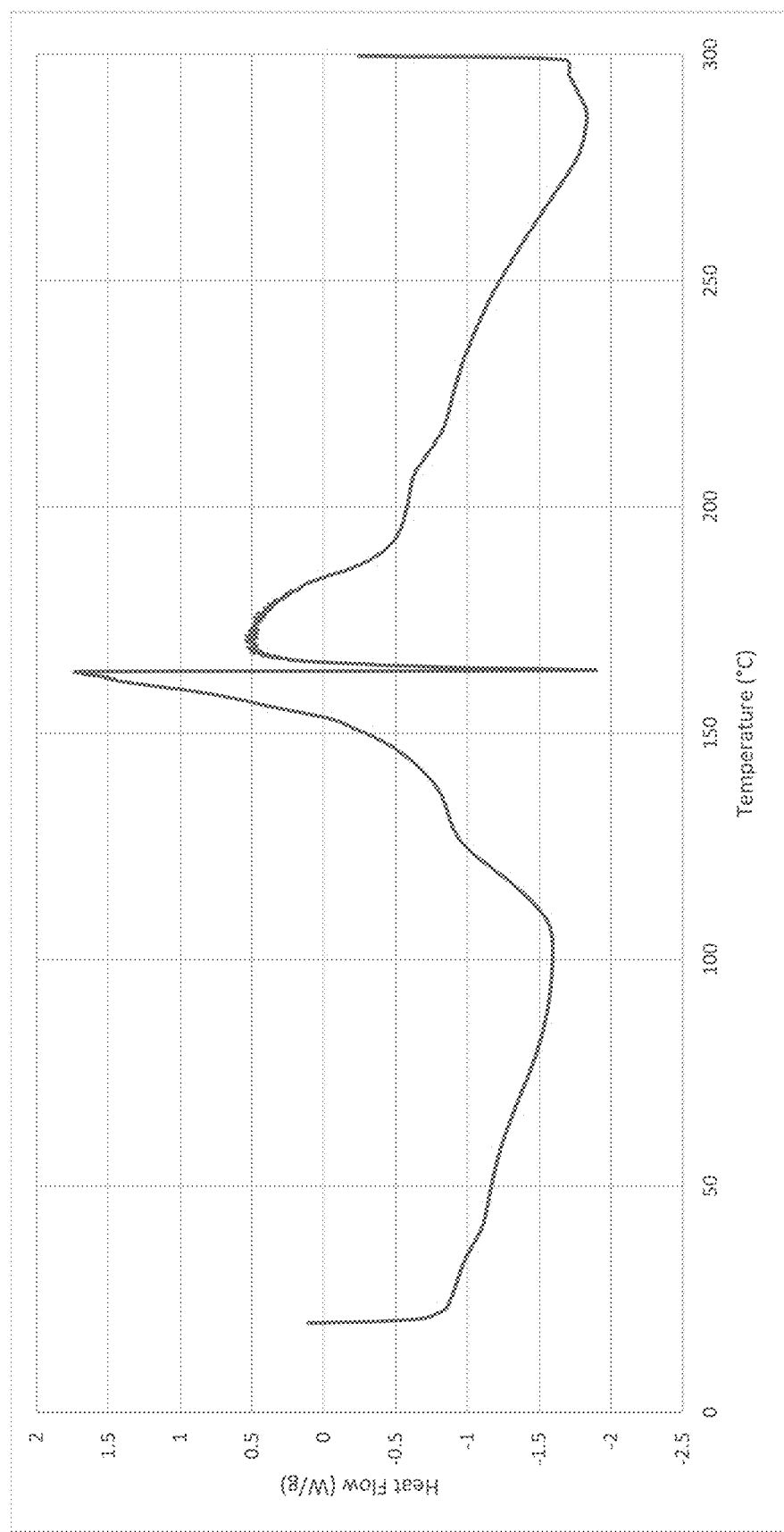
FIG. 34 provides a DSC thermogram for a sample of the presently disclosed amorphous solid form of nicotinamide mononucleotide (NMN), the compound having formula (XI), which was heated at a rate of 10 K/min.

In yet another embodiment, the amorphous solid form of nicotinamide mononucleotide (NMN) is characterized by a DSC thermogram substantially as shown in FIG. 34.

Preparation of Crystalline Form III of Nicotinamide Mononucleotide (NMN, Compound 6)

An amorphous solid form of nicotinamide mononucleotide (NMN, Compound 6) was added to a mixture of methanol and water in a 3:2 volume:volume ratio at room temperature in an amount of nicotinamide mononucleotide (NMN) of about 200 mg per milliliter of methanol-water mixture so as to dissolve the nicotinamide mononucleotide (NMN) in the methanol-water mixture. The solution of nicotinamide mononucleotide was filtered to remove any undissolved solids, and the solution was then diluted with a volume of acetone about 2 to about 5 times the total volume of methanol and water. The solution was cooled at −20° C. for two hours. The precipitated solid crystalline Form III of nicotinamide mononucleotide (NMN) was collected via filtration and dried overnight at room temperature.

Alternatively, an amorphous solid form of nicotinamide mononucleotide (NMN, Compound 6) was added to a mixture of methanol and water in a 3:2 volume:volume ratio at room temperature in an amount of nicotinamide mononucleotide (NMN) of about 200 mg per milliliter of methanol-water mixture so as to dissolve the nicotinamide mononucleotide (NMN) in the methanol-water mixture. The solution of nicotinamide mononucleotide was filtered to remove any undissolved solids, and the solution was then cooled at −20° C. for two hours. The methanol-water mixture was then decanted from the oily layer at the bottom of the solution. The oily layer was left to sit overnight at room temperature to crystallize into crystalline Form III of nicotinamide mononucleotide (NMN) and dry.

The crystalline Form III of nicotinamide mononucleotide (NMN, Compound 6) may be characterized by a powder X-ray diffraction pattern having peaks at 7.9, 22.9, and 24.8 degrees two theta±0.2 degrees two theta. The crystalline Form III of nicotinamide mononucleotide (NMN) may also or alternatively be characterized by a powder X-ray diffraction pattern having peaks at 7.9, 15.6, 17.2, 22.9, and 24.8 degrees two theta±0.2 degrees two theta. The crystalline Form III of nicotinamide mononucleotide (NMN) may also or alternatively be characterized by a powder X-ray diffraction pattern having peaks at 7.9, 15.6, 17.2, 17.9, 21.3, 21.9, 22.9, 24.8, 25.2, and 28.0 degrees two theta±0.2 degrees two theta.

Figure 20:
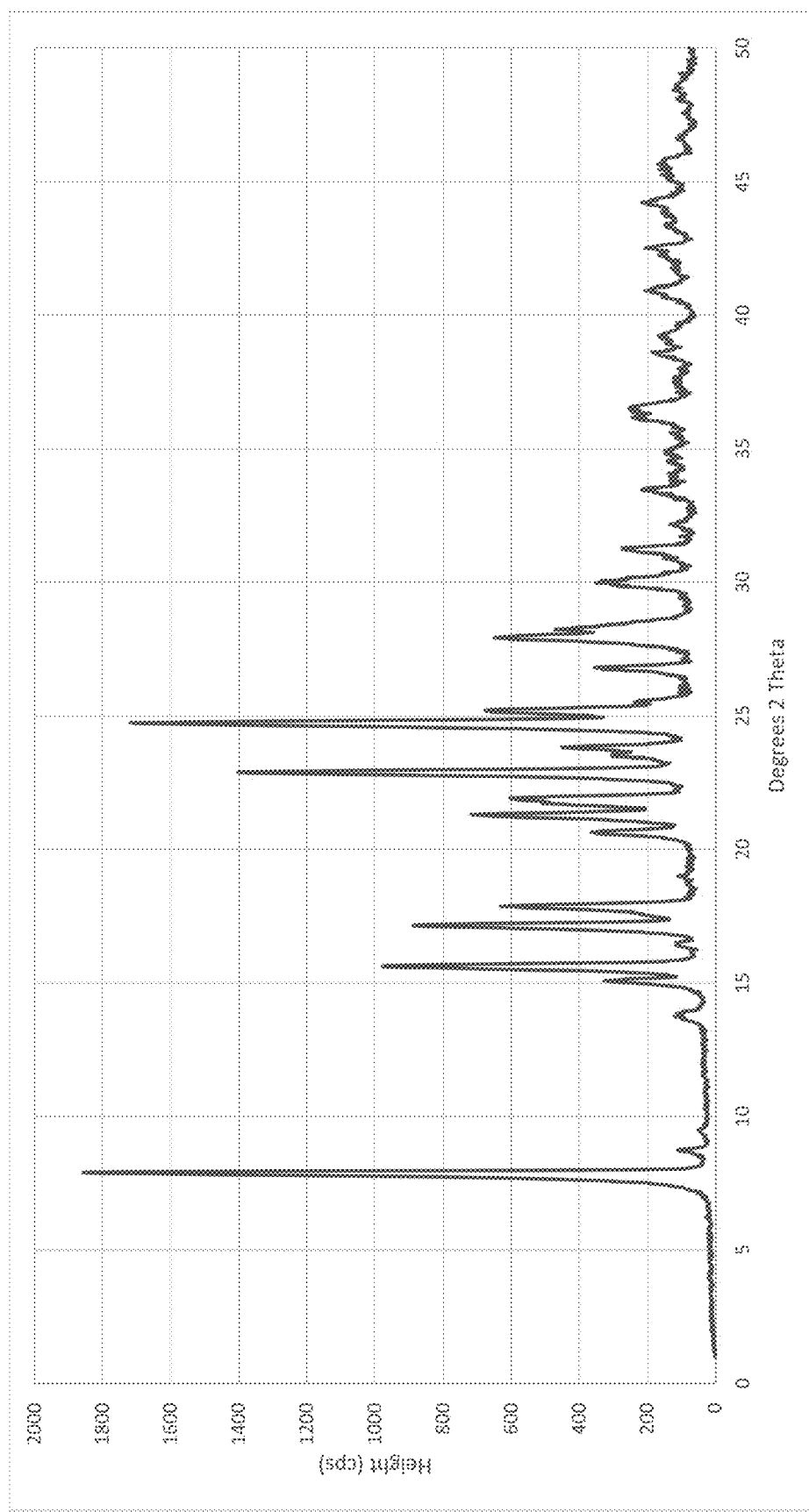
FIG. 20 provides an X-ray powder diffraction pattern for the presently disclosed Form III of crystalline nicotinamide mononucleotide (NMN), the compound having formula (XI), prepared according to an embodiment of the presently disclosed methods for the preparation of a compound or derivative having general formula (IIa), or a salt, solvate, or prodrug thereof.

In other embodiments, the crystalline Form III of nicotinamide mononucleotide (NMN) may be characterized by a powder X-ray diffraction pattern substantially as shown in FIG. 20. The crystalline Form III of nicotinamide mononucleotide (NMN) may also or alternatively be characterized by a powder X-ray diffraction pattern having peaks substantially as provided in Table 13, below, 0.2 degrees two theta.

TABLE 13

| Peak No. | Pos. [°2Th.] | d-spacing [Å] | Height [cts] | $I/I_{max}$ [%] |
|---|---|---|---|---|
| 1 | 7.9191 | 11.1553 | 1983 | 100 |
| 2 | 8.732 | 10.12 | 97 | 5 |
| 3 | 13.781 | 6.421 | 78 | 4 |
| 4 | 15.089 | 5.867 | 286 | 14 |
| 5 | 15.645 | 5.6597 | 1045 | 53 |
| 6 | 16.36 | 5.412 | 61 | 3 |
| 7 | 17.174 | 5.159 | 922 | 46 |
| 8 | 17.911 | 4.9484 | 551 | 28 |
| 9 | 20.626 | 4.3028 | 299 | 15 |
| 10 | 21.295 | 4.1689 | 656 | 33 |
| 11 | 21.702 | 4.0918 | 181 | 9 |
| 12 | 21.903 | 4.0547 | 564 | 28 |
| 13 | 22.891 | 3.8818 | 1462 | 74 |
| 14 | 23.542 | 3.776 | 211 | 11 |
| 15 | 23.807 | 3.7345 | 387 | 20 |
| 16 | 24.754 | 3.5938 | 1831 | 92 |
| 17 | 25.187 | 3.533 | 653 | 33 |
| 18 | 26.79 | 3.325 | 282 | 14 |
| 19 | 27.955 | 3.1891 | 610 | 31 |
| 20 | 28.184 | 3.1637 | 385 | 19 |
| 21 | 29.929 | 2.9831 | 269 | 14 |
| 22 | 31.276 | 2.8576 | 205 | 10 |
| 23 | 33.43 | 2.678 | 112 | 6 |
| 24 | 34.92 | 2.567 | 36 | 2 |
| 25 | 36.5 | 2.46 | 165 | 8 |
| 26 | 38.95 | 2.311 | 56 | 3 |
| 27 | 40.87 | 2.206 | 100 | 5 |
| 28 | 42.529 | 2.1239 | 111 | 6 |
| 29 | 44.2 | 2.047 | 109 | 5 |

Figure 26:
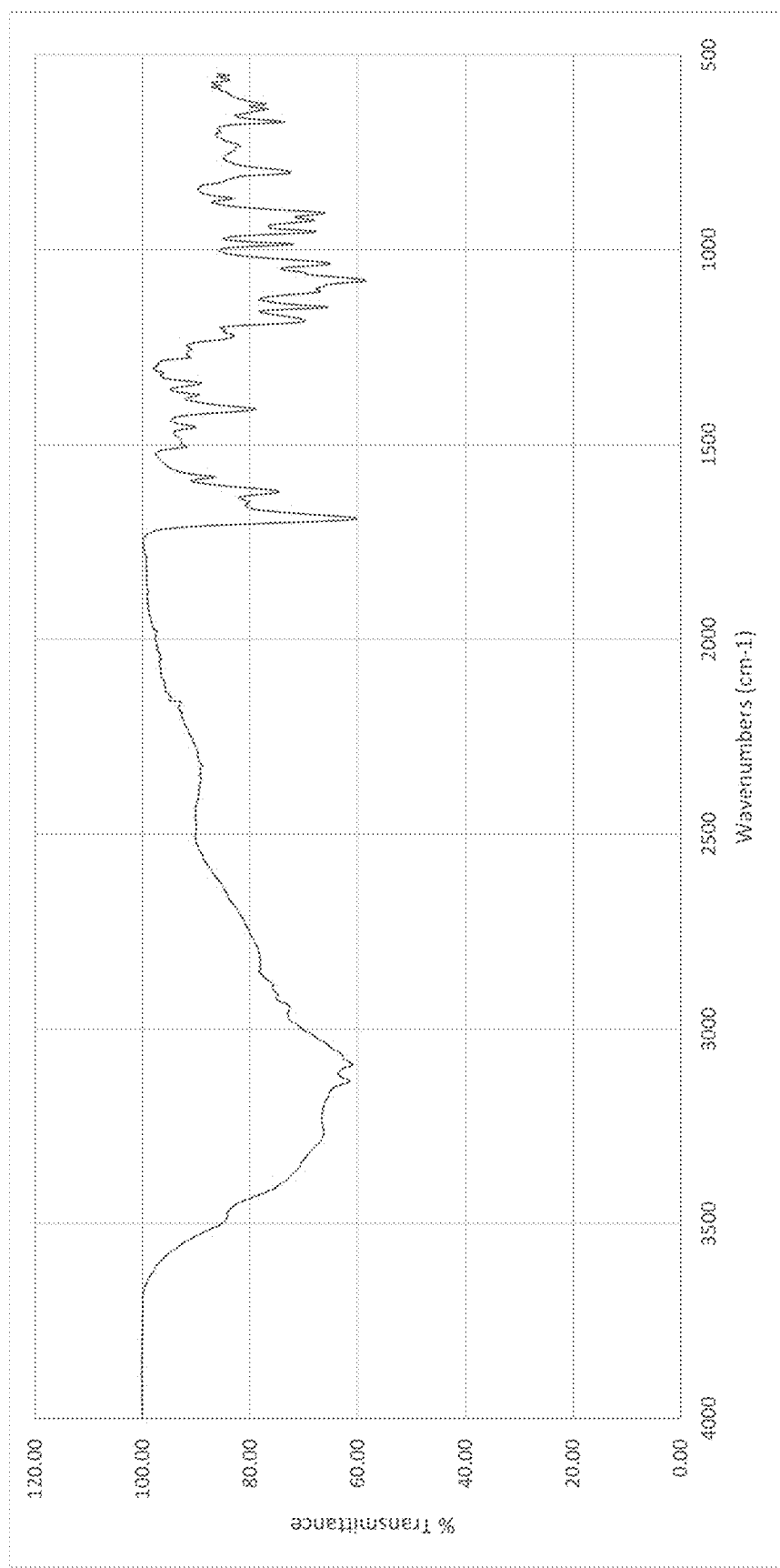
FIG. 26 provides a solid state IR spectrum for the presently disclosed Form III of crystalline nicotinamide mononucleotide (NMN), the compound having formula (XI).

The crystalline Form III of nicotinamide mononucleotide (NMN, Compound 6) may also or alternatively be characterized by a solid-state IR spectrum having peaks at 624.8, 626.8, 671.1, 802.3, and 906.4 $cm^{-1} \pm 0.2$ $cm^{-1}$. The crystalline Form III of nicotinamide mononucleotide (NMN) may also or alternatively be characterized by a solid-state IR spectrum having peaks at 624.8, 626.8, 671.1, 802.3, 906.4, 923.8, 952.7, 985.5, 1035.6, 1078.0, 1147.5, and 1182.2 $cm^{-1} \pm 0.2$ $cm^{-1}$. The crystalline Form III of nicotinamide mononucleotide (NMN) may also or alternatively be characterized by a solid-state IR spectrum having peaks at 624.8, 626.8, 671.1, 802.3, 906.4, 923.8, 952.7, 985.5, 1035.6, 1078.0, 1147.5, 1182.2, 1409.7, 1619.9, and 1689.4 $cm^{-1} \pm 0.2$ $cm^{-1}$. In certain embodiments, the crystalline Form III of nicotinamide mononucleotide (NMN) may be characterized by a solid-state IR spectrum substantially as shown in FIG. 26. In further embodiments, the crystalline Form III of nicotinamide mononucleotide (NMN) may be characterized by a solid-state IR spectrum having peaks substantially as provided in Table 14, below, ±0.2 $cm^{-1}$.

TABLE 14

| IR ($cm^{-1}$) |
|---|
| 3133.81 |
| 3091.38 |
| 1689.37 |
| 1619.94 |
| 1583.30 |
| 1504.23 |
| 1454.09 |
| 1409.73 |
| 1373.09 |
| 1342.24 |
| 1220.74 |
| 1182.17 |
| 1147.46 |
| 1078.03 |
| 1035.60 |
| 985.46 |
| 952.68 |
| 923.75 |
| 906.39 |
| 802.26 |
| 671.12 |
| 626.76 |
| 624.83 |

In another embodiment, crystalline Form III of nicotinamide mononucleotide (NMN, Compound 6) is characterized by a DSC thermogram obtained using a heating rate of 10 K/min comprising an endothermic event with an onset temperature of 105° C.±2° C.

In yet another embodiment, crystalline Form III of nicotinamide mononucleotide (NMN) is characterized by a DSC thermogram obtained using a heating rate of 10 K/min comprising an endothermic event with a peak temperature of 157° C.±2° C.

In yet another embodiment, crystalline Form III of nicotinamide mononucleotide (NMN) is characterized by a DSC thermogram obtained using a heating rate of 10 K/min comprising an endothermic event with an onset temperature of 105° C.±2° C., a peak temperature of 157° C.±2° C., or both.

Figure 35:
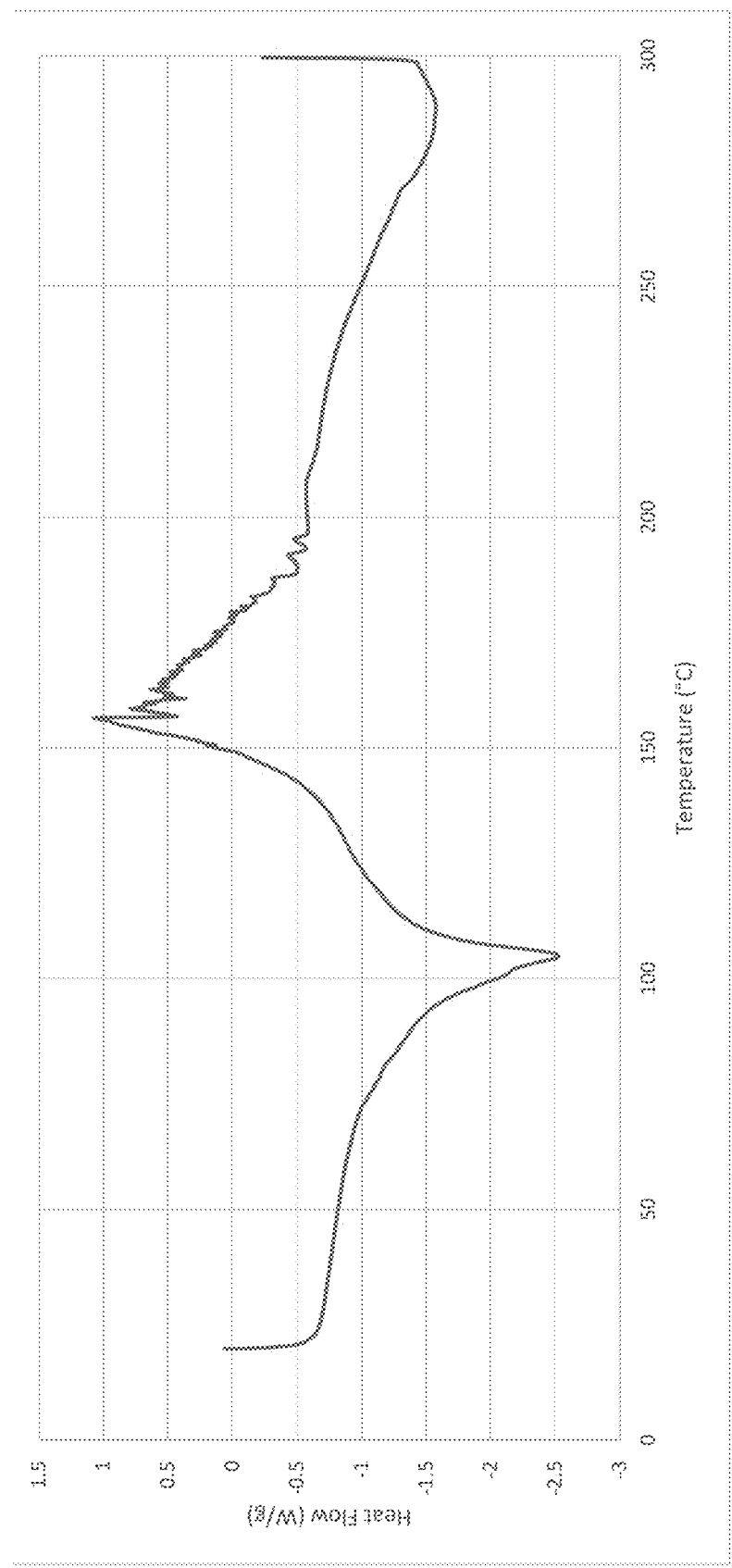
FIG. 35 provides a DSC thermogram for a sample of the presently disclosed Form III of crystalline nicotinamide mononucleotide (NMN), the compound having formula (XI), which was heated at a rate of 10 K/min.

In yet another embodiment, crystalline Form III of nicotinamide mononucleotide (NMN) is characterized by a DSC thermogram substantially as shown in FIG. 35.

Preparation of Crystalline Form IV of Nicotinamide Mononucleotide (NMN, Compound 6)

An amorphous solid form of nicotinamide mononucleotide (NMN, Compound 6) was added to a mixture of ethanol and water in a 3:2 volume:volume ratio at room temperature, in an amount of nicotinamide mononucleotide (NMN) of about 200 mg per milliliter of ethanol-water mixture so as to dissolve the nicotinamide mononucleotide (NMN) in the ethanol-water mixture. The solution of nicotinamide mononucleotide was filtered to remove any undissolved solids, and the solution was then cooled at −20° C. for about 48 hours. The ethanol-water mixture was decanted from the solid crystalline Form IV of nicotinamide mononucleotide (NMN), and the solid crystalline Form IV of nicotinamide mononucleotide (NMN) was dried under vacuum at room temperature overnight.

The crystalline Form IV of nicotinamide mononucleotide (NMN, Compound 6) may be characterized by a powder X-ray diffraction pattern having peaks at 9.6, 22.8, and 25.3 degrees two theta±0.2 degrees two theta. The crystalline Form IV of nicotinamide mononucleotide (NMN) may also or alternatively be characterized by a powder X-ray diffraction pattern having peaks at 9.6, 16.2, 22.0, 22.8, 25.3, and 25.6 degrees two theta±0.2 degrees two theta. The crystalline Form IV of nicotinamide mononucleotide (NMN) may also or alternatively be characterized by a powder X-ray diffraction pattern having peaks at 9.6, 16.2, 16.5, 17.4, 18.9, 19.9, 22.0, 22.8, 25.3, 25.6, 27.1, and 28.7 degrees two theta±0.2 degrees two theta.

Figure 28:
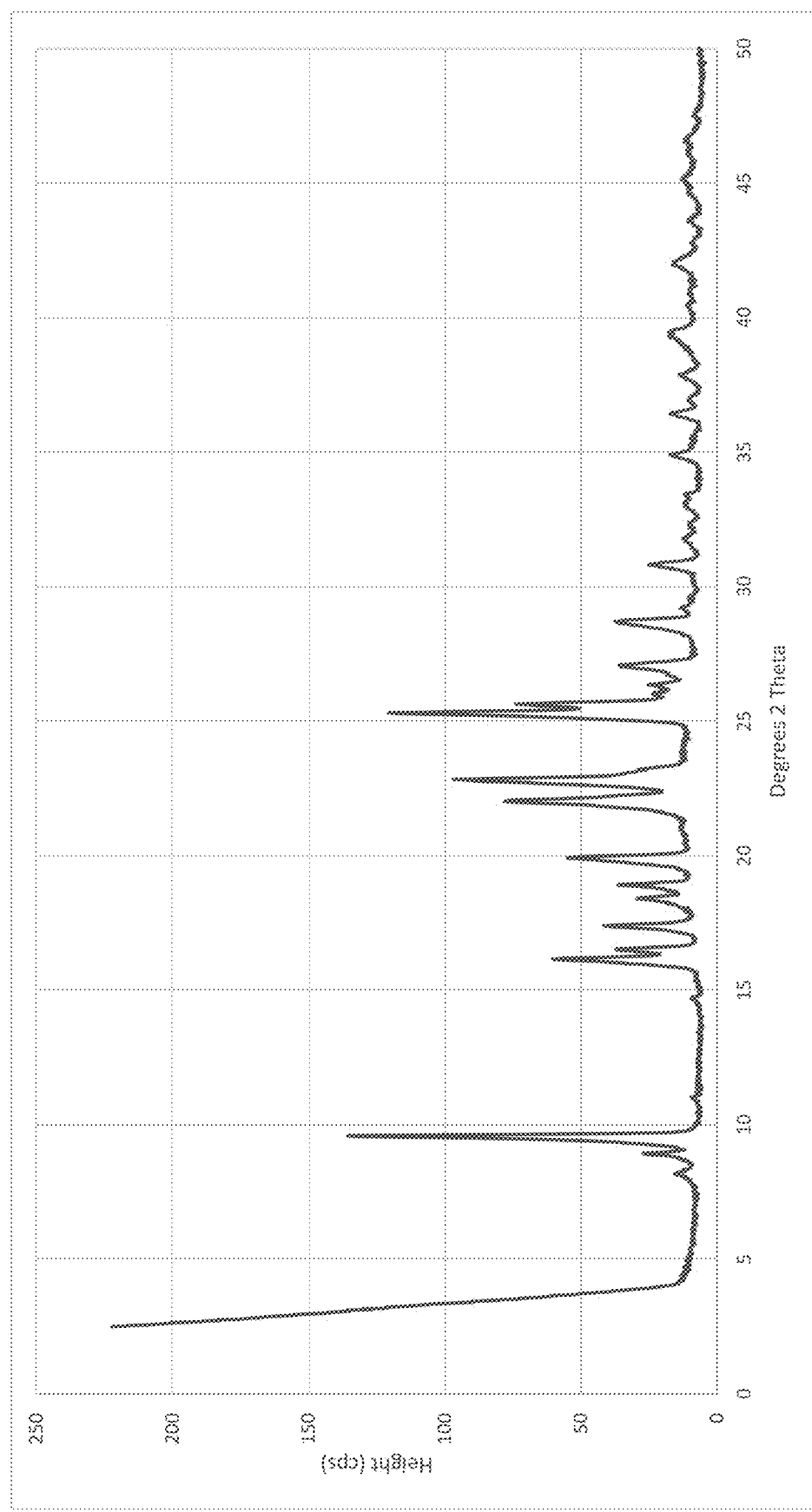
FIG. 28 provides an X-ray powder diffraction pattern for the presently disclosed Form IV of crystalline nicotinamide mononucleotide (NMN), the compound having formula (XI), prepared according to an embodiment of the presently disclosed methods for the preparation of a compound or derivative having general formula (IIa), or a salt, solvate, or prodrug thereof.

In other embodiments, the crystalline Form IV of nicotinamide mononucleotide (NMN) may be characterized by a powder X-ray diffraction pattern substantially as shown in FIG. 28. The crystalline Form IV of nicotinamide mononucleotide (NMN) may also or alternatively be characterized by a powder X-ray diffraction pattern having peaks substantially as provided in Table 15, below, 0.2 degrees two theta.

TABLE 15

| Peak No. | Pos. [°2Th.] | d-spacing [Å] | Height [cts] | $I/I_{max}$ [%] |
|---|---|---|---|---|
| 1 | 8.173 | 10.80927 | 268 | 5 |
| 2 | 8.924 | 9.90138 | 724 | 15 |
| 3 | 9.584 | 9.22091 | 4877 | 100 |
| 4 | 11.001 | 8.03636 | 108 | 2 |
| 5 | 14.677 | 6.03053 | 127 | 3 |
| 6 | 16.153 | 5.48262 | 2004 | 41 |
| 7 | 16.511 | 5.36452 | 1100 | 23 |
| 8 | 17.389 | 5.0958 | 1217 | 25 |
| 9 | 18.413 | 4.81467 | 740 | 15 |
| 10 | 18.917 | 4.68751 | 984 | 20 |
| 11 | 19.921 | 4.45333 | 1688 | 35 |
| 12 | 22.019 | 4.03354 | 2526 | 52 |
| 13 | 22.831 | 3.89188 | 3232 | 66 |
| 14 | 23.174 | 3.83503 | 565 | 12 |
| 15 | 25.301 | 3.51733 | 4175 | 86 |
| 16 | 25.627 | 3.47328 | 2371 | 49 |
| 17 | 25.985 | 3.42619 | 486 | 10 |
| 18 | 26.35 | 3.37957 | 568 | 12 |
| 19 | 27.063 | 3.29219 | 1006 | 21 |
| 20 | 28.696 | 3.10844 | 1107 | 23 |
| 21 | 29.174 | 3.05855 | 177 | 4 |
| 22 | 30.816 | 2.89927 | 646 | 13 |
| 23 | 31.776 | 2.8138 | 184 | 4 |
| 24 | 32.311 | 2.76846 | 85.8 | 2 |
| 25 | 33.077 | 2.70601 | 179 | 4 |
| 26 | 33.359 | 2.68382 | 136 | 3 |
| 27 | 34.897 | 2.56899 | 399 | 8 |
| 28 | 35.607 | 2.51932 | 96.1 | 2 |
| 29 | 36.438 | 2.4638 | 352 | 7 |
| 30 | 36.936 | 2.43167 | 120 | 2 |
| 31 | 37.871 | 2.3738 | 244 | 5 |
| 32 | 39.374 | 2.28655 | 350 | 7 |
| 33 | 40.439 | 2.22876 | 109 | 2 |
| 34 | 40.944 | 2.20242 | 87.6 | 2 |
| 35 | 42.022 | 2.14842 | 304 | 6 |
| 36 | 42.784 | 2.11187 | 102 | 2 |
| 37 | 43.584 | 2.07493 | 149 | 3 |
| 38 | 44.713 | 2.02515 | 132 | 3 |
| 39 | 45.149 | 2.00661 | 207 | 4 |
| 40 | 46.109 | 1.96702 | 140 | 3 |
| 41 | 46.617 | 1.94678 | 171 | 4 |
| 42 | 47.544 | 1.91095 | 61.1 | 1 |

Figure 29:
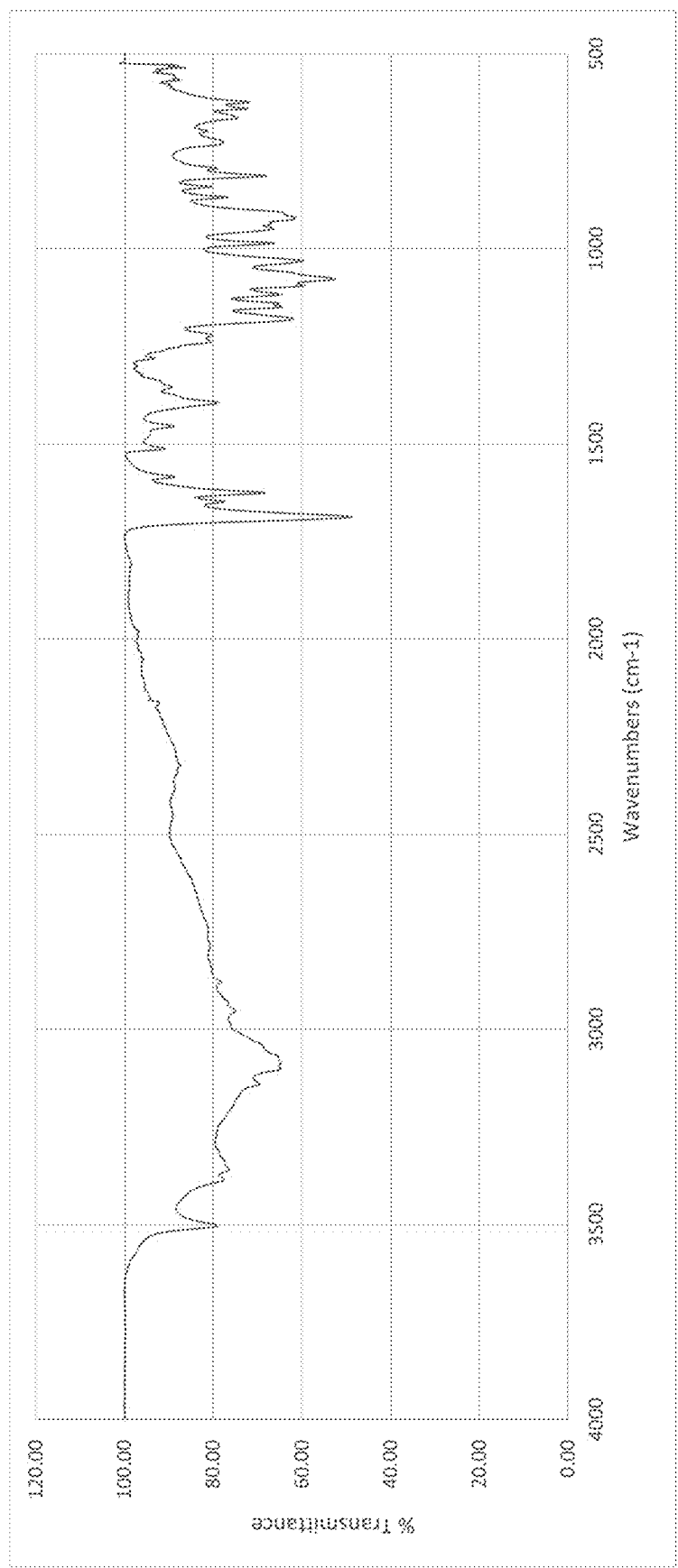
FIG. 29 provides a solid state IR spectrum for the presently disclosed Form IV of crystalline nicotinamide mononucleotide (NMN), the compound having formula (XI).

The crystalline Form IV of nicotinamide mononucleotide (NMN) may also or alternatively be characterized by a solid-state IR spectrum having peaks at 624.8, 640.3, 665.3, 725.1, 813.8, and 840.8 cm$^{-1}$±0.2 cm$^{-1}$. The crystalline Form IV of nicotinamide mononucleotide (NMN) may also or alternatively be characterized by a solid-state IR spectrum having peaks at 624.8, 640.3, 665.3, 725.1, 813.8, 840.8, 867.8, 921.8, 948.8, 985.5, 1029.8, and 1076.1 cm$^{-1}$±0.2 cm$^{-1}$. The crystalline Form IV of nicotinamide mononucleotide (NMN) may also or alternatively be characterized by a solid-state IR spectrum having peaks at 624.8, 640.3, 665.3, 725.1, 813.8, 840.8, 867.8, 921.8, 948.8, 985.5, 1029.8, 1076.1, 1625.7, 1646.9, and 1687.4 cm$^{-1}$±0.2 cm$^{-1}$. In certain embodiments, the crystalline Form IV of nicotinamide mononucleotide (NMN) may be characterized by a solid-state IR spectrum substantially as shown in FIG. 29. In further embodiments, the crystalline Form IV of nicotinamide mononucleotide (NMN) may be characterized by a solid-state IR spectrum having peaks substantially as provided in Table 16, below, ±0.2 cm$^{-1}$.

TABLE 16

| IR (cm$^{-1}$) |
|---|
| 3504.08 |
| 3085.60 |
| 1687.44 |
| 1646.94 |
| 1625.72 |
| 1585.23 |
| 1511.94 |
| 1456.02 |
| 1394.30 |
| 1238.10 |
| 1222.67 |
| 1180.24 |
| 1147.46 |
| 1139.74 |
| 1116.60 |
| 1095.39 |
| 1076.10 |
| 1029.82 |
| 985.46 |
| 948.82 |
| 921.82 |
| 867.82 |
| 840.83 |
| 813.83 |
| 725.12 |
| 665.33 |
| 640.26 |
| 624.83 |

In another embodiment, crystalline Form IV of nicotinamide mononucleotide (NMN, Compound 6) is characterized by a DSC thermogram obtained using a heating rate of 10 K/min comprising an endothermic event with an onset temperature of 144° C.±2° C.

In yet another embodiment, crystalline Form IV of nicotinamide mononucleotide (NMN) is characterized by a DSC thermogram obtained using a heating rate of 10 K/min comprising an endothermic event with an onset temperature of 165° C.±2° C.

In yet another embodiment, crystalline Form IV of nicotinamide mononucleotide (NMN) is characterized by a DSC thermogram obtained using a heating rate of 10 K/min comprising an endothermic event with an onset temperature of 144° C.±2° C., a peak temperature of 165° C.±2° C., or both.

Figure 36:
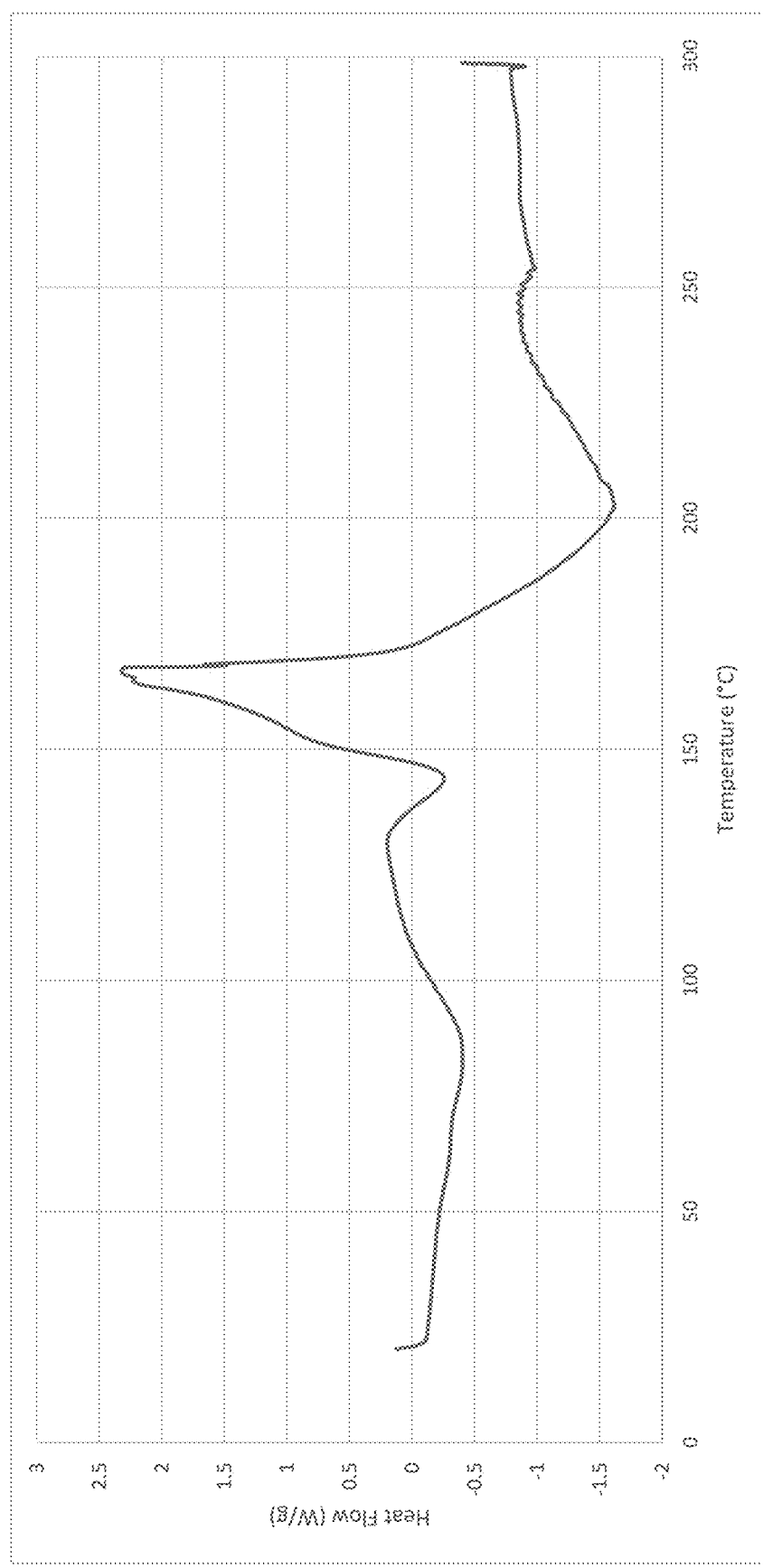
FIG. 36 provides a DSC thermogram for a sample of the presently disclosed Form IV of crystalline nicotinamide mononucleotide (NMN), the compound having formula (XI), which was heated at a rate of 10 K/min.

In yet another embodiment, crystalline Form IV of nicotinamide mononucleotide (NMN) is characterized by a DSC thermogram substantially as shown in FIG. 36.

It is expected through further experimentation that continuously processing a compound or derivative having formula (I), or a salt, solvate, or prodrug thereof, wherein R$^6$ is hydrogen, with a phosphorylating reagent, a phosphitylating reagent, or a thiophosphorylating reagent, and subsequently adding water to the mixture, and adjusting the pH with an aqueous base, will effect the preparation of a compound or derivative having formula (II), or a salt, solvate, or prodrug thereof, under almost solventless conditions. It is expected that the compound or derivative having formula (II), or salt, solvate, or prodrug thereof, can be purified and/or isolated, and the unreacted compound or derivative having formula (I), or salt, solvate, or prodrug thereof, wherein R$^6$ is hydrogen, can be separately isolated.

Example 3

It is expected that batch processing of or continuously processing a compound or derivative having formula (II), or a salt, solvate, or prodrug thereof, with a compound or derivative having formula (3), or a salt thereof, in the presence of a molar (x≤10) equivalent amount of a polar organic solvent co-reagent, and optionally in the presence of additional additives, then adding water to the mixture and adjusting the pH with an aqueous base, will effect the preparation of a compound or derivative having formula (III), or a salt, solvate, or prodrug thereof, under almost solventless conditions. It is expected that the compound or derivative having formula (III), or salt, solvate, or prodrug thereof, can be purified and/or isolated, and the unreacted compound or derivative having formula (II), or salt, solvate, or prodrug thereof, and the unreacted compound or derivative having formula (3), or salt thereof, can be separately isolated.

Example 4

A. Synthetic Preparation of Reduced Nicotinamide Riboside Triacetate (Compound 7): Compound of Formula (IVa): $R^1$=Hydrogen, n=0, $Z^2$=NH, $R^2$=$R^3$=$R^4$=$R^5$=Hydrogen, $R^6$=$R^7$=$R^8$=Acetyl Compound 7

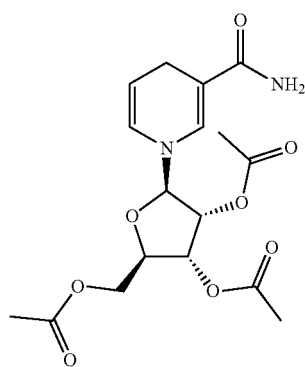

Nicotinamide riboside triacetate (0.500 g, 1.20 mmol, 1 eq.), sodium dithionite (0.246 g, 1.20 mmol, 1 eq.), and sodium hydrogen carbonate (0.201 g, 2.40 mmol, 1 eq.) were added to a 35-milliliter PTFE screw-top milling jar equipped with a 20-millimeter steel core Teflon grinding ball. Water (216 μL, 12.0 mmol, 10 eq.) was added to the solids and the mixture was shaken for 10 minutes in a Retsch MM400 mixer mill at 30 Hz. To the yellow suspension was added ethyl acetate (1.17 mL, 12 mmol, 10 eq.), and the mixture was milled for 5 minutes at 30 Hz. The ethyl acetate layer was removed from the mixture, filtered through a 0.2 μm filter, and added to a round-bottom flask for concentration. This procedure was repeated once more, the organic phases were combined, and the organic solvent was evaporated. 90 mg, 20% yield was obtained of a yellow solid, corresponding to reduced nicotinamide riboside triacetate, Compound 7.

The reduced nicotinamide riboside triacetate (NRH-TA, Compound 7) was dissolved in ethyl acetate in an amount of NRH-TA of approximately 250 mg per milliliter of ethyl acetate. Hexanes was added in a volume of approximately twice the volume of ethyl acetate, and the mixture was allowed to stand for ten minutes. A layer of yellow solution was decanted from the top, and a dark orange oil at the bottom of the flask was dried under vacuum at approximately 40° C. for about 1 hour. The resulting dried solids were grinded to a powder with mortar and pestle.

Figure 41:
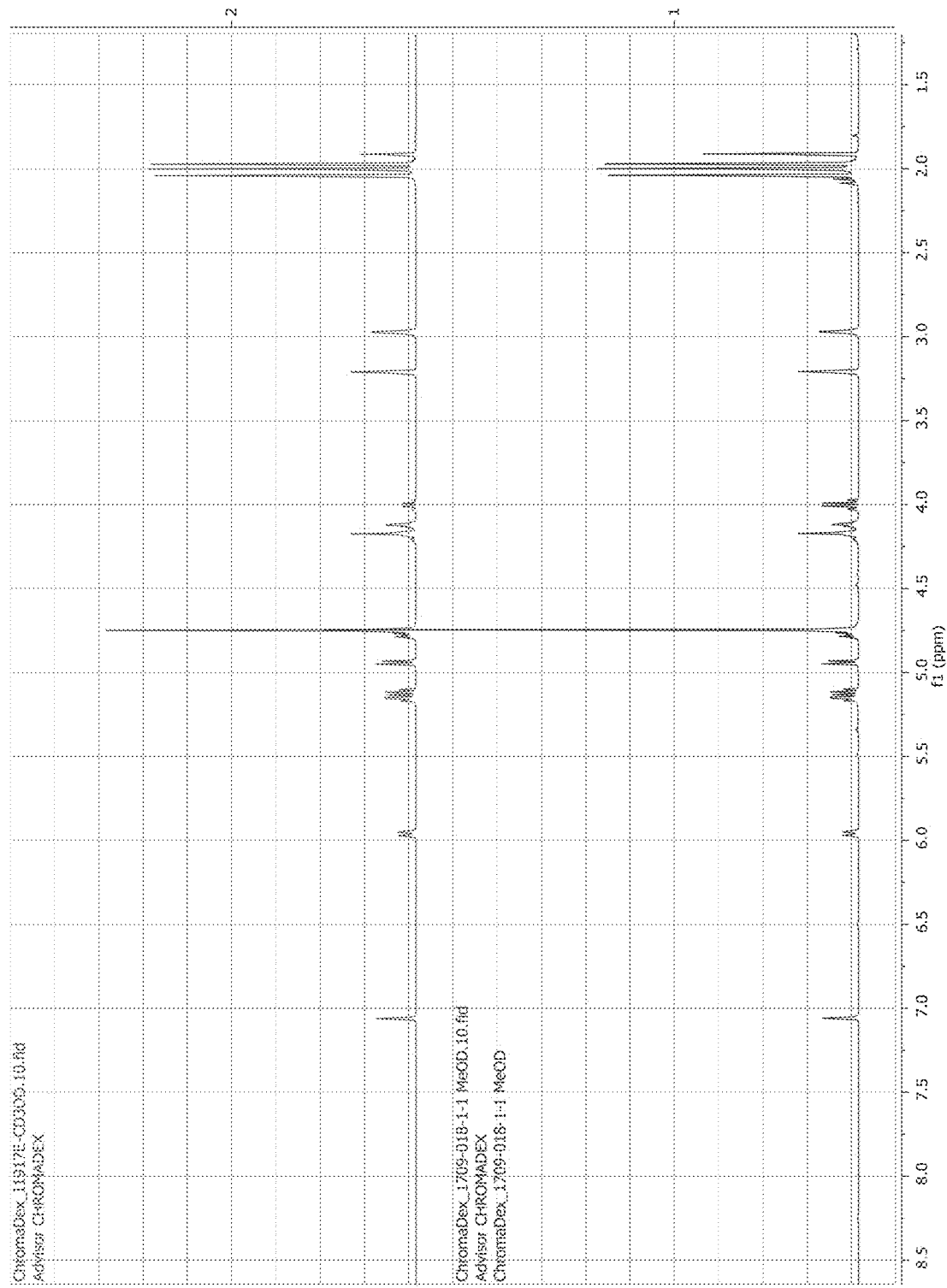
FIG. 41 depicts a comparison of $^1$H NMR spectra of reduced nicotinamide riboside triacetate (1-(2',3',5'-triacetyl-beta-D-ribofuranosyl)-1,4-dihydronicotinamide, "NRH triacetate," or "NRH-TA," Compound 7, infra), prepared using ordinary solvent-based laboratory techniques (top), with reduced nicotinamide riboside triacetate (NRH-TA), performed in accordance with one embodiment of the described methods for the preparation of a compound or derivative having general formula (IVa), or a salt, solvate, or prodrug thereof (bottom).

Reduced nicotinamide riboside triacetate (NRH-TA, Compound 7) was submitted to $^1$H NMR analysis, and the structure of NRH-TA from the above procedure was confirmed by comparison to a $^1$H NMR experiment performed on NRH-TA as prepared using ordinary solvent-based laboratory techniques. FIG. 41 provides a comparison of the $^1$H NMR spectra of NRH-TA as prepared using ordinary solvent-based laboratory techniques (top) with NRH-TA obtained according to the above procedure (bottom).

$^1$H NMR (MeOD, 400 MHz): δ ppm 7.07 (d, J=1.3 Hz, 1H, N—HC═C—C(═O)NH$_2$), 5.95 (dq, J=8.2, 1.6 Hz, 1H, N—HC═CH), 5.16 (dd, J=5.6, 2.5 Hz, 1H, H-3), 5.11 (dd, J=7.0, 5.8 Hz, 1H, H-2), 4.95 (d, J=7.0 Hz, 1H, H-1 (anomeric)), 4.79 (dt, J=8.2, 3.4 Hz, 1H, N—HC═CH), 4.11-4.21 (m, 3H, H-4, H-5, H-5'), 2.92 (dd, J=3.0, 1.5 Hz, 2H, N—HC═CH—CH$_2$), 2.05 (s, 3H, OAc), 2.00 (s, 3H, OAc), 1.97 (s, 3H, OAc). $^{13}$C NMR (MeOD, 100 MHz): δ ppm 172.9, 172.3, 171.5, 171.3 (3×O—C(═O)CH$_3$, C(═O)NH$_2$), 137.4 (N—HC═C—C(═O)NH$_2$), 126.7 (N—HC═CH), 105.2 (N—HC═C—C(═O)NH$_2$), 103.6 (N—HC═CH), 94.4 (C-1 (anomeric)), 80.3 (C-4), 72.1, 72.1 (C-2, C-3), 64.9 (C-5), 23.7 (N—HC═CH—CH$_2$), 20.8, 20.5, 20.3 (3×O—C(═O)CH$_3$). HRMS (ES, M+H$^+$) calculated 383.1454 for C$_{17}$H$_{23}$N$_2$O$_8$, found 383.1445.

Figure 39:
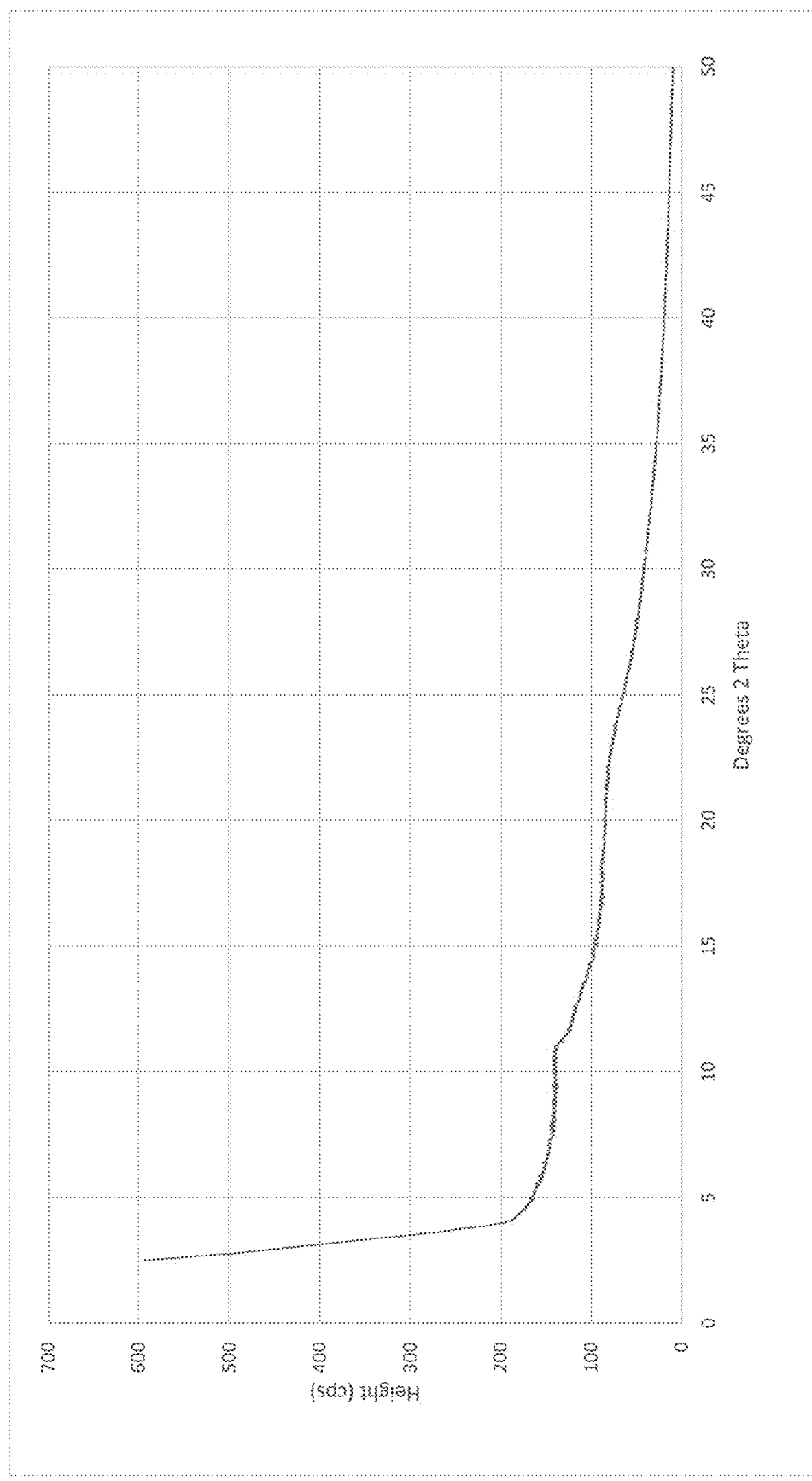
FIG. 39 provides an X-ray powder diffraction pattern for the presently disclosed amorphous solid form of crystalline reduced nicotinamide riboside triacetate (1-(2',3',5'-triacetyl-beta-D-ribofuranosyl)-1,4-dihydronicotinamide, "NRH triacetate," or "NRH-TA," Compound 7, infra) prepared according to an embodiment of the presently disclosed methods for the preparation of a compound or derivative having general formula (IVa), or a salt, solvate, or prodrug thereof.

In an embodiment, the amorphous form of reduced nicotinamide riboside triacetate (NRH-TA, Compound 7) may be characterized by a powder X-ray diffraction pattern substantially as shown in FIG. 39.

B. Synthetic Preparation of Reduced Nicotinic Acid Riboside Triacetate (Compound 8): Compound of Formula (IVa): $R^1$=Hydrogen, n=0, $Z^2$=Oxygen, $R^2$=$R^3$=$R^4$=$R^5$=Hydrogen, $R^6$=$R^7$=$R^8$=Acetyl Compound 8

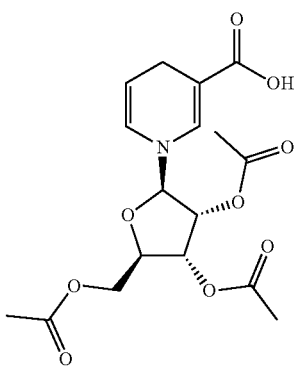

Nicotinic acid riboside triacetate (1.00 g, 2.40 mmol, 1 eq.), sodium dithionite (0.492 g, 2.40 mmol, 1 eq.), and sodium hydrogen carbonate (0.403 g, 4.80 mmol, 2 eq.) were added to a 35-milliliter PTFE screw-top milling jar equipped with a 20-millimeter steel core Teflon grinding ball. Water (216 μL, 12.0 mmol, 5 eq.) was added to the solids and the mixture was shaken for 10 minutes in a Retsch MM400 mixer mill at 30 Hz. To the yellow/orange suspension was added ethyl acetate (2.31 mL, 24 mmol, 10 eq.), and the mixture was milled for 5 minutes at 30 Hz. The ethyl acetate layer was removed from the mixture, filtered through a 0.2 μm filter and added to a round-bottom flask for concentration. This procedure was repeated once more, the organic phases were combined, and the organic solvent was evaporated. 75 mg, 8.4% yield was obtained of a yellow solid, corresponding to reduced nicotinic acid riboside triacetate, Compound 8.

The reduced nicotinic acid riboside triacetate (NARH-TA, Compound 8) was dissolved in ethyl acetate in an amount of NARH-TA of approximately 250 mg per milliliter of ethyl acetate. Hexanes was added in a volume of approximately twice the volume of ethyl acetate, and the mixture was allowed to stand for ten minutes. A layer of yellow solution was decanted from the top, and a dark orange oil at the bottom of the flask was dried under vacuum at approximately 40° C. for about 1 hour. The resulting dried solids were grinded to a powder with mortar and pestle.

Figure 42:
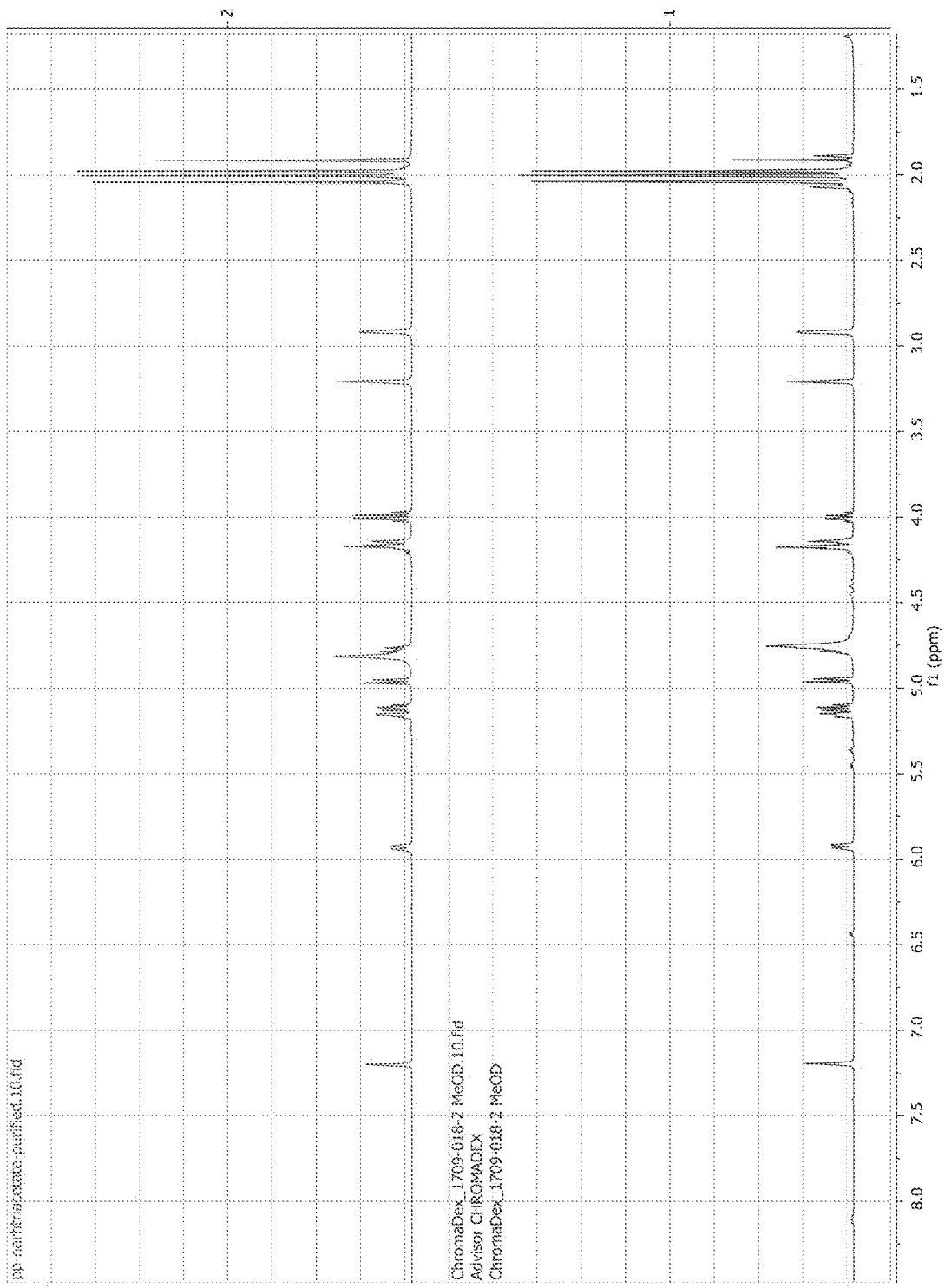
FIG. 42 depicts a comparison of $^1$H NMR spectra of reduced nicotinic acid riboside triacetate (1-(2',3',5'-triacetyl-beta-D-ribofuranosyl)-1,4-dihydronicotinic acid, "NARH triacetate," or "NARH-TA," Compound 8, infra), prepared using ordinary solvent-based laboratory techniques (top), with reduced nicotinic acid riboside triacetate (NARH-TA), performed in accordance with one embodiment of the described methods for the preparation of a compound or derivative having general formula (IVa), or a salt, solvate, or prodrug thereof (bottom).

Reduced nicotinic acid riboside triacetate (NARH-TA, Compound 8) was submitted to $^1$H NMR analysis, and the structure of NARH-TA from the above procedure was confirmed by comparison to a $^1$H NMR experiment performed on NARH-TA as prepared using ordinary solvent-based laboratory techniques. FIG. 42 provides a comparison of the $^1$H NMR spectra of NARH-TA as prepared using ordinary solvent-based laboratory techniques (top) with NARH-TA obtained according to the above procedure (bottom).

$^1$H NMR (MeOD, 400 MHz): δ ppm 7.19 (d, J=1.5 Hz, 1H, N—H$\underline{C}$=C—COOH), 5.93 (dq, J=8.3, 1.6 Hz, 1H, N—H$\underline{C}$=CH), 5.14 (dd, J=5.6, 2.6 Hz, 1H, H-3), 5.10 (dd, J=7.0, 5.8 Hz, 1H, H-2), 4.95 (d, J=7.0 Hz, 1H, H-1 (anomeric)), 4.76 (dt, J=8.0, 3.5 Hz, 1H, N—HC=C$\underline{H}$), 4.12-4.16 (m, 3H, H-4, H-5, H-5'), 2.90 (dd, J=3.0, 1.5 Hz, 2H, N—HC=CH—C$\underline{H}_2$), 2.03 (s, 3H, OAc), 1.99 (s, 3H, OAc), 1.96 (s, 3H, OAc). $^{13}$C NMR (MeOD, 100 MHz): δ ppm 172.2, 171.5, 171.5, 171.3 (3×O—$\underline{C}$(=O)CH$_3$, COOH), 140.0 (N—H$\underline{C}$=C—COOH), 126.8 (N—H $\underline{C}$=CH), 106.2 (N—HC=$\underline{C}$H), 101.6 (N—HC=$\underline{C}$—COOH), 94.2 (C-1 (anomeric)), 80.5 (C-4), 72.3, 72.2 (C-2, C-3), 64.5 (C-5), 23.4 (N—HC=CH—$\underline{C}$H$_2$), 20.8, 20.6, 20.4 (3×O—C(=O)$\underline{C}$H$_3$). HRMS (ES, M+H$^+$) calculated 384.1295 for C$_{17}$H$_{22}$NO$_9$, found 384.1300.

Figure 40:
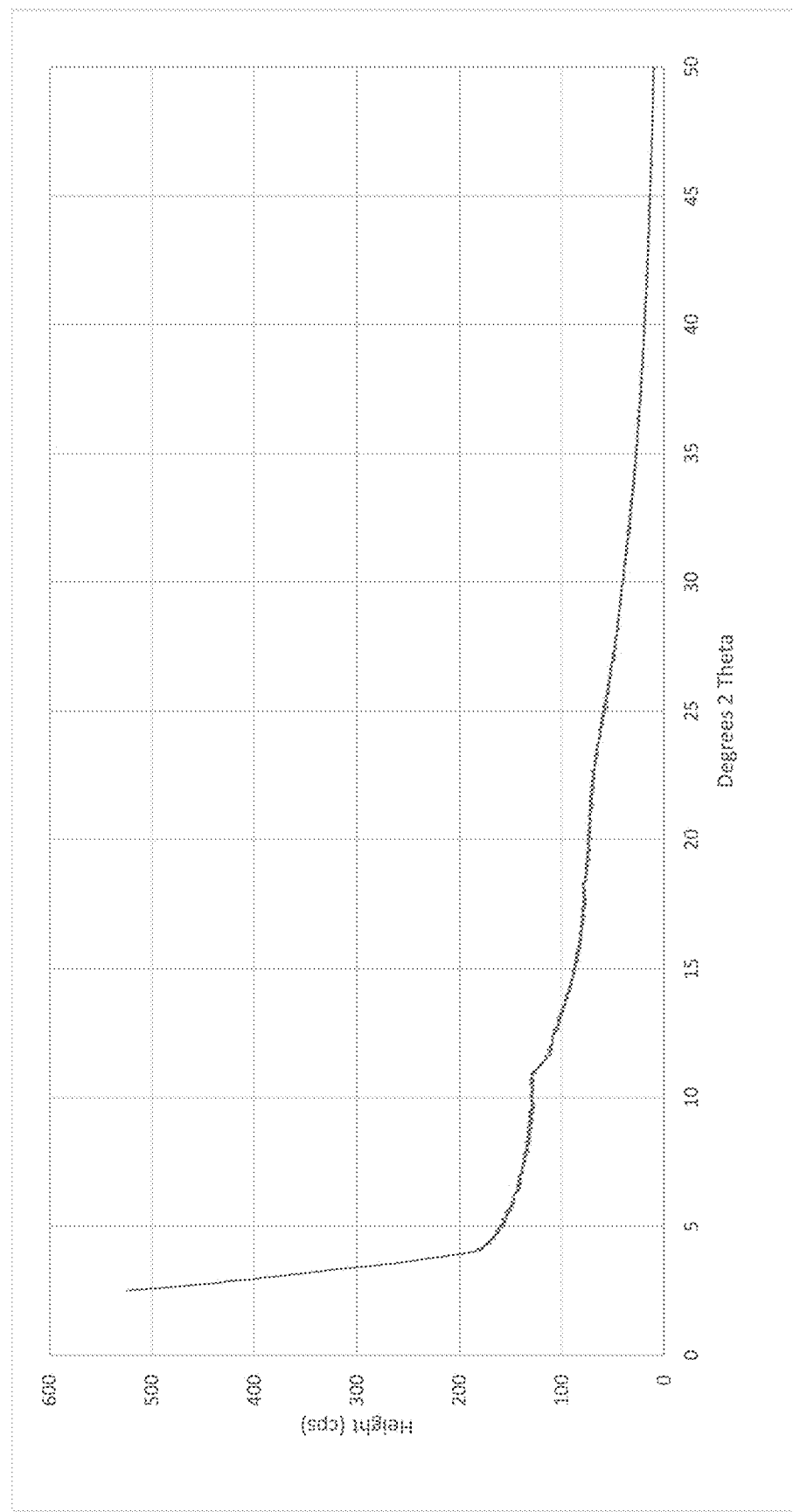
FIG. 40 provides an X-ray powder diffraction pattern for the presently disclosed amorphous solid form of crystalline reduced nicotinic acid triacetate (1-(2',3',5'-triacetyl-beta-D-ribofuranosyl)-1,4-dihydronicotinic acid, "NARH triacetate," or "NARH-TA," Compound 8, infra), prepared according to an embodiment of the presently disclosed methods for the preparation of a compound or derivative having general formula (IVa), or a salt, solvate, or prodrug thereof.

In an embodiment, the amorphous form of reduced nicotinic acid riboside triacetate (NARH-TA, Compound 8) may be characterized by a powder X-ray diffraction pattern substantially as shown in FIG. 40.

Thus, batch processing of or continuously processing a compound or derivative having formula (I), or a salt, solvate, or prodrug thereof, with a stoichiometric amount of a reducing agent reagent, in the presence of a molar equivalent (1<x<10) amount of a polar solvent co-reagent, then removing by-products under reduced pressure and temperature-controlled conditions, will effect the preparation of a compound or derivative having formula (IV), or a salt, solvate, or prodrug thereof, under almost solventless conditions, i.e., substantially free of solvent.

It is expected that the compound or derivative having formula (IV), or salt, solvate, or prodrug thereof, can be purified and/or isolated, and the unreacted compound or derivative having formula (I), or salt, solvate, or prodrug thereof, can be separately isolated.

Example 5

A. Synthetic Preparation of Reduced Nicotinamide Riboside (Compound 9): Compound of Formula (IVa-H): R$^1$=Hydrogen, n=0, Z$^2$=NH, R$^2$=R$^3$=R$^4$=R$^5$=R$^6$=R$^7$=R$^8$=Hydrogen

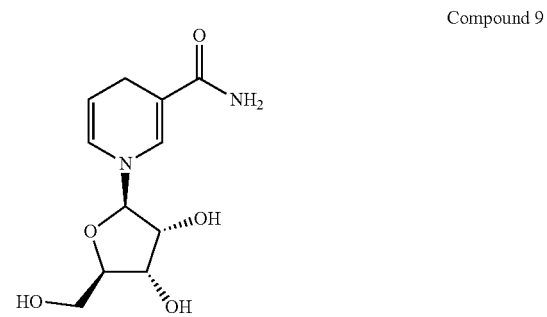 [SMILES: NC(=O)C1=CN([C@@H]2O[C@H](CO)[C@@H](O)[C@H]2O)C=CC1]

Compound 9

Reduced nicotinamide riboside triacetate (Compound 7) was deprotected using mechanochemical (MeOH, NaOMe) processes to remove the acetyl moieties, affording Compound 9 in quantitative yield. Compound 7 (500 mg, 1.35 mmol, 1 eq.), methanol (219 μL, 5.40 mmol, 4 eq.), and NaOMe (25% in MeOH, two drops, ~0.01 mL) were sequentially added to a 35-milliliter PTFE screw-top milling jar equipped with a 20-millimeter steel core Teflon grinding ball. The mixture was shaken for 10 minutes in a Retsch MM400 mixer mill at 30 Hz. The mixture was concentrated to provide a light brown solid in quantitative yield, corresponding to Compound 9.

The reduced nicotinamide riboside (NRH, Compound 9) was dissolved in methanol in an amount of NRH of approximately 100 mg per milliliter of methanol. Isopropyl alcohol was added in a volume of approximately five times the volume of methanol, the mixture was stirred for about 10 minutes, and the mixture was then allowed to stand at −20° C. overnight. The majority of solvent was evaporated under high air flow over the course of about two hours. Solids were collected from the remaining solvent mixture by filtering, and the solids were washed with isopropyl alcohol. The solids were dried under vacuum at room temperature overnight.

Figure 43:
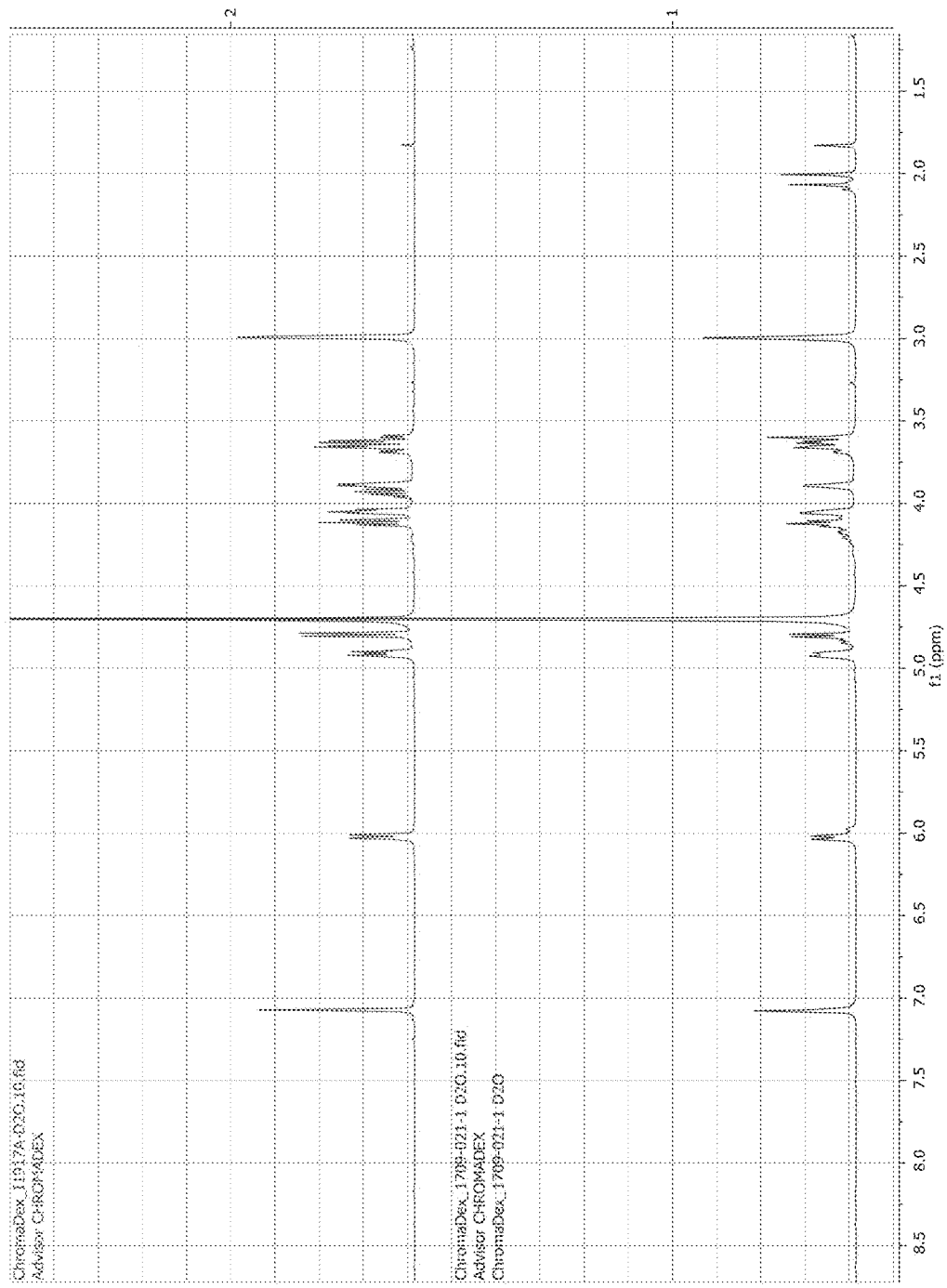
FIG. 43 depicts a comparison of $^1$H NMR spectra of reduced nicotinamide riboside (1-(beta-D-ribofuranosyl)-1,4-dihydronicotinamide, "NRH," Compound 9, infra) prepared using ordinary solvent-based laboratory techniques (top), with reduced nicotinamide riboside (NRH), performed in accordance with one embodiment of the described methods for the preparation of a compound or derivative having general formula (IVa-I), or a salt, solvate, or prodrug thereof, wherein $R^6$, $R^7$, and $R^8$ are each hydrogen (bottom).

Reduced nicotinamide riboside (NRH, Compound 9) was submitted to $^1$NMR analysis, and the structure of NRH from the above procedure was confirmed by comparison to a $^1$H NMR experiment performed on NRH as prepared using ordinary solvent-based laboratory techniques. FIG. 43 provides a comparison of the $^1$H NMR spectra of NRH as prepared using ordinary solvent-based laboratory techniques (top) with NRH obtained according to the above procedure (bottom).

$^1$H NMR (D$_2$O, 400 MHz): δ ppm 7.02 (d, 1H, N—H$\underline{C}$=C—C(O)NH$_2$), 5.97 (dq, J=8.3, 1.5 Hz, 1H, N—H$\underline{C}$=CH), 4.76 (dt, J=8.0, 3.5 Hz, 1H, N—HC=C$\underline{H}$), 4.74 (d, J=7.3 Hz, 1H, H-1 (anomeric)), 4.07 (dd, J=7.1, 5.5 Hz, 1H, H-2), 4.00 (dd, J=5.6, 2.9 Hz, 1H, H-3), 3.82-3.85 (m, 1H, H-4), 3.61 (AB$_X$, J$_{A,B}$=12.4 Hz, J$_{A,X}$=3.8 Hz, 1H, H-5), 3.55 (AB$_X$, J$_{A,B}$=12.4 Hz, J$_{B,X}$=4.5 Hz, 1H, H-5'), 2.94 (dd, J=3.1, 1.6 Hz, 2H, N—HC=CH—C$\underline{H}_2$). $^{13}$C NMR (D$_2$O, 100 MHz): δ ppm 172.9 ($\underline{C}$(=O)NH$_2$), 137.8 (N—H $\underline{C}$=C—C(=O)NH$_2$), 125.2 (N—H$\underline{C}$=CH), 105.1 (N—HC=$\underline{C}$H), 100.9 (N—HC=$\underline{C}$—C(=O)NH$_2$), 94.9

(C-1 (anomeric)), 83.5 (C-4), 70.9 (C-2), 70.1 (C-3), 61.5 (C-5), 22.0 (N—HC=CH—$CH_2$). HRMS (ES, M+H$^+$) calculated 257.1137 for $C_{11}H_{17}N_2O_5$, found 257.1130.

Figure 37:
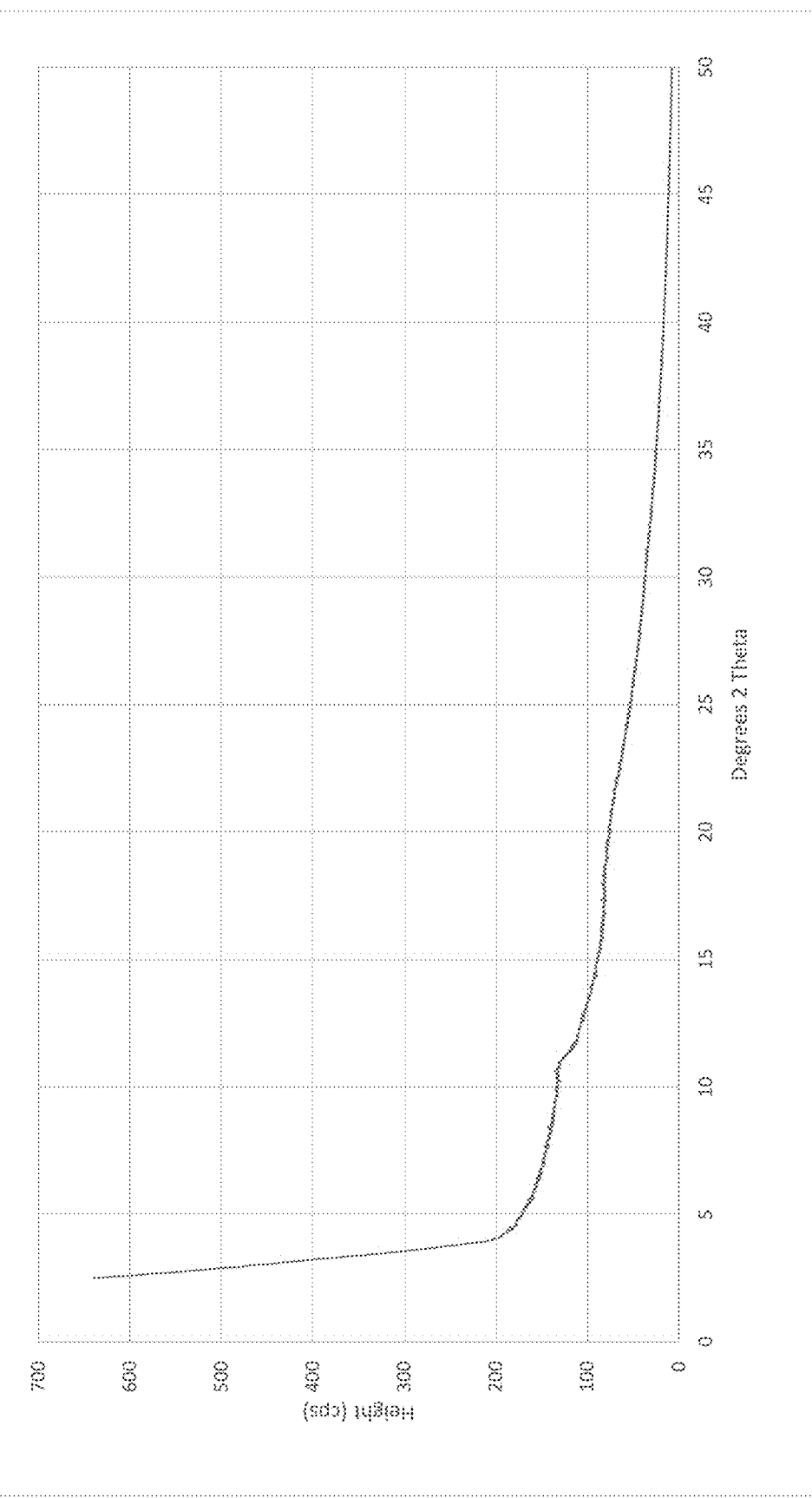
FIG. 37 provides an X-ray powder diffraction pattern for the presently disclosed amorphous solid form of reduced nicotinamide riboside (NRH, Compound 9, infra), prepared according to an embodiment of the presently disclosed methods for the preparation of a compound or derivative having general formula (IVa-H), or a salt, solvate, or prodrug thereof, wherein $R^6$, $R^7$, and $R^8$ are each hydrogen.

In an embodiment, the amorphous form of reduced nicotinamide riboside (NRH, Compound 9) may be characterized by a powder X-ray diffraction pattern substantially as shown in FIG. 37.

B. Synthetic Preparation of Reduced Nicotinic Acid Riboside (Compound 10): Compound of Formula (IVa-H): $R^1$=Hydrogen, n=0, $Z^2$=Oxygen, $R^2$=$R^3$=$R^4$=$R^5$=$R^6$=$R^7$=$R^8$=Hydrogen

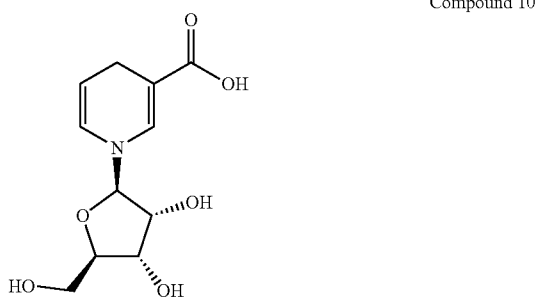

Compound 10

Reduced nicotinic acid riboside triacetate (Compound 8) was deprotected using mechanochemical (MeOH, NaOMe) processes to remove the acetyl moieties, affording Compound 10 in quantitative yield. Compound 8 (500 mg, 1.35 mmol, 1 eq.) and NaOMe (25% in MeOH, 340 μL, 1.49 mmol, 1.1 eq.) were sequentially added to a 35-milliliter PTFE screw-top milling jar equipped with a 20-millimeter steel core Teflon grinding ball. The mixture was shaken for 10 minutes in a Retsch MM400 mixer mill at 30 Hz. The mixture was concentrated to provide an orange solid in quantitative yield, corresponding to Compound 10.

The reduced nicotinic acid riboside (NARH, Compound 10) was dissolved in methanol in an amount of NARH of approximately 50 mg per milliliter of methanol. Isopropyl alcohol was added in a volume of approximately twice the volume of methanol. The mixture was filtered to collect the resulting solids, and the solids were vacuum dried at room temperature overnight.

Figure 44:
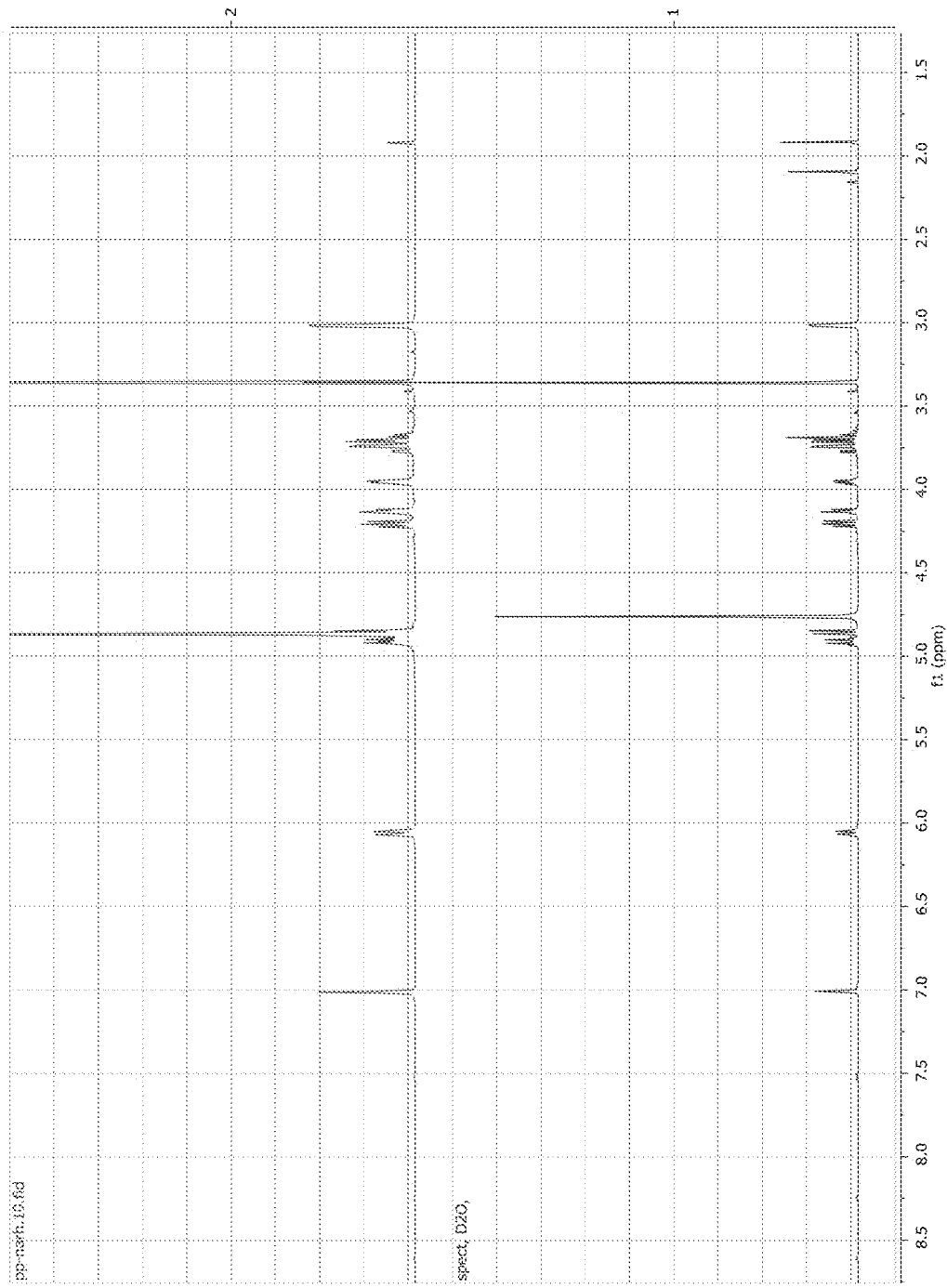
FIG. 44 depicts a comparison of $^1$H NMR spectra of reduced nicotinic acid riboside (1-beta-D-ribofuranosyl)-1,4-dihydronicotinic acid, "NARH," Compound 10, infra) prepared using ordinary solvent-based laboratory techniques (top), with reduced nicotinic acid riboside (NARH), performed in accordance with one embodiment of the described methods for the preparation of a compound or derivative having formula general (IVa-I), or a salt, solvate, or prodrug thereof, wherein $R^6$, $R^7$, and $R^8$ are each hydrogen (bottom).

Reduced nicotinic acid riboside (NARH, Compound 10) was submitted to $^1$H NMR analysis, and the structure of NARH from the above procedure was confirmed by comparison to a $^1$H NMR experiment performed on NARH as prepared using ordinary solvent-based laboratory techniques. FIG. 44 provides a comparison of the $^1$H NMR spectra of NARH as prepared using ordinary solvent-based laboratory technique (top) with NARH obtained according to the above procedure (bottom).

$^1$H NMR (D$_2$O, 400 MHz): δ ppm 6.86 (br s, 1H, N$\underline{H}C$=C—COOH), 5.91 (dq, J=8.3, 1.5 Hz, 1H, N—$\underline{H}C$=CH), 4.76 (dt, J=8.1, 3.5 Hz, 1H, N—HC=C$\underline{H}$), 4.74 (d, J=7.0 Hz, 1H, H-1 (anomeric)), 4.05 (dd, J=6.9, 5.9 Hz, 1H, H-2), 3.97 (dd, J=5.5, 3.0 Hz, 1H, H-3), 3.77-3.82 (m, 1H, H-4), 3.60 (AB$_X$, $J_{A,B}$=12.5 Hz, $J_{A,X}$=3.7 Hz, 1H, H-5), 3.55 (AB$_X$, $J_{A,B}$=12.5 Hz, $J_{B,X}$=4.8 Hz, 1H, H-5'), 2.87 (br s, 2H, N—HC=CH—$CH_2$). $^{13}$C NMR (D$_2$O, 100 MHz): δ ppm 171.1 ($\underline{C}$OOH), 136.4 (N—H$\underline{C}$=C—COOH), 126.1 (N—H$\underline{C}$=CH), 106.1 (N—H$\underline{C}$=C—COOH), 104.8 (N—HC=$\underline{C}$H), 94.9 (C-1 (anomeric)), 83.2 (C-4), 70.8 (C-2), 70.2 (C-3), 61.7 (C-5), 23.2 (N—HC=CH—$\underline{C}H_2$). HRMS (ES, M+Na$^+$) calculated 280.0797 for $C_{11}H_{15}NO_6Na$, found 280.0794.

Figure 38:
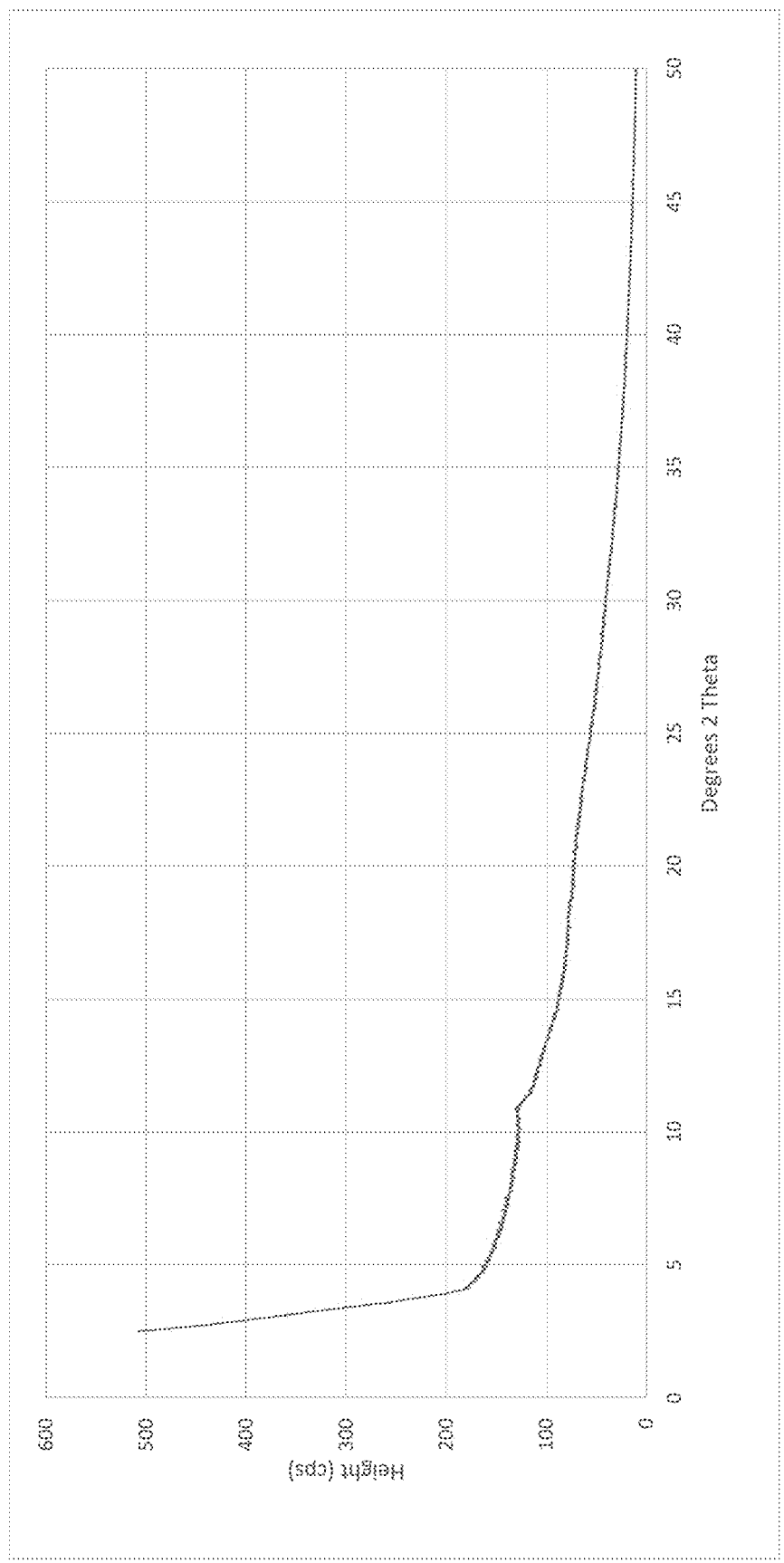
FIG. 38 provides an X-ray powder diffraction pattern for the presently disclosed amorphous solid form of reduced nicotinic acid riboside (NARH, Compound 10, infra), prepared according to an embodiment of the presently disclosed methods for the preparation of a compound or derivative having general formula (IVa-H), or a salt, solvate, or prodrug thereof, wherein $R^6$, $R^7$, and $R^8$ are each hydrogen.

In an embodiment, the amorphous form of reduced nicotinic acid riboside (NARH, Compound 10) may be characterized by a powder X-ray diffraction pattern substantially as shown in FIG. 38.

Thus, batch processing of or continuously processing a compound or derivative having formula (IV), or a salt, solvate, or prodrug thereof, with a molar equivalent of an alcohol and a sub-molar equivalent of a Brønsted base, will effect the preparation of a compound or derivative having formula (IV-H), or a salt, solvate, or prodrug thereof, under almost solventless conditions, i.e., substantially free of solvent. It is expected that the compound or derivative having formula (IV-H), or salt, solvate, or prodrug thereof, can be purified and/or isolated, and the unreacted compound or derivative having formula (IV), or salt, solvate, or prodrug thereof, can be separately isolated.

Example 6

Acidic Hydrolysis Methodology

A jacketed reaction vessel, fitted with addition ports and agitator, was set to 5° C. and charged with NR triacetate (NRTA) chloride (Compound 2, 50 g, 120 mmol, 1.0 eq.). HCl in methanol (3 M, 160 mL, 4 eq.) was slowly poured into the reaction vessel and stirred at a low agitation. The temperature of the solution was maintained at 5° C. and held until the reaction was complete, as seen by HPLC. The reaction mixture, a white suspension, was run off and washed from the reaction vessel using minimal methanol. The methanol suspension was filtered through a Buchner funnel equipped with Whatman filter paper (first isolation). The wet-cake and mother liquor were collected and tested for acetamide content by GC.

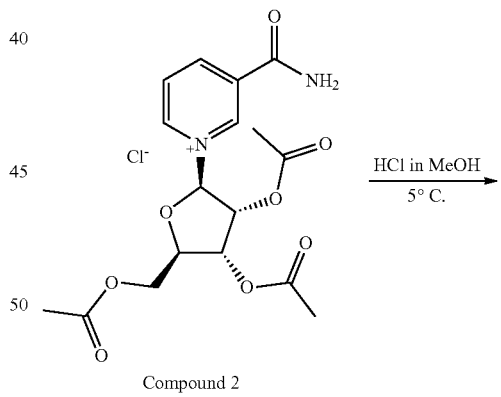

Compound 2

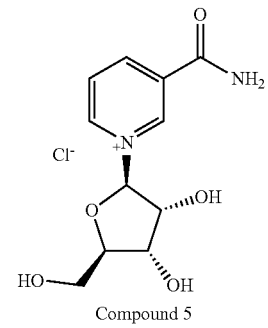

Compound 5

Basic Hydrolysis Methodology

NR triacetate (NRTA) chloride (Compound 2, 40C081, 1240 kg) was slurried into methanol (2453 kg, 2.5 vols.) and chilled to ≤−10° C. While maintaining the solution temperature at ≤−10° C., 30% ammonium hydroxide (248 kg) was slowly added and the reaction solution mixed until deacetylation was confirmed complete by HPLC. At ≤−10° C., the solution was placed under vacuum to strip the excess ammonia, then methyl tert-butyl ether (1376 kg, 1.5 vols.) was charged to precipitate the product. The slurry was isolated via centrifugation at ≤−10° C. and the product was tested for acetamide content by GC.

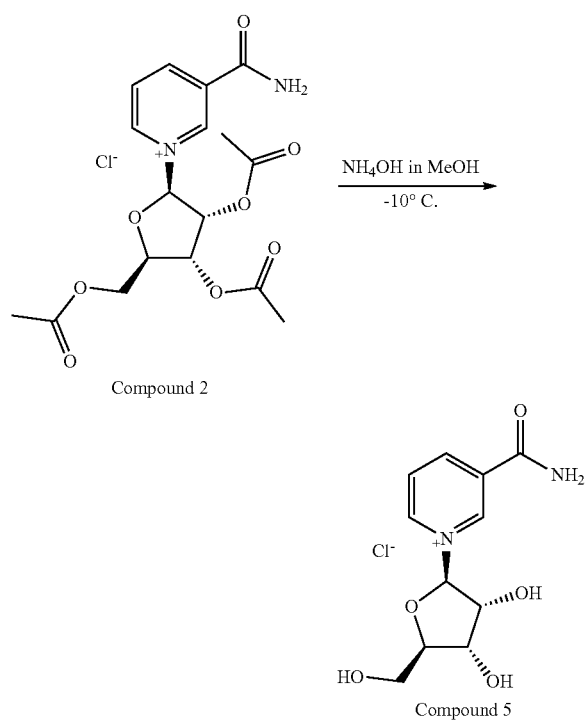

Compound 2

Compound 5

Results

| Sample ID | Hydrolysis Methodology | Acetamide (ppm) |
|---|---|---|
| 1710-013-1 (1st isolation) | Acidic | ND (<5 ppm) |
| 1710-013-1 (Mother Liquor) | Acidic | ND (<5 ppm) |
| Trial 1 (1st isolation) | Basic | 829.60 |
| Trial 2 (1st isolation) | Basic | 833.29 |
| Trial 3 (1st isolation) | Basic | 831.36 |

ND = Non-detect;
Basic = Basic ammonia;
Acidic = HCl methodology described above;
Sample ID relates to a wet-cake unless otherwise stated.

Acetamide was not detected in the acidic deprotection in either the filtered wet cake or the mother liquor, indicating that acetamide is not formed during the reaction. However, acetamide was detected in the basic deprotection in three filtered wet cakes.

Example 7

It is expected that batch processing of or continuously processing a compound or derivative having formula (I), or a salt, solvate, or prodrug thereof, a stoichiometric amount of a reducing agent, and a molar equivalent (1<x<10) amount of a polar organic solvent co-reagent, then removing by-products under reduced pressure and temperature-controlled conditions, then adding a molar equivalent of an alcohol and at least a catalytic amount of a Brønsted inorganic base and processing the mixture, then neutralizing the Brønsted inorganic base using a concentrated acid solution under controlled conditions, then evaporating any volatile by-products, will effect the preparation of a compound or derivative having formula (IV-H), or a salt, solvate, or prodrug thereof, under almost solventless conditions, i.e., substantially free of solvent. It is expected that the compound or derivative having formula (IV-H), or salt, solvate, or prodrug thereof, can be purified and/or isolated, and the unreacted compound or derivative having formula (I), or salt, solvate, or prodrug thereof, and the unreacted compound or derivative having formula (IV), or salt, solvate, or prodrug thereof, can each be separately isolated.

Example 8

It is expected that batch processing of or continuously processing a compound or derivative having formula (IVb), or a salt, solvate, or prodrug thereof, with a phosphorylating reagent, or, alternatively, a phosphitylating reagent followed by an oxidizing agent reagent, or, alternatively, a thiophosphorylating reagent, then adding the mixture to iced water, then adjusting the pH of the aqueous base, will effect the preparation of a compound or derivative having formula (V), or a salt, solvate, or prodrug thereof, under almost solventless conditions, i.e., substantially free of solvent. It is expected that the compound or derivative having (V), or salt, solvate, or prodrug thereof, can be purified and/or isolated, and the unreacted compound or derivative having formula (IVb), or salt, solvate, or prodrug thereof can be separately isolated.

Example 9

It is expected that batch processing of or continuously processing a compound or derivative having formula (IV-H), or a salt, solvate, or prodrug thereof, with a phosphorylating reagent, or, alternatively, a phosphitylating reagent followed by an oxidizing agent reagent, or, alternatively, a thiophosphorylating reagent, then adding the mixture to iced water, then adjusting the pH of the aqueous phase with an aqueous base, will effect the preparation of a compound or derivative having formula (V), or a salt, solvate, or prodrug thereof, under almost solventless conditions, i.e., substantially free of solvent. It is expected that the compound or derivative having formula (V), or salt, solvate, or prodrug thereof, can be purified and/or isolated, and the unreacted compound or derivative having formula (IV-H), or salt, solvate, or prodrug thereof, can be separately isolated.

Example 10

It is expected that batch processing of or continuously processing a compound or derivative having formula (V), or a salt, solvate, or prodrug thereof, with a compound or derivative having formula (3), or a salt thereof, in the presence of a molar (x≤10) equivalent amount of a polar organic solvent co-reagent, and optionally in the presence of additional additives, then adding the mixture to iced water and adjusting the pH with an aqueous base, will effect the preparation of a compound or derivative having formula (VI), or a salt, solvate, or prodrug thereof, under almost solventless conditions, i.e., substantially free of solvent. It is expected that the compound or derivative having formula (VI), or salt, solvate, or prodrug thereof, can be purified and/or isolated, and the unreacted compound or derivative having formula (V), or salt, solvate, or prodrug thereof, and the unreacted compound or derivative having formula (3), or salt thereof, can each be separately isolated.

Instrumentation

X-ray powder diffraction. The X-ray powder diffraction information concerning the crystalline and amorphous solid forms of the compounds or derivatives prepared according to embodiments of the methods of the present disclosure was obtained using MiniFlex 600 Benchtop X-ray RIGAKU Diffractometer, with a Cu K-alpha 0.15418 nm X-ray tube, run in a continuous scan mode with a scan speed of 2.0000 deg/min and a step width of 0.0200 deg; the scan axis in theta/2-theta with a scan range of 1.0000-50.0000 deg; and an incident slit of 1.250 deg with the receiving slit #1 set at 1.250 deg and the receiving slit #2 set at 0.3 deg.

Infrared Spectroscopy. Fourier-Transform Infrared Spectroscopy (FT-IR) spectra were obtained using a Thermo iS50 FT-IR spectrometer with a diamond Attenuated Total Reflection accessory.

Differential Scanning Calorimetry ("DSC"). DSC was conducted using a Model DSC Q20 V24.11 Differential Scanning Calorimeter at a heating rate of 10 K/min per ASTM D 3418-15. Samples were heated at 10 K/min from 20° C. to 300° C., held at 300° C., cooled to 20° C. at 10 K/min, held at 20° C. for 5 minutes, then reheated to 300° C. at 10 K/min. All testing was performed in a nitrogen environment.

It is well known that the DSC onset and peak temperatures as well as energy values may vary due to, for example, the purity of the sample and sample size and due to instrumental parameters, especially the temperature scan rate. Hence the DSC data presented are not to be taken as absolute values. A person skilled in the art can set up instrumental parameters for a Differential Scanning Calorimeter so that data comparable to the data presented here can be collected according to standard methods, for example, those described in G. W. H. HÖHNE ET AL., DIFFERENTIAL SCANNING CALORIMETRY (Springer 1996).

Gas chromatography ("GC"). Approximately 600 mg of each sample was added to a 20 mL scintillation vial and exactly 10 mL of acetone was added. The samples were sonicated for 30 minutes and filtered through a 0.45 µm PTFE syringe filter into a GC vial for analysis. Samples were analyzed against a six-point acetamide calibration curve. GC instrumental parameters: instrument, GC with a FID; DB-FFAP column, 30.0 m×0.250 mm×0.25 µm; inlet temperature, 250° C.; carrier gas flow rate, 2.0 mL/min helium; split ratio, 1:1 split; FID temperature, 260° C.; run time, 25.0 minutes; oven temperature program,

| Level | Rate (° C./min) | Temperature (° C.) | Hold (min) |
|---|---|---|---|
| Initial | NA | 40 | 4.0 |
| 1 | 10 | 190 | 0.0 |
| 2 | 30 | 250 | 4.0 |

Limit of detection ("LOD"), 5 ppm; Limit of quantification ("LOQ"), 10 ppm.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

We claim:

1. A method of making a compound having formula (I), a salt thereof, or a solvate thereof:

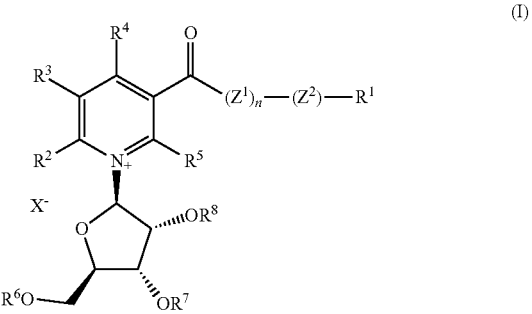

(I)

wherein $X^-$ is a counterion selected from the group consisting of citrate, gluconate, succinate, ascorbate, malate, tartrate, glycolate, glucuronate, maleate, fumarate, pyruvate, mandelate, nitrate, pantothenate, salicylate, galactarate, and galacturonate;

$Z^1$ of formula (I) is absent and n is 0;

$Z^2$ of formula (I) is NH;

$R^1$ of formula (I) is hydrogen;
$R^2$, $R^3$, $R^4$, and $R^5$ each of formula (I) are each hydrogen;
$R^6$, $R^7$ and $R^8$ each of formula (I) are each independently selected from the group consisting of hydrogen and —C(O)R'; and
R' is selected from the group consisting of methyl and substituted or unsubstituted aryl;
the method comprising the steps of:
(a) providing a compound having formula (2), or salt thereof:

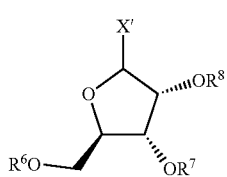

(2)

wherein X' is selected from the group consisting of fluoro, chloro, bromo, iodo, $HCO_2$, acetoxy, propionoxy, butyroxy, glutamyloxy, aspartyloxy, ascorbyloxy, benzoyloxy, $HOCO_2$, citryloxy, carbamyloxy, gluconyloxy, lactyloxy, succinyloxy, sulfoxy, trifluoromethanesulfoxy, trichloromethanesulfoxy, tribromomethanesulfoxy, trifluoroacetoxy, malateoxy, tartaroxy, glycoloxy, glucoronoxy, maleateoxy, fumaroxy, pyruvoxy, anthraniloxy, 4-hydroxybenzoxy, phenylacetoxy, mandeloxy, pamoatoxy, methanesulfoxy, ethanesulfoxy, benzenesulfoxy, panthothenoxy, trifluoroacetoxy, 2-hydroxyethanesulfoxy, p-toluenesulfoxy, sulfaniloxy, cyclohexylaminosulfoxy, stearoxy, alginoxy, beta-hydroxybutyroxy, salicyloxy, galactaroxy, and galacturonoxy;
$R^6$, $R^7$ and $R^5$ of formula (2) are each independently selected from the group consisting of hydrogen, —C(O)R', —C(O)OR', and —C(O)NHR'; and
R' is selected from the group consisting of hydrogen, methyl, substituted or unsubstituted $(C_3\text{-}C_8)$cycloalkyl, substituted or unsubstituted aryl, substituted or unsubstituted heteroaryl, and substituted or unsubstituted heterocycle;
(b) treating the compound having formula (2), or salt thereof, with a compound having formula (1), or a salt thereof;

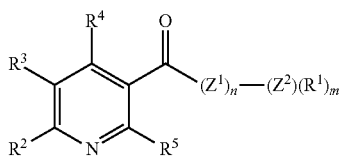

(1)

wherein $Z^1$ of formula (1) is absent and n is 0;
$Z^2$ of formula (1) is NH;
m is 1;
$R^1$ of formula (1) is hydrogen; and
$R^2$, $R^3$, $R^4$, and $R^5$ of formula (1) are each hydrogen;
(c) processing the compound having formula (2), or salt thereof, and the compound having formula (1), or salt thereof, so as to couple the compound of formula (2) to the compound of formula (1) and treating with an agent selected from the group consisting of a base, an acid, an acyl chloride, or combinations thereof, to produce the compound having formula (I), a salt thereof, or a solvate thereof; and
(d) isolating the compound having formula (I), a salt thereof, or a solvate thereof;
wherein the processing step (c) further comprises the steps of:
adding a volume of solvent comprising methanol, ethanol, water, or combinations thereof, to the compound having formula (I), a salt thereof, or a solvate thereof, at room temperature, so as to dissolve at least a portion of the compound having formula (I), a salt thereof, or a solvate thereof:
stirring the compound having formula (I), a salt thereof, or a solvate thereof, at about 25° C. to about 50° C. in the methanol, ethanol, water, or combinations thereof; and
cooling the compound having formula (I), a salt thereof, or a solvate thereof, in the methanol, ethanol, water, or combinations thereof, to a range of about 0° C. to about −10° C. with stirring so as to precipitate the compound having formula (I), a salt thereof, or a solvate thereof.

2. The method of claim 1, wherein the processing of step (c) is selected from the group consisting of batch processing, liquid-assisted mixing, milling, grinding, and extruding.

3. The method of claim 1, wherein the compound having formula (2), or salt thereof, the compound having formula (1), or salt thereof, or combination thereof, is further treated with a Lewis acid in step (b).

4. The method of claim 3, wherein the Lewis acid is selected from the group consisting of trimethylsilyl trifluoromethanesulfonate, boron trifluoride, and tin (IV) chloride.

5. The method of claim 3, wherein the compound having formula (I), a salt thereof, or a solvate thereof, is a beta-anomer.

6. The method of claim 1, wherein the compound of formula (I), a salt thereof, or a solvate thereof, is enriched with a beta-anomer of the compound of formula (I), a salt thereof, or a solvate thereof.

7. The method of claim 6, wherein the compound having formula (I), a salt thereof, or a solvate thereof, is enriched with the beta anomer by:
adding a solvent to a mixture comprising alpha and beta anomers of the compound having formula (I), a salt thereof, or a solvate thereof, to preferentially precipitate the beta-anomer of the compound having formula (I), a salt thereof, or a solvate thereof;
isolating the precipitate;
washing the precipitate with the solvent;
wherein the precipitate comprises the compound having formula (I), a salt thereof, or a solvate thereof, that is enriched with its beta anomer.

8. The method of claim 1, wherein $R^6$, $R^7$, and $R^8$ are each hydrogen.

9. The method of claim 8, wherein when the agent is an acid the processing step (c) further comprises adding a base to effect $X^-$ ion exchange.

10. The method of claim 1, wherein the compound of formula (I), a salt thereof, or a solvate thereof is nicotinamide riboside, or a salt thereof, or a solvate thereof, as shown in the following structure:

337

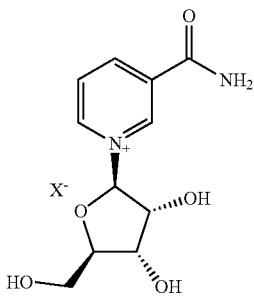

wherein X⁻ is as defined above in formula (I),
wherein the processing step (c) further comprises the steps of:
  forming nicotinamide riboside triacetate, a salt thereof, or a solvate thereof;
  treating the nicotinamide riboside triacetate, a salt thereof, or a solvate thereof, with a solvent, and an agent selected from the group consisting of a base, an acid, and an acyl chloride so as to produce the nicotinamide riboside, a salt thereof, or a solvate thereof; and
  wherein the isolating step (d) comprises isolating the nicotinamide riboside, a salt thereof, or a solvate thereof.

11. The method of claim 10, wherein, when the agent is a base, the method further comprises the step of adding an acid to effect X⁻ ion exchange.

12. The method of claim 11, wherein when the agent is an acid, the method further comprises the step adding a base to effect X⁻ ion exchange.

13. The method of claim 10, wherein the nicotinamide riboside compound, a salt thereof, or a solvate thereof, is selected from nicotinamide riboside malate or nicotinamide riboside tartrate.

14. The method of claim 13, wherein the agent is an acid.

15. The method of claim 8, further wherein the base, acid, or acyl chloride effects ion-exchange to provide the salt of the compound having formula (I).

16. The method of claim 1, wherein the compound having formula (I), a salt thereof, or a solvate thereof, is nicotinamide riboside malate or nicotinamide riboside tartrate.

17. The method of claim 1, wherein the compound having formula (I) is a salt of nicotinamide riboside or a salt of nicotinamide riboside triacetate, or a solvate of any of the foregoing.

18. The method of claim 17, wherein the compound having formula (I) is a nicotinamide riboside salt or nicotinamide riboside triacetate salt, wherein X⁻ is selected from the group consisting of malate and tartrate.

19. The method of claim 17, wherein the compound having formula (2) is represented by the following structure:

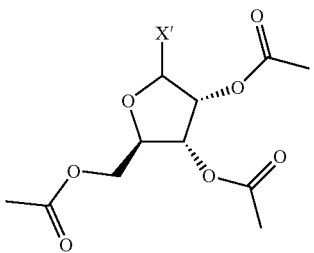

338 wherein X' is selected from the group consisting of chloro, bromo, and acetoxy.

20. The method of claim 19, wherein the compound having formula (1) is nicotinamide as represented by the following structure:

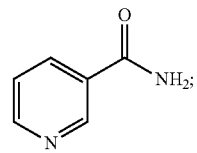

or a salt thereof.

21. A method of making a compound having formula (I), a salt thereof, or a solvate thereof:

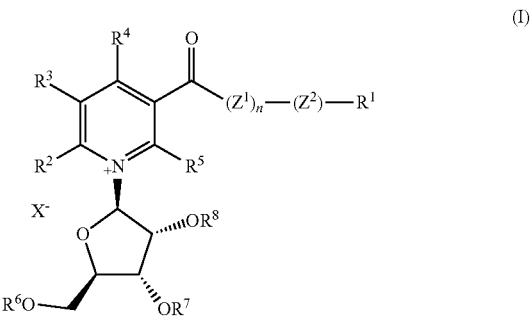

wherein X⁻ is a counterion selected from the group consisting of citrate, gluconate, succinate, ascorbate, malate, tartrate, glycolate, glucuronate, maleate, fumarate, pyruvate, mandelate, nitrate, pantothenate, salicylate, galactarate, and galacturonate;
$Z^1$ of formula (I) is absent and n is 0;
$Z^2$ of formula (I) is NH;
$R^1$ of formula (I) is hydrogen;
$R^2$, $R^3$, $R^4$, and $R^5$ each of formula (I) are each hydrogen;
$R^6$, $R^7$ and $R^8$ each of formula (I) are each independently selected from the group consisting of hydrogen and —C(O)R'; and
R' is selected from the group consisting of methyl and substituted or unsubstituted aryl;
the method comprising the steps of:
  (a) providing a compound having formula (2), or salt thereof:

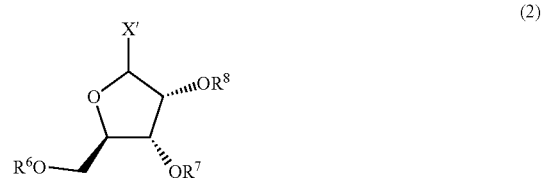

wherein X' is selected from the group consisting of fluoro, chloro, bromo, iodo, $HCO_2$, acetoxy, propionoxy, butyroxy, glutamyloxy, aspartyloxy, ascorbyloxy, benzoyloxy, $HOCO_2$, citryloxy, carbamyloxy, gluconyloxy, lactyloxy, succinyloxy, sulfoxy, trifluoromethanesulfoxy, trichloromethanesulfoxy, tribromomethanesulfoxy, trifluoroacetoxy, malateoxy, tartaroxy, glycoloxy, glucoronoxy, maleateoxy, fumaroxy, pyruvoxy, anthraniloxy, 4-hydroxybenzoxy, phenylacetoxy, mandeloxy, pamoatoxy, methanesulfoxy, ethanesulfoxy, benzenesulfoxy, panthothenoxy, trifluoroacetoxy, 2-hydroxyethanesulfoxy, p-toluenesulfoxy, sulfaniloxy, cyclohexylaminosulfoxy, stearoxy, alginoxy, beta-hydroxybutyroxy, salicyloxy, galactaroxy, and galacturonoxy;

$R^6$, $R^7$ and $R^8$ of formula (2) are each independently selected from the group consisting of hydrogen, —C(O)R', —C(O)OR', and —C(O)NHR'; and R' is selected from the group consisting of hydrogen, methyl, substituted or unsubstituted $(C_3-C_8)$cycloalkyl, substituted or unsubstituted aryl, substituted or unsubstituted heteroaryl, and substituted or unsubstituted heterocycle;

(b) treating the compound having formula (2), or salt thereof, with a compound having formula (1), or a salt thereof;

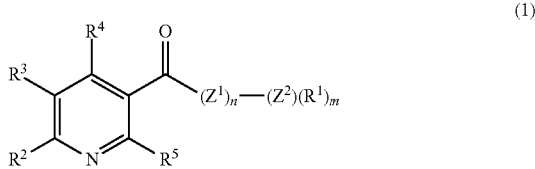

wherein $Z^1$ of formula (1) is absent and n is 0;
$Z^2$ of formula (1) is NH;
m is 1;
$R^1$ of formula (1) is hydrogen; and
$R^2$, $R^3$, $R^4$, and $R^5$ of formula (1) are each hydrogen;

(c) processing the compound having formula (2), or salt thereof, and the compound having formula (1), or salt thereof, so as to couple the compound of formula (2) to the compound of formula (1) and treating with an agent selected from the group consisting of a base, an acid, an acyl chloride, or combinations thereof, to produce the compound having formula (I), a salt thereof, or a solvate thereof; and (d) isolating the compound having formula (I), a salt thereof, or a solvate thereof;

wherein the compound of formula (I), a salt thereof, or a solvate thereof, is enriched with a beta-anomer of the compound of formula (I), a salt thereof, or a solvate thereof;

wherein the compound having formula (I), a salt thereof, or a solvate thereof, is enriched with the beta anomer by:

adding a solvent to a mixture comprising alpha and beta anomers of the compound having formula (I), a salt thereof, or a solvate thereof, to preferentially precipitate the beta-anomer of the compound having formula (I), a salt thereof, or a solvate thereof;

isolating the precipitate;
washing the precipitate with the solvent;
wherein the precipitate comprises the compound having formula (I), a salt thereof, or a solvate thereof, that is enriched with its beta anomer.

22. The method of claim 21, wherein the processing of step (c) is selected from the group consisting of batch processing, liquid-assisted mixing, milling, grinding, and extruding.

23. The method of claim 21, wherein the compound having formula (2), or salt thereof, the compound having formula (1), or salt thereof, or combination thereof, is further treated with a Lewis acid in step (b).

24. The method of claim 23, wherein the Lewis acid is selected from the group consisting of trimethylsilyl trifluoromethanesulfonate, boron trifluoride, and tin (IV) chloride.

25. The method of claim 23, wherein the compound having formula (I), a salt thereof, or a solvate thereof, is a beta-anomer.

26. The method of claim 21, wherein $R^6$, $R^7$, and $R^8$ are each hydrogen.

27. The method of claim 21, wherein the processing step (c) further comprises the steps of:

adding a volume of solvent comprising methanol, ethanol, water, or combinations thereof, to the compound having formula (I), a salt thereof, or a solvate thereof, at room temperature, so as to dissolve at least a portion of the compound having formula (I), a salt thereof, or a solvate thereof;

stirring the compound having formula (I), a salt thereof, or a solvate thereof, at about 25° C. to about 50° C. in the methanol, ethanol, water, or combinations thereof; and cooling the compound having formula (I), a salt thereof, or a solvate thereof, in the methanol, ethanol, water, or combinations thereof, to a range of about 0° C. to about −10° C. with stirring so as to precipitate the compound having formula (I), a salt thereof, or a solvate thereof.

28. The method of claim 26, wherein when the agent is an acid the processing step (c) further comprises adding a base to effect $X^-$ ion exchange.

29. The method of claim 21, wherein the compound of formula (I), a salt thereof, or a solvate thereof is nicotinamide riboside, or a salt thereof, or a solvate thereof, as shown in the following structure:

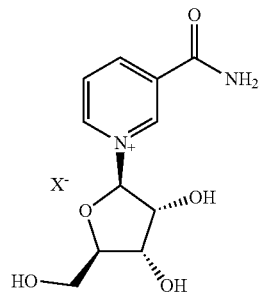

wherein $X^-$ is as defined above in formula (I),
wherein the processing step (c) further comprises the steps of:

forming nicotinamide riboside triacetate, a salt thereof, or a solvate thereof;

treating the nicotinamide riboside triacetate, a salt thereof, or a solvate thereof, with a solvent, and an agent selected from the group consisting of a base, an acid, and an acyl chloride so as to produce the nicotinamide riboside, a salt thereof, or a solvate thereof; and wherein the isolating step (d) comprises isolating the nicotinamide riboside, a salt thereof, or a solvate thereof.

30. The method of claim 29, wherein, when the agent is a base, the method further comprises the step of adding an acid to effect $X^-$ ion exchange.

31. The method of claim 29, wherein when the agent is an acid, the method further comprises the step adding a base to effect X⁻ ion exchange.

32. The method of claim 29, wherein the nicotinamide riboside compound, a salt thereof, or a solvate thereof, is selected from nicotinamide riboside malate or nicotinamide riboside tartrate.

33. The method of claim 32, wherein the agent is an acid.

34. The method of claim 26, further wherein the base, acid, or acyl chloride effects ion-exchange to provide the salt of the compound having formula (I).

35. The method of claim 21, wherein the compound having formula (I), a salt thereof, or a solvate thereof, is nicotinamide riboside malate or nicotinamide riboside tartrate.

36. The method of claim 21, wherein the compound having formula (I) is a salt of nicotinamide riboside or a salt of nicotinamide riboside triacetate, or a solvate of any of the foregoing.

37. The method of claim 36, wherein the compound having formula (I) is a nicotinamide riboside salt or nicotinamide riboside triacetate salt, wherein X⁻ is selected from the group consisting of malate and tartrate.

38. The method of claim 36, wherein the compound having formula (2) is represented by the following structure:

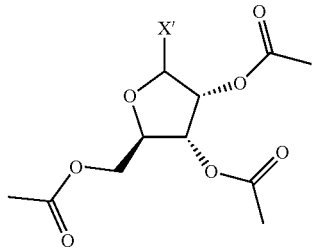

wherein X' is selected from the group consisting of chloro, bromo, and acetoxy.

39. The method of claim 38, wherein the compound having formula (1) is nicotinamide as represented by the following structure:

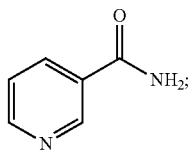

or a salt thereof.

* * * * *

UNITED STATES PATENT AND TRADEMARK OFFICE
CERTIFICATE OF CORRECTION

PATENT NO. : 11,242,364 B1
APPLICATION NO. : 17/323789
DATED : February 8, 2022
INVENTOR(S) : Marie E. Migaud et al.

It is certified that error appears in the above-identified patent and that said Letters Patent is hereby corrected as shown below:

In the Claims

In Claim 12, Column 337, Line 31, replace the term "11" with the term --10--.

Signed and Sealed this
Nineteenth Day of April, 2022

*Katherine Kelly Vidal*

Katherine Kelly Vidal
*Director of the United States Patent and Trademark Office*